United States Patent
Cappelletti et al.

(10) Patent No.: US 8,420,050 B2
(45) Date of Patent: *Apr. 16, 2013

(54) GASTRIN RELEASING PEPTIDE COMPOUNDS

(75) Inventors: Enrico Cappelletti, Sergno (IT); Luciano Lattuada, Bussero (IT); Karen E. Linder, Kingston, NJ (US); Edmund R. Marinelli, Lawrenceville, NJ (US); Palaniappa Nanjappan, Princeton, NJ (US); Adrian D. Nunn, Lambertville, NJ (US); Natarajan Raju, Kendall Park, NJ (US); Kondareddiar Ramalingam, Dayton, NJ (US); Rolf E. Swenson, Princeton, NJ (US); Michael F. Tweedle, Princeton, NJ (US); Mary Ellen Maddalena, Monmouth Jct., NJ (US)

(73) Assignee: Bracco Imaging S.p.A., Milan (IT)

( * ) Notice: Subject to any disclaimer, the term of this patent is extended or adjusted under 35 U.S.C. 154(b) by 584 days.

This patent is subject to a terminal disclaimer.

(21) Appl. No.: 12/137,079

(22) Filed: Jun. 11, 2008

(65) Prior Publication Data

US 2009/0175786 A1  Jul. 9, 2009

Related U.S. Application Data

(63) Continuation-in-part of application No. 11/751,337, filed on May 21, 2007, now abandoned, which is a continuation-in-part of application No. 11/352,156, filed on Feb. 10, 2006, now Pat. No. 7,850,947, which is a continuation-in-part of application No. 11/165,721, filed on Jun. 24, 2005, now Pat. No. 7,922,998, which is a continuation-in-part of application No. 10/828,925, filed on Apr. 20, 2004, now Pat. No. 7,611,692, which is a continuation-in-part of application No. PCT/US03/41328, filed on Dec. 24, 2003, which is a continuation-in-part of application No. 10/341,577, filed on Jan. 13, 2003, now Pat. No. 7,226,577.

(51) Int. Cl.
*A61K 51/00* (2006.01)
*A61M 36/14* (2006.01)

(52) U.S. Cl.
USPC .......... 424/1.69; 424/1.11; 424/1.65; 424/9.1; 530/328; 534/15

(58) Field of Classification Search .............. 424/1.11, 424/1.65, 1.69, 1.81, 1.85, 1.89, 9.1, 9.2, 424/9.3, 9.4, 9.5, 9.6, 9.7, 9.8; 534/7, 10–16; 514/1, 9, 16, 1.11; 530/300, 317, 328
See application file for complete search history.

(56) References Cited

U.S. PATENT DOCUMENTS

| | | |
|---|---|---|
| 4,885,363 A | 12/1989 | Tweedle et al. |
| 4,988,496 A | 1/1991 | Srinivasan et al. |
| 5,068,222 A | 11/1991 | Camble et al. |
| 5,084,555 A | 1/1992 | Coy et al. |
| 5,217,955 A | 6/1993 | Bogden et al. |
| 5,219,556 A | 6/1993 | Wolfangel |
| 5,244,883 A | 9/1993 | Cai et al. |
| 5,369,094 A | 11/1994 | Schally et al. |
| 5,393,512 A | 2/1995 | Vanderheyden et al. |
| 5,410,018 A | 4/1995 | Spindel et al. |
| 5,428,018 A | 6/1995 | Edwards et al. |
| 5,428,019 A | 6/1995 | Edwards et al. |
| 5,474,756 A | 12/1995 | Tweedle et al. |
| 5,534,497 A | 7/1996 | Verbruggen |
| 5,620,959 A | 4/1997 | Leban et al. |
| 5,620,995 A | 4/1997 | Weidmann et al. |

(Continued)

FOREIGN PATENT DOCUMENTS

| | | |
|---|---|---|
| EP | 0309297 | 3/1989 |
| EP | 0436005 | 3/1995 |

(Continued)

OTHER PUBLICATIONS

Hermanson (1996), Bioconjugate Techniques, Academic Press, Functional Targets, Chapter 1, pp. 3-136.*

(Continued)

*Primary Examiner* — D L Jones
(74) *Attorney, Agent, or Firm* — White & Case LLP

(57) ABSTRACT

Novel methods of treating prostate tumors or of delaying the progression of prostate tumors are also provided, including, methods of treating bone or soft tissue metastases of prostate cancer methods for treating hormone sensitive and hormone refractory prostate cancer, methods for delaying the progression of hormone sensitive prostate cancer, for facilitating combination therapy in patients with hormone sensitive prostate cancer and for decreasing aberrant vascular permeability in patients with hormone sensitive prostate cancer, said methods comprising the step of administering to a subject a dose comprising an amount of radioactively labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

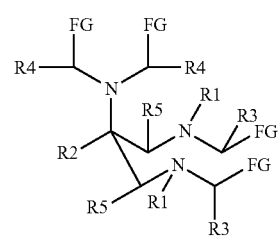

34 Claims, 105 Drawing Sheets

U.S. PATENT DOCUMENTS

| | | | |
|---|---|---|---|
| 5,649,537 | A | 7/1997 | Anelli et al. |
| 5,686,410 | A | 11/1997 | Albert et al. |
| 5,723,578 | A | 3/1998 | Coy |
| 5,833,985 | A | 11/1998 | Ball et al. |
| 5,834,433 | A | 11/1998 | Krstenansky |
| 5,965,595 | A | 10/1999 | Maurer et al. |
| 5,981,504 | A | 11/1999 | Buchsbaum et al. |
| 6,075,121 | A | 6/2000 | Simon et al. |
| 6,191,290 | B1 | 2/2001 | Safavy |
| 6,200,546 | B1 | 3/2001 | Hoffman et al. |
| 6,307,017 | B1 | 10/2001 | Coy et al. |
| 6,461,588 | B1 | 10/2002 | Anelli et al. |
| 6,803,030 | B2 | 10/2004 | De Haen et al. |
| 6,866,837 | B2 | 3/2005 | Reubi et al. |
| 6,921,526 | B2 | 7/2005 | Hoffman et al. |
| 7,060,247 | B2 | 6/2006 | Hoffman et al. |
| 7,147,838 | B2 | 12/2006 | Hoffman et al. |
| 7,226,577 | B2 * | 6/2007 | Cappelletti et al. ............. 424/9.1 |
| 7,611,692 | B2 * | 11/2009 | Cappelletti et al. ............. 424/9.1 |
| 7,850,947 | B2 | 12/2010 | Cappelletti |
| 7,922,998 | B2 | 4/2011 | Cappelletti et al. |
| 7,989,417 | B2 | 8/2011 | De Haen |
| 2002/0054855 | A1 | 5/2002 | Hoffman et al. |
| 2002/0164287 | A1 | 11/2002 | Rajagopalan |
| 2002/0176819 | A1 | 11/2002 | Hoffman et al. |
| 2003/0050436 | A1 | 3/2003 | Coy et al. |
| 2003/0171561 | A1 | 9/2003 | Pillai et al. |
| 2003/0224998 | A1 | 12/2003 | Reubi et al. |
| 2004/0136906 | A1 | 7/2004 | Cappelletti et al. |
| 2004/0253225 | A1 | 12/2004 | Cappelletti et al. |
| 2005/0163710 | A1 | 7/2005 | Hoffman et al. |
| 2005/0171014 | A1 | 8/2005 | Tarasova et al. |
| 2006/0067886 | A1 | 3/2006 | Hoffman et al. |
| 2007/0161047 | A1 | 7/2007 | Zhong et al. |
| 2007/0231257 | A1 | 10/2007 | Cappelletti et al. |
| 2007/0270575 | A1 | 11/2007 | Jacobovitz et al. |
| 2008/0008649 | A1 | 1/2008 | Capelletti et al. |
| 2008/0247946 | A1 | 10/2008 | Cappelletti et al. |
| 2011/0052491 | A1 | 3/2011 | Cappelletti et al. |

FOREIGN PATENT DOCUMENTS

| | | |
|---|---|---|
| EP | 0489089 | 6/1996 |
| EP | 0438519 | 5/1998 |
| EP | 1181936 | 2/2002 |
| EP | 0749325 | 6/2002 |
| EP | 1001977 | 10/2005 |
| WO | 89/02897 | 4/1989 |
| WO | 90/03980 | 4/1990 |
| WO | 91/01144 | 2/1991 |
| WO | 91/02746 | 3/1991 |
| WO | 95/24220 | 9/1995 |
| WO | 9532741 A | 12/1995 |
| WO | 96/03427 | 2/1996 |
| WO | 98/47524 | 10/1998 |
| WO | 9847524 A1 | 10/1998 |
| WO | 99/62563 | 12/1999 |
| WO | 0038738 A | 7/2000 |
| WO | 00/50059 | 8/2000 |
| WO | 01/09163 | 2/2001 |
| WO | 01/52900 | 7/2001 |
| WO | 0152900 A2 | 7/2001 |
| WO | 0162777 A | 8/2001 |
| WO | 02087631 A | 11/2002 |
| WO | 02087631 A1 | 11/2002 |
| WO | 03008390 A1 | 1/2003 |
| WO | 03/072754 | 9/2003 |
| WO | 03/72754 | 9/2003 |
| WO | 03092743 A1 | 11/2003 |
| WO | 2004062574 A | 7/2004 |
| WO | 2004065407 A | 8/2004 |
| WO | WO2004065407 | 8/2004 |
| WO | 2005009393 A2 | 2/2005 |

OTHER PUBLICATIONS

Eckelman et al (1993), Nuclear Imaging in Drug Discovery, Development, and Approval (eds), pp. 113-134.*

Taylor et al (1993), Annals New York Academy of Sciences, pp. 350-352.*

Radulovic et al (1992), P.S.E.B.M., vol. 200, pp. 394-401.*

International Search Report, PCT/US09/44447. Oct. 6, 2009, 3 pages.

Wen et al., "Poly(ethylene glycol)-Conjugated Anti-EGF Receptor Antibody C225 with Radiometal Chelator Attached to the Termini of Polymer Chains", Bioconjugate Chem. 2001; 12:545-553.

Hu et al., "PM-149 DOTA Bombesin Analogs for Potential Radiotherapy In Vivo Comparison with SM-153 and Lu-177 labeled DO3A-amide-βA1a-BBN(7-14)NH2", Nuclear Medicine and Biology 29 (2002) 423-430.

Safavy et al., "Paclitaxel Derivatives for Targeted Therapy of Cancer: Toward the Development of Smart Taxanes", J. Med. Chem. 1999, 42, 4919-4924.

Smith et al. "Radiochemical Investigations of 177Lu-DOTA-8-Aoc-BBN[7-14]NH2: A New Gastrin Releasing Peptide Receptor (GRPr) Targeting Radiopharmaceutical", J. Labelled Cpd. Radiopharm, 44 Suppl. I (2001).

Van De Wiele et al., "Technetium-99m RP527, GRP analogue for visualisation of GRP receptor-expressing malignancies: a feasibility study", European Journal of Nuclear Medicine vol. 27, No. 11 (Nov. 2000).

PCT International Preliminary Report on Patentability mailed Jan. 14, 2010; BRACCO, PCT/US07/61813 (Aug. 2, 2007).

Schibli, R., Karra, S.R., Gali, H., Katti, K.V., Higginbotham, C., Smith, C.J., Hoffman, T.J., and Volkert, W.A.; Conjugation of Small Biomolecules and Peptides with Water-Soluble Dithio-Bis-Hydroxymethylphosphine Ligands, Center Radiological Research, University of Missouri, Columbia, MO, USA. Book of Abstracts, 215th ACS National Meeting, Dallas, Mar. 29-Apr. 2, 1998, NUCL-062.

Smith, C.J., Hoffman, T.J., Gali, H., Hayes, D.L., Owen, N.K., Siekman, G.L. and Volkert, W.A.; Radiochemical investigations of 177Lu-DOTA-8-Aoc-BBN[7-14]NH2: A New Gastrin Releasing Peptide Receptor (GRPr) Targeting Radiopharmaceutical, J. Labeled Compounds and Radiopharmaceutical, J. Labeled Cpd. Radipharm., 44 (51):5706-5708, 2001.

Volkert, W.A., and Hoffman, T.J., Design and Development of Receptor-avid Peptide Conjugates for In Vivo Targeting of Cancer, Part of the SPIE Conference of Molecular Imaging: Reporters-Dyes, Markers and Instrumentation, SPIE vol. 3600:86-98, Jan. 1999.

Safavy et al. "Paclitaxel Derivatives for Targeted Therapy of Cancer: Toward the Development of Smart Taxanes", J. of Med. Chem., vol. 42, Jan. 1, 1999, pp. 4919-4924.

Wen et al. "Poly(ethylen glycol)-conjgated anti-EGF receptor antibody C225 with radiometal chelator attached to the termini of polymer chains". Bioconjugate Chemistry, vol. 12, No. 4, Jul. 1, 2001, pp. 545-553.

Hu et al. "Pm-149 DOTA bombesin analogs for potential radiotherapy—in vivo comparison with Sm-153 and Lu-177 labeled DO3A-amide-betaAla-BBN(7-14)NH", Nuclear Medicine and Biology, vol. 29, No. 4, May 1, 2002, pp. 423-430.

Smith et al. "Radiochemical investigation of 177 Lu-DOT-8-Aoc-BBN[7-14]NH2: an invitro/invivo assessment of the targeting ability of this new radiopharmaceutical for PC-3 human prostate cancer cells" Nuclear Medicine & Biology, vol. 30, 2003, pp. 101-109.

Bijsterbosch, MK; Selective Drug Delivery by Means of Receptor-Mediated Endocytosis, The Quarterly Journal of Nuclear Medicine, vol. 39, No. 1, pp. 4-19, Mar. 1995.

Parker, David; Tumor Targeting with Radiolabelled Macrocycle-Antibody Conjugates, Chemical Society Reviews, vol. 19, No. 3, Sep. 1990, pp. 271-291.

Wilbur, D. Scott; Radiohalogenation of Proteins: An Overview of Radionuclides, Labeling Methods, and Reagents for Conjugate Labeling, Bioconjugate Chem. Nov.-Dec. 1992:3(6):433-70.

Smythe, et al.; The Mechanism of Receptor-Mediated Endocytosis; Eur. J. Biochem. 202, pp. 689-699, 1991.

Wong, et al.; Rhenium(V), and Technetium(V) Oxo Complexes of an N2N's Peptide Chelator: Evidence of Inter-conversion between the Syn and Anti Conformations; Inorg. Chem., 1997, 36, pp. 5799-5808.

Schumbiger, et al.; Vehicles, Chelators, and Radionuclides: Choosing the "Building Blocks" of an Effective Therapeutic Radioimmunoconjugate; Bioconjugate Chemistry, vol. 7, No. 2, pp. 165-179, Mar./Apr. 1996.

Mattes, M.J.; Pharmacokinetics of Antibodies and their Radiolabels. In: Cancer Therapy with Radiolabelled Antibodies (ed) D.M. Goldenberg, CRC Press, Boca Raton, Florida, Chapter 8, pp. 89-99.

Li, et al.; Comparisons of Rh(III) Chloride Complexation with [14]aneNS, [14]aneN2S2 and [14]aneN4 Macrocycles in Aqueous Solution, Radiochemica Acta 75, pp. 83-95 (1996).

Lister-James, et al.; Pharmacokinetic considerations in the development of peptide-based imaging agents, The Quarterly Journal of Nuclear Medicine, vol. 41, No. 2, pp. 111-118.

Lamberts, S.W.J., Reubi, J.C., Krenning, E.P.; Somatostatin and the Concept of Peptide Receptor Scintigraphy in Oncology, Seminars in Oncology, vol. 21, No. 5, Suppl. 13 Oct. 1994, pp. 1-5.

Hoffken, K.; Peptides in Oncology II, Somatostatin Analogues and Bombesin Antagonists (1993), Springer-Verlag, Berlin-Heidleberg, pp. 87-112.

Krenning, et al.; Essentials of Peptide Receptor Scintigraphy with Emphasis on the Somatostatin Analog Octreotide, Seminars in Oncology, vol. 21, No. 5, Suppl. 13 (Oct. 1994), pp. 6-14.

Fischman, et al.; A ticket to ride: peptide radiopharmaceuticals, J Nucl Med. Dec. 1993;34(12):2253-63.

Duncan et al.; Indium-111-Diethylenetriaminepentaacetic Acid-Octreoide is Delivered in Vivo to Pancreatic, Tumor Cell, Renal, and Hepatocyte Lysosomes, Cancer Res. Feb. 15, 1997;57(4):659-71.

Eckelman, William c.; Radiolabeling with technetium-99m to study high-capacity and lo-capacity biochemical systems, Eur J Nucl Med. Mar. 1995;22(3):249-63.

Davis, et al.; Metabolic Stability and Tumor Inhibition of Bombesin/GRP Receptor Antagonists, Peptides. Mar.-Apr. 1992;13(2):401-7.

De Jong et al.; Yttrium-90 and indium-111 labeling, receptor binding and biodistribution of [DOTA0, d-Phe1,Tyr3] octreotide, a promising somatostatin analogue for radionuclide therapy, Eur J Nucl Med. Apr. 1997;24(4):368-71.

Fritzberg et al.; Targeted proteins for diagnostic imaging: does chemistry make a difference?; J Nucl Med. Mar. 1992;33(3):394-7.

Cai et al.; Pseudononapeptide Bombesin Antagonists Containing C-Terminal Trp or Tpi, Peptides, Mar.-Apr. 1992;13(2):267-71.

Coy et al.; Probing peptide backbone function in bombesin. A reduced peptide bond analogue with potent and specific receptor antagonist activity, J Biol Chem. Apr. 15, 1988;263(11):5056-60.

Donald J. Buchsbaum; Cancer Therapy with Radiolabelled Antibodies; Pharmacokinetics of Antibodies and their Radiolabels; Experimental Radioimmunotherapy and Methods to Increase Therapeutic Efficacy; CRC Press, Boca Raton, Chapter 10, pp. 115-140, 1995.

Zhu et al.; Binding, internalization, and processing of bombesin by rat pancreatic acini, Am J Physiol. Jul. 1991;261(1 Pt 1):G57-64.

Mulshine et al.; Autocrine growth factors as therapeutic targets in lung cancer, Chest. Jul. 1989;96(1 Suppl):31S-34S. Review.

Hoffken, K.; Peptides in Oncology II, Somatostatin Analogues: Mechanisms of Action, (1994), Springer-Verlag, Berlin-Heidleberg, pp. 1-136.

Gali, et al.; In Vitro and in Vivo Evaluation of 111In_Labeled DOTA_8_Aoc_BBN[7_14]NH2 Conjugate for Specific Targeting of Tumors Expressing Gastrin Releasing Peptide (GRP) Receptors, 47th Annual Meeting—Society of Nuclear Medicine, St. Louis, MO, J. Nucl. Med., 41(5), 119P, #471, 2000.

Gali, et al.; Influence of the Radiometal on the In Vivo Pharmacokinetic Properties of a Radiometal-labeled DOTA-Conjugated Peptide, 222nd American Chemical Society National Meeting, Chicago, Il, Aug. 2001 (Accepted).

Hoffman, et al.; Development and Characterization of a Receptor-Avid 111In-Labeled Peptide for Site Specific Targeting of Colon Cancer, 92nd Annual Meeting of the American Association for Cancer Research, New Orleans, LA, Proceedings of the American Association for Cancer Research, vol. 42, 139, #746, Mar. 2001.

Hoffman, et al.; Rh-105 Bombesin Analogs: Selective In Vivo Targeting of Prostate Cancer with a therapeutic Radionuclide, 45th Annual Meeting—Society of Nuclear Medicine, Jun. 1998;J.Nucl. Med., 39(5), #982, 222P.

Hoffman, et al.; Uptake in retention of a Rh-105 Labeled Bombesin Analogue in GRP Receptor Expressing Neoplasms: An In-Vitro Study, 44th Annual Meeting—Society of Nuclear Medicine, Jun. 1997;J.Nucl. Med., 38(5), #808, 188P, 1997.

Hoffman, et al.; Synthesis and Characterization of Rh-105 Labeled Bombesin Analogues: Enhancement of GRP Receptor Binding Affinity Utilizing Aliphatic Carbon Chain Linkers, 12th International Symposium on Radiopharmaceutical Chemistry, Jun. 1997.

Hoffman, et al.; Specific Uptake and retention of Rh-105 Labeled Bombesin Analogues in GRP-Receptor Expressing Cells, European Society of Nuclear Medicine, Aug. 1997; Eur. J. Nucl. Med., 24(8), 901, 1997.

Hoffman et al.; Radiometallated receptor-avid peptide conjugates for specific in vivo targeting of cancer cells, Nucl Med Biol. Jul. 2001;28(5):527-39.

Hoffman et al.; Targeting Small Cell Lung Cancer Using Iodinated Peptide Analogs, 11th International Symposium on Radiopharmaceutical Chemistry, Aug. 1995; J. Label. Comp'd Radiopharm., 37:321-323, 1995.

Hoffman et al.; Iodinated Bombesin Analogs: Effect of N-Terminal Chain Iodine Attachment on BBN/GRP Receptor Binding, 43rd Annual Meeting—Society of Nuclear Medicine, May 1996; J. Nucl. Med., 37(5), p185P, #850, 1996.

Hoffman et al.; Accumulation and Retention of 99mTc-RP591 by GRP Receptor Expressing Tumors in SCID Mice, Congress of the European Association of Nuclear Medicine, Barcelona, Spain, Eur. J. Nucl. Med., 26(9), 1157, #PS-416, Sep. 1999.

Hoffman et al.; Accumulation and Retention of 99mTc-RP527 by GRP Receptor Expressing Tumors in SCID Mice, 46th Annual Meting—Society of Nuclear Medicine, Jun. 9, 1999, Los Angeles, CA, J. Nucl. Med., 40(5), 104P, #419, 1999.

Hoffman et al.; 111In/90Y Radiolabelled Peptides for Targeting Prostate Cancer; A Matched Pair Gastrin Releasing Peptide (GRP) Receptor Localizing Radiopharmaceutical, 48th Annual Meting—Society of Nuclear Medicine, #1149, Toronto, Ontario, Canada, Jun. 2001. (Accepted).

Hoffman et al.; Vitro and in Vivo Evaluation of 111In/90Y Radiolabelled Peptides for Specific Targeting of Tumors Expressing Gastrin Releasing Peptide (GRP) Receptors, 92nd Annual Meting of the American Association for Cancer Research, New Orleans, LA. Proceedings of the American Association for Cancer Research, vol. 42, 773, #4148, Mar. 2001.

Hoffman et al.; Development of a Diagnostic Radiopharmaceutical for Visualization of Primary and Metastic Breast Cancer, 48th Annual Meting—Society of Nuclear Medicine, #1149, Toronto, Ontario, Canada, Jun. 2001, J. Nucl. Med., 45(5):245P, #1067.

Hoffman et al.; Targeting Gastrin Releasing Peptide (GRP-R) Expression in Prostate and Pancreatic Cancer Using Radiolabelled GRP Agonist Peptide Vectors, American Association for Cancer Research Annual Meeting, San Francisco, CA, Proceedings of the American Association for Cancer Research, vol. 41, 529, #3374, Apr. 2000.

Hoffman T.J., Smith, C.J., Simpson, S.D., Siekman, G., Higginbotham, C., Jiminez, H., Eshima, D., Thornback, J.R. and Volkert, W.A.; Optimizing Pharmacokinetics of Tc-99m-GRP Receptor Targeting Peptides Using Multi-Amino Acid Linking groups, 47th Annual Meting—Society of Nuclear Medicine, St. Louis, MO, J. Nucl. Med., 41(5), 228), #1013, 2000.

Jurrison, S., Cutler, C., Hu, F., Hoffman, T.J., Volkert, W.A.; DOTA Bombesin Complexes with Sm-153 and NCA PM-149, The International Chemical Congress of Pacific Basin Societies, Pacifichem 2000, Honolulu, HI, Dec. 2000.

Kara, S.R., Schibli, R., Gali, H., Katti, K.V., Hoffman, T.J., Higginbotham, C., Siekman, G., Volkert, W.A.; 99mTc-labeling and in vivo studies of a bombesin analogue with a novel water-soluble dithiadiphosphine-based bifunctional chelating agent, Bioconjug Chem. Mar.-Apr. 1999;10(2):254-60.

Katti, K.V., Gali, H., Schibli, R., Hoffman, T.J., and Volkert, W.A.; 99mTc/Re Coordination Chemistry and Biomolecule Conjugation Strategy of a Novel Water Soluble Phosphine-Based Bifunctional Chelating Agent, In Technetium, Rhenium and Other Metals in Chemistry and Nuclear Medicine (5), Ed by M. Nicolini and U. Mazzi, Servizi Grafici Editoriali, Padova, pp. 93-100, 1999.

Kothari, K.K. Katti, K.V., Prabhu, K.R., Gali, H., Pillarsetty, N.K., Hoffman, T.J., Owen, N.K., and Volkert, W.A.; Development of a Diamido-Diphosphine (N2P2)-BFCA for Labeling Cancer Seeking Peptides via the 99mTc(1)(CO)3(H2O)3 Intermediate, 47th Annual Meeting—Society of Nuclear Medicine, St. Louis, MO, J. Nucl. Med., 41(5), 244P, #1079, 2000.

Li, et al.; Development of an in vitro model for assessing the in vivo stability of lanthanide chelates, Nucl Med Biol. Feb. 2001;28(2):145-54.

Qin, et al.; Bombesin antagonists inhibit in vitro and in vivo growth of human gastric cancer and binding of bombesin to its receptors, J Cancer Res Clin Oncol., 1994; 120(9): 519-28.

Giblin et al. (1998), Proc. Natl. Aca. Sci., USA, vol. 95, pp. 12814-12818.

Walsh et al., Western Journal of Medicine, vol. 155, pp. 152-163, 1991.

Heppeler et al., Receptor Targeting for Tumor Localization and Therapy with Radiopeptides. Current Medicinal Chemistry 2000, 7:971-994.

Sethi et al., Growth of small cell lung cancer cells: stimulation by multiple neuropeptides and inhibition by broad spectrum antagonists in vitro and in vivo, Cancer Res. May 1, 1992:52(9 Suppl):2737s-2742s.

Halmos, T., Wittliff, J.L., and Schally, A.V., Characterization of bombesin/gastrin releasing peptide receptors on human breast cancer and their Relationship to steroid receptor expression, Cancer Research 55:280-287, 1995.

Kelly, K., Kane, M.A., and Bunn, P.A., "Growth factors in lung cancer: Possible etiologic role and clinical target", Medical and Pediatric Oncology 19:449-458, 1991.

Jensen, R.T., Mrozinski, J.E., and Coy, D.H., "Bombesin receptor antagonists: Different classes and cellular basis of action", Recent Results in Cancer Research 129:87-113.

Reile, H., Armatis, P.E., and Schally, A.V., Characterization of high-affinity receptors for bombesin/gastrin releasing peptide on the human prostate cancer cell lines PC-3 and DU-145: internalization of receptor bound 125I-(Tyr4) bombesin by tumor cells, Prostate, Jul. 1994;25(1):29-38.

Schutte, J., and Seeber, S., "Bombesin antagonists: Experimental and clinical results", Recent Results in Cancer Research 129:115-129, 1993.

Walsh, J.H., Karnes, W.E., Cuttitta, F., and Walker, A., "Autocrine growth factors and solid tumor malignancy", Western Journal of Medicine 155: 152-163, 1991.

Leban, et al., Potent gastrin-releasing peptide (GRP) antagonists derived from GRP (19-27) with a C-terminal DPro psi [CH2NH]Phe-NH2 and N-terminal aromatic residues, J Med Chem. Feb. 18, 1994;37(4):439-45.

Li, et al.; In-Vivo and In-Vitro Characterization of a Rh-105-Tetrathiamacrocycle Conjugate of a Bombesin Analogue, Proceedings of the 43rd Annual Meeting, vol. 37, No. 5, May 1996 Supplement, p. 61.

Zhu, et al.; Binding, internalization, and processing of bombesin by rat pancreatic acini, Bombesin Binding and Internalization, 1991, pp. G57-G64.

Moody, et al.; BW1023U90: A new GRP Receptor Antagonist for Small-Cell Lung Cancer Cells, Peptides vol. 17, No. 8, pp. 1337-1343, 1996.

Moody, et al.; A GRP Receptor Antagonist Which Inhibits Small-Cell Lung Cancer Growth; Life Sciences, vol. 56, No. 7, pp. 521-529, 1995.

Seifert, et al.; No Carrier Added Preparations of '3+1' Mixed-ligand 99mTc Complexes, Appl. Radiat. Isot. vol. 49, Nos. 1-2, pp. 5-11, 1998.

Smith, et al.; In Vivo and In Vitro Characterization of Novel Water-Soluble Dithio- Bisphosphine 99mTc Complexes, Nuclear Medicine & Biology, vol. 24, pp. 685-691, 1977.

Coy et al, "Short Chain Pseudopeptide bombesin receptor antagonists with enhanced binding affinities for pancreatic Acinar and swiss 3T3 cells display strong Antimitotic activity" J. Biol. Chem., vol. 264, No. 25, pp. 14691-14697, 1989.

Thomas et al., Antitumoral Activity of Bombesin Analogues on Small Cell Lung Cancer Xenografts: Relationship with Bombesin Receptor Expression, Cancer Res. Sep. 15, 1992;52(18):4872-7.

Radulovic et al., Inhibitory effects of antagonists of bombesin/gastrin releasing peptide (GRP) and somatostatin analog (RC-160) on growth of HT-29 human colon cancers in nude mice, Acta Oncol. 1994;33(6):693-701.

Qin, et al. Inhibitory effect of bombesin receptor antagonist RC-3095 on the growth of human pancreatic cancer cells in vivo and in vitro, Cancer Res. Feb. 15, 1994;54(4):1035-41.

Qin, et al., Antagonists of bombesin/gastrin-releasing peptide inhibit growth of SW-1990 human pancreatic adenocarcinoma and production of cyclic AMP, Int J Cancer. Oct. 9, 1995;63(2):257-62.

Cai et al., Potent Bombesin antagonists with C-Terminal Leu-(CH2-N)-Tac-NH2 or its Derivatives, (1994) Proc. Natl. Acad. Sci., 91:12664-12668.

Radulovic, et al., Biological effects and receptor binding affinities of new pseudononapeptide bombesin/GRP receptor antagonists with N-terminal D-Trp or D-Tpi, Int J Pept Protein Res. Dec. 1991;38(6):593-600.

Staley, et al., [Des-Met14]bombesin analogues function as small cell lung cancer bombesin receptor antagonists, Peptides. Jan.-Feb. 1991;12(1):145-9.

Wang et al., Desmethionine alkylamide bombesin analogues: a new class of bombesin receptor antagonists with potent antisecretory activity in pancreatic acini and antimitotic activity in Swiss 3T3 cells, Biochemistry. Jan. 23, 1990;29 (3):616-22.

Wang, Knezetic, Schally, Pour, Adrian; Bombesin May Stimulate Proliferation of Human Pancreatic Cancer Cells Through an Autocrine Pathway, Int. J. Cancer: 68, 528-534 (1996).

Yano, Pinski, Groot, Schally, Stimulation by bombesin and inhibition by bombesin/gastrin-releasing peptide antagonist RC-3095 of growth of human breast cancer cell lines, Cancer Res. Aug. 15, 1992;52(16):4545-7.

Kane, Auguayo, Portanova, Ross, Holley, Kelly, Miller, Isolation of the bombesin/gastrin-releasing peptide receptor from human small cell lung carcinoma NCI-H345 cells, J Biol Chem. May 25, 1991;266(15):9486-93.

Schuller, Receptor-mediated mitogenic signals and lung cancer, Cancer Cells. Dec. 1991;3(12):496-503.

Halmos et al., Characterization of bombesin/gastrin-releasing peptide receptors in human breast cancer and their relationship to steroid receptor expression, Cancer Res. Jan. 15, 1995;55(2):280-7.

Hajri et al., Gastrin-releasing peptide: in vivo and in vitro growth effects on an acinar pancreatic carcinoma, Cancer Res. Jul. 1, 1992;52(13):3726-32.

Fritzberg, et al., Radiolabeling of Antibodies for Targeted Diagnostics, Handbook of Targeted Delivery of Imaging Agents (ed) V.P. Torchilin, CRC Press, Boca Raton, Florida, Chapter 6, pp. 83-101, 1995.

Benya, et al., Gastrin-releasing peptide receptor-induced internalization, down-regulation, desensitization, and growth: possible role for cyclic AMP, Mol Pharmacol. Aug. 1994;46(2):235-45.

Yano, et al., Inhibitory effect of bombesin/gastrin-releasing peptide antagonist RC-3095 and luteinizing hormone-releasing hormone antagonist SB-75 on the growth of MCF-7 MIII human breast cancer xenografts in athymic nude mice, Cancer. Feb. 15, 1994;73(4):1229-38.

Kull, Jr., et al., Conveyance of partial agonism/antagonism to bombesin/gastrin-releasing peptide analogues on Swiss 3T3 cells by a carboxyl-terminal leucine insertion, J Biol Chem. Oct. 15, 1992;267(29):21132-8.

Heinz-Erian, et al., [D-Phe12]bombesin analogues: a new class of bombesin receptor antagonists, Am J Physiol. Mar. 1987;252(3 Pt 1):G439-42.

Halmos, et al., Characterization of bombesin/gastrin-releasing peptide receptors in membranes of MKN45 human gastric cancer, Cancer Lett. Sep. 30, 1994;85(1):111-8.

Coy, et al., Short-chain pseudopeptide bombesin receptor antagonists with enhanced binding affinities for pancreatic acinar and Swiss 3T3 cells display strong antimitotic activity, J Biol Chem. Sep. 5, 1989;264(25):14691-7.

Woll, et al., [D-Arg1,D-Phe5,D-Trp7,9,Leu11]substance P, a potent bombesin antagonist in murine Swiss 3T3 cells, inhibits the growth of human small cell lung cancer cells in vitro, Proc Natl Acad Sci U S A. Mar. 1988;85(6):1859-63.

Wang, et al., des-Met carboxyl-terminally modified analogues of bombesin function as potent bombesin receptor antagonists, partial agonists, or agonists, J Biol Chem. Sep. 15, 1990;265(26):15695-703.

Von Schrenck, et al., "Potent Bombesin Receptor Antagonists distinguish Receptor Subtypes", Amer. J. Physiol., vol. 259, pp. G468-G473, 1990.

Singh, et al., A novel bombesin receptor antagonist (2258U89), potently inhibits bombesin evoked release of gastrointestinal hormones from rats and dogs, in vitro and in vivo, Regul Pept. Jul. 2, 1992;40(1):75-86.

Leban, et al., Development of Potent Bombesin/Gastrin-Releasing Peptide antagonists Having a D-Pro-(CH2NH)-Phe-NH2 C Terminus, Proc Natl Acad Sci U S A. Mar. 1, 1993;90(5):1922-6.

Mahmoud, et al., "[Psi 13, 14] Bombesin Analogues Inhibit Growth of Small Cell Lung Cancer in Vitro and in Vivo", Cancer Res. Apr. 1, 1991;51(7):1798-802.

Troutner, David E., Chemical and Physical Properties of Radionuclides, Nucl. Med. Biol. vol. 14, No. 3, pp. 171-176, 1987.

Vallabhajosula, et al., Preclinical evaluation of technetium-99m-labeled somatostatin receptor-binding peptides, J Nucl Med. Jun. 1996;37(6):1016-22.

Gali, et al., Synthesis, characterization, and labeling with 99mTc/188Re of peptide conjugates containing a dithia-bisphosphine chelating agent, Bioconjugate Chem. May-Jun. 2001;12(3):354-63.

International Preliminary Examination Report for PCT/US09/44447; mailed Jul. 20, 2010.

International Preliminary Examination Report for PCT/US09/41328; mailed Jul. 21, 2006.

Schibli, R., Karra, S.R., Gali , H., Katti, K.V., Higginbotham, C., Smith, C.J., Hoffman, T.J., and Volkert, W.A.; Conjugation of Small Biomolecules and Peptides with Water-Soluble Dithio-Bis-Hydroxymethylphosphine Ligands, Center Radiological Research, University of Missouri, Columbia, MO, USA. Book of Abstracts, 215th ACS National Metting, Dallas, Mar. 29-Apr. 2, 1998, NUCL-062.

Schibli, R., Karra, S.R., Katti, K.V., Gali, H., Higginbotham, C., Siekman, G., Hoffman, T.J., and Volkert, W.A.; A Tc-99m-Dithia-Di(Bis-Hydroxy-methylene) Phosphine Conjugate of Bombesin: In Vitro and In Vivo Studies, 45th Annual Meeting—Society of Nuclear Medicine, May 1998; J. Nucl. Med., 39(5), 225P, #997.

Smith, C.J., Hoffman, T.J., Gali, H., Hayes, D.L., Owen, N.K., Siekman, G.L. and Volkert, W.A.; Radiochemical investigations of 177Lu-DOTA-8-Aoc-BBN[7-14]NH2: A New Gastrin Releasing Peptide Receptor (GRPr) Targeting Radiopharmaceutical, J. Labeled Compounds and Radiopharmaceutical, J. Labeled Cpd. Rapdipharm., 44(51):5706-5708, 2001.

Volkert, W.A.; Rh-105 Bombesin Analogs: Selective In Vivo Targeting of Prostate Cancer with a Therapeutic Radionuclide, 45th Annual Meeting—Society of Nuclear Medicine, Jun. 1998; J. Nucl. Med., 39(5):222P, #59, 1998.

Volkert, W.A., and Hoffman, T.J., Design and Development of Receptor-avid Peptide Conjugates for In Vivo Targeting of Cancer, Part of the SPIE Conference of Molecular Imaging: Reporters-Dyes, Markers and Instrumentation, SPIE vol. 3600;-86-98, Jan. 1999.

Volkert, W.A., Gali, H., Hoffman, T.J., Owen, N.K., Sieman, G.L., and Smith, C.J.; In-111/90Y Labeled GRP Analogs: A Structure-Activity Relationship, The International Chemical Congress of Pacific Basin Societies, Pacifichem 2000, Honolulu, HI, Dec. 2000.

Foster, B., and Volkert, W.A.; In-111/90Y Radiolabelled Peptides for targeting Prostate Cancer; A Matched Pair Gastrin releasing Peptide (GRP) Receptor Localizing Radiopharmaceutical, 48th Annual Meeting—Society of Nuclear Medicine, Toronto, Ontario, Canada, Jun. 2001. (Accepted).

Internationla Search Report and Written Opinion for International Application No. PCT/US07/61813 mailed Mar. 5, 2008.

Supplementary European Search Report for EP 03800223.4 dated Jun. 18, 2009.

Safavy et al. "Paclitaxel Derivaties for Targeted Therapy of Cancer: Toward the Development of Smart Taxanes", J. of Med. Chem., vol. 42, Jan. 1, 1999, pp. 4919-4924.

International Search Report and Written Opinion for International Application No. PCT/US07/61813 mailed Mar. 5, 2008.

Hoffman et al. "Radiometallated receptor-avid peptide conjugates for specific in vivo targeting of cancer cells" Nuclear Medicine & Biology (2001), vol. 28, pp. 527-539.

Smith et al. "Radiochemical investigation of 177 Lu-DOT-8-Aoc-BBN[7-14]NH2: an invitro/invivo assessment of the targeting ability of this new radiopharmaceutical for PC-3 human prostate cancer cells" Nuclear Medicine & Biology, vol. 30, (2003), pp. 101-109.

Supplemental European Search Report for European Application No. EP04777906, mailed on Oct. 28, 2008.

Smith et al., "Gastrin releasing peptide (GRP) receptor targeted radiopharmaceuticals: A concise update" Nuclear Medicine and Biology (2003), vol. 30, pp. 861-868.

Hoffman et al., "Novel Series of 111In-Labeled Bombesin Analogs as Potential Radiopharmaceuticals for Specific targeting of Gastin-Releasing Peptide Receptors Expressed on Human Prostate Cancer Cells" Journal of Nuclear Medicine (2003), vol. 44, pp. 823-831.

Rogers et al., "In Vitro and In Vivo Evaluation of a 64Cu-Labeled Polyethylene Glycol-Bombesin Conjugate" Cancer Biotherapy & Radiopharmaceuticals, (2004), vol. 19, No. 1, pp. 25-34.

Abstract: Samuel Achilefu et al., Synthesis In Vitro Receptor Binding, and In Vivo Evaluation of Fluorescin and Carbocyanine Peptide-Based Optical Contrast Agents, J. Med. Chem., 2002, vol. 454, pp. 2003-2015.

Blok et al., "Peptide Radiopharmaceuticals in Nuclear Medicine", European Journal of Nuclear Medicine, vol. 26, No. 11, pp. 1511-1519, 1999.

Extended European Search Report issued Feb. 7, 2012 in connection with European Patent Application No. 10178206.

Extended European Search Report issued in connection with European Patent Application No. 12 159 175.4 on Aug. 20, 2012.

Aime S et al., "[Gd-AAZTA] -A New Structural Entry for an Improved Generation of MRI Contrast Agents", Inorganic Chemistry, American Chemical Society, vol. 43, No. 24, Jan. 1, 2004, pp. 7588-7590.

Xuwan Liu et al., "Gastrin releasing peptide activates Akt through the epidermal growth factor receptor pathway and abrogates the effect of gefitnib", Experimental Cell Research, Academic Press, US, vol. 133, No. 7, Apr. 3, 2007, pp. 1361-1372.

Extended European Search Report issued Jul. 12, 2012 in connection with co-pending European Application No. 06 78 5507.

* cited by examiner

LINKERS:

L73

L115

L116

Where IBCF is isobutylchloroformate

1. Morpholine (50% in DMA)
2. C, DIC, HOBT, DMA
3. Morpholine (50% in DMA)
4. DOTA tri-t-butyl ester, DIC, HOBT, DIEA, DMA
5. Reagent B

L67

L67

1. Morpholine (50% in DMA)
2. 3a, DIC, HOBT, DMA
3. Morpholine (50% in DMA)
4. DOTA tri-t-butyl ester, DIC, HOBT, DIEA, DMA
5. Reagent B

L63

L64

2b

3a

3b

L63

L64

1. Morpholine (50% in DMA)
2. Fmoc-linker-OH, DIC, HOBT, DMA
3. Morpholine (50% in DMA)
4. DOTA tri-t-butyl ester, DIC, HOBT, DIEA, DMA
5. Reagent B L71 linker L72 linker

B

D

L124

L125

1. Morpholine (50% in DMA)
2. Fmoc-4-aminobenzoic acid, HATU, DMA
3. Morpholine (50% in DMA)
4. Fmoc-Gly-OH, HATU, DMA
5. Morpholine (50% in DMA)
6. H, DIC, HOBT, DIEA, DMA
7. Reagent B

L237

A

1. Morpholine (50% in DMA)
2. Fmoc-4-aminobenzoic acid,
   DIC, HOBT, DIEA, DMA
3. Morpholine (50% in DMA)
4. Fmoc-Gly-OH,
   DIC, HOBT, DIEA, DMA
5. Morpholine (50% in DMA)
6. Fmoc-Cys(Acm)-OH,
   DIC, HOBT, DIEA, DMA 8. Morpholine (50% in DMA)
9. Fmoc-Ser(tBu)-OH
   DIC, HOBT, DIEA, DMA
10. Morpholine (50% in DMA)
11. N,N-Me₂Gly-OH,
    DIC, HOBT, DIEA, DMA
13. Reagent B

L238

1. Morpholine (50% in DMA)
2. B, DIC, HOBT, DIEA, DMA
3. Morpholine (50% in DMA)
4. Fmoc-Gly-OH,
DIC, HOBT, DIEA, DMA
5. Morpholine (50% in DMA)
6. Fmoc-Cys(Acm)-OH,
DIC, HOBT, DIEA, DMA 8. Morpholine (50% in DMA)
9. Fmoc-Ser(tBu)-OH
DIC, HOBT, DIEA, DMA
10. Morpholine (50% in DMA)
11. N,N-Me$_2$Gly-OH,
DIC, HOBT, DIEA, DMA
13. Reagent B

L242

L65

L66

L70

L114

L144

L69

L146

Chart 1

A

X = H, Tmob, Xan, Trt
U = →O or null
Y = Trt, Bum, Boc, Cbz
P = Fmoc, Boc, Aloc, H, Cbz

B

X' = H, t-Bu, Bz, 2-Cl-Trt, Me, Et
Y' = CHO, Boc, H, 9-PhF, CBz
Z = H, Xan, Tmob, Trt
P' = Fmoc, Boc, Aloc, H, Cbz

C1

P" = Fmoc, Boc, Aloc, H, Cbz

C2

P" = Fmoc, Boc, Aloc, H, Cbz

D

X" = t-Bu, Me, Bz, H

1. Piperidine in DMF
2. Fmoc-4-aminobenzoic acid, HATU, NMP
3. Piperidine in DMF
4. Fmoc-Gly-OH, HATU, NMP
5. Piperidine in DMF
6. Boa-tetra-tbutylester, HBTU, NMP
7. Reagent B

L201

A

1. Piperidine in DMF
2. B, DIC, HOBT, DIEA, NMP
3. Piperidine in DMF
4. Fmoc-Gly-OH, HATU, NMP
5. Piperidine in DMF
6. DOTA tri-t-butyl ester, HBTU, NMP
7. Reagent B

L202

1. Piperidine in DMF
2. Fmoc-6-aminonicotinic acid, DIC, HOBT, NMP
3. Piperidine in DMF
4. Fmoc-Gly-OH, HATU, NMP
5. Piperidine in DMF
6. DOTA tri-t-butyl ester, HBTU, DIEA, NMP
7. Reagent B

L205

1. Piperidine in DMF
2. B, DIC, HOBT, NMP
3. piperidine in DMF
4. DOTA-tri-t-butyl ester, HBTU, DIEA, NMP
5. Reagent B

L206

L208

Resin A
1. Piperidine in DMF
2. Fmoc-8-amino-3,6-dioxaoctanoic acid, DIC, HOBT, NMP
3. Piperidine in DMF
4. Fmoc-8-amino-3,6-dioxaoctanoic acid, DIC, HOBT, NMP
5. Piperidine in DMF
6. Reagent B
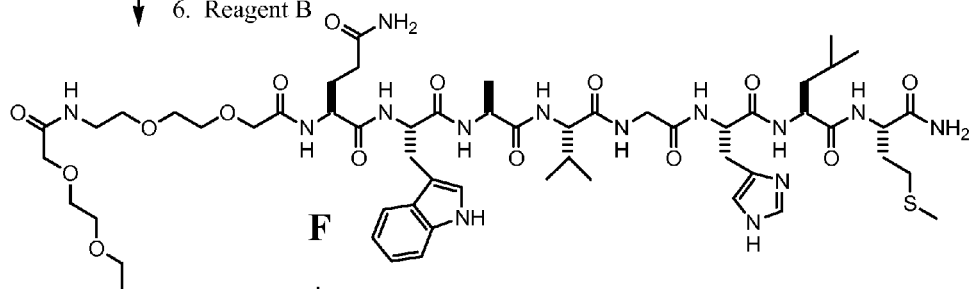
F
1. E, NHS, DIC, DIEA, CH₃CN/NMP
2. Reagent B
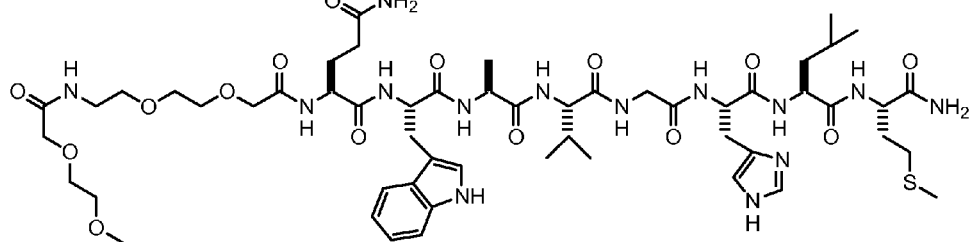
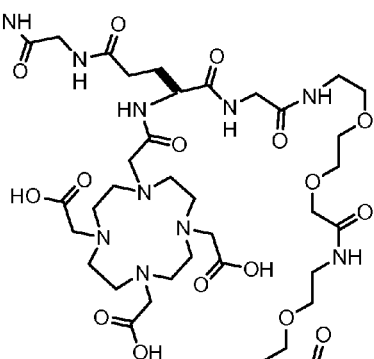
L209
Fig. 29B
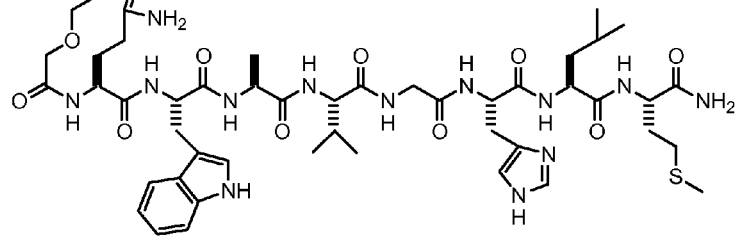

1. Piperidine in DMF
2. Fmoc-8-amino-3,6-dioxaoctanoic acid, DIC, HOBT, NMP
3. Piperidine in DMF
4. Fmoc-8-amino-3,6-dioxaoctanoic acid, DIC, HOBT, NMP
5. Piperidine in DMF
6. Reagent B

L210

L211

L212

L213

L214

L215

L216

L217

L219

L220

L221

L222

L223

L224

L225

L226

L227

L228

L301

GASTRIN RELEASING PEPTIDE COMPOUNDS

CROSS REFERENCE TO RELATED APPLICATIONS

This application is a continuation-in-part of U.S. Ser. No. 11/751,337, filed May 21, 2007 now abandoned, which is a continuation-in-part of U.S. Ser. No. 11/352,156, filed Feb. 10, 2006 now U.S. Pat. No. 7,850,947, which is a continuation-in-part of U.S. Ser. No. 11/165,721, filed Jun. 24, 2005 now U.S. Pat. No. 7,922,998, which is a continuation-in-part of U.S. Ser. No. 10/828,925, filed Apr. 20, 2004 now U.S. Pat. No. 7,611,692, which is a continuation-in-part application of International Application PCT/US2003/041328, filed Dec. 24, 2003, which is a continuation-in-part application of U.S. Ser. No. 10/341,577 filed Jan. 13, 2003, now U.S. Pat. No. 7,226,577. All of the above applications are hereby incorporated by reference in their entirety.

FIELD OF THE INVENTION

This invention relates to novel gastrin releasing peptide (GRP) compounds which are useful as diagnostic imaging agents or radiotherapeutic agents. These GRP compounds are labeled with radionuclides or labels detectable by in vivo light imaging and include the use of novel linkers between the label and the targeting peptide, which provides for improved pharmacokinetics.

BACKGROUND OF THE INVENTION

Prostate cancer encompasses a biological continuum ranging from a slow growing, indolent tumor to a highly aggressive and potentially fatal form. Most patients with metastatic prostate cancer receive drugs that block production of androgen, which promotes cancer cell proliferation. These drugs rarely cure cancer because the initial response is almost always followed by a relapse to an unresponsive, hormone-refractory stage (hormone refractory prostate cancer or HRPC). The relatively slow tumor progression coupled with the advancing age of the patients means that competing causes of death are substantive contributors to mortality in patients with prostate cancer. Thus while in HRPC patients tumor growth can be rapid and is a significant cause of death, in androgen dependent cancers it may be sufficient to slow down the progression to the more aggressive (HRPC) form.

Tumors stimulate the formation of new blood vessels (angiogenesis) in order to supply nutrients and oxygen to their structure. These vessels are formed rapidly without the controls of normal tissue and so exhibit various defects including leakiness, fragility, structural disorganization, aberrant morphology including large diameter and tortuosity, interrupted flow patterns, etc. The leakiness of the tumor vasculature is thought to be due in part to the abnormal expression of growth factors by tumor cells, and contributes to tumor growth and metastasis.1 The vessels have been shown to leak proteins such as fibrin, which forms a fibrinogen platform for stromal growth and further vessel development. A reduction in these abnormal vessels would result in a less favorable environment for tumor progression and an increase in the relative percentage of normal vessels to the area would lead to a more normal blood flow pattern to aid delivery of therapeutic agents.

The establishment of a prostate carcinoma primary cell line has thus far been unsuccessful (van Bokhoven A, Varella-Garcia M, Korch C, et al. Molecular Characteristics of Human Prostate Cell Lines. The Prostate (2003) 57:205-225). Cells from prostate tissue have proven to be among the most difficult from which to establish robust cultures. The cell lines PC-3 (ATCC #CRL1435), LNCaP (ATCC #CRL-1740), and DU145 (ATCC #HTB-41) are the classical cell models, all with metastatic sites of origin shown below:

| Cell Line | Tissue of Origin | Androgen Sensitivity |
| --- | --- | --- |
| PC-3 | Adenocarcinoma; bone metastasis. | No |
| LNCaP | Adenocarcinoma; supraclavicular lymph node metastasis. | Yes |
| DU145 | Carcinoma; brain metastasis. | No |

Human prostate cancer cell lines reflect the clinical range with LNCaP cells derived from a supraclavicular lymph node metastasis being androgen sensitive and representing the early forms and PC-3 cells derived from a bone metastasis being androgen insensitive and representing HRPC.

The use of radiopharmaceuticals (e.g., diagnostic imaging agents, radiotherapeutic agents) to detect and treat cancer is well known. In more recent years, the discovery of site-directed radiopharmaceuticals for cancer detection and/or treatment has gained popularity and continues to grow as the medical profession better appreciates the specificity, efficacy and utility of such compounds.

These newer radiopharmaceutical agents typically consist of a targeting agent connected to a metal chelator, which can be chelated to (e.g., complexed with) a diagnostic metal radionuclide such as, for example, technetium or indium, or a therapeutic metal radionuclide such as, for example, lutetium, yttrium, or rhenium. The role of the metal chelator is to hold (i.e., chelate) the metal radionuclide as the radiopharmaceutical agent is delivered to the desired site. A metal chelator which does not bind strongly to the metal radionuclide would render the radiopharmaceutical agent ineffective for its desired use since the metal radionuclide would therefore not reach its desired site. Thus, further research and development led to the discovery of metal chelators, such as that reported in U.S. Pat. No. 5,662,885 to Pollak et. al., hereby incorporated by reference, which exhibited strong binding affinity for metal radionuclides and the ability to conjugate with the targeting agent. Subsequently, the concept of using a "spacer" to create a physical separation between the metal chelator and the targeting agent was further introduced, for example in U.S. Pat. No. 5,976,495 to Pollak et. al., hereby incorporated by reference.

The role of the targeting agent, by virtue of its affinity for certain binding sites, is to direct the diagnostic agent, such as a radiopharmaceutical agent containing the metal radionuclide, to the desired site for detection or treatment. Typically, the targeting agent may include a protein, a peptide, or other macromolecule which exhibits a specific affinity for a given receptor. Other known targeting agents include monoclonal antibodies (MAbs), antibody fragments ($F_{ab}$'s and $(F_{ab})_2$'s), and receptor-avid peptides. Donald J. Buchsbaum, "Cancer Therapy with Radiolabeled Antibodies; Pharmacokinetics of Antibodies and Their Radiolabels; Experimental Radioimmunotherapy and Methods to Increase Therapeutic Efficacy," CRC Press, Boca Raton, Chapter 10, pp. 115-140, (1995); Fischman, et al. "A Ticket to Ride: Peptide Radiopharmaceuticals," The Journal of Nuclear Medicine, vol. 34, No. 12, (December 1993). These references are hereby incorporated by reference in their entirety.

In recent years, it has been learned that some cancer cells contain gastrin releasing peptide (GRP) receptors (GRP-R) of which there are a number of subtypes. In particular, it has been shown that several types of cancer cells have over-expressed or uniquely expressed GRP receptors. For this reason, much research and study have been done on GRP and GRP analogues which bind to the GRP receptor family. One such analogue is bombesin (BBN), a 14 amino acid peptide (i.e., tetradecapeptide) isolated from frog skin which is an analogue of human GRP and which binds to GRP receptors with high specificity and with an affinity similar to GRP. Bombesin and GRP analogues may take the form of agonists or antagonists.

Binding of GRP or BBN agonists to the GRP receptor increases the rate of cell division of these cancer cells and such agonists are internalized by the cell, while binding of GRP or BBN antagonists generally does not result in either internalization by the cell or increased rates of cell division. Such antagonists are designed to competitively inhibit endogenous GRP binding to GRP receptors and reduce the rate of cancer cell proliferation. See, e.g., Hoffken, K.; Peptides in Oncology II, Somatostatin Analogues and Bombesin Antagonists (1993), pp. 87-112. For this reason, a great deal of work has been, and is being pursued to develop BBN or GRP analogues that are antagonists. E.g., Davis et al., Metabolic Stability and Tumor Inhibition of Bombesin/GRP Receptor Antagonists, Peptides, vol. 13, pp. 401-407, 1992.

In designing an effective compound for use as a diagnostic or therapeutic agent for cancer, it is important that the drug have appropriate in vivo targeting and pharmacokinetic properties. For example, it is preferable that for a radiopharmaceutical, the radiolabeled peptide have high specific uptake by the cancer cells (e.g., via GRP receptors). In addition, it is also preferred that once the radionuclide localizes at a cancer site, it remains there for a desired amount of time to deliver a highly localized radiation dose to the site.

Moreover, developing radiolabeled peptides that are cleared efficiently from normal tissues is also an important factor for radiopharmaceutical agents. When biomolecules (e.g., MAb, $F_{ab}$ or peptides) labeled with metallic radionuclides (via a chelate conjugation), are administered to an animal such as a human, a large percentage of the metallic radionuclide (in some chemical form) can become "trapped" in either the kidney or liver parenchyma (i.e., is not excreted into the urine or bile). Duncan et al.; Indium-111-Diethylenetriaminepentaacetic Acid-Octreotide Is Delivered in Vivo to Pancreatic, Tumor Cell, Renal, and Hepatocyte Lysosomes, Cancer Research 57, pp. 659-671, (Feb. 15, 1997). For the smaller radiolabeled biomolecules (i.e., peptides or $F_{ab}$), the major route of clearance of activity is through the kidneys which can also retain high levels of the radioactive metal (i.e., normally >10-15% of the injected dose). Retention of metal radionuclides in the kidney or liver is clearly undesirable. Conversely, clearance of the radiopharmaceutical from the blood stream too quickly by the kidney is also undesirable if longer diagnostic imaging or high tumor uptake for radiotherapy is needed.

Subsequent work, such as that in U.S. Pat. No. 6,200,546 and US 2002/0054855 to Hoffman, et. al, hereby incorporated by reference in their entirety, have attempted to overcome this problem by forming a compound having the general formula X-Y-B wherein X is a group capable of complexing a metal, Y is a covalent bond on a spacer group and B is a bombesin agonist binding moiety. Such compounds were reported to have high binding affinities to GRP receptors, and the radioactivity was retained inside of the cells for extended time periods. In addition, in vivo studies in normal mice have shown that retention of the radioactive metal in the kidneys was lower than that known in the art, with the majority of the radioactivity excreted into the urine.

New and improved radiopharmaceutical and other diagnostic compounds which have improved pharmacokinetics and improved kidney excretion (i.e., lower retention of the radioactive metal in the kidney) have now been found for diagnostic imaging and therapeutic uses. For diagnostic imaging, rapid renal excretion and low retained levels of radioactivity are critical for improved images. For radiotherapeutic use, slower blood clearance to allow for higher tumor uptake and better tumor targeting with low kidney retention are critical. Furthermore, for therapeutic use, a reduction in tumor vasculature, i.e. abnormal vessels, would result in a less favorable environment for tumor progression and an increase in the relative percentage of normal vessels to the area would lead to a more normal blood flow pattern to aid delivery of therapeutic agents.

SUMMARY OF THE INVENTION

In an embodiment of the present invention, there is provided new and improved compounds for use in diagnostic imaging or radiotherapy. The compounds include a chemical moiety capable of complexing a medically useful metal ion or radionuclide (metal chelator) attached to a GRP receptor targeting peptide by a linker or spacer group. In another embodiment, these compounds include an optical label (e.g. a photolabel or other label detectable by light imaging, optoacoustical imaging or photoluminescence) attached to a GRP receptor targeting peptide by a linker or spacer group.

In general, compounds of the present invention may have the formula:

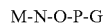

M-N-O-P-G wherein M is the metal chelator (in the form complexed with a metal radionuclide or not), or the optical label, N-O-P is the linker, and G is the GRP receptor targeting peptide.

The metal chelator M may be any of the metal chelators known in the art for complexing with a medically useful metal ion or radionuclide. Preferred chelators include DTPA, DOTA, DO3A, HP-DO3A, EDTA, TETA, EHPG, HBED, NOTA, DOTMA, TETMA, PDTA, TTHA, LICAM, MECAM, Aazta and derivatives thereof or peptide chelators, such as, for example, those discussed herein. The metal chelator may or may not be complexed with a metal radionuclide, and may include an optional spacer such as a single amino acid.

Preferred metal radionuclides for scintigraphy or radiotherapy include $^{99m}Tc$, $^{51}Cr$, $^{67}Ga$, $^{68}Ga$, $^{47}Sc$, $^{51}Cr$, $^{167}Tm$, $^{141}Ce$, $^{111}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{225}Ac$, $^{105}Rh$, $^{109}Pd$, $^{117m}Sn$, $^{149}Pm$, $^{161}Tb$, $^{177}Lu$, $^{198}Au$ and $^{199}Au$. The choice of metal will be determined based on the desired therapeutic or diagnostic application. For example, for diagnostic purposes the preferred radionuclides include $^{64}Cu$, $^{67}Ga$, $^{68}Ga$, $^{99m}Tc$, and $^{111}In$, with $^{99m}Tc$, and $^{111}In$ being particularly preferred. For therapeutic purposes, the preferred radionuclides include $^{64}Cu$, $^{90}Y$, $^{105}Rh$, $^{111}In$, $^{117m}Sn$, $^{149}Pm$, $^{153}Sm$, $^{161}Tb$, $^{166}Dy$, $^{166}Ho$, $^{175}Yb$, $^{177}Lu$, $^{186/188}Re$, and $^{199}Au$, with $^{177}Lu$ and $^{90}Y$ being particularly preferred. A preferred chelator used in compounds of the invention is 1-substituted 4,7,10-tricarboxymethyl 1,4,7,10 tetraazacyclododecane triacetic acid (DO3A).

The optical label M may be any of various optical labels known in the art. Preferred labels include, without limitation, optical dyes, including organic chromophores or fluorophores, such as cyanine dyes light absorbing compounds, light reflecting and scattering compounds, and bioluminescent molecules.

In one embodiment, the linker N-O-P contains at least one non-alpha amino acid.

In another embodiment, the linker N-O-P contains at least one substituted bile acid.

In yet another embodiment, the linker N-O-P contains at least one non-alpha amino acid with a cyclic group.

In the most preferred embodiment, M is a metal chelator and the linker N-O-P contains at least one non-alpha amino acid with a cyclic group. Additionally, M may be complexed with a radioactive or paramagnetic metal.

The GRP receptor targeting peptide may be GRP, bombesin or any derivatives or analogues thereof. In a preferred embodiment, the GRP receptor targeting peptide is a GRP or bombesin analogue which acts as an agonist. In a particularly preferred embodiment, the GRP receptor targeting peptide is a bombesin agonist binding moiety disclosed in U.S. Pat. No. 6,200,546 and US 2002/0054855, incorporated herein by reference.

There is also provided a novel method of imaging using the compounds of the present invention.

A single or multi-vial kit that contains all of the components needed to prepare the diagnostic or therapeutic agents of the invention is provided in an exemplary embodiment of the present invention.

There is further provided a novel method for preparing a diagnostic imaging agent comprising the step of adding to an injectable imaging medium a substance containing the compounds of the present invention.

A novel method of radiotherapy using the compounds of the invention is also provided, as is a novel method for preparing a radiotherapeutic agent comprising the step of adding to an injectable therapeutic medium a substance comprising a compound of the invention.

Improved methods of administration of labeled compounds of the invention are provided, as are methods of increasing targeting of GRP-expressing target tissue by labeled compounds of the invention.

Still further, novel methods of treating prostate tumors or of delaying the progression of prostate tumors are provided. In one embodiment, methods of treating bone or soft tissue metastases of prostate cancer are provided. In other embodiments, methods for treating hormone sensitive and methods for treating hormone refractory prostate cancer are provided. In yet other embodiments methods for delaying the progression of hormone sensitive prostate cancer, for facilitiating combination therapy in patients with hormone sensitive prostate cancer and for decreasing aberrant vascular permeability in patients with hormone sensitive prostate cancer are provided.

[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide (L233); N-[6-[[[[[4,7,10-Tris(carboxymethyl)-1,4,7,10-tetraazacyclododec-1-yl]acetyl]amino]acetyl]amino]naphthoyl]-L-glutaminyl-L-tryptophyl-L-alanyl-L-valyl-glycyl-L-histidyl-L-leucyl-L-methioninamide, (L234), and N-[4-[[[[[4,7,10-Tris(carboxymethyl)-1,4,7,10-tetraazacyclododec-1-yl]acetyl]amino]acetyl]methylamino]benzoyl]-L-glutaminyl-L-tryptophyl-L-alanyl-L-valyl-glycyl-L-histidyl-L-leucyl-L-methioninamide, (L235), as described in Example IX.

Figure 10A:
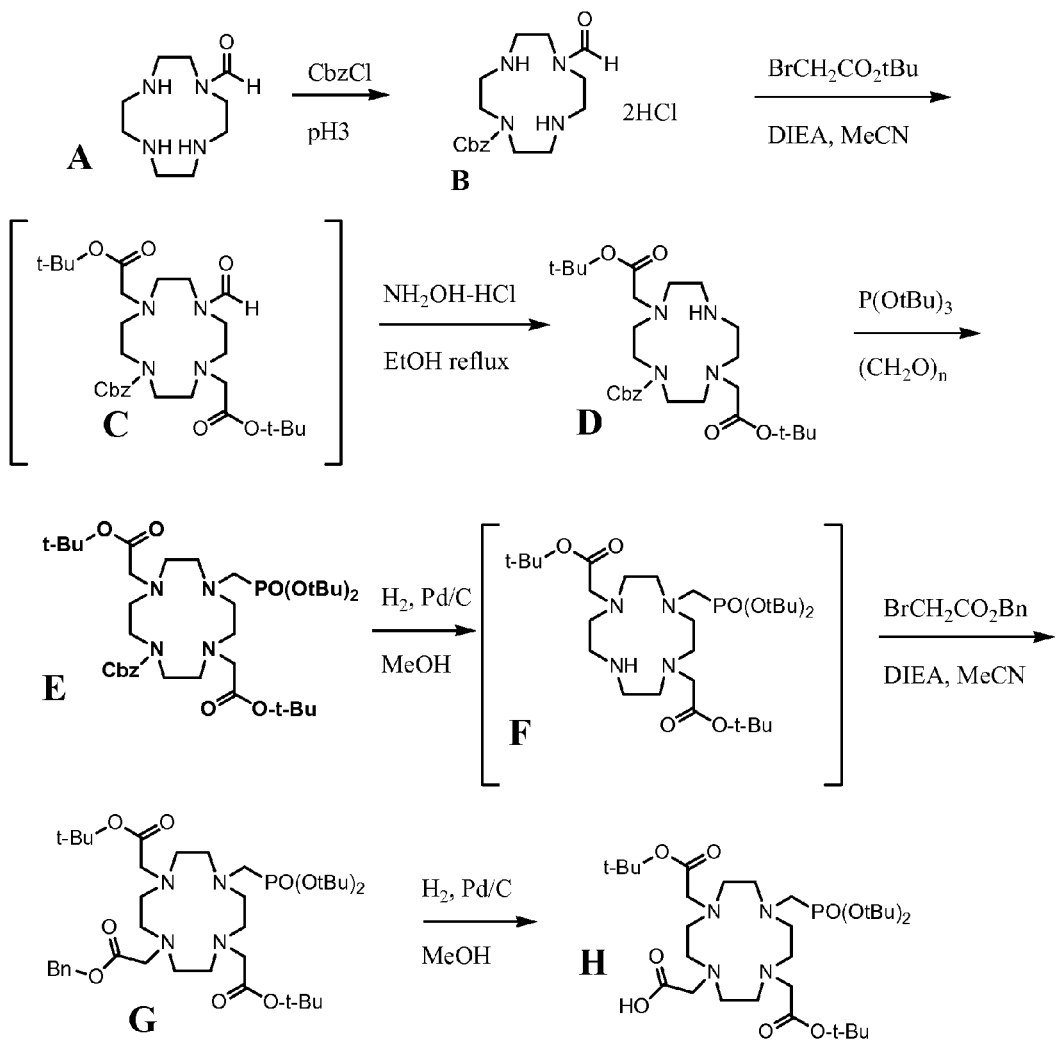

FIG. 10A is a graphical representation of a reaction for the synthesis of 7-[[Bis(1,1-dimethylethoxy)phosphinyl]methyl]-1,4,7,10-tetraazacyclododecane-1,4,10-triacetic acid 4,10-bis(1,1-dimethylethyl) ester H, as described in Example X.

Figure 10B:
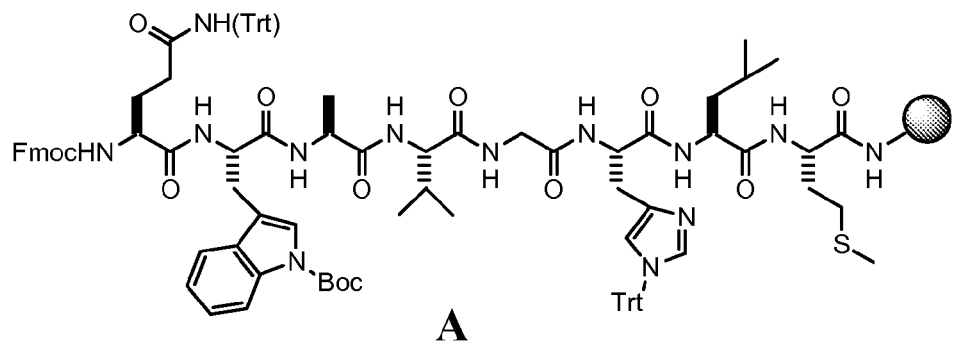
Figure 10B:
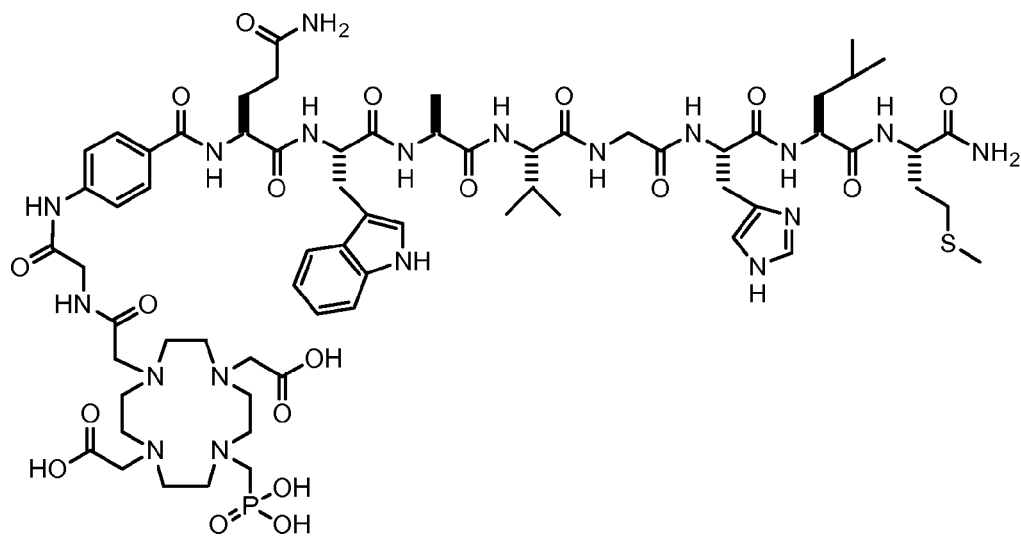

FIG. 10B is a graphical representation of a reaction for the synthesis of N-[4-[[[[[4,10-Bis(carboxymethyl)-7-(dihydroxyphosphinyl)methyl-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucil-L-methioninamide, (L237), as described in Example X.

Figure 11A:
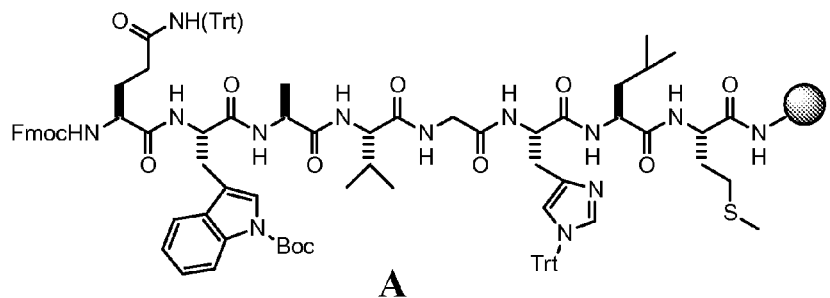
Figure 11A:
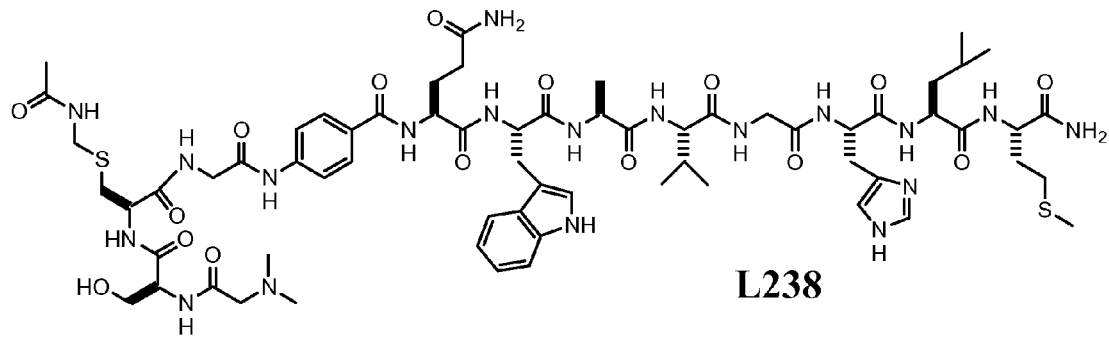

FIG. 11A is a graphical representation of a reaction for the synthesis of N,N-Dimethylglycyl-L-serinyl-[S-[(acetylamino)methyl]]-L-cysteinyl-glycyl-4-aminobenzoyl-L-glutaminyl-L-tryptophyl-L-alanyl-L-valyl-glycyl-L-histidyl-L-leucyl-L-methioninamide (L238), as described in Example XI.

Figure 11B:
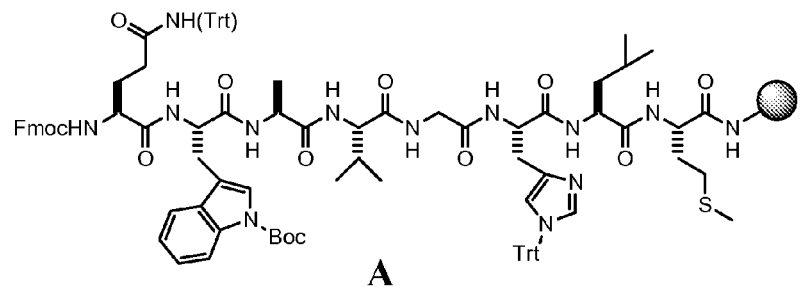
Figure 11B:
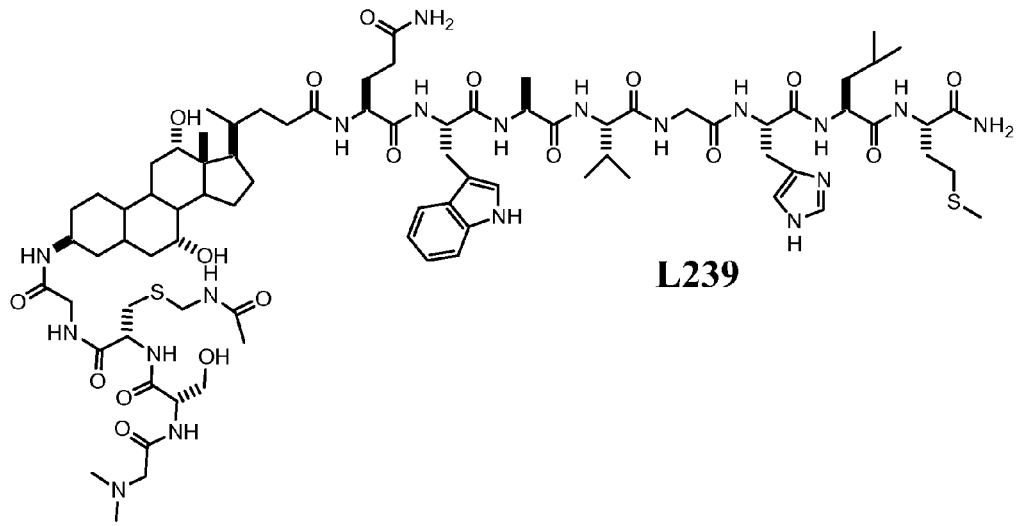

FIG. 11B is a graphical representation of a reaction for the synthesis of N,N-Dimethylglycyl-L-serinyl-[S-[(acetylamino)methyl]]-L-cysteinyl-glycyl-(3β,5β,7α,12α)-3-amino-7,12-dihydroxy-24-oxocholan-24-yl-L-glutaminyl-L-tryptophyl-L-alanyl-L-valyl-glycyl-L-histidyl-L-leucyl-L-methioninamide, (L239), as described in Example XI.

Figure 12A:
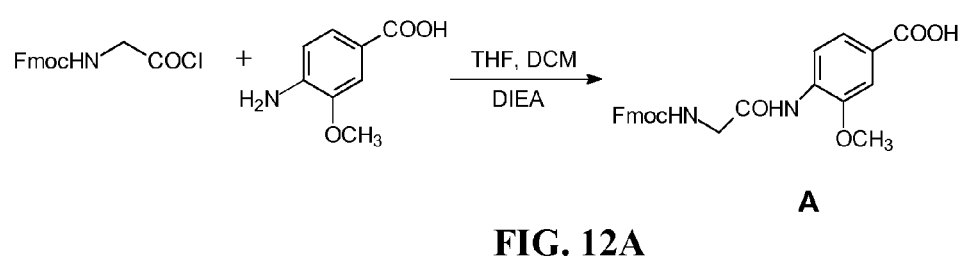

FIG. 12A is a graphical representation of a reaction for the synthesis of 4-[[[(9H-Fluoren-9-ylmethoxy)carbonyl]amino]acetyl]amino-3-methoxybenzoic acid (A), as described in Example XII.

Figure 12B:
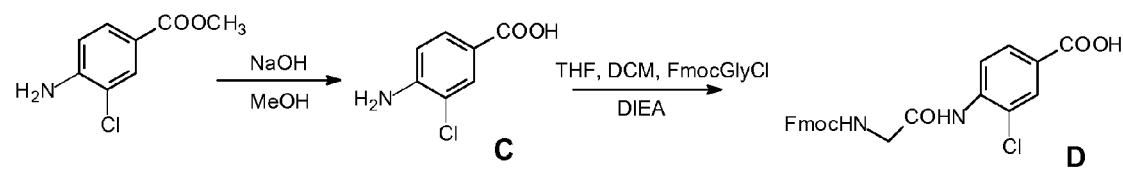

FIG. 12B is a graphical representation of a reaction for the synthesis of 4-[[[(9H-Fluoren-9-ylmethoxy)carbonyl]amino]acetyl]amino-3-chlorobenzoic acid, (D), as described in Example XII.

Figure 12C:
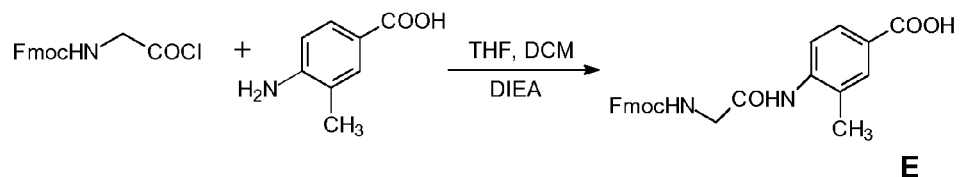

FIG. 12C is a graphical representation of a reaction for the synthesis of 4-[[[(9H-Fluoren-9-ylmethoxy)carbonyl]amino]acetyl]amino-3-methylbenzoic acid (E), as described in Example XII.

Figure 12D:
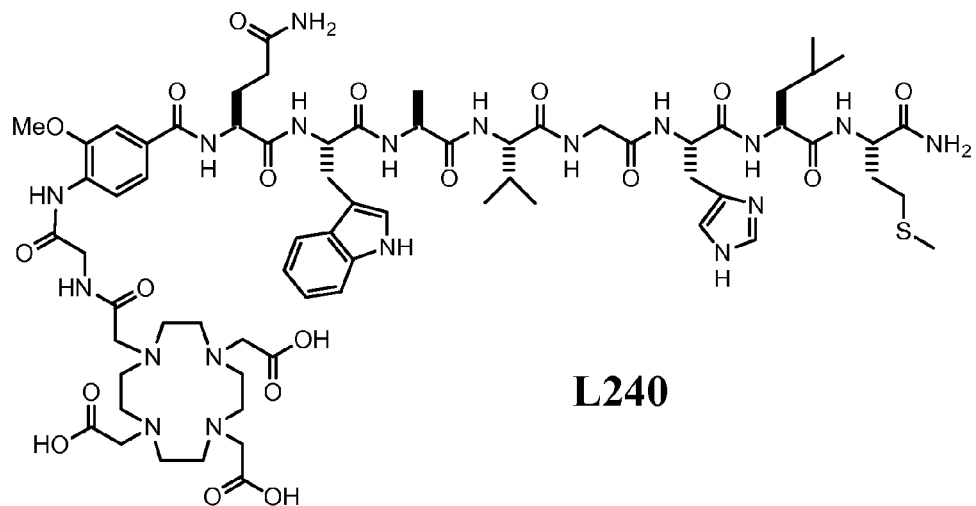

FIG. 12D is a chemical structure of N-[4-[[[[4,7,10-Tris(carboxymethyl)-1,4,7,10-tetraazacyclododec-1-yl]acetyl]glycyl]amino]-3-methoxybenzoyl]-L-glutaminyl-L-tryptophyl-1-alanyl-L-valyl-glycyl-L-histidyl-L-leucyl-L-methioninamide (L240) as described in Example XII.

Figure 12E:
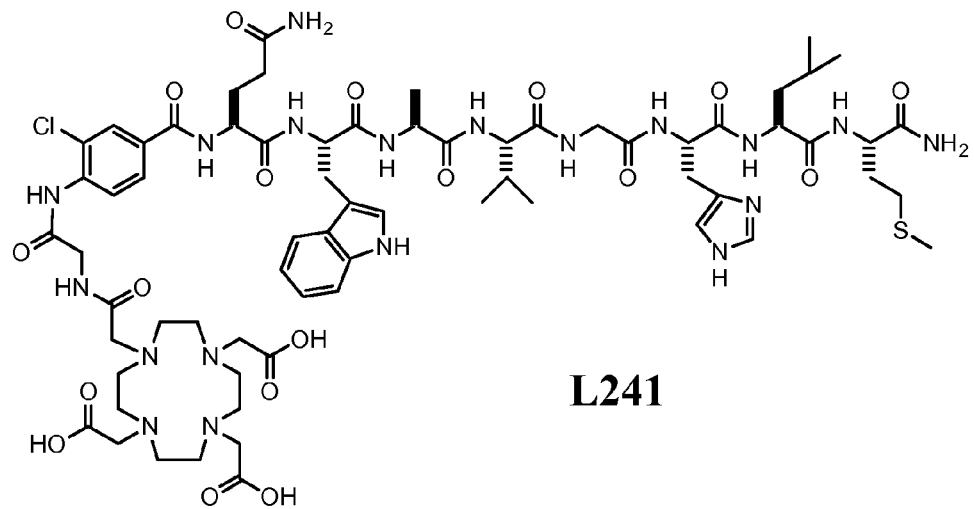

FIG. 12E is a chemical structure of compound N-[4-[[[[4,7,10-Tris(carboxymethyl)-1,4,7,10tetraazacyclododec-1-yl]acetyl]glycyl]amino]3-chlorobenzoyl]L-glutaminyl-L-tryptophyl-1-alanyl-L-valyl-glycyl-L-histidyl-L-leucyl-L-methioninamide, (L241) as described in Example XII.

Figure 12F:
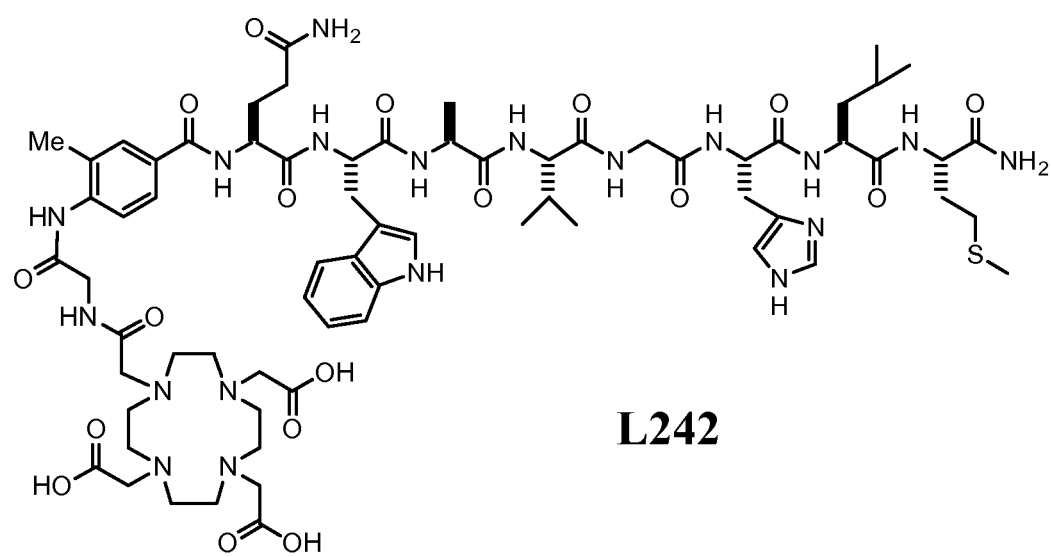

FIG. 12F is a chemical structure of N-[4-[[[[4,7,10-Tris(carboxymethyl)-1,4,7,10tetraazacyclododec-1-yl]acetyl]glycyl]amino]3-methylbenzoyl]L-glutaminyl-L-tryptophyl-1-alanyl-L-valyl-glycyl-L-histidyl-L-leucyl-L-methioninamide, (L242), as described in Example XII.

Figure 13A:
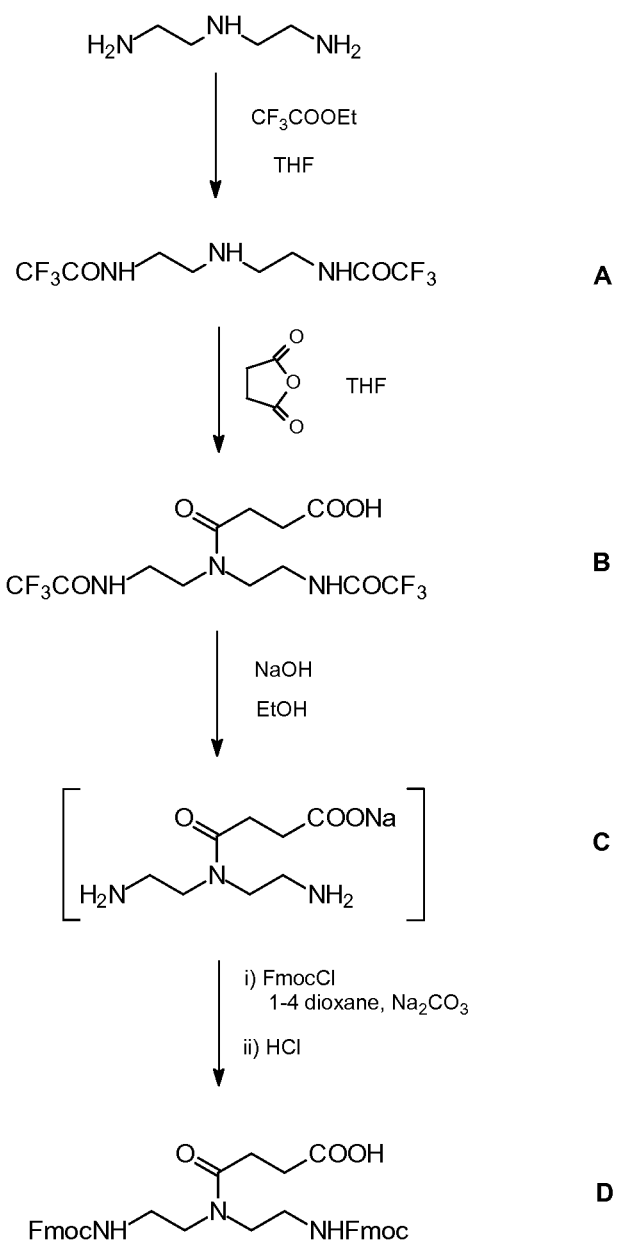

FIG. 13A is a graphical representation of a reaction for the synthesis of 4-[N,N'-Bis[2-[(9-H-fluoren-9-ylmethoxy)carbonyl]aminoethyl]amino]-4-oxobutanoic acid, (D), as described in Example XIII.

Figure 13B:
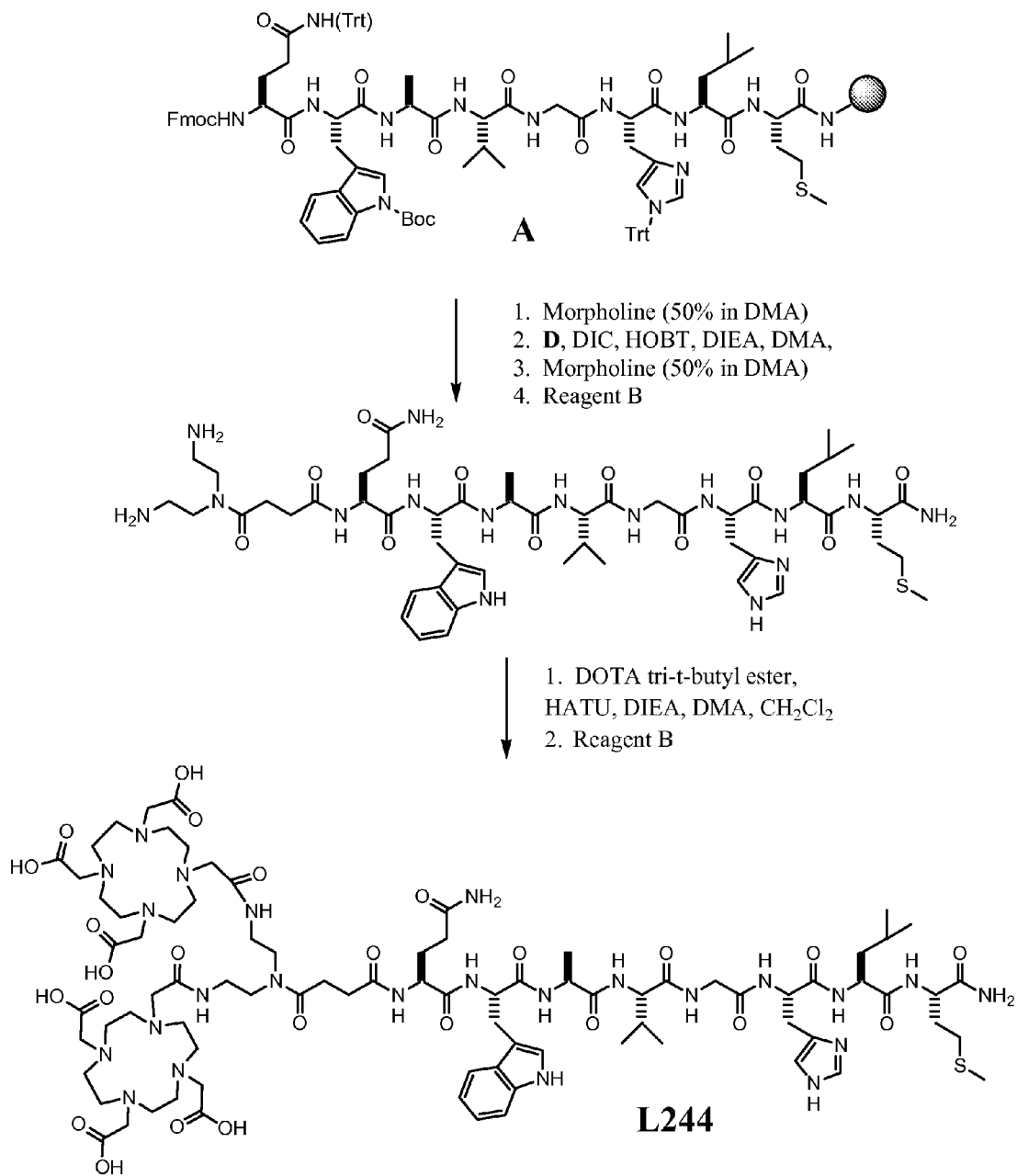

FIG. 13B is a graphical representation of a reaction for the synthesis of N-[4-[[4-[Bis[2-[[[4,7,10-tris(carboxymethyl)-1,4,7,10-tetraazacyclododec-1-yl]acetyl]amino]ethyl]amino-1,4-dioxobutyl]amino]benzoyl]-L-glutaminyl-L-tryptophyl-L-alanyl-L-valyl-glycyl-L-histidyl-L-leucyl-L-methioninamide, (L244), as described in Example XIII.

Figure 13C:
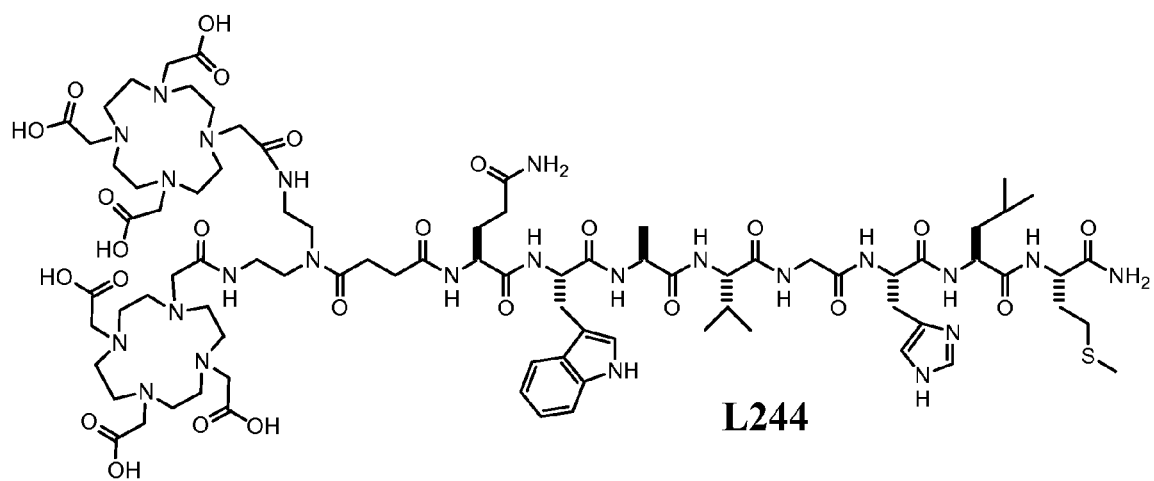

FIG. 13C is a chemical structure of compound L244, as described in Example XIII.

Figure 14A:
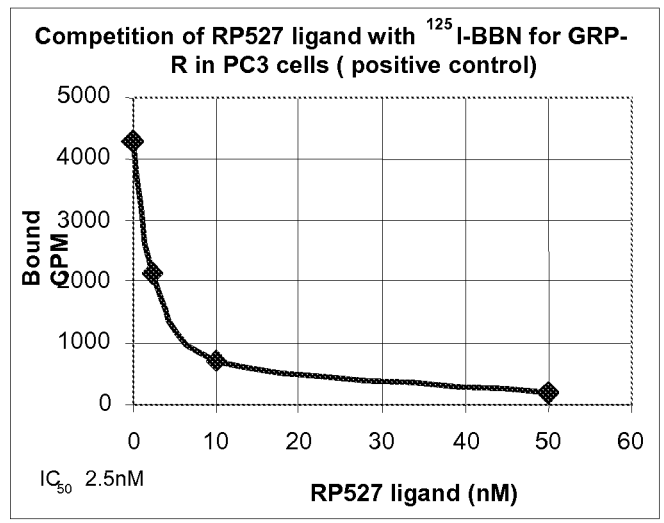
Figure 14B:
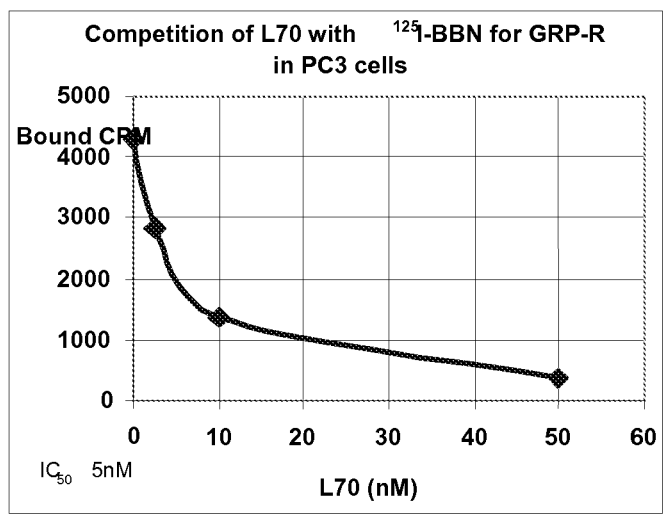

FIG. 14A and FIG. 14B are graphical representations of the binding and competition curves described in Example XLIII.

Figure 15A:
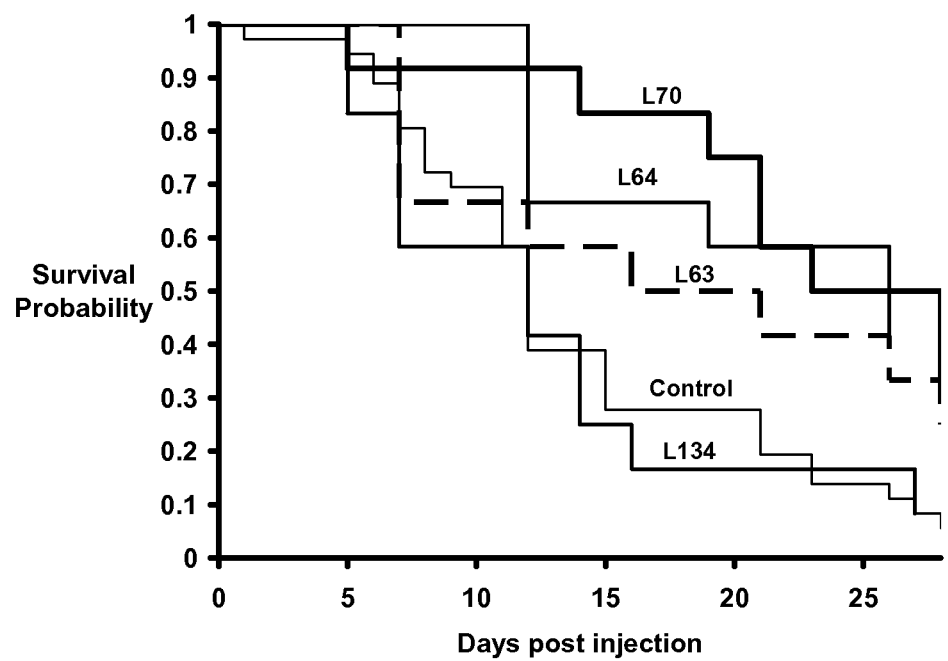

FIG. 15A is a graphical representation of the results of radiotherapy experiments described in Example LV.

Figure 15B:
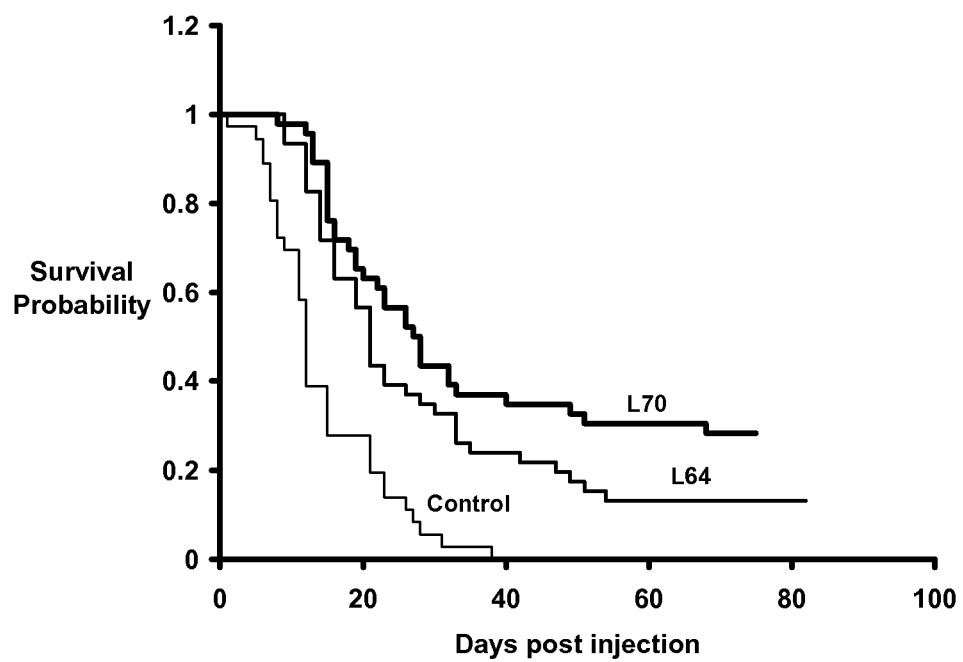

FIG. 15B is a graphical representation of the results of other radiotherapy experiments described in Example LV.

Figure 16:
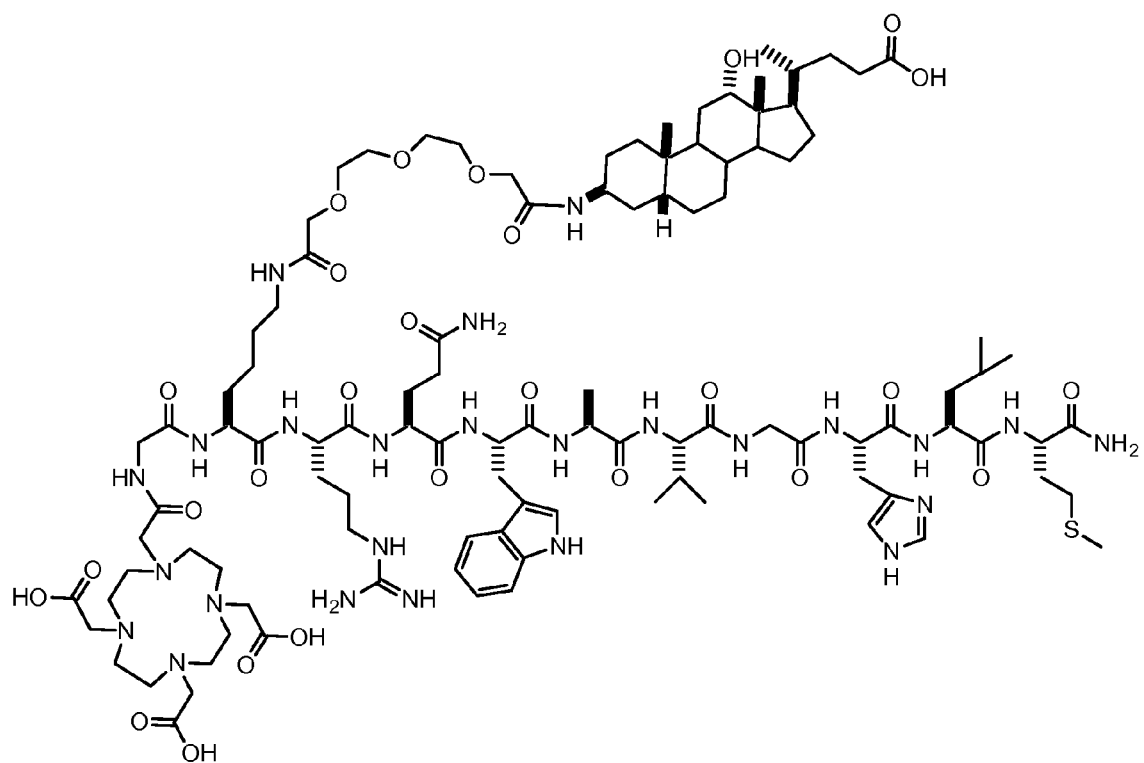

FIG. 16 is a chemical structure of N-[4-[[[[4,7,10-Tris(carboxymethyl)-1,4,7,10 tetraazacyclododec-1-yl]acetyl]glycyl]amino]-L-Lysinyl-(3,6,9)-trioxaundecane-1,11-dicarboxylic acid-3,7-dideoxy-3-aminocholic acid)-L-arginyl-L-glutaminyl-L-triptophyl-L-alanyl-L-valyl-glycyl-L-histidyl-L-leucyl-L-methioninamide (L65).

Figure 17:
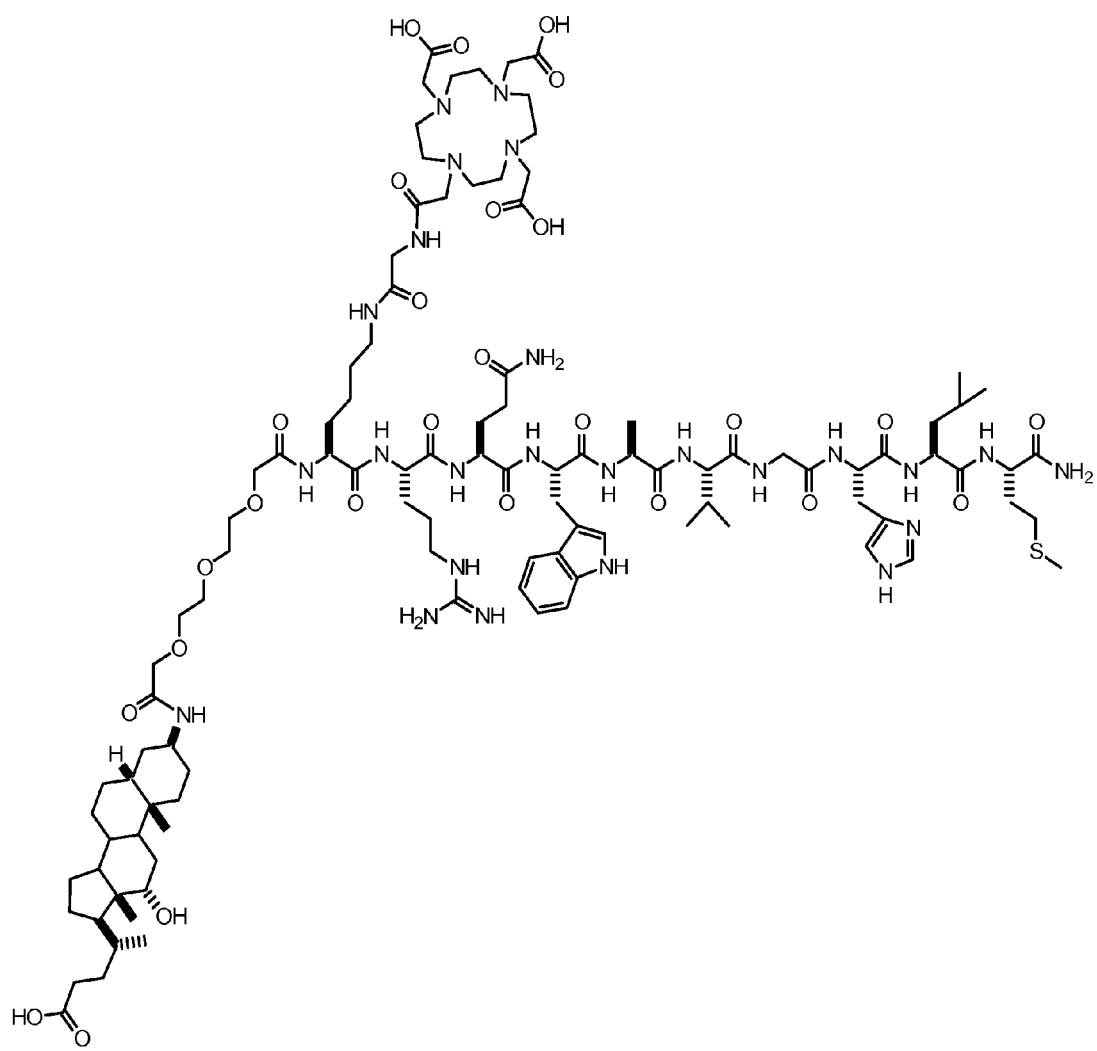

FIG. 17 is a chemical structure of N-[2-S-[[[[[12α-Hydroxy-17α-(1-methyl-3-carboxypropyl)etiocholan-3β-carbamoylmethoxyethoxyethoxyacetyl]-amino-6-[4,7,10-tris(carboxymethyl)-1,4,7,10-tetraazacyclododec-1-yl]acetyl]amino]acetyl]amino]hexanoyl]-L-glutaminyl-L-tryptophyl-L-alanyl-L-valyl-glycyl-L-histidyl-L-leucyl-L-methioninamide (L66).

Figure 18A:
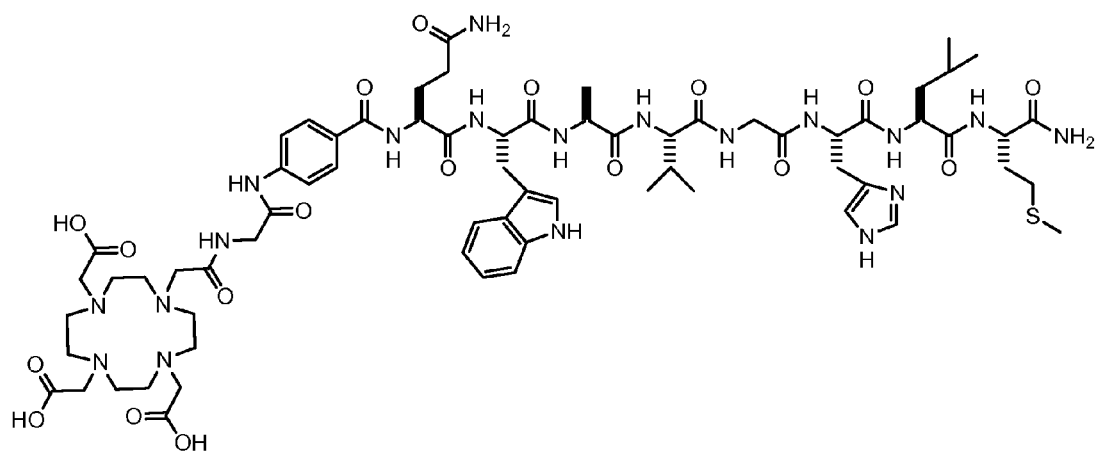

FIG. 18A is a chemical structure of N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide (L70).

Figure 18B:
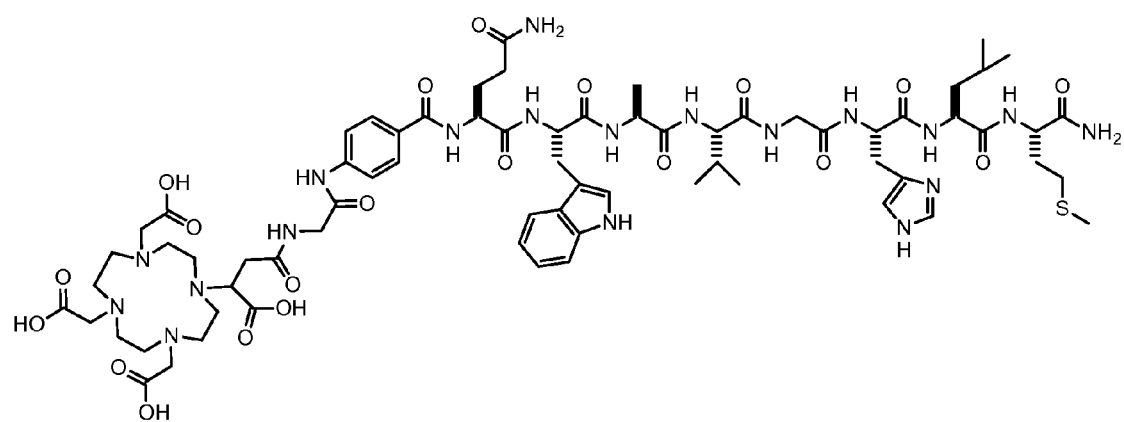

FIG. 18B is a chemical structure N-[4-[[[[[4,7,10-Tris(carboxymethyl)-1,4,7,10-tetraazacyclododec-1-yl]-3-carboxypropionyl]amino]acetyl]amino]benzoyl]-L-glutaminyl-L-tryptophyl-L-alanyl-L-valyl-glycyl-L-histidyl-L-leucyl-L-methioninamide (L114).

Figure 18C:
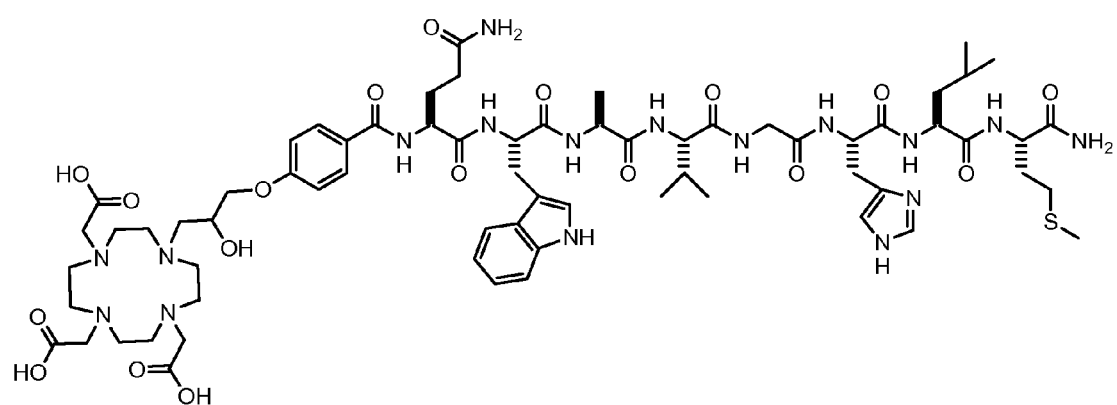

FIG. 18C is a chemical structure N-[4-[[4,7,10-Tris(carboxymethyl)-1,4,7,10-tetraazacyclododec-1-yl]-2-hydroxy-3-propoxy]benzoyl]-L-glutaminyl-L-tryptophyl-L-alanyl-L-valyl-glycyl-L-histidyl-L-leucyl-L-methioninamide (L144).

Figure 18D:
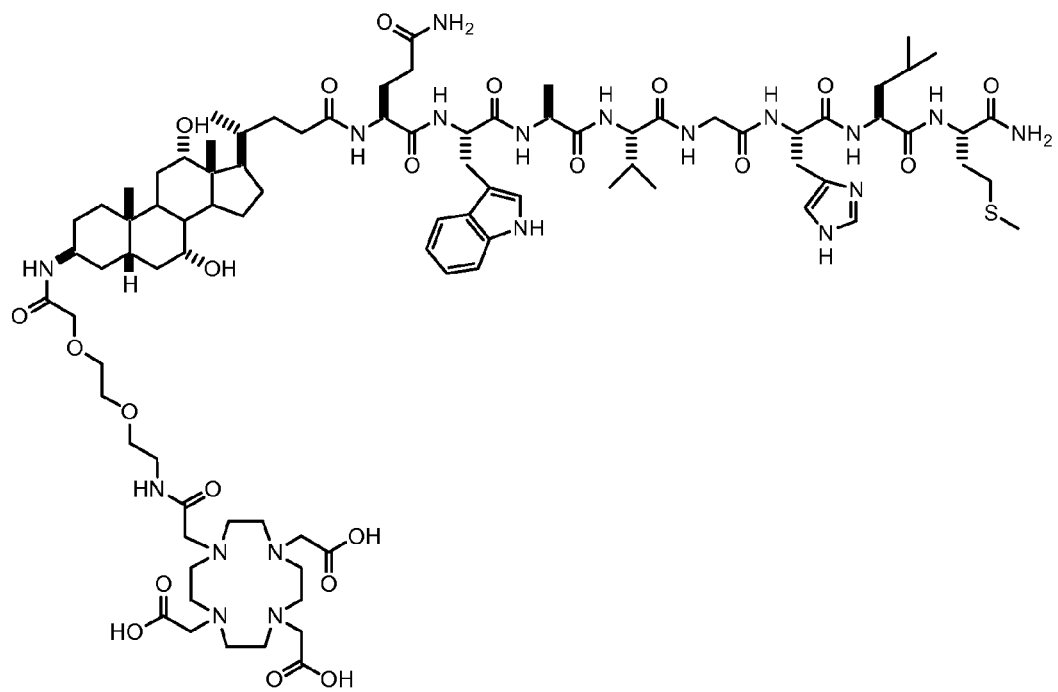

FIG. 18D is a chemical structure N-[(3β,5β,7α,12α)-3-[[[[[4,7,10-Tris(carboxymethyl)-1,4,7,10-tetraazacyclododec-1-yl]acetyl]amino]ethoxyethoxy]acetyl]amino]-7,12-dihydroxycholan-24-yl]-L-glutaminyl-L-tryptophyl-L-alanyl-L-valyl-glycyl-L-histidyl-L-leucyl-L-methioninamide (L69).

Figure 18E:
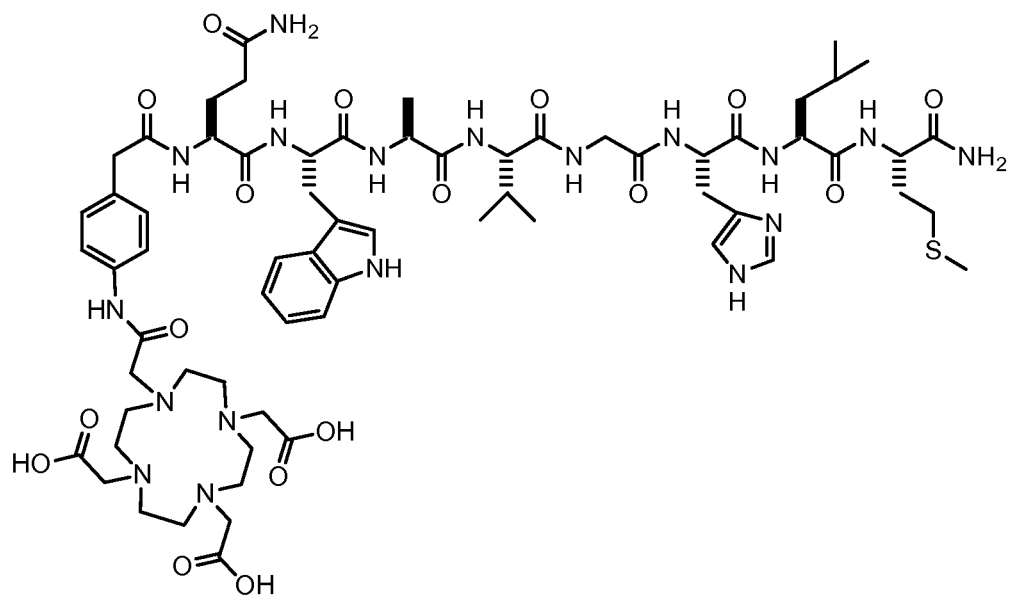

FIG. 18E is a chemical structure of N-[4-[[[[[4,7,10-Tris(carboxymethyl)-1,4,7,10-tetraazacyclododec-1-yl]acetyl]amino]acetyl]amino]phenylacetyl]-L-glutaminyl-L-tryptophyl-L-alanyl-L-valyl-glycyl-L-histidyl-L-leucyl-L-methioninamide (L146).

Figure 19:
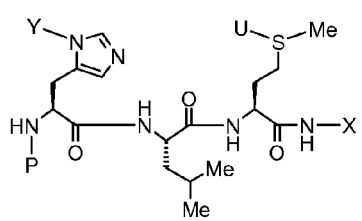
Figure 19:
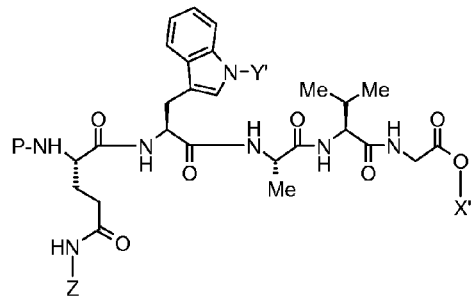
Figure 19:
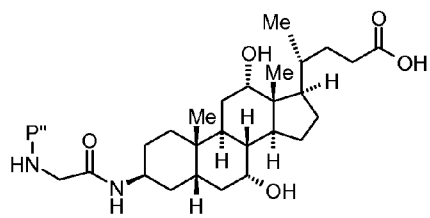
Figure 19:
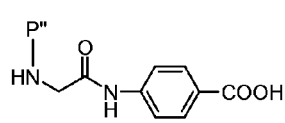
Figure 19:
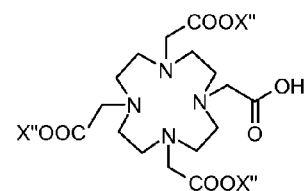

FIG. 19 discloses chemical structures of intermediates which may be used to prepare compounds L64 and L70 as described in Example LVI.

Figure 20:
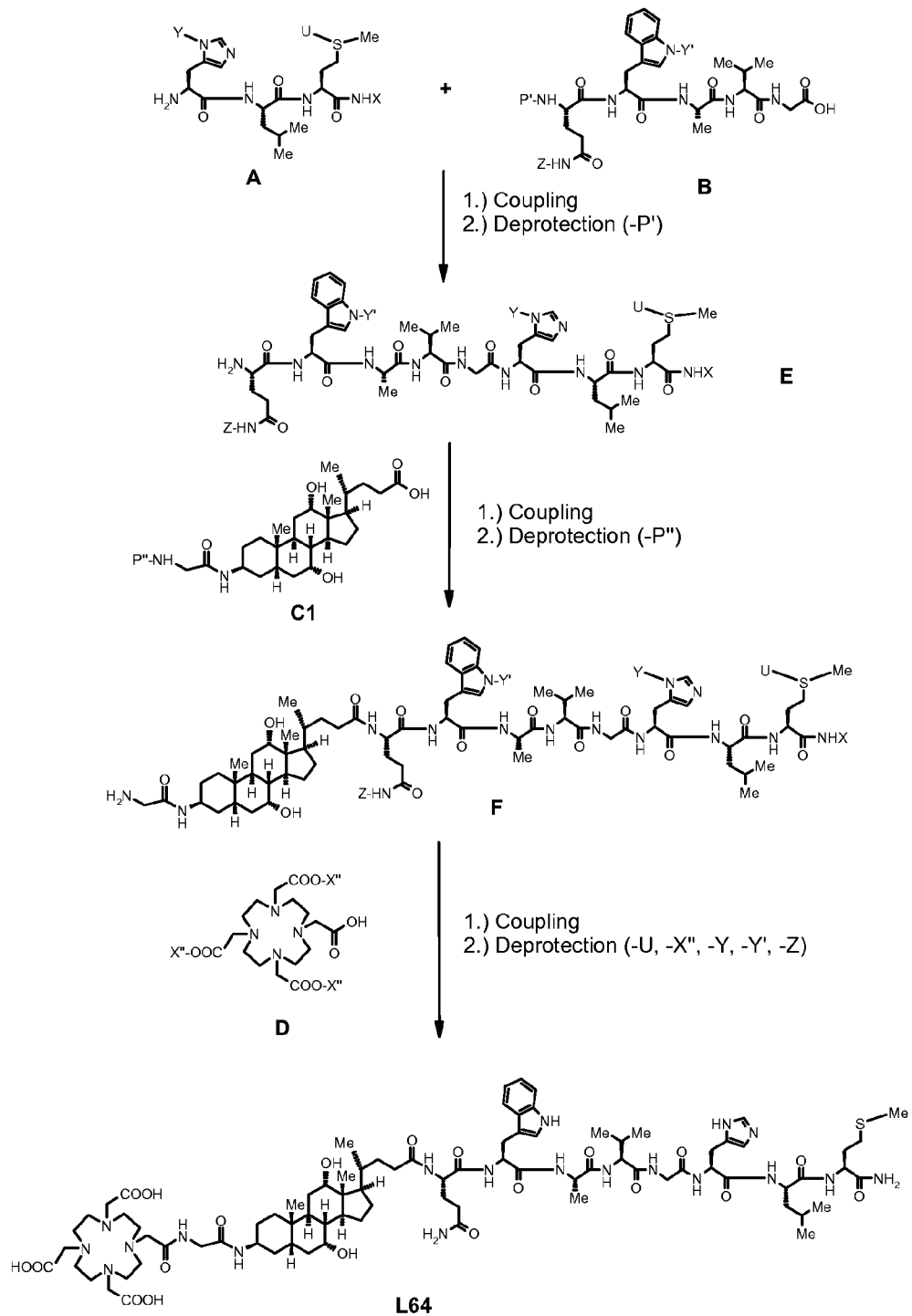

FIG. 20 is a graphical representation of the preparation of L64 using segment coupling as described in Example LVI.

Figure 21:
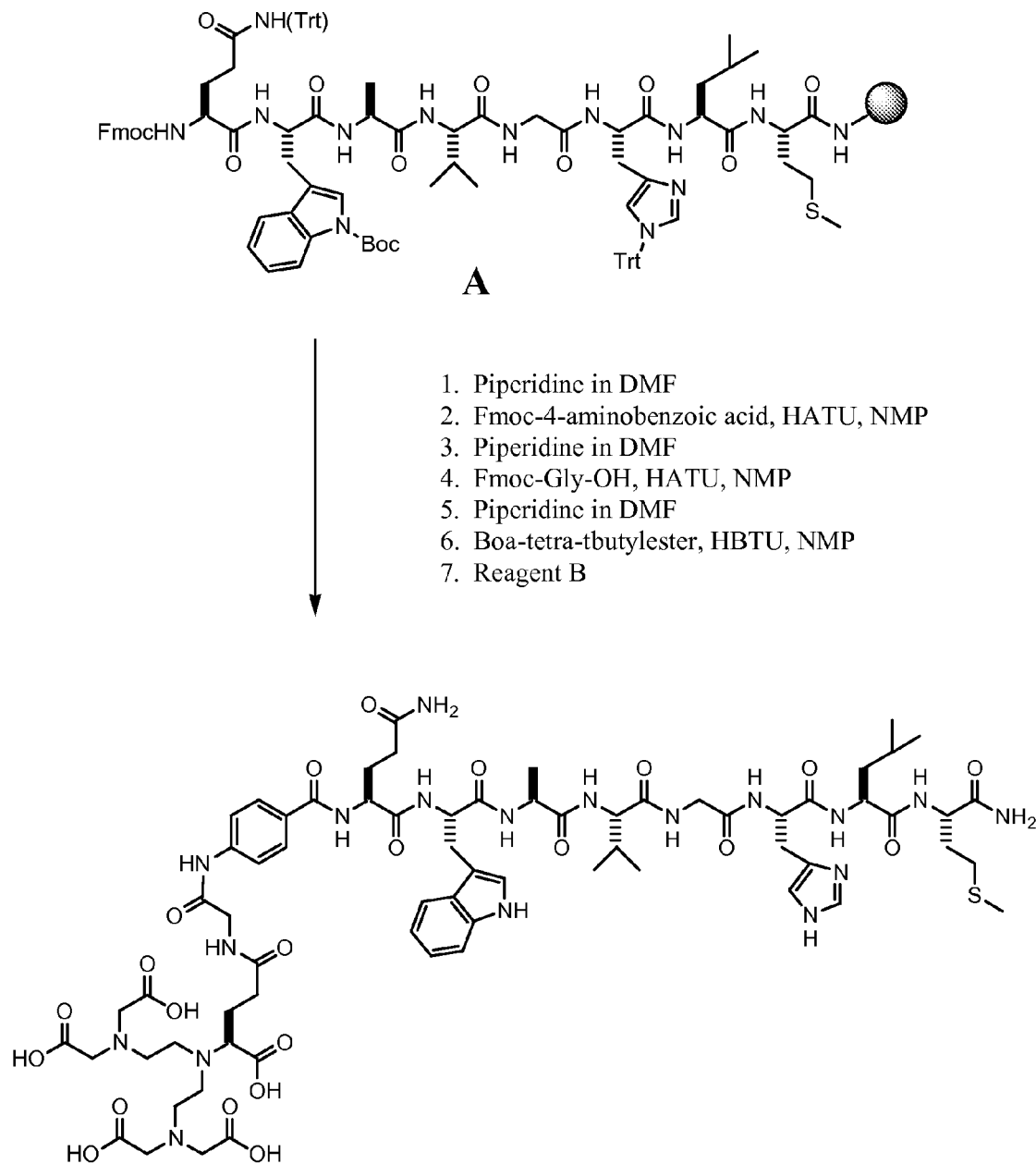

FIG. 21 is a graphical representation of the preparation of (1R)-1-(Bis{2-[bis(carboxymethyl)amino]ethyl}amino)propane-3-carboxylic acid-1-carboxyl-glycyl-4-aminobenzoyl-L-glutaminyl-L-tryptophyl-L-alanyl-L-valyl-glycyl-L-histidyl-L-leucyl-L-methioninamide (L201).

Figure 22A:
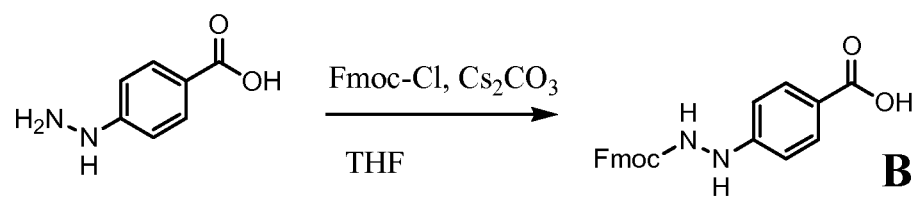

FIG. 22A is a graphical representation of chemical structure of chemical intermediates used to prepare L202.

Figure 22B:
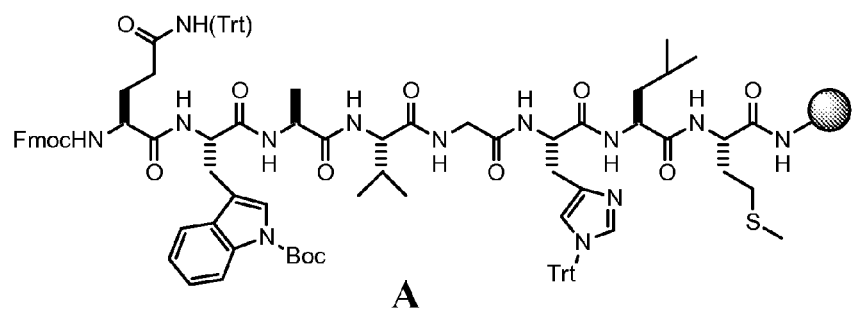
Figure 22B:
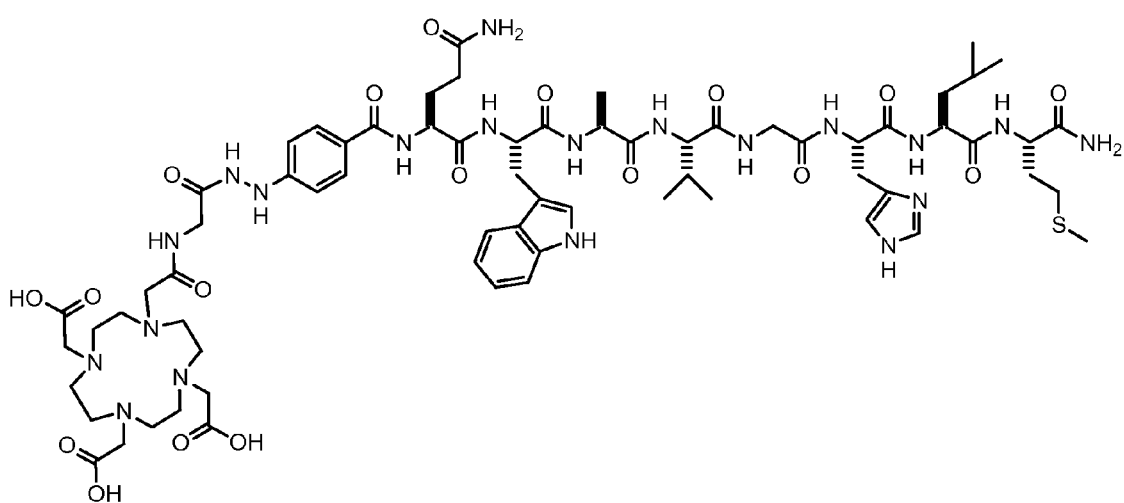

FIG. 22B is a graphical representation of the preparation of N-[(3β,5β,12α)-3-[[[[[4,7,10-Tris(carboxymethyl)-1,4,7,10-tetraazacyclododec-1-yl]acetyl]amino]acetyl]amino]-4-hydrazinobenzoyl-L-glutaminyl-L-tryptophyl-L-alanyl-L-valyl-glycyl-L-histidyl-L-leucyl-L-methioninamide (L202).

Figure 23A:
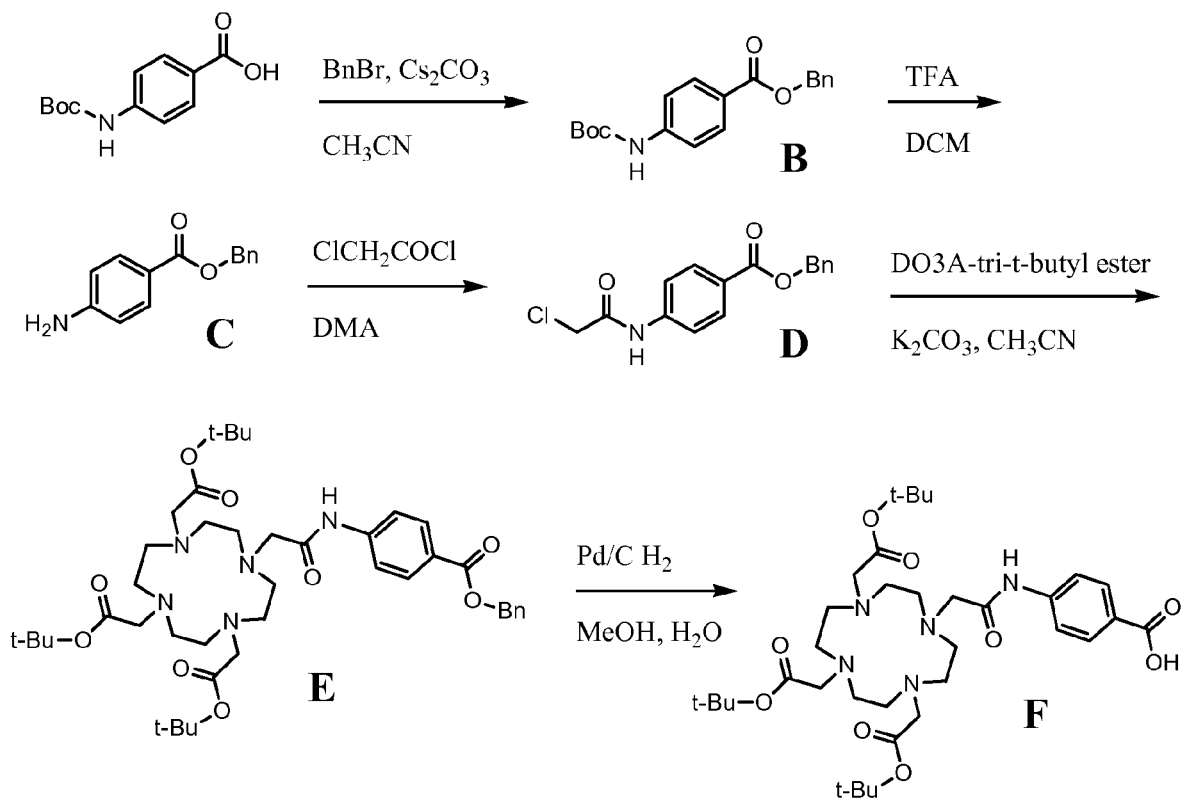

FIG. 23A is a graphical representation of chemical structure of chemical intermediates used to prepare L203.

Figure 23B:
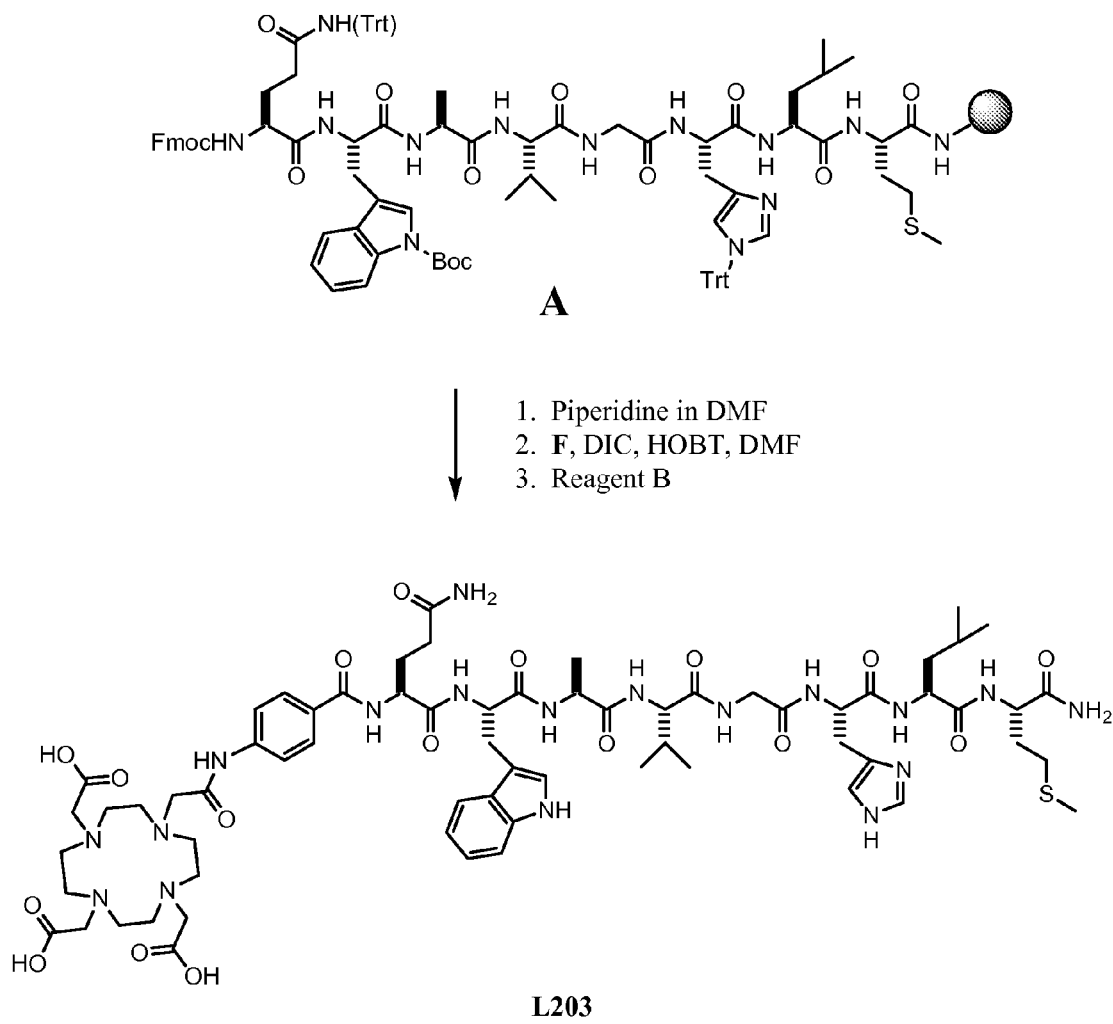

FIG. 23B is a graphical representation of the preparation of N-[(3β,5β,12α)-3-[[[4,7,10-Tris(carboxymethyl)-1,4,7,10-tetraazacyclododec-1-yl]acetyl]amino]-4-aminobenzoyl-L-glutaminyl-L-tryptophyl-L-alanyl-L-valyl-glycyl-L-histidyl-L-leucyl-L-methioninamide (L203).

Figure 24:
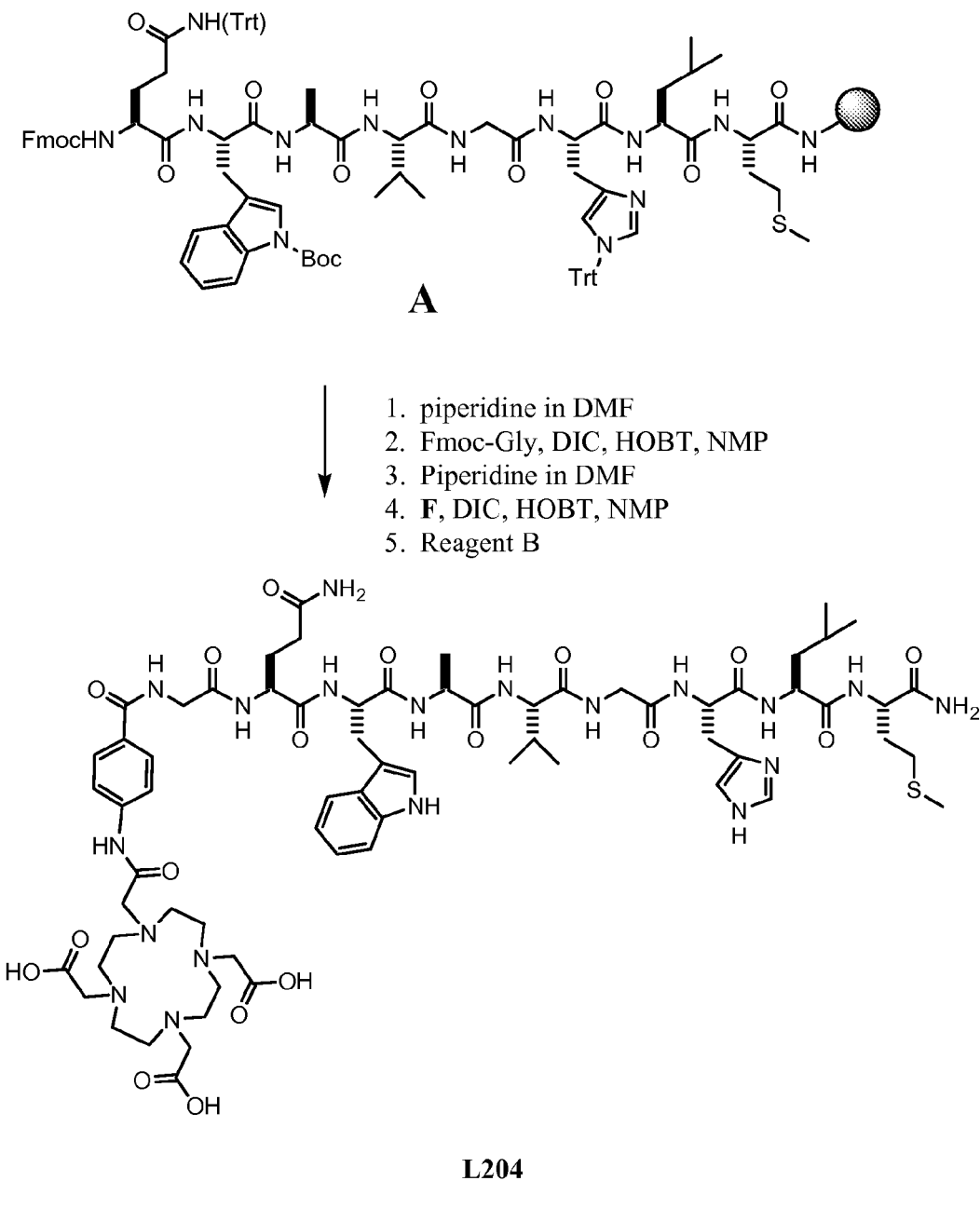

FIG. 24 is a graphical representation of the preparation of N-[(3β,5β,12α)-3-[[[4,7,10-Tris(carboxymethyl)-1,4,7,10-tetraazacyclododec-1-yl]acetyl]amino]-4-aminobenzoyl-glycyl-L-glutaminyl-L-tryptophyl-L-alanyl-L-valyl-glycyl-L-histidyl-L-leucyl-L-methioninamide (L204).

Figure 25:
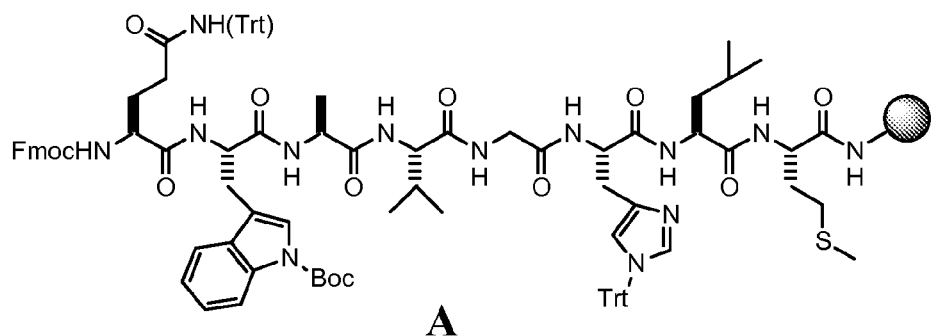
Figure 25:
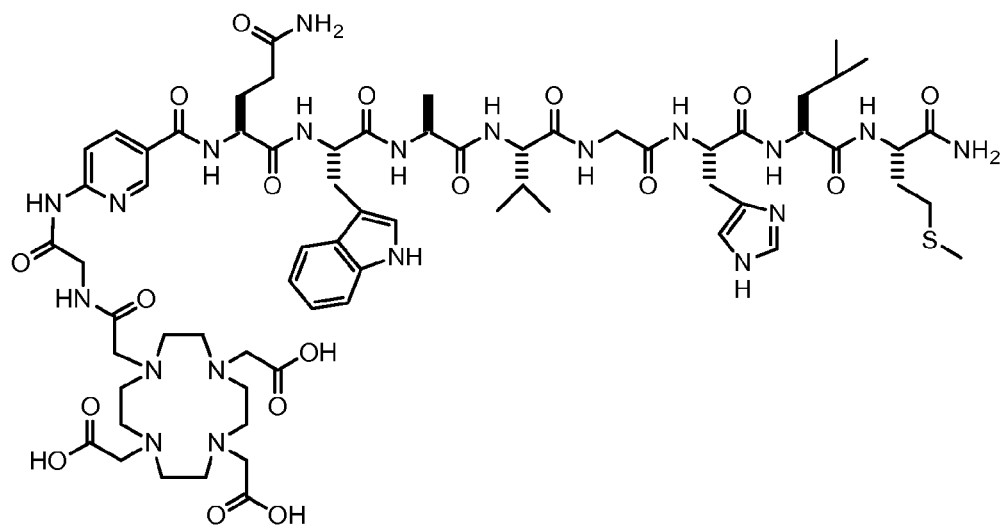

FIG. 25 is a graphical representation of the preparation of N-[(3β,5β,12α)-3-[[[4,7,10-Tris(carboxymethyl)-1,4,7,10-tetraazacyclododec-1-yl]acetyl]amino]-4-aminobenzoyl-glycyl-L-glutaminyl-L-tryptophyl-L-alanyl-L-valyl-glycyl-L-histidyl-L-leucyl-L-methioninamide (L205).

Figure 26A:
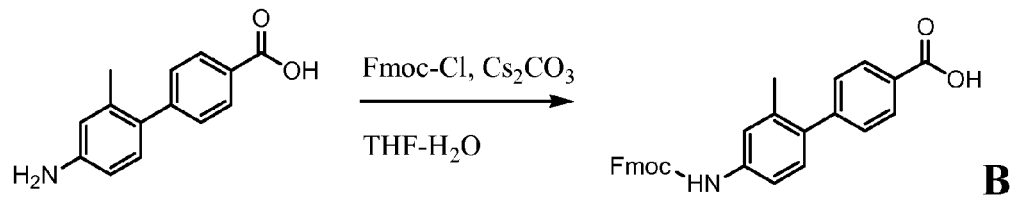

FIG. 26A is a graphical representation of chemical structures of chemical intermediates used to prepare L206.

Figure 26B:
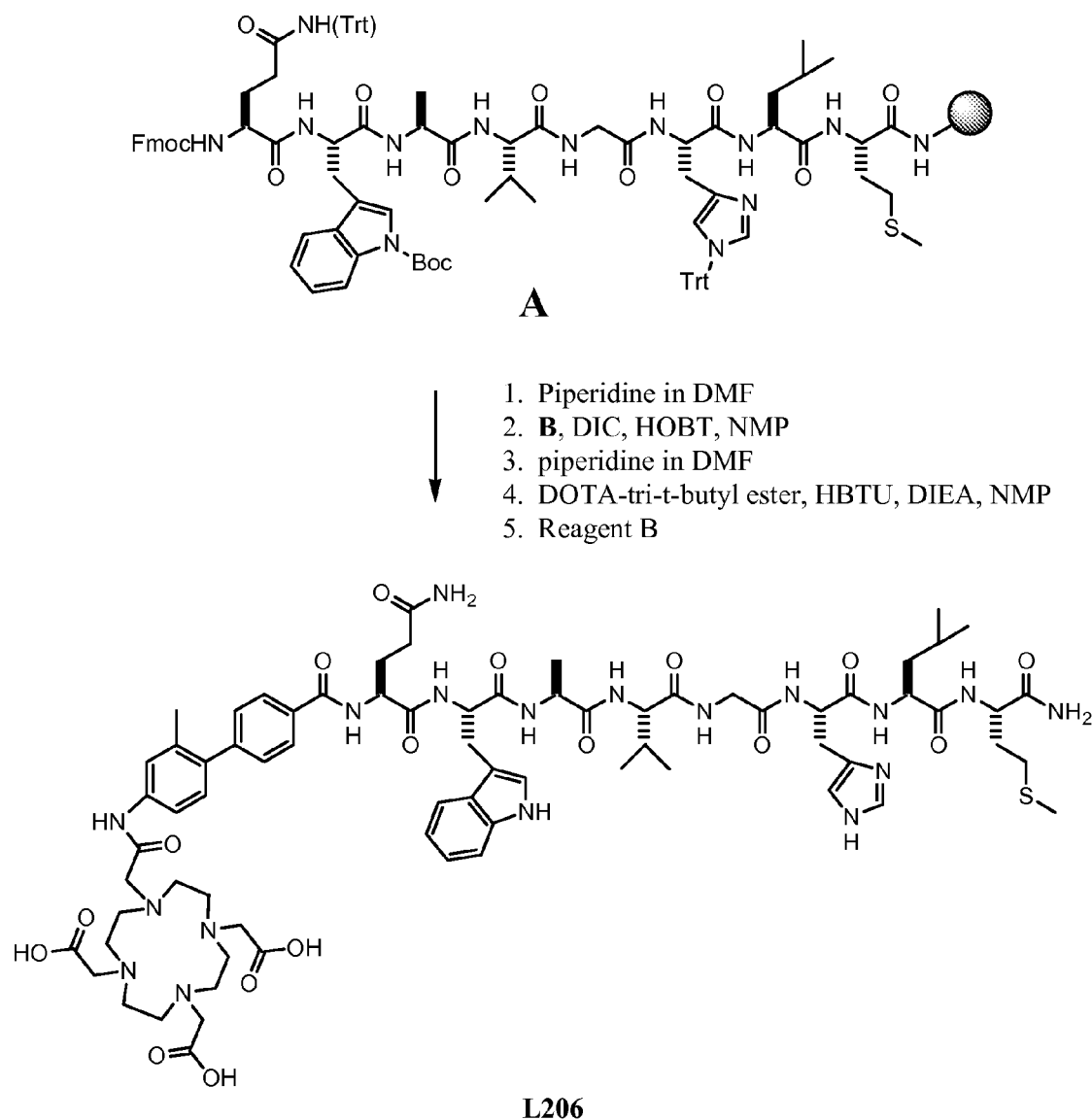

FIG. 26B is a graphical representation of the preparation of N-[(3β,5β,12α)-3-[[[[[4,7,10-Tris(carboxymethyl)-1,4,7,10-tetraazacyclododec-1-yl]acetyl]amino]acetyl]amino]-[4'-Amino-2'-methyl biphenyl-4-carboxyl]-L-glutaminyl-L-tryptophyl-L-alanyl-L-valyl-glycyl-L-histidyl-L-leucyl-L-methioninamide (L206).

Figure 27A:
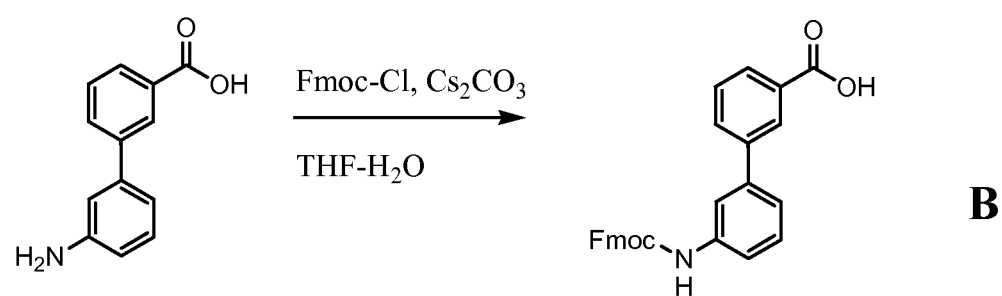

FIG. 27A is a graphical representation of chemical structures of chemical intermediates used to prepare L207.

Figure 27B:
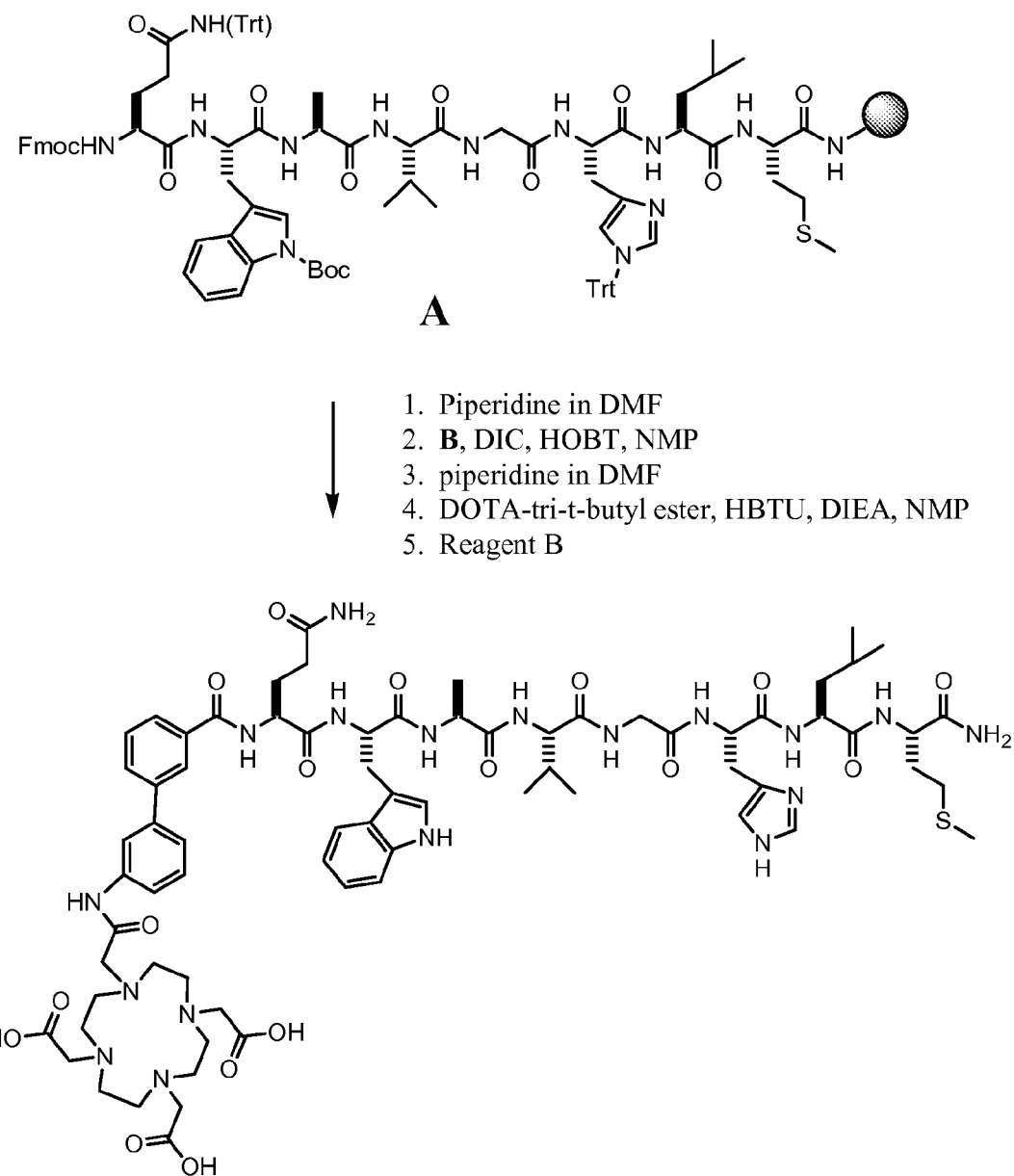

FIG. 27B is a graphical representation of the preparation of N-[(3β,5β,12α)-3-[[[[[4,7,10-Tris(carboxymethyl)-1,4,7,10-tetraazacyclododec-1-yl]acetyl]amino]acetyl]amino]-[3'-amino-biphenyl-3-carboxyl]-L-glutaminyl-L-tryptophyl-L-alanyl-L-valyl-glycyl-L-histidyl-L-leucyl-L-methioninamide (L207).

Figure 28:
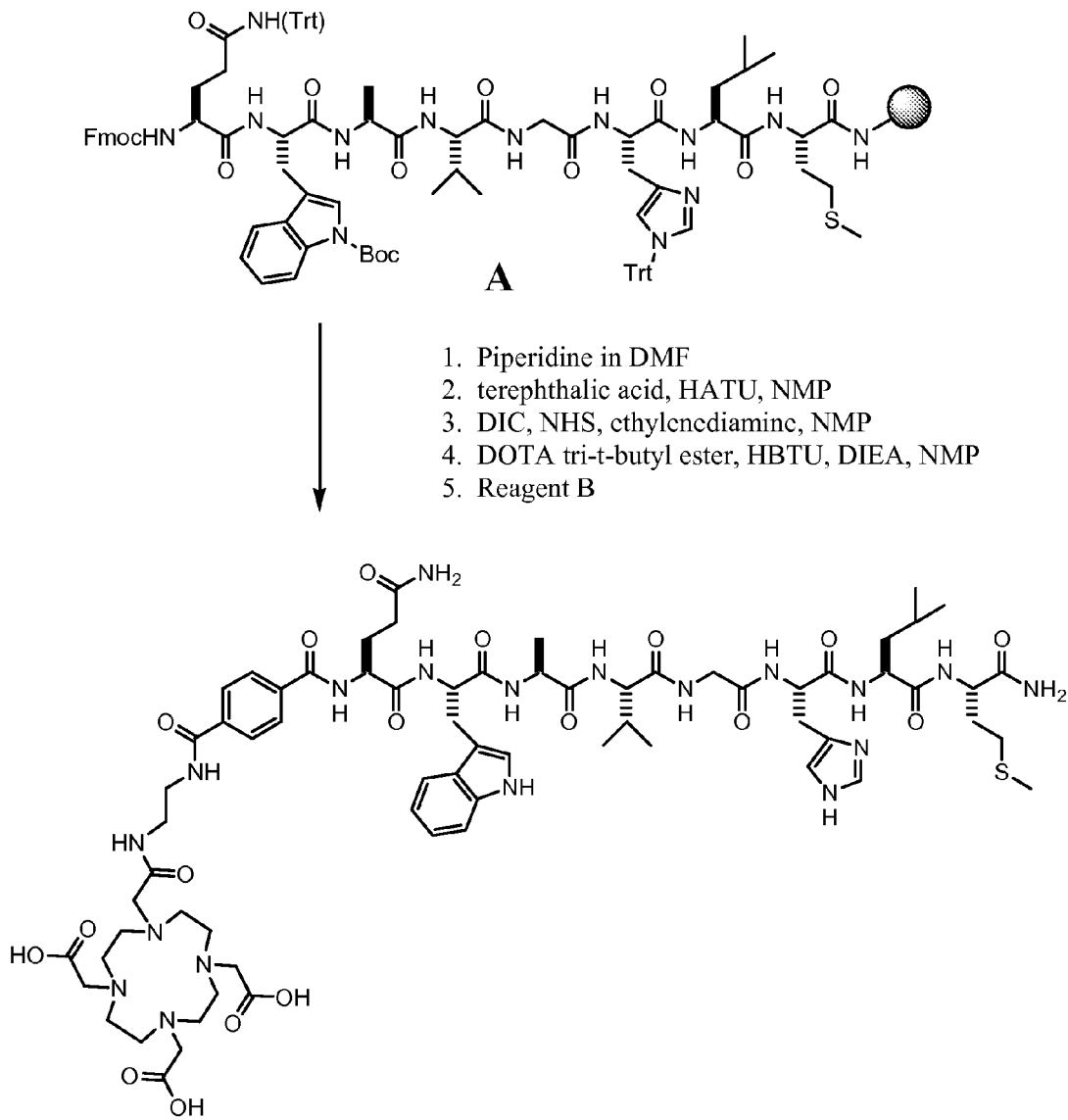

FIG. 28 is a graphical representation of the preparation of N-[(3β,5β,12α)-3-[[[[[4,7,10-Tris(carboxymethyl)-1,4,7,10-tetraazacyclododec-1-yl]acetyl]amino]acetyl]amino]-[1,2-d]aminoethyl-terephthalyl]-L-glutaminyl-L-tryptophyl-L-alanyl-L-valyl-glycyl-L-histidyl-L-leucyl-L-methioninamide (L208).

Figure 29A:
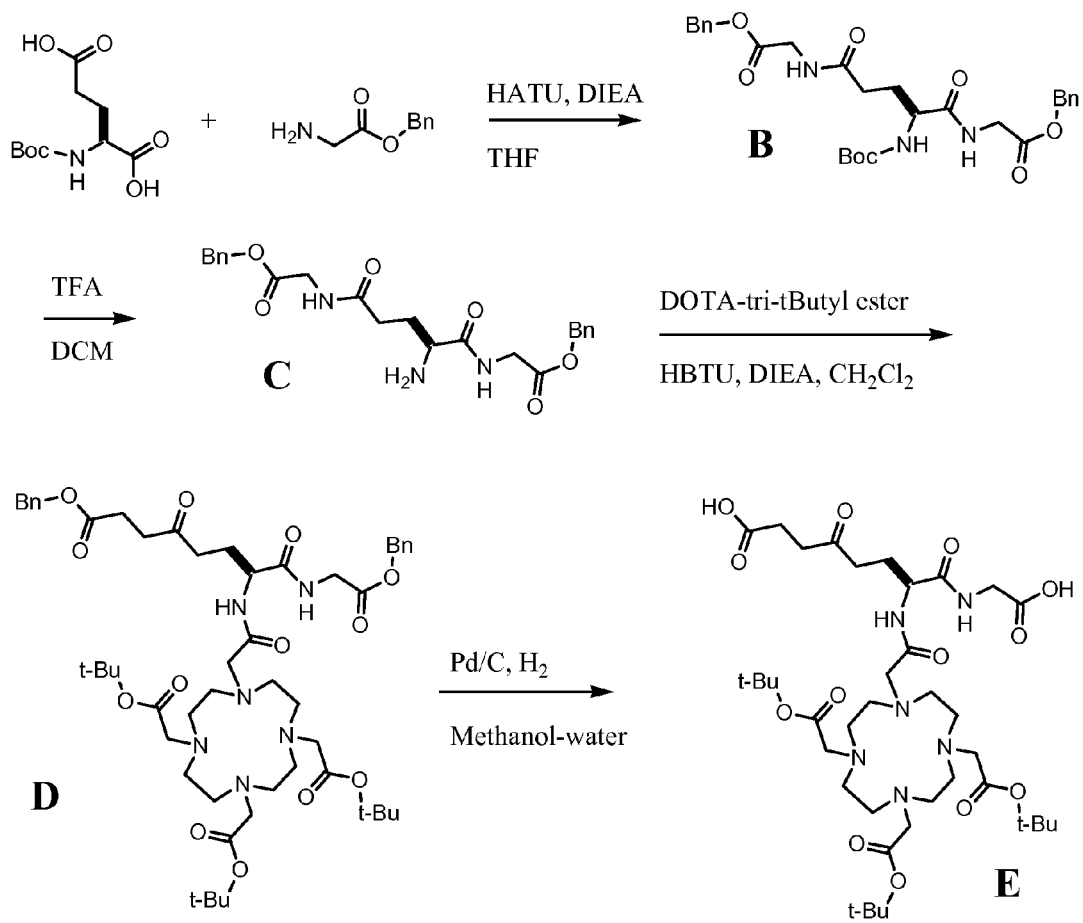

FIG. 29A is a graphical representation of chemical structures of chemical intermediates used to prepare L209.

FIG. 29B is a graphical representation of the preparation of L209.

Figure 30A:
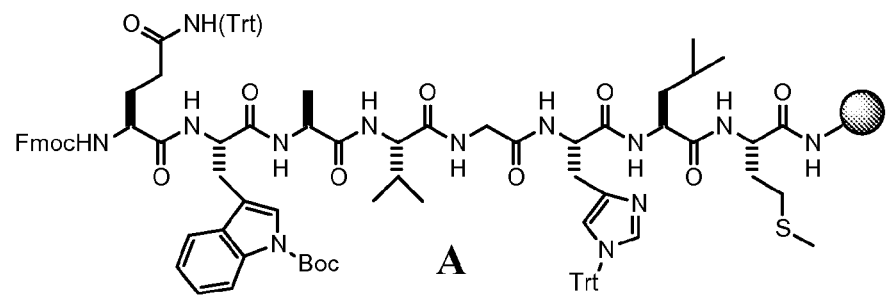
Figure 30A:
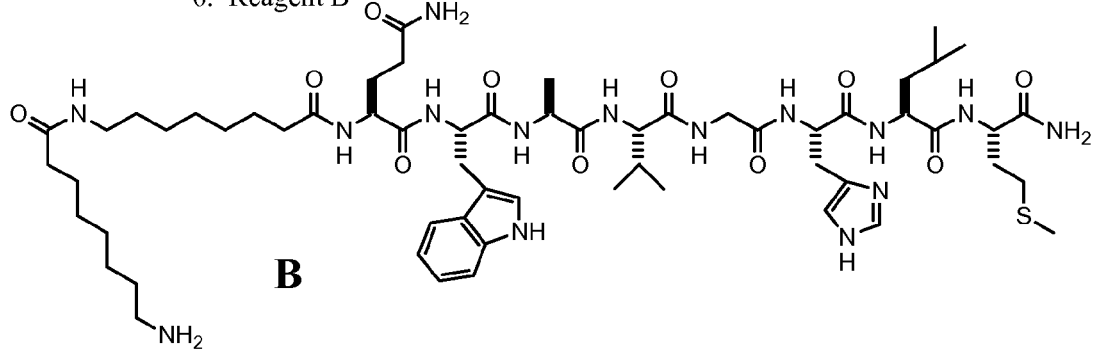

FIG. 30A is a graphical representation of chemical structures of chemical intermediates used to prepare L210.

Figure 30B:
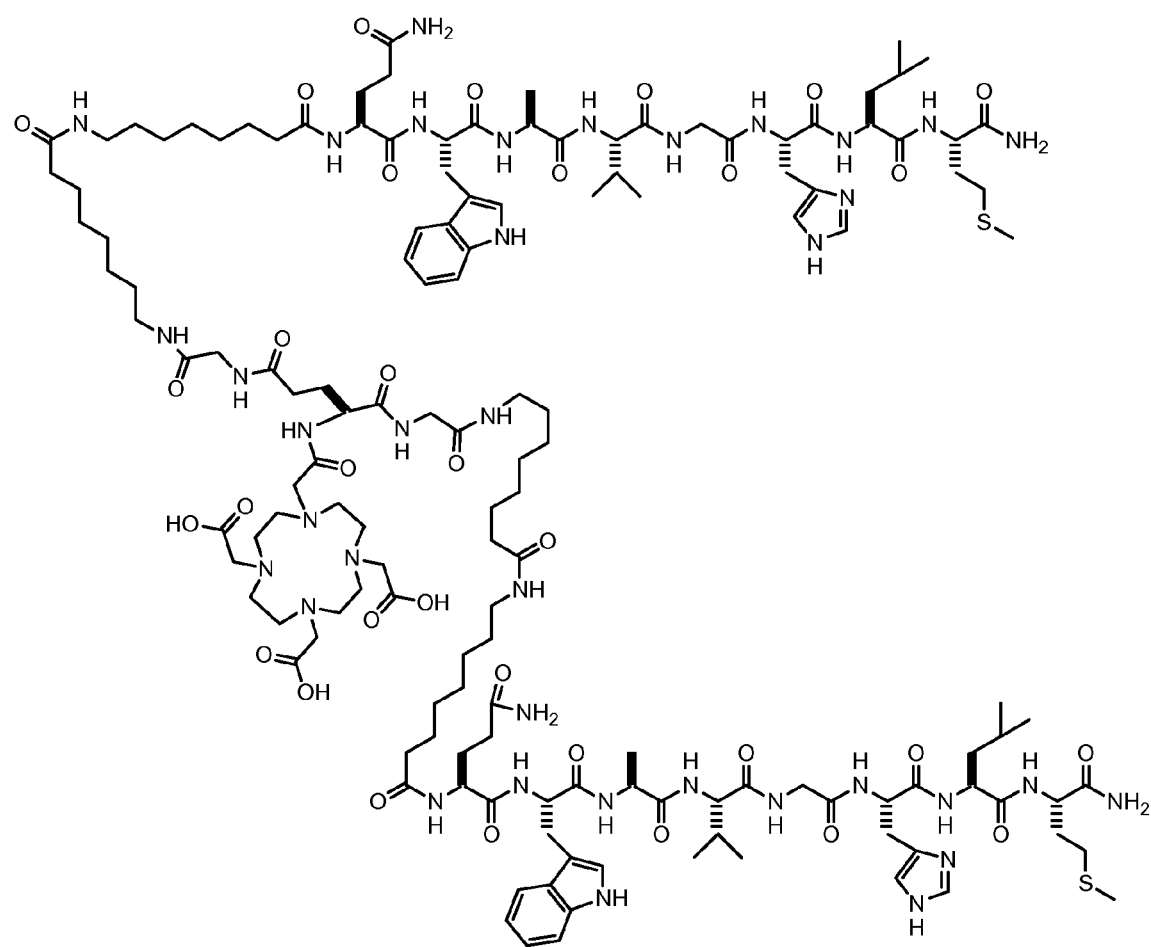

FIG. 30B is a chemical structure of L210.

Figure 31:
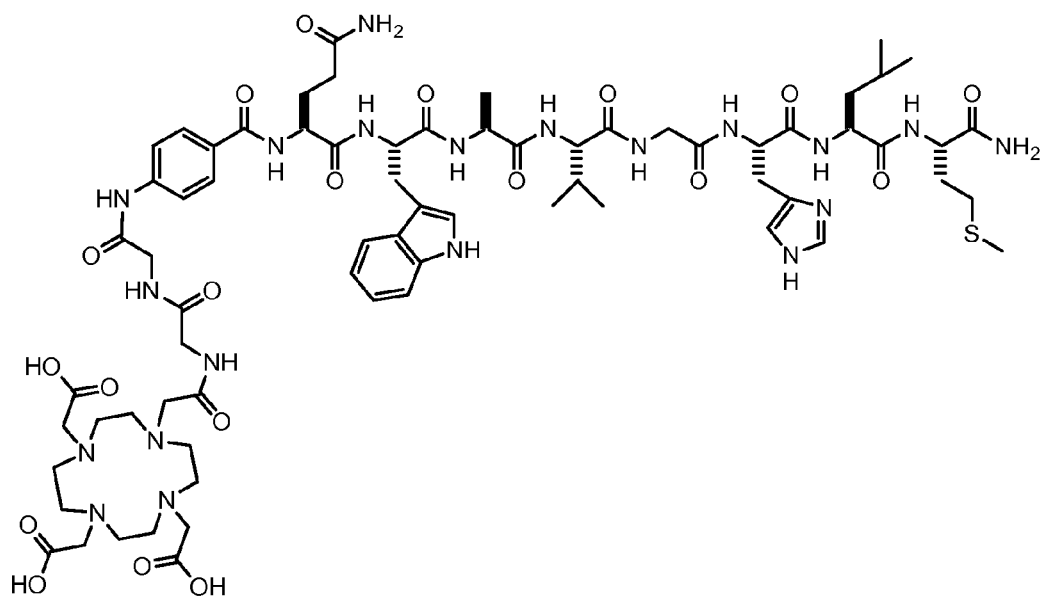

FIG. 31 is a chemical structure of N-[(3β,5β,12α)-3-[[[4,7,10-Tris(carboxymethyl)-1,4,7,10-tetraazacyclododec-1-yl]acetyl]amino]-glycyl-glycyl-4-aminobenzoyl-L-glutaminyl-L-tryptophyl-L-alanyl-L-valyl-glycyl-L-histidyl-L-leucyl-L-methioninamide L211.

Figure 32:
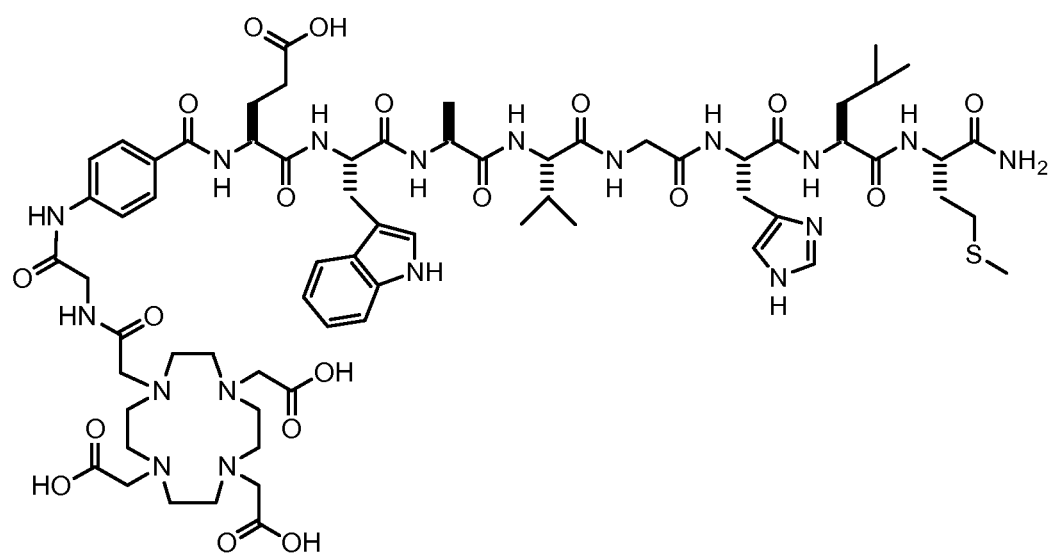

FIG. 32 is a chemical structure of N—[(3β,5β,12α)-3-[[[4,7,10-Tris(carboxymethyl)-1,4,7,10-tetraazacyclododec-1-yl]acetyl]amino]-glycyl-4-aminobenzoyl-L-glutamyl-L-tryptophyl-L-alanyl-L-valyl-glycyl-L-histidyl-L-leucyl-L-methioninamide L212.

Figure 33:
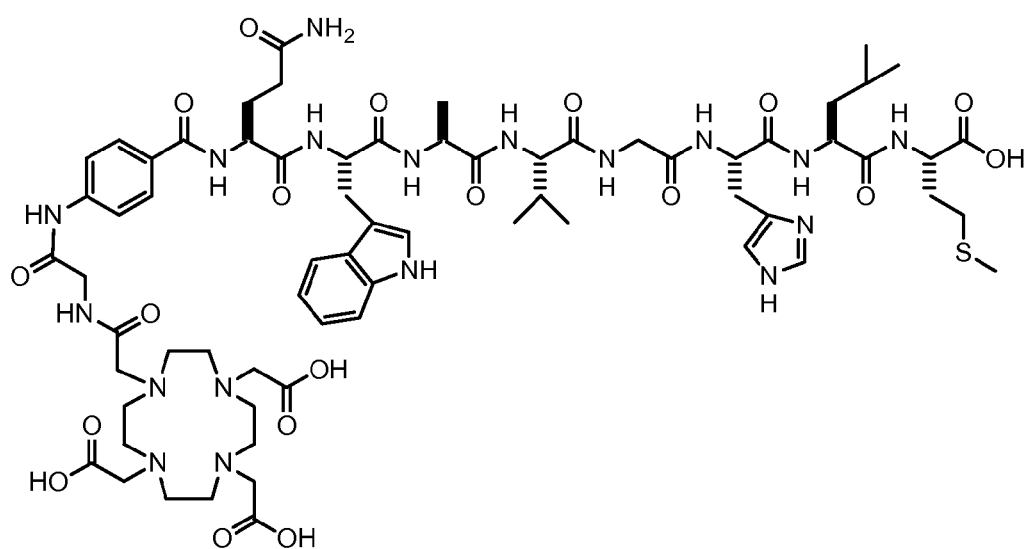

FIG. 33 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-L-glutaminyl-L-tryptophyl-L-alanyl-L-valyl-glycyl-L-histidyl-L-leucyl-L-methionine carboxylate L213.

Figure 34:
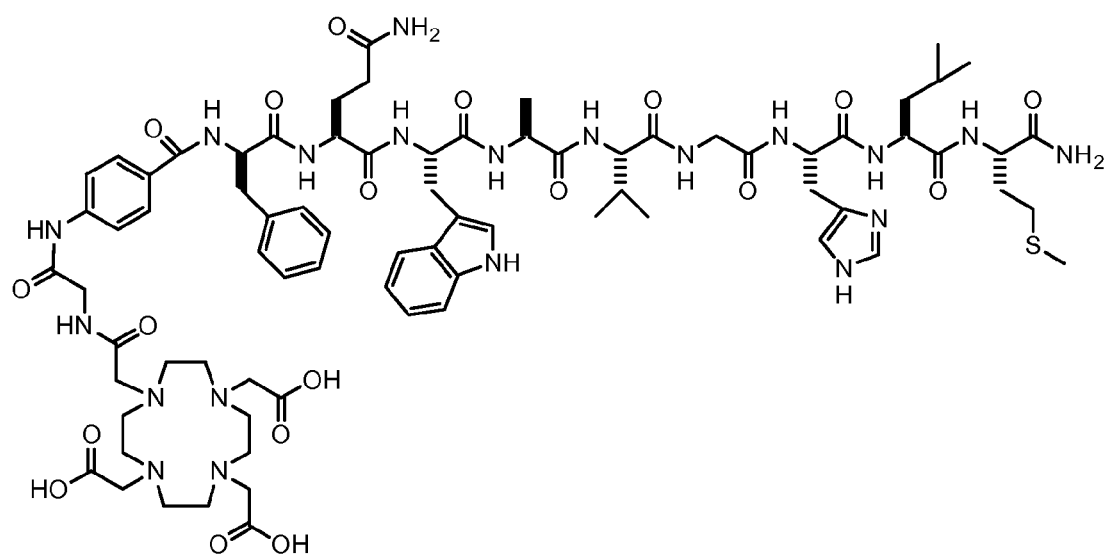

FIG. 34 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-D-phenylalanyl-L-glutaminyl-L-tryptophyl-L-alanyl-L-valyl-glycyl-L-histidyl-L-leucyl-L-methioninamide L214.

Figure 35:
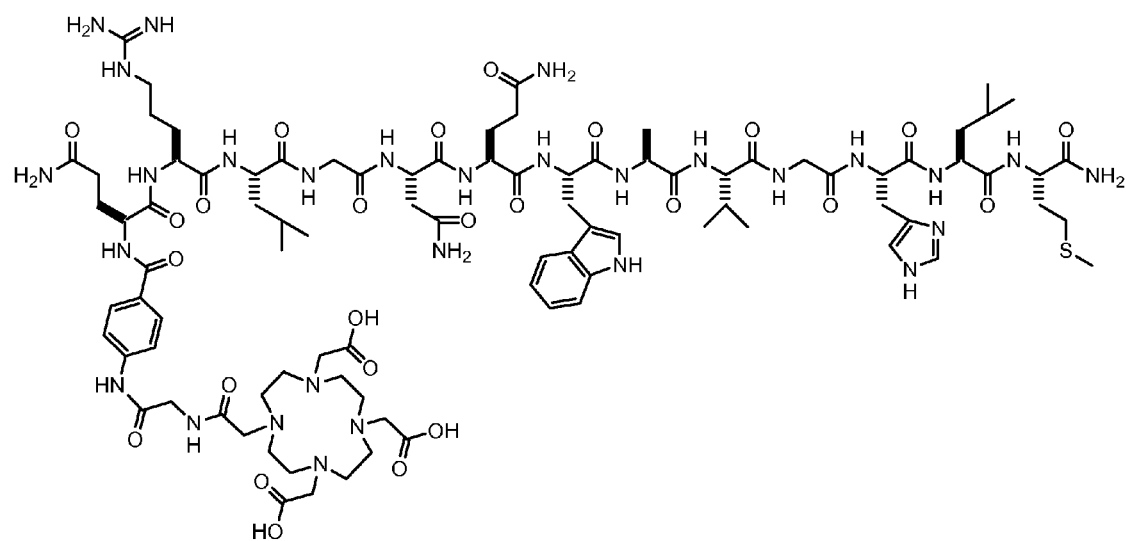

FIG. 35 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-L-glutaminyl-L-arginyl-L-leucyl-glycyl-L-asparginyl-L-glutaminyl-L-tryptophyl-L-alanyl-L-valyl-glycyl-L-histidyl-L-leucyl-L-methioninamide L215.

Figure 36:
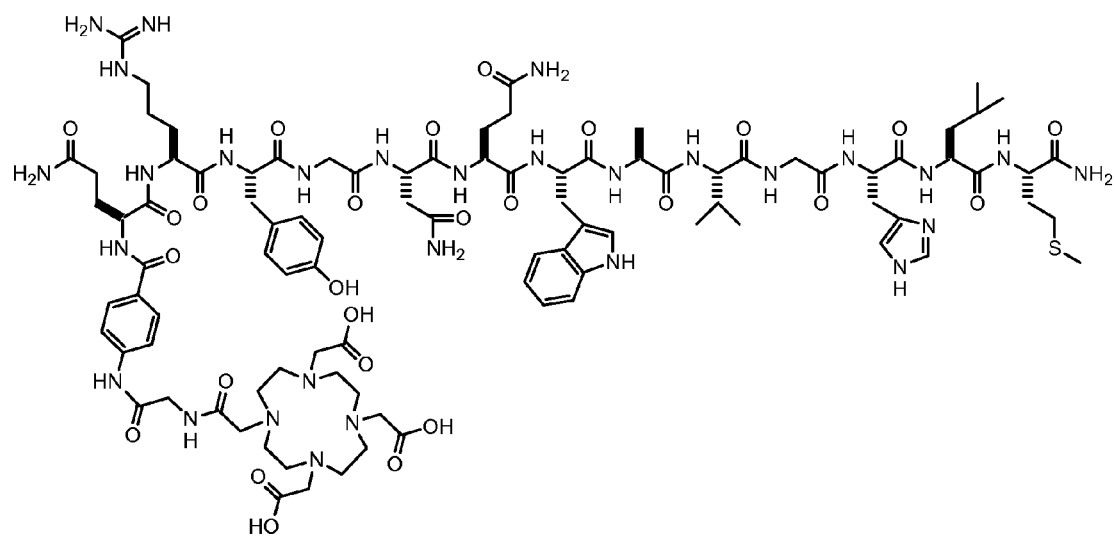

FIG. 36 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-L-glutaminyl-arginyl-L-tyrosinyl-glycyl-L-asparginyl-L-glutaminyl-L-tryptophyl-L-alanyl-L-valyl-glycyl-L-histidyl-L-leucyl-L-methioninamide L216.

Figure 37:
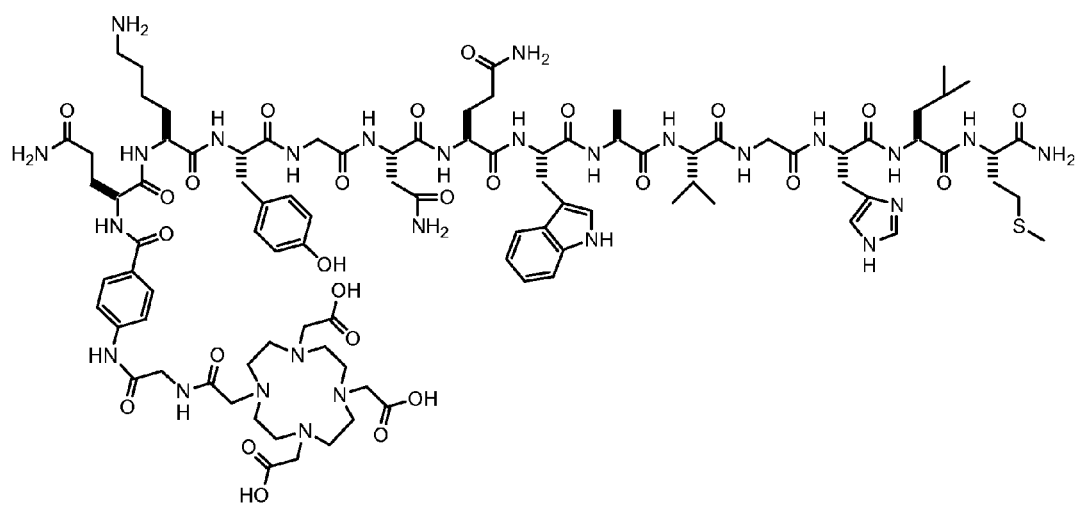

FIG. 37 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-L-glutaminyl-L-lysyl-L-tyrosinyl-glycyl-L-glutaminyl-L-tryptophyl-L-alanyl-L-valyl-glycyl-L-histidyl-L-leucyl-L-methioninamide L217.

Figure 38:
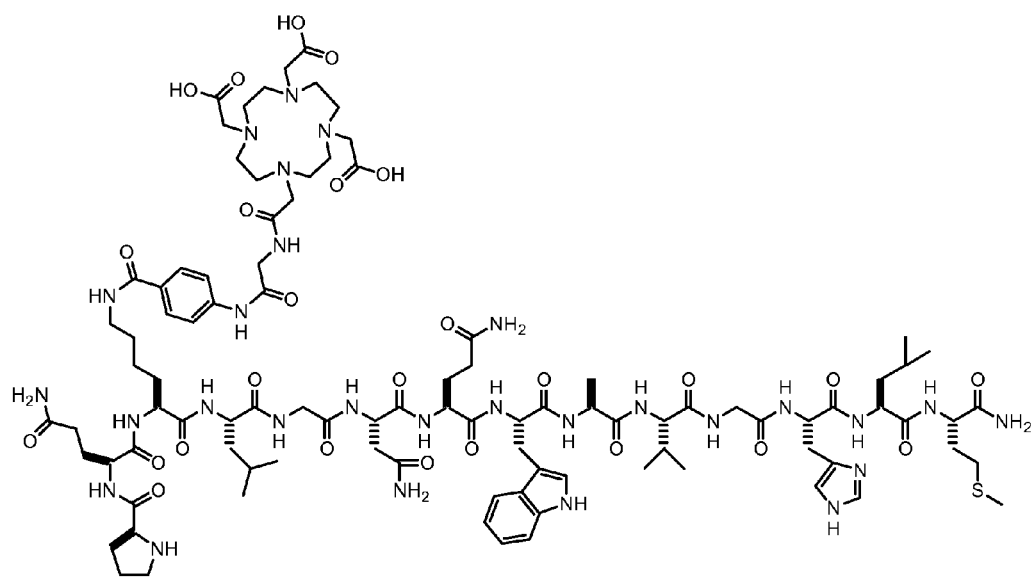

FIG. 38 is a chemical structure of L218.

Figure 39:
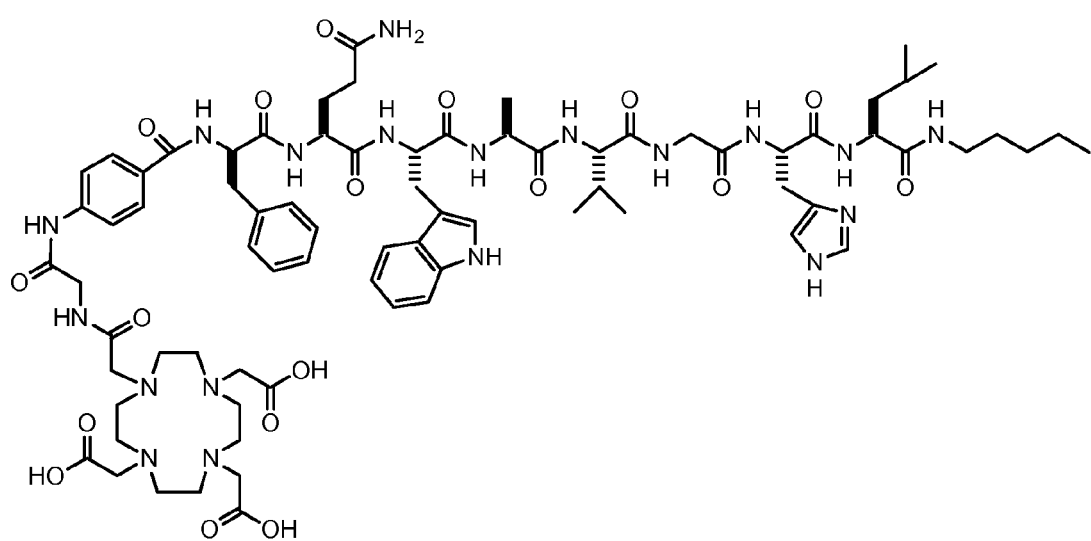

FIG. 39 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-D-phenylalanyl-L-glutaminyl-L-tryptophyl-L-alanyl-L-valyl-glycyl-L-histidyl-L-leucyl-aminopentyl, L219.

Figure 40:
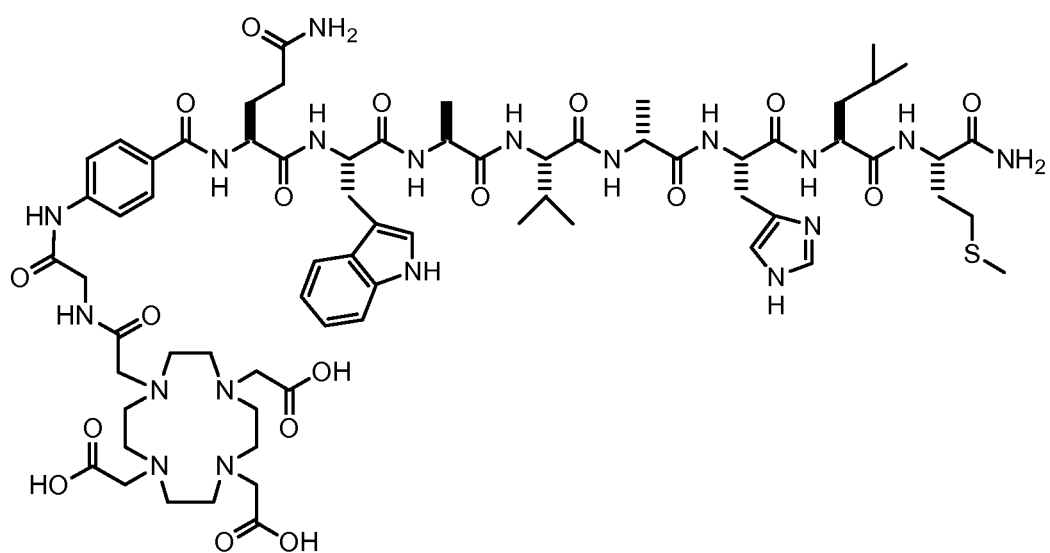

FIG. 40 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-L-glutaminyl-L-tryptophyl-L-serinyl-L-valyl-D-alanyl-L-histidyl-L-leucyl-L-methioninamide, L220.

Figure 41:
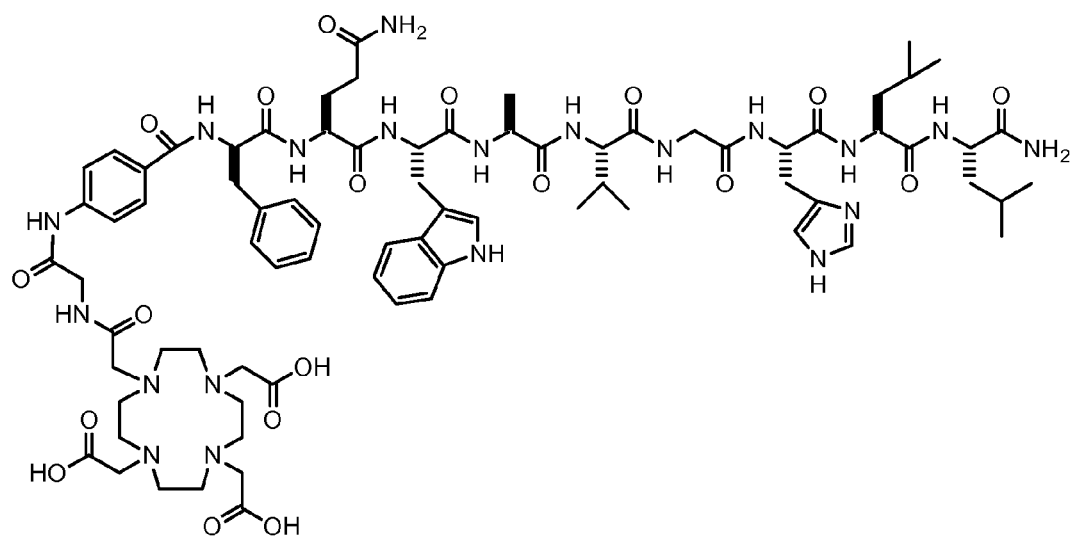

FIG. 41 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-D-phenylalanyl-L-glutaminyl-L-tryptophyl-L-alanyl-L-valyl-glycyl-L-histidyl-L-leucyl-L-leucinamide, L221.

Figure 42:
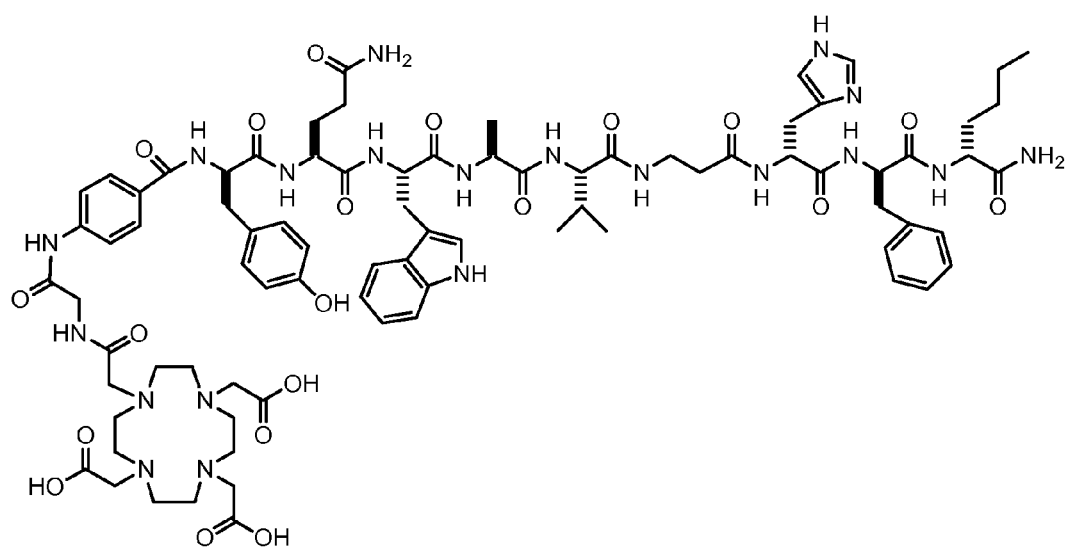

FIG. 42 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-D-tyrosinyl-L-glutaminyl-L-tryptophyl-L-alanyl-L-valyl-betaalanyl-L-histidyl-L-phenylalanyl-L-norleucinamide, L222.

Figure 43:
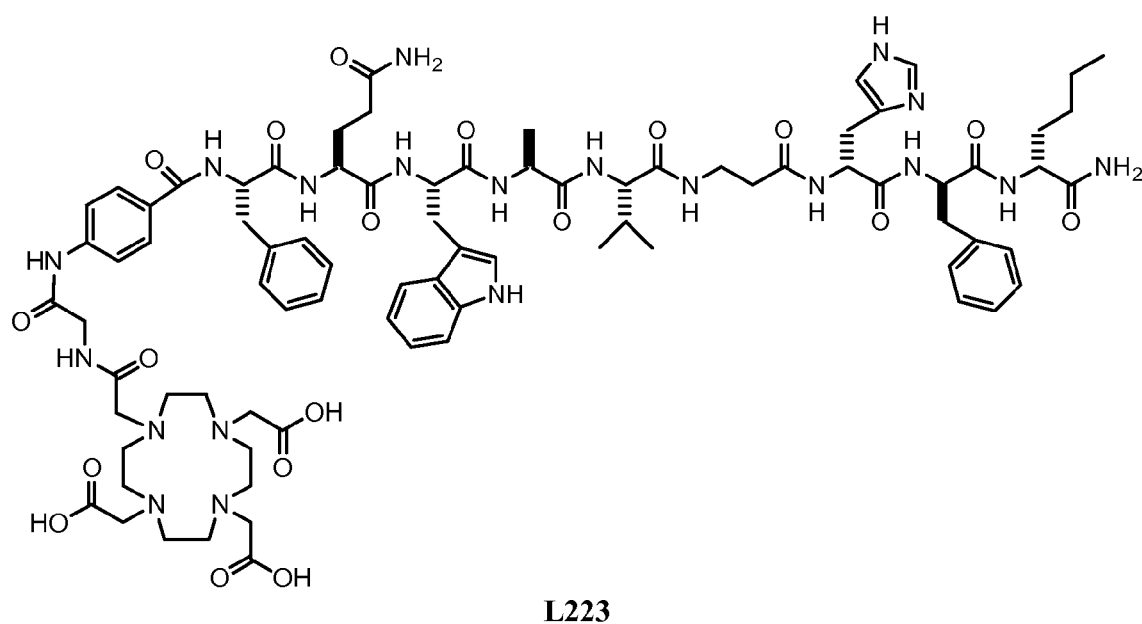

FIG. 43 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-L-phenylalanyl-L-glutaminyl-L-tryptophyl-L-alanyl-L-valyl-betaalanyl-L-histidyl-L-phenylalanyl-L-norleucinamide, L223.

Figure 44:
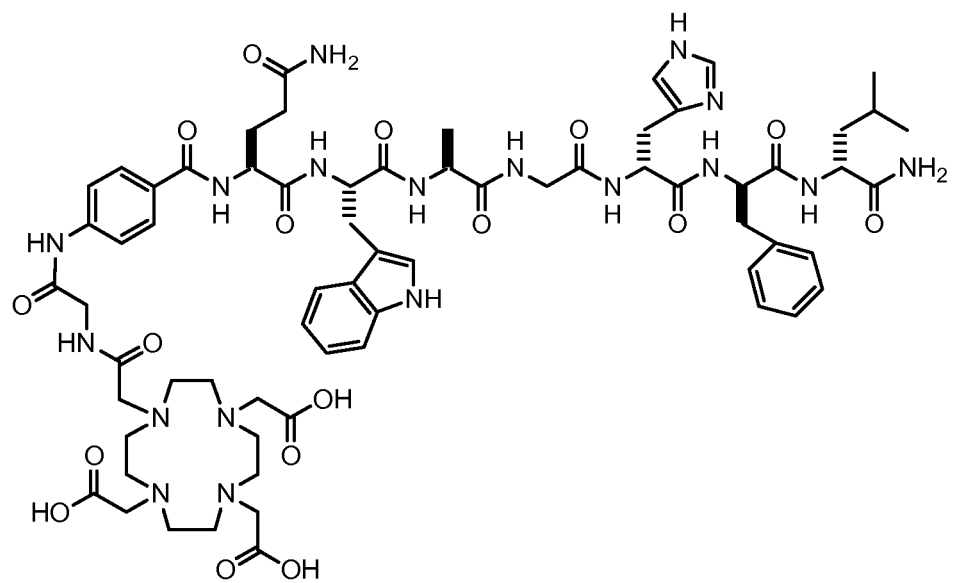

FIG. 44 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-L-glutaminyl-L-tryptophyl-L-alanyl-glycyl-L-histidyl-L-phenylalanyl-L-leucinamide, L224.

Figure 45:
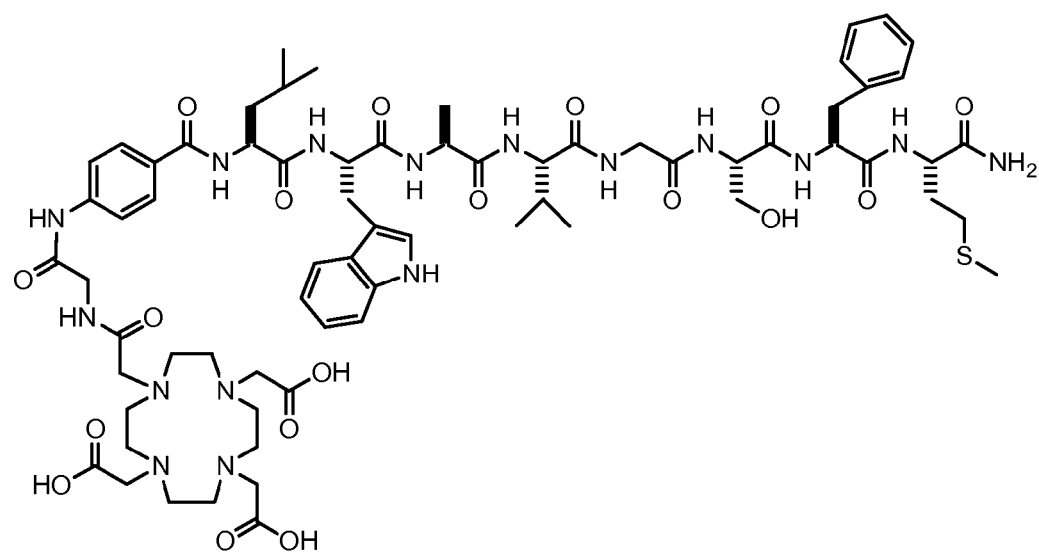

FIG. 45 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-L-leucyl-L-tryptophyl-L-alanyl-L-valinyl-glycyl-L-serinyl-L-phenylalanyl-L-methioninamide, L225.

Figure 46:
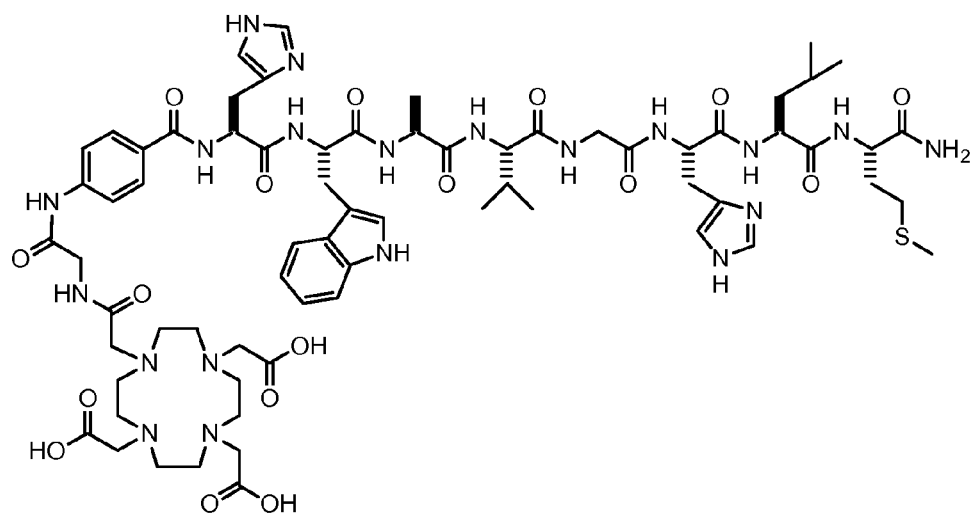

FIG. 46 is a chemical structure of N-[(3β,5β,12α)-3-[[[4,7,10-Tris(carboxymethyl)-1,4,7,10-tetraazacyclododec-1-yl]acetyl]amino]-glycyl-4-aminobenzoyl-L-histidyl-L-tryptophyl-L-alanyl-L-valyl-glycyl-L-histidyl-L-leucyl-L-methioninamide, L226.

Figure 47:
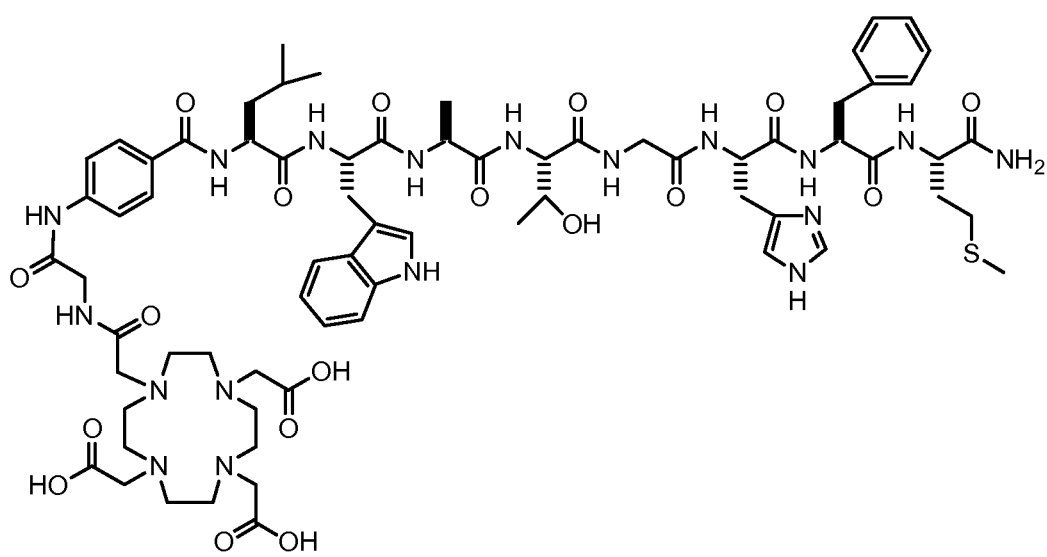

FIG. 47 is a chemical structure of N-[(3β,5β,12α)-3-[[[4, 7,10-Tris(carboxymethyl)-1,4,7,10-tetraazacyclododec-1-yl]acetyl]amino]-glycyl-4-aminobenzoyl-L-leucyl-L-tryptophyl-L-alanyl-L-valyl-glycyl-L-serinyl-L-phenylalanyl-L-methioninamide L227.

Figure 48:
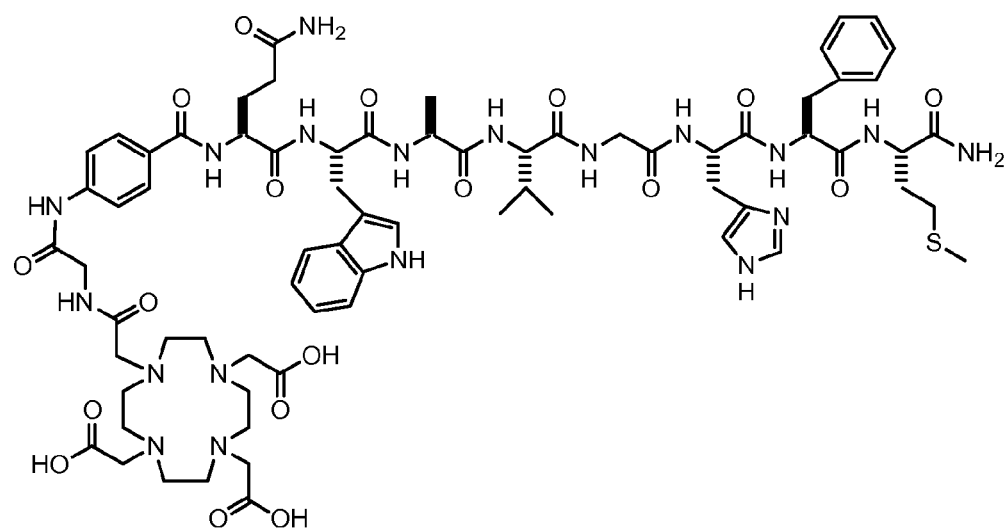

FIG. 48 is a chemical structure of N-[(3β,5β,12α)-3-[[[4, 7,10-Tris(carboxymethyl)-1,4,7,10-tetraazacyclododec-1-yl]acetyl]amino]-glycyl-4-aminobenzoyl-L-glutaminyl-L-tryptophyl-L-alanyl-L-valyl-glycyl-L-histidyl-L-phenylalanyl-L-methioninamide, L228.

Figure 49A:
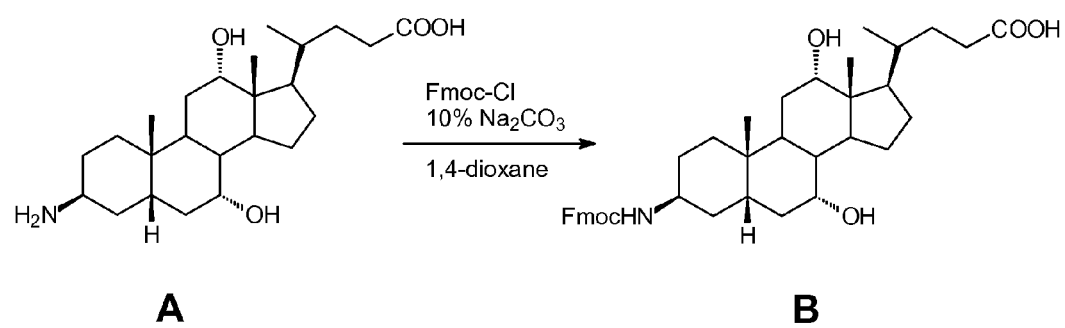

FIG. 49A is a graphical representation of a reaction for the synthesis of (3β,5β,7α,12α)-3-(9H-Fluoren-9-ylmethoxy) amino-7,12-dihydroxycholan-24-oic acid (B) as described in Example LVII.

Figure 49B:
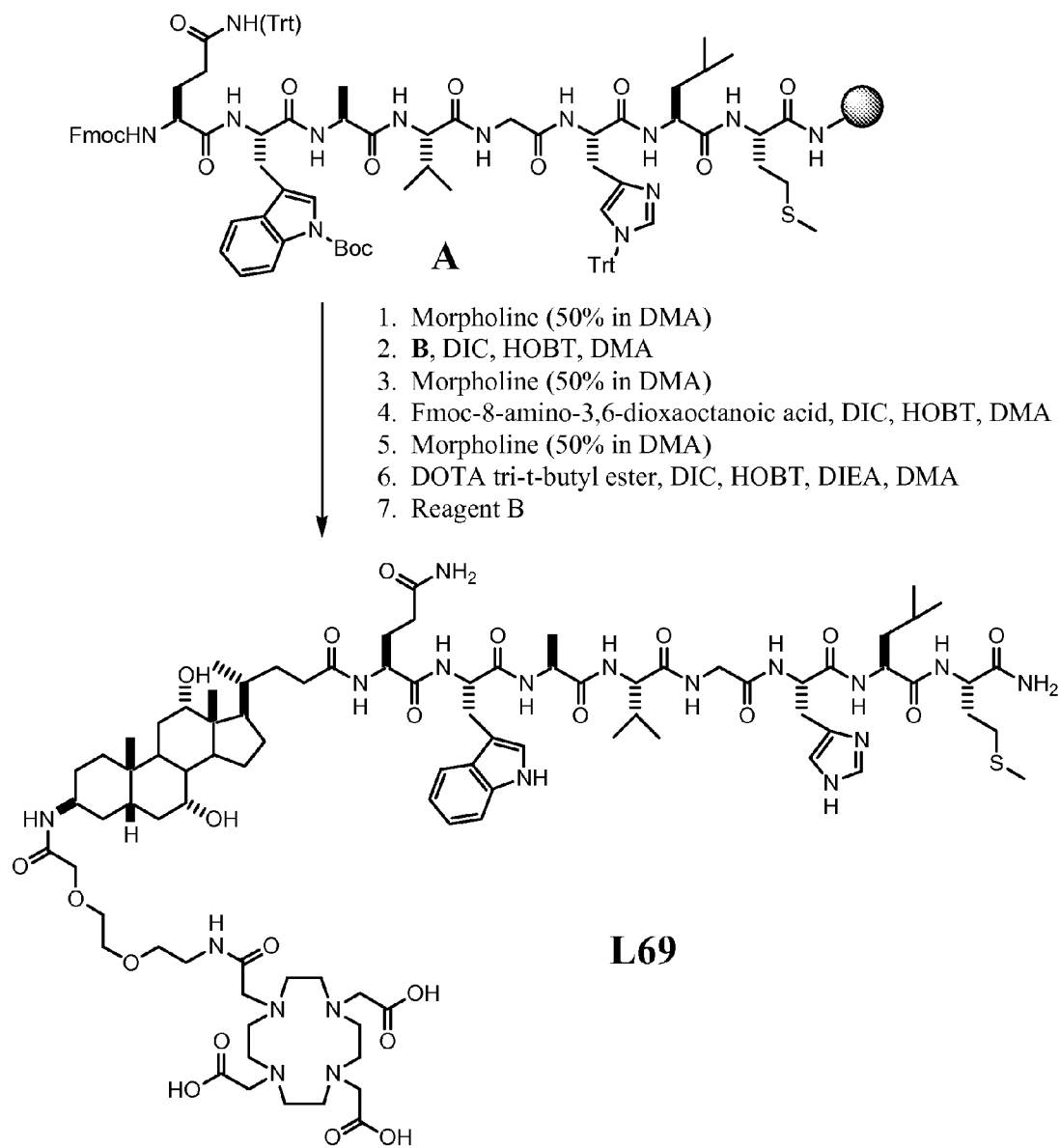

FIG. 49B is a graphical representation of a reaction for the synthesis of N-[(3β,5β,7α,12α)-3-[[[2-[2-[[[4,7,10-Tris(carboxymethyl)-1,4,7,10-tetraazacyclododec-1-yl]acetyl] amino]ethoxy]ethoxy]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide, (L69), as described in Example LVII.

Figure 50:
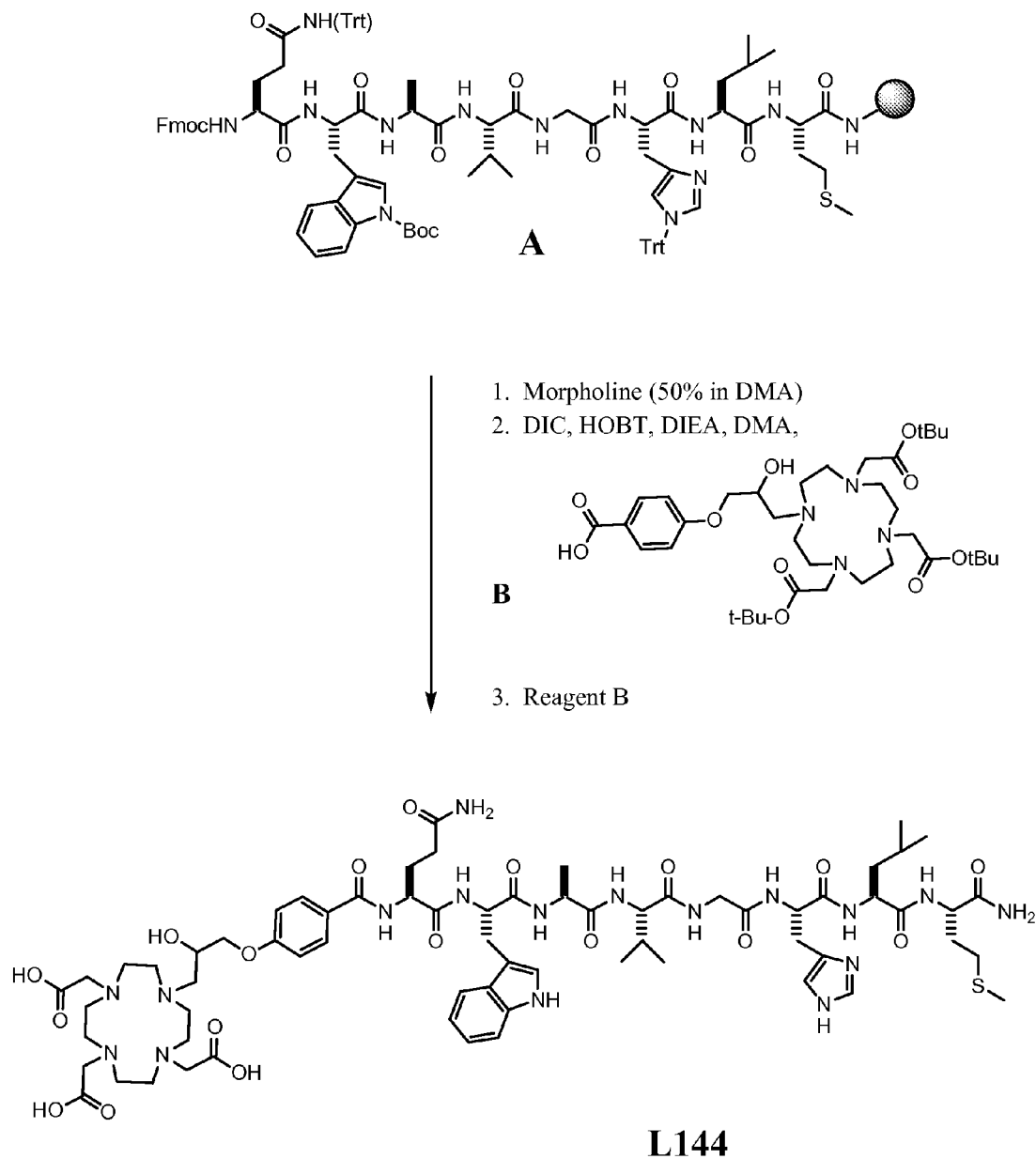

FIG. 50 is a graphical representation of a reaction for the synthesis of N-[4-[2-Hydroxy-3-[4,7,10-tris(carboxymethyl)-1,4,7,10-tetraazacyclododec-1-yl]propoxy]benzoyl]-L-glutaminyl-L-tryptophyl-L-alanyl-L-valyl-glycyl-L-histidyl-L-leucyl-L-methioninamide (L144), as described in Example LVIII.

Figure 51:
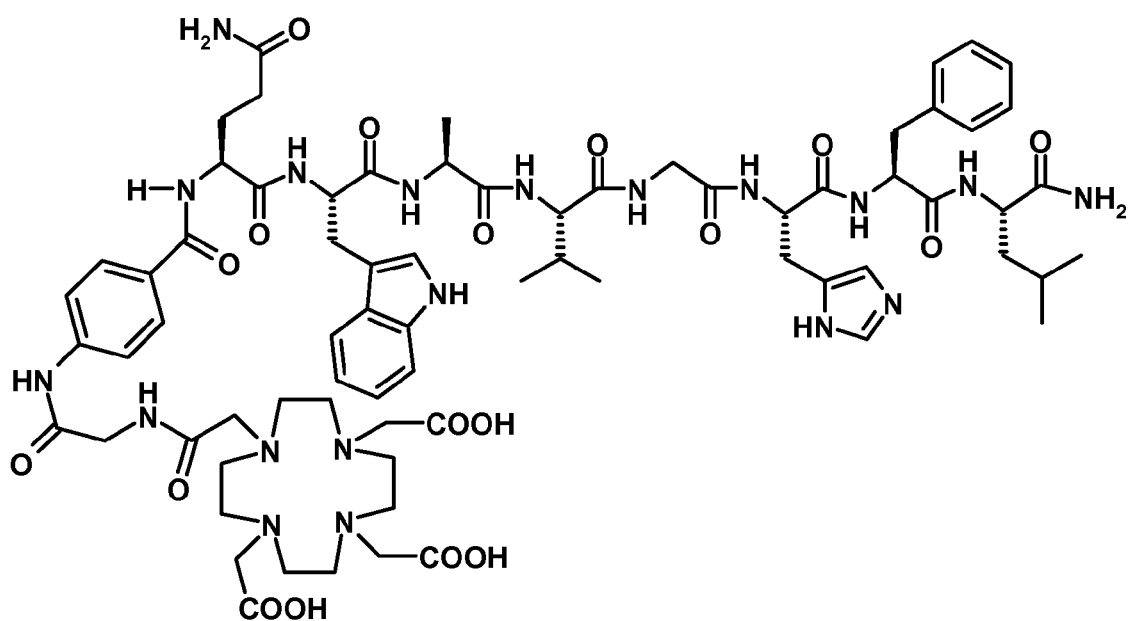

FIG. 51 is a chemical structure of L300.

Figure 52:
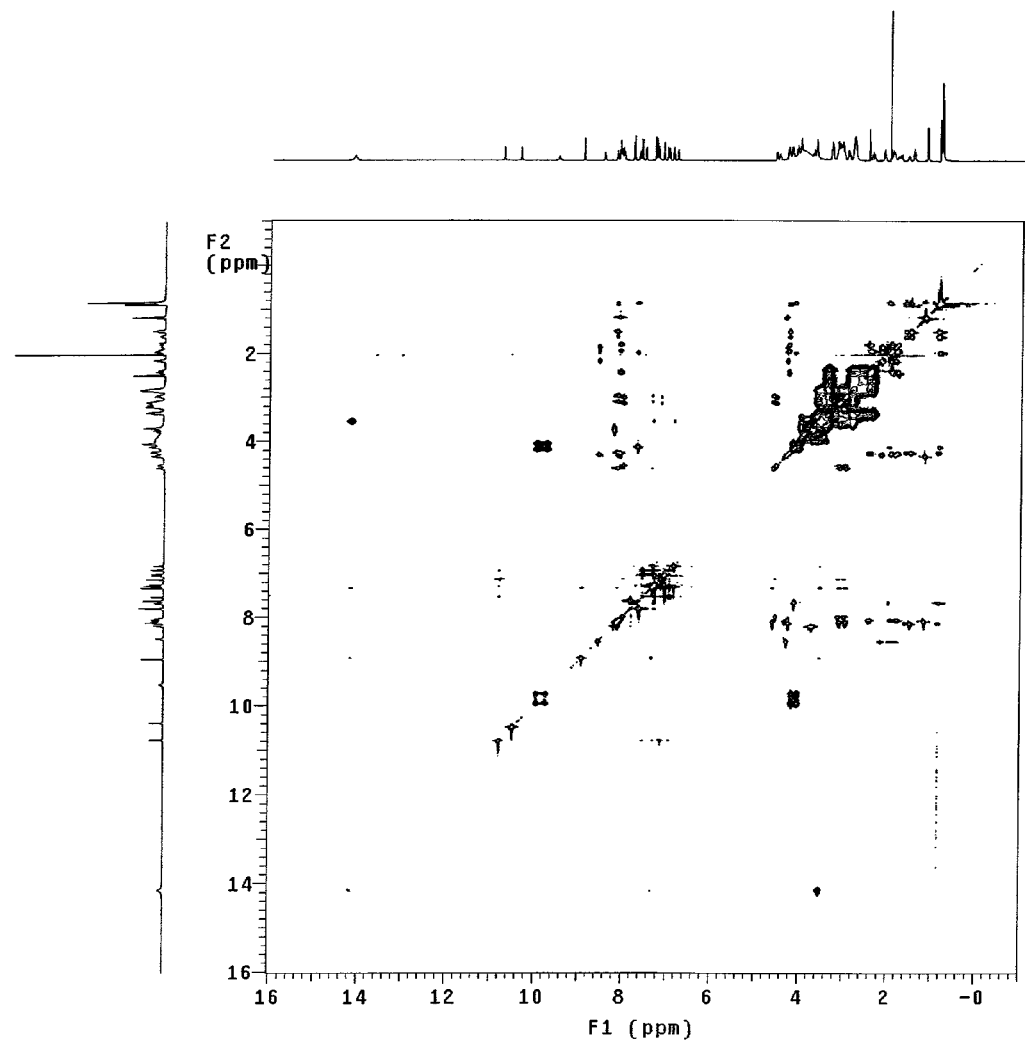

FIG. 52 is a TOCSY spectrum of Lu-L70 in DMSO-$d_6$ at 25° C.

Figure 53:
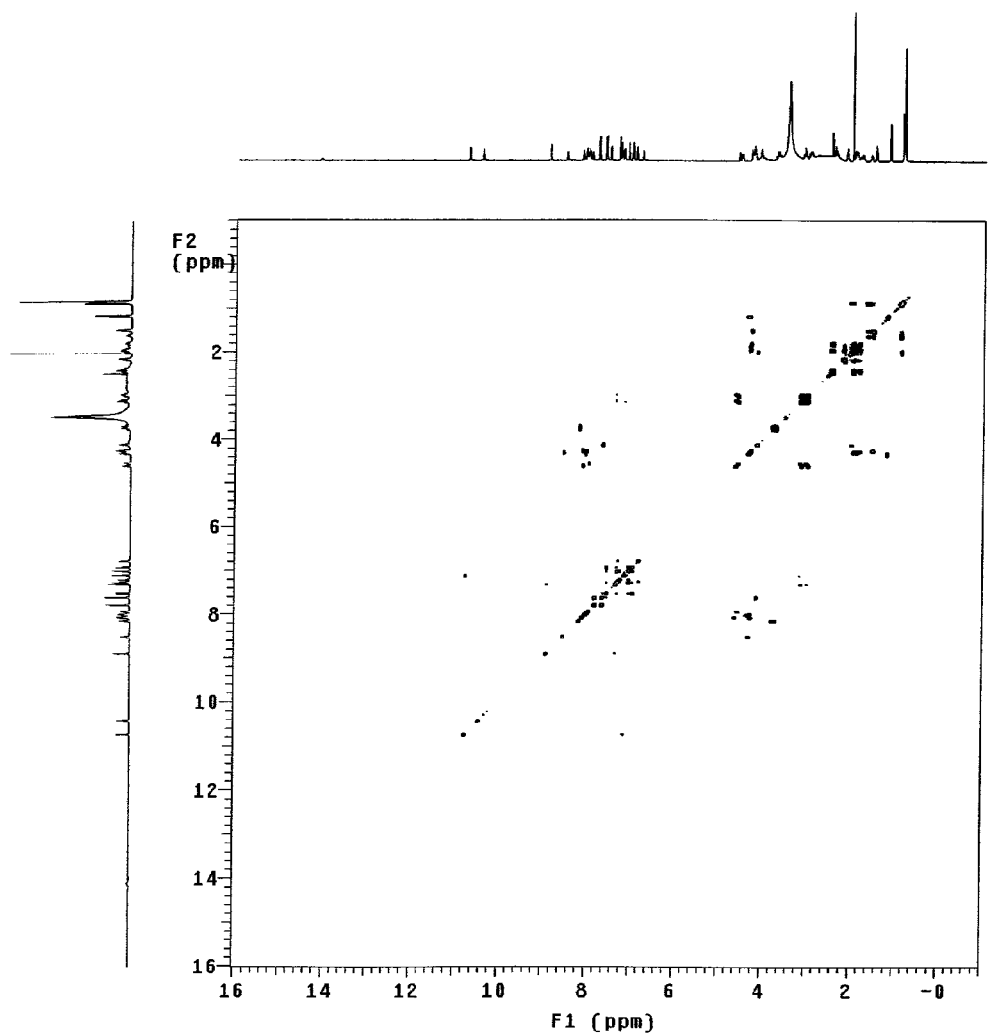

FIG. 53 is a COSY spectrum of Lu-L70 in DMSO-$d_6$ at 25° C.

Figure 54:
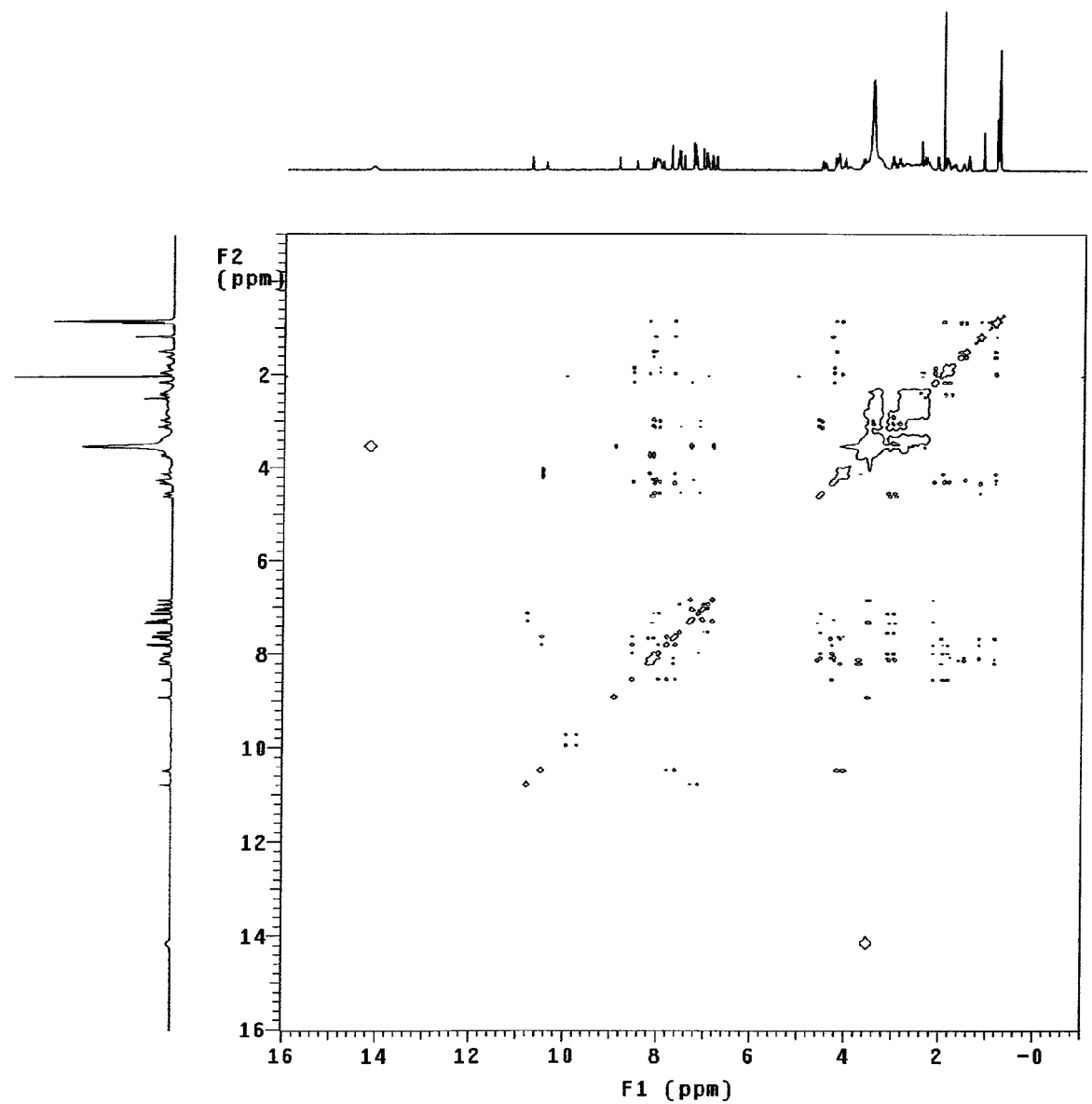

FIG. 54 is a NOESY spectrum of Lu-L70 in DMSO-$d_6$ at 25° C.

Figure 55:
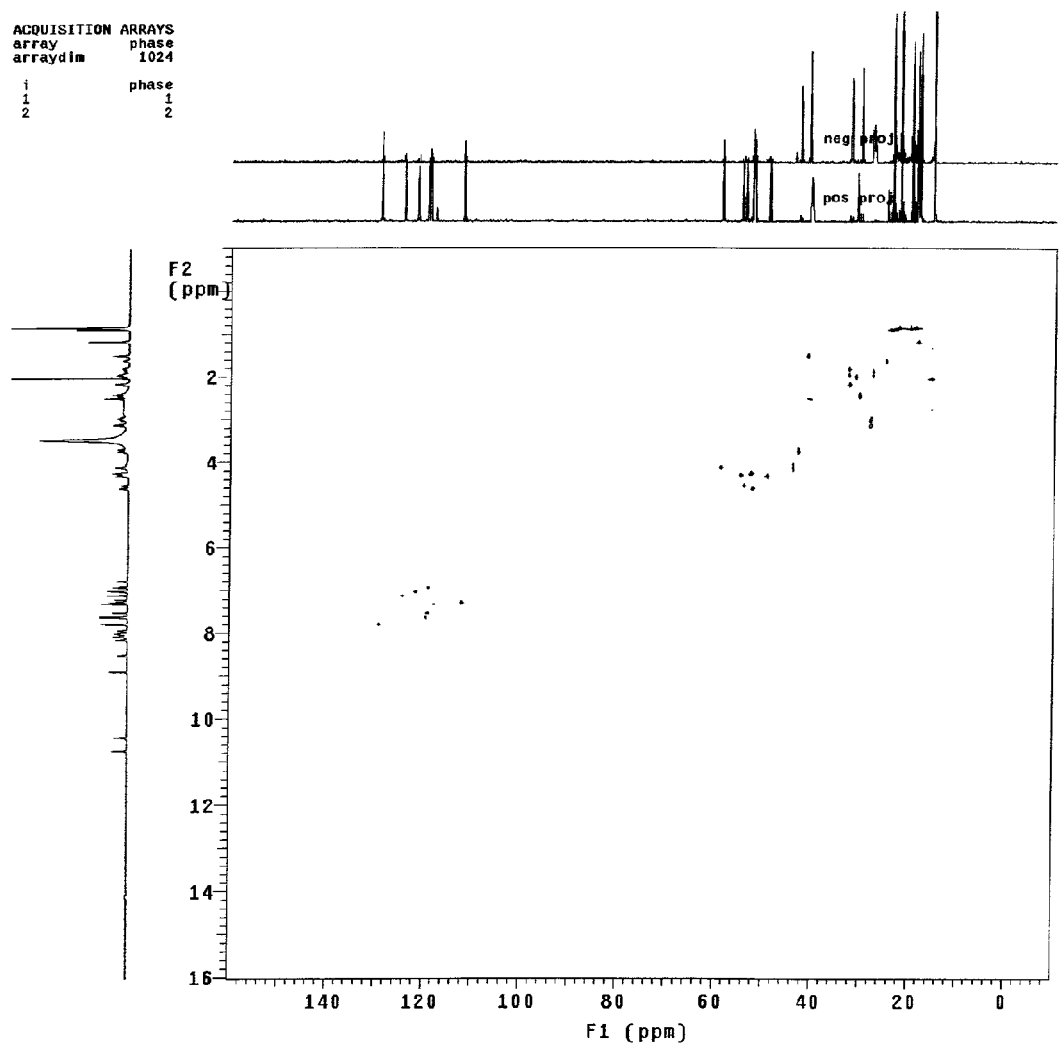

FIG. 55 is a gHSQC spectrum of Lu-L70 in DMSO-$d_6$ at 25° C.

Figure 56:
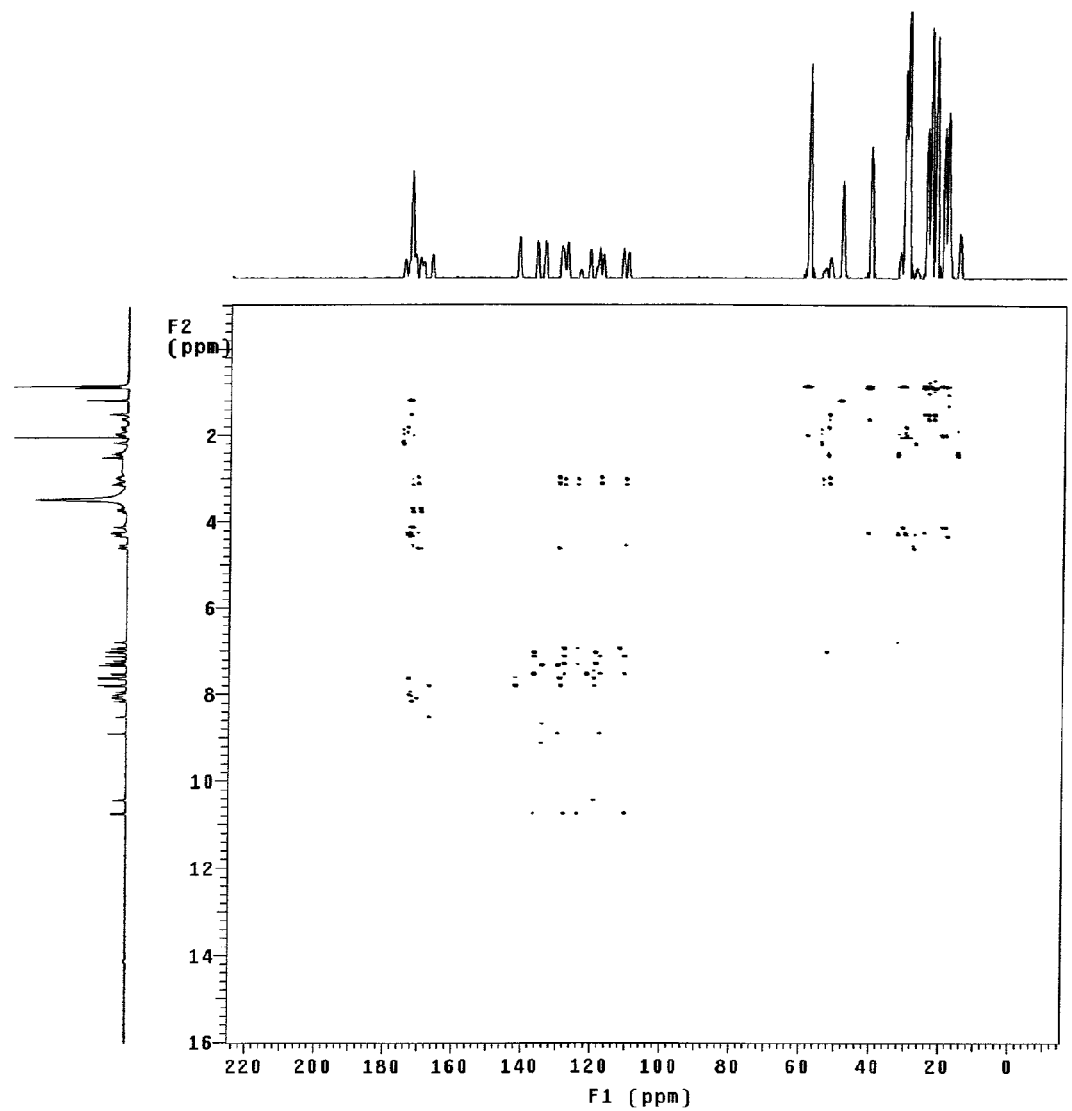

FIG. 56 is a gHMBC spectrum of Lu-L70 in DMSO-$d_6$ at 25° C.

Figure 57:
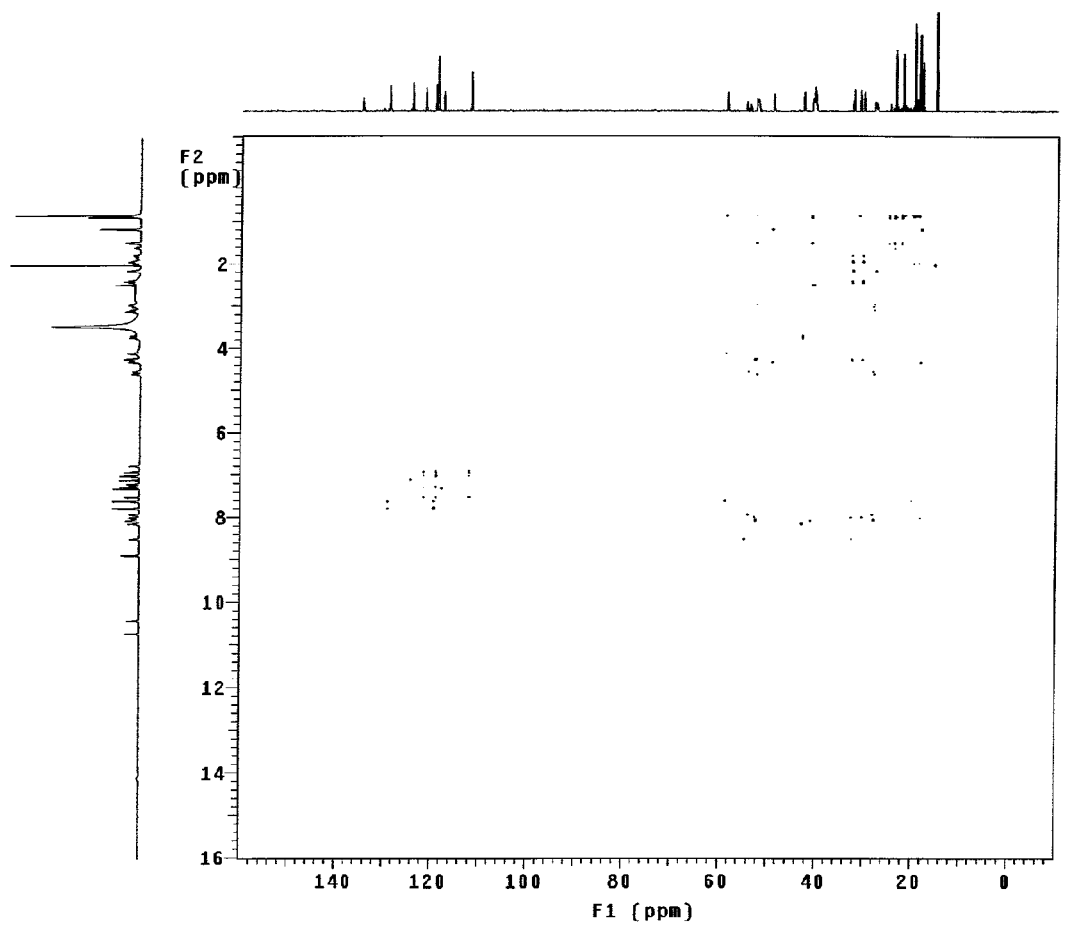

FIG. 57 is a gHSQCTOCSY spectrum of Lu-L70 in DMSO-$d_6$ at 25° C.

Figure 58:
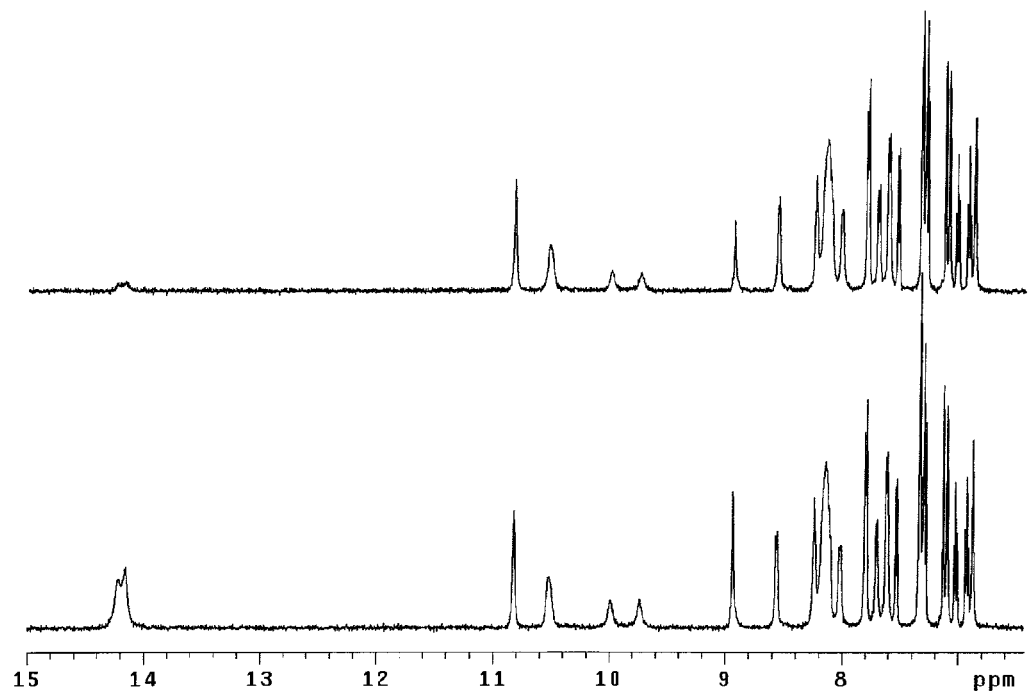

FIG. 58 is a Regular 1H-NMR (bottom) and selective homo-decoupling of the water peak at 3.5 ppm of Lu-L70 in DMSO-$d_6$ at 15° C.

Figure 59:
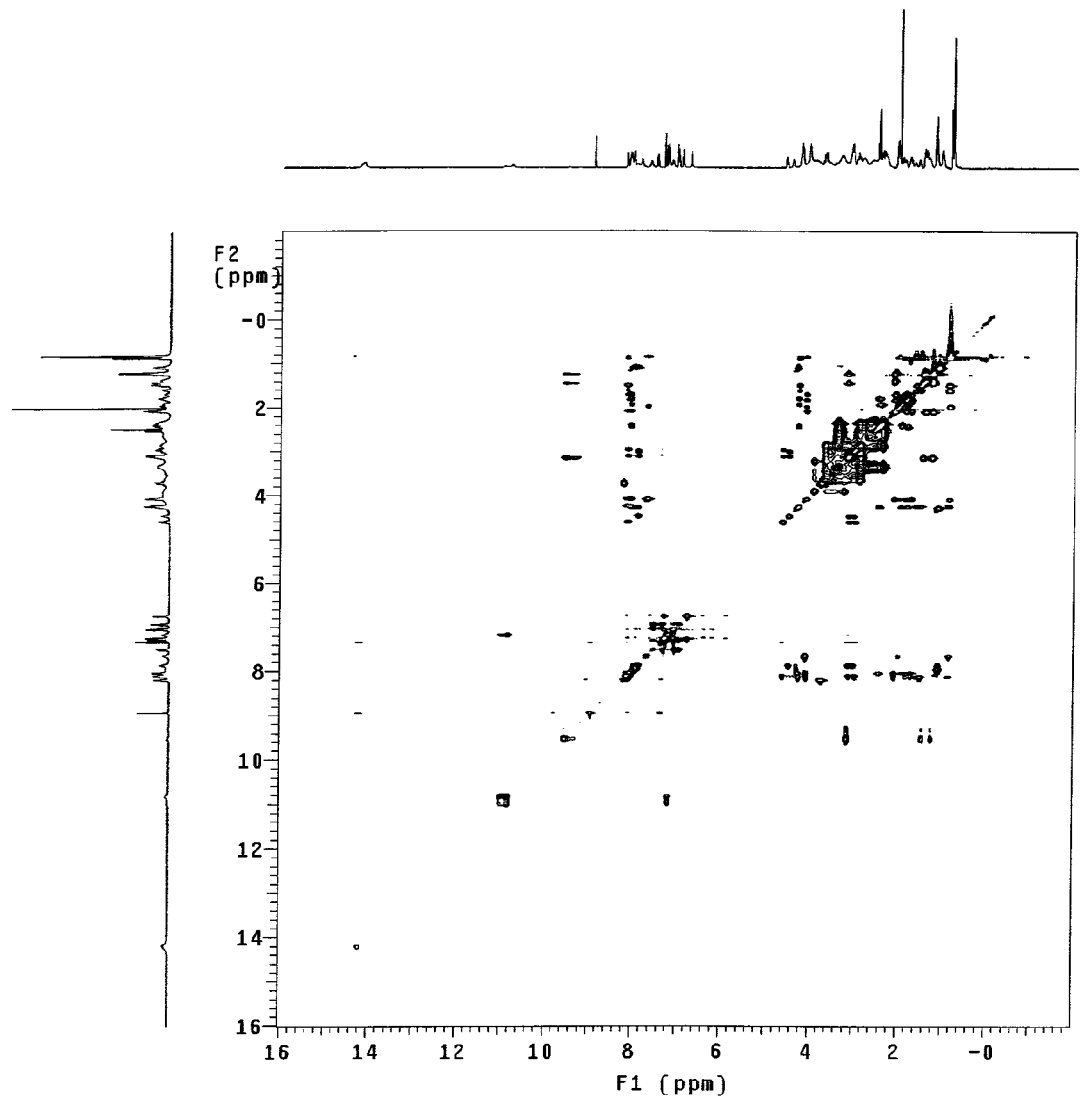

FIG. 59 is a TOCSY Spectrum of $^{175}$Lu-DO3A-monoamide-Aoc-QWAVGHLM-NH$_2$ in DMSO-$d_6$ at 25° C.

Figure 60:
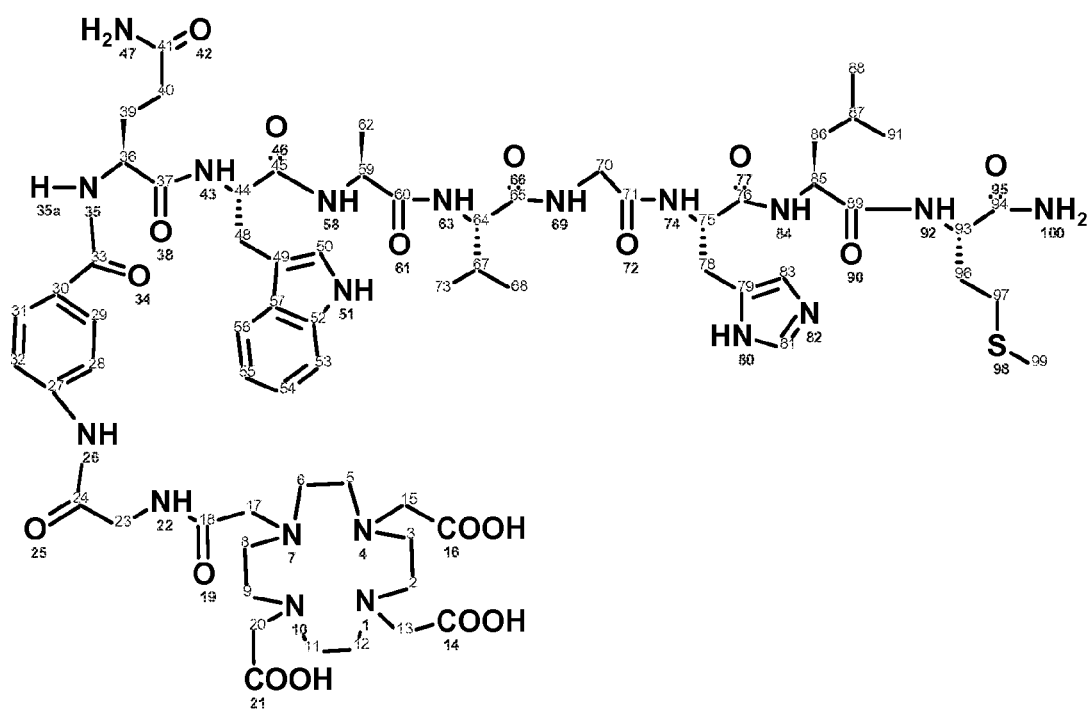

FIG. 60 is a chemical structure of L70.

Figure 61:
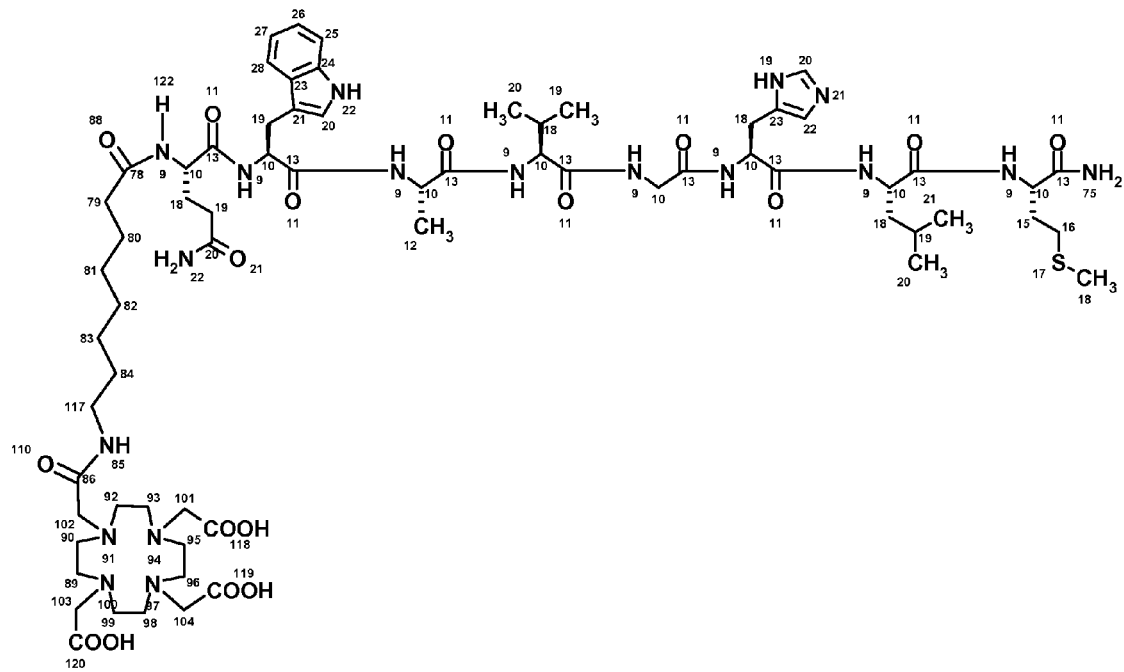

FIG. 61 is a chemical structure of $^{175}$Lu-DO3A-monoamide-Aoc-QWAVGHLM-NH$_2$.

Figure 62:
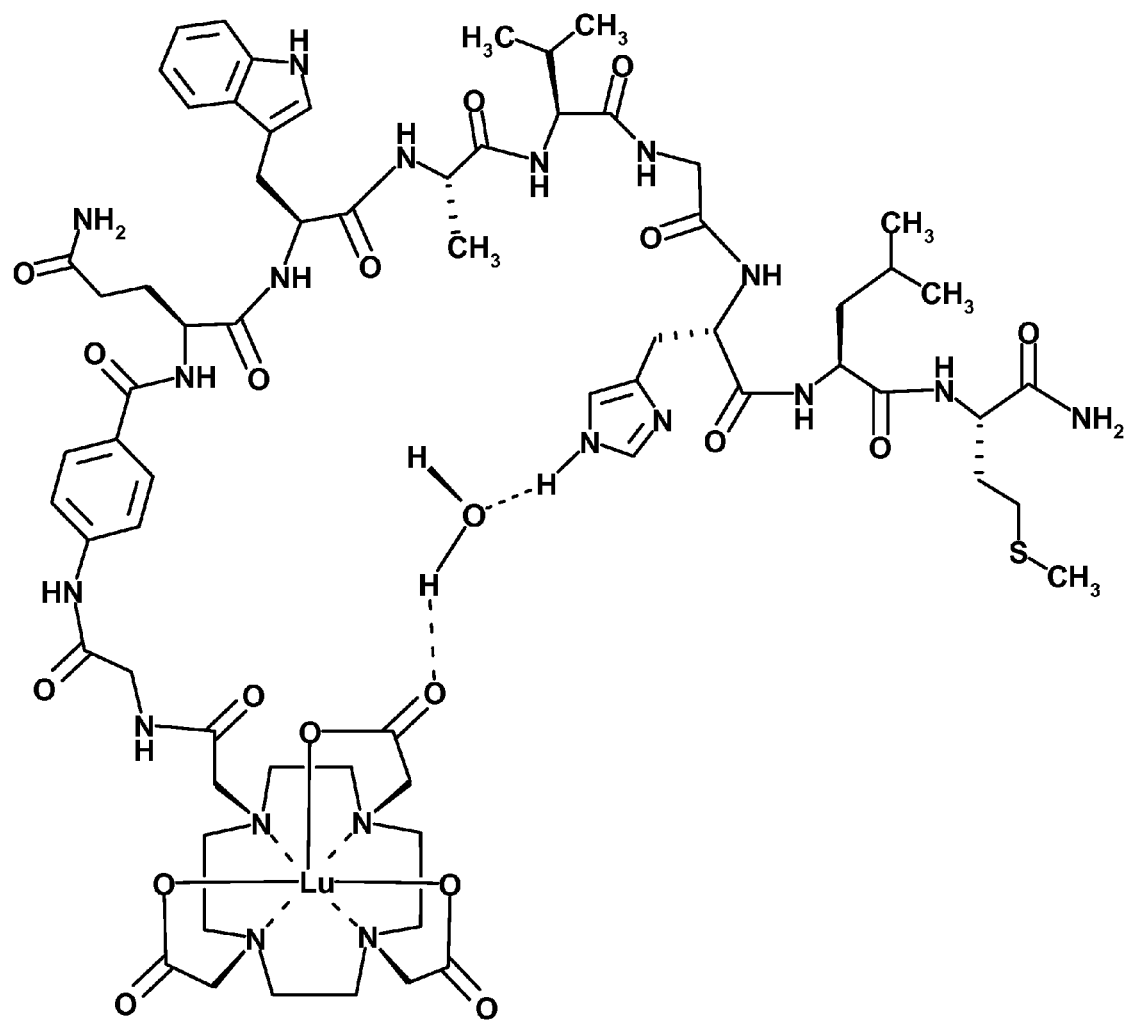

FIG. 62 is a chemical structure of $^{175}$Lu-L70 with a bound water molecule.

Figure 63:
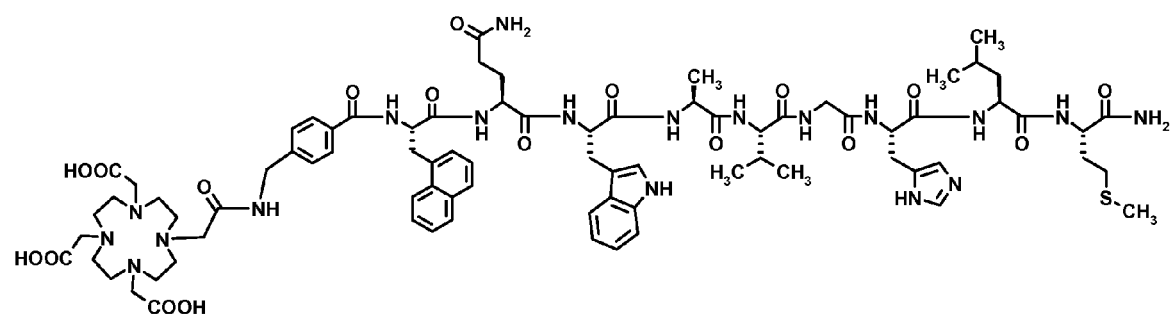

FIG. 63 is a chemical structure of L301.

Figure 64:
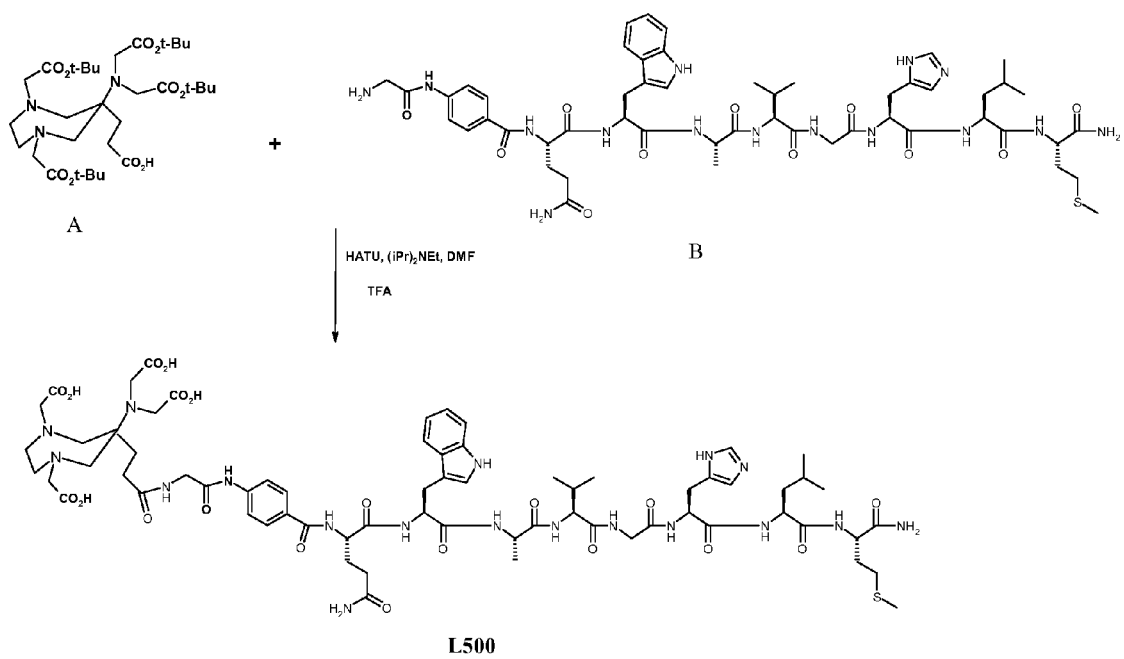

FIG. 64 is a graphical representation of the preparation of L500 as described in Example LXII.

Figure 65:
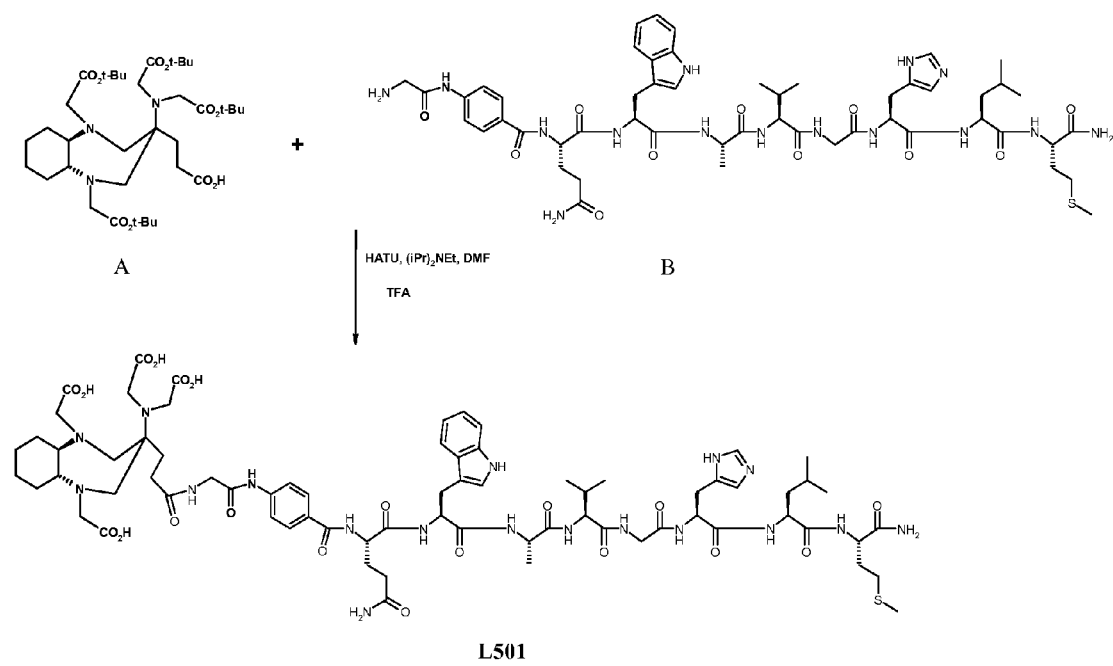

FIG. 65 is a graphical representation of the preparation of L501 as described in Example LXIII.

Figure 66:
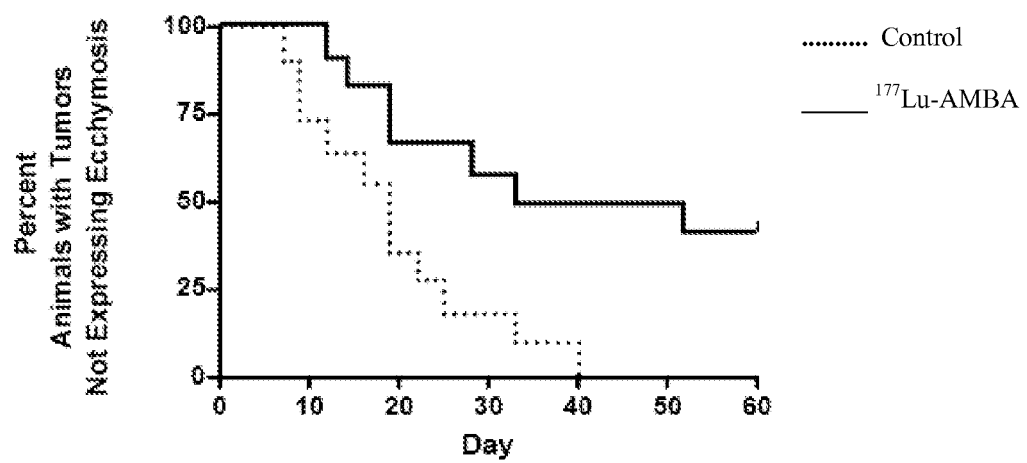

FIG. 66 is a graphical representation of occurrence of ecchymosis in control and $^{177}$Lu-AMBA ($^{177}$Lu-L70) treated mice over time.

Figure 67:
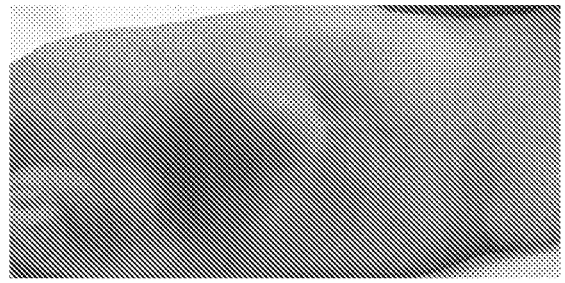

FIG. 67 is a photograph of a control group mouse from an experiment determining the occurrence of ecchymosis in control and $^{177}$Lu-AMBA ($^{177}$Lu-L70) treated mice over time.

Figure 68:
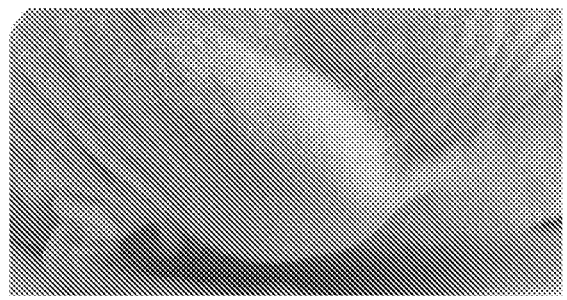

FIG. 68 is a photograph of an experimental group mouse from an experiment determining the occurrence of ecchymosis in control and $^{177}$Lu-AMBA ($^{177}$Lu-L70) treated mice over time.

Figure 69:
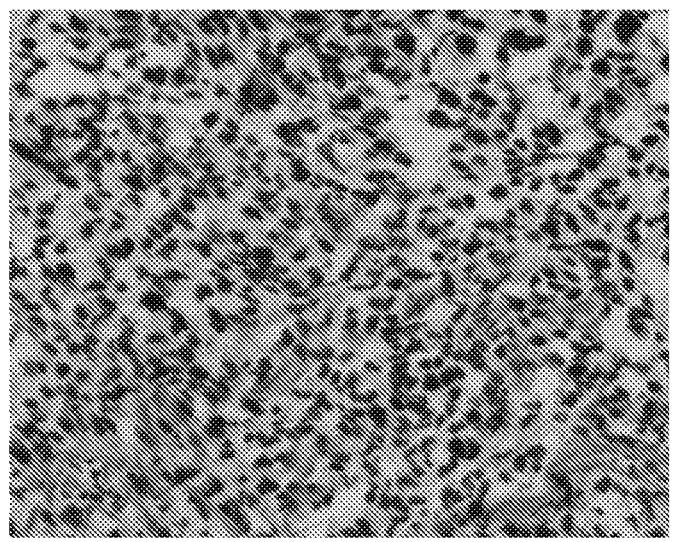

FIG. 69 is a photograph of anti-human Ki67 immunohistochemical staining of the DU145 radiotherapy control group xenograft at 400× magnification.

Figure 70:
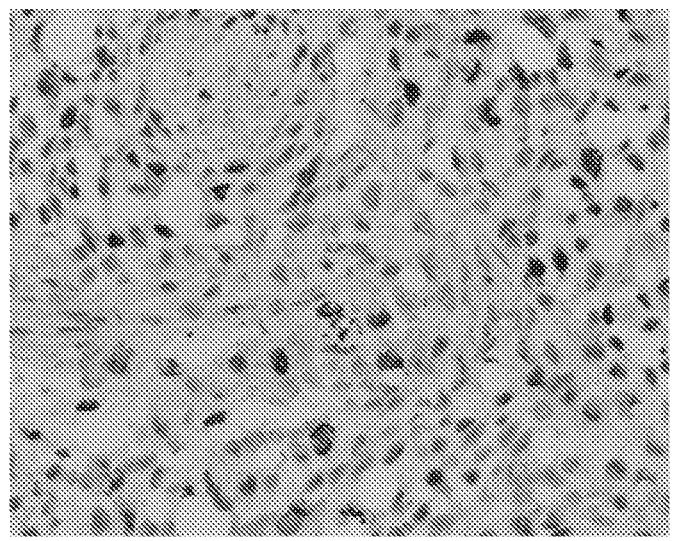

FIG. 70 is a photograph of anti-human Ki67 immunohistochemical staining of the DU145 radiotherapy treated group xenograft at 400× magnification.

ABBREVIATIONS USED IN THE APPLICATION

| | |
|---|---|
| Aazta | 1,4-Bis(carboxymethyl)-6-[bis(carboxymethyl)amino]-6-methyl-perhydro-1,4-diazepine |
| CyAazta | 2-{[(1S,7S)-2,6-diaza-2,6-bis(carboxymethyl)-4-methylbicyclo[5.4.0]undec-4-yl]carboxymethyl)amino}acetic acid |
| Aoc- | 8-aminooctanoic acid |
| Apa3- | 3-aminopropionic acid |
| Abu4- | 4-aminobutanoic acid |
| Adca3- | (3β,5β 7α,12α)-3-amino-7,12-dihydroxycholan-24-oic acid or 3-Amino-3-deoxycholic acid |
| Ah12ca- | (3β,5β,12α)-3-amino-12-hydroxycholan-24-oic acid |
| Akca- | (3β,5β,7α,12α)-3-amino-12-oxacholan-24-oic acid |
| Cha- | L-Cyclohexylalanine |
| Nal1- | L-1-Naphthylalanine |
| Bip- | L-Biphenylalanine |
| Mo3abz4- | 3-Methoxy-4-aminobenzoic acid or 4-aminomethyl-3-methoxybenzoic acid |
| Bpa4- | 4-benzoylphenylalanine |
| Cl3abz4- | 3-Chloro-4-aminobenzoic acid |
| M3abz4- | 3-methyl-4-aminobenzoic acid |
| Ho3abz4- | 3-hydroxy-4-aminobenzoic acid |
| Hybz4- | 4-hydrazinobenzoic acid |
| Nmabz4- | 4-methylaminobenzoic acid |
| Mo3amb4- | 3-methoxy-4-aminobenzoic acid |
| Amb4- | 4-aminomethylbenzoic acid |
| Aeb4- | 4-(2-aminoethoxy)benzoic acid |
| Dae- | 1,2-diaminoethyl |
| Tpa- | Terephthalic acid |
| A4m2biphc4- | 4'-Amino-2'-methyl biphenyl-4-carboxylic acid |
| A3biphc3- | 3-amino-3'-biphenylcarboxylic acid |
| Amc4- | trans-4-aminomethylcyclohexane carboxylic acid |
| Aepa4- | N-4-aminoethyl-N-1-piperazine-acetic acid |
| Inp- | Isonipecotic acid |
| Pia1- | N-1-piperazineacetic acid |
| Ckbp- | 4-(3-Carboxymethyl-2-keto-1-benzimidazoyl)-piperidine |
| Abz3 | 3-Aminobenzoic acid |
| Abz4 | 4-Aminobenzoic acid |
| J | 8-amino-3,6-dioxaoctanoic acid |
| Ava5 | 5-Aminovaleric acid |
| f | (D)-Phe |
| y | (D)-Tyr |
| Ala2 (also Bala) | Beta-alanine |

DETAILED DESCRIPTION OF THE INVENTION

In the following description, various aspects of the present invention will be further elaborated. For purposes of explanation, specific configurations and details are set forth in order to provide a thorough understanding of the present invention. However, it will also be apparent to one skilled in the art that the present invention may be practiced without the specific details. Furthermore, well known features may be omitted or simplified in order not to obscure the present invention.

In an embodiment of the present invention, there are provided new and improved compounds for use in diagnostic imaging or radiotherapy. The compounds include an optical label or a chemical moiety capable of complexing a medically useful metal ion or radionuclide (metal chelator) attached to a GRP receptor targeting peptide by a linker or spacer group.

In general, compounds of the present invention may have the formula:

M-N-O-P-G wherein M is the metal chelator (in the form complexed with a metal radionuclide or not), or an optical label, N-O-P is the linker, and G is the GRP receptor targeting peptide. Each of the metal chelator, optical label, linker, and GRP receptor targeting peptide is described in the discussion that follow.

In the most preferred embodiment of the invention, M is a metal chelator and the linker N-O-P contains at least one non-alpha amino acid with a cyclic group. In another preferred embodiment M is a metal chelator of formula 8 herein (preferably an Aazta chelator or a derivative thereof) and the linker N-O-P contains at least one non-alpha amino acid with a cyclic group.

In another embodiment of the present invention, there is provided a new and improved linker or spacer group which is capable of linking an optical label or a metal chelator to a GRP receptor targeting peptide. In general, linkers of the present invention may have the formula:

N-O-P wherein each of N, O and P are defined throughout the specification.

Compounds meeting the criteria defined herein were discovered to have improved pharmacokinetic properties compared to other GRP receptor targeting peptide conjugates known in the art. For example, compounds containing the linkers of the present invention were retained in the bloodstream longer, and thus had a longer half life than prior known compounds. The longer half life was medically beneficial because it permitted better tumor targeting which is useful for diagnostic imaging, and especially for therapeutic uses, where the cancerous cells and tumors receive greater amounts of the radiolabeled peptides. Additionally, compounds of the present invention had improved tissue receptor specificity compared to prior art compounds.

Furthermore, the instant invention includes a method of increasing targeting of a labeled compound of the invention to GRP receptor expressing target tissue comprising administering the appropriate mass of GRP receptor targeting peptide or conjugate, prior to or during administration of labeled compound of the invention. Similarly, the invention includes an improved method of administration of labeled compounds of the invention in which tumor targeting is optimized comprising administering the appropriate mass dose of GRP receptor targeting peptide or conjugate prior to or during administration of labeled compound of the invention. Such pre- or co-dosing has been found to saturate non-target GRP-receptors, decreasing their ability to compete with GRP receptors on target (e.g., tumor) tissue.

1A. Metal Chelator

The term "metal chelator" refers to a molecule that forms a complex with a metal atom, wherein said complex is stable under physiological conditions. That is, the metal will remain complexed to the chelator backbone in vivo. More particularly, a metal chelator is a molecule that complexes to a radionuclide metal to form a metal complex that is stable under physiological conditions and which also has at least one reactive functional group for conjugation with the linker N-O-P. The metal chelator M may be any of the metal chelators known in the art for complexing a medically useful metal ion or radionuclide. The metal chelator may or may not be complexed with a metal radionuclide. Furthermore, the metal chelator can include an optional spacer such as, for example, a single amino acid (e.g., Gly) which does not complex with the metal, but which creates a physical separation between the metal chelator and the linker.

The metal chelators of the invention may include, for example, linear, macrocyclic, terpyridine, and $N_3S$, $N_2S_2$, or $N_4$ chelators (see also, U.S. Pat. No. 5,367,080, U.S. Pat. No. 5,364,613, U.S. Pat. No. 5,021,556, U.S. Pat. No. 5,075,099, U.S. Pat. No. 5,886,142, the disclosures of which are incorporated by reference in their entirety), and other chelators known in the art including, but not limited to, HYNIC, DTPA, EDTA, DOTA, TETA, and bisamino bisthiol (BAT) chelators (see also U.S. Pat. No. 5,720,934). For example, $N_4$ chelators are described in U.S. Pat. Nos. 6,143,274; 6,093,382; 5,608,110; 5,665,329; 5,656,254; and 5,688,487, the disclosures of which are incorporated by reference in their entirety. Certain $N_3S$ chelators are described in PCT/CA94/00395, PCT/CA94/00479, PCT/CA95/00249 and in U.S. Pat. Nos. 5,662,885; 5,976,495; and 5,780,006, the disclosures of which are incorporated by reference in their entirety. The chelator may also include derivatives of the chelating ligand mercapto-acetyl-glycyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in Liu and Edwards, Chem. Rev. 1999, 99, 2235-2268 and references therein, the disclosures of which are incorporated by reference in their entirety.

The metal chelator may also include complexes containing ligand atoms that are not donated to the metal in a tetradentate array. These include the boronic acid adducts of technetium and rhenium dioximes, such as those described in U.S. Pat. Nos. 5,183,653; 5,387,409; and 5,118,797, the disclosures of which are incorporated by reference in their entirety.

Examples of preferred chelators include, but are not limited to, diethylenetriamine pentaacetic acid (DTPA), 1,4,7,10-tetraazacyclotetradecane-1,4,7,10-tetraacetic acid (DOTA), 1-substituted 1,4,7-tricarboxymethyl 1,4,7,10-tetraazacyclododecane triacetic acid (DO3A), ethylenediaminetetraacetic acid (EDTA), 4-carbonylmethyl-10-phosphonomethyl-1,4,7,10-Tetraazacyclododecane-1,7-diacetic acid (Cm4 pm10d2a); and 1,4,8,11-tetraazacyclotetradecane-1,4,8,11-tetraacetic acid (TETA). Additional chelating ligands are ethylenebis-(2-hydroxyphenylglycine) (EHPG), and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl-DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylenetetraaminehexaacetic acid (TTHA); derivatives of 1,5,10-N,N',N"-tris(2,3-dihydroxybenzoyl)-tricatecholate (LICAM) and 1,3,5-N,N',N"-tris(2,3-dihydroxybenzoyl) aminomethylbenzene (MECAM). Other preferred chelators include Aazta and derivatives thereof including CyAazta. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. No. 4,899,755, U.S. Pat. No. 5,474,756, U.S. Pat. No. 5,846,519 and U.S. Pat. No. 6,143,274, each of which is hereby incorporated by reference in its entirety.

Particularly preferred metal chelators include those of Formula 1, 2, 3 and 8 (for $^{111}$In and radioactive lanthanides, such as, for example $^{177}$Lu, $^{90}$Y, [153]Sm, and [166]Ho) and those of Formula 4, 5 and 6 (for radioactive [99]mTc, [186]Re, and [188]Re) set forth below. These and other metal chelating groups are described in U.S. Pat. Nos. 6,093,382 and 5,608,110, which are incorporated by reference in their entirety. Additionally, the chelating group of formula 3 is described in, for example, U.S. Pat. No. 6,143,274; the chelating group of formula 5 is described in, for example, U.S. Pat. Nos. 5,627,286 and 6,093,382, and the chelating group of formula 6 is described in, for example, U.S. Pat. Nos. 5,662,885; 5,780,006; and 5,976,495, all of which are incorporated by reference. The chelating group of formula 8 is described in copending U.S. Ser. No. 10/484,111 filed Jan. 15, 2004 and U.S. Ser. No. 11/165,793, filed Jun. 23, 2005, both of which are hereby incorporated by reference. Specific metal chelators of formula 6 include N,N-dimethylGly-Ser-Cys; N,N-dimethylGly-Thr-Cys; N,N-diethylGly-Ser-Cys; N,N-dibenzylGly-Ser-Cys; and other variations thereof. For example, spacers which do not actually complex with the metal radionuclide such as an extra single amino acid Gly, may be attached to these metal chelators (e.g., N,N-dimethylGly-Ser-Cys-Gly; N,N-dimethylGly-Thr-Cys-Gly; N,N-diethylGly-Ser-Cys-Gly; N,N-dibenzylGly-Ser-Cys-Gly). Other useful metal chelators such as all of those disclosed in U.S. Pat. No. 6,334,996, also incorporated by reference (e.g., Dimethylgly-L-t-Butylgly-L-Cys-Gly; Dimethylgly-D-t-Butylgly-L-Cys-Gly; Dimethylgly-L-t-Butylgly-L-Cys, etc.)

Furthermore, sulfur protecting groups such as Acm (acetamidomethyl), trityl or other known alkyl, aryl, acyl, alkanoyl, aryloyl, mercaptoacyl and organothiol groups may be attached to the cysteine amino acid of these metal chelators.

Additionally, other useful metal chelators include:

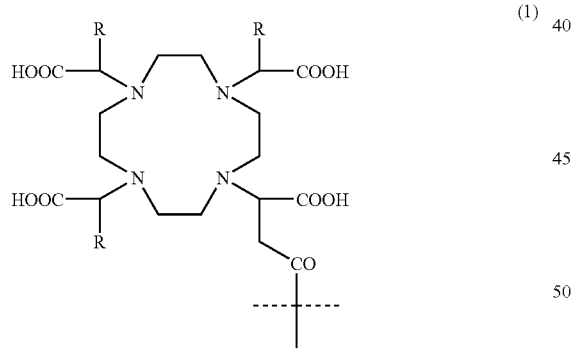

(1)

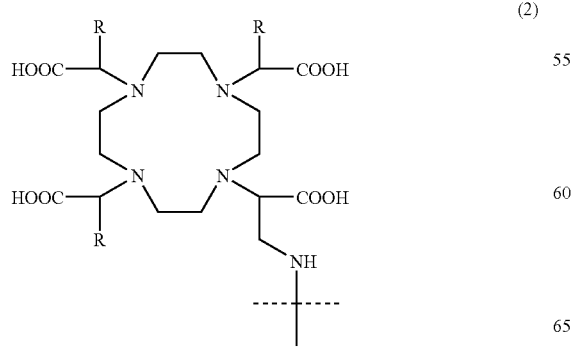

(2)

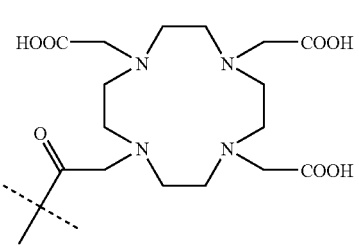

(3)

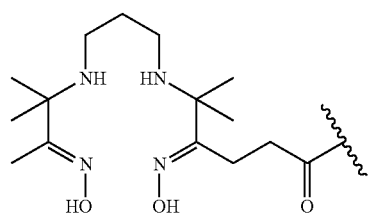

(4a)

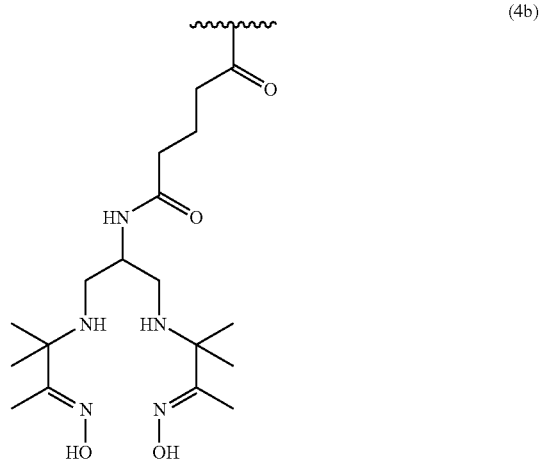

(4b)

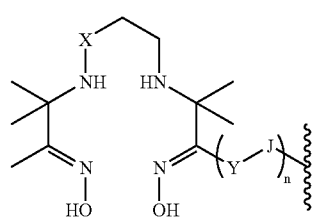

(5a)

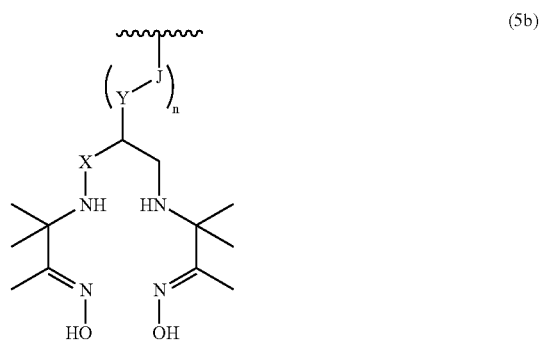

(5b)

-continued

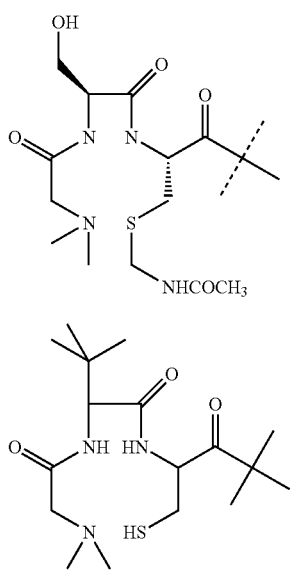

(6)

(7)

In the above Formulas 1 and 2, R is alkyl, preferably methyl. In the above Formulas 5a and 5b, X is either $CH_2$ or O; Y is $C_1$-$C_{10}$ branched or unbranched alkyl; aryl, aryloxy, arylamino, arylaminoacyl; arylalkyl—where the alkyl group or groups attached to the aryl group are $C_1$-$C_{10}$ branched or unbranched alkyl groups, $C_1$-$C_{10}$ branched or unbranched hydroxy or polyhydroxyalkyl groups or polyalkoxyalkyl or polyhydroxy-polyalkoxyalkyl groups; J is optional, but if present is C(=O)—, OC(=O)—, $SO_2$—, NC(=O)—, NC(=S)—, N(Y), NC(=NCH$_3$)—, NC(=NH)—, N=N—, homopolyamides or heteropolyamines derived from synthetic or naturally occurring amino acids; all where n is 1-100. Other variants of these structures are described, for example, in U.S. Pat. No. 6,093,382. In Formula 6, the group S—NHCOCH$_3$ may be replaced with SH or S—Z wherein Z is any of the known sulfur protecting groups such as those described above. Formula 7 illustrates one embodiment of t-butyl compounds useful as a metal chelator. The disclosures of each of the foregoing patents, applications and references are incorporated by reference in their entirety.

The metal chelators of the Aazta family generally have the following general formula: (8):

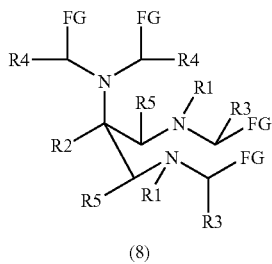

(8)

in which:
$R_1$ is hydrogen, $C_1$-$C_{20}$ alkyl optionally substituted with one or more carboxy groups, $C_3$-$C_{10}$ cycloalkyl, $C_4$-$C_{20}$ cycloalkylalkyl, aryl, arylalkyl or the two $R_1$ groups, taken together, form a straight or cyclic $C_2$-$C_{10}$ alkylene group or an ortho-disubstituted arylene;

$R_2$ is hydrogen, carboxy, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety, and a group bearing an amino moiety, each of which may be further optionally substituted with functional groups which allow conjugation with a suitable molecule able to interact with physiological systems;

$R_3$, $R_4$ and $R_5$, which can be the same or different, are hydrogen, carboxy, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amino moiety, each of which may be further optionally substituted with functional groups which allow conjugation with a suitable molecule able to interact with physiological systems;

FG, which can be the same or different, are carboxy, —PO$_3$H$_2$ or —RP(O)OH groups, wherein R is hydrogen, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amino moiety, each of which may be further optionally substituted with functional groups which allow conjugation with a suitable molecule able to interact with physiological systems.

Functional groups which allow conjugation with targeting molecules or other molecules that are able to interact with physiological systems are known to those skilled in the art. Such groups include, for example, carboxylic acids, amines, aldehydes, alkyl halogens, alkyl maleimides, sulfhydryl groups, hydroxyl groups, etc.

Specific examples of such Aazta metal chelators or derivatives thereof include, but are not limited to, CyAazta. Aazta derivatives also include:

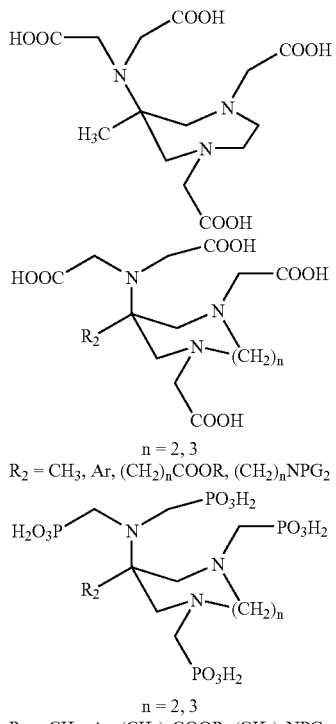

n = 2, 3
$R_2$ = CH$_3$, Ar, (CH$_2$)$_n$COOR, (CH$_2$)$_n$NPG$_2$ n = 2, 3
$R_2$ = CH$_3$, Ar, (CH$_2$)$_n$COOR, (CH$_2$)$_n$NPG$_2$

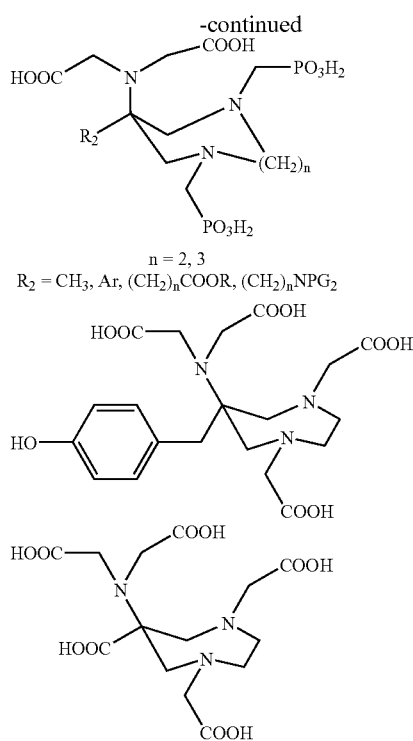

n = 2, 3
R₂ = CH₃, Ar, (CH₂)ₙCOOR, (CH₂)ₙNPG₂

In a preferred embodiment, the metal chelator includes cyclic or acyclic polyaminocarboxylic acids such as DOTA (1,4,7,10-tetraazacyclododecane-1,4,7,10-tetraacetic acid), DTPA (diethylenetriaminepentaacetic acid), DTPA-bismethylamide, DTPA-bismorpholineamide, Cm4 pm10d2a (1,4-carbonylmethyl-10-phosphonomethyl-1,4,7,10-Tetraazacyclododecane-1,7-diacetic acid), DO3A N-[[4,7,10-Tris(carboxymethyl)-1,4,7,10-tetraazacyclododec-1-yl]acetyl, HP-DO3A, DO3A-monoamide and derivatives thereof. In another preferred embodiment, the metal chelator includes Aazta or a derivative thereof.

Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au and oxides or nitrides thereof. The choice of metal will be determined based on the desired therapeutic or diagnostic application. For example, for diagnostic purposes (e.g., to diagnose and monitor therapeutic progress in primary tumors and metastases), the preferred radionuclides include $^{64}$Cu, $^{67}$Ga, $^{68}$Ga, $^{99m}$Tc, and $^{111}$In, with $^{99m}$Tc and $^{111}$In being especially preferred. For therapeutic purposes (e.g., to provide radiotherapy for primary tumors and metastasis related to cancers of the prostate, breast, lung, etc.), the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186/188}$Re, and $^{199}$Au, with $^{177}$Lu and $^{90}$Y being particularly preferred. $^{99m}$Tc is particularly useful and is a preferred for diagnostic radionuclide because of its low cost, availability, imaging properties, and high specific activity. The nuclear and radioactive properties of $^{99m}$Tc make this isotope an ideal scintigraphic imaging agent. This isotope has a single photon energy of 140 keV and a radioactive half-life of about 6 hours, and is readily available from a $^{99}$Mo$^{99m}$Tc generator. For example, the $^{99m}$Tc labeled peptide can be used to diagnose and monitor therapeutic progress in primary tumors and metastases. Peptides labeled with $^{177}$Lu, $^{90}$Y or other therapeutic radionuclides can be used to provide radiotherapy for primary tumors and metastasis related to cancers of the prostate, breast, lung, etc.

1B. Optical Labels

In an exemplary embodiment, the compounds of the invention may be conjugated with photolabels, such as optical dyes, including organic chromophores or fluorophores, having extensive delocalized ring systems and having absorption or emission maxima in the range of 400-1500 nm. The compounds of the invention may alternatively be derivatized with a bioluminescent molecule. The preferred range of absorption maxima for photolabels is between 600 and 1000 nm to minimize interference with the signal from hemoglobin. Preferably, photoabsorption labels have large molar absorptivities, e.g. $>10^5$ cm$^{-1}$M$^{-1}$, while fluorescent optical dyes will have high quantum yields. Examples of optical dyes include, but are not limited to those described in WO 98/18497, WO 98/18496, WO 98/18495, WO 98/18498, WO 98/53857, WO 96/17628, WO 97/18841, WO 96/23524, WO 98/47538, and references cited therein. For example, the photolabels may be covalently linked directly to compounds of the invention, such as, for example, compounds comprised of GRP receptor targeting peptides and linkers of the invention. Several dyes that absorb and emit light in the visible and near-infrared region of electromagnetic spectrum are currently being used for various biomedical applications due to their biocompatibility, high molar absorptivity, and/or high fluorescence quantum yields. The high sensitivity of the optical modality in conjunction with dyes as contrast agents parallels that of nuclear medicine, and permits visualization of organs and tissues without the undesirable effect of ionizing radiation. Cyanine dyes with intense absorption and emission in the near-infrared (NIR) region are particularly useful because biological tissues are optically transparent in this region. For example, indocyanine green, which absorbs and emits in the NIR region has been used for monitoring cardiac output, hepatic functions, and liver blood flow and its functionalized derivatives have been used to conjugate biomolecules for diagnostic purposes (R. B. Mujumdar, L. A. Ernst, S. R. Mujumdar, et al., Cyanine dye labeling reagents: Sulfoindocyanine succinimidyl esters. Bioconjugate Chemistry, 1993, 4(2), 105-111; Linda G. Lee and Sam L. Woo. "N-Heteroaromatic ion and iminium ion substituted cyanine dyes for use as fluorescent labels", U.S. Pat. No. 5,453,505; Eric Hohenschuh, et al. "Light imaging contrast agents", WO 98/48846; Jonathan Turner, et al. "Optical diagnostic agents for the diagnosis of neurodegenerative diseases by means of near infra-red radiation", WO 98/22146; Kai Licha, et al. "In-vivo diagnostic process by near infrared radiation", WO 96/17628; Robert A. Snow, et al., Compounds, WO 98/48838. Various imaging techniques and reagents are described in U.S. Pat. Nos. 6,663,847, 6,656,451, 6,641,798, 6,485,704, 6,423,547, 6,395,257, 6,280,703, 6,277,841, 6,264,920, 6,264,919, 6,228,344, 6,217,848, 6,190,641, 6,183,726, 6,180,087, 6,180,086, 6,180,085, 6,013,243, and published U.S. Patent Applications 2003185756, 20031656432, 2003158127, 2003152577, 2003143159, 2003105300, 2003105299, 2003072763, 2003036538, 2003031627, 2003017164, 2002169107, 2002164287, and 2002156117. All of the above references are incorporated by reference in their entirety.

2A. Linkers Containing At Least One Non-alpha Amino Acid

In one embodiment of the invention, the linker N-O-P contains at least one non-alpha amino acid. Thus, in this embodiment of the linker N-O-P, N is 0 (where 0 means it is absent), an alpha or non-alpha amino acid or other linking group;

O is an alpha or non-alpha amino acid; and

P is 0, an alpha or non-alpha amino acid or other linking group, wherein at least one of N, O or P is a non-alpha amino acid. Thus, in one example, N=Gly, O=a non-alpha amino acid, and P=0.

Alpha amino acids are well known in the art, and include naturally occurring and synthetic amino acids.

Non-alpha amino acids are also known in the art and include those which are naturally occurring or synthetic. Preferred non-alpha amino acids include:

8-amino-3,6-dioxaoctanoic acid;
N-4-aminoethyl-N-1-acetic acid; and
polyethylene glycol derivatives having the formula $NH_2$—$(CH_2CH_2O)n$-$CH_2CO_2H$ or $NH_2$—$(CH_2CH_2O)n$-$CH_2CH_2CO_2H$ where n=2 to 100.

Examples of compounds having the formula M-N-O-P-G which contain linkers with at least one non-alpha amino acid are listed in Table 1. These compounds may be prepared using the methods disclosed herein, particularly in the Examples, as well as by similar methods known to one skilled in the art.

TABLE 1

Table 1 - Compounds Containing Linkers With At Least One Non-alpha Amino Acid

| Compound | HPLC method[1] | HPLC RT[2] | MS[3] | IC50[5] | M | N | O | P | G |
|---|---|---|---|---|---|---|---|---|---|
| L1 | 10-40% B | 5.43 | 1616.6 | 5 | N,N-dimethylglycine-Ser-Cys(Acm)-Gly | Lys | 8-amino-3,6-dioxaoctanoic acid | none | BBN (7-14)* |
| L2 | 10-40% B | 5.47 | 1644.7 | 3 | N,N-dimethylglycine-Ser-Cys(Acm)-Gly | Arg | 8-amino-3,6-dioxaoctanoic acid | none | BBN (7-14)* |
| L3 | 10-40% B | 5.97 | 1604.6 | >50 | N,N-dimethylglycine-Ser-Cys(Acm)-Gly | Asp | 8-amino-3,6-dioxaoctanoic acid | none | BBN (7-14)* |
| L4 | 10-40% B | 5.92 | 1575.5 | 4 | N,N-dimethylglycine-Ser-Cys(Acm)-Gly | Ser | 8-amino-3,6-dioxaoctanoic acid | none | BBN (7-14)* |
| L5 | 10-40% B | 5.94 | 1545.5 | 9 | N,N-dimethylglycine-Ser-Cys(Acm)-Gly | Gly | 8-amino-3,6-dioxaoctanoic acid | none | BBN (7-14)* |
| L6 | 10-30% B | 7.82 | 1639 (M + Na) | >50 | N,N-dimethylglycine-Ser-Cys(Acm)-Gly | Glu | 8-amino-3,6-dioxaoctanoic acid | none | BBN (7-14)* |
| L7 | 10-30% B | 8.47 | 1581 (M + Na) | 7 | N,N-dimethylglycine-Ser-Cys(Acm)-Gly | Dala | 8-amino-3,6-dioxaoctanoic acid | none | BBN (7-14)* |
| L8 | 10-30% B | 6.72 | 1639 (M + Na) | 4 | N,N-dimethylglycine-Ser-Cys(Acm)-Gly | 8-amino-3,6-dioxaoctanoic acid | Lys | none | BBN (7-14)* |
| L9 | 10-30% B | 7.28 | 823.3 (M + 2/2) | 6 | N,N-dimethylglycine-Ser-Cys(Acm)-Gly | 8-amino-3,6-dioxaoctanoic acid | Arg | none | BBN (7-14)* |
| L10 | 10-30% B | 7.94 | 1625.6 (M + Na) | >50 | N,N-dimethylglycine-Ser-Cys(Acm)-Gly | 8-amino-3,6-dioxaoctanoic acid | Asp | none | BBN (7-14)* |
| L11 | 10-30% B | 7.59 | 1575.6 | 36 | N,N-dimethylglycine-Ser-Cys(Acm)-Gly | 8-amino-3,6-dioxaoctanoic acid | Ser | none | BBN (7-14)* |
| L12 | 10-30% B | 7.65 | 1567.5 (M + Na) | >50 | N,N-dimethylglycine-Ser-Cys(Acm)-Gly | 8-amino-3,6-dioxaoctanoic acid | Gly | none | BBN (7-14)* |
| L13 | 10-30% B | 7.86 | 1617.7 | >50 | N,N-dimethylglycine-Ser-Cys(Acm)-Gly | 8-amino-3,6-dioxaoctanoic acid | Glu | none | BBN (7-14)* |
| L14 | 10-30% B | 7.9 | 1581.7 (M + Na) | 11 | N,N-dimethylglycine-Ser-Cys(Acm)-Gly | 8-amino-3,6-dioxaoctanoic acid | Dala | none | BBN (7-14)* |
| L15 | 10-30% B | 7.84 | 1656.8 (M + Na) | 11.5 | N,N-dimethylglycine-Ser-Cys(Acm)-Gly | 8-amino-3,6-dioxaoctanoic acid | 8-amino-3,6-dioxaoctanoic acid | none | BBN (7-14)* |
| L16 | 10-30% B | 6.65 | 1597.4 (M + Na) | 17 | N,N-dimethylglycine-Ser-Cys(Acm)-Gly | 8-amino-3,6-dioxaoctanoic acid | 2,3-diaminopropionic acid | none | BBN (7-14)* |

TABLE 1-continued

Table 1 - Compounds Containing Linkers With At Least One Non-alpha Amino Acid

| Compound | HPLC method[1] | HPLC RT[2] | MS[3] | IC50[5] | M | N | O | P | G |
|---|---|---|---|---|---|---|---|---|---|
| L17 | 10-30% B | 7.6 | 1488.6 | 8 | N,N-dimethylglycine-Ser-Cys(Acm)-Gly | none | 8-amino-3,6-dioxaoctanoic acid | none | BBN (7-14)* |
| L18 | 10-30% B | 7.03 | 1574.6 | 7.8 | N,N-dimethylglycine-Ser-Cys(Acm)-Gly | 2,3-diaminopropionic acid | 8-amino-3,6-dioxaoctanoic acid | none | BBN (7-14)* |
| L19 | 10-35% B | 5.13 | 1603.6 | >50 | N,N-dimethylglycine-Ser-Cys(Acm)-Gly | Asp | 8-amino-3,6-dioxaoctanoic acid | Gly | BBN (7-14)* |
| L20 | 10-35% B | 5.19 | 1603.6 | 37 | N,N-dimethylglycine-Ser-Cys(Acm)-Gly | 8-amino-3,6-dioxaoctanoic acid | Asp | Gly | BBN (7-14)* |
| L21 | 10-35% B | 5.04 | 1575.7 | 46 | N,N-dimethylglycine-Ser-Cys(Acm)-Gly | 8-amino-3,6-dioxaoctanoic acid | Ser | Gly | BBN (7-14)* |
| L22 | 10-35% B | 4.37 | 1644.7 | 36 | N,N-dimethylglycine-Ser-Cys(Acm)-Gly | 8-amino-3,6-dioxaoctanoic acid | Arg | Gly | BBN (7-14)* |
| L23 | 10-35% B | 5.32 | 1633.7 | >50 | N,N-dimethylglycine-Ser-Cys(Acm)-Gly | 8-amino-3,6-dioxaoctanoic acid | 8-amino-3,6-dioxaoctanoic acid | Gly | BBN (7-14)* |
| L24 | 10-35% B | 4.18 | 1574.6 | 38 | N,N-dimethylglycine-Ser-Cys(Acm)-Gly | 8-amino-3,6-dioxaoctanoic acid | 2,3-diaminopropionic acid | Gly | BBN (7-14)* |
| L25 | 10-35% B | 4.24 | 1616.6 | 26 | N,N-dimethylglycine-Ser-Cys(Acm)-Gly | 8-amino-3,6-dioxaoctanoic acid | Lys | Gly | BBN (7-14)* |
| L26 | 10-35% B | 4.45 | 1574.6 | 30 | N,N-dimethylglycine-Ser-Cys(Acm)-Gly | 2,3-diaminopropionic acid | 8-amino-3,6-dioxaoctanoic acid | Gly | BBN (7-14)* |
| L27 | 10-35% B | 4.38 | 1627.3 | >50 | N,N-dimethylglycine-Ser-Cys(Acm)-Gly | N-4-aminoethyl-N-1-piperazineacetic acid | Asp | none | BBN (7-14)* |
| L28 | 10-35% B | 4.1 | 1600.3 | 25 | N,N-dimethylglycine-Ser-Cys(Acm)-Gly | N-4-aminoethyl-N-1-piperazineacetic acid | Ser | none | BBN (7-14)* |
| L29 | 10-35% B | 3.71 | 1669.4 | 36 | N,N-dimethylglycine-Ser-Cys(Acm)-Gly | N-4-aminoethyl-N-1-piperazineacetic acid | Arg | none | BBN (7-14)* |
| L30 | 10-35% B | 4.57 | 1657.2 | 36 | N,N-dimethylglycine-Ser-Cys(Acm)-Gly | N-4-aminoethyl-N-1-piperazineacetic acid | 8-amino-3,6-dioxaoctanoic acid | none | BBN (7-14)* |
| L31 | 10-35% B | 3.69 | 1598.3 | >50 | N,N-dimethylglycine-Ser-Cys(Acm)-Gly | N-4-aminoethyl-N-1-piperazineacetic acid | 2,3-diaminopropionic acid | none | BBN (7-14)* |
| L32 | 10-35% B | 3.51 | 1640.3 | 34 | N,N-dimethylglycine-Ser-Cys(Acm)-Gly | N-4-aminoethyl-N-1-piperazineacetic acid | Lys | none | BBN (7-14)* |
| L33 | 10-35% B | 4.29 | 1584.5 | >50 | N,N-dimethylglycine-Ser-Cys(Acm)-Gly | N-1-piperazineacetic acid | Asp | none | BBN (7-14)* |
| L34 | 10-35% B | 4.07 | 1578.7 (M + Na) | 38 | N,N-dimethylglycine-Ser-Cys(Acm)-Gly | N-1-piperazineacetic acid | Ser | none | BBN (7-14)* |
| L35 | 10-35% B | 3.65 | 1625.6 | 26 | N,N-dimethylglycine-Ser-Cys(Acm)-Gly | N-1-piperazineacetic acid | Arg | none | BBN (7-14)* |

TABLE 1-continued

Table 1 - Compounds Containing Linkers With At Least One Non-alpha Amino Acid

| Compound | HPLC method[1] | HPLC RT[2] | MS[3] | IC50[5] | M | N | O | P | G |
|---|---|---|---|---|---|---|---|---|---|
| L36 | 10-35% B | 4.43 | 1636.6 | 7 | N,N-dimethylglycine-Ser-Cys(Acm)-Gly | N-1-piperazineacetic acid | 8-amino-3,6-dioxaoctanoic acid | none | BBN (7-14)* |
| L37 | 10-35% B | 3.66 | 1555.7 | 23 | N,N-dimethylglycine-Ser-Cys(Acm)-Gly | N-1-piperazineacetic acid | 2,3-diaminopropionic acid | none | BBN (7-14)* |
| L38 | 10-35% B | 3.44 | 1619.6 | 7 | N,N-dimethylglycine-Ser-Cys(Acm)-Gly | N-1-piperazineacetic acid | Lys | none | BBN (7-14)* |
| L42 | 30-50% B | 5.65 | 1601.6 | 25 | N,N-dimethylglycine-Ser-Cys(Acm)-Gly | 4-Hydroxyproline | 8-amino-3,6-dioxaoctanoic acid | none | BBN (7-14)* |
| L48 | 30-50% B | 4.47 | 1600.5 | 40 | N,N-dimethylglycine-Ser-Cys(Acm)-Gly | 4-aminoproline | 8-amino-3,6-dioxaoctanoic acid | none | BBN (7-14)* |
| L51 | 15-35% B | 5.14 | 1673.7 | 49 | N,N-dimethylglycine-Ser-Cys(Acm)-Gly | Lys | 8-amino-3,6-dioxaoctanoic acid | Gly | BBN (7-14)* |
| L52 | 15-35% B | 6.08 | 1701.6 | 14 | N,N-dimethylglycine-Ser-Cys(Acm)-Gly | Arg | 8-amino-3,6-dioxaoctanoic acid | Gly | BBN (7-14)* |
| L53 | 15-35% B | 4.16 | 1632.6 | 10 | N,N-dimethylglycine-Ser-Cys(Acm)-Gly | Ser | 8-amino-3,6-dioxaoctanoic acid | Gly | BBN (7-14)* |
| L54 | 15-35% B | 4.88 | 1661.6 | >50 | N,N-dimethylglycine-Ser-Cys(Acm)-Gly | Asp | 8-amino-3,6-dioxaoctanoic acid | Gly | BBN (7-14)* |
| L55 | 15-35% B | 4.83 | 1683.4 (M + Na) | 43 | N,N-dimethylglycine-Ser-Cys(Acm)-Gly | 8-amino-3,6-dioxaoctanoic acid | Asp | Gly | BBN (7-14)* |
| L56 | 15-35% B | 4.65 | 1655.7 (M + Na) | 4 | N,N-dimethylglycine-Ser-Cys(Acm)-Gly | 8-amino-3,6-dioxaoctanoic acid | Ser | Gly | BBN (7-14)* |
| L57 | 15-35% B | 4.9 | 1701.8 | 50 | N,N-dimethylglycine-Ser-Cys(Acm)-Gly | 8-amino-3,6-dioxaoctanoic acid | Arg | Gly | BBN (7-14)* |
| L58 | 15-35% B | 4.22 | 846.4 (M + H/2) | >50 | N,N-dimethylglycine-Ser-Cys(Acm)-Gly | 8-amino-3,6-dioxaoctanoic acid | 8-amino-3,6-dioxaoctanoic acid | Gly | BBN (7-14)* |
| L59 | 15-35% B | 4.03 | 1635.5 | 42 | N,N-dimethylglycine-Ser-Cys(Acm)-Gly | 8-amino-3,6-dioxaoctanoic acid | 2,3-diaminopropionic acid | Gly | BBN (7-14)* |
| L60 | 15-35% B | 4.11 | 1696.6 (M + Na) | 20 | N,N-dimethylglycine-Ser-Cys(Acm)-Gly | 8-amino-3,6-dioxaoctanoic acid | Lys | Gly | BBN (7-14)* |
| L61 | 15-35% B | 4.32 | 1631.4 | 43 | N,N-dimethylglycine-Ser-Cys(Acm)-Gly | 2,3-diaminopropionic acid | 8-amino-3,6-dioxaoctanoic acid | Gly | BBN (7-14)* |
| L78 | 20-40% B | 6.13 | 1691.4 (M + Na) | 35 | DO3A-monoamide | 8-amino-3,6-dioxaoctanoic acid | Diaminopropionic acid | none | BBN (7-14)* |
| L79 | 20-40% B | 7.72 | 1716.8 (M + Na) | 42 | DO3A-monoamide | 8-amino-3,6-dioxaoctanoic acid | Biphenylalanine | none | BBN (7-14)* |
| L80 | 20-40% B | 7.78 | 1695.9 | >50 | DO3A-monoamide | 8-amino-3,6-dioxaoctanoic acid | Diphenylalanine | none | BBN (7-14)* |
| L81 | 20-40% B | 7.57 | 1513.6 | 37.5 | DO3A-monoamide | 8-amino-3,6-dioxaoctanoic acid | 4-Benzoylphenylalanine | none | BBN (7-14)* |
| L92 | 15-30% B | 5.63 | 1571.6 | 5 | DO3A-monoamide | 5-aminopentanoic acid | 8-amino-3,6-dioxaoctanoic acid | none | BBN (7-14)* |

TABLE 1-continued

Table 1 - Compounds Containing Linkers With At Least One Non-alpha Amino Acid

| Compound | HPLC method[1] | HPLC RT[2] | MS[3] | IC50[5] M | M | N | O | P | G |
|---|---|---|---|---|---|---|---|---|---|
| L94 | 20-36% B | 4.19 | 1640.8 (M + Na) | 6.2 | DO3A-monoamide | 8-amino-3,6-dioxaoctanoic acid | D-Phenylalanine | none | BBN (7-14)* |
| L110 | 15-45% B | 5.06 | 1612.7 | 36 | DO3A-monoamide | 8-aminooctanoic acid | 8-amino-3,6-dioxaoctanoic acid | none | BBN (7-14)* |
| L209 | 20-40% B over 6 minutes | 4.62 | 3072.54 | 37 | DO3A-monoamide | E(G8-amino-3,6-dioxaoctanoic acid-8-amino-3,6-dioxaoctanoic acid QWAVGHLM-NH$_2$) | 8-aminooctanoic acid | 8-aminooctanoic acid | BBN (7-14)* |
| L210 | 20-50% B over 10 minutes | 6.18 | 3056.76 | 11 | DO3A-monoamide | E(G-Aoa-Aoa-QWAVGHLM-NH$_2$) | 8-aminooctanoic acid | 8-aminooctanoic acid | BBN (7-14)* |

*BBN (7-14) corresponds to QWAVGHLM, which is (SEQ ID NO: 1)
[1]HPLC method refers to the 10 minute time for the HPLC gradient.
[2]HPLC RT refers to the retention time of the compound in the HPLC.
[3]MS refers to mass spectra where molecular weight is calculated from mass/unit charge (m/e).
[4]IC$_{50}$ refers to the concentration of compound to inhibit 50% binding of iodinated bombesin to a GRP receptor on cells.

2B. Linkers Containing at Least One Substituted Bile Acid

In another embodiment of the present invention, the linker N-O-P contains at least one substituted bile acid. Thus, in this embodiment of the linker N-O-P, N is 0 (where 0 means it is absent), an alpha amino acid, a substituted bile acid or other linking group;

O is an alpha amino acid or a substituted bile acid; and

P is 0, an alpha amino acid, a substituted bile acid or other linking group, wherein at least one of N, O or P is a substituted acid.

Bile acids are found in bile (a secretion of the liver) and are steroids having a hydroxyl group and a five carbon atom side chain terminating in a carboxyl group. In substituted bile acids, at least one atom such as a hydrogen atom of the bile acid is substituted with another atom, molecule or chemical group. For example, substituted bile acids include those having a 3-amino, 24-carboxyl function optionally substituted at positions 7 and 12 with hydrogen, hydroxyl or keto functionality.

Other useful substituted bile acids in the present invention include substituted cholic acids and derivatives thereof. Specific substituted cholic acid derivatives include:

(3β,5β)-3-aminocholan-24-oic acid;
(3β,5β,12α)-3-amino-12-hydroxycholan-24-oic acid;
(3β,5β,7α,12α)-3-amino-7,12-dihydroxycholan-24-oic acid;
Lys-(3,6,9)-trioxaundecane-1,11-dicarbonyl-3,7-dideoxy-3-aminocholic acid);
(3β,5β,7α)-3-amino-7-hydroxy-12-oxocholan-24-oic acid; and
(3β,5β,7α)-3-amino-7-hydroxycholan-24-oic acid.

Examples of compounds having the formula M-N-O-P-G which contain linkers with at least one substituted bile acid are listed in Table 2. These compounds may be prepared using the methods disclosed herein, particularly in the Examples, as well as by similar methods known to one skilled in the art.

TABLE 2

Table 2 - Compounds Containing Linkers With At Least One Substituted Bile Acid

| Compound | HPLC method[1] | HPLC RT[2] | MS[3] | IC50[5] M | M | N | O | P | G |
|---|---|---|---|---|---|---|---|---|---|
| L62 | 20-80% B | 3.79 | 1741.2 | >50 | DO3A-monoamide | Gly | (3β,5β)-3-aminocholan-24-oic acid | none | BBN (77-14)* |
| L63 | 20-80% B | 3.47 | 1757.0 | 23 | DO3A-monoamide | Gly | (3β,5β,12α)-3-amino-12-hydroxycholan-24-oic acid | none | BBN (77-14)* |
| L64 | 20-50% B | 5.31 | 1773.7 | 8.5 | DO3A-monoamide | Gly | (3β,5β,7α,12α)-3-amino-7,12-dihydroxycholan-24-oic acid | none | BBN (77-14)* |

TABLE 2-continued

Table 2 - Compounds Containing Linkers With At Least One Substituted Bile Acid

| Compound | HPLC method[1] | HPLC RT[2] | MS[3] | IC50[5] | M | N | O | P | G |
|---|---|---|---|---|---|---|---|---|---|
| L65 | 20-80% B | 3.57 | 2246.2 | >50 | DO3A-monoamide | Gly | Lys-(3,6,9-trioxaundecane-1,11-dicarbonyl-3,7-dideoxy-3-aminocholic acid) | Arg | BBN (77-14)* |
| L66 | 20-80% | 3.79 | 2245.8 | >50 | DO3A-monoamide | Gly | Lys-(3β,5β,7α,12α)-3-amino-7,12-dihydroxycholan-24-oic acid-3,6,9-trioxaundecane-1,11-dicarbonyl | Arg | BBN (77-14)* |
| L67 | 20-80% | 3.25 | 1756.9 | 4.5 | DO3A-monoamide | Gly | (3β,5β,7α,12α)-3-amino-12-oxacholan-24-oic acid | none | BBN (77-14)* |
| L69 | 20-80% | 3.25 | 1861.27 | 8 | DO3A-monoamide | 1-amino-3,6-dioxaoctanoic acid | (3β,5β,7α,12α)-3-amino-7,12-dihydroxycholan-24-oic acid | none | BBN (77-14)* |
| L280 | — | — | — | — | DO3A-monoamide | Gly | 3β,5β 7α,12α)-3-amino-7,12-dihydroxycholan-24-oic acid | none | QWAVaHLM-NH2 (SEQ ID NO: 14) |
| L281 | — | — | — | — | DO3A-monoamide | Gly | 3β,5β 7α,12α)-3-amino-7,12-dihydroxycholan-24-oic acid | f | QWAVGHLM-NH2* |
| L282 | — | — | — | — | DO3A-monoamide | Gly | 3β,5β 7α,12α)-3-amino-7,12-dihydroxycholan-24-oic acid | f | QWAVGHL-L-NH2 (SEQ ID NO: 8) |
| L283 | — | — | — | — | DO3A-monoamide | Gly | 3β,5β 7α,12α)-3-amino-7,12-dihydroxycholan-24-oic acid | f | QWAVGHL-NH-pentyl (SEQ ID NO: 6) |
| L284 | — | — | — | — | DO3A-monoamide | Gly | 3β,5β 7α,12α)-3-amino-7,12-dihydroxycholan-24-oic acid | y | QWAVBala-HFNle-NH$_2$ (SEQ ID NO: 9) |
| L285 | — | — | — | — | DO3A-monoamide | Gly | 3β,5β 7α,12α)-3-amino-7,12-dihydroxycholan-24-oic acid | f | QWAVBala-HFNle-NH$_2$ (SEQ ID NO; 9) |
| L286 | — | — | — | — | DO3A-monoamide | Gly | 3β,5β 7α,12α)-3-amino-7,12-dihydroxycholan-24-oic acid | none | QWAVGHFL-NH$_2$ (SEQ ID NO: 22) |
| L287 | — | — | — | — | DO3A-monoamide | Gly | 3β,5β 7α,12α)-3-amino-7,12-dihydroxycholan-24-oic acid | none | QWAVGNMeHis-LM-NH$_2$ (SEQ ID NO: 15) |
| L288 | — | — | — | — | DO3A-monoamide | Gly | 3β,5β 7α,12α)-3-amino-7,12-dihydroxycholan-24-oic acid | none | LWAVGSF-M-NH$_2$ (SEQ ID NO: 11) |
| L289 | — | — | — | — | DO3A-monoamide | Gly | 3β,5β 7α,12α)-3-amino-7,12-dihydroxycholan-24-oic acid | none | HWAVGHL-M-NH$_2$ (SEQ ID NO: 12) |
| L290 | — | — | — | — | DO3A-monoamide | Gly | 3β,5β 7α,12α)-3-amino-7,12-dihydroxycholan-24-oic acid | none | LWATGH-F-M-NH$_2$ (SEQ ID NO: 16) |
| L291 | — | — | — | — | DO3A-monoamide | Gly | 3β,5β 7α,12α)-3-amino-7,12-dihydroxycholan-24-oic acid | none | QWAVGH-FMNH$_2$ (SEQ ID NO: 17) |
| L292 | — | — | — | — | DO3A-monoamide | Gly | 3β,5β 7α,12α)-3-amino-7,12-dihydroxycholan-24-oic acid | QRLGN | QWAVGHLM-NH$_2$* |

TABLE 2-continued

Table 2 - Compounds Containing Linkers With At Least One Substituted Bile Acid

| Compound | HPLC method[1] | HPLC RT[2] | MS[3] | IC50[5] | M | N | O | P | G |
|---|---|---|---|---|---|---|---|---|---|
| L293 | — | — | — | — | DO3A-monoamide | Gly | 3β,5β 7α,12α)-3-amino-7,12-dihydroxycholan-24-oic acid | QRYGN | QWAVGHLM-NH$_2$* |
| L294 | — | — | — | — | DO3A-monoamide | Gly | 3β,5β 7α,12α)-3-amino-7,12-dihydroxycholan-24-oic acid | QKYGN | QWAVGHLM-NH$_2$* |
| L295 | — | — | — | — | Pglu-Q-Lys (DO3A-monoamide) | Gly | 3β,5β 7α,12α)-3-amino-7,12-dihydroxycholan-24-oic acid | LG-N | QWAVGHLM-NH$_2$* |
| L303 | — | — | — | — | DO3A-monoamide | Gly | 3-amino-3-deoxycholic acid | none | QRLGNQWAVGHLM-NH$_2$ (SEQ ID NO: 3) |
| L304 | — | — | — | — | DO3A-monoamide | Gly | 3-amino-3-deoxycholic acid | none | QRYGNQWAVGHLM-NH$_2$ (SEQ ID NO: 4) |
| L305 | — | — | — | — | DO3A-monoamide | Gly | 3-amino-3-deoxycholic acid | none | QKYGNQWAVGHLM-NH$_2$ (SEQ ID NO: 5) |
| L306 | — | — | — | — | DO3A-monoamide | Gly | 3-amino-3-deoxycholic acid | none | LGNQWAVGHLM-NH$_2$ (SEQ ID NO: 18) |
| L502 | — | — | — | — | Aazta | Gly | (3β,5β,7α,12α)-3-amino-7,12-dihydroxycholan-24-oic acid | none | BBN (77-14)* |
| L503 | — | — | — | — | CyAazta | Gly | (3β,5β,7α,12α)-3-amino-7,12-dihydroxycholan-24-oic acid | none | BBN (77-14)* |

*BBN (77-14) corresponds to QWAVGHLM, which is SEQ ID NO: 1
[1]HPLC method refers to the 10 minute time for the HPLC gradient.
[2]HPLC RT refers to the retention time of the compound in the HPLC.
[3]MS refers to mass spectra where molecular weight is calculated from mass/unit charge (m/e).
[4]IC$_{50}$ refers to the concentration of compound to inhibit 50% binding of iodinated bombesin to a GRP receptor on cells.

GRP receptor on cells.

2C. Linkers Containing at Least One Non-Alpha Amino Acid with a Cyclic Group In yet another embodiment of the present invention, the linker N-O-P contains at least one non-alpha amino acid with a cyclic group. Thus, in this embodiment of the linker N-O-P,
N is 0 (where 0 means it is absent), an alpha amino acid, a non-alpha amino acid with a cyclic group or other linking group;
O is an alpha amino acid or a non-alpha amino acid with a cyclic group; and
P is 0, an alpha amino acid, a non-alpha amino acid with a cyclic group, or other linking group,
wherein at least one of N, O or P is a non-alpha amino acid with a cyclic group.

Non-alpha amino acids with a cyclic group include substituted phenyl, biphenyl, cyclohexyl or other amine and carboxyl containing cyclic aliphatic or heterocyclic moieties. Examples of such include:
4-aminobenzoic acid (hereinafter referred to as "Abz4 in the specification")
3-aminobenzoic acid
4-aminomethyl benzoic acid
8-aminooctanoic acid
trans-4-aminomethylcyclohexane carboxylic acid
4-(2-aminoethoxy)benzoic acid
isonipecotic acid
2-aminomethylbenzoic acid
4-amino-3-nitrobenzoic acid
4-(3-carboxymethyl-2-keto-1-benzimidazolyl-piperidine
6-(piperazin-1-yl)-4-(3H)-quinazolinone-3-acetic acid
(2S,5S)-5-amino-1,2,4,5,6,7-hexahydro-azepino[3,21-hi]indole-4-one-2-carboxylic acid
(4S,7R)-4-amino-6-aza-5-oxo-9-thiabicyclo[4.3.0]nonane-7-carboxylic acid
3-carboxymethyl-1-phenyl-1,3,8-triazaspiro[4.5]decan-4-one
N1-piperazineacetic acid
N-4-aminoethyl-N-1-piperazineacetic acid
(3S)-3-amino-1-carboxymethylcaprolactam
(2S,6S,9)-6-amino-2-carboxymethyl-3,8-diazabicyclo-[4,3,0]-nonane-1,4-dione
3-amino-3-deoxycholic acid
4-hydroxybenzoic acid
4-aminophenylacetic acid
3-hydroxy-4-aminobenzoic acid
3-methyl-4-aminobenzoic acid
3-chloro-4-aminobenzoic acid
3-methoxy-4-aminobenzoic acid
6-aminonaphthoic acid
N,N'-Bis(2-aminoethyl)-succinamic acid Examples of compounds having the formula M-N-O-P-G which contain linkers with at least one alpha amino acid with a cyclic group are listed in Table 3. These compounds may be prepared using the methods disclosed herein, particularly in the Examples, as well as by similar methods known to one skilled in the art.

TABLE 3

Table 3 - Compounds Containing Linkers Related To Amino-(Phenyl, Biphenyl, Cycloalkyl Or Heterocyclic) Carboxylates

| Compound | HPLC method[1] | HPLC RT[2] | MS[3] | IC50[5] | M | N |
|---|---|---|---|---|---|---|
| L70 | 10-40% B | 6.15 | 1502.6 | 5 | DO3A-monoamide | Gly |
| L71 | 20-50% over 30 minutes | 14.14 | 59.68 (M + Na) | 7 | DO3A-monoamide | none |
| L72 | 20-50% over 30 minutes | 13.64 | 65.73 (M + K) | 8 | DO3A-monoamide | none |
| L73 | 5-35% | 7.01 | 1489.8 | 5 | DO3A-monoamide | none |
| L74 | 5-35% | 6.49 | 1494.8 | 7 | DO3A-monoamide | Gly |
| L75 | 5-35% | 6.96 | 1458.0 | 23 | DO3A-monoamide | none |
| L76 | 5-35% | 7.20] | 1502.7 | 4 | DO3A-monoamide | none |
| L77 | 20-40% B | 6.17 | 1691.8 (M + Na) | 17.5 | DO3A-monoamide | 8-amino-3,6-dioxaoctanoic acid |
| L82 | 20-40% B | 6.18 | 1584.6 | 8 | DO3A-monoamide | none |
| L83 | 20-40% B | 5.66 | 1597.5 | >50 | DO3A-monoamide | none |
| L84 | 20-40% B | 6.31 | 1555.5 | >50 | DO3A-monoamide | none |
| L85 | 20-40% B | 5.92 | 1525.5 | >50 | DO3A-monoamide | none |
| L86 | 20-40% B | 6.46 | 1598.6 | >50 | DO3A-monoamide | none |
| L87 | 20-40% B | 5.47 | 1593.8 (M + Na) | >50 | DO3A-monoamide | none |
| L88 | 20-40% B | 3.84 | 1452.7 | >50 | DO3A-monoamide | none |
| L89 | 20-40% B | 5.68 | 1518.5 (M + Na) | 23 | DO3A-monoamide | none |
| L90 | 20-40% B | 7.95 | 1495.4 | 50 | DO3A-monoamide | none |
| L91 | 20-40% B | 3.97 | 1535.7 | >50 | DO3A-monoamide | none |
| L93 | 15-30% B | 7.57 | 1564.7 | 5.8 | DO3A-monoamide | 5-aminopentanoic acid |
| L95 | 15-35% B | 5.41 | 1604.6 | 14 | DO3A-monoamide | trans-4-aminomethylcyclohexane-1-carboxylic acid |
| L96 | 20-36% B | 4.75 | 1612.7 | 35 | DO3A-monoamide | 4-aminomethylbenzoic acid |
| L97 | 15-35% B | 5.86 | 1598.8 | 4.5 | DO3A-monoamide | 4-benzoyl-(L)-phenylalanine |
| L98 | 15-35% B | 4.26 | 1622.7 | 16 | DO3A-monoamide | trans-4-aminomethylcyclohexane-1-carboxylic acid |
| L99 | 15-35% B | 4.1 | 1594.7 | 22 | DO3A-monoamide | trans-4-aminomethylcyclohexane-1-carboxylic acid |
| L100 | 15-35% B | 4.18 | 1613.6 | 10 | DO3A-monoamide | trans-4-aminomethylcyclohexane-1-carboxylic acid |

TABLE 3-continued

Table 3 - Compounds Containing Linkers Related To Amino-(Phenyl, Biphenyl, Cycloalkyl Or Heterocyclic) Carboxylates

| | | | | | | |
|---|---|---|---|---|---|---|
| L101 | 15-35% B | 5.25 | 1536.7 | 25 | DO3A-monoamide | trans-4-aminomethylcyclohexane-1-carboxylic acid |
| L102 | 15-35% B | 5.28 | 1610.8 | 9.5 | DO3A-monoamide | trans-4-aminomethylcyclohexane-1-carboxylic acid |
| L103 | 15-35% B | 4.75 | 1552.7 | 24 | DO3A-monoamide | trans-4-aminomethylcyclohexane-1-carboxylic acid |
| L104 | 15-35% B | 3.91 | 1551.7 | 32 | DO3A-monoamide | trans-4-aminomethylcyclohexane-1-carboxylic acid |
| L105 | 20-45% B | 7.68 | 1689.7 | 3.5 | DO3A-monoamide | trans-4-aminomethylcyclohexane-1-carboxylic acid |
| L106 | 20-45% B | 6.97 | 1662.7 | 3.8 | DO3A-monoamide | trans-4-aminomethylcyclohexane-1-carboxylic acid |
| L107 | 15-35% B | 5.79 | 1604.7 | 5 | DO3A-monoamide | trans-4-aminomethylcyclohexane-1-carboxylic acid |
| L108 | 15-45% B | 6.38 | 1618.7 | 10 | DO3A-monoamide | 8-amino-3,6-dioxaoctanoic acid |
| L109 | 15-45% B | 6.85 | 1612.7 | 6 | DO3A-monoamide | trans-4-aminomethylcyclohexane-1-carboxylic acid |
| L111 | 20-45% B | 3.75 | 1628.6 | 8 | DO3A-monoamide | 8-aminooctanoic acid |
| L112 | 20-47% B in 9 min | 3.6 | 1536.5 | 4.5 | DO3A-monoamide | none |
| L113 | 20-47% B in 9 min | 3.88 | 1558.6 (M + Na) | 5 | DO3A-monoamide | none |
| L114 | 10-40% B | 5.47 | 1582.8 | 4.5 | CMDOTA | Gly |
| L124 | 5-35% B | 7.04 | 1489.9 | 8.0 | DO3A-monoamide | none |
| L143 | 5-35% B | 6.85 | 1516.8 | 11 | DO3A-monoamide | Gly |
| L144 | 5-35% B | 6.85 | 1462.7 | 9 | HPDO3A | none |
| L145 | 20-80% B | 1.58 | 1459.8 | 5 | DO3A-monoamide | none |
| L146 | 20-80% B | 1.53 | 1473.7 | 9 | DO3A-monoamide | none |
| L147 | 20-80% B | 1.68 | 1489.7 | 3.5 | DO3A-monoamide | none |
| L201 | 10-46% B over 12 minutes | 5.77 | 1563.7 | 36 | Boa*** | none |
| L202 | 10-46% B over 12 minutes | 5.68 | 1517.74 | 13 | DO3A-monoamide | none |
| L203 | 10-46% B over 12 minutes | 5.98 | 1444.69 | 9 | DO3A-monoamide | none |
| L204 | 10-46% B over 12 minutes | 5.82 | 1502.73 | 50 | DO3A-monoamide | none |

TABLE 3-continued

Table 3 - Compounds Containing Linkers Related To Amino-(Phenyl, Biphenyl, Cycloalkyl Or Heterocyclic) Carboxylates

| | | | | | | |
|---|---|---|---|---|---|---|
| L205 | 10-46% B over 12 minutes | 5.36 | 1503.72 | 45 | DO3A-monoamide | Gly |
| L206 | 10-46% B over 12 minutes | 7.08 | 1592.85 | 4.5 | DO3A-monoamide | Gly |
| L207 | 10-46% B over 12 minutes | 7.59 | 1578.83 | 2.5 | DO3A-monoamide | Gly |
| L208 | 10-46% B over 12 minutes | 5.9 | 1516.75 | 7.5 | DO3A-monoamide | Gly |
| L211 | 10-46% B over 12 minutes | 5.76 | 1560.77 | 4 | DO3A-monoamide | Gly |
| L212 | 10-46% B over 12 minutes | 6.05 | 1503.71 | NT** | DO3A-monoamide | none |
| L213 | 10-46% B over 12 minutes | 5.93 | 1503.71 | NT** | DO3A-monoamide | Gly |
| L214 | 10-46% B over 12 minutes | 7.36 | 1649.91 | NT** | DO3A-monoamide | Gly |
| L215 | 10-46% B over 12 minutes | 5.08 | 2071.37 | NT** | DO3A-monoamide | Gly |
| L216 | 10-46% B over 12 minutes | 4.94 | 2121.38 | NT** | DO3A-monoamide | Gly |
| L217 | 10-46% B over 12 minutes | 4.38 | 2093.37 | NT** | DO3A-monoamide | Gly |
| L218 | 10-46% B over 12 minutes | 6.13 | 2154.45 | NT** | DO3A-monoamide | Gly |
| L219 | 10-46% B over 12 minutes | 8.61 | 1588.84 | NT** | DO3A-monoamide | Gly |
| L220 | 10-46% B over 12 minutes | 5.96 | 1516.75 | NT** | DO3A-monoamide | Gly |
| L221 | 10-46% B over 12 minutes | 7.96 | 1631.87 | NT** | DO3A-monoamide | Gly |
| L222 | 10-46% B over 12 minutes | 6.61 | 1695.91 | NT** | DO3A-monoamide | Gly |
| L223 | 10-46% B over 12 minutes | 7.48 | 1679.91 | NT** | DO3A-monoamide | Gly |
| L224 | 10-46% B over 12 minutes | 5.40 | 1419.57 | NT** | DO3A-monoamide | Gly |
| L225 | 10-46% B over 12 minutes | 8.27 | 1471.71 | NT** | DO3A-monoamide | Gly |
| L226 | 10-46% B over 12 minutes | 5.12 | 1523.75 | NT** | DO3A-monoamide | Gly |
| L227 | 10-46% B over 12 minutes | 6.61 | 1523.75 | NT** | DO3A-monoamide | Gly |
| L228 | 10-46% B over 12 minutes | 5.77 | 1511 | NT** | DO3A-monoamide | Gly |
| L233 | 5-35% B over 10 min | 7.04 | 1502.71 | 4.8 | DO3A-monoamide | Gly |
| L234 | 20-80% over 10 minutes | 1.95 | 1552.76 | 3 | DO3A-monoamide | Gly |
| L235 | 20-80% over 10 minutes | 1.95 | 1515.72 | 7 | DO3A-monoamide | Gly |
| L237 | 20-80% over 10 minutes | 1.52 | 1538.68 | 5 | Cm4pm10d2a | Gly |

TABLE 3-continued

Table 3 - Compounds Containing Linkers Related To Amino-(Phenyl, Biphenyl, Cycloalkyl Or Heterocyclic) Carboxylates

| | | | | | | |
|---|---|---|---|---|---|---|
| L238 | 5-35% B over 10 min | 7.17 | 1462.70 | 1.5 | N,N-dimethylglycine-Ser-Cys(Acm)-Gly | Gly |
| L239 | 20-80% over 10 minutes | 3.36 | 1733.16 | 4.5 | N,N-dimethylglycine-Ser-Cys(Acm)-Gly | Gly |
| L240 | 20-80% over 10 minutes | 1.55 | 1532.73 | 4 | DO3A-monoamide | Gly |
| L241 | 20-80% over 10 minutes | 1.63 | 1535.68 | 4 | DO3A-monoamide | Gly |
| L242 | 20-80% over 10 minutes | 1.55 | 1516.75 | 5 | DO3A-monoamide | Gly |
| L243 | 20-80% over 10 minutes | 1.57 | 1518.70 | 14 | DO3A-monoamide | Gly |
| L244 | 5-50% over 10 minutes | 4.61 | 1898.16 | >50 | (DO3A-monoamide)$_2$ | N,N'-Bis(2-aminoethyl)-succinamic acid |
| L300 | 10-46% over 10 minutes | — | — | — | DO3A-monoamide | Gly |
| L301 | 20-45% over 15 minutes | 7.18 | — | — | DO3A-monoamide | none |
| L302 | — | — | — | — | DO3A-monoamide | Gly |
| L500 | — | — | 1515.7 | — | Aazta | Gly |
| L501 | — | — | 1569.7 | — | CyAazta | Gly |

| Compound | O | P | G |
|---|---|---|---|
| L70 | 4-aminobenzoic acid | none | BBN (77-14)* |
| L71 | 4-aminomethyl benzoic acid | none | BBN (77-14)* |
| L72 | trans-4-aminomethylcyclohexyl carboxylic acid | none | BBN (77-14)* |
| L73 | 4-(2-aminoethoxy)benzoic acid | none | BBN (77-14)* |
| L74 | isonipecotic acid | none | BBN (77-14)* |
| L75 | 2-aminomethylbenzoic acid | none | BBN (77-14)* |
| L76 | 4-aminomethyl-3-nitrobenzoic acid | none | BBN (77-14)* |
| L77 | 1-Naphthylalanine | none | BBN (77-14)* |
| L82 | 4-(3-carboxymethyl-2-keto-1-benzimidazolyl-piperidine | none | BBN (77-14)* |
| L83 | 6-(piperazin-1-yl)-4-(3H)-quinazolinone-3-acetic acid | none | BBN (77-14)* |
| L84 | (2S,5S)-5-amino-1,2,4,5,6,7-hexahydro-azepino[3,21-hi]indole-4-one-2-carboxylic acid | none | BBN (77-14)* |

TABLE 3-continued

Table 3 - Compounds Containing Linkers Related To Amino-(Phenyl, Biphenyl, Cycloalkyl Or Heterocyclic) Carboxylates

| | | | |
|---|---|---|---|
| L85 | (4S,7R)-4-amino-6-aza-5-oxo-9-thiabicyclo[4.3.0]nonane-7-carboxylic acid | none | BBN (77-14)* |
| L86 | N,N-dimethylglycine | none | BBN (77-14)* |
| L87 | 3-carboxymethyl-1-phenyl-1,3,8-triazaspiro[4.5]decan-4-one | none | BBN (77-14)* |
| L88 | N1-piperazineacetic acid | none | BBN (77-14)* |
| L89 | N-4-aminoethyl-N-1-piperazine-acetic acid | none | BBN (77-14)* |
| L90 | (3S)-3-amino-1-carboxymethylcaprolactam | none | BBN (77-14)* |
| L91 | (2S,6S,9)-6-amino-2-carboxymethyl-3,8-diazabicyclo-[4,3,0]-nonane-1,4-dione | none | BBN (77-14)* |
| L93 | trans-4-aminomethylcyclohexane-1-carboxylic acid | none | BBN (77-14)* |
| L95 | D-Phenylalanine | none | BBN (77-14)* |
| L96 | 8-amino-3,6-dioxaoctanoic acid | none | BBN (77-14)* |
| L97 | trans-4-aminomethylcyclohexane-1-carboxylic acid | none | BBN (77-14)* |
| L98 | Arg | none | BBN (77-14)* |
| L99 | Lys | none | BBN (77-14)* |
| L100 | Diphenylalanine | none | BBN (77-14)* |
| L101 | 1-Naphthylalanine | none | BBN (77-14)* |
| L102 | 8-amino-3,6-dioxaoctanoic acid | none | BBN (77-14)* |
| L103 | Ser | none | BBN (77-14)* |
| L104 | 2,3-diaminopropionic acid | none | BBN (77-14)* |
| L105 | Biphenylalanine | none | BBN (77-14)* |
| L106 | (2S,5S)-5-amino-1,2,4,5,6,7-hexahydro-azepino[3,21-hi]indole-4-one-2-carboxylic acid | none | BBN (77-14)* |
| L107 | trans-4-aminomethylcyclohexane-1-carboxylic acid | none | BBN (77-14)* |
| L108 | Phenylalanine | none | BBN (77-14)* |
| L109 | Phenylalanine | none | BBN (77-14)* |
| L111 | trans-4-aminomethylcyclohexane-1-carboxylic acid | none | BBN (77-14)* |
| L112 | 4'-aminomethyl-biphenyl-1-carboxylic acid | none | BBN (77-14)* |
| L113 | 3'-aminomethyl-biphenyl-3-carboxylic acid | none | BBN (77-14)* |
| L114 | 4-aminobenzoic acid | none | BBN (77-14)* |

TABLE 3-continued

Table 3 - Compounds Containing Linkers Related To Amino-(Phenyl, Biphenyl, Cycloalkyl Or Heterocyclic) Carboxylates

| | | | |
|---|---|---|---|
| L124 | 4-aminomethylphenoxyacetic acid | none | BBN (77-14)* |
| L143 | 4-aminophenylacetic acid | none | BBN (77-14)* |
| L144 | 4-phenoxy | none | BBN (77-14)* |
| L145 | 3-aminomethylbenzoic acid | none | BBN (77-14)* |
| L146 | 4-aminomethylphenylacetic acid | none | BBN (77-14)* |
| L147 | 4-aminomethyl-3-methoxybenzoic acid | none | BBN (77-14)* |
| L201 | Gly | 4-amino benzoic acid | BBN (77-14)* |
| L202 | Gly | 4-hydrazinobenzoyl | BBN (77-14)* |
| L203 | none | 4-amino benzoic acid | BBN (77-14)* |
| L204 | 4-aminobenzoic acid | Gly | BBN (77-14)* |
| L205 | 6-Aminonicotinic acid | none | BBN (77-14)* |
| L206 | 4'-Amino-2'-methyl biphenyl-4-carboxylic acid | none | BBN (77-14)* |
| L207 | 3'-Aminobiphenyl-3-carboxylic acid | none | BBN (77-14)* |
| L208 | 1,2-diaminoethyl | Terephthalic acid | BBN (77-14)* |
| L211 | Gly | 4-amino benzoic acid | BBN (77-14)* |
| L212 | Gly | 4-amino benzoic acid | EWAVGHLM-NH$_2$ (SEQ ID NO: 2) |
| L213 | 4-aminobenzoic acid | none | QWAVGHLM-OH* |
| L214 | 4-aminobenzoic acid | (D)-Phe | BBN (77-14)* |
| L215 | 4-aminobenzoic acid | none | QRLGNQWAVGHLM-NH$_2$ (SEQ ID NO: 3) |
| L216 | 4-aminobenzoic acid | none | QRYGNQWAVGHLM-NH$_2$ (SEQ ID NO: 4) |
| L217 | 4-aminobenzoic acid | none | QKYGNQWAVGHLM-NH$_2$ (SEQ ID NO: 5) |
| L218 | 4-aminobenzoic acid | none | LGNQWAVGHLM-NH$_2$ (SEQ ID NO: 18) |
| L219 | 4-aminobenzoic acid | (D)-Phe | QWAVGHL-NH-Pentyl (SEQ ID NO: 6) |
| L220 | 4-aminobenzoic acid | none | QWSVaHLM-NH$_2$ (SEQ ID NO: 7) |
| L221 | 4-aminobenzoic acid | (D)-Phe | QWAVGHLL-NH$_2$ (SEQ ID NO: 8) |

TABLE 3-continued

Table 3 - Compounds Containing Linkers Related To Amino-(Phenyl, Biphenyl, Cycloalkyl Or Heterocyclic) Carboxylates

| | | | | |
|---|---|---|---|---|
| L222 | 4-aminobenzoic acid | (D)-Tyr | QWAV-Bala-HFNle-NH$_2$ (SEQ ID NO: 9) | |
| L223 | 4-aminobenzoic acid | Phe | QWAV-Bala-HFNle-NH$_2$ (SEQ ID NO: 9) | |
| L224 | 4-aminobenzoic acid | none | QWAGHFL-NH$_2$ (SEQ ID NO: 10) | |
| L225 | 4-aminobenzoic acid | none | LWAVGSFM-NH$_2$ (SEQ ID NO: 11) | |
| L226 | 4-aminobenzoic acid | none | HWAVGHLM-NH$_2$ (SEQ ID NO: 12) | |
| L227 | 4-aminobenzoic acid | none | LWATGHFM-NH$_2$ (SEQ ID NO: 16) | |
| L228 | 4-aminobenzoic acid | none | QWAVGHFM-NH$_2$ (SEQ ID NO: 13) | |
| L233 | 3-aminobenzoic acid | none | BBN (77-14)* | |
| L234 | 6-aminonaphthoic acid | none | BBN (77-14)* | |
| L235 | 4-methylaminobenzoic acid | none | BBN (77-14)* | |
| L237 | 4-aminobenzoic acid | none | BBN (77-14)* | |
| L238 | 4-aminobenzoic acid | none | BBN (77-14)* | |
| L239 | 3-amino-3-deoxycholic acid | none | BBN (77-14)* | |
| L240 | 3-methoxy-4-aminobenzoic acid | none | BBN (77-14)* | |
| L241 | 3-chloro-4-aminobenzoic acid | none | BBN (77-14)* | |
| L242 | 3-methyl-4-aminobenzoic acid | none | BBN (77-14)* | |
| L243 | 3-hydroxy-4-aminobenzoic acid | none | BBN (77-14)* | |
| L244 | none | none | BBN (77-14)* | |
| L300 | 4-aminobenzoic acid | none | QWAVGHFL-NH$_2$ (SEQ ID NO: 22) | |
| L301 | 4-aminomethylbenzoic acid | L-1-Naphthylalanine | BBN (77-14)* | |
| L302 | 4-aminobenzoic acid | none | QWAVGNMeH-L-M-NH$_2$ (SEQ ID NO: 15) | |
| L500 | 4-aminobenzoic acid | none | BBN (77-14)* | |
| L501 | 4-aminobenzoic acid | none | BBN (77-14)* | |

*BBN (77-14) is the sequence QWAVGHLM (SEQ ID NO: 1)
**NT is defined as "not tested."
***BOA is defined as (1R)-1-(Bis{2-[bis(carboxymethyl)amino]ethyl}amino)propane-1,3-dicarboxylic acid.
[1] HPLC method refers to the 10 minute time for the HPLC gradient.
[2] HPLC RT refers to the retention time of the compound in the HPLC.
[3] MS refers to mass spectra where molecular weight is calculated from mass/unit charge (m/e).
[4] IC$_{50}$ refers to the concentration of compound to inhibit 50% binding of iodinated bombesin to a GRP receptor on cells.

A subset of compounds containing preferred linkers and various GRP receptor targeting peptides are set forth in Table 4. These compounds may be prepared using the methods disclosed herein, particularly in the Examples, as well as by similar methods known to one skilled in the art.

TABLE 4

Table 4 - Compounds Containing Linkers of the Invention With Various GRP-R Targeting Moities

| Compound | HPLC method[1] | HPLC RT[2] | MS[3] | IC50[5] | M | N | O | P | G |
|---|---|---|---|---|---|---|---|---|---|
| L214 | 10-46% B over 12 minutes | 7.36 | 1649.91 | NT** | DO3A-monoamide | Gly | 4-aminobenzoic acid | (D)-Phe | BBN(7-14)* |
| L215 | 10-46% B over 12 minutes | 5.08 | 2071.37 | NT** | DO3A-monoamide | Gly | 4-aminobenzoic acid | none | QRLGNQWAVGHLM-NH$_2$ (SEQ ID NO: 3) |
| L216 | 10-46% B over 12 minutes | 4.94 | 2121.38 | NT** | DO3A-monoamide | Gly | 4-aminobenzoic acid | none | QRYGNQWAVGHLM-NH$_2$ (SEQ ID NO: 4) |
| L217 | 10-46% B over 12 minutes | 4.38 | 2093.37 | NT** | DO3A-monoamide | Gly | 4-aminobenzoic acid | none | QKYGNQWAVGHLM-NH (SEQ ID NO: 5) |
| L218 | 10-46% B over 12 minutes | 6.13 | 2154.45 | NT** | DO3A-monoamide | Gly | 4-aminobenzoic acid | none | LGNQWAVGHLM-NH$_2$ (SEQ ID NO: 18) |
| L219 | 10-46% B over 12 minutes | 8.61 | 1588.84 | NT** | DO3A-monoamide | Gly | 4-aminobenzoic acid | (D)-Phe | QWAVGHL-NH-Pentyl (SEQ ID NO: 6) |
| L220 | 10-46% B over 12 minutes | 5.96 | 1516.75 | NT** | DO3A-monoamide | Gly | 4-aminobenzoic acid | none | QWAVaHLM-NH$_2$ (SEQ ID NO: 7) |
| L221 | 10-46% B over 12 minutes | 7.96 | 1631.87 | NT** | DO3A-monoamide | Gly | 4-aminobenzoic acid | (D)-Phe | QWAVGHLL-NH$_2$ (SEQ ID NO: 8) |
| L222 | 10-46% B over 12 minutes | 6.61 | 1695.91 | NT** | DO3A-monoamide | Gly | 4-aminobenzoic acid | (D)-Tyr | QWAV-Bala-HF-Nle-NH$_2$ (SEQ ID NO: 9) |
| L223 | 10-46% B over 12 minutes | 7.48 | 1679.91 | NT** | DO3A-monoamide | Gly | 4-aminobenzoic acid | Phe | QWAV-Bala-HF-Nle-NH$_2$ (SEQ ID NO: 9) |
| L224 | 10-46% B over 12 minutes | 5.40 | 1419.57 | NT** | DO3A-monoamide | Gly | 4-aminobenzoic acid | none | QWAGHFL-NH$_2$ (SEQ ID NO: 10) |
| L225 | 10-46% B over 12 minutes | 8.27 | 1471.71 | NT** | DO3A-monoamide | Gly | 4-aminobenzoic acid | none | LWAVGSFM-NH$_2$ (SEQ ID NO: 11) |
| L226 | 10-46% B over 12 minutes | 5.12 | 1523.75 | NT** | DO3A-monoamide | Gly | 4-aminobenzoic acid | none | HWAVGHLM-NH$_2$ (SEQ ID NO: 12) |
| L227 | 10-46% B over 12 minutes | 6.61 | 1523.75 | NT** | DO3A-monoamide | Gly | 4-aminobenzoic acid | none | LWATGHFM-NH$_2$ (SEQ ID NO: 16) |
| L228 | 10-46% B over 12 minutes | 5.77 | 1511 | NT** | DO3A-monoamide | Gly | 4-aminobenzoic acid | none | QWAVGHFM-NH$_2$ (SEQ ID NO: 13) |
| L280 | — | — | — | — | DO3A-monoamide | Gly | (3β,5β 7a,12a)-3-amino-7,12-dihydroxycholan-24-oic acid | none | QWAVaHLM-NH$_2$ (SEQ ID NO: 14) |
| L281 | — | — | — | — | DO3A-monoamide | Gly | (3β,5β 7a,12a)-3-amino-7,12-dihydroxycholan-24-oic acid | f | QWAVGH-LM-NH$_2$* |
| L282 | — | — | — | — | DO3A-monoamide | Gly | (3β,5β 7a,12a)-3-amino-7,12-dihydroxycholan-24-oic acid | f | QWAVGHLL-NH$_2$ (SEQ ID NO: 8) |
| L283 | — | — | — | — | DO3A-monoamide | Gly | (3β,5β 7a,12a)-3-amino-7,12-dihydroxycholan-24-oic acid | f | QWAVGHLNH-pentyl (SEQ ID NO: 6) |
| L284 | — | — | — | — | DO3A-monoamide | Gly | (3β,5β 7a,12a)-3-amino-7,12-dihydroxycholan-24-oic acid | y | QWAVBalaHF-Nle-NH$_2$ (SEQ ID NO: 9) |
| L285 | — | — | — | — | DO3A-monoamide | Gly | (3β,5β 7a,12a)-3-amino-7,12-dihydroxycholan-24-oic acid | f | QWAVBala-HF-Nle-NH$_2$ (SEQ ID NO: 9) |

TABLE 4-continued

Table 4 - Compounds Containing Linkers of the Invention With Various GRP-R Targeting Moities

| Compound | HPLC method[1] | HPLC RT[2] | MS[3] | IC50[5] | M | N | O | P | G |
|---|---|---|---|---|---|---|---|---|---|
| L286 | — | — | — | — | DO3A-monoamide | Gly | (3β,5β 7a,12a)-3-amino-7,12-dihydroxycholan-24-oic acid | none | QWAVGHFL-NH$_2$ (SEQ ID NO: 22) |
| L287 | — | — | — | — | DO3A-monoamide | Gly | (3β,5β 7a,12a)-3-amino-7,12-dihydroxycholan-24-oic acid | none | QWAVGNMeHis-L-M-NH$_2$ (SEQ ID NO: 15) |
| L288 | — | — | — | — | DO3A-monoamide | Gly | (3β,5β 7a,12a)-3-amino-7,12-dihydroxycholan-24-oic acid | none | LWAVGSFM-NH$_2$ (SEQ ID NO: 11) |
| L289 | — | — | — | — | DO3A-monoamide | Gly | (3β,5β 7a,12a)-3-amino-7,12-dihydroxycholan-24-oic acid | none | HWAVGHLM-NH$_2$ (SEQ ID NO: 12) |
| L290 | — | — | — | — | DO3A-monoamide | Gly | (3β,5β 7a,12a)-3-amino-7,12-dihydroxycholan-24-oic acid | none | LWATGHFM-NH$_2$ (SEQ ID NO: 16) |
| L291 | — | — | — | — | DO3A-monoamide | Gly | (3β,5β 7a,12a)-3-amino-7,12-dihydroxycholan-24-oic acid | none | QWAVGHFM-NH$_2$ (SEQ ID NO: 13) |
| L292 | — | — | — | — | DO3A-monoamide | Gly | 3β,5β 7α,12α)-3-amino-7,12-dihydroxycholan-24-oic acid | QRLGN | QWAVGHLM-NH$_2$* |
| L293 | — | — | — | — | DO3A-monoamide | Gly | 3β,5β 7α,12α)-3-amino-7,12-dihydroxycholan-24-oic acid | QRYGN | QWAVGHLM-NH$_2$* |
| L294 | — | — | — | — | DO3A-monoamide | Gly | 3β,5β 7α,12α)-3-amino-7,12-dihydroxycholan-24-oic acid | QKYGN | QWAVGHLM-NH$_2$* |
| L295 | — | — | — | — | Pglu-Q-Lys (DO3A-monoamide) | Gly | 3β,5β 7α,12α)-3-amino-7,12-dihydroxycholan-24-oic acid | LG-N | QWAVGHLM-NH$_2$* |
| L304 | — | — | — | — | DO3A-monoamide | Gly | 3-amino-3-deoxycholic acid | none | QRYGNQWAVGHLM-NH$_2$ (SEQ ID NO: 4) |
| L305 | — | — | — | — | DO3A-monoamide | Gly | 3-amino-3-deoxycholic acid | none | QKYGNQWAVGHLM-NH$_2$ (SEQ ID NO: 5) |
| L306 | — | — | — | — | DO3A-monoamide | Gly | 3-amino-3-deoxycholic acid | none | LGNQWAVGHLM-NH$_2$ (SEQ ID NO: 18) |

*BBN(7-14) is the sequence QWAVGHLM (SEQ ID NO: 1)

2D. Other Linking Groups

Other linking groups which may be used within the linker N-O-P include a chemical group that serves to couple the GRP receptor targeting peptide to the metal chelator or optical label while not adversely affecting either the targeting function of the GRP receptor targeting peptide or the metal complexing function of the metal chelator or the detectability of the optical label. Suitable other linking groups include peptides (i.e., amino acids linked together) alone, a non-peptide group (e.g., hydrocarbon chain) or a combination of an amino acid sequence and a non-peptide spacer.

In one embodiment, other linking groups for use within the linker N-O-P include L-glutamine and hydrocarbon chains, or a combination thereof.

In another embodiment, other linking groups for use within the linker N-O-P include a pure peptide linking group consisting of a series of amino acids (e.g., diglycine, triglycine, gly-gly-glu, gly-ser-gly, etc.), in which the total number of atoms between the N-terminal residue of the GRP receptor targeting peptide and the metal chelator or the optical label in the polymeric chain is ≦12 atoms.

In yet a further embodiment, other linking groups for use within the linker N-O-P can also include a hydrocarbon chain [i.e., $R_1$—$(CH_2)_n$—$R_2$] wherein n is 0-10, preferably n=3 to 9, $R_1$ is a group (e.g., $H_2N$—, HS—, —COOH) that can be used as a site for covalently linking the ligand backbone or the preformed metal chelator or metal complexing backbone or optical label; and $R_2$ is a group that is used for covalent coupling to the N-terminal $NH_2$-group of the GRP receptor targeting peptide (e.g., $R_2$ is an activated COOH group). Several chemical methods for conjugating ligands (i.e., chelators) or preferred metal chelates to biomolecules have been well described in the literature [Wilbur, 1992; Parker, 1990; Hermanson, 1996; Frizberg et al., 1995]. One or more of these methods could be used to link either the uncomplexed ligand (chelator) or the radiometal chelate or optical label to the linker or to link the linker to the GRP receptor targeting peptides. These methods include the formation of acid anhydrides, aldehydes, arylisothiocyanates, activated esters, or N-hydroxysuccinimides [Wilbur, 1992; Parker, 1990; Hermanson, 1996; Frizberg et al., 1995].

In a preferred embodiment, other linking groups for use within the linker N-O-P may be formed from linker precursors having electrophiles or nucleophiles as set forth below:

LP1: a linker precursor having on at least two locations of the linker the same electrophile E1 or the same nucleophile Nu1;

LP2: a linker precursor having an electrophile E1 and on another location of the linker a different electrophile E2;

LP3: a linker precursor having a nucleophile Nu1 and on another location of the linker a different nucleophile Nu2; or LP4: a linker precursor having one end functionalized with an electrophile E1 and the other with a nucleophile Nu1.

The preferred nucleophiles Nu1/Nu2 include —OH, —NH, —NR, —SH, —HN—NH$_2$, —RN—NH$_2$, and —RN—NHR', in which R' and R are independently selected from the definitions for R given above, but for R' is not H.

The preferred electrophiles E1/E2 include —COOH, —CH=O (aldehyde), —CR=OR' (ketone), —RN=C=S, —RN=C=O, —S—S-2-pyridyl, —SO$_2$—Y, —CH$_2$C(=O)Y, and

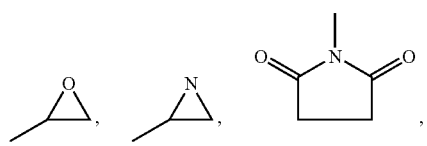

wherein Y can be selected from the following groups:

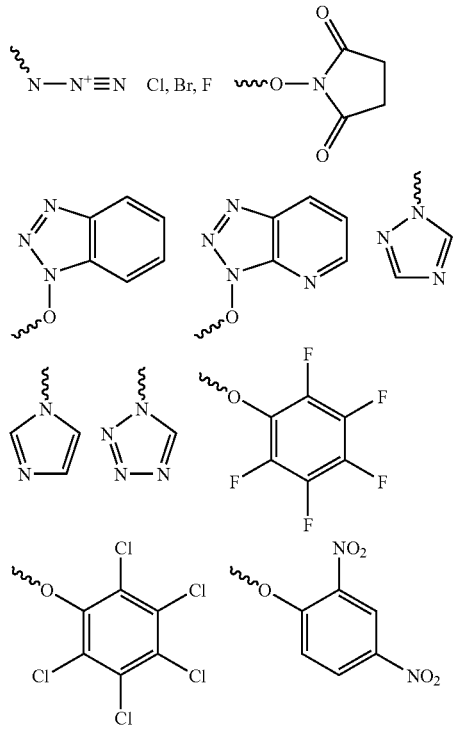

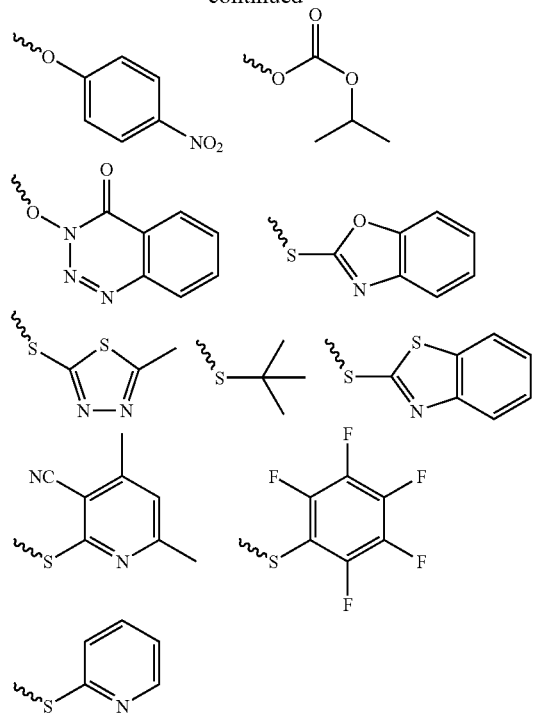

3. GRP Receptor Targeting Peptide

The GRP receptor targeting peptide (i.e., G in the formula M-N-O-P-G) is any peptide, equivalent, derivative or analogue thereof which has a binding affinity for the GRP receptor family.

The GRP receptor targeting peptide may take the form of an agonist or an antagonist. A GRP receptor targeting peptide agonist is known to "activate" the cell following binding with high affinity and may be internalized by the cell. Conversely, GRP receptor targeting peptide antagonists are known to bind only to the GRP receptor on the cell without being internalized by the cell and without "activating" the cell. In a preferred embodiment, the GRP receptor targeting peptide is an agonist.

In a more preferred embodiment of the present invention, the GRP agonist is a bombesin (BBN) analogue and/or a derivative thereof. The BBN derivative or analog thereof preferably contains either the same primary structure of the BBN binding region (i.e., BBN(7-14) (SEQ ID NO:1) or similar primary structures, with specific amino acid substitutions that will specifically bind to GRP receptors with better or similar binding affinities as BBN alone (i.e., Kd<25 nM). Suitable compounds include peptides, peptidomimetics and analogues and derivatives thereof. The presence of L-methionine (Met) at position BBN-14 will generally confer agonistic properties while the absence of this residue at BBN-14 generally confers antagonistic properties [Hoffken, 1994]. Some useful bombesin analogues are disclosed in U.S. Patent Pub. 2003/0224998, incorporated here in its entirety.

It is well documented in the art that there are a few and selective number of specific amino acid substitutions in the BBN (8-14) binding region (e.g., D-Ala[11] for L-Gly[11] or D-Trp[8] for L-Trp[8]), which can be made without decreasing binding affinity [Leban et al., 1994; Qin et al., 1994; Jensen et al., 1993]. In addition, attachment of some amino acid chains or other groups to the N-terminal amine group at position BBN-8 (i.e., the Trp[8] residue) can dramatically decrease the binding affinity of BBN analogues to GRP receptors [Davis et al., 1992; Hoffken, 1994; Moody et al., 1996; Coy, et al., 1988; Cai et al., 1994]. In a few cases, it is possible to append additional amino acids or chemical moieties without decreasing binding affinity.

Analogues of BBN receptor targeting peptides include molecules that target the GRP receptors with avidity that is greater than or equal to BBN, as well as muteins, retropeptides and retro-inverso-peptides of GRP or BBN. One of ordinary skill will appreciate that these analogues may also contain modifications which include substitutions, and/or deletions and/or additions of one or several amino acids, insofar that these modifications do not negatively alter the biological activity of the peptides described therein. These substitutions may be carried out by replacing one or more amino acids by their synonymous amino acids. Synonymous amino acids within a group are defined as amino acids that have sufficient physicochemical properties to allow substitution between members of a group in order to preserve the biological function of the molecule.

Deletions or insertions of amino acids may also be introduced into the defined sequences provided they do not alter the biological functions of said sequences. Preferentially such insertions or deletions should be limited to 1, 2, 3, 4 or 5 amino acids and should not remove or physically disturb or displace amino acids which are critical to the functional conformation. Muteins of the GRP receptor targeting peptides described herein may have a sequence homologous to the sequence disclosed in the present specification in which amino acid substitutions, deletions, or insertions are present at one or more amino acid positions. Muteins may have a biological activity that is at least 40%, preferably at least 50%, more preferably 60-70%, most preferably 80-90% of the peptides described herein. However, they may also have a biological activity greater than the peptides specifically exemplified, and thus do not necessarily have to be identical to the biological function of the exemplified peptides. Analogues of GRP receptor targeting peptides also include peptidomimetics or pseudopeptides incorporating changes to the amide bonds of the peptide backbone, including thioamides, methylene amines, and E-olefins. Also peptides based on the structure of GRP, BBN or their peptide analogues with amino acids replaced by N-substituted hydrazine carbonyl compounds (also known as aza amino acids) are included in the term analogues as used herein.

The GRP receptor targeting peptide can be prepared by various methods depending upon the selected chelator. The peptide can generally be most conveniently prepared by techniques generally established and known in the art of peptide synthesis, such as the solid-phase peptide synthesis (SPPS) approach. Solid-phase peptide synthesis (SPPS) involves the stepwise addition of amino acid residues to a growing peptide chain that is linked to an insoluble support or matrix, such as polystyrene. The C-terminal residue of the peptide is first anchored to a commercially available support with its amino group protected with an N-protecting agent such as a t-butyloxycarbonyl group (Boc) or a fluorenylmethoxycarbonyl (Fmoc) group. The amino protecting group is removed with suitable deprotecting agents such as TFA in the case of Boc or piperidine for Fmoc and the next amino acid residue (in N-protected form) is added with a coupling agent such as N,N'-dicyclohexylcarbodiimide (DCC), or N,N'-diisopropylcarbodiimide (DIC) or 2-(1H-benzotriazol-1-yl)-1,1,3,3-tetramethyluronium hexafluorophosphate (HBTU). Upon formation of a peptide bond, the reagents are washed from the support. After addition of the final residue, the peptide is cleaved from the support with a suitable reagent such as trifluoroacetic acid (TFA) or hydrogen fluoride (HF).

The linker may then be coupled to form a conjugate by reacting the free amino group of the Trp[8] residue of the GRP receptor targeting peptide with an appropriate functional group of the linker. The entire construct of chelator, linker and targeting moiety discussed above may also be assembled on resin and then cleaved by agency of suitable reagents such as trifluoroacetic acid or HF, as well.

Bombesin (7-14) is subject to proteolytic cleavage in vitro and in vivo, which shortens the half-life of the peptide. It is well known in the literature that the amide bond of the backbone of the polypeptide may be substituted and retain activity, while resisting proteolytic cleavage. For example, to reduce or eliminate undesired proteolysis, or other degradation pathways that diminish serum stability, resulting in reduced or abolished bioactivity, or to restrict or increase conformational flexibility, it is common to substitute amide bonds within the backbone of the peptides with functionality that mimics the existing conformation or alters the conformation in the manner desired. Such modifications may produce increased binding affinity or improved pharmacokinetic behavior. It is understood that those knowledgeable in the art of peptide synthesis can make the following amide bond-changes for any amide bond connecting two amino acids (e.g., amide bonds in the targeting moiety, linker, chelator, etc.) with the expectation that the resulting peptides could have the same or improved activity: insertion of alpha-N-methylamides or backbone thioamides, removal of the carbonyl to produce the cognate secondary amines, replacement of one amino acid with an aza-aminoacid to produce semicarbazone derivatives, and use of E-olefins and substituted E-olefins as amide bond surrogates. The hydrolysis can also be prevented by incorporation of a D-amino acid of one of the amino acids of the labile amide bond, or by alpha-methyl aminoacid derivatives. Backbone amide bonds have also been replaced by heterocycles such as oxazoles, pyrrolidinones, imidazoles, as well as ketomethylenes and fluoroolefins.

Some specific compounds including such amide bond modifications are listed in Table 4a. The abbreviations used in Table 4a for the various amide bond modifications are exemplified below:

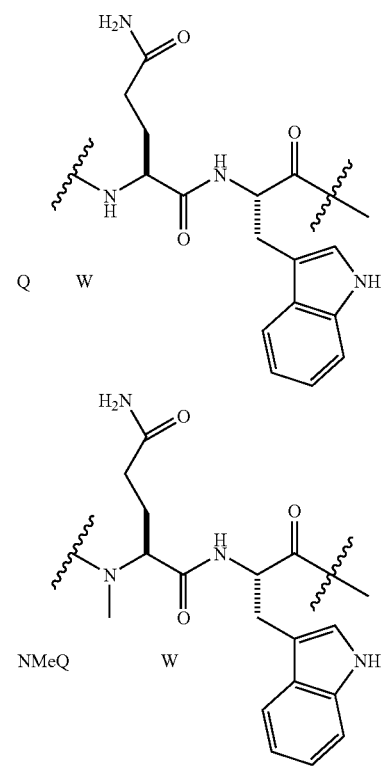

Q    W

NMeQ    W

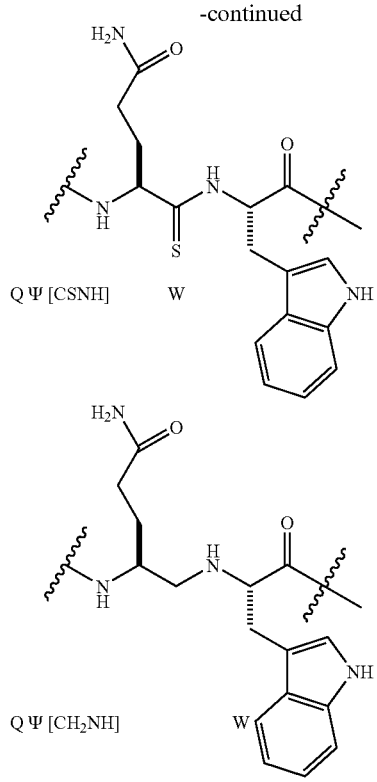

Q Ψ [CSNH]   W

Q Ψ [CH₂NH]   W

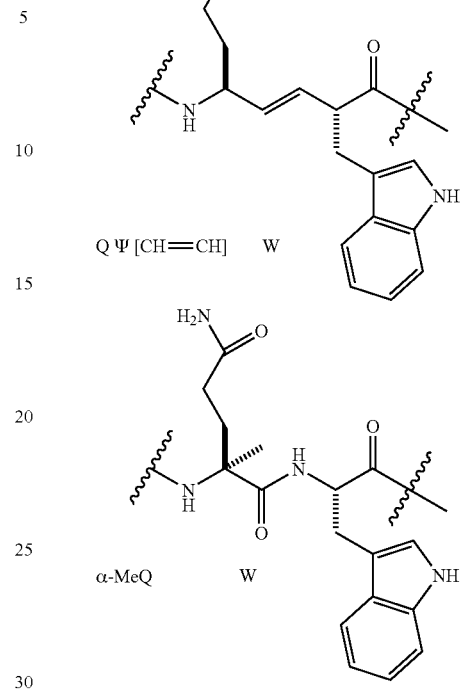

Q Ψ [CH=CH]   W

α-MeQ   W

TABLE 4A

Table 4A - Preferred Amide Bond Modified Analogs

| Compound | M-N-O-P | | | BBN Analogue | | | | | |
|---|---|---|---|---|---|---|---|---|---|
| L401 | DO3A-monoamide-G-Abz4 | Nme-Q | W | A | V | G | H | L | M-NH₂ |
| L402 | DO3A-monoamide-G-Abz4 | Q-Ψ[CSNH] | W | A | V | G | H | L | M-NH₂ |
| L403 | DO3A-monoamide-G-Abz4 | Q-Ψ[CH₂NH] | W | A | V | G | H | L | M-NH₂ |
| L404 | DO3A-monoamide-G-Abz4 | Q-Ψ[CH=CH] | W | A | V | G | H | L | M-NH₂ |
| L405 | DO3A-monoamide-G-Abz4 | α-MeQ | W | A | V | G | H | L | M-NH₂ |
| L406 | DO3A-monoamide-G-Abz4 | Q | Nme-W | A | V | G | H | L | M-NH₂ |
| L407 | DO3A-monoamide-G-Abz4 | Q | W-Ψ[CSNH] | A | V | G | H | L | M-NH₂ |
| L408 | DO3A-monoamide-G-Abz4 | Q | W-Ψ[CH₂NH] | A | V | G | H | L | M-NH₂ |
| L409 | DO3A-monoamide-G-Abz4 | Q | W-Ψ[CH=CH] | A | V | G | H | L | M-NH₂ |
| L410 | DO3A-monoamide-G-Abz4 | Q | α-MeW | A | V | G | H | L | M-NH₂ |
| L411 | DO3A-monoamide-G-Abz4 | Q | W | Nme-A | V | G | H | L | M-NH₂ |
| L412 | DO3A-monoamide-G-Abz4 | Q | W | A-Ψ[CSNH] | V | G | H | L | M-NH₂ |

TABLE 4A-continued

Table 4A - Preferred Amide Bond Modified Analogs

| Compound | M-N-O-P | | | BBN Analogue | | | | | |
|---|---|---|---|---|---|---|---|---|---|
| L413 | DO3A-monoamide-G-Abz4 | Q | W | A-Ψ[CH$_2$NH] | V | G | H | L | M-NH$_2$ |
| L414 | DO3A-monoamide-G-Abz4 | Q | W | Aib | V | G | H | L | M-NH$_2$ |
| L415 | DO3A-monoamide-G-Abz4 | Q | W | A | V | Sar | H | L | M-NH$_2$ |
| L416 | DO3A-monoamide-G-Abz4 | Q | W | A | V | G-Ψ[CSNH] | H | L | M-NH$_2$ |
| L417 | DO3A-monoamide-G-Abz4 | Q | W | A | V | G-Ψ[CH=CH] | H | L | M-NH$_2$ |
| L418 | DO3A-monoamide-G-Abz4 | Q | W | A | V | Dala | H | L | M-NH$_2$ |
| L419 | DO3A-monoamide-G-Abz4 | Q | W | A | V | G | Nme-His | L | M-NH$_2$ |
| L420 | DO3A-monoamide-G-Abz4 | Q | W | A | V | G | H-Ψ[CSNH] | L | M-NH$_2$ |
| L421 | DO3A-monoamide-G-Abz4 | Q | W | A | V | G | H-Ψ[CH$_2$NH] | L | M-NH$_2$ |
| L422 | DO3A-monoamide-G-Abz4 | Q | W | A | V | G | H-Ψ[CH=CH] | L | M-NH$_2$ |
| L423 | DO3A-monoamide-G-Abz4 | Q | W | A | V | G | α-MeH | L | M-NH$_2$ |
| L424 | DO3A-monoamide-G-Abz4 | Q | W | A | V | G | H | Nme-L | M-NH$_2$ |
| L425 | DO3A-monoamide-G-Abz4 | Q | W | A | V | G | H | α-MeL | M-NH$_2$ |
| L300 | DO3A-monoamide-G-ABz4 | Q | W | A | V | G | H | F-L | NH$_2$ |

In the above table, QWAVGHLM-NH$_2$ is SEQ ID NO: 1 and QWAVGHFL-NH$_2$ (L300) is SEQ ID NO: 22.

4. Labeling and Administration of Radiopharmaceutical Compounds

Incorporation of the metal within the radiopharmaceutical conjugates can be achieved by various methods commonly known in the art of coordination chemistry. When the metal is $^{99m}$Tc, a preferred radionuclide for diagnostic imaging, the following general procedure can be used to form a technetium complex. A peptide-chelator conjugate solution is formed by initially dissolving the conjugate in water, dilute acid, or in an aqueous solution of an alcohol such as ethanol. The solution is then optionally degassed to remove dissolved oxygen. When an —SH group is present in the peptide, a thiol protecting group such as Acm (acetamidomethyl), trityl or other thiol protecting group may optionally be used to protect the thiol from oxidation. The thiol protecting group(s) are removed with a suitable reagent, for example with sodium hydroxide, and are then neutralized with an organic acid such as acetic acid (pH 6.0-6.5). Alternatively, the thiol protecting group can be removed in situ during technetium chelation. In the labeling step, sodium pertechnetate obtained from a molybdenum generator is added to a solution of the conjugate with a sufficient amount of a reducing agent, such as stannous chloride, to reduce technetium and is either allowed to stand at room temperature or is heated. The labeled conjugate can be separated from the contaminants $^{99m}$TcO$_4^-$ and colloidal $^{99m}$TcO$_2$ chromatographically, for example with a C-18 Sep Pak cartridge [Millipore Corporation, Waters Chromatography Division, 34 Maple Street, Milford, Mass. 01757] or by HPLC using methods known to those skilled in the art.

In an alternative method, the labeling can be accomplished by a transchelation reaction. In this method, the technetium source is a solution of technetium that is reduced and complexed with labile ligands prior to reaction with the selected chelator, thus facilitating ligand exchange with the selected chelator. Examples of suitable ligands for transchelation includes tartrate, citrate, gluconate, and heptagluconate. It will be appreciated that the conjugate can be labeled using the techniques described above, or alternatively, the chelator itself may be labeled and subsequently coupled to the peptide to form the conjugate; a process referred to as the "prelabeled chelate" method. Re and Tc are both in row VIIB of the Periodic Table and they are chemical congeners. Thus, for the most part, the complexation chemistry of these two metals with ligand frameworks that exhibit high in vitro and in vivo stabilities are the same [Eckelman, 1995] and similar chelators and procedures can be used to label with Re. Many $^{99m}$Tc or $^{186/188}$Re complexes, which are employed to form stable radiometal complexes with peptides and proteins, chelate these metals in their +5 oxidation state [Lister-James et al., 1997]. This oxidation state makes it possible to selectively place $^{99m}$Tc- or $^{186/188}$Re into ligand frameworks already conjugated to the biomolecule, constructed from a variety of $^{99m}$Tc(V) and/or $^{186/188}$Re(V) weak chelates (e.g., $^{99m}$Tc-glucoheptonate, citrate, gluconate, etc.) [Eckelman, 1995; Lister-James et al., 1997; Pollak al., 1996]. These references are hereby incorporated by reference in their entirety.

5. Diagnostic and Therapeutic Uses

When labeled with diagnostically and/or therapeutically useful metals or optical labels, compounds of the present invention can be used to treat and/or detect any pathology involving overexpression of GRP receptors (or NMB receptors) by procedures established in the art of radiodiagnostics, radiotherapeutics and optical imaging. [See, e.g., Bushbaum, 1995; Fischman et al., 1993; Schubiger et al., 1996; Lowbertz et al., 1994; Krenning et al., 1994; examples of optical dyes include, but are not limited to those described in WO 98/18497, WO 98/18496, WO 98/18495, WO 98/18498, WO 98/53857, WO 96/17628, WO 97/18841, WO 96/23524, WO 98/47538, and references cited therein, hereby incorporated by reference in their entirety.]

GRP-R expression is highly upregulated in a variety of human tumors. See e.g., WO 99/62563. Thus, compounds of the invention may be widely useful in treating and diagnosing cancers, including prostate cancer (primary and metastatic), breast cancer (primary and metastatic), colon cancer, gastric cancer, pancreatic cancer, non small cell lung cancer, small cell lung cancer, gastrinomas, melanomas, glioblastomas, neuroblastomas, uterus leiomyosarcoma tumors, prostatic intraepithelial neoplasias [PIN], and ovarian cancer. Additionally, compounds of the invention may be useful to distinguish between conditions in which GRP receptors are upregulated and those in which they are not (e.g. chronic pancreatitis and ductal pancreatic carcinoma, respectively The compounds of the invention, which, as explained in more detail in the Examples, show greater specificity and higher uptake in tumors in vivo than compounds without the novel linkers disclosed herein, exhibit an improved ability to target GRP receptor-expressing tumors and thus to image or deliver radiotherapy to these tissues. Indeed, as shown in the Examples, radiotherapy is more effective (and survival time increased) using compounds of the invention. Moreover, as shown in the Examples, compounds of the invention are particularly useful in the treatment of prostate cancer, including bone or soft tissue metastases of prostate cancer and in both hormone sensitive and hormone refractory prostate cancer. Compounds of the invention, particularly radiolabeled L70, are also useful in methods of delaying progression and decreasing vascular permeability of prostate cancer, particularly hormone sensitive prostate cancer. Indeed, as shown in the Examples, compounds of the invention may delay time to progression by about 100%. This is significant particularly as some drugs have been approved which decrease time to progression by as little as 15%. The compounds of the invention are also useful in facilitating combination therapy of hormone sensitive prostate cancer. Combination therapy includes administration of a compound of the invention as well as another substance useful in treating prostate cancer such, as for example, a chemotherapeutic. Compounds of the invention facilitate such combination therapy by, for example, normalizing the blood flow to tumors, facilitating the delivery of the additional therapeutic agent.

Furthermore, the instant invention includes a method of increasing targeting of a labeled compound of the invention to GRP receptor expressing target tissue as compared to normal (e.g. non-target) GRP receptor expressing tissue. This method comprises administering the appropriate mass of GRP receptor targeting peptide or conjugate, prior to or during administration of labeled compound of the invention. Similarly, the invention includes an improved method of administration of labeled compounds of the invention in which tumor targeting is optimized comprising administering the appropriate mass dose of GRP receptor targeting peptide or conjugate prior to or during administration of labeled compound of the invention. Such pre- or co-dosing has been found to saturate non-target GRP receptors, decreasing their ability to compete with GRP receptors on tumor tissue.

It has previously been demonstrated that it can be beneficial to pre- or co-dose with increased masses of an active ingredient to occupy circulating binding sites or binding sites on normal (e.g., non-target) tissue which would otherwise compete with the target tissue binding sites for the active ingredient. The goal of such pre-dosing or co-dosing is to increase targeting to and uptake in the target tissue. For instance, unlabeled anti-CD20 antibodies have been administered prior to administration of radioactive anti-CD20 antibodies to occupy binding sites on circulating cells in an attempt to improve visualization of disease sites. In another example, increasing masses of cold somatostatin have been administered in an attempt to saturate the binding sites of normal tissue and thus improve visualization of disease.

No circulating GRP receptor targeting peptide binding proteins have been identified to date. However, there are some normal tissues in the body that express appreciable levels of GRP receptors, which may compete with GRP receptor expressing target tissue. Increasing mass dose would be expected to saturate the binding sites in such tissues. However, it has been unexpectedly found that when mass doses of compounds of the invention are administered, the behaviour of GRP receptor-expressing tumor tissue is different from that of GRP receptor-expressing normal tissues. Specifically, while normal tissue expressing GRP receptors exhibit the expected saturation by the mass dose and thus decreased uptake of labeled compounds of the invention, GRP expressing tumor tissue is unexpectedly resistant to saturation as the mass dose is increased, retaining the ability to bind labeled compounds of the invention. The difference in response between the normal tissue and the tumor tissue may be a reflection of the escape from control of the tumor tissues. Thus this beneficial effect is most likely to occur in those cases where the binding site for a regulatory peptide or compound which is normally closely controlled by the physiology of the normal tissue escapes such control when present in tumor tissue, as in for example the case of GRP receptor expressing tumor tissue.

Thus, in order to optimize tumor targeting, an appropriate mass dose of compound of the invention may be administered prior to or during administration of the labeled compounds of the invention. It should be noted that while administration of a mass dose of unlabeled compounds of the invention is preferred, any active peptide that binds to and interacts with the GRP receptor may be used, whether or not conjugated to a linker and/or a metal chelator or detectable label and whether or not labeled. Preferably, a mass dose of a GRP receptor agonist is used and more preferably it is conjugated to a linker and/or a metal chelator or detectable label, such as those disclosed herein. Most preferably a mass dose of a compound of the invention is administered. While use of unlabeled compounds is preferred for some embodiments, the mass dose may include labeled compound. Indeed, for co-administration applications, administration of a single dose which includes the mass dose and the diagnostic or therapeutic dose of the labeled compound is preferred. In this instance, a labeled, but low specific activity dose is administered which delivers both the appropriate mass dose of unlabeled compound as well as the diagnostically or therapeutically useful dose of labeled compound.

The appropriate mass dose will depend on the specifics of the patient and application, but selection of such dose is within the skill in the art. Useful mass doses are in the range of about 1 to about 20 µg/m$^2$ and preferred doses are in the range of about 2 to about 10 µg/m$^2$. Where the mass dose is given before the labeled compound of the invention (e.g. pre-dosing) the mass dose is preferably administered no more than about 60 minutes before the diagnostic or therapeutic dose.

The diagnostic application of these compounds can be as a first line diagnostic screen for the presence of neoplastic cells using scintigraphic, optical, sonoluminescence or photoacoustic imaging, as an agent for targeting neoplastic tissue using hand-held radiation detection instrumentation in the field of radioimmuno guided surgery (RIGS), as a means to obtain dosimetry data prior to administration of the matched pair radiotherapeutic compound, and as a means to assess GRP receptor population as a function of treatment over time.

The therapeutic application of these compounds can be defined as an agent that will be used as a first line therapy in the treatment of cancer, as combination therapy with a chemotherapeutic or other drug, and/or as a matched pair therapeutic agent. Treatment encompasses at least partial amelioration or alleviation of symptoms of a given condition. For example, treatment may result in a decrease in the size of a tumor or other diseased area, prevention of an increase in size of the tumor or diseased area, reduction in aberrant blood flow or otherwise normalizing the blood flow in the tumor, delaying time to progression of the tumor, increasing survival of the patient, etc. The matched pair concept refers to a single unmetallated compound which can serve as both a diagnostic and a therapeutic agent depending on the radiometal that has been selected for binding to the appropriate chelate. If the chelator cannot accommodate the desired metals, appropriate substitutions can be made to accommodate the different metal while maintaining the pharmacology such that the behavior of the diagnostic compound in vivo can be used to predict the behavior of the radiotherapeutic compound. When utilized in conjunction with combination therapy any suitable chemotherapeutic or drug may be used, including for example, antineoplastic agents, such as platinum compounds (e.g., spiroplatin, cisplatin, and carboplatin), methotrexate, adriamycin, mitomycin, ansamitocin, bleomycin, cytosine, arabinoside, arabinosyl adenine, mercaptopolylysine, vincristine, busulfan, chlorambucil, melphalan (e.g., PAM, a, L-PAM or phennylalanine mustard), mercaptopurine, mitotane. procarbazine hydrochloride, dactinomycin (actinomycin D), daunorubcin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) *Erwina aparaginase*, etoposide-(VP-16), interferon α-2a, interferon α-2b, teniposide (VM-26), vinblastine sulfate (VLB), and arabinosyl. In certain embodiments, the therapeutic may be monoclonal antibody, such as a monoclonal antibody capable of binding to melanoma antigen.

A conjugate labeled with a radionuclide metal, such as $^{177}$Lu or $^{99m}$Tc, can be administered to a mammal, including human patients or subjects, by, for example, intravenous, subcutaneous or intraperitoneal injection in a pharmaceutically acceptable carrier and/or solution such as salt solutions like isotonic saline. Radiolabeled scintigraphic imaging agents provided by the present invention are provided having a suitable amount of radioactivity. In forming $^{99m}$Tc radioactive complexes, it is generally preferred to form radioactive complexes in solutions containing radioactivity at concentrations of from about 0.01 millicurie (mCi) to 100 mCi per mL. Generally, the unit dose to be administered has a radioactivity of about 0.01 mCi to about 100 mCi, preferably 1 mCi to 30 mCi. The solution to be injected at unit dosage is from about 0.01 mL to about 10 mL. The amount of labeled conjugate appropriate for administration is dependent upon the distribution profile of the chosen conjugate in the sense that a rapidly cleared conjugate may need to be administered in higher doses than one that clears less rapidly. In vivo distribution and localization can be tracked by standard scintigraphic techniques at an appropriate time subsequent to administration; typically between thirty minutes and 180 minutes depending upon the rate of accumulation at the target site with respect to the rate of clearance at non-target tissue. For example, after injection of the diagnostic radionuclide-labeled compounds of the invention into the patient, a gamma camera calibrated for the gamma ray energy of the nuclide incorporated in the imaging agent can be used to image areas of uptake of the agent and quantify the amount of radioactivity present in the site. Imaging of the site in vivo can take place in a few minutes. However, imaging can take place, if desired, hours or even longer, after the radiolabeled peptide is injected into a patient. In most instances, a sufficient amount of the administered dose will accumulate in the area to be imaged within about 0.1 hour to permit the taking of scintiphotos.

The compounds of the present invention can be administered to a patient alone or as part of a composition that contains other components such as excipients, diluents, radical scavengers, stabilizers, and carriers, all of which are well-known in the art. The compounds can be administered to patients either intravenously or intraperitoneally.

There are numerous advantages associated with the present invention. The compounds made in accordance with the present invention form stable, well-defined $^{99m}$Tc or $^{186/188}$Re labeled compounds. Similar compounds of the invention can also be made by using appropriate chelator frameworks for the respective radiometals, to form stable, well-defined products labeled with $^{153}$Sm, $^{90}$Y, $^{166}$Ho, $^{105}$Rh, $^{199}$Au, $^{149}$Pm, $^{171}$Lu, $^{111}$In or other radiometals. The radiolabeled GRP receptor targeting peptides selectively bind to neoplastic cells expressing GRP receptors, and if an agonist is used, become internalized, and are retained in the tumor cells for extended time periods. The radioactive material that does not reach (i.e., does not bind) the cancer cells is preferentially excreted efficiently into the urine with minimal retention of the radiometal in the kidneys.

6. Optical Imaging, Sonoluminescence, Photoacoustic Imaging and Phototherapy In accordance with the present invention, a number of optical parameters may be employed to determine the location of a target with in vivo light imaging after injection of the subject with an optically-labeled compound of the invention. Optical parameters to be detected in the preparation of an image may include transmitted radiation, absorption, fluorescent or phosphorescent emission, light reflection, changes in absorbance amplitude or maxima, and elastically scattered radiation. For example, biological tissue is relatively translucent to light in the near infrared (NIR) wavelength range of 650-1000 nm. NIR radiation can penetrate tissue up to several centimeters, permitting the use of compounds of the present invention to image target-containing tissue in vivo. The use of visible and near-infrared (NIR) light in clinical practice is growing rapidly. Compounds absorbing or emitting in the visible, NIR, or long-wavelength (UV-A, >350 nm) region of the electromagnetic spectrum are potentially useful for optical tomographic imaging, endoscopic visualization, and phototherapy.

A major advantage of biomedical optics lies in its therapeutic potential. Phototherapy has been demonstrated to be a safe and effective procedure for the treatment of various surface lesions, both external and internal. Dyes are important to enhance signal detection and/or photosensitizing of tissues in optical imaging and phototherapy. Previous studies have shown that certain dyes can localize in tumors and serve as a powerful probe for the detection and treatment of small cancers (D. A. Bellnier et al., Murine pharmacokinetics and antitumor efficacy of the photodynamic sensitizer 2-[1-hexyloxyethyl]-2-devinyl pyropheophorbide-a, J. Photochem. Photobiol., 1993, 20, pp. 55-61; G. A. Wagnieres et al., In vivo fluorescence spectroscopy and imaging for oncological applications, Photochem. Photobiol., 1998, 68, pp. 603-632; J. S. Reynolds et al., Imaging of spontaneous canine mammary tumors using fluorescent contrast agents, Photochem. Photobiol., 1999, 70, pp. 87-94). All of these listed references are hereby incorporated by reference in their entirety. However, these dyes do not localize preferentially in malignant tissues.

In an exemplary embodiment, the compounds of the invention may be conjugated with photolabels, such as optical dyes, including organic chromophores or fluorophores, having extensive delocalized ring systems and having absorption or emission maxima in the range of 400-1500 nm. The compounds of the invention may alternatively be derivatized with a bioluminescent molecule. The preferred range of absorption maxima for photolabels is between 600 and 1000 nm to minimize interference with the signal from hemoglobin. Preferably, photoabsorption labels have large molar absorptivities, e.g. >$10^5$ cm$^{-1}$M$^{-1}$, while fluorescent optical dyes will have high quantum yields. Examples of optical dyes include, but are not limited to those described in U.S. Pat. No. 6,641, 798, WO 98/18497, WO 98/18496, WO 98/18495, WO 98/18498, WO 98/53857, WO 96/17628, WO 97/18841, WO 96/23524, WO 98/47538, and references cited therein, all hereby incorporated by reference in their entirety. For example, the photolabels may be covalently linked directly to compounds of the invention, such as, for example, compounds comprised of GRP receptor targeting peptides and linkers of the invention. Several dyes that absorb and emit light in the visible and near-infrared region of electromagnetic spectrum are currently being used for various biomedical applications due to their biocompatibility, high molar absorptivity, and/or high fluorescence quantum yields. The high sensitivity of the optical modality in conjunction with dyes as contrast agents parallels that of nuclear medicine, and permits visualization of organs and tissues without the undesirable effect of ionizing radiation. Cyanine dyes with intense absorption and emission in the near-infrared (NIR) region are particularly useful because biological tissues are optically transparent in this region (B. C. Wilson, Optical properties of tissues. Encyclopedia of Human Biology, 1991, 5, 587-597). For example, indocyanine green, which absorbs and emits in the NIR region has been used for monitoring cardiac output, hepatic functions, and liver blood flow (Y-L. He, H. Tanigami, H. Ueyama, T. Mashimo, and I. Yoshiya, Measurement of blood volume using indocyanine green measured with pulse-spectrometry: Its reproducibility and reliability. Critical Care Medicine, 1998, 26(8), 1446-1451; J. Caesar, S. Shaldon, L. Chiandussi, et al., The use of Indocyanine green in the measurement of hepatic blood flow and as a test of hepatic function. Clin. Sci. 1961, 21, 43-57) and its functionalized derivatives have been used to conjugate biomolecules for diagnostic purposes (R. B. Mujumdar, L. A. Ernst, S. R. Mujumdar, et al., Cyanine dye labeling reagents: Sulfoindocyanine succinimidyl esters. Bioconjugate Chemistry, 1993, 4(2), 105-111; Linda G. Lee and Sam L. Woo. "N-Heteroaromatic ion and iminium ion substituted cyanine dyes for use as fluorescent labels", U.S. Pat. No. 5,453,505; Eric Hohenschuh, et al. "Light imaging contrast agents", WO 98/48846; Jonathan Turner, et al. "Optical diagnostic agents for the diagnosis of neurodegenerative diseases by means of near infra-red radiation", WO 98/22146; Kai Licha, et al. "In-vivo diagnostic process by near infrared radiation", WO 96/17628; Robert A. Snow, et al., Compounds, WO 98/48838, U.S. Pat. No. 6,641, 798. All of these listed references are hereby incorporated by reference in their entirety.

After injection of the optically-labeled compound, the patient is scanned with one or more light sources (e.g., a laser) in the wavelength range appropriate for the photolabel employed in the agent. The light used may be monochromatic or polychromatic and continuous or pulsed. Transmitted, scattered, or reflected light is detected via a photodetector tuned to one or multiple wavelengths to determine the location of target-containing tissue (e.g., tissue containing GRP) in the subject. Changes in the optical parameter may be monitored over time to detect accumulation of the optically-labeled reagent at the target site (e.g. the tumor or other site with GRP receptors). Standard image processing and detecting devices may be used in conjunction with the optical imaging reagents of the present invention.

The optical imaging reagents described above may also be used for acousto-optical or sonoluminescent imaging performed with optically-labeled imaging agents (see, U.S. Pat. No. 5,171,298, WO 98/57666, and references therein). In acousto-optical imaging, ultrasound radiation is applied to the subject and affects the optical parameters of the transmitted, emitted, or reflected light. In sonoluminescent imaging, the applied ultrasound actually generates the light detected. Suitable imaging methods using such techniques are described in WO 98/57666.

Various imaging techniques and reagents are described in U.S. Pat. Nos. 6,663,847, 6,656,451, 6,641,798, 6,485,704, 6,423,547, 6,395,257, 6,280,703, 6,277,841, 6,264,920, 6,264,919, 6,228,344, 6,217,848, 6,190,641, 6,183,726, 6,180,087, 6,180,086, 6,180,085, 6,013,243, and published U.S. Patent Applications 2003185756, 20031656432, 2003158127, 2003152577, 2003143159, 2003105300, 2003105299, 2003072763, 2003036538, 2003031627, 2003017164, 2002169107, 2002164287, and 2002156117, all of which are hereby incorporated by reference.

7. Radiotherapy

Radioisotope therapy involves the administration of a radiolabeled compound in sufficient quantity to damage or destroy the targeted tissue. After administration of the compound (by e.g., intravenous, subcutaneous, or intraperitonal injection), the radiolabeled pharmaceutical localizes preferentially at the disease site (in this instance, tumor tissue or other tissue that expresses the pertinent GRP receptor). Once localized, the radiolabeled compound then damages or destroys the diseased tissue with the energy that is released during the radioactive decay of the isotope that is administered. As discussed herein, the invention also encompasses use of radiotherapy in combination with chemotherapy (or in combination with any other appropriate therapeutic agent). Compounds of the invention may facilitate such combination therapy by, inter alia, improving delivery of the chemotherapy to the tumor.

The design of a successful radiotherapeutic involves several critical factors:

1. selection of an appropriate targeting group to deliver the radioactivity to the disease site;
2. selection of an appropriate radionuclide that releases sufficient energy to damage that disease site, without substantially damaging adjacent normal tissues; and
3. selection of an appropriate combination of the targeting group and the radionuclide without adversely affecting the ability of this conjugate to localize at the disease site. For radiometals, this often involves a chelating group that coordinates tightly to the radionuclide, combined with a linker that couples said chelate to the targeting group, and that affects the overall biodistribution of the compound to maximize uptake in target tissues and minimize uptake in normal, non-target organs.

The present invention provides radiotherapeutic agents that satisfy all three of the above criteria, through proper selection of targeting group, radionuclide, metal chelate and linker.

Radiotherapeutic agents may contain a chelated 3+ metal ion from the class of elements known as the lanthanides (elements of atomic number 57-71) and their analogs (i.e. $M^{3+}$ metals such as yttrium and indium). Typical radioactive metals in this class include the isotopes 90-Yttrium, 111-Indium, 149-Promethium, 153-Samarium, 166-Dysprosium, 166-Holmium, 175-Ytterbium, and $^{177}$-Lutetium. All of these metals (and others in the lanthanide series) have very similar chemistries, in that they remain in the +3 oxidation state, and prefer to chelate to ligands that bear hard (oxygen/nitrogen) donor atoms, as typified by derivatives of the well known chelate DTPA (diethylenetriaminepentaacetic acid) and polyaza-polycarboxylate macrocycles such as DOTA (1,4,7,10-tetrazacyclododecane-N,N',N'',N'''-tetraacetic acid and its close analogs. The structures of these chelating ligands, in their fully deprotonated form are shown below.

These chelating ligands encapsulate the radiometal by binding to it via multiple nitrogen and oxygen atoms, thus preventing the release of free (unbound) radiometal into the body. This is important, as in vivo dissociation of $3^+$ radiometals from their chelate can result in uptake of the radiometal in the liver, bone and spleen [Brechbiel M W, Gansow O A, "Backbone-substituted DTPA ligands for $^{90}$Y radioimmunotherapy", Bioconj. Chem. 1991; 2: 187-194; Li, W P, Ma D S, Higginbotham C, Hoffman T, Ketring A R, Cutler C S, Jurisson, S S, "Development of an in vitro model for assessing the in vivo stability of lanthanide chelates." Nucl. Med. Biol. 2001; 28(2): 145-154; Kasokat T, Urich K. Arzneim.-Forsch, "Quantification of dechelation of gadopentetate dimeglumine in rats". 1992; 42(6): 869-76]. Unless one is specifically targeting these organs, such non-specific uptake is highly undesirable, as it leads to non-specific irradiation of non-target tissues, which can lead to such problems as hematopoietic suppression due to irradiation of bone marrow.

For radiotherapy applications any of the chelators for therapeutic radionuclides disclosed herein may be used. However, forms of the DOTA chelate [Tweedle M F, Gaughan G T, Hagan J T, "1-Substituted-1,4,7-triscarboxymethyl-1,4,7,10-tetraazacyclododecane and analogs." U.S. Pat. No. 4,885,363, Dec. 5, 1989] are particularly preferred, as the DOTA chelate is expected to de-chelate less in the body than DTPA or other linear chelates. Compounds L64 and L70 (when labeled with an appropriate therapeutic radionuclide) are particularly preferred for radiotherapy.

General methods for coupling DOTA-type macrocycles to targeting groups through a linker (e.g. by activation of one of the carboxylates of the DOTA to form an active ester, which is then reacted with an amino group on the linker to form a stable amide bond), are known to those skilled in the art. (See e.g. Tweedle et al. U.S. Pat. No. 4,885,363). Coupling can also be performed on DOTA-type macrocycles that are modified on the backbone of the polyaza ring.

The selection of a proper nuclide for use in a particular radiotherapeutic application depends on many factors, including:

a. Physical half-life—This should be long enough to allow synthesis and purification of the radiotherapeutic construct from radiometal and conjugate, and delivery of said construct to the site of injection, without significant radioactive decay prior to injection. Preferably, the radionuclide should have a physical half-life between about 0.5 and 8 days.

b. Energy of the emission(s) from the radionuclide—Radionuclides that are particle emitters (such as alpha emitters, beta emitters and Auger electron emitters) are particularly useful, as they emit highly energetic particles that deposit their energy over short distances, thereby producing highly localized damage. Beta emitting radionuclides are particularly preferred, as the energy from beta particle emissions from these isotopes is deposited within 5 to about 150 cell diameters. Radiotherapeutic agents prepared from these nuclides are capable of killing diseased cells that are relatively close to their site of localization, but cannot travel long distances to damage adjacent normal tissue such as bone marrow.

c. Specific activity (i.e. radioactivity per mass of the radionuclide)-Radionuclides that have high specific activity (e.g.

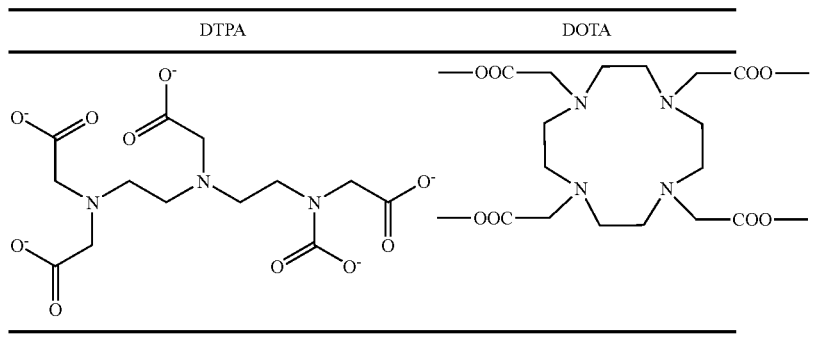

generator produced 90-Y, 111-In, 177-Lu) are particularly preferred. The specific activity of a radionuclide is determined by its method of production, the particular target that is used to produce it, and the properties of the isotope in question.

Many of the lanthanides and lanthanoids include radioisotopes that have nuclear properties that make them suitable for use as radiotherapeutic agents, as they emit beta particles. Some of these are listed in the table below.

| Isotope | Half-Life (days) | Max b-energy (MeV) | Gamma energy (keV) | Approximate range of b-particle (cell diameters) |
|---|---|---|---|---|
| $^{149}$-Pm | 2.21 | 1.1 | 286 | 60 |
| $^{153}$-Sm | 1.93 | 0.69 | 103 | 30 |
| $^{166}$-Dy | 3.40 | 0.40 | 82.5 | 15 |
| $^{166}$-Ho | 1.12 | 1.8 | 80.6 | 117 |
| $^{175}$-Yb | 4.19 | 0.47 | 396 | 17 |
| $^{177}$-Lu | 6.71 | 0.50 | 208 | 20 |
| $^{90}$-Y | 2.67 | 2.28 | — | 150 |
| $^{111}$-In | 2.810 | Auger electron emitter | 173, 247 | <5 μm |

Pm: Promethium,
Sm: Samarium,
Dy: Dysprosium,
Ho: Holmium,
Yb: Ytterbium,
Lu: Lutetium,
Y: Yttrium,
In: Indium Methods for the preparation of radiometals such as beta-emitting lanthanide radioisotopes are known to those skilled in the art, and have been described elsewhere [e.g., Cutler C S, Smith C J, Ehrhardt G J.; Tyler T T, Jurisson S S, Deutsch E. "Current and potential therapeutic uses of lanthanide radioisotopes." Cancer Biother. Radiopharm. 2000; 15(6): 531-545]. Many of these isotopes can be produced in high yield for relatively low cost, and many (e.g. $^{90}$-Y, $^{149}$-Pm, 177-Lu) can be produced at close to carrier-free specific activities (i.e. the vast majority of atoms are radioactive). Since non-radioactive atoms can compete with their radioactive analogs for binding to receptors on the target tissue, the use of high specific activity radioisotope is important, to allow delivery of as high a dose of radioactivity to the target tissue as possible.

Radiotherapeutic derivatives of the invention containing beta-emitting isotopes of rhenium ($^{186}$-Re and $^{188}$-Re) are also particularly preferred.

As shown in the Examples, radiotherapeutic derivatives of the invention are particularly useful at treating prostate cancer and may be used in th treatment of primary or metastatic prostate cancer, whether hormone sensitive or hormone refractory. Additionally, radiotherapeutic compounds of the invention may be utilized to treat both bone and soft tissue metastases of prostate cancer as well as to delay progression and/or to decrease aberrant vascular permeability associated with prostate cancer.

8. Dosages And Additives

Proper dose schedules for the compounds of the present invention are known to those skilled in the art. The compounds can be administered using many methods which include, but are not limited to, a single or multiple IV or IP injections. For radiopharmaceuticals, one administers a quantity of radioactivity that is sufficient to permit imaging or, in the case of radiotherapy, to cause damage or ablation of the targeted GRP-R bearing tissue, but not so much that substantive damage is caused to non-target (normal tissue). The quantity and dose required for scintigraphic imaging is discussed supra. The quantity and dose required for radiotherapy is also different for different constructs, depending on the energy and half-life of the isotope used, the degree of uptake and clearance of the agent from the body and the mass of the tumor. In general, doses can range from a single dose of about 30-50 mCi to a cumulative dose of up to about 3 Curies.

As explained herein the administration of an appropriately selected mass dose can decrease the proportion of the administered dose of labeled compound of the invention in normal tissues having functioning GRP receptors, thus improving the perspicuity of the tumor signal and/or increasing the dose of a therapeutic radionuclide in the tumor.

For optical imaging compounds, dosages sufficient to achieve the desired image enhancement are known to those skilled in the art and may vary widely depending on the dye or other compound used, the organ or tissue to be imaged, the imaging equipment used, etc.

The compositions of the invention can include physiologically acceptable buffers, and can require radiation stabilizers to prevent radiolytic damage to the compound prior to injection. Radiation stabilizers are known to those skilled in the art, and may include, for example, para-aminobenzoic acid, ascorbic acid, gentistic acid and the like.

A single, or multi-vial kit that contains all of the components needed to prepare the diagnostic or therapeutic agents of this invention is an integral part of this invention. In the case of radiopharmaceuticals, such kits will often include all necessary ingredients except the radionuclide.

For example, a single-vial kit for preparing a radiopharmaceutical of the invention preferably contains a chelator/linker/targeting peptide conjugate of the formula M-N-O-P-G, a source of stannous salt (if reduction is required, e.g., when using technetium), or other pharmaceutically acceptable reducing agent, and is appropriately buffered with pharmaceutically acceptable acid or base to adjust the pH to a value of about 3 to about 9. The quantity and type of reducing agent used will depend highly on the nature of the exchange complex to be formed. The proper conditions are well known to those that are skilled in the art. It is preferred that the kit contents be in lyophilized form. Such a single vial kit may optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or α, β, or γ-cyclodextrin that serve to improve the radiochemical purity and stability of the final product. The kit may also contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial may contain all of the ingredients that are required to form a labile Tc(V) complex on addition of pertechnetate (e.g. the stannous source or other reducing agent). Pertechnetate is added to this vial, and after waiting an appropriate period of time, the contents of this vial are added to a second vial that contains the chelator and targeting peptide, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. may be present in either or both vials.

General Preparation of Compounds

The compounds of the present invention can be prepared by various methods depending upon the selected chelator. The peptide portion of the compound can be most conveniently prepared by techniques generally established and known in the art of peptide synthesis, such as the solid-phase peptide synthesis (SPPS) approach. Because it is amenable to solid phase synthesis, employing alternating FMOC protection and deprotection is the preferred method of making short peptides. Recombinant DNA technology is preferred for producing proteins and long fragments thereof.

Solid-phase peptide synthesis (SPPS) involves the stepwise addition of amino acid residues to a growing peptide chain that is linked to an insoluble support or matrix, such as polystyrene. The C-terminal residue of the peptide is first anchored to a commercially available support with its amino group protected with an N-protecting agent such as a t-butyloxycarbonyl group (Boc) or a fluorenylmethoxycarbonyl (Fmoc) group. The amino protecting group is removed with suitable deprotecting agents such as TFA in the case of Boc or piperidine for Fmoc and the next amino acid residue (in N-protected form) is added with a coupling agent such as diisopropylcarbodiimide (DIC). Upon formation of a peptide bond, the reagents are washed from the support. After addition of the final residue, the peptide is cleaved from the support with a suitable reagent such as trifluoroacetic acid (TFA) or hydrogen fluoride (HF).

Alternative Preparation of the Compounds Via Segment Coupling

The compounds of the invention may also be prepared by the process known in the art as segment coupling or fragment condensation (Barlos, K. and Gatos, D.; 2002 "Convergent Peptide Synthesis" in *Fmoc Solid Phase Synthesis—A Practical Approach*; Eds. Chan, W. C. and White, P. D.; Oxford University Press, New York; Chap. 9, pp 215-228). In this method segments of the peptide usually in side-chain protected form, are prepared separately by either solution phase synthesis or solid phase synthesis or a combination of the two methods. The choice of segments is crucial and is made using a division strategy that can provide a manageable number of segments whose C-terminal residues and N-terminal residues are projected to provide the cleanest coupling in peptide synthesis. The C-terminal residues of the best segments are either devoid of chiral alpha carbons (glycine or other moieties achiral at the carbon $\propto$ to the carboxyl group to be activated in the coupling step) or are compromised of amino acids whose propensity to racemization during activation and coupling is lowest of the possible choices. The choice of N-terminal amino acid for each segment is based on the ease of coupling of an activated acyl intermediate to the amino group. Once the division strategy is selected the method of coupling of each of the segments is chosen based on the synthetic accessibility of the required intermediates and the relative ease of manipulation and purification of the resulting products (if needed). The segments are then coupled together, both in solution, or one on solid phase and the other in solution to prepare the final structure in fully or partially protected form.

The protected target compound is then subjected to removal of protecting groups, purified and isolated to give the final desired compound. Advantages of the segment coupling approach are that each segment can be purified separately, allowing the removal of side products such as deletion sequences resulting from incomplete couplings or those derived from reactions such as side-chain amide dehydration during coupling steps, or internal cyclization of side-chains (such as that of Gln) to the alpha amino group during deprotection of Fmoc groups. Such side products would all be present in the final product of a conventional resin-based 'straight through' peptide chain assembly whereas removal of these materials can be performed, if needed, at many stages in a segment coupling strategy. Another important advantage of the segment coupling strategy is that different solvents, reagents and conditions can be applied to optimize the synthesis of each of the segments to high purity and yield resulting in improved purity and yield of the final product. Other advantages realized are decreased consumption of reagents and lower costs.

EXAMPLES

The following examples are provided as examples of different methods which can be used to prepare various compounds of the present invention. Within each example, there are compounds identified in single bold capital letter (e.g., A, B, C), which correlate to the same labeled corresponding compounds in the drawings identified.

General Experimental

A. Definitions of Additional Abbreviations Used

The following common abbreviations are used throughout this specification:
1,1-dimethylethoxycarbonyl (Boc or Boc);
9-fluorenylmethyloxycarbonyl (Fmoc);
allyloxycarbonyl (Aloc);
1-hydroxybenozotriazole (HOBt or HOBT);
N,N'-diisopropylcarbodiimide (DIC);
N-methylpyrrolidinone (NMP);
acetic anhydride ($Ac_2O$);
(4,4-dimethyl-2,6-dioxocyclohex-1-ylidene)-3-methylbutyl (iv-Dde);
trifluoroacetic acid (TFA);
Reagent B (TFA:$H_2O$:phenol:triisopropylsilane, 88:5:5:2);
diisopropylethylamine (DIEA);
0-(1H-benzotriazole-1-yl)-N,N,N',N'-tetramethyluronium hexafluorophosphate (HBTU);
O-(7-azabenzotriazol-1-yl)-1,1,3,3-tetramethyluronium hexafluorphosphate (HATU);
N-hydroxysuccinimide (NHS);
solid phase peptide synthesis (SPPS);
dimethylsulfoxide (DMSO);
dichloromethane (DCM);
dimethylformamide (DMF);
dimethylacetamide (DMA);
1,4,7,10-tetraazacyclotetradecane-1,4,7,10-tetraacetic acid (DOTA);
Triisopropylsilane (TIPS);
1,4,7,10-tetraazacyclotetradecane-1,4,7,10-tetraacetic acid (DOTA)
(1R)-1-[1,4,7,10-tetraaza-4,7,10-tris(carboxymethyl)cyclododecyl]ethane-1,2-dicarboxylic acid (CMDOTA);
fetal bovine serum (FBS);
human serum albumin (HSA);
human prostate cancer cell line (PC3);
isobutylchloroformate (IBCF);
tributyl amine (TBA);
radiochemical purity (RCP); and
high performance liquid chromatography (HPLC).

B. Materials

The Fmoc-protected amino acids used were purchased from Nova-Biochem (San Diego, Calif., USA), Advanced Chem Tech (Louisville, Ky., USA), Chem-Impex International (Wood Dale Ill., USA), and Multiple Peptide Systems (San Diego, Calif., USA). Other chemicals, reagents and adsorbents required for the syntheses were procured from Aldrich Chemical Co. (Milwaukee, Wis., USA) and VWR Scientific Products (Bridgeport, N.J., USA). Solvents for peptide synthesis were obtained from Pharmco Co. (Brookfield Conn., USA). Columns for HPLC analysis and purification were obtained from Waters Co. (Milford, Mass., USA). Experimental details are given below for those that were not commercially available.

C. Instrumentation for Peptide Synthesis

Peptides were prepared using an Advanced ChemTech 496Ω MOS synthesizer, an Advanced ChemTech 357 FBS synthesizer and/or by manual peptide synthesis. However the protocols for iterative deprotection and chain extension employed were the same for all.

D. Automated Synthesis with the Symphony Instrument (Made by Rainin)

The synthesis was run with Symphony Software (Version 3) supplied by Protein Technologies Inc. Novagel TGR resin, with a substitution of 0.25 mmol/g, was used, and each well contained 0.2 g of the resin (50 μmol). The amino acids were dissolved in NMP and the concentration was 0.25M. A 0.25M solution of HBTU and N-Methylmorpholine in DMF was prepared and used for the coupling. All the couplings were carried out for 2.0 h. The cleavage was done outside the machine by transferring the resin to another reaction vessel and using Reagent B as in the manual synthesis E. Instrumentation Employed for Analysis and Purification Analytical HPLC was performed using a Shimadzu-LC-10A dual pump gradient analytical LC system employing Shimadzu-ClassVP software version 4.1 for system control, data acquisition, and post run processing. Mass spectra were acquired on a Hewlett-Packard Series 1100 MSD mass spectrometer interfaced with a Hewlett-Packard Series 1100 dual pump gradient HPLC system fitted with an Agilent Technologies 1100 series autosampler fitted for either direct flow injection or injection onto a Waters Associates XTerra MS C18 column (4.6 mm×50 mm, 5μ particle, 120 Å pore). The instrument was driven by a HP Kayak workstation using 'MSD Anyone' software for sample submission and HP Chemstation software for instrument control and data acquisition. In most cases the samples were introduced via direct injection using a 5 μL injection of sample solution at a concentration of 1 mg/mL and analyzed using positive ion electrospray to obtain m/e and m/z (multiply charged) ions for confirmation of structure. $^1$H-NMR spectra were obtained on a Varian Innova spectrometer at 500 MHz. $^{13}$C-NMR spectra were obtained on the same instrument at 125.73 MHz. Generally the residual $^1$H absorption, or in the case of $^{13}$C-NMR, the $^{13}$C absorption of the solvent employed, was used as an internal reference; in other cases tetramethylsilane (δ=0.00 ppm) was employed. Resonance values are given in δ units. Micro analysis data was obtained from Quantitative Technologies Inc., Whitehouse N.J. Preparative HPLC was performed on a Shimadzu-LC-8A dual pump gradient preparative HPLC system employing Shimadzu-ClassVP software version 4.3 for system control, data acquisition, fraction collection and post run processing.

F. General Procedures for Peptide Synthesis

Rink Amide-Novagel HL resin (0.6 mmol/g) was used as the solid support.

G. Coupling Procedure

In a typical experiment, the first amino acid was loaded onto 0.1 g of the resin (0.06 mmol). The appropriate Fmoc-amino acid in NMP (0.25M solution; 0.960 mL was added to the resin followed by N-hydroxybenzotriazole (0.5M in NMP; 0.48 mL) and the reaction block (in the case of automated peptide synthesis) or individual reaction vessel (in the case of manual peptide synthesis) was shaken for about 2 min. To the above mixture, diisopropylcarbodiimide (0.5M in NMP; 0.48 mL) was added and the reaction mixture was shaken for 4 h at ambient temperature. Then the reaction block or the individual reaction vessel was purged of reactants by application of a positive pressure of dry nitrogen.

H. Washing Procedure

Each well of the reaction block was filled with 1.2 mL of NMP and the block was shaken for 5 min. The solution was drained under positive pressure of nitrogen. This procedure was repeated three times. The same procedure was used, with an appropriate volume of NMP, in the case of manual synthesis using individual vessels.

I. Removal of Fmoc Protecting Group

The resin bearing the Fmoc-protected amino acid was treated with 1.5 mL of 20% piperidine in DMF (v/v) and the reaction block or individual manual synthesis vessel was shaken for 15 min. The solution was drained from the resin. This procedure was repeated once and the resin was washed employing the washing procedure described above.

J. Final Coupling of Ligand (DOTA and CMDOTA)

The N-terminal amino group of the resin bound peptide linker construct was deblocked and the resin was washed. A 0.25M solution of the desired ligand and HBTU in NMP was made, and was treated with a two-fold equivalency of DIEA. The resulting solution of activated ligand was added to the resin (1.972 mL; 0.48 mmol) and the reaction mixture was shaken at ambient temperature for 24-30 h. The solution was drained and the resin was washed. The final wash of the resin was conducted with 1.5 mL dichloromethane (3×).

K. Deprotection and Purification of the Final Peptide

A solution of Reagent B (2 mL; 88:5:5:2-TFA:phenol: water:TIPS) was added to the resin and the reaction block or individual vessel was shaken for 4.5 h at ambient temperature. The resulting solution containing the deprotected peptide was drained into a vial. This procedure was repeated two more times with 1 mL of Reagent B. The combined filtrate was concentrated under reduced pressure using a Genevac HT-12 series II centrifugal concentrator. The residue in each vial was then triturated with 2 mL of Et$_2$O and the supernatant was decanted. This procedure was repeated twice to provide the peptides as colorless solids. The crude peptides were dissolved in water/acetonitrile and purified using either a Waters XTerra MS C18 preparative HPLC column (50 mm×19 mm, 5 micron particle size, 120A pore size) or a Waters-YMC C18 ODS column (250 mm×30 mm i.d., 10 micron particle size. 120 Å pore size). The product-containing fractions were collected and analyzed by HPLC. The fractions with >95% purity were pooled and the peptides isolated by lyophilization.

Conditions for Preparative HPLC (Waters XTerra Column):

Elution rate: 50 mL/min

Detection: UV, λ=220 nm

Eluent A: 0.1% aq. TFA; Eluent B: Acetonitrile (0.1% TFA). Conditions for HPLC Analysis:

Column: Waters XTerra (Waters Co.; 4.6×50 mm; MS C18; 5 micron particle, 120 Å pore).

Elution rate: 3 mL/min; Detection: UV, λ=220 nm.

Eluent A: 0.1% aq. TFA; Eluent B: Acetonitrile (0.1% TFA).

Example 1

FIGS. 1A-B

Synthesis of L62

Figure 1A:
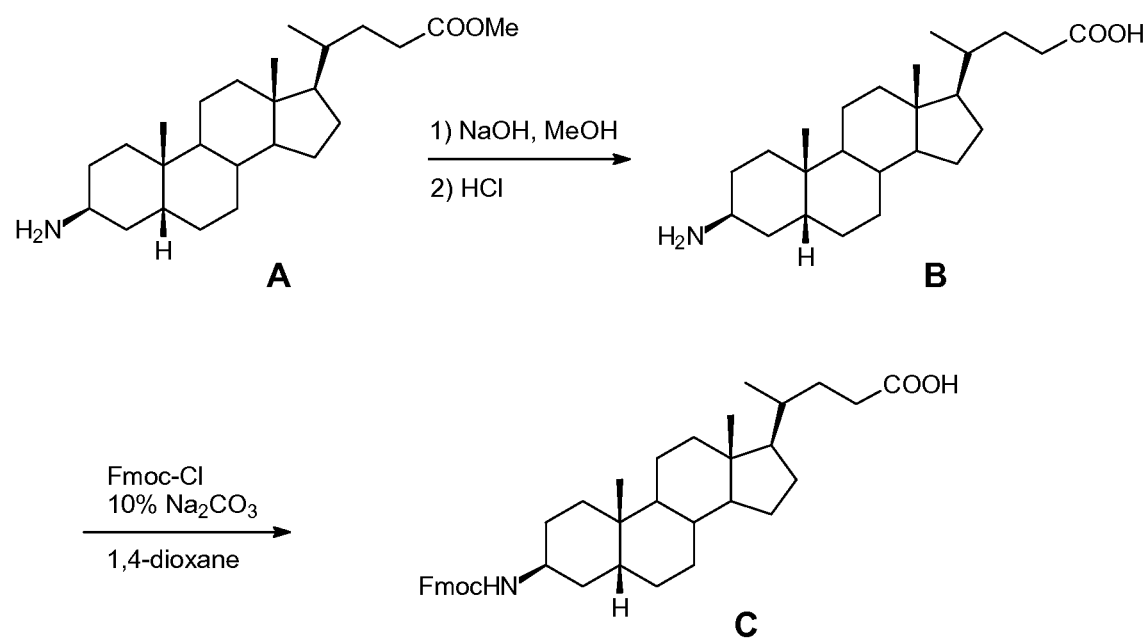
FIG. 1A is a graphical representation of a series of chemical reactions for the synthesis of intermediate C ((3β,5β)-3-(9H-Fluoren-9-ylmethoxy)aminocholan-24-oic acid), from A (Methyl-(3β,5β)-3-aminocholan-24-ate) and B ((3β,5β)-3-aminocholan-24-oic acid), as described in Example I.
Figure 1B:
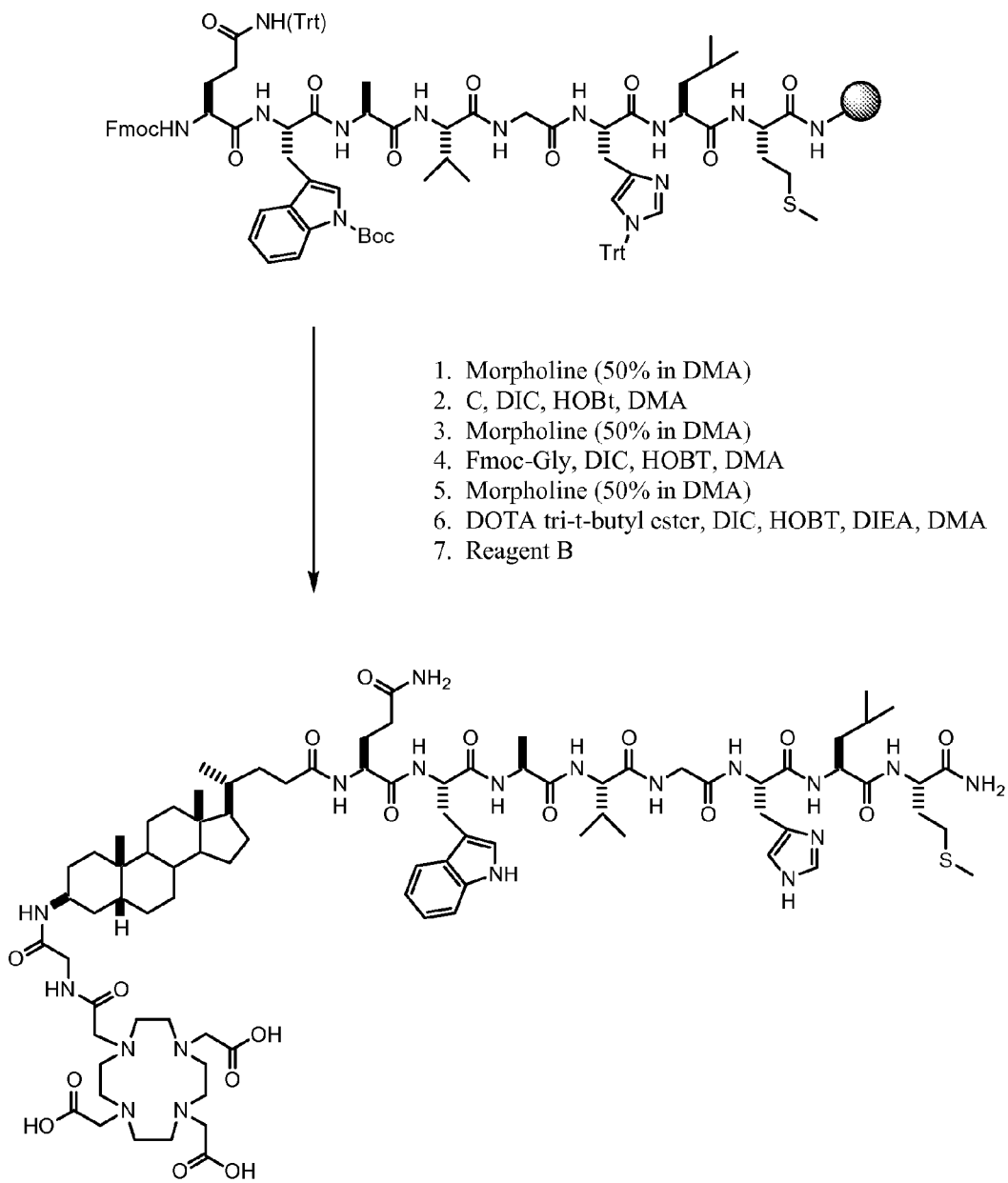
FIG. 1B is a graphical representation of the sequential reaction for the synthesis of N—[(3β,5β)-3-[[[[[4,7,10-Tris(carboxymethyl)-1,4,7,10-tetraazacyclododec-1-yl]acetyl]amino]acetyl]amino]cholan-24-yl]-L-glutaminyl-L-tryptophyl-L-alanyl-L-valyl-glycyl-L-histidyl-L-leucyl-L-methioninamide (L62), as described in Example I.

Summary: As shown in FIGS. 1A-B, L62 was prepared using the following steps: Hydrolysis of (3β,5β)-3-aminocholan-24-oic acid methyl ester A with NaOH gave the corresponding acid B, which was then reacted with Fmoc-Cl to give intermediate C. Rink amide resin functionalised with the octapeptide Gln-Trp-Ala-Val-Gly-His-Leu-Met-NH$_2$ (BBN[7-14] (SEQ ID NO: 1) was sequentially reacted with C, Fmoc-glycine and DOTA tri-t-butyl ester. After cleavage and deprotection with Reagent B the crude was purified by preparative HPLC to give L62. Overall yield: 2.5%. More details are provided below:

A. Rink Amide Resin Functionalised with Bombesin[7-14] (SEQ ID NO: 1), (A)

In a solid phase peptide synthesis vessel (see enclosure No. 1) Fmoc-aminoacid (24 mmol), N-hydroxybenzotriazole (HOBt) (3.67 g; 24 mmol), and N,N'-diisopropylcarbodiimide (DIC) (3.75 mL; 24 mmol) were added sequentially to a suspension of Rink amide NovaGel™ resin (10 g; 6.0 mmol) A in DMF (45 mL). The mixture was shaken for 3 h at room temperature using a bench top shaker, then the solution was emptied and the resin was washed with DMF (5×45 mL). The resin was shaken with 25% piperidine in DMF (45 mL) for 4 min, the solution was emptied and fresh 25% piperidine in DMF (45 mL) was added. The suspension was shaken for 10 min, then the solution was emptied and the resin was washed with DMF (5×45 mL).

This procedure was applied sequentially for the following amino acids: N-α-Fmoc-L-methionine, N-α-Fmoc-L-leucine, N-α-Fmoc-N$^{im}$-trityl-L-histidine, N-α-Fmoc-glycine, N-α-Fmoc-L-valine, N-α-Fmoc-L-alanine, N-α-Fmoc-N$^{in}$-Boc-L-tryptophan.

In the last coupling reaction N-α-Fmoc-N-γ-trityl-L-glutamine (14.6 g; 24 mmol), HOBt (3.67 g; 24 mmol), and DIC (3.75 mL; 24 mmol) were added to the resin in DMF (45 mL). The mixture was shaken for 3 h at room temperature, the solution was emptied and the resin was washed with DMF (5×45 mL), CH$_2$Cl$_2$ (5×45 mL) and vacuum dried.

B. Preparation of Intermediates B and C (FIG. 1A):

1. Synthesis of (3β,5β)-3-Aminocholan-24-oic acid (B)

A 1 M solution of NaOH (16.6 mL; 16.6 mmol) was added dropwise to a solution of (3β,5β)-3-aminocholan-24-oic acid methyl ester (5.0 g; 12.8 mmol) in MeOH (65 mL) at 45° C. After 3 h stirring at 45° C., the mixture was concentrated to 25 mL and H$_2$O (40 mL) and 1 M HCl (22 mL) were added. The precipitated solid was filtered, washed with H$_2$O (2×50 mL) and vacuum dried to give B as a white solid (5.0 g; 13.3 mmol). Yield 80%.

2. Synthesis of (3β,5β)-3-(9H-Fluoren-9-ylmethoxy)aminocholan-24-oic acid (C)

A solution of 9-fluorenylmethoxycarbonyl chloride (0.76 g; 2.93 mmol) in 1,4-dioxane (9 mL) was added dropwise to a suspension of (3β,5β)-3-aminocholan-24-oic acid B (1.0 g; 2.66 mmol) in 10% aq. Na$_2$CO$_3$ (16 mL) and 1,4-dioxane (9 mL) stirred at 0° C. After 6 h stirring at room temperature H$_2$O (90 mL) was added, the aqueous phase washed with Et$_2$O (2×90 mL) and then 2 M HCl (15 mL) was added (final pH: 1.5). The aqueous phase was extracted with EtOAc (2×100 mL), the organic phase dried over Na$_2$SO$_4$ and evaporated. The crude was purified by flash chromatography to give C as a white solid (1.2 g; 2.0 mmol). Yield 69%.

C. Synthesis of L62 (N-[(3β,5β)-3-[[[[[4,7,10-Tris(carboxymethyl)-1,4,7,10-tetraazacyclododec-1-yl]acetyl]amino]acetyl]amino]-cholan-24-yl]-L-glutaminyl-L-tryptophyl-L-alanyl-L-valyl-glycyl-L-histidyl-L-leucyl-L-methioninamide) (FIG. 1B):

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was shaken for 20 min then the solution was emptied and the resin washed with DMA (5×7 mL). (3β,5β)-3-(9H-Fluoren-9-ylmethoxy)aminocholan-24-oic acid C (0.72 g; 1.2 mmol), N-hydroxybenzotriazole (HOBt) (0.18 g; 1.2 mmol), N,N'-diisopropylcarbodiimide (DIC) (0.19 mL; 1.2 mmol) and DMA (7 mL) were added to the resin, the mixture shaken for 24 h at room temperature, and the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture shaken for another 20 min. The solution was emptied and the resin washed with DMA (5×7 mL). N-α-Fmoc-glycine (0.79 g; 1.2 mmol), HOBt (0.18 g; 1.2 mmol), DIC (0.19 mL: 1.2 mmol) and DMA (7 mL) were added to the resin. The mixture was shaken for 3 h at room temperature, the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture shaken for another 20 min. The solution was emptied and the resin washed with DMA (5×7 mL) followed by addition of 1,4,7,10-tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) to the resin. The mixture was shaken for 24 h at room temperature, the solution was emptied and the resin washed with DMA (5×7 mL), CH$_2$Cl$_2$ (5×7 mL) and vacuum dried. The resin was shaken in a flask with Reagent B (25 mL) for 4.5 h. The resin was filtered and the solution was evaporated under reduced pressure to afford an oily crude which was triturated with Et$_2$O (20 mL) gave a precipitate. The precipitate was collected by centrifugation and washed with Et$_2$O (3×20 mL), then analysed by HPLC and purified by preparative HPLC. The fractions containing the product were lyophilised to give L62 (6.6 mg; 3.8×10$^{-3}$ mmol) as a white solid. Yield 4.5%.

Example II

FIGS. 2A-F

Synthesis of L70, L73, L74, L115 and L116

Summary: The products were obtained by coupling of the octapeptide Gln-Trp-Ala-Val-Gly-His-Leu-Met-NH$_2$ (BBN (7-14) (SEQ ID NO:1) (with appropriate side chain protection) on the Rink amide resin with different linkers, followed by functionalization with DOTA tri-t-butyl ester. After cleavage and deprotection with Reagent B the final products were purified by preparative HPLC. Overall yields 3-9%.

Figure 2A:
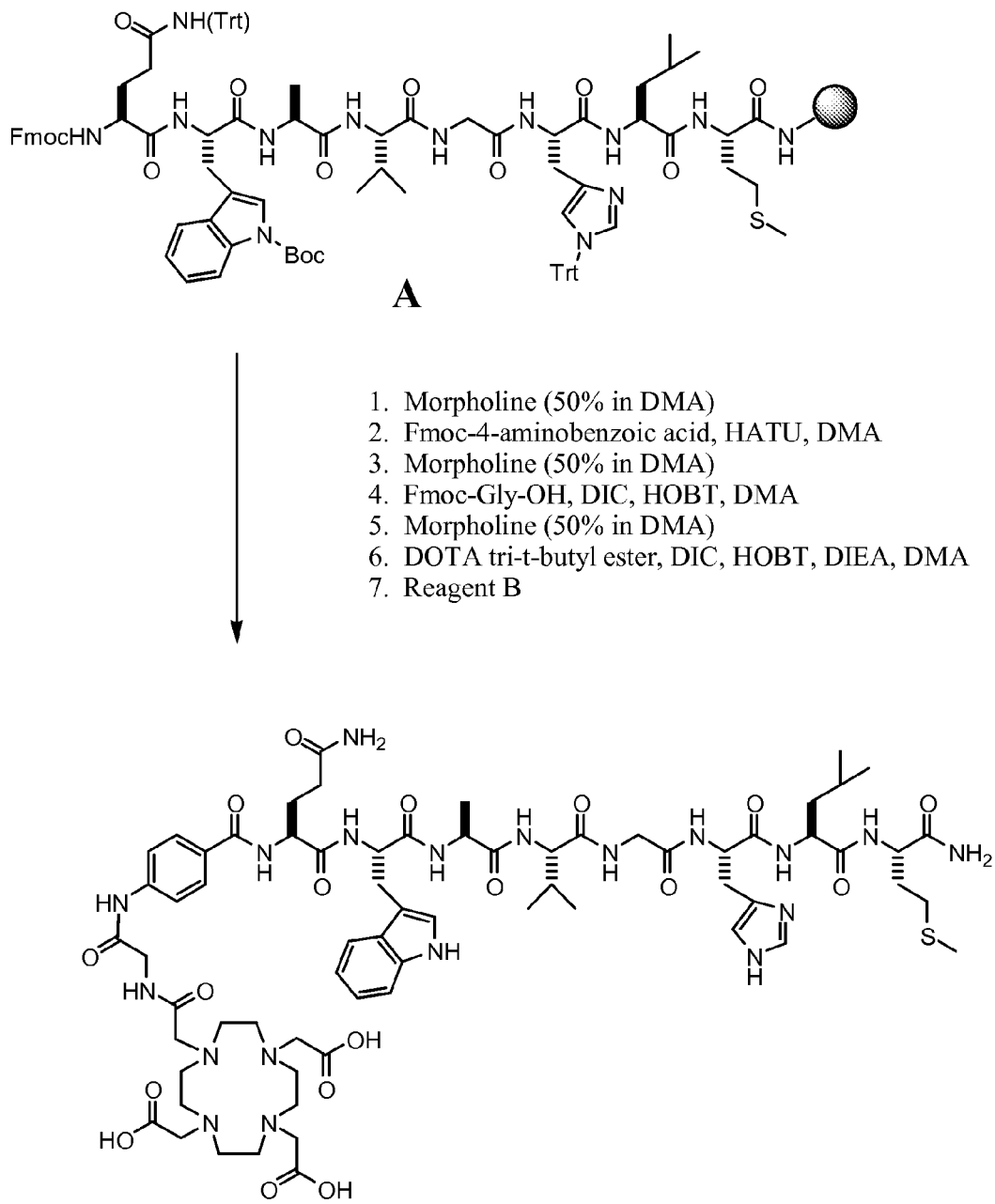
FIG. 2A is a graphical representation of the sequential reaction for the synthesis of N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide (L70), as described in Example II.
Figure 2B:
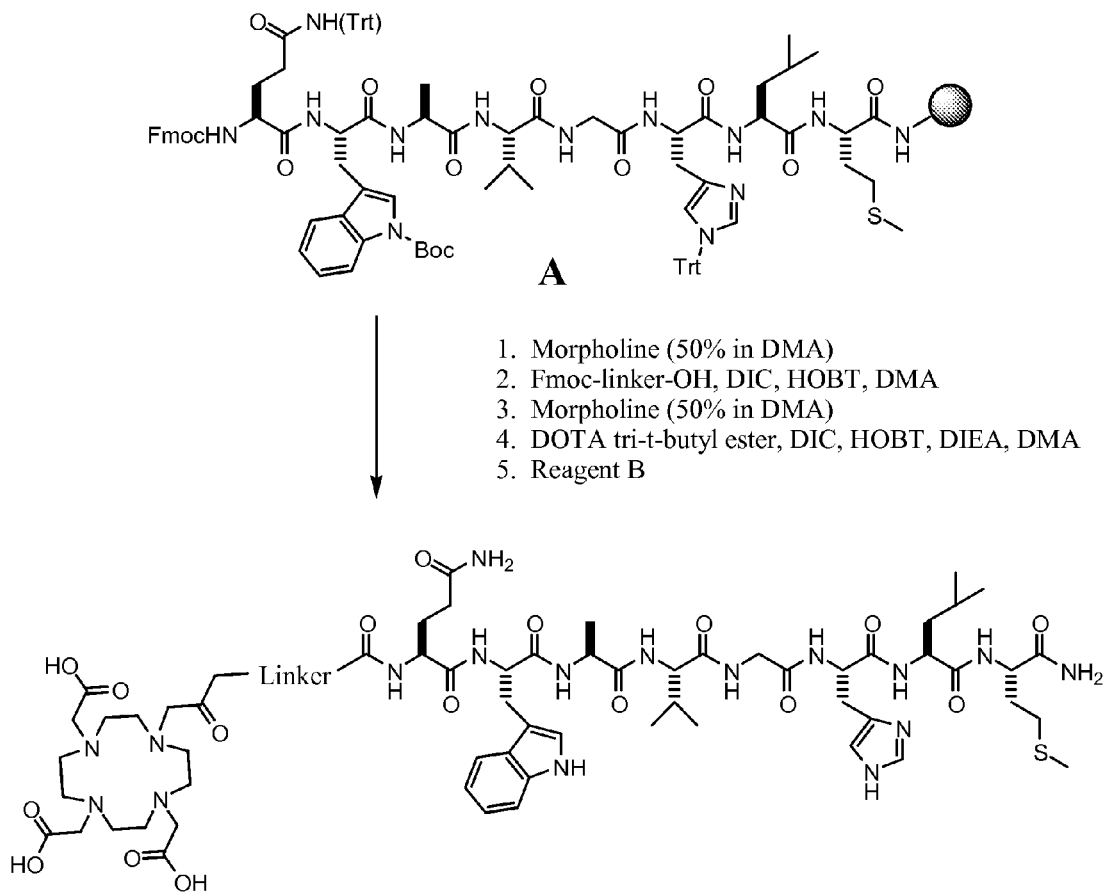
FIG. 2B is a general graphical representation of the sequential reaction for the synthesis of N-[4-[2-[[[4,7,10-Tris(carboxymethyl)-1,4,7,10-tetraazacyclododec-1-yl]acetyl]amino]ethoxy]benzoyl]-L-glutaminyl-L-tryptophyl-L-alanyl-L-valyl-glycyl-L-histidyl-L-leucyl-L-methioninamide (L73), N-[3-[[[[4,7,10-Tris(carboxymethyl)-1,4,7,10-tetraazacyclododec-1-yl]acetyl]amino]methyl]benzoyl]-L-glutaminyl-L-tryptophyl-L-alanyl-L-valyl-glycyl-L-histidyl-L-leucyl-L-methioninamide (L115), and N-[4-[[[[4,7,10-Tris(carboxymethyl)-1,4,7,10-tetraazacyclododec-1-yl]acetyl]amino]methyl]phenylacetyl]-L-glutaminyl-L-tryptophyl-L-alanyl-L-valyl-glycyl-L-histidyl-L-leucyl-L-methioninamide (L116), as described in Example II.
Figure 2C:
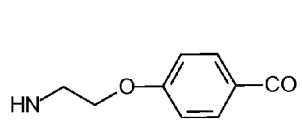
FIG. 2C is a chemical structure of the linker used in the synthesis reaction of FIG. 2B for synthesis of N-[4-[2-[[[4,7,10-Tris(carboxymethyl)-1,4,7,10-tetraazacyclododec-1-yl]acetyl]amino]ethoxy]benzoyl]-L-glutaminyl-L-tryptophyl-L-alanyl-L-valyl-glycyl-L-histidyl-L-leucyl-L-methioninamide (L73), as described in Example II.
Figure 2D:
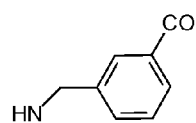
FIG. 2D is a chemical structure of the linker used in the synthesis reaction of FIG. 2B for synthesis of N-[3-[[[[4,7,10-Tris(carboxymethyl)-1,4,7,10-tetraazacyclododec-1-yl]acetyl]amino]methyl]benzoyl]-L-glutaminyl-L-tryptophyl-L-alanyl-L-valyl-glycyl-L-histidyl-L-leucyl-L-methioninamide (L115), as described in Example II.
Figure 2E:
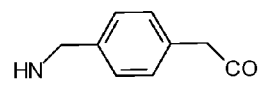
FIG. 2E is a chemical structure of the linker used in the synthesis reaction of FIG. 2B for synthesis of N-[4-[[[[4,7,10-Tris(carboxymethyl)-1,4,7,10-tetraazacyclododec-1-yl]acetyl]amino]methyl]phenylacetyl]-L-glutaminyl-L-tryptophyl-L-alanyl-L-valyl-glycyl-L-histidyl-L-leucyl-L-methioninamide (L116), as described in Example II.

A. Synthesis of L70 (FIG. 2A):

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin washed with DMA (5×7 mL). Fmoc-4-aminobenzoic acid (0.43 g; 1.2 mmol), HOBt (0.18 g; 1.2 mmol), DIC (0.19 mL; 1.2 mmol) and DMA (7 mL) were added to the resin, the mixture shaken for 3 h at room temperature, the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture was shaken for 20 min. The solution was emptied and the resin washed with DMA (5×7 mL). Fmoc-glycine (0.36 g; 1.2 mmol) HATU (0.46 g; 1.2 mmol) and DIEA (0.40 mL; 2.4 mmol) were stirred for 15 min in DMA (7 mL) then the solution was added to the resin, the mixture shaken for 2 h at room temperature, the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture was shaken for 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin washed with DMA (5×7 mL), $CH_2Cl_2$ (5×7 mL) and vacuum dried. The resin was shaken in a flask with Reagent B (25 mL) for 4 h. The resin was filtered and the filtrate solution was evaporated under reduced pressure to afford an oily crude that was triturated with $Et_2O$ (5 mL). The precipitate was collected by centrifugation and washed with $Et_2O$ (5×5 mL), then analysed by HPLC and purified by preparative HPLC. The fractions containing the product were lyophilised to give L70 as a white fluffy solid (6.8 mg; 0.005 mmol). Yield 3%.

B. Synthesis of L73, L115 and L116 (FIGS. 2B-2E):

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin washed with DMA (5×7 mL). Fmoc-linker-OH (1.2 mmol), HOBt (0.18 g; 1.2 mmol), DIC (0.19 mL; 1.2 mmol) and DMA (7 mL) were added to the resin, the mixture was shaken for 3 h at room temperature, the solution was emptied and the resin was washed with DMA (5×7 mL). The resin was shaken with 50% morpholine in DMA (7 mL) for 10 min, the solution was emptied, fresh 50% morpholine in DMA (7 mL) was added and the mixture was shaken for 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin washed with DMA (5×7 mL), $CH_2Cl_2$ (5×7 mL) and vacuum dried. The resin was shaken in a flask with Reagent B (25 mL) for 4 h. The resin was filtered and the solution was evaporated under reduced pressure to afford an oily crude that was triturated with $Et_2O$ (5 mL). The precipitate was collected by centrifugation and washed with $Et_2O$ (5×5 mL), then analysed by HPLC and purified by preparative HPLC. The fractions containing the product were lyophilised.

Figure 2F:
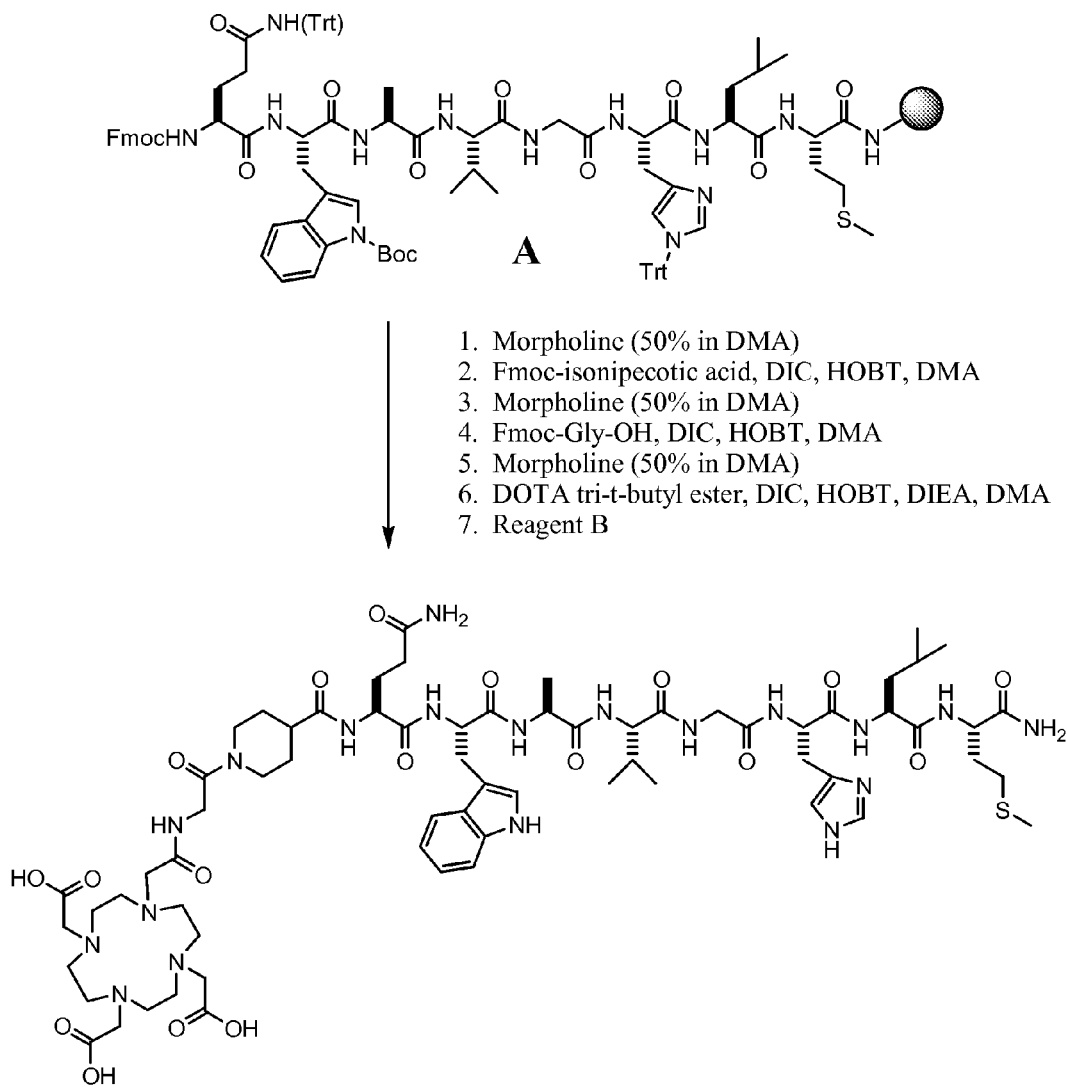
FIG. 2F is a graphical representation of the sequential reaction for the synthesis of N-[[4,7,10-Tris(carboxymethyl)-1,4,7,10-tetraazacyclododec-1-yl]acetyl]glycyl-4-piperidinecarbonyl-L-glutaminyl-L-tryptophyl-L-alanyl-L-valyl-glycyl-L-histidyl-L-leucyl-L-methioninamide (L74), as described in Example II.

C. Synthesis of L74 (FIG. 2F):

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). Fmoc-isonipecotic acid (0.42 g; 1.2 mmol), HOBt (0.18 g; 1.2 mmol), DIC (0.19 mL; 1.2 mmol) and DMA (7 mL) were added to the resin, the mixture was shaken for 3 h at room temperature, the solution was emptied and the resin was washed with DMA (5×7 mL). The resin was shaken with 50% morpholine in DMA (7 mL) for 10 min, the solution was emptied, fresh 50% morpholine in DMA (7 mL) was added and the mixture was shaken for 20 min. The solution was emptied and the resin was washed with DMA (5×7 mL). Fmoc-glycine (0.36 g; 1.2 mmol), HOBt (0.18 g; 1.2 mmol), DIC (0.19 mL; 1.2 mmol) and DMA (7 mL) were added to the resin, the mixture was shaken for 3 h at room temperature, the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture shaken for 20 minutes. The solution was emptied and the resin was washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin was washed with DMA (5×7 mL), $CH_2Cl_2$ (5×7 mL) and vacuum dried. The resin was shaken in a flask with Reagent B (25 mL) for 4 h. The resin was filtered and the solution was evaporated under reduced pressure to afford an oily crude that was triturated with $Et_2O$ (5 mL). The precipitate was collected by centrifugation and washed with $Et_2O$ (5×5 mL), then analysed by HPLC and purified by HPPLC. The fractions containing the product were lyophilised to give L74 as a white fluffy solid (18.0 mg; 0.012 mmol). Yield 8%.

Example III

FIGS. 3A-E

Synthesis of L67

Summary: Hydrolysis of (3β,5β)-3-amino-12-oxocholan-24-oic acid methyl ester A with NaOH gave the corresponding acid B, which was then reacted with Fmoc-Glycine to give intermediate C. Rink amide resin functionalised with the octapeptide Gln-Trp-Ala-Val-Gly-His-Leu-Met-$NH_2$ (BBN [7-14] (SEQ ID NO:1) was sequentially reacted with C, and DOTA tri-t-butyl ester. After cleavage and deprotection with Reagent B the crude was purified by preparative HPLC to give L67. Overall yield: 5.2%.

Figure 3A:
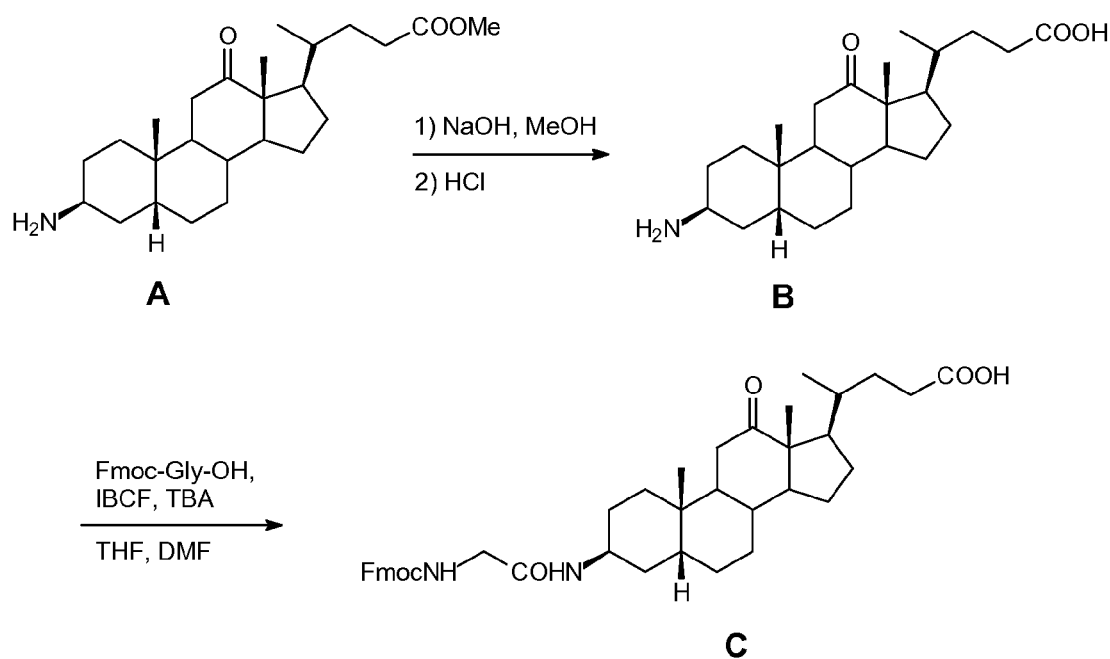
FIG. 3A is a graphical representation of a series of chemical reactions for the synthesis of intermediate (3β,5β)-3-[[(9H-Fluoren-9-ylmethoxy)amino]acetyl]amino-12-oxocholan-24-oic acid (C), as described in Example III.

A. Synthesis (3β,5β)-3-Amino-12-oxocholan-24-oic acid, (B) (FIG. 3A)

A 1 M solution of NaOH (6.6 mL; 6.6 mmol) was added dropwise to a solution of (3β,5β)-3-amino-12-oxocholan-24-oic acid methyl ester A (2.1 g; 5.1 mmol) in MeOH (15 mL) at 45° C. After 3 h stirring at 45° C., the mixture was concentrated to 25 mL then H$_2$O (25 mL) and 1 M HCl (8 mL) were added. The precipitated solid was filtered, washed with H$_2$O (2×30 mL) and vacuum dried to give B as a white solid (1.7 g; 4.4 mmol). Yield 88%.

B. Synthesis of (3β,5β)-3-[[(9H-Fluoren-9-ylmethoxy)amino]acetyl]amino-12-oxocholan-24-oic acid (C) (FIG. 3A)

Tributylamine (0.7 mL; 3.1 mmol) was added dropwise to a solution of N-α-Fmoc-glycine (0.9 g; 3.1 mmol) in THF (25 mL) stirred at 0° C. Isobutyl chloroformate (0.4 mL; 3.1 mmol) was subsequently added and, after 10 min, a suspension of tributylamine (0.6 mL; 2.6 mmol) and (3β,5β)-3-amino-12-oxocholan-24-oic acid B (1.0 g; 2.6 mmol) in DMF (30 mL) was added dropwise, over 1 h, into the cooled solution. The mixture was allowed to warm up and after 6 h the solution was concentrated to 40 mL, then H$_2$O (50 mL) and 1 N HCl (10 mL) were added (final pH: 1.5). The precipitated solid was filtered, washed with H$_2$O (2×50 mL), vacuum dried and purified by flash chromatography to give C as a white solid (1.1 g; 1.7 mmol). Yield 66%.

Figure 3B:
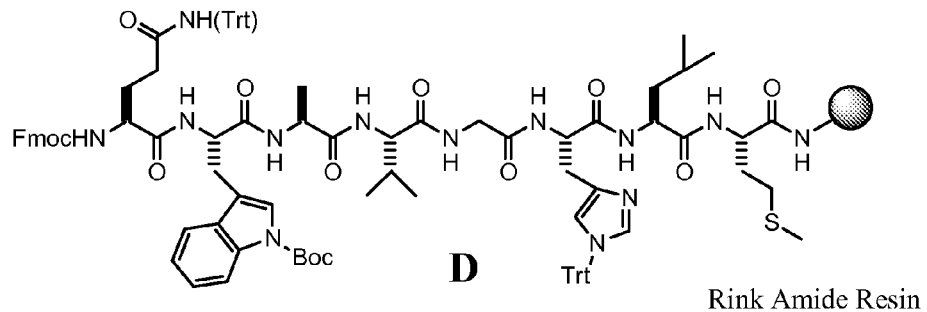
FIG. 3B is a graphical representation of the sequential reaction for the synthesis of N-[(3β,5β)-3-[[[[4,7,10-Tris(carboxymethyl)-1,4,7,10-tetraazacyclododec-1-yl]acetyl]amino]acetyl]amino]-12,24-dioxocholan-24-yl]-L-glutaminyl-L-tryptophyl-L-alanyl-L-valyl-glycyl-L-histidyl-L-leucyl-L-methioninamide (L67), as described in Example III.
Figure 3B:
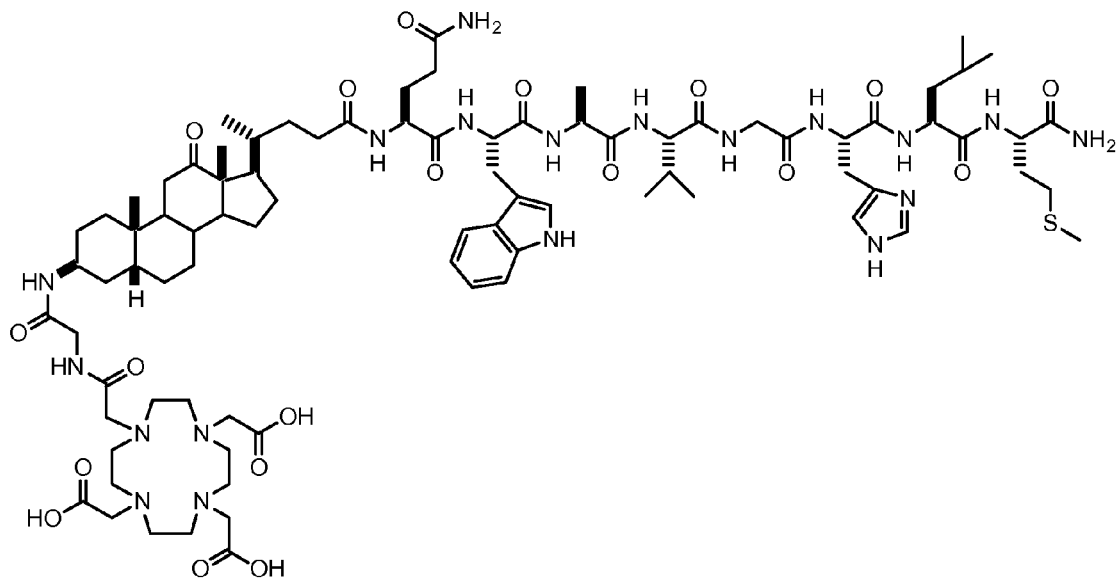
Figure 3C:
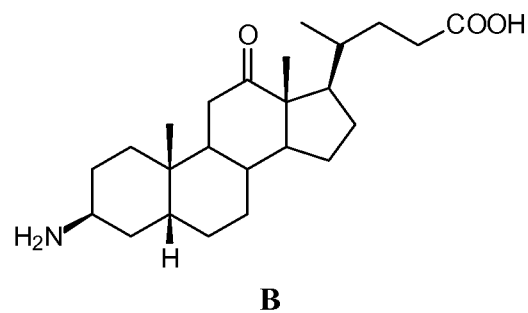
FIG. 3C is a chemical structure of (3β,5β)-3-Amino-12-oxocholan-24-oic acid (B), as described in Example III.
Figure 3D:
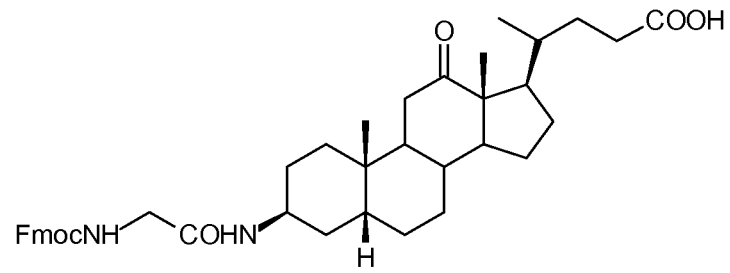
FIG. 3D is a chemical structure of (3β,5β)-3-[[(9H-Fluoren-9-ylmethoxy)amino]acetyl]amino-12-oxocholan-24-oic acid (C), as described in Example III.
Figure 3E:
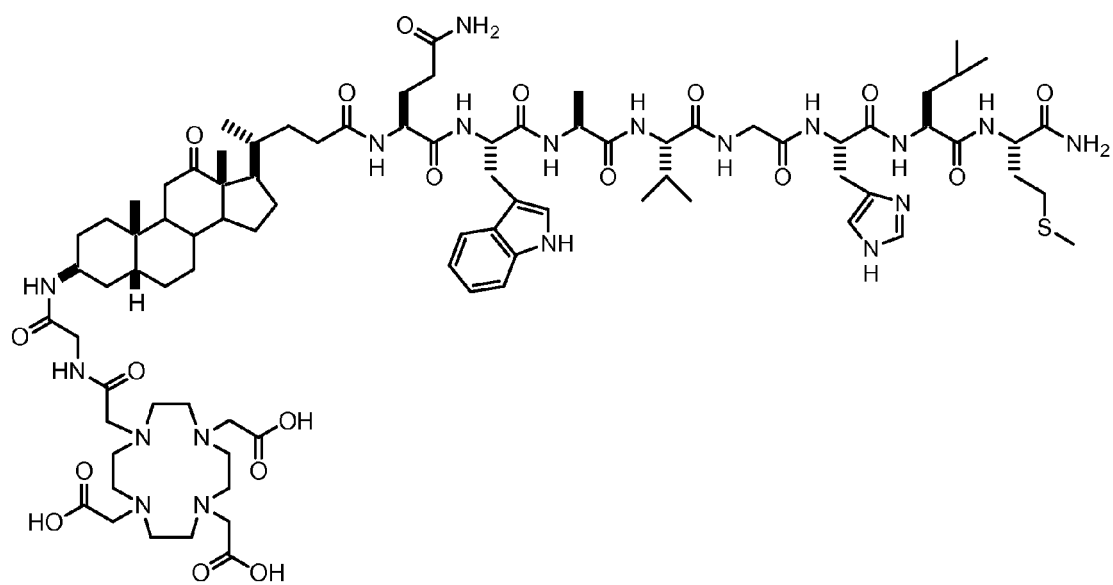
FIG. 3E is a chemical structure of N-[(3β,5β)-3-[[[[4,7,10-Tris(carboxymethyl)-1,4,7,10-tetraazacyclododec-1-yl]acetyl]amino]acetyl]amino]-12,24-dioxocholan-24-yl]-L-glutaminyl-L-tryptophyl-L-alanyl-L-valyl-glycyl-L-histidyl-L-leucyl-L-methioninamide (L67), as described in Example III.

C. Synthesis of L67 (N-[(3β,5β)-3-[[[[[4,7,10-Tris(carboxymethyl)-1,4,7,10-tetraazacyclododec-1-yl]acetyl]amino]acetyl]amino]-12,24-dioxocholan-24-yl]-L-glutaminyl-L-tryptophyl-L-alanyl-L-valyl-glycyl-L-histidyl-L-leucyl-L-methioninamide) (FIG. 3B and FIG. 3E).

Resin D (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). (3β,5β)-3-[[(9H-Fluoren-9-ylmethoxy)amino]acetyl]amino]-12-oxocholan-24-oic acid C (0.80 g; 1.2 mmol), HOBt (0.18 g; 1.2 mmol), DIC (0.19 mL; 1.2 mmol) and DMA (7 mL) were added to the resin, the mixture was shaken for 24 h at room temperature, the solution was emptied and the resin was washed with DMA (5×7 mL). The resin was shaken with 50% morpholine in DMA (7 mL) for 10 min, the solution was emptied, fresh 50% morpholine in DMA (7 mL) was added and the mixture was shaken for 20 min. The solution was emptied and the resin was washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin was washed with DMA (5×7 mL), CH$_2$Cl$_2$ (5×7 mL) and vacuum dried. The resin was shaken in a flask with Reagent B (25 mL) for 4.5 h. The resin was filtered and the solution was evaporated under reduced pressure to afford an oily crude that was triturated with Et$_2$O (20 mL).

Example IV

FIGS. 4A-H

Synthesis of L63 and L64

Summary: Hydrolysis of (3β,5β,7α,12α)-3-amino-7,12-dihydroxycholan-24-oic acid methyl ester 1b with NaOH gave the intermediate 2b, which was then reacted with Fmoc-glycine to give 3b. Rink amide resin functionalised with the octapeptide Gln-Trp-Ala-Val-Gly-His-Leu-Met-NH$_2$ (BBN [7-14] (SEQ ID NO:1) was reacted with 3b and then with DOTA tri-t-butyl ester. After cleavage and deprotection with Reagent B the crude was purified by preparative HPLC to give L64. The same procedure was repeated starting from intermediate 2a, already available, to give L63. Overall yields: 9 and 4%, respectively.

Figure 4A:
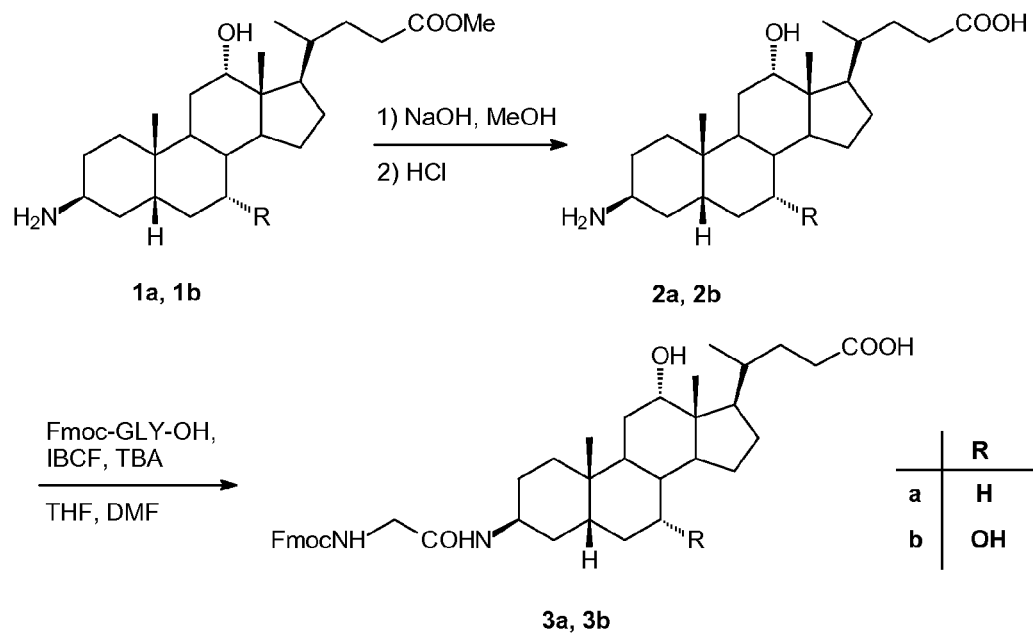
FIG. 4A is a graphical representation of a sequence of reactions to obtain intermediates (3β,5β,12α)-3-[[(9H-Fluoren-9-ylmethoxy)amino]acetyl]amino-12-hydroxycholan-24-oic acid (3a) and (3β,5β,7α,12α)-3-[[(9H-Fluoren-9-ylmethoxy)amino]acetyl]amino-7,12-dihydroxycholan-24-oic acid (3b), as described in Example IV.

A. Synthesis of (3β,5β,7α,12α)-3-Amino-7,12-dihydroxycholan-24-oic acid, (2b) (FIG. 4A)

A 1 M solution of NaOH (130 mL; 0.13 mol) was added dropwise to a solution of (3β,5β,7α,12α)-3-amino-7,12-dihydroxycholan-24-oic acid methyl ester 1b (42.1 g; 0.10 mol) in MeOH (300 mL) heated at 45° C. After 3 h stirring at 45° C., the mixture was concentrated to 150 mL and H$_2$O (350 mL) was added. After extraction with CH$_2$Cl$_2$ (2×100 mL) the aqueous solution was concentrated to 200 mL and 1 M HCl (150 mL) was added. The precipitated solid was filtered, washed with H$_2$O (2×100 mL) and vacuum dried to give 2b as a white solid (34.8 g; 0.08 mol). Yield 80%.

B. Synthesis of (3β,5β,12α)-3-[[(9H-Fluoren-9-ylmethoxy)amino]acetyl]amino-12-hydroxycholan-24-oic acid, (3a) (FIG. 4A)

Tributylamine (4.8 mL; 20.2 mmol) was added dropwise to a solution of N-α-Fmoc-glycine (6.0 g; 20.2 mmol) in THF (120 mL) stirred at 0° C. Isobutyl chloroformate (2.6 mL; 20.2 mmol) was subsequently added and, after 10 min, a suspension of tributylamine (3.9 mL; 16.8 mmol) and (3β,5β,12α)-3-amino-12-hydroxycholan-24-oic acid 2a (6.6 g; 16.8 mmol) in DMF (120 mL) was added dropwise, over 1 h, into the cooled solution. The mixture was allowed to warm up and after 6 h the solution was concentrated to 150 mL, then H$_2$O (250 mL) and 1 N HCl (40 mL) were added (final pH: 1.5). The precipitated solid was filtered, washed with H$_2$O (2×100 mL), vacuum dried and purified by flash chromatography to give 3a as a white solid (3.5 g; 5.2 mmol). Yield 31%.

C. Synthesis of (3β,5β,7α,12α)-3-[[(9H-Fluoren-9-ylmethoxy)amino]acetyl]amino-7,12-dihydroxycholan-24-oic acid, (3b) (FIG. 4A)

Tributylamine (3.2 mL; 13.5 mmol) was added dropwise to a solution of N-α-Fmoc-glycine (4.0 g; 13.5 mmol) in THF (80 mL) stirred at 0° C. Isobutyl chloroformate (1.7 mL; 13.5 mmol) was subsequently added and, after 10 min, a suspension of tributylamine (2.6 mL; 11.2 mmol) and (3β,5β,7α,12α)-3-amino-7,12-dihydroxycholan-24-oic acid 3a (4.5 g; 11.2 mmol) in DMF (80 mL) was added dropwise, over 1 h, into the cooled solution. The mixture was allowed to warm up and after 6 h the solution was concentrated to 120 mL, then H$_2$O (180 mL) and 1 N HCl (30 mL) were added (final pH: 1.5). The precipitated solid was filtered, washed with H$_2$O (2×100 mL), vacuum dried and purified by flash chromatography to give 3a as a white solid (1.9 g; 2.8 mmol). Yield 25%.

In an alternative method, (3β,5β,7α,12α)-3-[[(9H-Fluoren-9-ylmethoxy)amino]acetyl]amino-7,12-dihydroxycholan-24-oic acid, (3b) can be prepared as follows:

N-Hydroxysuccinimide (1.70 g, 14.77 mmol) and DIC (1.87 g, 14.77 mmol) were added sequentially to a stirred solution of Fmoc-Gly-OH (4.0 g, 13.45 mmol) in dichloromethane (15 mL); the resulting mixture was stirred at room temperature for 4 h. The N,N'-diisopropylurea formed was removed by filtration and the solid was washed with ether (20 mL). The volatiles were removed and the solid Fmoc-Gly-succinimidyl ester formed was washed with ether (3×20 mL). Fmoc-Gly-succinimidyl ester was then redissolved in dry DMF (15 mL) and 3-aminodeoxycholic acid (5.21 g, 12.78 mmol) was added to the clear solution. The reaction mixture was stirred at room temperature for 4 h, water (200 mL) was added and the precipitated solid was filtered, washed with water, dried and purified by silica gel chromatography (TLC (silica): ($R_f$: 0.50, silica gel, $CH_2Cl_2$/$CH_3OH$, 9:1) (eluant: $CH_2Cl_2$/$CH_3OH$ (9:1)) to give (3β,5β,7α,12α)-3-[[(9H-Fluoren-9-ylmethoxy)amino]acetyl]amino-7,12-dihydroxycholan-24-oic acid as a colorless solid. Yield: 7.46 g (85%).

Figure 4B:
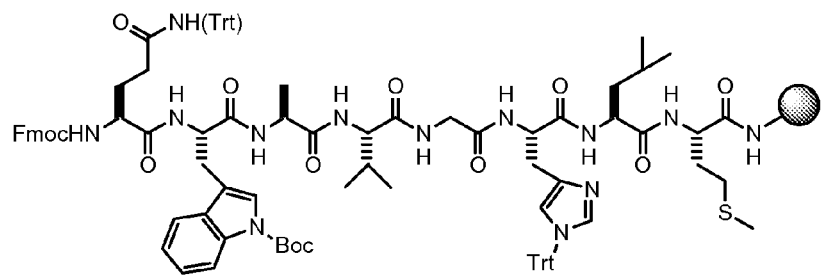
FIG. 4B is a graphical representation of the sequential reaction for the synthesis of N-[(3β,5β,12α)-3-[[[[[4,7,10-Tris(carboxymethyl)-1,4,7,10-tetraazacyclododec-1-yl]acetyl]amino]acetyl]amino]-[2-hydroxy-24-oxocholan-24-yl]-L-glutaminyl-L-tryptophyl-L-alanyl-L-valyl-glycyl-L-histidyl-L-leucyl-L-methioninamide (L63), as described in Example IV.
Figure 4B:
Figure 4B:
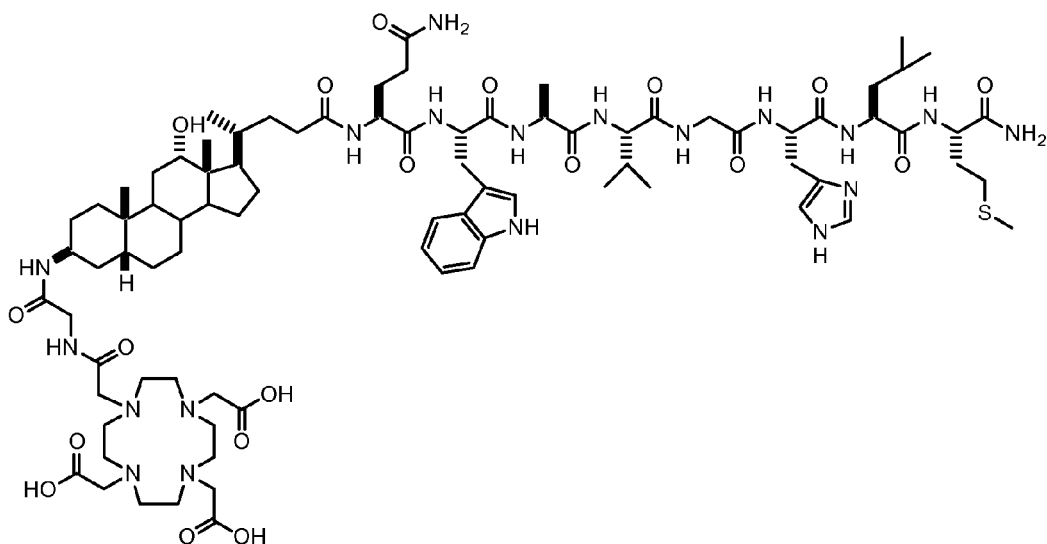

D. Synthesis of L63 (N-[(3β,5β,12α)-3-[[[[[4,7,10-Tris(carboxymethyl)-1,4,7,10-tetraazacyclododec-1-yl]acetyl]amino]acetyl]amino]-12-hydroxy-24-oxocholan-24-yl]-L-glutaminyl-L-tryptophyl-L-alanyl-L-valyl-glycyl-L-histidyl-L-leucyl-L-methioninamide) (FIG. 4B)

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin washed with DMA (5×7 mL). (3β,5β,12α)-3-[[(9H-Fluoren-9-ylmethoxy)amino]acetyl]amino-12-hydroxycholan-24-oic acid 3a (0.82 g; 1.2 mmol), HOBt (0.18 g; 1.2 mmol), DIC (0.19 mL; 1.2 mmol) and DMA (7 mL) were added to the resin, the mixture was shaken for 24 h at room temperature, the solution was emptied and the resin was washed with DMA (5×7 mL). The resin was then shaken with 50% morpholine in DMA (7 mL) for 10 min, the solution was emptied, fresh 50% morpholine in DMA (7 mL) was added and the mixture was shaken for 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin washed with DMA (5×7 mL), $CH_2Cl_2$ (5×7 mL) and vacuum dried. The resin was shaken in a flask with Reagent B (25 mL) for 4 h. The resin was filtered and the solution was evaporated under reduced pressure to afford an oily crude that after treatment with $Et_2O$ (5 mL) gave a precipitate. The precipitate was collected by centrifugation and washed with $Et_2O$ (5×5 mL), then analysed and purified by HPLC. The fractions containing the product were lyophilised to give L63 as a white fluffy solid (12.8 mg; 0.0073 mmol). Yield 9%.

Figure 4C:
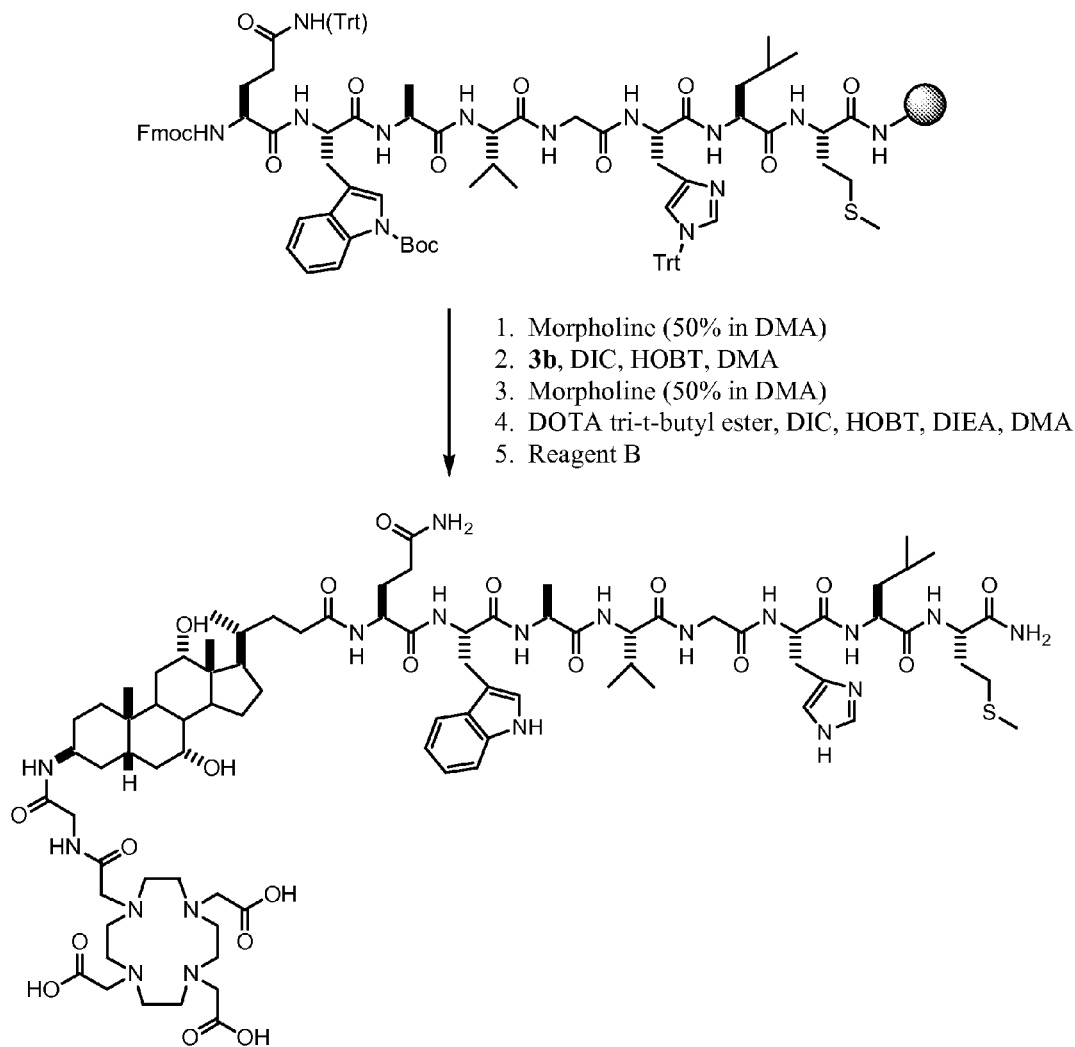
FIG. 4C is a graphical representation of the sequential reaction for the synthesis of N-[(3β,5β,7α,12α)-3-[[[[[4,7,10-Tris(carboxymethyl)-1,4,7,10-tetraazacyclododec-1-yl]acetyl]amino]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide (L64), as described in Example IV.
Figure 4D:
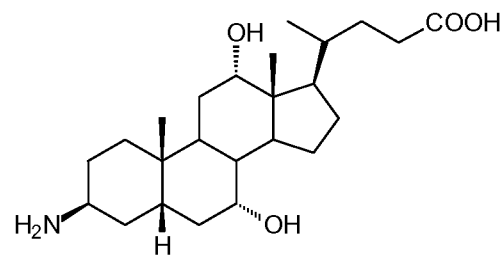
FIG. 4D is a chemical structure of (3β,5β,7α,12α)-3-amino-7,12-dihydroxycholan-24-oic acid (2b), as described in Example IV.
Figure 4E:
FIG. 4E is a chemical structure of (3β,5β,12α)-3-[[(9H-Fluoren-9-ylmethoxy)amino]acetyl]amino-12-hydroxycholan-24-oic acid (3a), as described in Example IV.
Figure 4F:
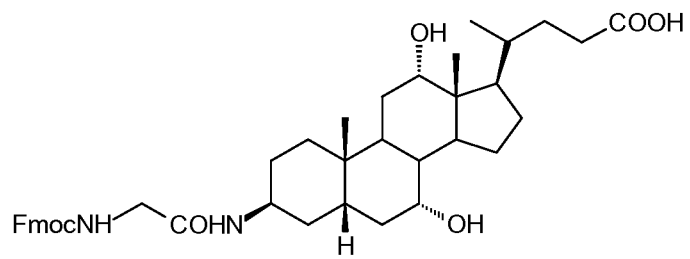
FIG. 4F is a chemical structure of (3β,5β,7α,12α)-3-[[(9H-Fluoren-9-ylmethoxy)amino]acetyl]amino-7,12-dihydroxycholan-24-oic acid (3b), as described in Example IV.
Figure 4G:
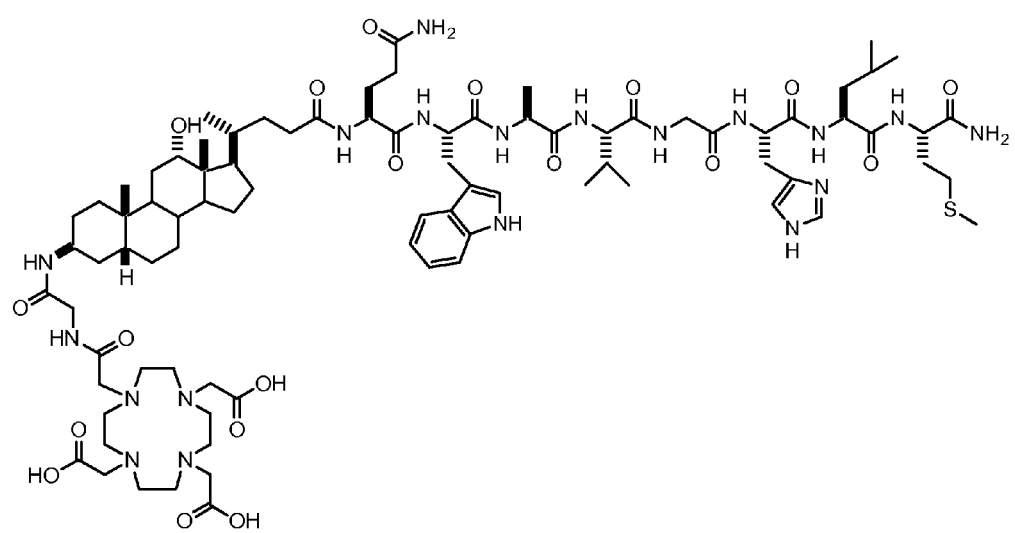
FIG. 4G is a chemical structure of N-[(3β,5β,12α)-3-[[[[[4,7,10-Tris(carboxymethyl)-1,4,7,10-tetraazacyclododec-1-yl]acetyl]amino]acetyl]amino]-12-hydroxy-24-oxocholan-24-yl]-L-glutaminyl-L-tryptophyl-L-alanyl-L-valyl-glycyl-L-histidyl-L-leucyl-L-methioninamide (L63), as described in Example IV.
Figure 4H:
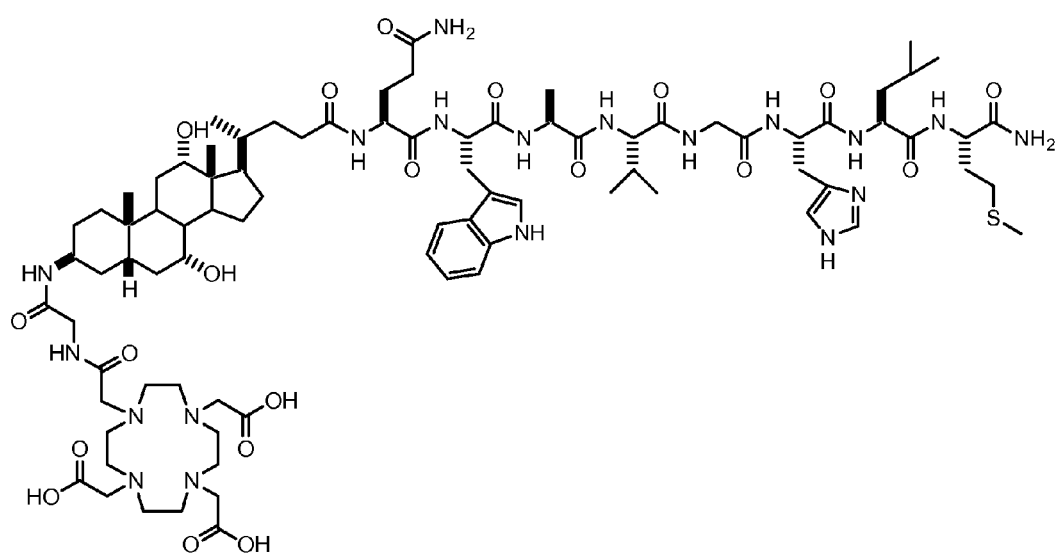
FIG. 4H is a chemical structure of N-[(3β,5β,7α,12α)-3-[[[[[4,7,10-Tris(carboxymethyl)-1,4,7,10-tetraazacyclododec-1-yl]acetyl]amino]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide (L64), as described in Example IV.

E. Synthesis of L64 (N-[(3β,5β,7α,12α)-3-[[[[[4,7,10-Tris(carboxymethyl)-1,4,7,10-tetraazacyclododec-1-yl]acetyl]amino]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide) (FIG. 4C)

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min, the solution was emptied and the resin was washed with DMA (5×7 mL). (3β,5β,7α,12α)-3-[[(9H-Fluoren-9-ylmethoxy)amino]acetyl]amino-7,12-dihydroxycholan-24-oic acid 3b (0.81 g; 1.2 mmol), HOBt (0.18 g; 1.2 mmol), DIC (0.19 mL; 1.2 mmol) and DMA (7 mL) were added to the resin, the mixture was shaken for 24 h at room temperature, the solution was emptied and the resin was washed with DMA (5×7 mL). The resin was shaken with 50% morpholine in DMA (7 mL) for 10 min, the solution was emptied, fresh 50% morpholine in DMA (7 mL) was added and the mixture was shaken for 20 min. The solution was emptied and the resin was washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL; 1.2 mmol), DIEA (0.40 mL; 2.4 mmol) and DMA (7 mL) were added to the resin. The mixture was shaken for 24 h at room temperature, the solution was emptied and the resin washed with DMA (5×7 mL), $CH_2Cl_2$ (5×7 mL) and vacuum dried. The resin was shaken in a flask with Reagent B (25 mL) for 4 h. The resin was filtered and the solution was evaporated under reduced pressure to afford an oily crude that was triturated with $Et_2O$ (5 mL). The precipitate was collected by centrifugation and washed with $Et_2O$ (5×5 mL). Then it was dissolved in $H_2O$ (20 mL), and $Na_2CO_3$ (0.10 g; 0.70 mmol) was added; the resulting mixture was stirred 4 h at room temperature. This solution was purified by HPLC, the fractions containing the product lyophilised to give L64 as a white fluffy solid (3.6 mg; 0.0021 mmol). Yield 4%.

Example V

FIGS. 5A-E

Synthesis of L71 and L72

Summary: The products were obtained in two steps. The first step was the solid phase synthesis of the octapeptide Gln-Trp-Ala-Val-Gly-His-Leu-Met-$NH_2$ (BBN[7-14] (SEQ ID NO:1) (with appropriate side chain protecting groups) on the Rink amide resin discussed supra. The second step was the coupling with different linkers followed by functionalization with DOTA tri-t-butyl ester. After cleavage and deprotection with Reagent B the final products were purified by preparative HPLC. Overall yields 3-9%.

Figure 5A:
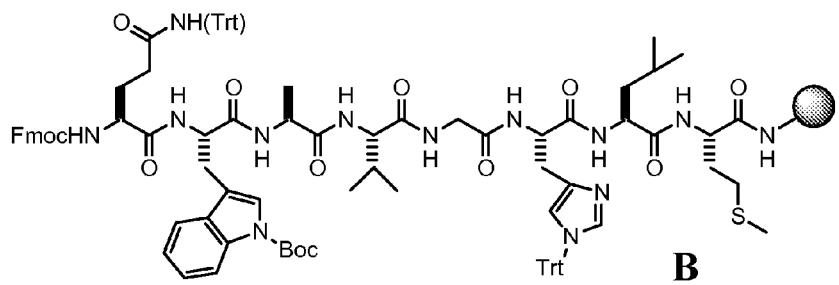
FIG. 5A is a general graphical representation of the sequential reaction for the synthesis of 4-[[[[4,7,10-Tris(carboxymethyl)-1,4,7,10-tetraazacyclododec-1-yl]acetyl]amino]methyl]benzoyl-L-glutaminyl-L-tryptophyl-L-alanyl-L-valyl-glycyl-L-histidyl-L-leucyl-L-methioninamide (L71); and Trans-4-[[[[4,7,10-tris(carboxymethyl)-1,4,7,10-tetraazacyclododec-1-yl]acetyl]amino]methyl]cyclohexyl-carbonyl-L-glutaminyl-L-tryptophyl-L-alanyl-L-valyl-glycyl-L-histidyl-L-leucyl-L-methioninamide (L72) as described in Example V, wherein the linker is from FIG. 5B and FIG. 5C, respectively.
Figure 5A:
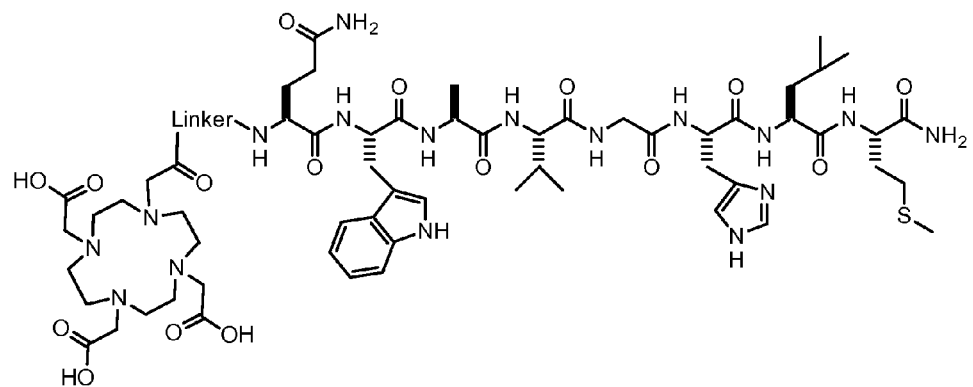
Figure 5B:
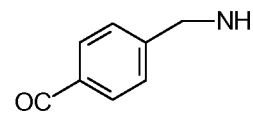
FIG. 5B is a chemical structure of the linker used in compound L71 as shown in FIG. 5A and as described in Example V.
Figure 5C:
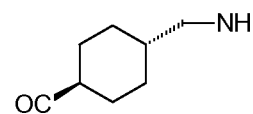
FIG. 5C is a chemical structure of the linker used in compound L72 as shown in FIG. 5A and as described in Example V.
Figure 5D:
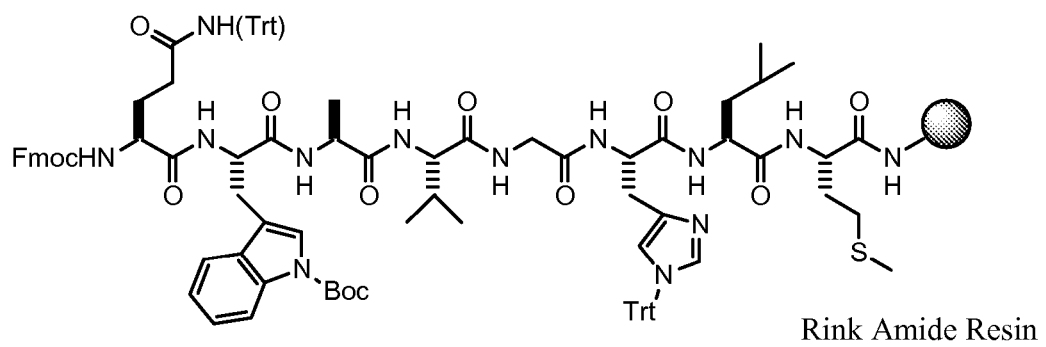
FIG. 5D is a chemical structure of Rink amide resin functionalised with bombesin[7-14] (B), as described in Example V.

A. Bombesin [7-14] Functionalisation and Cleavage Procedure (FIGS. 5A and 5D)

The resin B (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). The Fmoc-linker-OH (1.2 mmol), HOBt (0.18 g; 1.2 mmol), DIC (0.19 mL; 1.2 mmol) and DMA (7 mL) were added to the resin. The mixture was shaken for 3 h at room temperature, the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture was shaken for 20 min. The solution was emptied and the resin was washed with DMA (5×7 mL). 1,4,7,10-Tetraazacyclododecane-1,4,7,10-tetraacetic acid tris(1,1-dimethylethyl) ester adduct with NaCl C (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature. The solution was emptied and the resin washed with DMA (5×7 mL), $CH_2Cl_2$ (5×7 mL)

and vacuum dried. The resin was shaken in a flask with Reagent B (25 mL) for 4 h. The resin was filtered and the filtrate was evaporated under reduced pressure to afford an oily crude that was triturated with ether (5 mL). The precipitate was collected by centrifugation and washed with ether (5×5 mL), then analyzed by analytical HPLC and purified by preparative HPLC. The fractions containing the product were lyophilized.

B. Products
1. L71 (4-[[[[4,7,10-Tris(carboxymethyl)-1,4,7,10-tetraazacyclododec-1-yl]acetyl]amino]methyl]benzoyl-L-glutaminyl-L-tryptophyl-L-alanyl-L-valyl-glycyl-L-histidyl-L-leucyl-L-methioninamide)
   The product was obtained as a white fluffy solid (7.3 mg; 0.005 mmol). Yield 7.5%.
2. L72 (Trans-4-[[[[4,7,10-tris(carboxymethyl)-1,4,7,10-tetraazacyclododec-1-yl]acetyl]amino]methyl]cyclohexylcarbonyl-L-glutaminyl-L-tryptophyl-L-alanyl-L-valyl-glycil-L-histidyl-L-leucyl-L-methioninamide)
   The product was obtained as a white fluffy solid (7.0 mg; 0.005 mmol). Yield 4.8%.

Figure 5E:
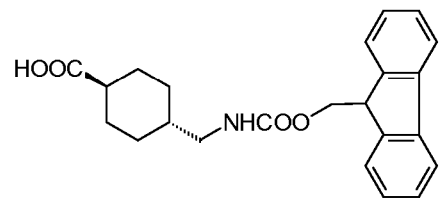
FIG. 5E is a chemical structure of Trans-4-[[[(9H-fluoren-9-ylmethoxy)carbonyl]amino]methyl]cyclohexanecarboxylic acid (D), as described in Example V.

C. Trans-4-[[[(9H-fluoren-9-ylmethoxy)carbonyl]amino]methyl]cyclohexanecarboxylic acid, (D) (FIG. 5E)

A solution of N-(9-fluorenylmethoxycarbonyloxy)succinimide (4.4 g; 14.0 mmol) in 1,4-dioxane (40 mL) was added dropwise to a solution of trans-4-(aminomethyl)cyclohexanecarboxylic acid (2.0 g; 12.7 mmol) in 10% $Na_2CO_3$ (30 mL) cooled to 0° C. The mixture was then allowed to warm to ambient temperature and after 1 h stirring at room temperature was treated with 1 N HCl (32 mL) until the final pH was 2. The resulting solution was extracted with n-BuOH (100 mL); the volatiles were removed and the crude residue was purified by flash chromatography to give D as a white solid (1.6 g; 4.2 mmol). Yield 33%.

Example VI

FIGS. 6A-F

Synthesis of L75 and L76

Summary: The two products were obtained by coupling of the octapeptide Gln-Trp-Ala-Val-Gly-His-Leu-Met-$NH_2$ (BBN[7-14], which is SEQ ID NO:1) (A) on the Rink amide resin with the two linkers E and H, followed by functionalization with DOTA tri-t-butyl ester. After cleavage and deprotection with Reagent B the final products were purified by preparative HPLC. Overall yields: 8.5% (L75) and 5.6% (L76).

Figure 6A:
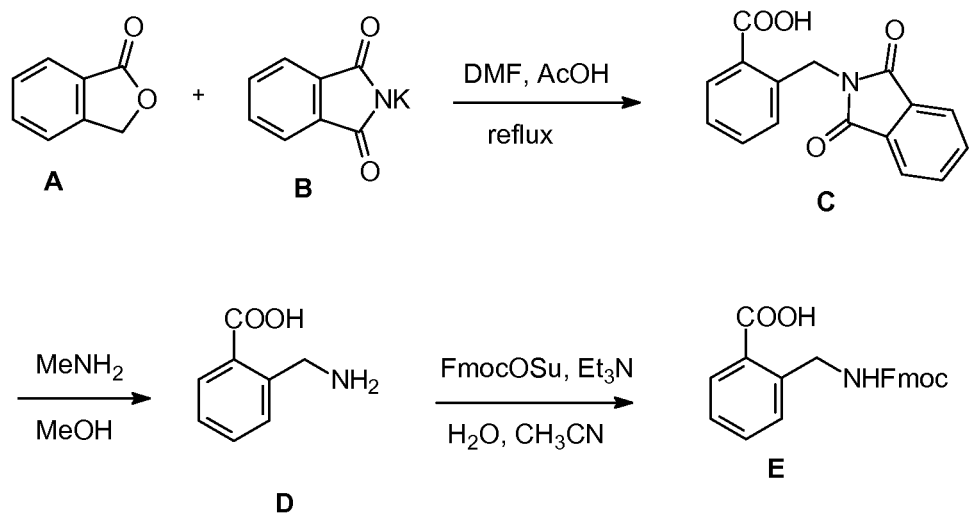
FIG. 6A is a graphical representation of a sequence of reactions for the synthesis of intermediate linker 2-[[[9H-Fluoren-9-ylmethoxy)carbonyl]amino]methyl]benzoic acid (E), as described in Example VI.

A. 2-[(1,3-Dihydro-1,3-dioxo-2H-isoindol-2-yl)methyl]benzoic acid, (C) (FIG. 6A)
   The product was synthesized following the procedure reported in the literature (Bornstein, J; Drummon, P. E.; Bedell, S. F. Org. Synth. Coll. Vol. IV 1963, 810-812).

B. 2-(Aminomethyl)benzoic acid, (D) (FIG. 6A)
A 40% solution of methylamine (6.14 mL; 7.1 mmol) was added to 2-[(1,3-dihydro-1,3-dioxo-2H-isoindol-2-yl)methyl]benzoic acid C (2 g; 7.1 mmol) and then EtOH (30 mL) was added. After 5 minutes stirring at room temperature the reaction mixture was heated at 50° C. After 2.5 h, the mixture was cooled and the solvent was evaporated under reduced pressure. The crude product was suspended in 50 mL of absolute ethanol and the suspension was stirred at room temperature for 1 h. The solid was filtered and washed with EtOH to afford 2-(aminomethyl)benzoic acid D (0.87 g; 5.8 mmol). Yield 81%.

C. 2-[[[(9H-Fluoren-9-ylmethoxy)carbonyl]amino]methyl]benzoic acid, (E) (FIG. 6A)
   The product was synthesized following the procedure reported in the literature (Sun, J-H.; Deneker, W. F. Synth. Commun. 1998, 28, 4525-4530).

Figure 6B:
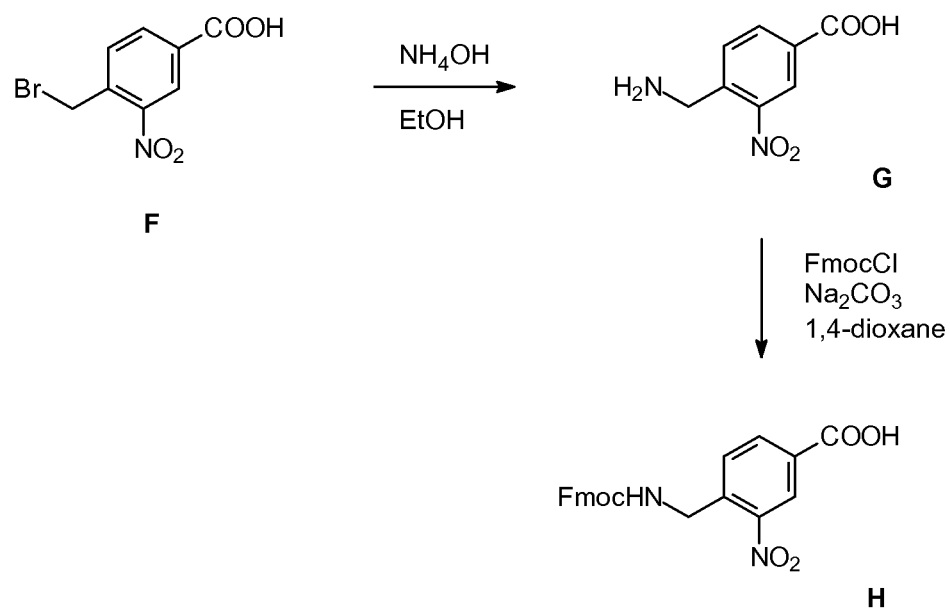
FIG. 6B is a graphical representation of a sequence of reactions for the synthesis of intermediate linker 4-[[[9H-Fluoren-9-ylmethoxy)carbonyl]amino]methyl]-3-nitrobenzoic acid (H), as described in Example VI.

D. 4-(Aminomethyl)-3-nitrobenzoic acid, (G) (FIG. 6B)
   4-(Bromomethyl)-3-nitrobenzoic acid (3.2 g; 12.3 mmol) was dissolved in 8% $NH_3$ in EtOH (300 mL) and the resulting solution was stirred at room temperature. After 22 h the solution was evaporated and the residue suspended in $H_2O$ (70 mL). The suspension was stirred for 15 min and filtered. The collected solid was suspended in $H_2O$ (40 mL) and dissolved by the addition of few drops of 25% aq. $NH_4OH$ (pH 12), then the pH of the solution was adjusted to 6 by addition of 6 N HCl. The precipitated solid was filtered, and washed sequentially with MeOH (3×5 mL), and $Et_2O$ (10 mL) and was vacuum dried (1.3 kPa; $P_2O_5$) to give 4-(aminomethyl)-3-nitrobenzoic acid as a pale brown solid (1.65 g; 8.4 mmol). Yield 68%.

E. 4-[[[(9H-Fluoren-9-ylmethoxy)carbonyl]amino]methyl]-3-nitrobenzoic acid, (H) (FIG. 6B)
   4-(Aminomethyl)-3-nitrobenzoic acid G (0.8 g; 4 mmol) was dissolved in 10% aq. $Na_2CO_3$ (25 mL) and 1,4-dioxane (10 mL) and the solution was cooled to 0° C. A solution of 9-fluorenylmethyl chloroformate (Fmoc-Cl) (1.06 g; 4 mmol) in 1,4-dioxane (10 mL) was added dropwise for 20 min. After 2 h at 0-5° C. and 1 h at 10° C. the reaction mixture was filtered and the solution was acidified to pH 5 by addition of 1 N HCl. The precipitate was filtered, washed with $H_2O$ (2×2 mL) dried under vacuum (1.3 kPa; $P_2O_5$) to give 4-[[[9H-fluoren-9-ylmethoxy)carbonyl]amino]methyl]-3-nitrobenzoic acid as a white solid (1.6 g; 3.7 mmol). Yield 92%.

Figure 6C:
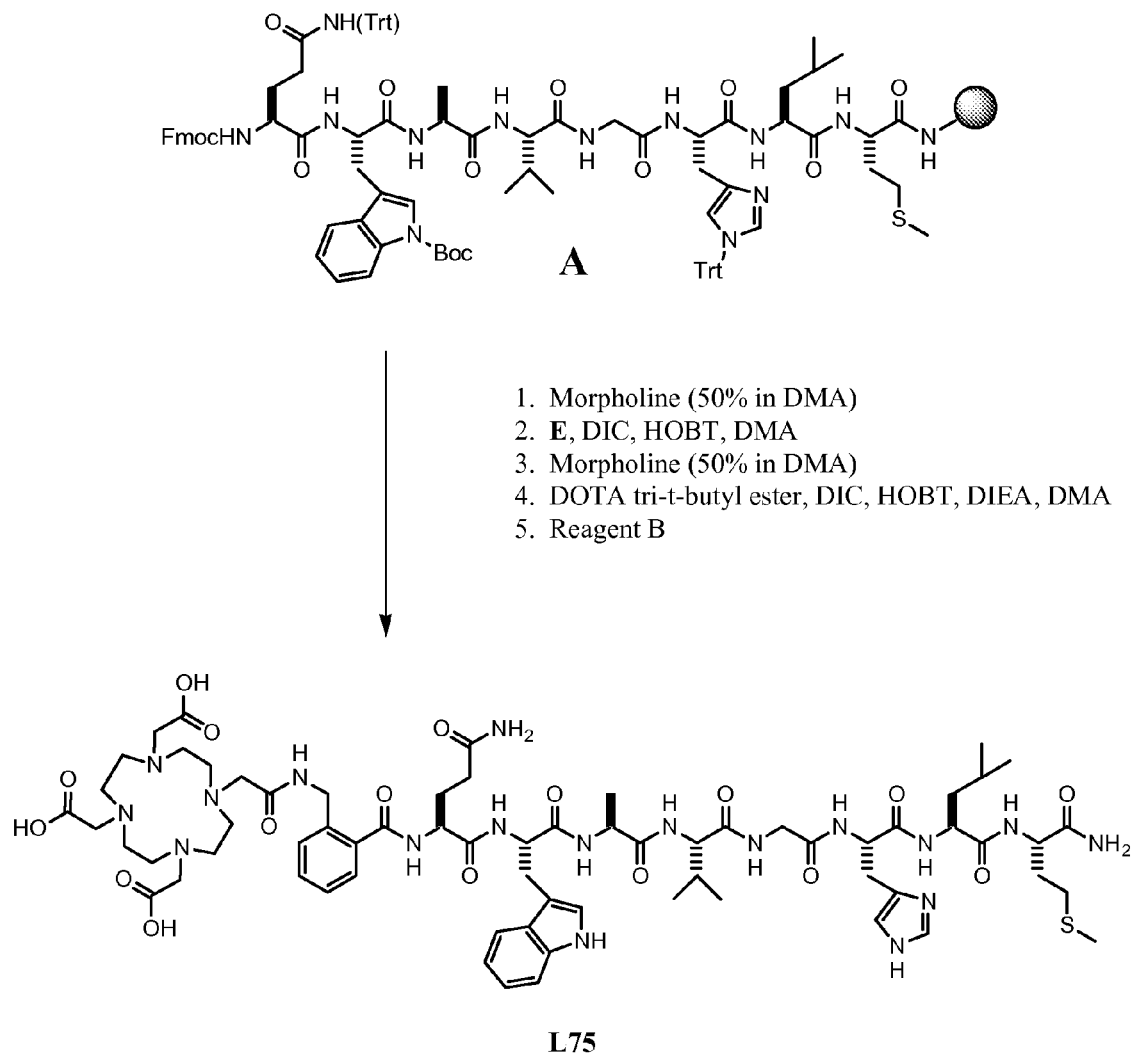
FIG. 6C is a graphical representation of the synthesis of N-[2-[[[[4,7,10-Tris(carboxymethyl)-1,4,7,10-tetraazacyclododec-1-yl]acetyl]amino]methyl]benzoyl]-L-glutaminyl-L-tryptophyl-L-alanyl-L-valyl-glycyl-L-histidyl-L-leucyl-L-methioninamide (L75), as described in Example VI.

F. L75 (N-[2-[[[[4,7,10-Tris(carboxymethyl)-1,4,7,10-tetraazacyclododec-1-yl]acetyl]amino]methyl]benzoyl]-L-glutaminyl-L-tryptophyl-L-alanyl-L-valyl-glycyl-L-histidyl-L-leucyl-L-methioninamide) (FIG. 6C)
   Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin washed with DMA (5×7 mL). 2-[[[(9H-Fluoren-9-ylmethoxy)carbonyl]amino]methyl]benzoic acid, E (0.45 g; 1.2 mmol), N-hydroxybenzotriazole (HOBt) (0.18 g; 1.2 mmol), N,N'-diisopropylcarbodiimide (DIC) (0.19 mL; 1.2 mmol) and DMA (7 mL) were added to the resin, the mixture shaken for 24 h at room temperature, the solution was emptied and the resin was washed with DMA (5×7 mL). The resin was then shaken with 50% morpholine in DMA (7 mL) for 10 min, the solution was emptied, fresh 50% morpholine in DMA (7 mL) was added and the mixture shaken for 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (DOTA tri-t-butyl ester) (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin was washed with DMA (5×7 mL), $CH_2Cl_2$ (5×7 mL) and vacuum dried. The resin was shaken in a flask with Reagent B (25 mL) for 4.5 h. The resin was filtered and the filtrate was evaporated under reduced pressure to afford an oily crude that after treatment with Et$_2$O (20 mL) gave a precipitate. The resulting precipitate was collected by centrifugation and was washed with Et$_2$O (3×20 mL) to give L75 (190 mg; 0.13 mmol) as a white solid. Yield 44%.

Figure 6D:
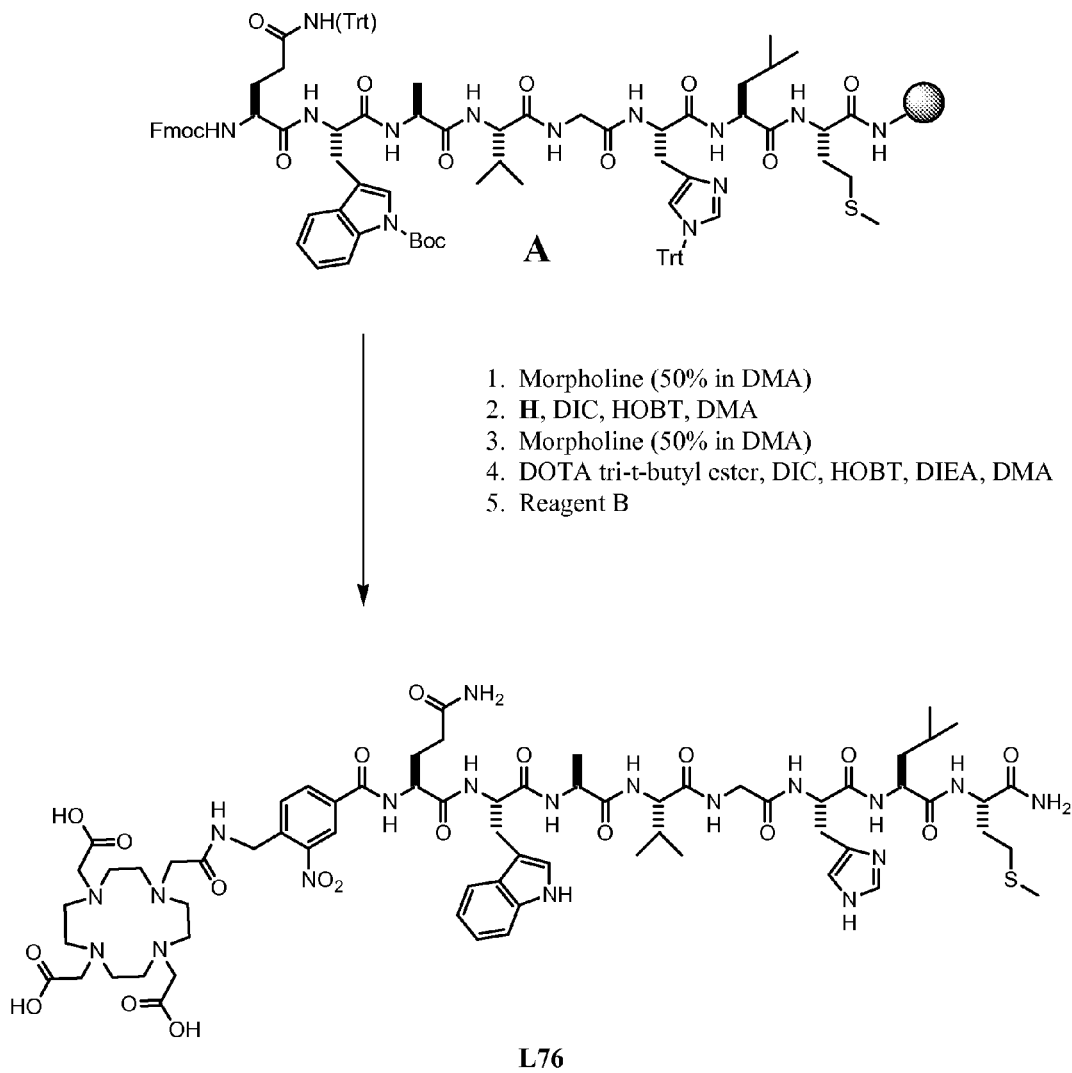
FIG. 6D is a graphical representation of the synthesis of N-[4-[[[[4,7,10-Tris(carboxymethyl)-1,4,7,10-tetraazacyclododec-1-yl]acetyl]amino]methyl]-3-nitrobenzoyl]-L-glutaminyl-L-tryptophyl-L-alanyl-L-valyl-glycyl-L-histidyl-L-leucyl-L-methioninamide (L76), as described in Example VI.

G. L76 (N-[4-[[[[4,7,10-Tris(carboxymethyl)-1,4,7,10-tetraazacyclododec-1-yl]acetyl]amino]methyl]-3-nitrobenzoyl]-L-glutaminyl-L-tryptophyl-L-alanyl-L-valyl-glycyl-L-histidyl-L-leucyl-L-methioninamide) (FIG. 6D)

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). 4-[[[9H-Fluoren-9-ylmethoxy)carbonyl]amino]methyl]-3-nitrobenzoic acid, H (0.50 g; 1.2 mmol), HOBt (0.18 g; 1.2 mmol), DIC (0.19 mL; 1.2 mmol) and DMA (7 mL) were added to the resin, the mixture was shaken for 24 h at room temperature, the solution was emptied and the resin was washed with DMA (5×7 mL). The resin was then shaken with 50% morpholine in DMA (7 mL) for 10 min, the solution was emptied, fresh 50% morpholine in DMA (7 mL) was added and the mixture was shaken for 20 min. The solution was emptied and the resin was washed with DMA (5×7 mL). DOTA tri-t-butyl ester (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin was washed with DMA (5×7 mL), CH$_2$Cl$_2$ (5×7 mL) and vacuum dried. The resin was shaken in a flask with Reagent B (25 mL) for 4.5 h. The resin was filtered and the solution was evaporated under reduced pressure to afford an oily crude that was triturated with Et$_2$O (20 mL). The precipitate was collected by centrifugation and was washed with Et$_2$O (3×20 mL) to give a solid (141 mg) which was analysed by HPLC. A 37 mg portion of the crude was purified by preparative HPLC. The fractions containing the product were lyophilised to give L76 (10.8 mg; 7.2×10$^{-3}$ mmol) as a white solid. Yield 9%.

Example VII

FIGS. 7A-C

Synthesis of L124

Summary: 4-Cyanophenol A was reacted with ethyl bromoacetate and K$_2$CO$_3$ in acetone to give the intermediate B, which was hydrolysed with NaOH to the corresponding acid C. Successive hydrogenation of C with H$_2$ and PtO$_2$ at 355 kPa in EtOH/CHCl$_3$ gave the corresponding aminoacid D, which was directly protected with FmocOSu to give E. Rink amide resin functionalised with the octapeptide Gln-Trp-Ala-Val-Gly-His-Leu-Met-NH$_2$ (BBN[7-14], which is SEQ ID NO:1) was reacted with E and then with DOTA tri-t-butyl ester. After cleavage and deprotection with Reagent B the crude was purified by preparative HPLC to give L124. Overall yield: 1.3%

Figure 7A:
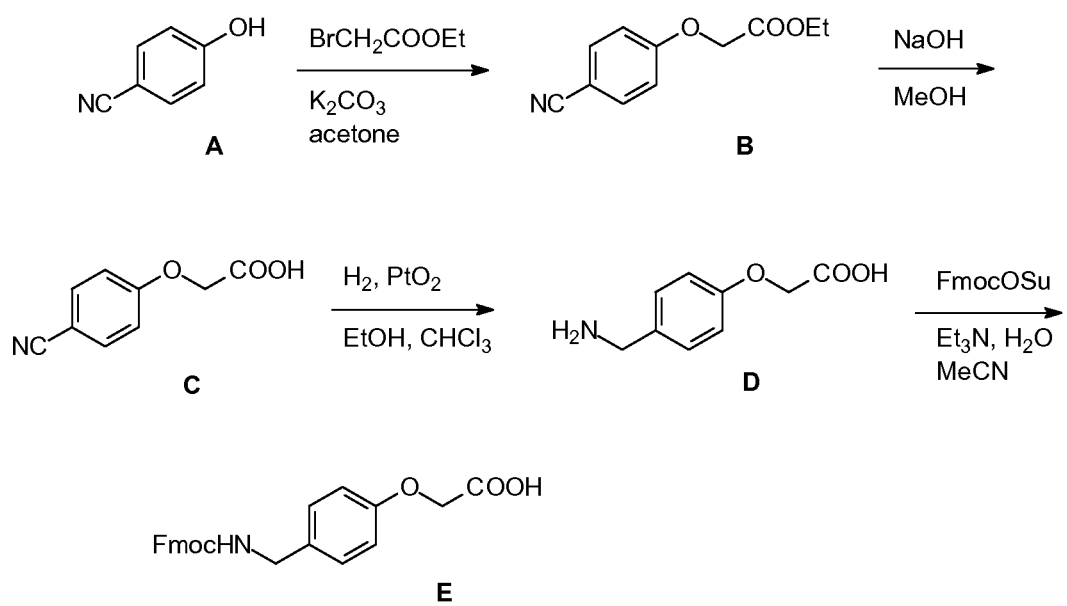
FIG. 7A is a graphical representation of a sequence of reactions for the synthesis of intermediate linker [4-[[[9H-Fluoren-9-ylmethoxy)carbonyl]amino]methyl]phenoxy]acetic acid (E), as described in Example VII.

A. Synthesis of (4-Cyanophenoxy)acetic acid ethyl ester, (B) (FIG. 7A)

The product was synthesized following the procedure reported in the literature (Archimbault, P.; LeClerc, G.; Strosberg, A. D.; Pietri-Rouxel, F. PCT Int. Appl. WO 980005, 1998).

B. Synthesis of (4-Cyanophenoxy)acetic acid, (C) (FIG. 7A)

A 1 N solution of NaOH (7.6 mL; 7.6 mmol) was added dropwise to a solution of (4-cyanophenoxy)acetic acid ethyl ester B (1.55 g; 7.6 mmol) in MeOH (15 mL). After 1 h the solution was acidified with 1 N HCl (7.6 mL; 7.6 mmol) and evaporated. The residue was taken up with water (20 mL) and extracted with CHCl$_3$ (2×30 mL). The organic phases were evaporated and the crude was purified by flash chromatography to give (4-cyanophenoxy)acetic acid C (0.97 g; 5.5 mmol) as a white solid. Yield 72%.

C. Synthesis of [4-[[[9H-Fluoren-9-ylmethoxy)carbonyl]amino]methyl]phenoxy]acetic acid, (E) (FIG. 7A)

PtO$_2$ (150 mg) was added to a solution of (4-cyanophenoxy)acetic acid C (1.05 g; 5.9 mmol) in EtOH (147 mL) and CHCl$_3$ (3 mL). The suspension was stirred 30 h under a hydrogen atmosphere (355 kPa; 20° C.). The mixture was filtered through a Celite® pad and the solution evaporated under vacuum. The residue was purified by flash chromatography to give acid D (0.7 g) which was dissolved in H$_2$O (10 mL), MeCN (2 mL) and Et$_3$N (0.6 mL) at 0° C., then a solution of N-(9-fluorenylmethoxycarbonyloxy)succinimide (1.3 g; 3.9 mmol) in MeCN (22 mL) was added dropwise. After stirring 16 h at room temperature the reaction mixture was filtered and the volatiles were removed under vacuum. The residue was treated with 1 N HCl (10 mL) and the precipitated solid was filtered and purified by flash chromatography to give [4-[[[9H-fluoren-9-ylmethoxy)carbonyl]amino]methyl]phenoxy]acetic acid E (0.56 g; 1.4 mmol) as a white solid. Overall yield 24%.

Figure 7B:
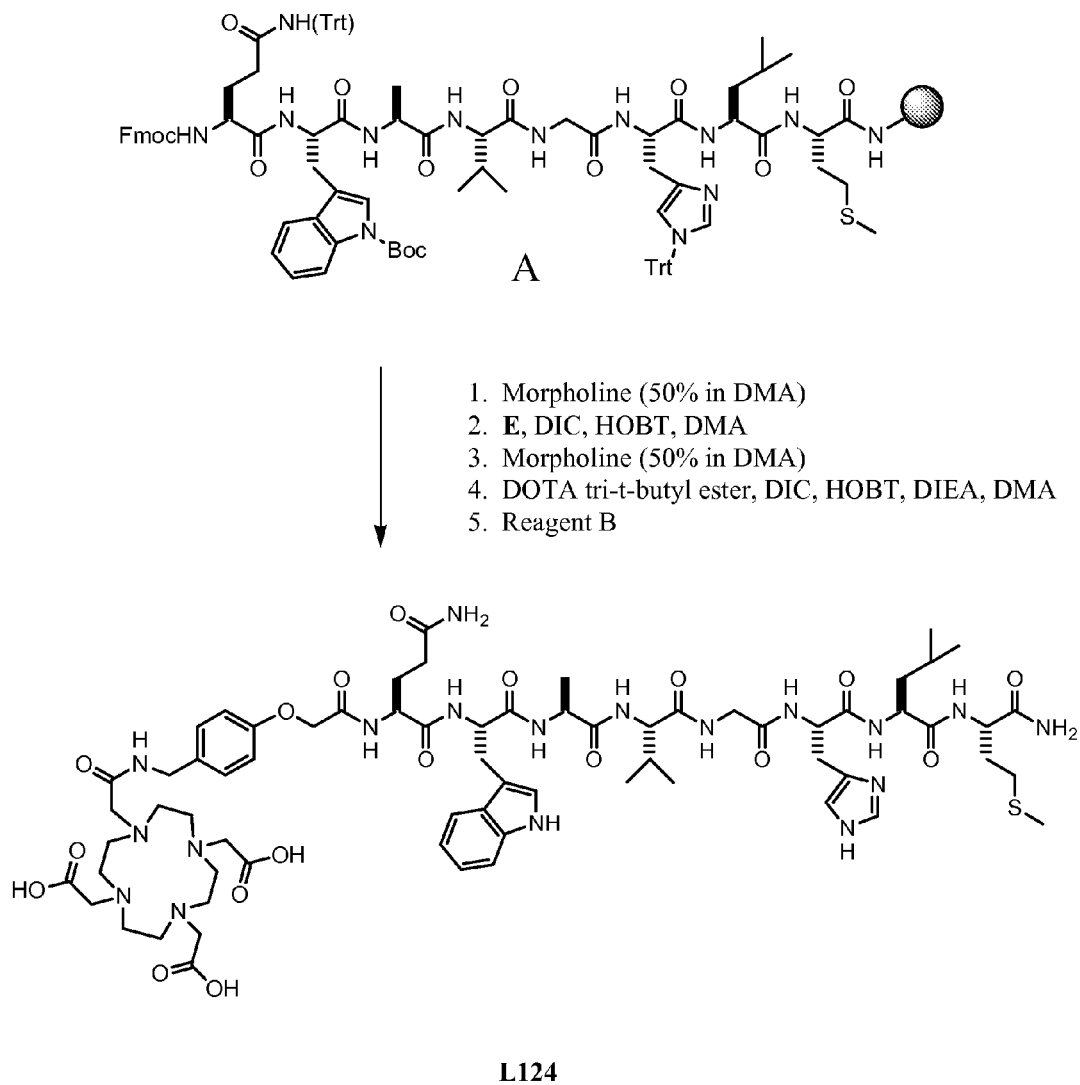
FIG. 7B is a graphical representation of the synthesis of N-[[4-[[[[4,7,10-Tris(carboxymethyl)-1,4,7,10-tetraazacyclododec-1-yl]acetyl]amino]methyl]phenoxy]acetyl]-L-glutaminyl-L-tryptophyl-L-alanyl-L-valyl-glycyl-L-histidyl-L-leucyl-L-methioninamide (L124), as described in Example VII.

D. Synthesis of L124 (N-[[4-[[[[4,7,10-Tris(carboxymethyl)-1,4,7,10-tetraazacyclododec-1-yl]acetyl]amino]methyl]phenoxy]acetyl]-L-glutaminyl-L-tryptophyl-L-alanyl-L-valyl-glycyl-L-histidyl-L-leucyl-L-methioninamide) (FIG. 7B)

Figure 7C:
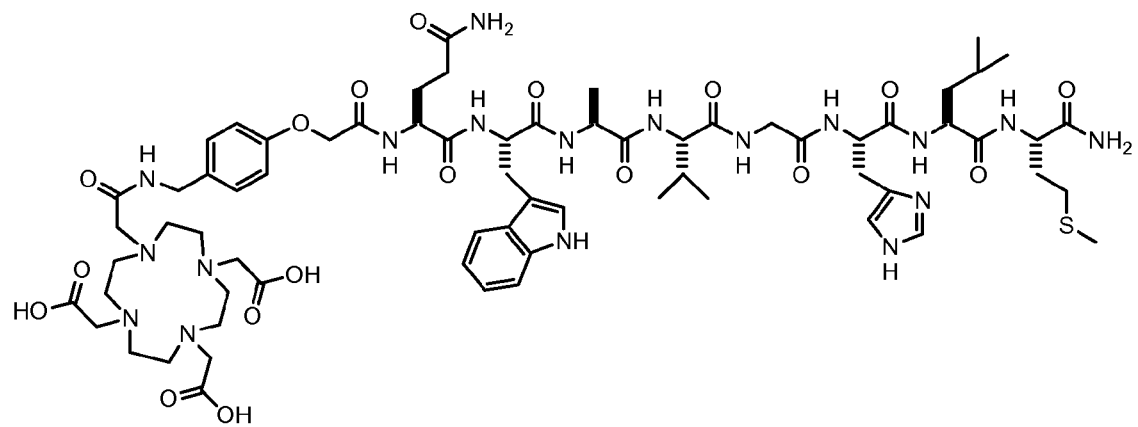
FIG. 7C is a chemical structure of N-[[4-[[[[4,7,10-Tris(carboxymethyl)-1,4,7,10-tetraazacyclododec-1-yl]acetyl]amino]methyl]phenoxy]acetyl]-L-glutaminyl-L-tryptophyl-L-alanyl-L-valyl-glycyl-L-histidyl-L-leucyl-L-methioninamide (L124), as described in Example VII.

Resin A (480 mg; 0.29 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min, the solution was emptied and the resin was washed with DMA (5×7 mL). [4-[[[9H-Fluoren-9-ylmethoxy)carbonyl]amino]methyl]phenoxy]acetic acid E (480 mg; 1.19 mmol), N-hydroxybenzotriazole (HOBt) (182 mg; 1.19 mmol), N,N'-diisopropylcarbodiimide (DIC) (185 µL; 1.19 mmol) and DMA (7 mL) were added to the resin, the mixture was shaken for 24 h at room temperature, the solution was emptied and the resin was washed with DMA (5×7 mL). The resin was then shaken with 50% morpholine in DMA (6 mL) for 10 min, the solution was emptied, fresh 50% morpholine in DMA (6 mL) was added and the mixture was shaken for 20 min. The solution was emptied and the resin was washed with DMA (5×7 mL). 1,4,7,10-Tetraazacyclododecane-1,4,7,10-tetraacetic acid tris(1,1-dimethylethyl) ester adduct with NaCl (750 mg; 1.19 mmol), HOBt (182 mg; 1.19 mmol), DIEA (404 µL; 2.36 mmol), DIC (185 µL; 1.19 mmol) and DMA (6 mL) were added to the resin. The mixture was shaken for 24 h at room temperature, the solution was emptied, the resin was washed with DMA (2×7 mL), CH$_2$Cl$_2$ (5×7 mL) and vacuum dried. The resin was shaken in a flask with Reagent B (25 mL) for 4 h. The resin was filtered and the filtrate was evaporated under reduced pressure to afford an oily crude that was triturated with Et$_2$O (5 mL). The precipitate was collected by centrifugation and washed with Et$_2$O (5×5 mL) to give a solid (148 mg) which was analysed by HPLC. A 65 mg portion of the crude was purified by preparative HPLC. The fractions containing the product were lyophilised to give L124 (FIG. 7C) as a white solid (15 mg; 0.01 mmol). Yield 7.9%.

Example VIII

FIGS. 8A-C

Synthesis of L125

Summary: 4-(Bromomethyl)-3-methoxybenzoic acid methyl ester A was reacted with NaN$_3$ in DMF to give the intermediate azide B, which was then reduced with Ph$_3$P and H$_2$O to amine C. Hydrolysis of C with NaOH gave acid D, which was directly protected with FmocOSu to give E. Rink amide resin functionalised with the octapeptide Gln-Trp-Ala-Val-Gly-His-Leu-Met-NH$_2$ (BBN[7-14], which is SEQ ID NO:1) (A) was reacted with E and then with DOTA tri-t-butyl ester. After cleavage and deprotection with Reagent B the crude was purified by preparative HPLC to give L125. Overall yield: 0.2%.

A. Synthesis of 4-(Azidomethyl)-3-methoxybenzoic acid methyl ester, (B) (FIG. 8A)

A solution of 4-(bromomethyl)-3-methoxybenzoic acid methyl ester (8 g; 31 mmol) and NaN$_3$(2 g; 31 mmol) in DMF (90 mL) was stirred overnight at room temperature. The volatiles were removed under vacuum and the crude product was dissolved in EtOAc (50 mL). The solution was washed with water (2×50 mL) and dried. The volatiles were evaporated to provide 4-(azidomethyl)-3-methoxybenzoic acid methyl ester (6.68 g; 30 mmol). Yield 97%.

Figure 8A:
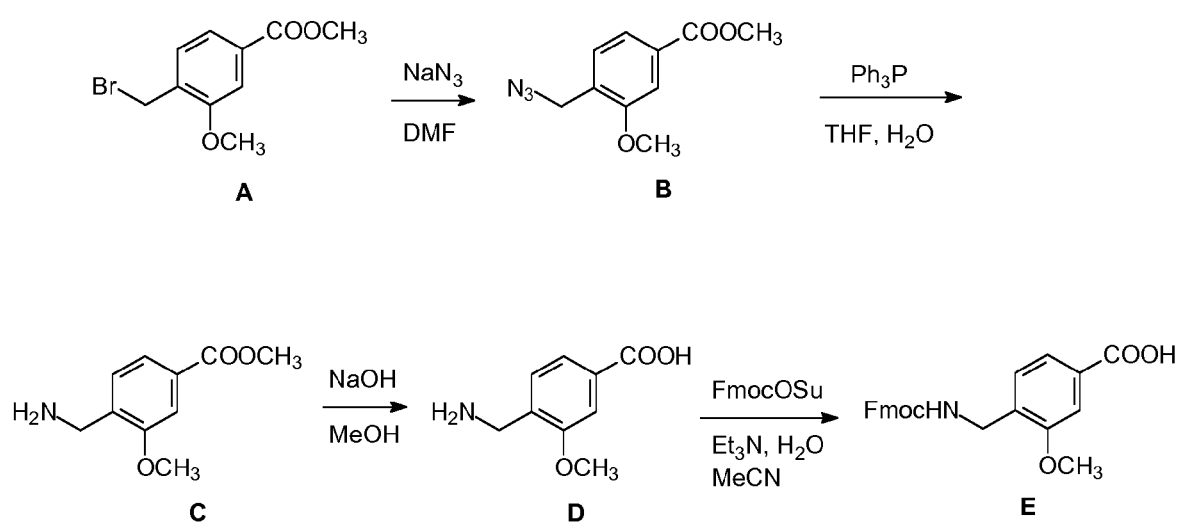
FIG. 8A is a graphical representation of a sequence of reactions for the synthesis of intermediate 4-[[[9H-Fluoren-9-ylmethoxy)carbonyl]amino]methyl]-3-methoxybenzoic acid (E), as described in Example VIII.

B. 4-(Aminomethyl)-3-methoxybenzoic acid methyl ester, (C) (FIG. 8A)

Triphenylphosphine (6.06 g; 23 mmol) was added to a solution of (4-azidomethyl)-3-methoxybenzoic acid methyl ester B (5 g; 22 mmol) in THF (50 mL): hydrogen evolution and formation of a white solid was observed. The mixture was stirred under nitrogen at room temperature. After 24 h more triphenylphosphine (0.6 g; 2.3 mmol) was added. After 24 h the azide was consumed and H$_2$O (10 mL) was added. After 4 h the white solid disappeared. The mixture was heated at 45° C. for 3 h and was stirred overnight at room temperature. The solution was evaporated to dryness and the crude was purified by flash chromatography to give 4-(aminomethyl)-3-methoxybenzoic acid methyl ester C (1.2 g; 6.1 mmol). Yield 28%.

C. 4-[[[9H-Fluoren-9-ylmethoxy)carbonyl]amino]methyl]-3-methoxybenzoic acid, (E) (FIG. 8A)

A 1 N solution of NaOH (6.15 mL; 6.14 mmol) was added dropwise to a solution of 4-(aminomethyl)-3-methoxybenzoic acid methyl ester C (1.2 g; 6.14 mmol) in MeOH (25 mL) heated at 40° C. After stirring 8 h at 45° C. the solution was stirred over night at room temperature. A 1 N solution of NaOH (0.6 mL; 0.6 mmol) was added and the mixture heated at 40° C. for 4 h. The solution was concentrated, acidified with 1 N HCl (8 mL; 8 mmol), extracted with EtOAc (2×10 mL) then the aqueous layer was concentrated to 15 mL. This solution (pH 4.5) was cooled at 0° C. and Et$_3$N (936 µL; 6.75 mmol) was added (pH 11). A solution of N-(9-fluorenylmethoxycarbonyloxy)succinimide (3.04 g; 9 mmol) in MeCN (30 mL) was added dropwise (final pH 9) and a white solid precipitated. After stirring 1 h at room temperature the solid was filtered, suspended in 1N HCl (15 mL) and the suspension was stirred for 30 min. The solid was filtered to provide 4-[[[9H-fluoren-9-ylmethoxy)carbonyl]amino]methyl]-3-methoxybenzoic acid E as a white solid (275 mg; 0.7 mmol).

The filtrate was evaporated under vacuum and the resulting white residue was suspended in 1N HCl (20 mL) and stirred for 30 minutes. The solid was filtered and purified by flash chromatography to give more acid E (198 mg; 0.5 mmol). Overall yield 20%.

Figure 8B:
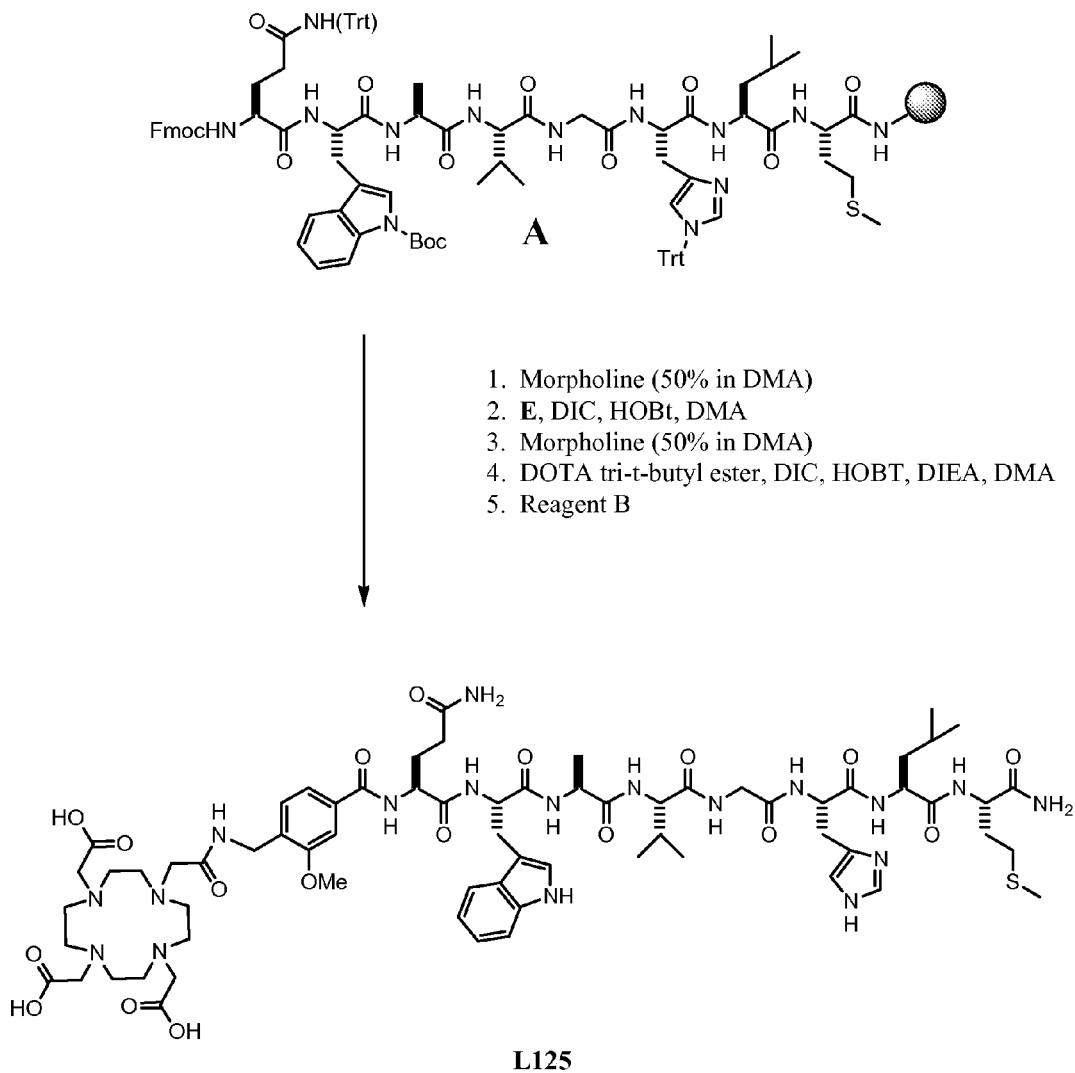
FIG. 8B is a graphical representation of the synthesis of N-[4-[[[[4,7,10-Tris(carboxymethyl)-1,4,7,10-tetraazacyclododec-1-yl]acetyl]amino]methyl]-3-methoxybenzoyl]-L-glutaminyl-L-tryptophyl-L-alanyl-L-valyl-glycyl-L-histidyl-L-leucyl-L-methioninamide, (L125), as described in Example VIII.

D. L125 (N-[4-[[[[4,7,10-Tris(carboxymethyl)-1,4,7,10-tetraazacyclododec-1-yl]acetyl]amino]methyl]-3-methoxybenzoyl]-L-glutaminyl-L-tryptophyl-L-alanyl-L-valyl-glycyl-L-histidyl-L-leucyl-L-methioninamide) (FIG. 8B)

Figure 8C:
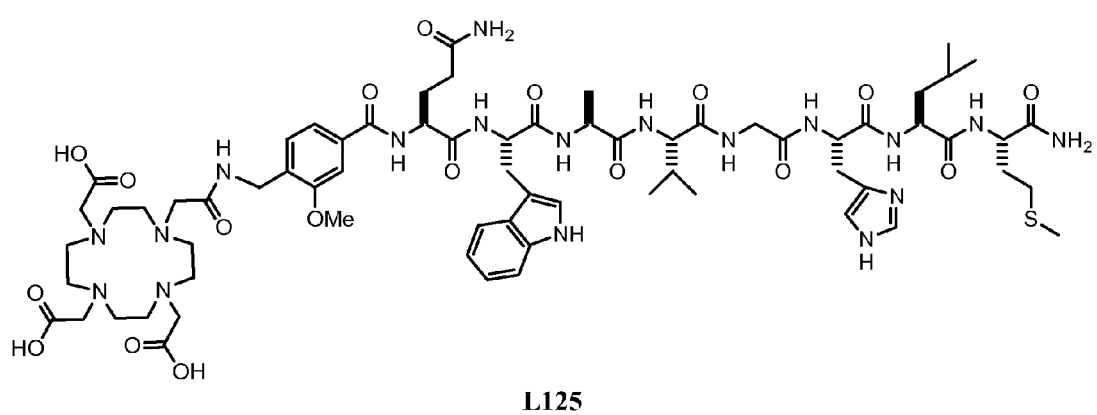
FIG. 8C is a chemical structure of N-[4-[[[[4,7,10-Tris(carboxymethyl)-1,4,7,10-tetraazacyclododec-1-yl]acetyl]amino]methyl]-3-methoxybenzoyl]-L-glutaminyl-L-tryptophyl-L-alanyl-L-valyl-glycyl-L-histidyl-L-leucyl-L-methioninamide, (L125), as described in Example VIII.

Resin A (410 mg; 0.24 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). 4-[[[9H-Fluoren-9-ylmethoxy)carbonyl]amino]methyl]-3-methoxybenzoic acid E (398 mg; 0.98 mmol), HOBt (151 mg; 0.98 mmol), DIC (154 µL; 0.98 mmol) and DMA (6 mL) were added to the resin; the mixture was shaken for 24 h at room temperature, the solution was emptied and the resin was washed with DMA (5×7 mL). The resin was then shaken with 50% morpholine in DMA (6 mL) for 10 min, the solution was emptied, fresh 50% morpholine in DMA (6 mL) was added and the mixture was shaken for 20 min. The solution was emptied and the resin washed with DMA (5×7 mL). 1,4,7,10-Tetraazacyclododecane-1,4,7,10-tetraacetic acid tris (1,1-dimethylethyl) ester adduct with NaCl (618 mg; 0.98 mmol), HOBt (151 mg; 0.98 mmol), DIC (154 µL; 0.98 mmol), DIEA (333 µL; 1.96 mmol) and DMA (6 mL) were added to the resin. The mixture was shaken for 24 h at room temperature, the solution was emptied and the resin was washed with DMA (5×7 mL), CH$_2$Cl$_2$ (5×7 mL) and vacuum dried. The resin was shaken in a flask with Reagent B (25 mL) for 4 h. The resin was filtered and the solution was evaporated under reduced pressure to afford an oily crude that was triturated with Et$_2$O (5 mL). The resulting precipitate was collected by centrifugation, was washed with Et$_2$O (5×5 mL), was analysed by HPLC and purified by preparative HPLC. The fractions containing the product were lyophilised to give L125 (FIG. 8C) as a white solid (15.8 mg; 0.011 mmol). Yield 4.4%.

Example IX

FIGS. 9A-9D

Synthesis of L146, L233, L234, and L235

Summary: The products were obtained in several steps starting from the octapeptide Gln-Trp-Ala-Val-Gly-His-Leu-Met-NH$_2$(BBN[7-14]) (A) on the Rink amide resin. After final cleavage and deprotection with Reagent B the crudes were purified by preparative HPLC to give L146, L233, L234 and L235. Overall yields: 10%, 11%, 4.5%, 5.7% respectively.

Figure 9A:
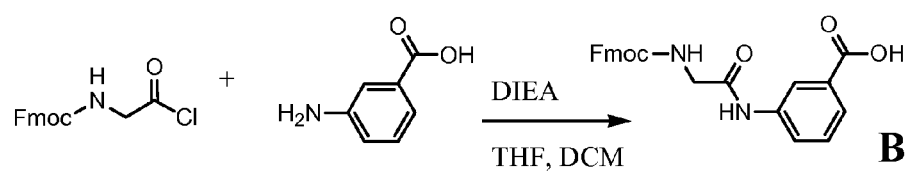
FIG. 9A is a graphical representation of a reaction for the synthesis of 3-[[[(9H-Fluoren-9-ylmethoxy)carbonyl]amino]acetyl]aminobenzoic acid, (B), as described in Example IX.

A. 3-[[[(9H-Fluoren-9-ylmethoxy)carbonyl]amino]acetyl]aminobenzoic acid, B (FIG. 9A)

A solution of 3-aminobenzoic acid (0.5 g; 3.8 mmol) and N-ethyldiisopropylamine (DIEA) (0.64 mL; 3.8 mmol) in THF (20 mL) was added dropwise to a solution of Fmoc-glycine chloride (1.2 g; 4.0 mmol) (3) in THF (10 mL) and $CH_2Cl_2$ (10 mL). After 24 h stirring at room temperature 1 M HCl (50 mL) was added (final pH: 1.5). The precipitate was filtered, washed with $H_2O$ (2×100 mL), vacuum dried and crystallised from $CHCl_3$/$CH_3OH$ (1:1) to give B as a white solid (0.7 g; 1.6 mmol). Yield 43%.

B. N-[3-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide, L233 (FIG. 9D)

Resin A (0.5 g; 0.3 mmol) was shaken in a solid phase peptide synthesis vessel with 50% morpholine in DMA (7 mL) for 10 min, the solution emptied and fresh 50% morpholine in DMA (7 mL) was added.

The suspension was stirred for another 20 min then the solution was emptied and the resin washed with DMA (5×7 mL). 3-[[[(9H-Fluoren-9-ylmethoxy)carbonyl]amino]acetyl]aminobenzoic acid, B (0.50 g; 1.2 mmol), HOBt (0.18 g; 1.2 mmol), DIC (0.19 mL; 1.2 mmol) and DMA (7 mL) were added to the resin, the mixture shaken for 6 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). DOTA tri-t-butyl ester adduct with $NaCl^2$ (0.79 g; 1.2 mmol) (5), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, emptied and the resin washed with DMA (5×7 mL), $CH_2Cl_2$ (5×7 mL) and vacuum dried. The resin was shaken in a flask with Reagent B (25 mL) for 4.5 h. The resin was filtered and the solution was evaporated under reduced pressure to afford an oily crude that after treatment with $Et_2O$ (20 mL) gave a precipitate. The precipitate was collected by centrifugation and washed with $Et_2O$ (3×20 mL) to give a solid (152 mg) which was analysed by HPLC. An amount of crude (50 mg) was purified by preparative HPLC. The fractions containing the product were lyophilised to give L233 (17.0 mg; 11.3×10⁻³ mmol) as a white solid. Yield 11%.

C. N-[4-[[[[[4,7,10-Tris(carboxymethyl)-1,4,7,10-tetraazacyclododec-1-yl]acetyl]amino]acetyl]amino]phenylacetyl]-L-glutaminyl-L-tryptophyl-L-alanyl-L-valyl-glycyl-L-histidyl-L-leucyl-L-methioninamide, L146 (FIG. 9D)

Resin A (0.5 g; 0.3 mmol) was shaken in a solid phase peptide synthesis vessel with 50% morpholine in DMA (7 mL) for 10 min, the solution filtered and fresh 50% morpholine in DMA (7 mL) was added. The suspension was stirred for another 20 min then the solution was filtered and the resin washed with DMA (5×7 mL). Fmoc-4-aminophenylacetic acid (0.45 g; 1.2 mmol), HOBt (0.18 g; 1.2 mmol), DIC (0.19 mL; 1.2 mmol) and DMA (7 mL) were added to the resin, the mixture shaken for 6 h at room temperature, filtered and the resin washed with DMA (5×7 mL). The resin was then shaken with 50% morpholine in DMA (7 mL) for 10 min, the solution filtered, fresh 50% morpholine in DMA (7 mL) was added and the mixture shaken for another 20 min. The solution was filtered and the resin washed with DMA (5×7 mL). Fmoc-glycine (0.36 g; 1.2 mmol), HATU (0.46 g; 1.2 mmol) and DIEA (0.40 mL; 2.4 mmol) were stirred for 15 min in DMA (7 mL) then the solution was added to the resin, the mixture shaken for 2 h at room temperature, filtered and the resin washed with DMA (5×7 mL). The resin was then shaken with 50% morpholine in DMA (7 mL) for 10 min, the solution filtered, fresh 50% morpholine in DMA (7 mL) was added and the mixture shaken for another 20 min. The solution was filtered and the resin washed with DMA (5×7 mL). DOTA tri-t-butyl ester adduct with NaCl (0.79 g; 1.2 mmol), HOBt (0.18 g; 1.2 mmol), DIC (0.19 mL; 1.2 mmol), DIEA (0.40 mL; 2.4 mmol) and DMA (7 mL) were added to the resin. The mixture was shaken for 24 h at room temperature, filtered and the resin washed with DMA (5×7 mL), $CH_2Cl_2$ (5×7 mL) and vacuum dried. The resin was shaken in a flask with Reagent B (25 mL) for 4.5 h. The resin was filtered and the solution was evaporated under reduced pressure to afford an oily crude that after treatment with $Et_2O$ (20 mL) gave a precipitate. The precipitate was collected by centrifugation and washed with $Et_2O$ (3×20 mL) to give a solid (203 mg) which was analysed by HPLC. An amount of crude (50 mg) was purified by preparative HPLC. The fractions containing the product were lyophilised to give L146 (11.2 mg; 7.4×10⁻³ mmol) as a white solid. Yield 10%.

Figure 9B:
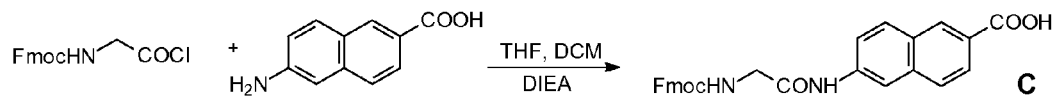
FIG. 9B is a graphical representation of a reaction for the synthesis of 6-[[[(9H-Fluoren-9-ylmethoxy)carbonyl]amino]acetyl]aminonaphthoic acid (C), as described in Example IX.

D. 6-[[[(9H-Fluoren-9-ylmethoxy)carbonyl]amino]acetyl]aminonaphthoic acid, C (FIG. 9B)

A solution of 6-aminonaphthoic acid (500 mg; 2.41 mmol); and DIEA (410 µL 2.41 mmol) in THF (20 mL) was added dropwise to a solution of Fmoc-glycine chloride (760 mg; 2.41 mmol) in $CH_2Cl_2$/THF 1:1 (10 mL) and stirred at room temperature. After 24 h the solvent was evaporated under vacuum. The residue was taken up with 0.5 N HCl (50 mL) and stirred for 1 h. The white solid precipitated was filtered and dried. The white solid was suspended in methanol (30 mL) and boiled for 5 min, then was filtered to give product C (690 mg; 1.48 mmol). Yield 62%.

E. N-[6-[[[[[4,7,10-Tris(carboxymethyl)-1,4,7,10-tetraazacyclododec-1-yl]acetyl]amino]acetyl]amino]naphthoyl]-L-glutaminyl-L-tryptophyl-L-alanyl-L-valyl-glycyl-L-histidyl-L-leucyl-L-methioninamide, L234

Resin A (500 mg; 0.3 mmol) was shaken in a solid phase peptide synthesis vessel with 50% morpholine in DMA (7 mL) for 10 min, the solution emptied and fresh 50% morpholine in DMA (7 mL) was added. The suspension was stirred for another 20 min then the solution was emptied and the resin washed with DMA (5×7 mL). 6-[[[(9H-Fluoren-9-ylmethoxy)carbonyl]amino]acetyl]aminonaphthoic acid C (560 mg; 1.2 mmol), HOBt (184 mg; 1.2 mmol), DIC (187 µL; 1.2 mmol) and DMA (7 mL) were added to the resin, the mixture shaken for 6 h at room temperature, emptied and the resin washed with DMA (5×7 mL). The resin was then shaken with 50% morpholine in DMA (6 L) for 10 min, the solution emptied, fresh 50% morpholine in DMA (7 mL) was added and the mixture shaken for another 20 min. The solution was emptied and the resin washed with DMA (5×7 mL). DOTA tri-t-butyl ester adduct with NaCl (757 mg; 1.2 mmol), HOBt (184 mg; 1.2 mmol), DIC (187 µL; 1.2 mmol), and DIEA (537 µL; 2.4 mmol) and DMA (7 mL) were added to the resin. The mixture was shaken in a flask, emptied and the resin washed with DMA (2×7 mL), CH$_2$Cl$_2$ (5×7 mL) and vacuum dried. The resin was shaken in a flask with Reagent B (25 mL) for 4.5 h. The resin was filtrated and the solution was evaporated under reduced pressure to afford an oil crude that after treatment with Et$_2$O (20 mL) gave a precipitate. The precipitate was collected by centrifugation and washed with Et$_2$O (3×20 mL) to give a solid (144 mg) which was analysed by HPLC. An amount of crude (54 mg) was purified by preparative HPLC. The fractions containing the product were lyophilised to give L234 (8 mg; 5.1× 10$^{-3}$ mmol) as a white solid. Yield 4.5%.

Figure 9C:
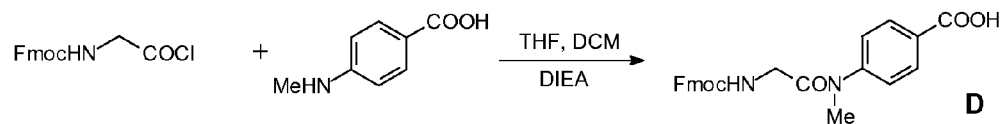
FIG. 9C is a graphical representation of a reaction for the synthesis of 4-[[[[(9H-Fluoren-9-ylmethoxy)carbonyl]amino]acetyl]methylamino]benzoic acid, (D), as described in Example IX.
Figure 9D:
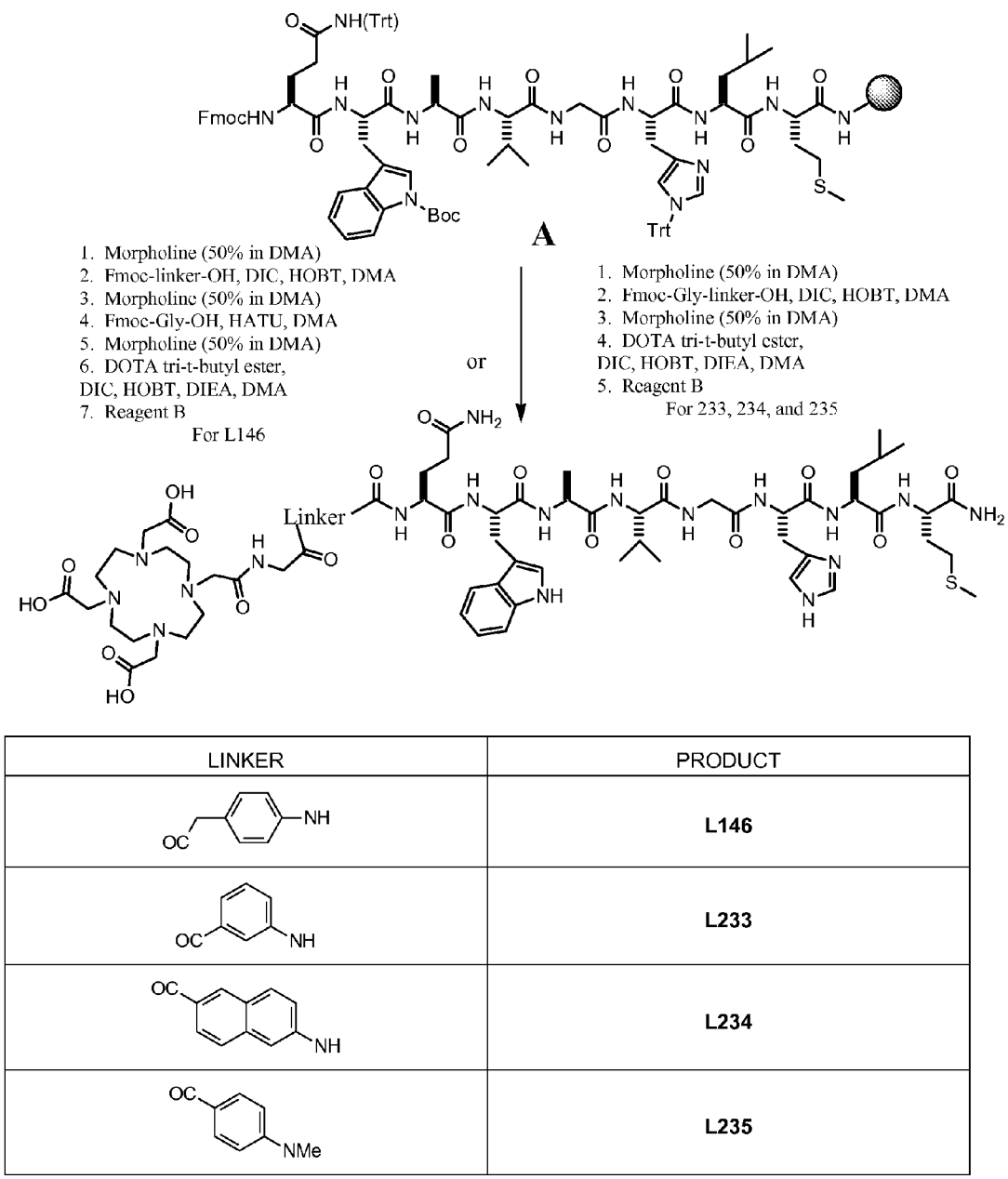
FIG. 9D is a graphical representation of a reaction for the synthesis of N44-[[[[[4,7,10-Tris(carboxymethyl)-1,4,7,10-tetraazacyclododec-1-yl]acetyl]amino]acetyl]amino]phenylacetyl]-L-glutaminyl-L-tryptophyl-L-alanyl-L-valyl-glycyl-L-histidyl-L-leucyl-L-methioninamide, (L146); N-[3-

F. 4-[[[[(9H-Fluoren-9-ylmethoxy)carbonyl]amino] acetyl]methylamino]benzoic acid, D (FIG. 9C)

A solution of 4-N-methylaminonaphthoic acid (500 mg; 3.3 mmol) and DIEA (562 µL 3.3 mmol) in THF (20 mL) was added to a solution of Fmoc-glycine chloride (1.04 g; 3.3 mmol) in CH$_2$Cl$_2$/THF 1:1 (10 mL) and stirred at room temperature. After 24 h the solvent was evaporated under vacuum. The residue was taken up with 0.5 N HCl (30 mL) and was stirred for 3 h at 0° C. The white solid precipitated was filtered and dried. The crude was purified by flash chromatography to give Compound D (350 mg; 0.81 mmol). Yield 25%.

G. N-[4-[[[[[4,7,10-Tris(carboxymethyl)-1,4,7,10-tetraazacyclododec-1-yl]acetyl]amino]acetyl]methylamino] benzoyl]-L-glutaminyl-L-tryptophyl-L-alanyl-L-valyl-glycyl-L-histidyl-L-leucyl-L-methioninamide, L235 (FIG. 9D)

Resin A (500 mg; 0.3 mmol) was shaken in a solid phase peptide synthesis vessel with 50% morpholine in DMA (7 mL) for 10 min, the solution emptied and fresh 50% morpholine in DMA (7 mL) was added. The suspension was stirred for another 20 min then the solution was emptied and the resin washed with DMA (5×7 mL). 4-[[[[9H-Fluoren-9-ylmethoxy)carbonyl]amino] acetyl]-N-methyl]amino-benzoic acid D (510 mg; 1.2 mmol), HOBt (184 mg; 1.2 mmol), DIC (187 µL; 1.2 mmol) and DMA (7 mL) were added to the resin, the mixture shaken for 6 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). DOTA tri-t-butyl ester adduct with NaCl (757 mg; 1.2 mmol), HOBt (184 mg; 1.2 mmol), DIC (187 µL; 1.2 mmol), and DIEA (537 µL; 2.4 mmol) and DMA (7 mL) were added to the resin. The mixture was shaken in a flask, emptied and the resin washed with DMA (2×7 mL), CH$_2$Cl$_2$ (5×7 mL) and vacuum dried. The resin was shaken in a flask with Reagent B (25 mL) for 4.5 h. The resin was filtrated and the solution was evaporated under reduced pressure to afford an oil crude that after treatment with Et$_2$O (20 mL) gave a precipitate. The precipitate was collected by centrifugation and washed with Et$_2$O (3×20 mL) to give a solid (126 mg) which was analysed by HPLC. An amount of crude (53 mg) was purified by preparative HPLC. The fractions containing the product were lyophilised to give L235 (11 mg; 7.2×10$^{-3}$ mmol) as a white solid. Yield 5.7%.

Example X

FIGS. 10A-B

Synthesis of L237

Summary: 1-Formyl-1,4,7,10-tetraazacyclododecane (A) was selectively protected with benzyl chloroformate at pH 3 to give B, which was alkylated with t-butyl bromoacetate and deformylated with hydroxylamine hydrochloride to give D. Reaction with P(OtBu)$_3$ and paraformaldehyde gave E, which was deprotected by hydrogenation and alkylated with benzyl bromoacetate to give G, which was finally hydrogenated to H. Rink amide resin functionalized with the octapeptide Gln-Trp-Ala-Val-Gly-His-Leu-Met-NH$_2$ (BBN[7-14]) (A) was sequentially reacted with Fmoc-4-aminobenzoic acid, Fmocglycine and H. After cleavage and deprotection with Reagent B the crude was purified by preparative HPLC to give L237. Overall yield 0.21%.

A. 7-Formyl-1,4,7,10-tetraazacyclododecane-1-carboxylic acid phenylmethyl ester dihydrochloride, B (FIG. 10A)

1-Formyl-1,4,7,10-tetraazacyclododecane A (14 g; 69.9 mmol) was dissolved in H$_2$O (100 mL) and 12 N HCl (11 mL) was added until pH 3 then 1,4-dioxane (220 mL) was added. A solution of benzyl chloroformate (13.8 g; 77 mmol) in 1,4-dioxane (15 mL) was slowly added dropwise in 3.5 h, constantly maintaining the reaction mixture at pH 3 by continuous addition of 2 N NaOH (68.4 mL) with a pHstat apparatus. At the end of the addition the reaction was stirred for 1 h then washed with n-hexane (4×100 mL) and $^i$Pr$_2$O (4×100 mL). The aqueous phase was brought to pH 13 by addition of 10 N NaOH (6.1 mL) and extracted with CHCl$_3$ (4×100 mL). The organic phase was washed with brine (100 mL), dried (Na$_2$SO$_4$), filtered and evaporated. The oily residue was dissolved in acetone (200 mL) and 6 N HCl (26 mL) was added. The solid precipitated was filtered, washed with acetone (2×50 mL) and dried under vacuum to give compound B (23.6 g; 58 mmol) as a white crystalline solid. Yield 83%.

B. 4-(Phenylmethoxy)carbonyl-1,4,7,10-tetraazacyclododecane-1,7-diacetic acid bis(1,1-dimethylethyl) ester, D (FIG. 10A)

A solution of B (14.4 g; 35.3 mmol) in H$_2$O (450 mL) and 1 N NaOH (74 mL; 74 mmol) was stirred for 20 min then extracted with CHCl$_3$ (4×200 mL). The organic layer was evaporated to obtain an oily residue (12.3 g) which was dissolved in CH$_3$CN (180 mL) and N-ethyldiisopropylamine (DIEA) (15 mL; 88.25 mmol). A solution of t-butyl bromoacetate (16.8 g; 86.1 mmol) in CH$_3$CN (15 mL) was added dropwise to the previous solution in 2.5 h. After 20 h at room temperature the solvent was evaporated and the oily residue was dissolved in CHCl$_3$ (150 mL) and washed with H$_2$O (5×100 mL). The organic layer was dried (Na$_2$SO$_4$), filtered and evaporated to dryness to give C as a yellow oil. Crude C (22 g) was dissolved in EtOH (250 mL), NH$_2$OH.HCl (2.93 g; 42.2 mmol) was added and the solution heated to reflux. After 48 h the solvent was evaporated and the residue dissolved in CH$_2$Cl$_2$ (250 mL), washed with H$_2$O (3×250 mL) then with brine (3×250 mL). The organic layer was dried (Na$_2$SO$_4$), filtered and evaporated. The oily residue (18.85 g) was purified by flash chromatography. The fractions containing the product were collected and evaporated to obtain a glassy white solid (17.62 g) which was dissolved in H$_2$O (600 mL) and 1 N NaOH (90 mL; 90 mmol) and extracted with CHCl$_3$ (3×250 ml). The organic layer was dried (Na$_2$SO$_4$) and evaporated to dryness to give D (16.6 g; 31 mmol) as an oil. Yield 88%.

C. 4-(Phenylmethoxy)carbonyl-10-[[bis(1,1-dimethylethoxy)phosphinyl]methyl]-1,4,7,10-tetraazacyclododecane-1,7-diacetic acid bis(1,1-dimethylethyl) ester, E (FIG. 10A)

A mixture of Compound D (13.87 g; 26 mmol), P(OtBu)$_3$ (7.6 g; 28.6 mmol) (10) and paraformaldeyde (0.9 g; 30 mmol) was heated at 60° C. After 16 h more P(OtBu)$_3$ (1 g; 3.76 mmol) and paraformaldeyde (0.1 g; 3.33 mmol) were added. The reaction was heated at 60° C. for another 20 h then at 80° C. for 8 h under vacuum to eliminate the volatile impurities. The crude was purified by flash chromatography to give E (9.33 g; 8 mmol) as an oil. Yield 31%.

D. 7-[[Bis(1,1-dimethylethoxy)phosphinyl]methyl]-1,4,7,10-tetraazacyclododecane-1,4,10-triacetic acid 1-phenylmethyl 4,10-bis(1,1-dimethylethyl) ester, G (FIG. 10A)

To the solution of E (6.5 g; 5.53 mmol) in CH$_3$OH (160 mL) 5% Pd/C (1 g; 0.52 mmol) was added and the mixture was stirred under hydrogen atmosphere at room temperature. After 4 h (consumed H$_2$ 165 mL; 6.7 mmol) the mixture was filtered through a Millipore® filter (FT 0.45 μm) and the solution evaporated under reduced pressure. The crude (5.9 g) was purified by flash chromatography to give F (4.2 g) as an oil. Benzyl bromoacetate (1.9 g; 8.3 mmol) dissolved in CH$_3$CN (8 mL) was added dropwise in 1 h to a solution of F (4.2 g) in CH$_3$CN (40 mL) and DIEA (1.5 mL; 8.72 mmol). After 36 h at room temperature the solvent was evaporated and the residue (5.76 g) dissolved in CHCl$_3$ (100 mL), washed with H$_2$O (2×100 mL) then with brine (2×70 mL). The organic layer was dried (Na$_2$SO$_4$), filtered and evaporated. The crude (5.5 g) was purified twice by flash chromatography, the fractions were collected and evaporated to dryness to afford G (1.12 g; 1.48 mmol) as an oil. Yield 27%.

E. 7-[[Bis(1,1-dimethylethoxy)phosphinyl]methyl]-1,4,7,10-tetraazacyclododecane-1,4,10-triacetic acid 4,10-bis(1,1-dimethylethyl) ester, H (FIG. 10A)

5% Pd/C (0.2 g; 0.087 mmol) was added to a solution of G (1.12 g; 1.48 mmol) in CH$_3$OH (27 mL) and the mixture was stirred under hydrogen atmosphere at room temperature. After 2 h (consumed H$_2$ 35 mL; 1.43 mmol) the mixture was filtered through a Millipore® filter (FT 0.45 μm) and the solution evaporated to dryness to give H (0.94 g; 1.41 mmol) as a pale yellow oil. Yield 97%.

F. N-[4-[[[[[4,10-Bis(carboxymethyl)-7-(dihydroxyphosphinyl)methyl-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucil-L-methioninamide, L237 (FIG. 10B)

Resin A (330 mg; 0.20 mmol) (17) was shaken in a solid phase peptide synthesis vessel with 50% morpholine in DMA (5 mL) for 10 min, the solution emptied and fresh 50% morpholine in DMA (5 mL) was added. The suspension was stirred for another 20 min then the solution was emptied and the resin washed with DMA (5×5 mL). Fmoc-4-aminobenzoic acid (290 mg; 0.80 mmol), HOBt (120 mg; 0.80 mmol), DIC (130 μL; 0.80 mmol) and DMA (5 mL) were added to the resin, the mixture shaken for 3 h at room temperature, emptied and the resin washed with DMA (5×5 mL). The resin was then shaken with 50% morpholine in DMA (5 mL) for 10 min, the solution emptied, fresh 50% morpholine in DMA (5 mL) was added and the mixture shaken for another 20 min. The solution was emptied and the resin washed with DMA (5×5 mL). Fmoc-glycine (240 mg; 0.8 mmol), HATU (310 mg; 0.8 mmol) and DIEA (260 μL; 1.6 mmol) were stirred for 15 min in DMA (5 mL) then the solution was added to the resin, the mixture shaken for 2 h at room temperature, emptied and the resin washed with DMA (5×5 mL). The resin was then shaken with 50% morpholine in DMA (5 mL) for 10 min, the solution emptied, fresh 50% morpholine in DMA (5 mL) was added and the mixture shaken for another 20 min. The solution was emptied and the resin washed with DMA (5×5 mL). H (532 mg; 0.80 mmol), HOBt (120 mg; 0.80 mmol), DIC (130 μL; 0.80 mmol), and DIEA (260 μL; 1.6 mmol) and DMA (5 mL) were added to the resin. The mixture was shaken in a flask for 40 h at room temperature, emptied and the resin washed with DMA (5×5 mL), CH$_2$Cl$_2$ (5×5 mL) and vacuum dried. The resin was shaken in a flask with Reagent B (25 mL) for 4 h. The resin was filtered and the solution was evaporated under reduced pressure to afford an oily crude that after treatment with Et$_2$O (20 mL) gave a precipitate. The precipitate was collected by centrifugation and washed with Et$_2$O (3×20 mL) to give a solid (90 mg) which was analysed by HPLC. An amount of crude (50 mg) was purified by preparative HPLC. The fractions containing the product were lyophilised to give L237 (6 mg; 3.9×10$^{-3}$ mmol) as a white solid. Yield 3.5%.

Example XI

FIGS. 11A-B

Synthesis of L238 and L239

Summary: The products were obtained in several steps starting from the octapeptide Gln-Trp-Ala-Val-Gly-His-Leu-Met-NH$_2$ (BBN[7-14]) (A) on the Rink amide resin. After cleavage and deprotection with Reagent B the crude was purified by preparative HPLC to give L238 and L239. Overall yields: 14 and 9%, respectively.

A. N,N-Dimethylglycyl-L-seryl-[S-[(acetylamino)methyl]]-L-cysteinyl-glycyl-4-aminobenzoyl-L-glutaminyl-L-tryptophyl-L-alanyl-L-valyl-glycyl-L-histidyl-L-leucyl-L-methioninamide, L238 (FIG. 11A)

Resin A (0.5 g; 0.3 mmol) was shaken in a solid phase peptide synthesis vessel with 50% morpholine in DMA (7 mL) for 10 min, the solution emptied and fresh 50% morpholine in DMA (7 mL) was added. The suspension was stirred for another 20 min then the solution was emptied and the resin washed with DMA (5×7 mL). Fmoc-4-aminobenzoic acid (0.43 g; 1.2 mmol), HOBt (0.18 g; 1.2 mmol), DIC (0.19 mL; 1.2 mmol) and DMA (7 mL) were added to the resin, the mixture shaken for 3 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). Fmoc-glycine (0.36 g; 1.2 mmol), HATU (0.46 g; 1.2 mmol) and N-ethyldiisopropylamine (0.40 mL; 2.4 mmol) were stirred for 15 min in DMA (7 mL) then the solution was added to the resin, the mixture shaken for 2 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). N-α-Fmoc-5-acetamidomethyl-L-cysteine (0.50 g; 1.2 mmol), HOBt (0.18 g; 1.2 mmol), DIC (0.19 mL; 1.2 mmol) and DMA (7 mL) were added to the resin, the mixture shaken for 3 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). N-α-Fmoc-O-t-butyl-L-serine (0.46 g; 1.2 mmol), HOBt (0.18 g; 1.2 mmol), DIC (0.19 mL: 1.2 mmol), and DMA (7 mL) were added to the resin, the mixture was shaken for 3 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min.

The solution was emptied and the resin washed with DMA (5×7 mL). N,N-Dimethylglycine (0.12 g; 1.2 mmol), HATU (0.46 g; 1.2 mmol) and N-ethyldiisopropylamine (0.40 mL; 2.4 mmol) were stirred for 15 min in DMA (7 mL) then the solution was added to the resin. The mixture was shaken for 2 h at room temperature, emptied and the resin washed with DMA (5×7 mL), $CH_2Cl_2$ (5×7 mL) and vacuum dried. The resin was shaken in a flask with Reagent B (25 mL) for 4.5 h. The resin was filtered and the solution was evaporated under reduced pressure to afford an oily crude that after treatment with $Et_2O$ (20 mL) gave a precipitate. The precipitate was collected by centrifugation and washed with $Et_2O$ (3×20 mL) to give a solid (169 mg) which was analysed by HPLC. An amount of crude (60 mg) was purified by preparative HPLC. The fractions containing the product were lyophilised to give L238 (22.0 mg; 0.015 mmol) as a white solid. Yield 14%.

B. N,N-Dimethylglycyl-L-seryl-[S-[(acetylamino)methyl]]-L-cysteinyl-glycyl-(3β,5β,7α,12α)-3-amino-7,12-dihydroxy-24-oxocholan-24-yl-L-glutaminyl-L-tryptophyl-L-alanyl-L-valyl-glycyl-L-histidyl-L-leucyl-L-methioninamide, L239 (FIG. 11B)

Resin A (0.5 g; 0.3 mmol) was shaken in a solid phase peptide synthesis vessel with 50% morpholine in DMA (7 mL) for 10 min, the solution emptied and fresh 50% morpholine in DMA (7 mL) was added. The suspension was stirred for another 20 min then the solution was emptied and the resin washed with DMA (5×7 mL). (3β,5β,7α,12α)-3-[[(9H-Fluoren-9-ylmethoxy)amino]acetyl]amino-7,12-dihydroxycholan-24-oic acid B (0.82 g; 1.2 mmol) (7), HOBt (0.18 g; 1.2 mmol), DIC (0.19 mL; 1.2 mmol) and DMA (7 mL) were added to the resin, the mixture shaken for 24 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). N-α-Fmoc-5-acetamidomethyl-L-cysteine (0.50 g; 1.2 mmol), HOBt (0.18 g; 1.2 mmol), DIC (0.19 mL; 1.2 mmol) and DMA (7 mL) were added to the resin, the mixture was shaken for 3 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). N-α-Fmoc-O-t-butyl-L-serine (0.46 g; 1.2 mmol), HOBt (0.18 g; 1.2 mmol), DIC (0.19 mL: 1.2 mmol), and DMA (7 mL) were added to the resin, the mixture was shaken for 3 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). N,N-Dimethylglycine (0.12 g; 1.2 mmol), HATU (0.46 g; 1.2 mmol) and N-ethyldiisopropylamine (0.40 mL; 2.4 mmol) were stirred for 15 min in DMA (7 mL) then the solution was added to the resin.

Resin A (0.5 g; 0.3 mmol) was shaken in a solid phase peptide synthesis vessel with 50% morpholine in DMA (7 mL) for 10 min, the solution emptied and fresh 50% morpholine in DMA (7 mL) was added. The suspension was stirred for another 20 min then the solution was emptied and the resin washed with DMA (5×7 mL). (3β,5β,7α,12α)-3-[[(9H-Fluoren-9-ylmethoxy)amino]acetyl]amino-7,12-dihydroxycholan-24-oic acid B (0.82 g; 1.2 mmol) HOBt (0.18 g; 1.2 mmol), DIC (0.19 mL; 1.2 mmol) and DMA (7 mL) were added to the resin, the mixture shaken for 24 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). N-α-Fmoc-5-acetamidomethyl-L-cysteine (0.50 g; 1.2 mmol), HOBt (0.18 g; 1.2 mmol), DIC (0.19 mL; 1.2 mmol) and DMA (7 mL) were added to the resin, the mixture was shaken for 3 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). N-α-Fmoc-O-t-butyl-L-serine (0.46 g; 1.2 mmol), HOBt (0.18 g; 1.2 mmol), DIC (0.19 mL: 1.2 mmol), and DMA (7 mL) were added to the resin, the mixture was shaken for 3 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). N,N-Dimethylglycine (0.12 g; 1.2 mmol), HATU (0.46 g; 1.2 mmol) and N-ethyldiisopropylamine (0.40 mL; 2.4 mmol) were stirred for 15 min in DMA (7 mL) then the solution was added to the resin.

Example XII

FIGS. 12A-F

Synthesis of L240, L241, L242

Summary: The products were obtained in several steps starting from the octapeptide Gln-Trp-Ala-Val-Gly-His-Leu-Met-NH$_2$ (BBN[7-14]) (A) on the Rink amide resin. After cleavage and deprotection with Reagent B the crudes were A. 4-[[[(9H-Fluoren-9-ylmethoxy)carbonyl]amino]acetyl]amino-3-methoxybenzoic acid A (FIG. 12A)

A solution of 4-amino-3-methoxybenzoic acid (1.0 g; 5.9 mmol); and N-ethyldiisopropylamine (1.02 mL 5.9 mmol) in THF (20 mL) was added dropwise to a solution of Fmoc-glycylchloride (1.88 g; 5.9 mmol) in $CH_2Cl_2$/THF 1:1 (20 mL) and stirred at room temperature under $N_2$. After 3 h the solvent was evaporated under vacuum. The residue was taken up with 0.5 N HCl (50 mL), was stirred for 1 h at 0° C. then filtered and dried. The white solid was suspended in MeOH (30 mL) and stirred for 1 h, then was filtered and suspended in a solution of $CHCl_3$/hexane 1:4 (75 mL). The suspension was filtered to give compound A as a with solid (1.02 g; 2.28 mmol). Yield 39%.

B. N-[4-[[[[4,7,10-Tris(carboxymethyl)-1,4,7,10tetraaza-cyclododec-1-yl]acetyl]glycyl]amino]-3-methoxybenzoyl]-L-glutaminyl-L-tryptophyl-1-alanyl-L-valyl-glycyl-L-histi-dyl-L-leucyl-L-methioninamide L240

Resin A (0.5 g; 0.3 mmol) was shaken in a solid phase peptide synthesis vessel with 50% morpholine in DMA (7 mL) for 10 min, the solution emptied and fresh 50% morpholine in DMA (7 mL) was added. The suspension was stirred for another 20 min then the solution was emptied and the resin washed with DMA (5×7 mL). 4-[[[(9H-Fluoren-9-ylmethoxy)carbonyl]amino]acetyl]amino-3-methoxybenzoic acid, A (0.50 g; 1.2 mmol), HOBt (0.18 g; 1.2 mmol), DIC (0.19 mL; 1.2 mmol) and DMA (7 mL) were added to the resin, the mixture shaken for 5 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), N-ethyldiisopropylamine (0.40 mL; 2.4 mmol) and DMA (7 mL) were added to the resin. The mixture was shaken for 24 h at room temperature, emptied and the resin washed with DMA (5×7 mL), $CH_2Cl_2$ (5×7 mL) and vacuum dried. The resin was shaken in a flask with Reagent B (25 mL) for 4.5 h. The resin was filtered and the solution was evaporated under reduced pressure to afford an oil crude that after treatment with $Et_2O$ (20 mL) gave a precipitate. The precipitate was collected by centrifugation and washed with $Et_2O$ (5×20 mL) to give a solid (152 mg) which was analysed by HPLC. An amount of crude (52 mg) was purified by preparative HPLC. The fractions containing the product were lyophilised to give L240 (12.0 mg; $7.8 \times 10^{-3}$ mmol) as a white solid. Yield 7.4%.

C. 4-amino-3-chlorobenzoic acid C (FIG. 12B)

1 N NaOH (11 mL; 11 mmol) was added to a solution of methyl 4-amino-3-chlorobenzoate (2 g; 10.8 mmol) in MeOH (20 mL) at 45° C. The reaction mixture was stirred for 5 h at 45° C. and overnight at room temperature. More 1N NaOH was added (5 mL; 5 mmol) and the reaction was stirred at 45° C. for 2 h. After concentration of solvent was added 1N HCl (16 ml). The solid precipitate was filtered and dried to give 4-amino-3-chlorobenzoic acid, C, as a with solid (1.75 g; 10.2 mmol). Yield 94.6%.

D. 4-[[[(9H-Fluoren-9-ylmethoxy)carbonyl]amino]acetyl]amino-3-chlorobenzoic acid, D (FIG. 12B)

A solution of 4-amino-3-chlorobenzoic acid (1.5 g; 8.75 mmol) and N-ethyldiisopropylamine (1.46 mL 8.75 mmol) in THF (50 mL) was added dropwise to a solution of Fmoc-glycylchloride (2.76 g; 8.75 mmol) in $CH_2Cl_2$/THF 1:1 (30 mL) and stirred at room temperature under $N_2$. After 3 h the solvent was evaporated under vacuum. The residue was taken up with 0.5N HCl (50 mL), filtered and dried.

The white solid was suspended in MeOH (30 mL) and stirred for 1 h, then was filtered and dried to give 4-[[[(9H-fluoren-9-ylmethoxy)carbonyl]amino]acetyl]amino-3-chlorobenzoic acid (2.95 g; 6.5 mmol). Yield 75%.

E. N-[4-[[[[4,7,10-Tris(carboxymethyl)-1,4,7,10tetraaza-cyclododec-1-yl]acetyl]glycyl]amino]3-chlorobenzoyl]L-glutaminyl-L-tryptophyl-1-alanyl-L-valyl-glycyl-L-histi-dyl-L-leucyl-L-methioninamide, L241 (FIG. 12E)

Resin A (0.5 g; 0.3 mmol) was shaken in a solid phase peptide synthesis vessel with 50% morpholine in DMA (7 mL) for 10 min, the solution emptied and fresh 50% morpholine in DMA (7 mL) was added. The suspension was stirred for another 20 min then the solution was emptied and the resin washed with DMA (5×7 mL). 4-[[[(9H-Fluoren-9-ylmethoxy)carbonyl]amino]acetyl]amino-3-chlorobenzoic acid, D (0.54 g; 1.2 mmol), HOBt (0.18 g; 1.2 mmol), DIC (0.19 mL; 1.2 mmol) and DMA (7 mL) were added to the resin, the mixture shaken for 5 h at room temperature, emptied and the resin washed with DMA (5×7 mL).

The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), N-ethyldiisopropylamine (0.40 mL; 2.4 mmol) and DMA (7 mL) were added to the resin. The mixture was shaken for 40 h at room temperature, emptied and the resin washed with DMA (5×7 mL), $CH_2Cl_2$ (5×7 mL) and vacuum dried. The resin was shaken in a flask with Reagent B (25 mL) for 4.5 h. The resin was filtered and the solution was evaporated under reduced pressure to afford an oil crude that after treatment with $Et_2O$ (20 mL) gave a precipitate. The precipitate was collected by centrifugation and washed with $Et_2O$ (5×20 mL) to give a solid (151 mg) which was analysed by HPLC. An amount of crude (56 mg) was purified by preparative HPLC. The fractions containing the product were lyophilised to give L241 (5.6 mg; $3.6 \times 10^{-3}$ mmol) as a white solid. Yield 3.2%.

F. 4-[[[(9H-Fluoren-9-ylmethoxy)carbonyl]amino]acetyl]amino-3-methylbenzoic acid, E (FIG. 12C)

A solution of 4-amino-3-methylbenzoic acid (0.81 g; 5.35 mmol) and N-ethyldiisopropylamine (0.9 mL 5.35 mmol) in THF (30 mL) was added dropwise to a solution of Fmoc-glycylchloride (1.69 g; 5.35 mmol) in $CH_2Cl_2$/THF 1:1 (20 mL) and stirred at room temperature under $N_2$. After 3 h the solvent was evaporated under vacuum. The residue was taken up with HCl 0.5 N (50 mL)and was stirred for 3 h at 0° C. then was filtered and dried. The white solid was suspended in MeOH (50 mL) and stirred for 1 h, then filtered and dried to give Compound E (1.69 g; 3.9 mmol). Yield 73%.

G. N-[4-[[[[4,7,10-Tris(carboxymethyl)-1,4,7,10-tetraazacyclododec-1-yl]acetyl]glycyl]amino]3-methylbenzoyl]L-glutaminyl-L-tryptophyl-L-alanyl-L-valyl-glycyl-L-histidyl-L-leucyl-L-methioninamide L242 (FIG. 12F)

Resin A (0.5 g; 0.3 mmol) was shaken in a solid phase peptide synthesis vessel with 50% morpholine in DMA (7 mL) for 10 min, the solution emptied and fresh 50% morpholine in DMA (7 mL) was added. The suspension was stirred for another 20 min then the solution was emptied and the resin washed with DMA (5×7 mL). 4-[[(9H-Fluoren-9-ylmethoxy)amino]acetyl]amino-3-methylbenzoic acid, E (0.52 g; 1.2 mmol), HOBt (0.18 g; 1.2 mmol), DIC (0.19 mL; 1.2 mmol) and DMA (7 mL) were added to the resin, the mixture shaken for 5 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (0.76 g; 1.2 mmol), HOBt (0.18 g; 1.2 mmol), DIC (0.19 mL; 1.2 mmol), N-ethyldiisopropylamine (0.40 mL; 2.4 mmol) and DMA (7 mL) were added to the resin.

The mixture was shaken for 40 h at room temperature, emptied and the resin washed with DMA (5×7 mL), $CH_2Cl_2$ (5×7 mL) and vacuum dried. The resin was shaken in a flask with Reagent B (25 mL) for 4.5 h. The resin was filtered and the solution was evaporated under reduced pressure to afford an oil crude that after treatment with $Et_2O$ (20 mL) gave a precipitate. The precipitate was collected by centrifugation and washed with $Et_2O$ (5×20 mL) to give a solid (134 mg) which was analysed by HPLC. An amount of crude (103 mg) was purified by preparative HPLC. The fractions containing the product were lyophilised to give L242 (4.5 mg; 2.9× $10^{-3}$ mmol) as a white solid. Yield 1.3%.

Example XIII

FIGS. 13A-C

Synthesis of L244

Summary: The product was obtained in several steps starting from the octapeptide Gln-Trp-Ala-Val-Gly-His-Leu-Met-$NH_2$(BBN[7-14]) on the Rink amide resin (A). The final coupling step with DOTA tri-t-butyl ester was done in solution phase after cleavage and deprotection with Reagent B of Linker-BBN [7-14]. The crude was purified by preparative HPLC to give L244. Overall yield: 0.4%.

A. N,N'-(Iminodi-2,1-ethanediyl)bis[2,2,2-trifluoroacetamide], A (FIG. 13A)

Trifluoroacetic acid ethyl ester (50 g; 0.35 mol) was dropped into a solution of diethylenetriamine (18 g; 0.175 mol) in THF (180 mL) at 0° C. in 1 h. After 20 h at room temperature, the mixture was evaporated to an oily residue (54 g). The oil was crystallized from $Et_2O$ (50 mL), filtered, washed with cooled $Et_2O$ (2×30 mL) and dried to obtain A as a white solid (46 g; 0.156 mol). Yield 89%.

B. 4-[N,N'-Bis[2-(trifluoroacetyl)aminoethyl]amino]-4-oxobutanoic acid, B (FIG. 13A)

Succinic anhydride (0.34 g; 3.4 mmol) was added in a solution of A (1 g; 3.4 mmol) in THF (5 mL) at room temperature. After 28 h the crude was concentrated to residue (1.59 g), washed with EtOAc (2×10 mL) and 1 N HCl (2×15 mL). The organic layer was dried on $Na_2SO_4$, filtered and evaporated to give an oily residue (1.3 g) that was purified by flash chromatography (5) to afford B as an oil (0.85 g; 2.15 mmol). Yield 63%.

C. 4-[N,N'-Bis[2-[(9-H-fluoren-9-ylmethoxy)carbonyl]aminoethyl]amino]-4-oxobutanoic acid, D (FIG. 13A)

Succinic anhydride (2 g; 20 mmol) was added in a solution of A (5 g; 16.94 mmol) in THF (25 mL) at room temperature. After 28 h the crude was concentrated to residue (7 g), washed in ethyl acetate (100 mL) and in 1 N HCl (2×50 mL). The organic layer was dried on $Na_2SO_4$, filtered and evaporated to give crude B as an oily residue (6.53 g). 2 N NaOH (25 mL) was added to suspension of crude B (5 g) in EtOH (35 mL) obtaining a complete solution after 1 h at room temperature. After 20 h the solvent was evaporated to obtain C as an oil (8.48 g). A solution of 9-fluorenylmethyl chloroformate (6.54 g, 25.3 mmol) in 1,4-dioxane (30 mL), was dropped in the solution of C in 10% aq. $Na_2CO_3$ (30 mL) in 1 h at 0° C. After 20 h at r.t. a gelatinous suspension was obtained and filtered to give a white solid (3.5 g) and a yellow solution. The solution was evaporated and the remaining aqueous solution was diluted in $H_2O$ (150 mL) and extracted with EtOAc (70 mL). Fresh EtOAc (200 mL) was added to aqueous phase, obtaining a suspension which was cooled to 0° C. and acidified to pH 2 with conc. HCl. The organic layer was washed with $H_2O$ (5×200 mL) until neutral pH, then dried to give a glassy solid (6.16 g). The compound was suspended in boiling n-Hexane (60 mL) for 1 h, filtered to give D as a white solid (5.53 g, 8.54 mmol). Overall yield 50%.

D. N-[4-[[4-[Bis[2-[[[4,7,10-tris(carboxymethyl)-1,4,7,10-tetraazacyclododec-1-yl]acetyl]amino]ethyl]amino-1,4-dioxobutyl]amino]benzoyl]-L-glutaminyl-L-tryptophyl-L-alanyl-L-valyl-glycyl-L-histidyl-L-leucyl-L-methioninamide, L244 (FIG. 13B)

Resin A (0.5 g; 0.3 mmol) was shaken in a solid phase peptide synthesis vessel with 50% morpholine in DMA (7 mL) for 10 min, the solution emptied and fresh 50% morpholine in DMA (7 mL) was added. The suspension was stirred for another 20 min then the solution was emptied and the resin washed with DMA (5×7 mL). 4-[N,N'-Bis[2-[(9-H-fluoren-9-ylmethoxy)carbonyl]aminoethyl]amino]-4-oxo butanoic acid (777.3 mg; 1.2 mmol), HOBt (184 mg; 1.2 mmol), DIC (187 μL; 1.2 mmol) and DMA (7 mL) were added to the resin, the mixture shaken for 40 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for 20 min. The solution was emptied and the resin washed with DMA (2×7 mL) and with $CH_2Cl_2$ (5×7 mL) then it was shaken in a flask with Reagent B (25 mL) for 4.5 h. The resin was filtered and the solution was evaporated under reduced pressure to afford an oily crude that after treatment with $Et_2O$ (20 mL) gave a precipitate. The precipitate was collected by centrifugation and washed with $Et_2O$ (5×20 mL) to give F as a white solid (140 mg). DOTA tri-t-butyl ester (112 mg; 0.178 mmol) HATU (70 mg; 0.178 mmol) and DIEA (60 μL; 0.356 mmol) were added to a solution of F (50 mg; 0.0445 mmol) in DMA (3 mL) and $CH_2Cl_2$ (2 mL) and stirred for 24 h at room temperature. The crude was evaporated to reduced volume (1 mL) and shaken with Reagent B (25 mL) for 4.5 h. After evaporation of the solvent, the residue was treated with Et$_2$O (20 mL) to give a precipitate. The precipitate was collected by centrifugation and washed with Et$_2$O (5×20 mL) to afford a beige solid (132 mg) that was analyzed by HPLC. An amount of crude (100 mg) was purified by preparative HPLC. The fractions containing the product were lyophilized to give L244 (FIG. 13C) (3.5 mg; 1.84×10$^{-3}$ mmol) as a white solid. Yield 0.8%.

General Experimentals for Examples XIV-Example XLII

L201-L228

A. Manual Couplings
6.0 equivalents of the appropriately protected amino acid was treated with 6.0 equivalents each of HOBt and DIC and activated outside the reaction vessel. This activated carboxylic acid in NMP was then transferred to the resin containing the amine and the reaction was carried out for 4-6 h and then the resin was drained and washed.

B. Special Coupling of Fmoc-Gly-OH to 4-aminobenzoic acid and aminobiphenylcarboxylic acid amides:
Fmoc-Gly-OH (10.0 equiv.) was treated with HATU (10.0 equiv.) and DIEA (20.0 equiv.) in NMP (10 mL of NMP was used for one gram of the amino acid by weight) and the solution was stirred for 10-15 min at RT before transferring to the vessel containing the amine loaded resin. The volume of the solution was made to 15.0 ml for every gram of the resin. The coupling was continued for 20 h at RT and the resin was drained of all the reactants. This procedure was repeated one more time and then washed with NMP before moving on to the next step.

C. Preparation of DO3A Monoamide:
8.0 equivalents of DOTA mono acid was dissolved in NMP and treated with 8.0 equivalents of HBTU and 16.0 equivalents of DIEA. This solution was stirred for 15 min at RT and then transferred to the amine on the resin and the coupling was continued for 24 h at RT. The resin was then drained, washed and then the peptide was cleaved and purified.

D. Cleavage of the Crude Peptides from the Resin and Purification:
The resin was suspended in Reagent B (15.0 ml/g) and shaken for 4 h at RT. The resin was then drained and washed with 2×5 mL of Reagent B again and combined with the previous filtrate. The filtrate was then concentrated under reduced pressure to a paste/liquid at RT and triturated with 25.0 mL of anhydrous ether (for every gram of the resin used). The suspension was then centrifuged and the ether layer was decanted. This procedure was repeated two more times and the colorless precipitate after ether wash was purified by preparative HPLC.

Example XIV

FIG. 21

Synthesis of L201

0.5 g of the Fmoc-Q(Trt)-W(Boc)-A-V-G-H(Trt)-M-Resin (0.4 mmol/g, 0.5 g, 0.2 mmol) (Resin A) was used. The rest of the amino acid units were added as described in the general procedure to prepare (1R)-1-(Bis {2-[bis(carboxymethyl)amino]ethyl}amino)propane-3-carboxylic acid-1-carboxyl-glycyl-4-aminobenzoyl-L-glutaminyl-L-tryptophyl-L-alanyl-L-valyl-glycyl-L-histidyl-L-leucyl-L-methioninamide (L201), Yield: 17.0 mg (5.4%)

Example XV

FIGS. 22A and 22B

Synthesis of L202

A. 4-Fmoc-hydrazinobenzoic acid (FIG. 22A):
A suspension of 4-hydrazinobenzoic acid (5.0 g, 32.9 mmol) in water (100 ml) was treated with cesium carbonate (21.5 g, 66.0 mmol). Fmoc-Cl (9.1 g, 35.0 mmol) in THF (25 mL) was added dropwise to the above solution with stirring over a period of 1 h. The solution was stirred for 4 h more after the addition and the reaction mixture was concentrated to about 75 mL and extracted with ether (2×100 mL). The ether layer was discarded and the aqueous layer was acidified with 2N HCl. The separated solid was filtered, washed with water (5×100 mL) and then recrystallized from acetonitrile to yield the product (compound B) as a colorless solid. Yield: 11.0 g (89%). $^1$H NMR (DMSO-d$_6$): δ 4.5 (m, 1H, Ar—CH$_2$—CH), 4.45 (m, 2H, Ar—CH$_2$), 6.6 (bs, 1H, Ar—H), 7.4-7.9 (m, 9, Ar—H and Ar—CH$_2$), 8.3 (s, 2H, Ar—H), 9.6 (s, 2H, Ar—H). M. S. –m/z 373.2 [M–H]

0.5 g of the Fmoc-Q(Trt)-W(Boc)-A-V-G-H(Trt)-M-Resin (0.4 mmol/g, 0.5 g, 0.2 mmol) (Resin A) was used. The amino acid units were added as described in the general procedure, including Compound B to prepare N-[(3β, 5β,12α)-3-[[[[[4,7,10-Tris(carboxymethyl)-1,4,7,10-tetraazacyclododec-1-yl]acetyl]amino]acetyl]amino]-4-hydrazinobenzoyl-L-glutaminyl-L-tryptophyl-L-alanyl-L-valyl-glycyl-L-histidyl-L-leucyl-L-methioninamide (L202) (FIG. 22B), Yield: 25.0 mg (8.3%)

Example XVI

FIGS. 23A and 23B

Synthesis of L203

A. Preparation of 4-Boc-aminobenzyl benzoate Compound B (FIG. 23A):
A suspension of 4-boc-aminobenzoic acid (0.95 g, 4.0 mmol) in dry acetonitrile (10.0 mL) was treated with powdered cesium carbonate (1.3 g, 4.0 mmol) and stirred vigorously under nitrogen. Benzyl bromide (0.75 g, 4.4 mmol) was added and the reaction mixture was refluxed for 20 h under nitrogen. The reaction mixture was then poured into ice cold water (200 mL) and the solid separated was filtered and washed with water (5×50 mL). The crude material was then recrystallized from aqueous methanol to yield the product as a colorless solid (Compound B). Yield: 0.8 g (61%). $^1$H NMR (CDCl$_3$): δ 1.5 (s, 9H, Tertiary methyls), 5.4 (s, 2H, Ar—CH$_2$), 7.4 (m, 7H, Ar—H) and 8.0 (m, 2H, Ar—H). M. S. –m/z 326.1 [M+H].

B. 4-Aminobenzyl benzoate Compound C (FIG. 23A):
4-Boc-aminobenzyl benzoate (0.8 g, 2.5 mmol) was dissolved in DCM (20 mL) containing TFA (25% by volume) and stirred for 2 h at RT. The reaction mixture was poured into 100.0 g of crushed ice and neutralized with saturated sodium bicarbonate solution until the pH reached about 8.5. The organic layer was separated and the aqueous layer was extracted with DCM (3×20 mL) and all the organic layers were combined. The DCM layer was then washed with 1×50 mL of saturated sodium bicarbonate, water (2×50 mL) and dried (sodium sulfate). Removal of the solvent yielded a colorless solid (Compound C) that was taken to the next step without further purification. Yield: 0.51 g (91%). $^1$H NMR (CDCl$_3$): δ 5.3 (s, 2H, Ar—CH$_2$), 6.6 (d, 2H, Ar—H, j=1.0 Hz), 7.4 (m, 5H, Ar—H, J=1.0 Hz) and 7.9 (d, 2H, Ar—H, J=1.0 Hz).

C. 4-(2-Chloroacetyl)aminobenzyl benzoate Compound D (FIG. 23A):

The amine (0.51 g, 2.2 mmol) was dissolved in dry dimethylacetamide (5.0 mL) and cooled in ice. Chloroacetyl chloride (0.28 g, 2.5 mmol) was added dropwise via a syringe and the solution was allowed to come to RT and stirred for 2 h. An additional, 2.5 mmol of chloroacetyl chloride was added and stirring was continued for 2 h more. The reaction mixture was then poured into ice cold water (100 mL). The precipitated solid was filtered and washed with water and then recrystallized from hexane/ether to yield a colorless solid (Compound D). Yield: 0.38 g (56%). $^1$H NMR (CDCl$_3$): δ 4.25 (s, 2H, CH$_2$—Cl), 5.4 (s, 2H, Ar—H), 7.4 (m, 5H, Ar—H), 7.6 (d, 2H, Ar—H), 8.2 (d, 2H, Ar—H) and 8.4 (s, 1H, —CONH).

tert-Butyl 2-{1,4,7,10-tetraaza-7,10-bis{[(tert-butyl)oxycarbonyl]methyl}-4-[(N-{4-[benzyloxycarbonyl]phenyl}carbamoyl]cyclododecyl}acetate, Compound E (FIG. 23A):

DO3A-tri-t-butyl ester.HCl (5.24 g, 9.5 mmol) was suspended in 30.0 mL of dry acetonitrile and anhydrous potassium carbonate (2.76 g, 20 mmol) was added and stirred for 30 min. The chloroacetamide D (2.8 g, 9.2 mmol) in dry acetonitrile (20.0 mL) was then added dropwise to the above mixture for 10 min. The reaction mixture was then stirred overnight. The solution was filtered and then concentrated under reduced pressure to a paste. The paste was dissolved in about 200.0 mL of water and extracted with 5×50 mL of ethyl acetate. The combined organic layer was washed with water (2×100 mL) and dried (sodium sulfate). The solution was filtered and evaporated under reduced pressure to a paste and the paste was chromatographed over flash silica gel (600.0 g). Elution with 5% methanol in DCM eluted the product. All the fractions that were homogeneous on TLC were pooled and evaporated to yield a colorless gum. The gum was recrystallized from isopropylether and DCM to prepare Compound E. Yield: 4.1 g (55%). $^1$H NMR (CDCl$_3$): δ 1.5 (s, 27H, methyls), 2.0-3.75 (m, 24H, NCH$_2$s), 5.25 (d, 2H, Ar—CH$_2$), 7.3 (m, 5H, Ar—H), 7.8 (d, 2H, Ar—H) and 7.95 (d, 2H, Ar–H). M. S.: m/z 804.3 [M+H].

D. Reduction of the Above Acid E to Prepare Compound F, (FIG. 23a):

The benzyl ester E from above (1.0 g, 1.24 mmol) was dissolved in methanol-water mixture (10.0 mL, 95:5) and palladium on carbon was added (10%, 0.2 g). The solution was then hydrogenated using a Parr apparatus at 50.0 psi for 8 h. The solution was filtered off the catalyst and then concentrated under reduced pressure to yield a colorless fluffy solid F. It was not purified further and was taken to the next step immediately. MS: m/z 714.3 [M+Na].

E. Preparation of L203 (FIG. 23B)

The above acid F was coupled to the amine on the resin [H-Q(Trt)-W(Boc)-A-V-G-H(Trt)-L-M-Resin] Resin A and F from above using standard coupling procedures described above. 0.5 g (0.2 mmol) of the resin yielded 31.5 mg of the final purified peptide (10.9%) N-[(3β,5β,12α)-3-[[[4,7,10-Tris(carboxymethyl)-1,4,7,10-tetraazacyclododec-1-yl]acetyl]amino]-4-aminobenzoyl-L-glutaminyl-L-tryptophyl-L-alanyl-L-valyl-glycyl-L-histidyl-L-leucyl-L-methioninamide (L203) (FIG. 23B).

Example XVII

FIG. 24

Synthesis of L204

Fmoc-Q(Trt)-W(Boc)-A-V-G-H(Trt)-L-M-resin (0.5 g, 0.2 mmol) (Resin A) was used. Fmoc-Gly-OH was loaded first followed by F from the above procedure (FIG. 23A) employing standard coupling conditions. Yield: 24.5 mg (8.16%) of N-[(3β,5β,12α)-3-[[[4,7,10-Tris(carboxymethyl)-1,4,7,10-tetraazacyclododec-1-yl]acetyl]amino]-4-aminobenzoyl-glycyl-L-glutaminyl-L-tryptophyl-L-alanyl-L-valyl-glycyl-L-histidyl-L-leucyl-L-methioninamide (L204) (FIG. 24).

Example XVIII

FIG. 25

Synthesis of L205

Fmoc-6-aminonicotinic acid[1] was prepared as described in the literature ("Synthesis of diacylhydrazine compounds for therapeutic use". Hoelzemann, G.; Goodman, S. (Merck Patent G.m.b.H., Germany). Ger. Offen. 2000, 16 pp. CODEN: GWXXBX DE 19831710 A1 20000120) and coupled with preloaded Fmoc-Q(Trt)-W(Boc)-A-V-G-H(Trt)-L-M-resin (0.5 g, 0.2 mmol) Resin A, followed by the other amino groups as above to prepare N-[(3β,5β,12α)-3-[[[4,7,10-Tris(carboxymethyl)-1,4,7,10-tetraazacyclododec-1-yl]acetyl]amino]-4-aminobenzoyl-glycyl-L-glutaminyl-L-tryptophyl-L-alanyl-L-valyl-glycyl-L-histidyl-L-leucyl-L-methioninamide (L205) Yield: 1.28 mg (0.4%).

Example XIX

FIGS. 26A and 26B

Synthesis of L206

A. 4'-Fmoc-amino-3'-methylbiphenyl-4-carboxylic acid B:

The amino acid (0.41 g, 1.8 mmol) was dissolved in a solution of cesium carbonate (0.98 g, 3.0 mmol) in 10.0 mL of water. See "Rational Design of Diflunisal Analogues with Reduced Affinity for Human Serum Albumin" Mao, H. et al J. Am. Chem. Soc., 2001, 123(43), 10429-10435. This solution was cooled in an ice bath and a solution of Fmoc-Cl (0.52 g, 2.0 mmol) in THF (10.0 mL) was added dropwise with vigorous stirring. After the addition, the reaction mixture was stirred at RT for 20 h. The solution was then acidified with 2N HCl. The precipitated solid was filtered and washed with water (3×20 mL) and air dried. The crude solid was then recrystallized from acetonitrile to yield a colorless fluffy solid B (FIG. 26A). Yield: 0.66 g (75%). $^1$H NMR (DMSO-d$_6$): δ 2.2 (s, Ar-Me), 4.25 (t, 1H, Ar—CH, j=5 Hz), 4.5 (d, 2H, O—CH2, j=5.0 Hz), 7.1 (bs, 1H, CONH), 7.4-8.0 (m, 8H, Ar—H) and 9.75 (bs, 1H, —COOH). M. S.: m/z 472.0 [M-H].

The acid B from above was coupled to Fmoc-Q(Trt)-W(Boc)-A-V-G-H(Trt)-L-M-resin (0.2 g, 0.08 mmol) resin A with the standard coupling conditions. Additional groups were added as above to prepare N-[(3β,5β,12α)-3-[[[[[4,7,10-Tris(carboxymethyl)-1,4,7,10-tetraazacyclododec-1-yl]acetyl]amino]acetyl]amino]-[4'-Amino-2'-methyl biphenyl-4-carboxyl]-L-glutaminyl-L-tryptophyl-L-alanyl-L-valyl-glycyl-L-histidyl-L-leucyl-L-methioninamide (L206). Yield: 30.5 mg (24%).

Example XX

FIGS. 27A-B

Synthesis of L207

3'-Fmoc-amino-biphenyl-3-carboxylic acid was prepared from the corresponding amine using the procedure described above. See "Synthesis of 3'-methyl-4-'-nitrobiphenylcarboxylic acids by the reaction of 3-methyl-4-nitrobenzenenediazonium acetate with methyl benzoate", Boyland, E. and Gorrod, J., J. Chem. Soc., Abstracts (1962), 2209-11. 0.7G of the amine yielded 0.81 g of the Fmoc-derivative (58%) (Compound B, FIG. 27A). $^1$H NMR (DMSO-$d_6$): δ 4.3 (t, 1H, Ar—CH), 4.5 (d, 2H, O—$CH_2$), 7.25-8.25 (m, 16H, Ar—H) and 9.9 (s, 1H, —COOH). M. S. -m/z 434 [M—H]

Fmoc-Q(Trt)-W(Boc)-A-V-G-H(Trt)-L-M-resin (0.2 g, 0.08 mmol) resin A was coupled to the above acid B and additional groups as above (FIG. 27B). 29.0 mg of N-[(3β,5β,12α)-3-[[[[[4,7,10-Tris(carboxymethyl)-1,4,7,10-tetraazacyclododec-1-yl]acetyl]amino]acetyl]amino]-[3'-amino-biphenyl-3-carboxyl]-L-glutaminyl-L-tryptophyl-L-alanyl-L-valyl-glycyl-L-histidyl-L-leucyl-L-methioninamide (L207) was prepared (23%).

Example XXI

FIG. 28

Synthesis of L208

Fmoc-Q(Trt)-W(Boc)-A-V-G-H(Trt)-L-M-resin (0.2 g, 0.08 mmol) A was deblocked and coupled to terephthalic acid employing HATU as the coupling agent. The resulting acid on the resin was activated with DIC and NHS and then coupled to ethylenediamine. DOTA-mono acid was finally coupled to the amine on the resin. N-[(3β,5β,12α)-3-[[[[[4,7,10-Tris(carboxymethyl)-1,4,7,10-tetraazacyclododec-1-yl]acetyl]amino]acetyl]amino]-[1,2-d]aminoethyl-terephthalyl]-L-glutaminyl-L-tryptophyl-L-alanyl-L-valyl-glycyl-L-histidyl-L-leucyl-L-methioninamide (L208) was prepared for a yield of 17.5 mg (14%)

Example XXII

FIGS. 29A-B

Synthesis of L209

A. Boc-Glu(G-OBn)-G-OBn:
Boc-Glutamic acid (5.0 g, 20.2 mol) was dissolved in THF (50.0 mL) and cooled to 0° C. in an ice bath. HATU (15.61 g, 41.0 mmol) was added followed by DIEA (6.5 g, 50.0 mmol). The reaction mixture was stirred at 0° C. for 30 min. Benzyl ester of glycine [8.45 g, 50 mmol, generated from neutralizing benzyl glycine hydrochloride with sodium carbonate and by extraction with DCM and solvent removal] was added in THF (25.0 mL). The reaction mixture was allowed to come to RT and stirred for 20 h at RT. All the volatiles were removed under reduced pressure. The residue was treated with saturated sodium carbonate solution (100 mL) and extracted with ethyl acetate (3×100 mL). The organic layers were combined and washed with 1N HCl (2×100 mL) and water (2×100 mL) and dried (sodium sulfate). The solution was filtered and solvent was removed under reduced pressure to yield a paste that was chromatographed over flash silica gel (500.0 g). Elution with 2% methanol in DCM yielded the product as a colorless paste (Compound B, FIG. 29A). Yield: 8.5 g (74.5%). $^1$H NMR (CDCl$_3$): δ 1.4 (s, 9H, —$CH_3$s), 2.0-2.5 (m, 4H, —CH—$CH_2$ and CO—CH), 4.2 (m, 5H, N—C$H_2$—CO), 5.15 (s, 4H, Ar—$CH_2$), 5.45 (bs, 1H, Boc-NH), 7.3 (m, 10H, Ar—H) and 7.6 (2bs, 2H, CONH). M. S. -m/z 564.1 [M+H]. Analytical HPLC retention time—8.29 min (>97% pure, 20-65% B over 15 min).

B. H-Glu(G-OBn)-G-OBn:
The fully protected glutamic acid derivative (1.7 g, 3.2 mmol) B from above was dissolved in DCM/TFA (4:1, 20 mL) and stirred until the starting material disappeared on TLC (2 h). The reaction mixture was poured into ice cold saturated sodium bicarbonate solution (200 mL) and the organic layer was separated and the aqueous layer was extracted with 2×50 mL of DCM and combined with the organic layer. The DCM layer was washed with saturated sodium bicarbonate (2×100 mL), water (2×100 mL) and dried (sodium sulfate). The solution was filtered and evaporated under reduced pressure and the residue was dried under vacuum to yield a glass (Compound C, FIG. 29A) that was taken to the next step without further purification. Yield: 0.72 g (95%). M. S. -m/z 442.2 [M+H].

C. (DOTA-tri-t-butyl)-Glu-(G-OBn)-G-OBn:
The amine C from above (1.33 g, 3 mmol) in anhydrous DCM (10.0 mL) was added to an activated solution of DOTA-tri-t-butyl ester [2.27 g, 3.6 mmol was treated with HBTU, 1.36 g, 3.6 mmol and DIEA 1.04 g, 8 mmol and stirred for 30 min at RT in 25 mL of dry DCM] and stirred at RT for 20 h]. The reaction mixture was diluted with 200 mL of DCM and washed with saturated sodium carbonate (2×150 mL) and dried (sodium sulfate). The solution was filtered and solvent was removed under reduced pressure to yield a brown paste. The crude product was chromatographed over flash silica gel (500.0 g). Elution with 2% methanol in DCM furnished the product as a colorless gum (Compound D, FIG. 29A). Yield: 1.7 g (56.8%). $^1$H NMR (CDCl$_3$): δ 1.3 and 1.4 (2s, 9H, three methyls each from the free base and the sodium adduct of DOTA), 2.0-3.5 (m, 20H, N—$CH_2$s and —CH—$CH_2$ and CO—$CH_2$), 3.75-4.5 (m, 13H, N—C$H_2$—CO), 5.2 (m, 4H, Ar—$CH_2$) and 7.25 (m, 10H, Ar—H). M. S. m/z -1018.3 [M+Na] and 996.5 [M+H] and 546.3 [M+Na+H]/2. HPLC—Retention Time: 11.24 min (>90%, 20-80% B over 30 min).

D. (DOTA-tri-t-butyl)-Glu-(G-OH)-G-OH:
The bis benzyl ester (0.2 g, 0.2 mmol) D from above was dissolved in methanol-water (20 mL, 9:1) and hydrogenated at 50 psi in the presence of 10% Pd/C catalyst (0.4 g, 50% by wt. water). After the starting material disappeared on HPLC and TLC (4 h), the solution was filtered off the catalyst and the solvent was removed under reduced pressure and the residue was dried under high vacuum for about 20 h (<0.1 mm) to yield the product as a colorless foam (Compound E, FIG. 29A). Yield: 0.12 g (73.5%). $^1$H NMR (DMSO-d$_6$): δ 1.3 and 1.4 (2s, 9H corresponding to methyls of free base and the sodium adduct of DOTA), 1.8-4.7 (m, 33H, NCH$_2$s, COCH$_2$ and CH—CH$_2$ and NH—CH—CO), 8.1, 8.2 and 8.4 (3bs, N HCO). M. S.: m/z −816.3 [M+H] and 838.3 [M+Na]. HPLC Retention Time: 3.52 min (20-80% B over 30 min, >95% pure).

E. H-8-amino-3,6-dioxaoctanoyl-8-amino-3,6-dioxaoctanoyl-Gln-Trp-Ala-Val-Gly-His-Leu-Met-NH$_2$:

Fmoc-Q(Trt)-W(Boc)-A-V-G-H(Trt)-L-M-resin (0.5 g, 0.2 mmol) A was deblocked and coupled twice sequentially to 8-amino-3,6-dioxaoctanoic acid to yield the above deprotected peptide (Compound F, FIG. 29B) after preparative HPLC purification. Yield: 91.0 mg (37%).

HPLC Retention Time: 8.98 min (>95% purity, 10-40% B in over 10 min). M. S.: m/z −1230.6 [M+H], 615.9 [M+2H]/2.

F. Solution Phase Coupling of the Bis-Acid E and the Amine F from Above: (FIG. 29B)

The bis-acid (13.5 mg, 0.0166 mmol) E was dissolved in 100 µL of dry acetonitrile and treated with NHS (4.0 mg, 0.035 mmol) and DIC (5.05 mg, 0.04 mmol) and stirred for 24 h at RT. To the above activated acid, the free amine F (51.0 mg, 0.41 mmol)[generated from the TFA salt by treatment with saturated sodium bicarbonate and freeze drying the solution to yield the amine as a fluffy solid] was added followed by 100 µL of NMP and the stirring was continued for 40 h more at RT. The solution was diluted with anhydrous ether (10 mL) and the precipitate was collected by centrifugation and washed with 2×10 mL of anhydrous ether again. The crude solid was then purified by preparative HPLC to yield the product as a colorless fluffy solid L209 as in FIG. 29B with a yield of 7.5 mg (14.7%).

Example XXIII

FIGS. 30A-B

Synthesis of L210

A. H-8-aminooctanoyl-8-aminooctanoyl-Gln-Trp-Ala-Val-Gly-His-Leu-Met-NH$_2$:

This was also prepared exactly the same way as in the case of Compound F (FIG. 29B), but using 1-aminooctanoic acid and the amine (Compound B, FIG. 30A) was purified by preparative HPLC. Yield: 95.0 mg (38.9%). HPLC Retention Time: 7.49 min (>95% purity; 10-40% B over 10.0 min). M. S.: m/z −1222.7 [M+H], 611.8 [M+2H]/2.

(DOTA-tri-t-butyl)-Glu-(G-OH)-G-OH (0.0163 g, 0.02 mmol) was converted to its bis-NHS ester as in the case of L209 in 100 µL of acetonitrile and treated with the free base, Compound B (60.0 mg, 0.05 mmol) in 100 µL of NMP and the reaction was continued for 40 h and then worked up and purified as above to prepare L210 (FIG. 30B) for a yield of 11.0 mg (18%).

Example XXIV

FIG. 31

Synthesis of L211

Prepared from 0.2 g 0f the Fmoc-Q(Trt)-W(Boc)-A-V-G-H(Trt)-L-M-resin (0.08 mmol) using standard protocols. N-[(3β,5β,12α)-3-[[[4,7,10-Tris(carboxymethyl)-1,4,7,10-tetraazacyclododec-1-yl]acetyl]amino]-glycyl-glycyl-4-aminobenzoyl-L-glutaminyl-L-tryptophyl-L-alanyl-L-valyl-glycyl-L-histidyl-L-leucyl-L-methioninamide L211 was prepared in a yield of 4.7 mg (3.7%) (FIG. 31).

Example XXV

FIG. 32

Synthesis of L212

Prepared from Rink Amide Novagel resin (0.47 mmol/g, 0.2 g, 0.094 mmol) by building the sequence on the resin by standard protocols. N-[(3β,5β,12α)-3-[[[4,7,10-Tris(carboxymethyl)-1,4,7,10-tetraazacyclododec-1-yl]acetyl] amino]-glycyl-4-aminobenzoyl-L-glutamyl-L-tryptophyl-L-alanyl-L-valyl-glycyl-L-histidyl-L-leucyl-L-methioninamide L212 was prepared for a yield of 25.0 mg (17.7%) (FIG. 32).

Example XXVI

FIG. 33

Synthesis of L213

Prepared from Fmoc-Met-2-chlorotrityl chloride resin (NovaBioChem, 0.78 mmol/g, 0.26 g, 0.2 mmol) and the rest of the sequence were built using standard methodology. N-[(3β,5β,12α)-3-[[[4,7,10-Tris(carboxymethyl)-1,4,7,10-tetraazacyclododec-1-yl]acetyl]amino]-glycyl-4-aminobenzoyl-L-glutaminyl-L-tryptophyl-L-alanyl-L-valyl-glycyl-L-histidyl-L-leucyl-L-methionine L213 was prepared for a yield of 49.05 mg (16.4%) (FIG. 33).

Example XXVII

FIG. 34

Synthesis of L214

Fmoc-Q(Trt)-W(Boc)-A-V-G-H(Trt)-L-M-resin (0.2 g, 0.08 mmol) A was used to prepare N-[(3β,5β,12α)-3-[[[4,7,10-Tris(carboxymethyl)-1,4,7,10-tetraazacyclododec-1-yl] acetyl]amino]-glycyl-4-aminobenzoyl-D-phenylalanyl-L-glutaminyl-L-tryptophyl-L-alanyl-L-valyl-glycyl-L-histidyl-L-leucyl-L-methioninamide L214 using standard conditions. 8.5 mg of the product (6.4%) was obtained (FIG. 34).

Example XXVIII

FIG. 35

Synthesis of L215

Fmoc-Q(Trt)-W(Boc)-A-V-G-H(Trt)-L-M-resin (0.2 g, 0.08 mmol) A was used to prepare N-[(3β,5β,12α)-3-[[[4,7, 10-Tris(carboxymethyl)-1,4,7,10-tetraazacyclododec-1-yl] acetyl]amino]-glycyl-4-aminobenzoyl-L-glutaminyl-L-arginyl-L-leucyl-glycyl-L-asparginyl-L-glutaminyl-L-tryptophyl-L-alanyl-L-valyl-glycyl-L-histidyl-L-leucyl-L-methioninamide L215. 9.2 mg (5.5%) was obtained (FIG. 35).

Example XXIX

FIG. 36

Synthesis of L216

Fmoc-Q(Trt)-W(Boc)-A-V-G-H(Trt)-L-M-resin (0.2 g, 0.08 mmol) A was used to prepare N-[(3β,5β,12α)-3-[[[4,7,10-Tris(carboxymethyl)-1,4,7,10-tetraazacyclododec-1-yl]acetyl]amino]-glycyl-4-aminobenzoyl-L-glutaminyl-arginyl-L-tyrosinyl-glycyl-L-asparginyl-L-glutaminyl-L-tryptophyl-L-alanyl-L-valyl-glycyl-L-histidyl-L-leucyl-L-methioninamide L216. 25.0 mg (14.7%) was obtained (FIG. 36).

Example XXX

FIG. 37

Synthesis of L217

Fmoc-Q(Trt)-W(Boc)-A-V-G-H(Trt)-L-M-resin A (0.2 g, 0.08 mmol) was used to prepare N-[(3β,5β,12α)-3-[[[4,7,10-Tris(carboxymethyl)-1,4,7,10-tetraazacyclododec-1-yl]acetyl]amino]-glycyl-4-aminobenzoyl-L-glutaminyl-L-lysyl-L-tyrosinyl-glycyl-L-glutaminyl-L-tryptophyl-L-alanyl-L-valyl-glycyl-L-histidyl-L-leucyl-L-methioninamide L217. 58.0 mg (34.7%) was obtained (FIG. 37).

Example XXXI

FIG. 38

Synthesis of L218

Fmoc-Q(Trt)-W(Boc)-A-V-G-H(Trt)-L-M-resin A (0.2 g, 0.08 mmol) was used. Fmoc-Lys(ivDde) was employed for the introduction of lysine. After the linear sequence was completed, the protecting group of the lysine was removed using 10% hydrazine in DMF (2×10 mL; 10 min each and then washed). The rest of the amino acids were then introduced using procedures described in the "general" section to complete the required peptide sequence. L218 in FIG. 38 as obtained in a yield of 40.0 mg (23.2%).

Example XXXII

FIG. 39

Synthesis of L219

4-Sulfamylbutyryl AM Novagel resin was used (1.1 mmol/g; 0.5 g; 0.55 mmol). The first amino acid was loaded on to this resin at −20° C. for 20 h. The rest of the sequence was completed utilizing normal coupling procedures. After washing, the resin was alkylated with 20.0 eq. of iodoacetonitrile and 10.0 equivalents of DIEA for 20 h. The resin was then drained of the liquids and washed and then cleaved with 2.0 eq. of pentylamine in 5.0 mL of THF for 20 h. The resin was then washed with 2×5.0 mL of THF and all the filtrates were combined. THF was then evaporated under reduced pressure and the residue was then deblocked with 10.0 mL of Reagent B and the peptide N-[(3β,5β,12α)-3-[[[4,7,10-Tris(carboxymethyl)-1,4,7,10-tetraazacyclododec-1-yl]acetyl]amino]-glycyl-4-aminobenzoyl-D-phenylalanyl-L-glutaminyl-L-tryptophyl-L-alanyl-L-valyl-glycyl-L-histidyl-L-leucyl-aminopentyl, L219 was purified as previously described. 28.0 mg (2.8%) was obtained (FIG. 39).

Example XXXIII

FIG. 40

Synthesis of L220

NovaSyn TGR (0.25 mmol/g; 0.15 g, 0.05 mmol) resin A was used to prepare N-[(3β,5β,12α)-3-[[[4,7,10-Tris(carboxymethyl)-1,4,7,10-tetraazacyclododec-1-yl]acetyl]amino]-glycyl-4-aminobenzoyl-L-glutaminyl-L-tryptophyl-L-alanyl-L-valyl-D-alanyl-L-histidyl-L-leucyl-L-methioninamide, L220. 31.5 mg (41.4%) was obtained (FIG. 40).

Example XXXIV

FIG. 41

Synthesis of L221

NovaSyn TGR (0.25 mmol/g; 0.15 g, 0.05 mmol) resin A was used to prepare N-[(3β,5β,12α)-3-[[[4,7,10-Tris(carboxymethyl)-1,4,7,10-tetraazacyclododec-1-yl]acetyl]amino]-glycyl-4-aminobenzoyl-D-phenylalanyl-L-glutaminyl-L-tryptophyl-L-alanyl-L-valyl-glycyl-L-histidyl-L-leucyl-L-leucinamide, L221. 28.0 mg (34.3%) was obtained (FIG. 41).

Example XXXV

FIG. 42

Synthesis of L222

NovaSyn TGR (0.25 mmol/g; 0.15 g, 0.05 mmol) resin A was used to prepare N-[(3β,5β,12α)-3-[[[4,7,10-Tris(carboxymethyl)-1,4,7,10-tetraazacyclododec-1-yl]acetyl]amino]-glycyl-4-aminobenzoyl-D-tyrosinyl-L-glutaminyl-L-tryptophyl-L-alanyl-L-valyl-betaalanyl-L-histidyl-L-phenylalanyl-L-norleucinamide, L222. 34.0 mg (40.0%) was obtained (FIG. 42).

Example XXXVI

FIG. 43

Synthesis of L223

NovaSyn TGR (0.25 mmol/g; 0.15 g, 0.05 mmol) resin A was used to prepare N-[(3β,5β,12α)-3-[[[4,7,10-Tris(carboxymethyl)-1,4,7,10-tetraazacyclododec-1-yl]acetyl]amino]-glycyl-4-aminobenzoyl-L-phenylalanyl-L-glutaminyl-L-tryptophyl-L-alanyl-L-valyl-betaalanyl-L-histidyl-L-phenylalanyl-L-norleucinamide, L223. 31.2 mg (37.1%) was obtained (FIG. 43).

Example XXXVII

FIG. 44

Synthesis of L224

NovaSyn TGR (0.25 mmol/g; 0.15 g, 0.05 mmol) resin A was used to prepare N—[(3β,5β,12α)-3-[[[4,7,10-Tris(carboxymethyl)-1,4,7,10-tetraazacyclododec-1-yl]acetyl] amino]-glycyl-4-aminobenzoyl-L-glutaminyl-L-tryptophyl-L-alanyl-glycyl-L-histidyl-L-phenylalanyl-L-leucinamide, L224. 30.0 mg (42.2%) was obtained (FIG. 44).

Example XXXVIII

FIG. 45

Synthesis of L225

NovaSyn TGR (0.25 mmol/g; 0.15 g, 0.05 mmol) resin A was used to prepare N-[(3β,5β,12α)-3-[[[4,7,10-Tris(carboxymethyl)-1,4,7,10-tetraazacyclododec-1-yl]acetyl] amino]-glycyl-4-aminobenzoyl-L-leucyl-L-tryptophyl-L-alanyl-L-valinyl-glycyl-L-serinyl-L-phenylalanyl-L-methioninamide, L225. 15.0 mg (20.4%) was obtained (FIG. 45).

Example XXXIX

FIG. 46

Synthesis of L226

NovaSyn TGR (0.25 mmol/g; 0.15 g, 0.05 mmol) resin A was used to prepare N-[(3β,5β,12α)-3-[[[4,7,10-Tris(carboxymethyl)-1,4,7,10-tetraazacyclododec-1-yl]acetyl] amino]-glycyl-4-aminobenzoyl-L-histidyl-L-tryptophyl-L-alanyl-L-valyl-glycyl-L-histidyl-L-leucyl-L-methioninamide, L226. 40.0 mg (52.9%) was obtained (FIG. 46).

Example XL

FIG. 47

Synthesis of L227

NovaSyn TGR (0.25 mmol/g; 0.15 g, 0.05 mmol) resin A was used to prepare N-[(3β,5β,12α)-3-[[[4,7,10-Tris(carboxymethyl)-1,4,7,10-tetraazacyclododec-1-yl]acetyl] amino]-glycyl-4-aminobenzoyl-L-leucyl-L-tryptophyl-L-alanyl-L-threonyll-glycyl-L-histidyl-L-phenylalanyl-L-methioninamide L227. 28.0 mg (36.7%) was obtained (FIG. 47).

Example XLI

FIG. 48

Synthesis of L228

NovaSyn TGR (0.25 mmol/g; 0.15 g, 0.05 mmol) resin A was used to prepare N-[(3β,5β,12α)-3-[[[4,7,10-Tris(carboxymethyl)-1,4,7,10-tetraazacyclododec-1-yl]acetyl] amino]-glycyl-4-aminobenzoyl-L-glutaminyl-L-tryptophyl-L-alanyl-L-valyl-glycyl-L-histidyl-L-phenylalanyl-L-methioninamide, L228. 26.0 mg (33.8%) was obtained (FIG. 48).

Example XLII

Synthesis of Additional GRP Compounds

A. General procedure for the preparation of 4,4'-Aminomethylbiphenylcarboxylic acid (B2) and 3,3'-aminomethylbiphenylcarboxylic acid (B3):

1. Methyl-hydroxymethylbiphenylcarboxylates:

Commercially available (Aldrich Chemical Co.) 4-hydroxymethylphenylboric acid or 3-hydroxymethylphenylboric acid (1.0 g, 6.58 mmol) was stirred with isopropanol (10 mL) and 2M sodium carbonate (16 mL) until the solution became homogeneous. The solution was degassed by passing nitrogen through the solution and then treated with solid methyl-3-bromobenzoate, or methyl-4-bromobenzoate (1.35 g, 6.3 mmol) followed by the Pd (0) catalyst {[($C_6H_5$)$_3$P]$_4$Pd; 0.023 g, 0.003 mmol}. The reaction mixture was kept at reflux under nitrogen until the starting bromobenzoate was consumed as determined by TLC analysis (2-3 h). The reaction mixture was then diluted with 250 mL of water and extracted with ethyl acetate (3×50 mL). The organic layers were combined and washed with saturated sodium bicarbonate solution (2×50 mL) and dried ($Na_2SO_4$). The solvent was removed under reduced pressure and the residue was chromatographed over flash silica gel (100 g). Elution with 40% ethyl acetate in hexanes yielded the product either as a solid or oil.

Yield:

B2 –0.45 g (31%); m. p. –170-171° C.

B3 –0.69 g (62%); oil.

$^1$H NMR (CDCl$_3$) δ B2 –3.94 (s, 3H, —COOCH$_3$), 4.73 (s, 2H, —CH$_2$-Ph), 7.475 (d, 2H, J=5 Hz), 7.6 (d, 2H, J=10 Hz), 7.65 (d, 2H, J=5 Hz) and 8.09 (d, 2H, J=10 Hz).

M. S. –m/e –243.0 [M+H]

B3 –3.94 (s, 3H, —COOCH$_3$), 4.76 (s, 2H, —CH$_2$-Ph), 7.50 (m, 4H), 7.62 (s, 1H), 7.77 (s, 1H), 8.00 (s, 1H) and 8.27 (s, 1H).

M. S. –m/e –243.2 [M+H]

2. Azidomethylbiphenyl carboxylates:

The above biphenyl alcohols (2.0 mmol) in dry dichloromethane (10 mL) were cooled in ice and treated with diphenylphosphoryl azide (2.2 mol) and DBU (2.0 mmol) and stirred under nitrogen for 24 h. The reaction mixture was diluted with water and extracted with ethyl acetate (2×25 mL). The organic layers were combined and washed successfully with 0.5 M citric acid solution (2×25 mL), water (2×25 mL) and dried (Na$_2$SO$_4$). The solution was filtered and evaporated under reduced pressure to yield the crude product. The 4,4'-isomer was crystallized from hexane/ether and the 3,3'-isomer was triturated with isopropyl ether to remove all the impurities; the product was homogeneous as determined on TLC analysis and further purification was not required.

Yield:

Methyl-4-azidomethyl-4-biphenylcaroxylate –0.245 g (46%); m. p. –106-108° C.

Methyl-4-azidomethyl-4-biphenylcaroxylate –0.36 g (59%, oil)

$^1$H NMR (CDCl$_3$) δ-4,4'-isomer –3.95 (s, 3H, —COOCH$_3$), 4.41 (s, 2H, —CH$_2$N$_3$), 7.42 (d, 2H, J=5 Hz), 7.66 (m, 4H) and 8.11 (d, 2H, J=5 Hz)

3,3'-Isomer –3.94 (s, 3H, —COOCH$_3$), 4.41 (s, 2H, —CH$_2$N$_3$), 7.26-7.6 (m, 5H), 7.76 (d, 1H, J=10 Hz), 8.02 (d, 1H, J=5 Hz) and 8.27 (s, 1H).

3. Hydrolysis of the methyl esters of biphenylcarboxylates:

About 4 mmol of the methyl esters were treated with 20 mL of 2M lithium hydroxide solution and stirred until the solution was homogeneous (20-24 h). The aqueous layer was extracted with 2×50 mL of ether and the organic layer was discarded. The aqueous layer was then acidified with 0.5 M citric acid and the precipitated solid was filtered and dried. No other purification was necessary and the acids were taken to the next step.

Yield:
4,4'-isomer −0.87 g of methyl ester yielded 0.754 g of the acid (86.6%); m. p. −205-210° C.

3,3'-isomer −0.48 g of the methyl ester furnished 0.34 g of the acid (63.6%); m. p. −102-105° C.

$^1$H NMR (DMSO-d$_6$) δ: 4,4'-isomer −4.52 (s, 2H, —CH$_2$N$_3$), 7.50 (d, 2H, J=5 Hz), 7.9 (m, 4H), and 8.03 (d, 2H, J=10 Hz)

3,3'-isomer −4.54 (s, 2H, —CH$_2$N$_3$), 7.4 (d, 1H, J=10 Hz), 7.5-7.7 (m, 4H), 7.92 (ABq, 2H) and 8.19 (s, 1H).

4. Reduction of the azides to the amine:

This was carried out on the solid phase and the amine was never isolated. The azidocarboxylic acid was loaded on the resin using the standard peptide coupling protocols. After washing, the resin containing the azide was shaken with 20 equivalents of triphenylphosphine in THF/water (95:5) for 24 h. The solution was drained under a positive pressure of nitrogen and then washed with the standard washing procedure. The resulting amine was employed in the next coupling.

5. (3β,5β,7α,12α)-3-[{(9H-Flouren-9-ylmethoxy)amino]acetyl}amino-7,12-dihydroxycholan-24-oic acid:

Tributylamine (3.2 mL); 13.5 mmol) was added dropwise to a solution of Fmoc-glycine (4.0 g, 13.5 mmol) in THF (80 mL) stirred at 0° C. Isobutylchloroformate (1.7 mL; 13.5 mmol) was subsequently added and, after 10 min, a suspension of tributylamine (2.6 mL; 11.2 mmol) and (3β,5β,7α,12α)-3-amino-7,12-dihydroxycholan-24-oic acid (4.5 g; 11.2 mmol) in DMF (80 mL) was added dropwise, over 1 h, into the cooled solution. The mixture was allowed to warm up to ambient temperature and after 6 h, the solution was concentrated to 120 mL, then water (180 mL) and 1N HCl (30 mL) were added (final pH 1.5). The precipitated solid was filtered, washed with water (2×100 mL), vacuum dried and purified by flash chromatography. Elution with chloroform/methanol (8:2) yielded the product as a colorless solid.

Yield: 1.9 g (25%). TLC: R$_f$ 0.30 (CHCl$_3$/MeOH/NH$_4$OH—6:3:1).

In Vitro and In Vivo Testing of Compounds

Example XLIII

In Vitro Binding Assay for GRP Receptors in PC3 Cell Lines—FIGS. 14 A-B

To identify potential lead compounds, an in vitro assay that identifies compounds with high affinity for GRP-R was used. Since the PC3 cell line, derived from human prostate cancer, is known to exhibit high expression of GRP-R on the cell surface, a radio ligand binding assay in a 96-well plate format was developed and validated to measure the binding of $^{125}$I-BBN to GRP-R positive PC3 cells and the ability of the compounds of the invention to inhibit this binding. This assay was used to measure the IC$_{50}$ for RP527 ligand, DO3A-monoamide-Aoc-QWAVGHLM-NH$_2$ (controls) and compounds of the invention which inhibit the binding of $^{125}$I-BBN to GRP-R. (RP527=N,N-dimethylglycine-Ser-Cys (Acm)-Gly-5-aminopentanoic acid-BBN (7-14), which is SEQ ID NO: 1), which has MS=1442.6 and IC50-0.84). Van de Wiele C, Dumont F et al., Technetium-99m RP527, a GRP analogue for visualization of GRP receptor-expressing malignancies: a feasibility study. Eur. J. Nucl. Med., (2000) 27; 1694-1699.; DO3A-monoamide-Aoc-QWAVGHLM-NH$_2$ is also referred to as DO3A-monoamide-8-amino-octanoic acid-BBN (7-14), which is SEQ ID NO: 1, and has MS=1467.0. DO3A monoamide-aminooctanyl-BBN[7-14]

The Radioligand Binding Plate Assay was validated for BBN and BBN analogues (including commercially available BBN and L1) and also using $^{99m}$Tc RP527 as the radioligand.

A. Materials and Methods:

1. Cell culture:

PC3 (human prostate cancer cell line) were obtained from the American Type Culture Collection and cultured in RPMI 1640 (ATCC) in tissue culture flasks (Corning). This growth medium was supplemented with 10% heat inactivated FBS (Hyclone, SH30070.03), 10 mM HEPES (GibcoBRL, 15630-080), and antibiotic/antimycotic (GibcoBRL, 15240-062) for a final concentration of penicillin-streptomycin (100 units/mL), and fungizone (0.25 µg/mL). All cultures were maintained in a humidified atmosphere containing 5% CO$_2$/95% air at 37° C., and passaged routinely using 0.05% trypsin/EDTA (GibcoBRL 25300-054) where indicated. Cells for experiments were plated at a concentration of 2.0× 10$^4$/well either in 96-well white/clear bottom microtiter plates (Falcon Optilux-I) or 96 well black/clear collagen I cellware plates (Beckton Dickinson Biocoat). Plates were used for binding studies on day 1 or 2 post-plating.

2. Binding buffer:

RPMI 1640 (ATCC) supplemented with 20 mM HEPES, 0.1% BSA (w/v), 0.5 mM PMSF (AEBSF), bacitracin (50 mg/500 ml), pH 7.4. $^{125}$I-BBN (carrier free, 2200 Ci/mmole) was obtained from Perkin-Elmer.

B. Competition Assay with $^{125}$I-BBN for GRP-R in PC3 Cells:

A 96-well plate assay was used to determine the IC$_{50}$ of various compounds of the invention to inhibit binding of $^{125}$I-BBN to human GRP-R. The following general procedure was followed:

All compounds tested were dissolved in binding buffer and appropriate dilutions were also done in binding buffer. PC3 cells (human prostate cancer cell line) for assay were plated at a concentration of 2.0×10$^4$/well either in 96-well white/clear bottomed microtiter plates (Falcon Optilux-I) or 96 well black/clear collagen I cellware plates (Beckton Dickinson Biocoat). Plates were used for binding studies on day 1 or 2 post-plating. The plates were checked for confluency (>90% confluent) prior to assay. For the assay, RP527 or DO3A-monoamide-Aoc-QWAVGHLM-NH$_2$ ligand, (controls), or compounds of the invention at concentrations ranging from 1.25×10$^{-9}$ M to 5×10$^{-9}$ M, was co-incubated with $^{125}$I-BBN (25, 000 cpm/well). These studies were conducted with an assay volume of 75 µl per well. Triplicate wells were used for each data point. After the addition of the appropriate solutions, plates were incubated for 1 h at 4° C. to prevent internalization of the ligand-receptor complex. Incubation was ended by the addition of 200 µl of ice-cold incubation buffer. Plates were washed 5 times and blotted dry. Radioactivity was detected using either the LKB CompuGamma counter or a microplate scintillation counter.

Competition binding curves for RP527 (control) and L70, a compound of the invention can be found in FIGS. 14A-B. These data show that the IC50 of the RP527 control is 2.5 nM and that of L70, a compound of this invention is 5 nM. The IC50 of the DO3A-monoamide-Aoc-QWAVGHLM-NH$_2$ control was 5 nM. IC50 values for those compounds of the invention tested can be found in Tables 1-3, supra, and show that they are comparable to that of the controls and thus would be expected to have sufficient affinity for the receptor to allow uptake by receptor bearing cells in vivo.

C. Internalization & Efflux Assay:

These studies were conducted in a 96-well plate. After washing to remove serum proteins, PC3 cells were incubated with $^{125}$I-BBN, $^{177}$Lu-DO3A-monoamide-Aoc-QWAVGHLM-NH$_2$ or radiolabeled compounds of this invention for 40 min, at 37° C. Incubations were stopped by the addition of 200 µl of ice-cold binding buffer. Plates were washed twice with binding buffer. To remove surface-bound radioligand, the cells were incubated with 0.2M acetic acid (in saline), pH 2.8 for 2 min. Plates were centrifuged and the acid wash media were collected to determine the amount of radioactivity which was not internalized. The cells were collected to determine the amount of internalized $^{125}$I-BBN, and all samples were analyzed in the gamma counter. Data for the internalization assay was normalized by comparing counts obtained at the various time points with the counts obtained at the final time point (T40 min).

For the efflux studies, after loading the PC3 cells with $^{125}$I-BBN or radiolabeled compounds of the invention for 40 min at 37° C., the unbound material was filtered, and the % of internalization was determined as above. The cells were then resuspended in binding buffer at 37° C. for up to 3 h. At 0.5, 1, 2, or 3 h, the amount remaining internalized relative to the initial loading level was determined as above and used to calculate the percent efflux recorded in Table 5.

TABLE 5

Internalisation and efflux of $^{125}$I-BBN and the Lu-177 complexes of DO3A-monoamide-Aoc-QWAVGHLM-NH$_2$ (control) and compounds of this invention

|  | I-BBN | DO3A-monoamide-Aoc-QWAVGHLM-NH$_2$ (control) | L63 | L64 | L70 |
|---|---|---|---|---|---|
| Internalisation (40 minutes) | 59 | 89 | 64 | 69 | 70 |
| Efflux (2 h) | 35 | 28 | 0 | 20 | 12 |

These data show that the compounds of this invention are internalized and retained by the PC3 cells to a similar extent to the controls.

Example XLIV

Preparation of Tc-Labeled GRP Compounds

Peptide solutions of compounds of the invention identified in Table 6 were prepared at a concentration of 1 mg/mL in 0.1% aqueous TFA. A stannous chloride solution was prepared by dissolving SnCl$_2$.2H$_2$O (20 mg/mL) in 1 N HCl. Stannous gluconate solutions containing 20 lug of SnCl$_2$.2H$_2$O/100 µL were prepared by adding an aliquot of the SnCl$_2$ solution (10 µL) to a sodium gluconate solution prepared by dissolving 13 mg of sodium gluconate in water. A hydroxypropyl gamma cyclodextrin [HP-γ-CD] solution was prepared by dissolving 50 mg of HP-γ-CD in 1 mL of water.

The $^{99m}$Tc labeled compounds identified below were prepared by mixing 20 µL of solution of the unlabeled compounds (20 µg), 50 µL of HP-γ-CD solution, 100 µL of Sn-gluconate solution and 20 to 50 µL of $^{99m}$Tc pertechnetate (5 to 8 mCi, Syncor). The final volume was around 200 µL and final pH was 4.5-5. The reaction mixture was heated at 100° C. for 15 to 20 min. and then analyzed by reversed phase HPLC to determine radiochemical purity (RCP). The desired product peaks were isolated by HPLC, collected into a stabilizing buffer containing 5 mg/mL ascorbic acid, 16 mg/mL HP-γ-CD and 50 mM phosphate buffer, pH 4.5, and concentrated using a speed vacuum to remove acetonitrile. The HPLC system used for analysis and purification was as follows: C18 Vydac column, 4.6×250 mm, aqueous phase: 0.1% TFA in water, organic phase: 0.085% TFA in acetonitrile. Flow rate: 1 mL/min. Isocratic elution at 20%-25% acetonitrile/0.085% TFA was used, depending on the nature of individual peptide.

Labeling results are summarized in Table 6.

TABLE 6

| Compound[1] | Sequence[2] | HPLC retention time (min) | Initial RCP[3] (%) | RCP[4] (%) immediately following purification |
|---|---|---|---|---|
| L2 | -RJQWAVGHLM-NH$_2$ | 5.47 | 89.9 | 95.6 |
| L4 | -SJQWAVGHLM-NH$_2$ | 5.92 | 65 | 97 |
| L8 | -JKQWAVGHLM-NH$_2$ | 6.72 | 86 | 94 |
| L1 | -KJQWAVGHLM-NH$_2$ | 5.43 | 88.2 | 92.6 |
| L9 | -JRQWAVGHLM-NH$_2$ | 7.28 | 91.7 | 96.2 |
| L7 | -aJQWAVGHLM-NH$_2$ | 8.47 | 88.6 | 95.9 | n.d. = not detected
[1]All compounds were conjugated with an N,N'-dimethylglycyl-Ser-Cys-Gly metal chelator. The Acm protected form of the ligand was used. Hence, the ligand used to prepare the 99mTc complex of L2 was N,N'-dimethylglycyl-Ser-Cys (Acm)-Gly-RJQWAVGHLM-NH$_2$. The Acm group was removed during chelation to Tc.
[2]In the Sequence, "J" refers to 8-amino-3,6-dioxaoctanoic acid and "a" refers to D-alanine.
[3]Initial RCP measurement taken immediately after heating and prior to HPL purification.
[4]RCP determined following HPLC isolation and acetonitrile removal via speed vacuum.

Example XLV

Preparation of $^{177}$Lu-L64 for Cell Binding and Biodistribution Studies

This compound was synthesized by incubating 10 µg L64 ligand (10 µL of a 1 mg/mL solution in water), 100 µL ammonium acetate buffer (0.2M, pH 5.2) and ~1-2 mCi of $^{177}$LuCl$_3$ in 0.05N HCl (MURR) at 90° C. for 15 min. Free $^{177}$Lu was scavenged by adding 20 µL of a 1% Na$_2$EDTA.2H$_2$O (Aldrich) solution in water. The resulting radiochemical purity (RCP) was ~95%. The radiolabeled product was separated from unlabeled ligand and other impurities by HPLC, using a YMC Basic C8 column [4.6×150 mm], a column temperature of 30° C. and a flow rate of 1 mL/min, with a gradient of 68% A/32% B to 66% A/34% B over 30 min., where A is citrate buffer (0.02M, pH 3.0), and B is 80% CH$_3$CN/20% CH$_3$OH. The isolated compound had an RCP of ~100% and an HPLC retention time of 23.4 minutes.

Samples for biodistribution and cell binding studies were prepared by collecting the desired HPLC peak into 1000 µL of citrate buffer (0.05 M, pH 5.3, containing 1% ascorbic acid, and 0.1% HSA). The organic eluent in the collected eluate was removed by centrifugal concentration for 30 min. For cell binding studies, the purified sample was diluted with cell-binding media to a concentration of 1.5 µCi/mL within 30 minutes of the in vitro study. For biodistribution studies, the sample was diluted with citrate buffer (0.05 M, pH 5.3, containing 1% sodium ascorbic acid and 0.1% HSA) to a final concentration of 50 µCi/mL within 30 minutes of the in vivo study.

Example XLVI

Preparation of $^{177}$Lu-L64 for Radiotherapy Studies

This compound was synthesized by incubating 70 µg L64 ligand (70 µL of a 1 mg/mL solution in water), 200 µL ammonium acetate buffer (0.2M, pH 5.2) and ~30-40 mCi of $^{177}$LuCl$_3$ in 0.05N HCl (MURR) at 85° C. for 10 min. After cooling to room temperature, free $^{177}$Lu was scavenged by adding 20 µL of a 2% Na$_2$EDTA.2H$_2$O (Aldrich) solution in water. The resulting radiochemical purity (RCP) was ~95%. The radiolabeled product was separated from unlabeled ligand and other impurities by HPLC, using a 300VHP Anion Exchange column (7.5×50 mm) (Vydac) that was sequentially eluted at a flow rate of 1 mL/min with water, 50% acetonitrile/water and then 1 g/L aqueous ammonium acetate solution. The desired compound was eluted from the column with 50% CH$_3$CN and mixed with ~1 mL of citrate buffer (0.05 M, pH 5.3) containing 5% ascorbic acid, 0.2% HSA, and 0.9% (v:v) benzyl alcohol. The organic part of the isolated fraction was removed by spin vacuum for 40 min, and the concentrated solution (~20-25 mCi) was adjusted within 30 minutes of the in vivo study to a concentration of 7.5 mCi/mL using citrate buffer (0.05 M, pH 5.3) containing 5% ascorbic acid, 0.2% HSA, and 0.9% (v:v) benzyl alcohol. The resulting compound had an RCP of >95%.

Example XLVII

Preparation of $^{111}$In-L64

This compound was synthesized by incubating 10 µg L64 ligand (5 µL of a 2 mg/mL solution in 0.01 N HCl), 60 µL ethanol, 1.12 mCi of $^{111}$InCl$_3$ in 0.05N HCl (80 µL) and 155 µL sodium acetate buffer (0.5M, pH 4.5) at 85° C. for 30 min. Free $^{111}$In was scavenged by adding 20 µL of a 1% Na$_2$EDTA.2H$_2$O (Aldrich) solution in water. The resulting radiochemical purity (RCP) was 87%. The radiolabeled product was separated from unlabeled ligand and other impurities by HPLC, using a Vydac C18 column, [4,6×250 mm], a column temperature of 50° C. and a flow rate of 1.5 mL/min. with a gradient of 75% A/25% B to 65% A/35% B over 20 min where A is 0.1% TFA in water, B is 0.085% TFA in acetonitrile. With this system, the retention time for $^{111}$In-L64 is 15.7 min. The isolated compound had an RCP of 96.7%.

Example XLVIII

Preparation of $^{177}$Lu-DO3A-monoamide-Aoc-QWAVGHLM-NH$_2$ (Control)

A stock solution of peptide was prepared by dissolving DO3A-monoamide-Aoc-QWAVGHLM-NH$_2$ ligand (prepared as described in US Application Publication No. 2002/0054855 and WO 02/87637, both incorporated by reference) in 0.01 N HCl to a concentration of 1 mg/mL. $^{177}$Lu-DO3A-monoamide-Aoc-QWAVGHLM-NH$_2$ was prepared by mixing the following reagents in the order shown.

| | |
|---|---|
| 0.2 M NH$_4$OAc, pH 6.8 | 100 µL |
| Peptide stock, 1 mg/mL, in 0.01 N HCl | 5 µL |
| $^{177}$LuCl$_3$ (MURR) in 0.05M HCl | 1.2 µL (1.4 mCi) |

The reaction mixture was incubated at 85° C. for 10 min. After cooling down to room temperature in a water bath, 20 µL of a 1% EDTA solution and 20 µl of EtOH were added. The compound was analyzed by HPLC using a C18 column (VYDAC Cat # 218TP54) that was eluted at flow rate of 1 mL/min with a gradient of 21 to 25% B over 20 min, where A is 0.1% TFA/H$_2$O and B is 0.1% TFA/CH$_3$CN). $^{177}$Lu-DO3A-monoamide-Aoc-QWAVGHLM-NH$_2$ was formed in 97.1% yield (RCP) and had a retention time of ~16.1 min on this system.

Example XLIX

Preparation of $^{177}$Lu-L63

This compound was prepared as described for $^{177}$Lu-DO3A-monoamide-Aoc-QWAVGHLM-NH$_2$, wherein QWAVGHLM-NH$_2$ is the BBN(7-14) sequence (SEQ ID NO: 1). The compound was analyzed by HPLC using a C18 column (VYDAC Cat # 218TP54) that was eluted at flow rate of 1 mL/min with a gradient of 30-34% B over 20 min (where solvent is A. 0.1% TFA/H$_2$O and B is 0.1% TFA/CH$_3$CN). The $^{177}$Lu-L63 that formed had an RCP of 97.8% and a retention time of ~14.2 min on this system.

Example L

Preparation of $^{177}$Lu-L70 for Cell Binding and Biodistribution Studies

This compound was prepared following the procedures described above, but substituting L70 (the ligand of Example II). Purification was performed using a YMC Basic C8 column (4.6×150 mm), a column temperature of 30° C. and a flow rate of 1 mL/min. with a gradient of 80% A/20% B to 75% A/25% B over 40 min., where A is citrate buffer (0.02M, pH 4.5), and B is 80% CH$_3$CN/20% CH$_3$OH. The isolated compound had an RCP of ~100% and an HPLC retention time of 25.4 min.

Example LI

Preparation of $^{177}$Lu-L70 for Radiotherapy Studies

This compound was prepared as described above for L64.

Example LII

Preparation of $^{111}$In-L70 for Cell Binding and Biodistribution Studies

This compound was synthesized by incubating 10 µg L70 ligand (10 µL of a 1 mg/mL solution in 0.01 N HCl), 180 µL ammonium acetate buffer (0.2M, pH 5.3), 1.1 mCi of $^{111}$InCl$_3$ in 0.05N HCl (61 µL, Mallinckrodt) and 50 µL of saline at 85° C. for 30 min. Free $^{111}$In was scavenged by adding 20 µL of a 1% Na$_2$EDTA.2H$_2$O (Aldrich) solution in water. The resulting radiochemical purity (RCP) was 86%. The radiolabeled product was separated from unlabeled ligand and other impurities by HPLC, using a Waters XTerra C18 cartridge linked to a Vydac strong anion exchange column [7.5×50 mm], a column temperature of 30° C. and a flow rate of 1 mL/min. with the gradient listed in the Table below, where A is 0.1 mM NaOH in water, pH 10.0, B is 1 g/L ammonium acetate in water, pH 6.7 and C is acetonitrile. With this system, the retention time for $^{111}$In-L70 is 15 min while the retention time for L70 ligand is 27 to 28 min. The isolated compound had an RCP of 96%.

Samples for biodistribution and cell binding studies were prepared by collecting the desired HPLC peak into 500 µL of citrate buffer (0.05 M, pH 5.3, containing 5% ascorbic acid, 1 mg/mL L-methionine and 0.2% HSA). The organic part of the collection was removed by spin vacuum for 30 min. For cell binding studies, the purified, concentrated sample was used within 30 minutes of the in vitro study. For biodistribution studies, the sample was diluted with citrate buffer (0.05 M, pH 5.3, containing 5% sodium ascorbic acid and 0.2% HSA) to a final concentration of 10 µCi/mL within 30 minutes of the in vivo study.

| Time, min | A | B | C |
|---|---|---|---|
| 0-10 | 100% | | |
| 10-11 | 100-50% | | 0-50% |
| 11-21 | 50% | | 50% |
| 21-22 | 50-0% | 0-50% | 50% |
| 22-32 | | 50% | 50% |

Example LIII

In Vivo Pharmacokinetic Studies

A. Tracer Dose Biodistribution:

Low dose pharmacokinetic studies (e.g., biodistribution studies) were performed using the below-identified compounds of the invention in xenografted, PC3 tumor-bearing nude mice ([Ncr]-Foxn1<nu>). In all studies, mice were administered 100 µL of $^{177}$Lu-labeled test compound at 200 µCi/kg, i.v., with a residence time of 1 and 24 h per group (n=3-4). Tissues were analyzed in an LKB 1282 CompuGamma counter with appropriate standards.

TABLE 7

Pharmacokinetic comparison at 1 and 24 h in PC3 tumor-bearing nude mice (200 µCi/kg; values as % ID/g, except where otherwise indicated) of $^{177}$Lu-177 labeled compounds of this invention compared to control

| Tissue | DO3A-monoamide-Aoc-QWAVGHLM-NH$_2$ control | | L63 | | L64 | | L70 | |
|---|---|---|---|---|---|---|---|---|
|  | 1 hr | 24 hr | 1 hr | 24 hr | 1 hr | 24 hr | 1 hr | 24 hr |
| Blood (% ID) | 0.44 | 0.03 | 7.54 | 0.05 | 1.87 | 0.02 | 0.33 | 0.03 |
| Liver (% ID) | 0.38 | 0.04 | 12.15 | 0.20 | 2.89 | 0.21 | 0.77 | 0.10 |
| Kidneys | 7.65 | 1.03 | 7.22 | 0.84 | 10.95 | 1.45 | 6.01 | 2.31 |
| Tumor | 3.66 | 1.52 | 9.49 | 2.27 | 9.83 | 3.60 | 6.42 | 3.50 |
| Pancreas | 28.60 | 1.01 | 54.04 | 1.62 | 77.78 | 6.56 | 42.34 | 40.24 |

Whereas the distribution of radioactivity in the blood, liver and kidneys after injection of L64 and L70 is similar to that of the control compound, DO3A-monoamide-Aoc-QWAVGHLM-NH$_2$, wherein QWAVGHLM-NH$_2$ is the BBN(7-14) sequence (SEQ ID NO: 1), the uptake in the tumor is much higher at 1 and 24 h for both L64 and L70. L63 also shows high tumor uptake although with increased blood and liver values at early times. Uptake in the mouse pancreas, a normal organ known to have GRP receptors is much higher for L64, L70 and L63 than for the control compound DO3A-monoamide-Aoc-QWAVGHLM-NH$_2$, wherein QWAVGHLM-NH$_2$ is the BBN(7-14) sequence (SEQ ID NO: 1).

B. The Effect of Mass Peptide Dose of L70 in Tumor and Normal Tissues.

The following biodistribution studies were performed in the human PC-3 nude mouse model (Tac:Cr:(NCr)-Fox1$^{nu}$).

Mice received one i.v. tail vein dose (0.1 mL) of the appropriate solution of $^{177}$Lu-L70 to which sufficient L70 ligand was added to achieve the peptide mass recorded in the following tables. The radioactive dose of $^{177}$Lu-L70 given was 10-750 µCi.

Subjects of all studies were terminated at the end of the residence interval and the organs and tissues were harvested. Radioactivity was assayed in a gamma counter. The data is expressed as percentage of the total administered radioactivity per gram of tissue (% ID/g).

|  | Administered Dose (µg) | | | | | |
|---|---|---|---|---|---|---|
| Organ | 0.0025 | 0.08 | 0.22 | 0.43 | 0.64 | 0.85 |
| Mouse % IDg, 1 h | | | | | | |
| Blood | 0.24 | 0.77 | 0.49 | 0.85 | 0.48 | 0.71 |
| Liver | 0.21 | 0.44 | 0.27 | 0.44 | 0.26 | 0.35 |
| Kidneys | 7.09 | 5.17 | 3.46 | 4.13 | 4.75 | 5.31 |
| Tumor | 6.35 | 3.13 | 4.36 | 3.13 | 3.97 | 5.78 |
| Pancreas | 49.59 | 51.15 | 25.11 | 11.60 | 7.19 | 5.27 |
| GI | 6.38 | 4.08 | 1.41 | 1.39 | 0.94 | 0.83 |
| Mouse % ID/g, 24 h | | | | | | |
| Blood | 0.02 | 0.01 | 0.01 | 0.02 | 0.01 | 0.01 |
| Liver | 0.08 | 0.18 | 0.15 | 0.11 | 0.12 | 0.12 |
| Kidneys | 2.26 | 1.2 | 1.70 | 1.28 | 0.90 | 1.47 |
| Tumor | 3.39 | 2.59 | 2.13 | 1.64 | 0.57 | 2.85 |
| Pancreas | 35.11 | 35.18 | 19.68 | 9.55 | 4.86 | 3.29 |
| GI | 3.26 | 1.31 | 0.78 | 0.53 | 0.25 | 0.24 |

The data show that those normal organs in mice, e.g. pancreas and gastrointestinal tract, known to express the GRP receptor, demonstrate an expected mass dose effect (i.e. reduction in uptake of radioactivity with increasing mass dose), however, the tumor is unexpectedly resistant to saturation as the mass dose is increased.

A similar effect can be obtained by administering a dose of L70 ligand prior to the administration of the radioactive material. In this study, biodistribution studies were performed in the human PC-3 nude mouse model (Tac:Cr:(NCr)-Fox1$^{nu}$) where the animals were pretreated with 1 intravenous injection of L70 ligand (0.64 µg) or buffer control at 5, 15, or 60 minutes prior to intravenous administration of $^{177}$Lu-L70; mass peptide dose 0.1 µg/kg mouse. Animals were sacrificed 1 hour after administration of $^{177}$Lu-L70 and tissues counted to determine if pre-treatment with L70 had any effect on biodistribution.

Down-regulation In Vivo, % Injected Dose/Organ* in PC-3 Mice,
at 1 h Post Injection of $^{177}$Lu-L70

| | Time between L70 predose injection and administration of $^{177}$Lu-L70 | | | |
|---|---|---|---|---|
| | No Predose (Control) | 5 min | 15 min | 60 min |
| Blood$^a$ | 0.20 ± 0.04 | 0.46 ± 0.12** | 0.49 ± 0.32 | 0.22 ± 0.02 |
| Lung | 0.04 ± 0.01 | 0.09 ± 0.02** | 0.09 ± 0.04 | 0.04 ± 0.01 |
| Kidneys | 5.10 ± 2.61 | 1.73 ± 0.69* | 2.25 ± 1.30 | 3.93 ± 2.26 |
| Pancreas | 15.87 ± 4.48 | 1.22 ± 0.25**** | 2.83 ± 0.22*** | 10.14 ± 1.73 |
| Spleen | 0.10 ± 0.03 | 0.02 ± 0.01*** | 0.02 ± 0.01*** | 0.04 ± 0.01** |
| Tumor$^a$ | 4.37 ± 1.42 | 5.40 ± 1.85 | 4.07 ± 1.05 | 3.21 ± 1.49 |
| G.I. | 9.50 ± 0.20 | 1.29 ± 0.77**** | 1.98 ± 0.54**** | 5.86 ± 2.46* |
| Urine | 40.59 ± 6.12 | 65.06 ± 7.25*** | 68.66 ± 12.50** | 57.88 ± 10.42* |

$^a$% injected dose/g tissue.
Level of Significance:
*p < 0.05,
**p < 0.01,
***p < 0.005,
****p < 0.001.

As before, a significant decrease in the amount of radioactivity in the pancreas was seen in animals that had been pretreated with L70 either 5 or 15 minutes prior to $^{177}$Lu-L70 administration, while decreases in gastrointestinal radioactivity were seen in all L70 pre-treatment groups (5, 15, and 60 minutes). Renal effects were transient and only significantly different from control in the 5-minute predose group; however, urinary excretion differences persisted out to 60 minutes post L70 administration. The results indicate that the target tumor was unaffected by pre-treatment with L70 and demonstrated uptake of $^{177}$Lu-L70 under all predose conditions. Combined, these results show a beneficial effect of pre-dosing or co-dosing with compounds of the invention.

Example LIV

Receptor Subtype Specificity

Currently, four mammalian members of the GRP receptor family are known: the GRP-preferring receptor (GRP-R), neuromedin-B preferring receptor (NMB-R), the bombesin receptor subtype 3 (BB3-R) and the bombesin receptor subtype 4 (BB4-R). The receptor subtype specificity of $^{177}$Lu-L70 was investigated. The results indicate $^{177}$Lu-L70 binds specifically to GRP-R and NMB-R, and has little affinity for BB3-R.

The subtype specificity of the Lutetium complex of L70 (here, $^{177}$Lu-L70) (prepared as described supra) was determined by in vitro receptor autoradiography using the procedure described in Reubi et al., "Bombesin Receptor Subtypes in Human Cancers: Detection with the Universal Radioligand $^{125}$I-[D-Tyr$^6$, beta-Ala, Phe$^{13}$, Nle$^{14}$]", Clin. Cancer Res. 8:1139-1146 (2002) and tissue samples that had been previously found to express only one subtype of GRP receptor, as well as non-neoplastic tissues including normal pancreas and colon, as well as chronic pancreatitis (shown below in Table 8a). Human ileal carcinoid tissue was used as a source for NMB-R, human prostate carcinoma for GRP-R and human bronchial carcinoid for BB3-R subtype receptors. For comparison, receptor autoradiography was also performed with other bombesin radioligands, such as $^{125}$I-Tyr$^4$-bombesin or a compound known as the Universal ligand, $^{125}$I-[DTyr$^6$, βAla$^{11}$, Phe$^{13}$, Nle$^{14}$]-BBN(6-14), which binds to all three subsets of GRP-R, on adjacent tissue sections. For further discussion, see Fleischmann et al., "Bombesin Receptors in Distinct Tissue Compartments of Human Pancreatic Diseases," Lab. Invest. 80:1807-1817 (2000); Markwalder et al., "Gastin-Releasing Peptide Receptors in the Human Prostate: Relation to Neoplastic Transformation," Cancer Res. 59:1152-1159 (1999); Gugger et al., "GRP Receptors in Non-Neoplastic and Neoplastic Human Breast," Am. J. Pathol. 155:2067-2076 (1999).

TABLE 8A

Detection of bombesin receptor subtypes in various human tissues using different radioligands.

| | | Receptor autoradiography using $^{177}$Lu-L70 | | | Receptor autoradiography using standard BN radioligands* | | |
|---|---|---|---|---|---|---|---|
| Tumor | n | GRP-R | NMB-R | BB3 | GRP-R | NMB-R | BB3 |
| Mammary Ca | 8 | 8/8 | 0/8 | 0/8 | 8/8 | 0/8 | 0/8 |
| Prostate Ca | 4 | 4/4 | 0/4 | 0/4 | 4/4 | 0/4 | 0/4 |
| Renal Ca | 6 | 5/6 | 0/6 | 0/6 | 4/6 | 0/6 | 0/6 |
| Ileal carcinoid | 8 | 0/8 | 8/8 | 0/8 | 0/8 | 8/8 | 0/8 |
| Bronchial carcinoid | 6 | 2/6 (weak) | 0/6 | 0/6 | 2/6 (weak) | 0/6 | 6/6 |
| Colon Ca | | | | | | | |
| tumor | 7 | 3/7 (weak) | 0/7 | 0/7 | 3/7 (weak) | 0/7 | 0/7 |
| smooth muscle | 7 | 7/7 | 0/7 | 0/7 | 7/7 | 0/7 | 0/7 |
| Pancreas Ca | 4 | 0/4 | 0/4 | 0/4 | 0/4 | 0/4 | 0/4 |

TABLE 8A-continued

Detection of bombesin receptor subtypes in various human tissues using different radioligands.

| Tumor | n | Receptor autoradiography using $^{177}$Lu-L70 | | | Receptor autoradiography using standard BN radioligands* | | |
|---|---|---|---|---|---|---|---|
| | | GRP-R | NMB-R | BB3 | GRP-R | NMB-R | BB3 |
| Chronic pancreatitis (acini) | 5 | 5/5 | 0/5 | 0/5 | 5/5 | 0/5 | 0/5 |
| Human pancreas (acini) | 7 | 1/7 (weak) | 0/7 | 0/7 | 0/7 | 0/7 | 0/7 |
| Mouse pancreas (acini) | 4 | 4/4 | 0/4 | 0/4 | 4/4 | 0/4 | 0/4 |

*$^{125}$I-[DTyr$^6$, βAla$^{11}$, Phe$^{13}$, Nle$^{14}$]-BBN(6-14) and $^{125}$I-Tyr$^4$-BBN.

As seen from Table 8a, all GRP-R-expressing tumors such as prostatic, mammary and renal cell carcinomas, identified as such with established radioligands, were also visualized in vitro with $^{177}$Lu-L70. Due to a better sensitivity, selected tumors with low levels of GRP-R could be identified with $^{177}$Lu-L70, but not with $^{125}$I-Tyr$^4$-BBN, as shown in Table 8a. All NMB-R-expressing tumors identified with established radioligands were also visualized with $^{177}$Lu-L70. Conversely, none of the BB3 tumors were detected with $^{177}$Lu-L70. One should not make any conclusion on the natural incidence of the receptor expression in the various types of tumors listed in Table 8a, as the tested cases were chosen as receptor-positive in the majority of cases, with only a few selected negative controls. The normal human pancreas is not labeled with $^{177}$Lu-L70, whereas the mouse pancreas is strongly labeled under identical conditions. Although the normal pancreas is a very rapidly degradable tissue and one can never completely exclude degradation of protein, including receptors, factors suggesting that the human pancreas data are truly negative include the positive control of the mouse pancreas under similar condition and the strongly labeled BB3 found in the islets of the respective human pancreas, which represent a positive control for the quality of the investigated human pancreas. Furthermore, the detection of GRP-R in pancreatic tissues that are pathologically altered (chronic pancreatitis) indicate that GRP-R, when present, can be identified under the chosen experimental conditions in this tissue. In fact, $^{177}$Lu-L70 identifies these GRP-R in chronic pancreatitis with greater sensitivity than $^{125}$I-Tyr$^4$-BBN. While none of the pancreatic cancers had measurable amounts of GRP-R, a few colon carcinomas showed a low density of heterogeneously distributed GRP receptors measured with $^{177}$Lu-L70 (Table 8a). It should further be noticed that the smooth muscles of the colon express GRP-R and were detected in vitro with $^{177}$Lu-L70 as well as with the established bombesin ligands.

TABLE 8B

Binding affinity of $^{175}$Lu-L70 to the 3 bombesin receptor subtypes expressed in human cancers. Data are expressed as IC$_{50}$ in nM (mean ± SEM. n = number of experiments in parentheses).

| Compound | D. NMB-R | E. GRP-R | BB3 |
|---|---|---|---|
| Universal ligand | 0.8 ± 0.1 (3) | 0.7 ± 0.1 (3) | 1.1 ± 0.1 (3) |
| $^{175}$Lu-L70 | 0.9 ± 0.1 (4) | 0.8 ± 0.1 (5) | >1,000 (3) |

As shown in Table 8b, the cold labeled $^{175}$Lu-L70 had a very high affinity for human GRP and NMB receptors expressed in human tissues while it had only low affinity for BB3 receptors. These experiments used $^{125}$I-[DTyr$^6$, βAla$^{11}$, Phe$^{13}$, Nle$^{14}$]-BBN(6-14) as radiotracer. Using the $^{177}$Lu-labeled L70 as radiotracer, the above mentioned data are hereby confirmed and extended. All GRP-R-expressing human cancers were very strongly labeled with $^{177}$Lu-L70. The same was true for all NMB-R-positive tumors. Conversely, tumors with BB3 were not visualized. The sensitivity of $^{177}$Lu-L70 seems better than that of $^{125}$I-Tyr$^4$-BBN or the $^{125}$I-labeled universal bombesin analog. Therefore, a few tumors expressing a low density of GRP-R can be readily identified with $^{177}$Lu-L70, while they are not positive with $^{125}$I-Tyr$^4$-BBN. The binding characteristics of $^{177}$Lu-L70 could also be confirmed in non-neoplastic tissues. While the mouse pancreas, as control, was shown to express a very high density of GRP-R, the normal human pancreatic acini were devoid of GRP-R. However, in conditions of chronic pancreatitis GRP-R could be identified in acini, as reported previously in Fleischmann et al., "Bombesin Receptors in Distinct Tissue Compartments of Human Pancreatic Diseases", Lab. Invest. 80:1807-1817 (2000) and tissue, again with better sensitivity by using $^{177}$Lu-L70 than by using $^{125}$I-Tyr$^4$-BBN. Conversely, the BB$_3$-expressing islets were not detected with $^{177}$Lu-L70, while they were strongly labeled with the universal ligand, as reported previously in Fleischmann et al., "Bombesin Receptors in Distinct Tissue Compartments of Human Pancreatic Diseases", Lab. Invest. 80:1807-1817 (2000). While a minority of colon carcinomas had GRP-R, usually in very low density and heterogeneously distributed, the normal colonic smooth muscles expressed a high density of GRP-R.

The results in Tables 8a and 8b indicate that Lu labeled L70 derivatives are expected to bind well to human prostate carcinoma, which primarily expresses GRP-R. They also indicate that Lu labeled L70 derivatives are not expected to bind well to normal human pancreas (which primarily expresses the BB3-R receptor), or to cancers which primarily express the BB3-R receptor subtype.

Example LV

Radiotherapy Studies

A. Efficacy Studies:
Radiotherapy studies were performed using the PC3 tumor-bearing nude mouse model. In Short Term Efficacy Studies, $^{177}$Lu labeled compounds of the invention L64, L70, L63 and the treatment control compound DO3A-monoamide-Aoc-QWAVGHLM-NH$_2$ were compared to an untreated control group. (n=12 for each treatment group for up to 30 days, and n=36 for the pooled untreated control group for up to 31 days). For all efficacy studies, mice were administered 100 µL of $^{177}$Lu-labeled compound of the invention at 30 mCi/kg, i.v, or s.c. under sterile conditions. The subjects were housed in a barrier environment for the duration of the study. Body weight and tumor size (by caliper measurement) were collected on each subject 3 times per week for the duration of the study. Criteria for early termination included: death; loss of total body weight (TBW) equal to or greater than 20%; tumor size equal to or greater than 2 cm$^3$. Results of the Short Term Efficacy Study are displayed in FIG. 15A. These results show that animals treated with L70, L64 or L63 have increased survival over the control animals given no treatment and over those animals given the same dose of the DO3A-monoamide-Aoc-QWAVGHLM-NH$_2$ control.

Long Term Efficacy Studies were performed with L64 and L70 using the same dose as before but using more animals per compound (n=46) and following them for up to 120 days. The results of the Long Term Efficacy Study are displayed in FIG. 15B. Relative to the same controls as before (n=36), both L64 and L70 treatment gave significantly increased survival (p<0.0001) with L70 being better than L64, although not statistically different from each other (p<0.067).

Example LVI

Alternative Preparation of L64 and L70 Using Segment Coupling

Compounds L64 and L70 can be prepared employing the collection of intermediates generally represented by A-D (FIG. 19), which themselves are prepared by standard methods known in the art of solid and solution phase peptide synthesis (Synthetic Peptides—A User's Guide 1992, Grant, G., Ed. WH. Freeman Co., NY, Chap 3 and Chap 4 pp 77-258; Chan, W. C. and White, P. D. Basic Procedures in Fmoc Solid Phase Peptide Synthesis—A Practical Approach 2002, Chan, W.C. and White, P.D. Eds Oxford University Press, New York, Chap. 3 pp 41-76; Barlos, K. and Gatos, G. Convergent Peptide Synthesis in Fmoc Solid Phase Peptide Synthesis—A Practical Approach 2002, Chan, W. C. and White, P. D. Eds Oxford University Press, New York, Chap. 9 pp 216-228) which are incorporated herein by reference.

These methods include Aloc, Boc, Fmoc or benzyloxycarbonyl-based peptide synthesis strategies or judiciously chosen combinations of those methods on solid phase or in solution. The intermediates to be employed for a given step are chosen based on the selection of appropriate protecting groups for each position in the molecule, which may be selected from the list of groups shown in FIG. 1. Those of ordinary skill in the art will also understand that intermediates, compatible with peptide synthesis methodology, comprised of alternative protecting groups can also be employed and that the listed options for protecting groups shown above serves as illustrative and not inclusive, and that such alternatives are well known in the art.

This is amply illustrated in FIG. 20 which outlines the approach. Substitution of the intermediate C2 in place of C1 shown in the synthesis of L64, provides L70 when the same synthetic strategies are applied.

Example LVII

FIGS. 49A and 49B

Synthesis of L69

Summary: Reaction of (3β,5β,7α,12α)-3-amino-7,12-dihydroxycholan-24-oic acid A with Fmoc-Cl gave intermediate B. Rink amide resin functionalised with the octapeptide Gln-Trp-Ala-Val-Gly-His-Leu-Met-NH$_2$ (BBN[7-14]) (SEQ ID NO: 1) (A), was sequentially reacted with B, Fmoc-8-amino-3,6-dioxaoctanoic acid and DOTA tri-t-butyl ester. After cleavage and deprotection with Reagent B the crude was purified by preparative HPLC to give L230. Overall yield: 4.2%.

A. (3β,5β,7α,12α)-3-(9H-Fluoren-9-ylmethoxy)amino-7, 12-dihydroxycholan-24-oic acid, B (FIG. 49A)

A solution of 9-fluorenylmethoxycarbonyl chloride (1.4 g; 5.4 mmol) in 1,4-dioxane (18 mL) was added dropwise to a suspension of (3β,5β,7α,12α)-3-amino-7,12-dihydroxycholan-24-oic acid A (2.0 g; 4.9 mmol) (3) in 10% aq. Na$_2$CO$_3$ (30 mL) and 1,4-dioxane (18 mL) stirred at 0° C. After 6 h stirring at room temperature H2O (100 mL) was added, the aqueous phase washed with Et$_2$O (2×90 mL) and then 2 M HCl (15 mL) was added (final pH: 1.5). The precipitated solid was filtered, washed with H$_2$O (3×100 mL), vacuum dried and then purified by flash chromatography to give B as a white solid (2.2 g; 3.5 mmol). Yield 71%.

B. N-[3β,5β,7α,12α)-3-[[[2-[2-[[[4,7,10-Tris(carboxymethyl)-1,4,7,10-tetraazacyclododec-1-yl]acetyl]amino] ethoxy]ethoxy]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide, L69 (FIG. 49B)

Resin A (0.5 g; 0.3 mmol) was shaken in a solid phase peptide synthesis vessel with 50% morpholine in DMA (7 mL) for 10 min, the solution filtered and fresh 50% morpholine in DMA (7 mL) was added. The suspension was stirred for another 20 min then the solution was filtered and the resin washed with DMA (5×7 mL). (3β, 5β,7α,12α)-3-(9H-Fluoren-9-ylmethoxy)amino-7,12-dihydroxycholan-24-oic acid B (0.75 g; 1.2 mmol), N-hydroxybenzotriazole (HOBt) (0.18 g; 1.2 mmol), N,N'-diisopropylcarbodiimide (DIC) (0.19 mL; 1.2 mmol) and DMA (7 mL) were added to the resin, the mixture shaken for 24 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). Fmoc-8-amino-3,6-dioxaoctanoic acid (0.79 g; 1.2 mmol), HOBt (0.18 g; 1.2 mmol), DIC (0.19 mL; 1.2 mmol) and DMA (7 mL) were added to the resin. The mixture was shaken for 3 h at room temperature, emptied and the resin washed with DMA (5×7 mL). The resin was then shaken with 50% morpholine in DMA (7 mL) for 10 min, the solution filtered, fresh 50% morpholine in DMA (7 mL) was added and the mixture shaken for another 20 min. The solution was filtered and the resin washed with DMA (5×7 mL) 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), N-ethyldiisopropylamine (0.40 mL; 2.4 mmol) and DMA (7 mL) were added to the resin. The mixture was shaken for 24 h at room temperature, filtered and the resin washed with DMA (5×7 mL), CH$_2$Cl$_2$ (5×7 mL) and vacuum dried. The resin was shaken in a flask with Reagent B (25 mL) (2) for 4.5 h. The resin was filtered and the solution was evaporated under reduced pressure to afford an oily crude that after treatment with Et$_2$O (20 mL) gave a precipitate. The precipitate was collected by centrifugation and washed with Et$_2$O (3×20 mL) to give a solid (248 mg) which was analysed by HPLC. An amount of crude (50 mg) was purified by preparative HPLC. The fractions containing the product were lyophilised to give L69 (6.5 mg; 3.5×10$^{-3}$ mmol) (FIG. 49B) as a white solid. Yield 5.8%.

Example LVIII

FIG. 50

Synthesis of L144

Summary: Rink amide resin functionalised with the octapeptide Gln-Trp-Ala-Val-Gly-His-Leu-Met-NH$_2$ (BBN [7-14]) (SEQ ID NO: 1) (A) was reacted with 4-[2-hydroxy-3-[4,7,10-tris[2-(1,1-dimethylethoxy)-2-oxoethyl]-1,4,7,10-tetrazacyclododec-1-yl]propoxy]benzoic acid. After cleavage and deprotection with Reagent B (2) the crude was purified by preparative HPLC to give L144. Overall yield: 12%.

A. N-[4-[2-Hydroxy-3-[4,7,10-tris(carboxymethyl)-1,4,7,10-tetraazacyclododec-1-yl]propoxy]benzoyl]-L-glutaminyl-L-tryptophyl-L-alanyl-L-valyl-glycyl-L-histidyl-L-leucyl-L-methioninamide, L144 (FIG. 50)

Resin A (0.4 g; 0.24 mmol) was shaken in a solid phase peptide synthesis vessel with 50% morpholine in DMA (7 mL) for 10 min, the solution filtered and fresh 50% morpholine in DMA (7 mL) was added. The suspension was stirred for another 20 min then the solution was filtered and the resin washed with DMA (5×7 mL). 4-[2-Hydroxy-3-[4,7,10-tris[2-(1,1-dimethylethoxy)-2-oxoethyl]-1,4,7,10-tetrazacyclododec-1-yl]propoxy]benzoic acid B (0.5 g; 0.7 mmol), HOBt (0.11 g; 0.7 mmol), DIC (0.11 mL; 0.7 mmol)), N-ethyldiisopropylamine (0.24 mL; 1.4 mmol) and DMA (7 mL) were added to the resin. The mixture was shaken for 24 h at room temperature, emptied and the resin washed with DMA (5×7 mL), CH$_2$Cl$_2$ (5×7 mL) and vacuum dried. The resin was shaken in a flask with Reagent B (25 mL) (2) for 4.5 h. The resin was filtered and the solution was evaporated under reduced pressure to afford an oily crude that after treatment with Et$_2$O (20 mL) gave a precipitate. The precipitate was collected by centrifugation and washed with Et$_2$O (3×20 mL) to give a solid (240 mg) which was analysed by HPLC. An amount of crude (60 mg) was purified by preparative HPLC. The fractions containing the product were lyophilised to give L144 (10.5 mg; 7.2×10$^{-3}$ mmol) as a white solid. Yield 12%.

Example LIX

Preparation of L300 and $^{177}$Lu-L300

From 0.2 g of Rink amide Novagel resin (0.63 mmol/g, 0.126 mmol), L300 (0.033 g, 17%) was obtained after preparative column chromatography. The retention time was 6.66 minutes. The molecular formula is C$_{72}$H$_{99}$N$_{19}$O$_{18}$. The calculated molecular weight is 1518.71; 1519.6 observed. The sequence is DO3A-Gly-Abz4-Gln-Trp-Ala-Val-Gly-His-Phe-Leu-NH$_2$, wherein Gln-Trp-Ala-Val-Gly-His-Phe-Leu-NH$_2$ (i.e., QWAVGHFL-NH$_2$) is SEQ ID NO: 22. The structure of L300 is shown in FIG. 51.

L300 (13.9 μg in 13.9 μL of 0.2M pH 4.8 sodium acetate buffer) was mixed with 150 μL of 0.2M pH 4.8 sodium acetate buffer and 4 μL of $^{177}$LuCl$_3$ (1.136 mCi, Missouri Research Reactor). After 10 min at 100° C., the radiochemical purity (RCP) was 95%. The product was purified on a Vydac C18 peptide column (4.6×250 mm, 5 um pore size) eluted at a flow rate of 1 mL/min using an aqueous/organic gradient of 0.1% TFA in water (A) and 0.085% TFA in acetonitrile (B). The following gradient was used: isocratic 22% B for 30 min, to 60% B in 5 min, hold at 60% B for 5 min. The compound, which eluted at a retention time of 18.8 min., was collected into 1 mL of an 0.8% human serum albumin solution that was prepared by adding HSA to a 9:1 mixture of normal saline and Ascorbic Acid, Injection. Acetonitrile was removed using a Speed Vacuum (Savant). After purification, the compound had an RCP of 100%.

Example LX

Characterization of Linker Specificity in Relation to GRP Receptor Subtypes

Two cell lines, C6, an NMB-R expressing rodent glioblastoma cell line and PC3, a GRP-R expressing human prostate cancer cell line, were used in this assay. The affinity of various unlabeled compounds for each receptor subtype (NMB-R and GRP-R) was determined indirectly by measuring its ability to compete with the binding of $^{125}$I-NMB or $^{125}$I-BBN to its corresponding receptors in C6 and PC3 cells.

A. Materials and Methods:

1. Cell Culture:

C6 cells were obtained from ATCC(CCL-107) and cultured in F12K media (ATCC) supplemented with 2 mM L-glutamine, 1.5 g/L Sodium bicarbonate, 15% horse serum and 2.5% FBS. Cells for the assays were plated at a concentration of 9.6×10$^4$/well in 48 well poly-lysine coated plates (Beckton Dickinson Biocoat). PC3 were obtained from ATCC(CRL-1435) and cultured in RPMI 1640 (ATCC) supplemented with 2 mM L-glutamine, 1.5 g/L Sodium bicarbonate, 10 mM HEPES and 10% FBS. Both cultures were maintained in a humidified atmosphere containing 5% CO$_2$/95% air at 37° C. PC3 cells for the assays were plated at a concentration of 2.0×10$^4$ cells/well in 96-well white/clear bottom plates (Falcon Optilux-I). Plates were used for the assays on day 2 of the post-plating.

2. Binding Buffer, and Radio-Ligands:

RPMI 1640 (ATCC) containing 25 mM HEPES, 0.2% BSA fraction V, 1.0 mMAEBSF (CAS # 3087-99-7) and 0.1% Bacitracin (CAS # 1405-87-4), pH 7.4.

Custom made $^{125}$I-[Tyr$^0$]NIMB, >2.0 Ci/μmole (Amersham Life Science) [$^{125}$I-NMB] and commercially available $^{125}$I-[Tyr$^4$]BBN, >2.0 Ci/μmole (Perkin Elmer Life Science) [$^{125}$I-BBN] were used as radioligands.

B. In Vitro Assay:

Using a 48-well plate assay system (for C6 study) competition experiments were performed using $^{125}$I-NMB. All of the PC3 studies were performed as described in Example XLIII using $^{125}$I-BBN. Selection of compounds for the assay was based on linker subtype. Results are shown in Table 9.

TABLE 9

Number of selected compounds for the assay and their linkers

| LINKER TYPE | NUMBER OF COMPOUNDS |
|---|---|
| Neutral, Basic or combination of neutral, basic & acidic | 8 |
| Linear aliphatic (ω-aminoalkanoic & ω-aminoalkoxynoic acid | 4 |
| Bile acids (cholic acids) | 3 |
| Substituted alanine (cycloalkyl, aromatic and heteroaromatic) | 5 |
| Aromatic (aminobenzoic acid and aminoalkyl benzoic acid, biphenyl) | 12 |
| Cyclic non-aromatic | 5 |
| Heterocyclic (aromatic and non-aromatic) | 5 |

TABLE 9-continued

Number of selected compounds for the assay and their linkers

| LINKER TYPE | NUMBER OF COMPOUNDS |
|---|---|
| Miscellaneous (DOTA-NMB, DOTA-G-Abz4-NMB, DOTA-Abz4-G-NMB, BBN$_{7-14}$, BBN$_{8-14}$, DOTA-BBN$_{7-14}$) | 6 |

The binding parameters obtained from the studies were analyzed using a one-site competition non-linear regression analysis with GraphPad Prism. The relative affinity of various compounds for NMB-R in C6 cells were compared with those obtained using commercially available [Tyr$^4$]-BBN and [Tyr$^0$]-NMB. To distinguish the GRP-R preferring compounds from NMB-R plus GRP-R preferring compounds, IC$_{50}$ values obtained for each compound was compared with those obtained from [Tyr$^0$]-BBN with $^{125}$I-NMB on C6 cells. The cut off point between the two classes of compounds was taken as 10× the IC$_{50}$ of [Tyr$^4$]-BBN. Among the compounds tested, 8 compounds preferentially bind to GRP-R (as shown in Table 10) while 32 compounds bind to both GRP-R and NMB-R with similar affinity, and two show preference for NMB-R.

TABLE 10

The IC$_{50}$ values obtained from competition experiments using 125I-NMB and 125I-BBN

| | | IC$_{50}$ (nM) | | | |
|---|---|---|---|---|---|
| L # | COMPOUND | $^{125}$I-BBN/ PC3 | $^{125}$I-NMB/ C6 | GRP-R | GRP-R & NMB-R |
| na | N,N-dimethylglycine-Ser-Cys(Acm)-Gly-SS-QWAVGHLM-NH$_2$* | 10 | 10.4 | — | yes |
| na | N,N-dimethylglycine-Ser-Cys(Acm)-Gly-G-QWAVGHLM-NH$_2$* | 25 | 7.9 | — | yes |
| na | N,N-dimethylglycine-Ser-Cys(Acm)-Gly-GG-QWAVGHLM-NH$_2$* | 48 | 20.2 | — | yes |
| na | N,N-dimethylglycine-Ser-Cys(Acm)-Gly-KK-QWAVGHLM-NH$_2$* | 13 | 6.4 | — | yes |
| na | N,N-dimethylglycine-Ser-Cys(Acm)-Gly-SK-QWAVGHLM-NH$_2$* | 2 | 2.2 | — | yes |
| na | N,N-dimethylglycine-Ser-Cys(Acm)-Gly-SR-QWAVGHLM-NH$_2$* | 1.9 | 2.0 | — | yes |
| na | N,N-dimethylglycine-Ser-Cys(Acm)-Gly-KS-QWAVGHLM-NH$_2$* | 7.5 | 24.1 | yes | — |
| na | N,N-dimethylglycine-Ser-Cys(Acm)-Gly-KE-QWAVGHLM-NH$_2$* | 32 | 60.0 | yes | — |
| na | DO3A-monoamide-Aoc-QWAVGHLM-NH$_2$* | 3.4 | 3.1 | — | yes |
| na | DO3A-monoamide-Apa3-QWAVGHLM-NH$_2$* | 36 | 18.9 | — | yes |
| na | DO3A-monoamide-Abu4-QWAVGHLM-NH$_2$* | 19.8 | 5.2 | — | yes |
| L3 | N,N-dimethylglycine-Ser-Cys(Acm)-Gly-DJ-QWAVGHLM-NH$_2$* | 70 | 33 | — | yes |
| L64 | DO3A-monoamide-G-Adca3-QWAVGHLM-NH$_2$* | 8.5 | 3.3 | — | yes |
| L63 | DO3A-monoamide-G-Ah12ca-QWAVGHLM-NH$_2$* | 23 | 3.8 | — | yes |
| L67 | DO3A-monoamide-G-Akca-QWAVGHLM-NH$_2$* | 5.5 | 2.3 | — | yes |
| na | DO3A-monoamide-Cha-Cha-QWAVGHLM-NH$_2$* | 22 | 77 | yes | — |

TABLE 10-continued

The IC$_{50}$ values obtained from competition experiments using 125I-NMB and 125I-BBN

| L # | COMPOUND | $^{125}$I-BBN/ PC3 IC$_{50}$ (nM) | $^{125}$I-NMB/ C6 IC$_{50}$ (nM) | GRP-R | GRP-R & NMB-R |
|---|---|---|---|---|---|
| na | DO3A-monoamide-Nal1-Bip-QWAVGHLM-NH$_2$* | 30 | 210.9 | yes | — |
| na | DO3A-monoamide-Cha-Nal1-QWAVGHLM-NH$_2$* | 8 | 66.5 | yes | — |
| na | DO3A-monoamide-Nal1-Bpa4-QWAVGHLM-NH$_2$* | 17 | 89.9 | yes | — |
| L301 | DO3A-monoamide-Amb4-Nal1-QWAVGHLM-NH$_2$* | 10 | 6.8 | | yes |
| L147 | DO3A-monoamide-G-Mo3abz4-QWAVGHLM-NH$_2$* | 4 | 32 | yes | — |
| L241 | DO3A-monoamide-G-Cl3abz4QWAVGHLM-NH$_2$* | 4 | 0.8 | — | yes |
| L242 | DO3A-monoamide-G-M3abz4-QWAVGHLM-NH$_2$* | 5 | 2.2 | — | yes |
| L243 | DO3A-monoamide-G-Ho3abz4-QWAVGHLM-NH$_2$* | 14 | 9.9 | — | yes |
| L202 | DO3A-monoamide-G-Hybz4-QWAVGHLM-NH$_2$* | 13 | 2.7 | — | yes |
| L204 | DO3A-monoamide-Abz4-G-QWAVGHLM-NH$_2$* | 50 | 1.2 | — | yes |
| L233 | DO3A-monoamide-G-Abz3-QWAVGHLM-NH$_2$* | 4.8 | 1.6 | — | yes |
| L235 | DO3A-monoamide-G-Nmabz4-QWAVGHLM-NH$_2$* | 7 | 1.5 | — | yes |
| L147 | DO3A-monoamide-Mo3amb4-QWAVGHLM-NH$_2$* | 3.5 | 1.2 | — | yes |
| L71 | DO3A-monoamide-Amb4-QWAVGHLM-NH$_2$* | 7.2 | 0.2 | — | yes |
| L73 | DO3A-monoamide-Aeb4-QWAVGHLM-NH$_2$* | 5 | 1.8 | — | yes |
| L208 | DO3A-monoamide-Dae-Tpa-QWAVGHLM-NH$_2$* | 8 | 0.9 | — | yes |
| L206 | DO3A-monoamide-G-A4m2biphc4-QWAVGHLM-NH$_2$* | 5 | 1.3 | — | yes |
| L207 | DO3A-monoamide-G-A3biphc3-QWAVGHLM-NH$_2$* | 3 | 15.1 | — | yes |
| L72 | DO3A-monoamide-Amc4-QWAVGHLM-NH$_2$* | 8.2 | 2.6 | — | yes |
| L107 | DO3A-monoamide-Amc4-Amc4-QWAVGHLM-NH$_2$* | 5 | 0.3 | — | yes |
| L89 | DO3A-monoamide-Aepa4-QWAVGHLM-NH$_2$* | 23 | 114 | yes | — |
| L28 | N,N-dimethylglycine-Ser-Cys(Acm)-Gly-Aepa4-S-QWAVGHLM-NH$_2$* | 25 | 13 | — | yes |
| L74 | DO3A-monoamide-G-Inp-QWAVGHLM-NH$_2$* | 6.5 | 3.4 | — | Yes |
| L36 | N,N-dimethylglycine-Ser-Cys(Acm)-Gly-Pia1-J-QWAVGHLM-NH$_2$* | 7 | 12.1 | — | Yes |
| L82 | DO3A-monoamide-Ckbp-QWAVGHLM-NH$_2$* | 8 | 1.7 | — | Yes |
| na | DO3A-monoamide-Aoc-QWAVGHL-Nle-NH$_2$* | 11 | 14 | — | Yes |
| L70 | DO3A-monoamide-G-Abz4-QWAVGHLM-NH$_2$* | 4.5 | 1.5 | — | Yes |
| na | DO3A-monoamide-QWAVGHLM-NH$_2$* | 366 | >250 | No selective preference | |
| na | QWAVGHLM-NH$_2$* | 369 | 754 | No selective preference | |
| na | WAVGHLM-NH$_2$ (SEQ ID NO: 25) | >800 | >800 | No selective preference | |
| L204 | DO3A-monoamide-Abz4-G-QWAVGHLM-NH$_2$* | >50 | 1.2 | preference to NMB-R | |

TABLE 10-continued

The IC$_{50}$ values obtained from competition experiments using 125I-NMB and 125I-BBN

| | | IC$_{50}$ (nM) | | | |
|---|---|---|---|---|---|
| L # | COMPOUND | $^{125}$I-BBN/ PC3 | $^{125}$I-NMB/ C6 | GRP-R | GRP-R & NMB-R |
| na | GNLWATGHFM-NH$_2$ (SEQ ID NO: 24) | >500 | 0.7 | preference to NMB-R | |
| L227 | DO3A-monoamide-G-Abz4-LWATGHFM-NH$_2$ wherein LWATGHFM-NH$_2$ is SEQ ID NO: 16 | 28 | 0.8 | — | Yes |

*QWAVGHLM-NH$_2$ is the sequence BBN(7-14) which is SEQ ID NO: 1

In the above Table "na" indicates "not applicable" (e.g. the compound does not contain a linker of the invention and thus was not assigned an L#).

Based on the above, several results were observed. The receptor binding region alone (BBN$_{7-14}$ or BBN$_{8-14}$) did not show any preference to GRP-R or NMB-R. The addition of a chelator alone to the receptor binding region did not contribute to the affinity of the peptide to GRP-R or NMB-R (DO3A-monoamide-QWAVGHLM-NH$_2$, wherein QWAVGHLM-NH$_2$ is the BBN(7-14) sequence (SEQ ID NO: 1). Coupling the chelator to the peptide through a linker did contribute to the affinity of the peptide towards the receptor. However, depending on the type of linker this affinity varied from being dual (preference for both NMB-R and GRP-R) to GRP-R (preferring GRP-R). In the above paragraph, QWAVGHLM-NH$_2$ is the BBN(7-14) sequence (SEQ ID NO: 1).

The ω-Aminoalkanoic acids tested (8-Aminooctanoic acid in $^{175}$Lu-DO3A-monoamide-Aoc-QWAVGHLM-NH$_2$ and DO3A-monoamide-Aoc-QWAVGHL-Nle-NH$_2$, 3-aminopropionic acid in DO3A-monoamide-Apa3-QWAVGHLM-NH$_2$ and 4-aminobutanoic acid in DO3A-monoamide-Abu4-QWAVGHLM-NH$_2$) as linkers, conferred the peptide with dual affinity for both GRP-R and NMB-R. Replacement of 'Met' in $^{175}$Lu-DOTA-Aoc-QWAVGHLM-NH$_2$ by 'Nle' did not change this dual affinity of the peptide. In the above paragraph, QWAVGHLM-NH$_2$ is the BBN(7-14) sequence (SEQ ID NO: 1).

Cholic acid containing linkers (3-aminocholic acid in L64, 3-amino-12-hydroxycholanic in L63 and 3-amino-12-ketocholanic in L67 conferred the peptides with dual affinity for both GRP-R and NMB-R. Cycloalkyl and aromatic substituted alanine containing linkers (3-cyclohexylalanine in DO3A-monoamide-Cha-Cha-QWAVGHLM-NH$_2$, 1-Naphthylalanine in DO3A-monoamide-Cha-NalI-QWAVGHLM-NH$_2$, 4-Benzoylphenylalanine in DO3A-monoamide-NalI-Bpa4-QWAVGHLM-NH$_2$ and Biphenylalanine in DO3A-monoamide-NalI-Bip-QWAVGHLM-NH$_2$) imparted the peptides with selective affinity towards GRP-R. A linker containing only 4-(2-Aminoethylpiperazine)-1 also contributed to the peptides with GRP-R selectivity (L89). In the above paragraph, QWAVGHLM-NH$_2$ is the BBN(7-14) sequence (SEQ ID NO: 1).

Introduction of G-4-amino benzoic acid linker to NMB sequence conferred the compound with an affinity to GRP-R in addition to its inherent NMB-R affinity (L227 vs GNL-WATGHFM-NH$_2$ (SEQ ID NO: 24). Shifting the position of Gly around the linker altered the affinity of L70 from its dual affinity to a selective affinity to NMB-R (L204). 3-methoxy substitution in 4-aminobenzoic acid in L70 (as in L240) changed the dual affinity to a selective affinity to GRP-R.

It is apparent from the preceding data that the linker has a significant effect on the receptor subtype specificity. Three groups of compounds can be identified:

Those that are Active at the GRP-R

These compounds provide information specific to this receptor in vitro and in vivo, which can be used for diagnostic purposes. When these compounds are radiolabeled with a therapeutic radionuclide, therapy can be performed on tissues containing only this receptor, sparing those that contain the NMB-R Those that are Active at the NMB-R These compounds provide information specific to this receptor in vitro and in vivo, which can be used for diagnostic purposes. When radiolabeled with a therapeutic radionuclide, therapy can be performed on tissues containing only this receptor, sparing those that contain the GRP-R Those that are Active at Both the GRP-R and the NMB-R These compounds provide information on the combined presence of these two receptor subtypes in vitro and in vivo, that can be used for diagnostic purposes. Targeting both receptors may increase the sensitivity of the examination at the expense of specificity. When these compounds are radiolabeled with a therapeutic radionuclide, therapy can be performed on tissues containing both receptors, which may increase the dose delivered to the desired tissues.

Example LXI

Competition Studies of Modified Bombesin (BBN) Analogs with $^{125}$I-BBN for GRP-R in Human Prostate Cancer (PC3) Cells To determine the effect of replacing certain amino acids in the BBN$^{7-14}$ analogs, peptides modified in the targeting portion were made and assayed for competitive binding to GRP-R in human prostate cancer (PC3) cells. All these peptides have a common linker conjugated to a metal chelating moiety (DOTA-Gly-Abz4-). The binding data (IC$_{50}$ nM) are given below in Table 13.

A. Materials and Methods:

1. Cell Culture:

PC3 cell lines were obtained from ATCC(CRL-1435) and cultured in RPMI 1640 (ATCC) supplemented with 2 mM L-glutamine, 1.5 g/L Sodium bicarbonate, 10 mM HEPES and 10% FBS. Cultures were maintained in a humidified atmosphere containing 5% CO$_2$/95% air at 37° C. PC3 cells for the assays were plated at a concentration of 2.0×10$^4$ cells/well in a 96-well white/clear bottom plates (Falcon Optilux-I). Plates were used for the assays on day 2 of the post-plating.

2. Binding Buffer:
RPMI 1640 (ATCC) containing 25 mM HEPES, 0.2% BSA fraction V, 1.0 mM AEBSF (CAS # 3087-99-7) and 0.1% Bacitracin (CAS # 1405-87-4), pH 7.4.
3. $^{125}$I-Tyr$^4$-Bombesin [$^{125}$I-BBN]
$^{125}$I-BBN (Cat # NEX258) was obtained from PerkinElmer Life Sciences.

Radioactivity was detected using either a LKB CompuGamma counter or a microplate scintillation counter. The bound radioactivity of $^{125}$I-BBN was plotted against the inhibition concentrations of the competitors, and the concentration at which $^{125}$I-BBN binding was inhibited by 50% ($IC_{50}$) was obtained from the binding curve.

TABLE 13

Competition studies with $^{125}$I-BBN for GRP-R in PC3 cells

|  | L # | PEPTIDES | $IC_{50}$ [nM] |
|---|---|---|---|
| Ref | Na | N,N-dimethylglycyl-Ser-Cys(Acm)-Gly-Ava5-QWAVGHLM-NH$_2$* | 2.5 |
| 1 | L70 | DO3A-monoamide-G-Abz4-QWAVGHLM-NH$_2$* | 4.5 |
| 2 | L214 | DO3A-monoamide-G-Abz4-fQWAVGHLM-NH$_2$* | 18 |
| 3 | L215 | DO3A-monoamide-G-Abz4-QRLGNQWAVGHLM-NH$_2$ (wherein QRLGNQWAVGHLM-NH$_2$ is SEQ ID NO: 3) | 6 |
| 4 | L216 | DO3A-monoamide-G-Abz4-QRYGNQWAVGHLM-NH$_2$ (wherein QRYGNQWAVGHLM-NH$_2$ is SEQ ID NO: 4) | 4.5 |
| 5 | L217 | DO3A-monoamide-G-Abz4-QKYGNQWAVGHLM-NH$_2$ (wherein QKYGNQWAVGHLM-NH$_2$ is SEQ ID NO: 5) | 10 |
| 6 | L218 | >EQ-[K(DO3A-monoamide-G-Abz4)-LGNQWAVGHLM-NH$_2$ (wherein LGNQWAVGHLM-NH$_2$ is SEQ ID NO: 18) | 53 |
| 7 | L219 | DO3A-monoamide-G-Abz4-fQWAVGHLM-NH-C$_5$H$_{12}$ (wherein QWAVGHLM-NH-C$_5$H$_{12}$ is SEQ ID NO: 21) | 75 |
| 8 | L220 | DO3A-monoamide-G-Abz4-QWAVaHLM-NH$_2$ (wherein QWAVaHLM-NH$_2$ is SEQ ID NO: 14) | 13 |
| 9 | L221 | DO3A-monoamide-G-Abz4-fQWAVGHLL-NH$_2$ (wherein QWAVGHLL-NH$_2$ is SEQ ID NO: 8) | 340 |
| 10 | L222 | DO3A-monoamide-G-Abz4-yQWAV-Ala2-HF-Nle-NH$_2$ (wherein QWAV-Ala2-HF-Nle-NH$_2$ is SEQ ID NO: 23) | 46 |
| 11 | L223 | DO3A-monoamide-G-Abz4-fQWAV-Ala2-HF-Nle-NH$_2$ (wherein QWAV-Ala2-HF-Nle-NH$_2$ is SEQ ID NO: 23) | 52 |
| 12 | L224 | DO3A-monoamide-G-Abz4-QWAGHFL-NH$_2$ (wherein QWAGHFL-NH$_2$ is SEQ ID NO: 10) | >500 |
| 13 | L225 | DO3A-monoamide-G-Abz4-LWAVGSFM-NH$_2$ (wherein LWAVGSFM-NH$_2$ is SEQ ID NO: 11) | 240 |
| 14 | L226 | DO3A-monoamide-G-Abz4-HWAVGHLM-NH$_2$ (wherein HWAVGHLM-NH$_2$ is SEQ ID NO: 12) | 5.5 |
| 15 | L227 | DO3A-monoamide-G-Abz4-LWATGHFM-NH$_2$ (wherein LWATGHFM-NH$_2$ is SEQ ID NO: 16) | 39 |
| 16 | L228 | DO3A-monoamide-G-Abz4-QWAVGHFM-NH$_2$ (wherein QWAVGHFM-NH$_2$ is SEQ ID NO: 13) | 5.5 |
| 17 | na | GNLWATGHFM-NH$_2$ (SEQ ID NO: 24) | >500 |
| 18 | na | yGNLWATGHFM-NH$_2$ (wherein GNLWATGHFM-NH$_2$ is SEQ ID NO: 24) | 450 |
| 19 | L300 | DO3A-monoamide-G-Abz4-QWAVGHFL-NH$_2$ (wherein QWAVGHFL-NH$_2$ is SEQ ID NO: 22) | 2.5 |

*QWAVGHLM-NH$_2$ is the BBN(7-14) sequence (SEQ ID NO: 1)

C. In Vitro Assay:
Competition assay with $^{125}$I-BBN for GRP-R in PC3 cells:
All compounds tested were dissolved in binding buffer and appropriate dilutions were also done in binding buffer. PC3 cells for assay were seeded at a concentration of 2.0×10$^4$/well either in 96-well black/clear collagen I cellware plates (Beckton Dickinson Biocoat). Plates were used for binding studies on day 2 post-plating. The plates were checked for confluency (>90% confluent) prior to assay. For competition assay, N,N-dimethylglycyl-Ser-Cys(Acm)-Gly-Ava5-QWAVGHLM-NH$_2$, wherein QWAVGHLM-NH$_2$ is the BBN(7-14) sequence (SEQ ID NO: 1) (control) or other competitors at concentrations ranging from 1.25×10$^{-9}$ M to 500×10$^{-9}$ M, was co-incubated with $^{125}$I-BBN (25,000 cpm/well). The studies were conducted with an assay volume of 75 µL per well. Triplicate wells were used for each data point. After the addition of the appropriate solutions, plates were incubated for 1 hour at 4° C. Incubation was ended by the addition of 200 µL of ice-cold incubation buffer. Plates were washed 5 times and blotted dry.

Results/Conclusions: Analysis of the binding results of various peptides modified in the targeting portion indicated the following:

Neuromedin analogs (GNLWATGHFM-NH$_2$, yGNLWATGHFM-NH$_2$ wherein GNLWATGHFM-NH$_2$ is SEQ ID NO: 24) are unable to compete for the GRP-R except when conjugated to DO3A-monoamide-G-Abz4 (L227). They are, however, effective NMB competitors. This is similar to the requirement for derivatisation of the amino end of the bombesin sequence as reflected in QWAVGHLM-NH$_2$, DO3A-monoamide-QWAVGHLM-NH$_2$ (wherein QWAVGHLM-NH$_2$ is the BBN(7-14) sequence SEQ ID NO: 1) & L70. Replacement of the histidine (L225) reduces competition at the GRP-R.

Reversal of the two linker components in L70 to give L204 changes the subtype specificity to favor the NMB subtype. L$^{13}$F substitution in the bombesin sequence maintains GRP-R activity. (L228).

TABLE 14

| L Number | Sequence | IC$_{50}$ C6/NMB-R | IC$_{50}$ PC3/GRP-R |
|---|---|---|---|
| na | GNLWATGHFM-NH$_2$ (SEQ ID NO: 24) | 0.69 | >500 |
| na | yGNLWATGHFM-NH$_2$ (wherein GNLWATGHFM-NH$_2$ is SEQ ID NO: 24) | 0.16 | 884.6 |
| L227 | DO3A-monoamide-G-Abz4-LWATGHFM-NH$_2$ (wherein LWATGHFM-NH$_2$ is SEQ ID NO: 16) | 0.07 | 28.0 |
| L225 | DO3A-monoamide-G-Abz4-LWAVGSFM-NH$_2$ (wherein LWAVGSFM-NH$_2$ is SEQ ID NO: 11) | — | 240 |
| na | WAVGHLM-NH$_2$ (SEQ ID NO: 25) | >800 | >800 |
| na | QWAVGHLM-NH$_2$* | 369 | 754 |
| na | DO3A-monoamide-QWAVGHLM-NH$_2$* | 161 | 366 |
| L70 | DO3A-monoamide-G-Abz4-QWAVGHLM-NH$_2$* | 4.5 | 1.5 |
| L204 | DO3A-monoamide-Abz4-GQWAVGHLM-NH$_2$ (wherein GQWAVGHLM-NH$_2$ is SEQ ID NO: 19) | 1.19 | >50 |
| L228 | DO3A-monoamide-G-Abz4-QWAVGHFM-NH$_2$ wherein QWAVGHFM-NH$_2$ is SEQ ID NO: 13) | — | 5.5 |

*QWAVGHLM-NH$_2$ is the BBN(7-14) sequence (SEQ ID NO: 1)

As seen here, $F^{13}M^{14}$ to $F^{13}L^{14}$ substitution in L228 produces a compound (L300) with high activity at the GRP-R. The removal of the methionine has advantages as it is prone to oxidation. This benefit does not occur if the $L^{13}F$ substitution is not also performed (L221). Removal of $V^{10}$ resulted in complete loss of binding as seen in L224.

TABLE 15

| Number | Sequence | IC50 C6/NMB-R | IC50 PC3/GRP-R |
|---|---|---|---|
| L300 | DO3A-monoamide-G-Abz4-QWAVGHFL-NH$_2$ (wherein QWAVGHFL-NH$_2$ is SEQ ID NO: 22) | — | 2.5 |
| L221 | DO3A-monoamide-G-Abz4-fQWAVGHLL-NH$_2$ (wherein QWAVGHLL-NH$_2$ is SEQ ID NO: 8) | — | 340 |
| L224 | DO3A-monoamide-G-Abz4-QWAGHFL-NH$_2$ (wherein QWAGHFL-NH$_2$ is SEQ ID NO: 10) | — | >500 |

TABLE 16

| Number | Sequence | IC50 C6/NMB-R | IC50 PC3/GRP-R |
|---|---|---|---|
| na | pEQRYGNQWAVGHLM-NH$_2$ (SEQ ID NO: 28) | 3.36 | 2.2 |
| L214 | DO3A-monoamide-G-Abz4-fQWAVGHLM-NH$_2$* | — | 18 |
| L215 | DO3A-monoamide-G-Abz4-QRLGNQWAVGHLM-NH$_2$ (wherein QRLGNQWAVGHLM-NH$_2$ is SEQ ID NO: 3) | — | 6 |
| L216 | DO3A-monoamide-G-Abz4-QRYGNQWAVGHLM-NH$_2$ (wherein QRYGNQWAVGHLM-NH$_2$ is SEQ ID NO: 4) | — | 4.5 |
| L217 | DO3A-monoamide-G-Abz4-QKYGNQWAVGHLM-NH$_2$ (wherein QKYGNQWAVGHLM-NH$_2$ is SEQ ID NO: 5) | — | 10 |
| L226 | DO3A-monoamide-G-Abz4-HWAVGHLM-NH$_2$ (wherein HWAVGHLM-NH$_2$ is SEQ ID NO: 12) | — | 5.5 |

*QWAVGHLM-NH$_2$ is the BBN(7-14) sequence (SEQ ID NO: 1)
As seen in Table 16, various substitutions are allowed in the BBN$^{2-6}$ region (L214-L217, L226)

TABLE 17

| Name | Number | Sequence | IC50 C6/NMB-R | IC50 PC3/GRP-R |
|---|---|---|---|---|
| Universal agonist | L222 | DO3A-monoamide-G-Abz4-yQWAV-Ala2-HF-Nle-NH$_2$ (wherein QWAV-Ala2-HF-Nle-NH$_2$ is SEQ ID NO: 23) | — | 46 |
| Universal agonist | L224 | DO3A-monoamide-G-Abz4-fQWAV-Ala2-HF-Nle-NH$_2$ (wherein QWAV-Ala2-HF-Nle-NH$_2$ is SEQ ID NO: 23) | — | 52 |

As expected, results from Table 17 show that the universal agonists (L222 & L223) compete reasonably well at ~50 nM level.

Example LXI

NMR Structural Comparison of $^{175}$Lu-L70 and $^{175}$Lu-DO3A-monoamide-Aoc-QWAVGHLM-NH$_2$ The purpose of this NMR study was to provide complete structural characterization of Lu-L70 and compare it to the structure of $^{175}$Lu-DOTA-Aoc-QWAVGHLM. L70 and $^{175}$Lu-DOTA-Aoc-QWAVGHLM are both bombesin analogues (see FIGS. 60 and 61), differing only in the linker between the chelating group and the targeting peptide. In L70 there is a glycyl-4-aminobenzoyl group, whereas in $^{175}$Lu-DOTA-Aoc-QWAVGHLM there is an 8-aminooctanoyl group. However, the biological data of these two compounds is strikingly different. Detailed NMR studies were performed to explain this difference.

A. Experimental

1. Materials 5 mg of $^{175}$Lu-DO3A-monoamide-Aoc-QWAVGHLM-NH$_2$ was dissolved in 225 uL of DMSO-d$_6$ (Aldrich 100% atom % D).

5 mg of $^{175}$Lu-L70 was dissolved in 225 μL of DMSO-d$_6$ (Aldrich 100% atom % D).

2. Acquisition of NMR Data

All NMR experiments were performed on a Varian Inova-500 Fourier Transform NMR spectrometer equipped with a 3 mm broad-band inverse (z-axis gradient) probe. The chemical shifts were referenced to the residual CH peaks of DMSO-d$_6$ at 2.50 ppm for the proton and 40.19 ppm for $^{13}$C. The sample temperatures were controlled by a Varian digital temperature controller. The data were processed using NMRPipe, VNMR, PROSA, and VNMRJ software on the Sun Blade 2000 Unix computer and analyzed using NMRView and SPARKY software on the Linux computer. The modeling of the peptides was performed employing CYANA software on the Linux computer and further analyzed using MOLMOL software on a Compaq Deskpro Workstation.

B. Results and Discussion

The proton chemical shifts of $^{175}$Lu-L70 were assigned as follows. A quick survey of the methyl region (0.5 to 2.5 ppm) in the 1D spectrum allowed the identification of a sharp singlet at 2.02 ppm as the methyl peak of methionine. In the same region of the TOCSY spectrum, the chemical shift at 1.16 ppm which correlates to only one peak at 4.32 ppm indicates that they belong to alanine. The methyl peaks at 0.84 and 0.85 ppm which correlate to two peaks at 1.98 and 4.12 ppm must belong to valine. The remaining methyl peaks at 0.84 and 0.88 ppm which correlate to peaks at 1.60, 1.48, and 4.23 ppm belong to leucine. These chemical shifts and the chemical shifts of other amino acids are also present in the "fingerprint" region (see Wuthrich, K. "NMR of Proteins and Nucleic Acids", John Wiley & Sons, 1986)—the backbone NH-αH region of the TOCSY spectrum (see FIG. 52). All the chemical shifts belonging to a spin system of an amino acid will align themselves vertically. After a careful examination of the spectrum, all chemical shifts were assigned. The chemical shifts were further verified by reviewing other spectra such as COSY (see FIG. 53) and NOESY (see FIG. 54). After the proton chemical shifts were assigned, their carbon chemical shifts were identified through the gHSQC spectrum (see FIG. 55) and further verified by reviewing the gHMBC (see FIG. 56) and gHSQCTOCSY (see FIG. 57) spectra. The chemical shifts of Lu-L70 are listed in Table 19 (the atom numbers are referenced to FIG. 60).

Interestingly, in the TOCSY spectrum of $^{175}$Lu-L70, the chemical shift of the NH proton at 14.15 ppm shows strong correlations to two other peaks of the histidine ring, and also to a water molecule. This water molecule is not freely exchanging and is clearly seen in the NMR timeframe. To see which proton of the histidine interacts more strongly with the water molecule, a selective homo-decoupling experiment was performed on the $^{175}$Lu-L70 at 15° C. When the water peak was selectively saturated with a low power, the intensities of the NH peaks of histidine at 14.16 and 14.23 ppm were dramatically reduced while the intensities of the two remaining peaks of histidine at 7.32 and 8.90 ppm were partially reduced (see FIG. 58). The observation of the water protons on the NMR time scale suggests a rigid confirmation.

A proposed chemical structure of $^{175}$Lu-L70 with a water molecule can be seen in FIG. 62. A water molecule occupies a ninth coordination site by capping the square plane described by the coordinated oxygens. This has other precedents. Coordination of water at the ninth site of Lu in Na[Lu (DOTA)H$_2$O)].4H$_2$O was observed in an x-ray structure, as shown by Aime et al, Inorg. Chim. Acta 1996, 246, 423-429, which is incorporated by reference.

In contrast, in the TOCSY spectrum of $^{175}$Lu-DO3A-monoamide-Aoc-QWAVGHLM-NH$_2$, the chemical shift of the NH proton only shows strong correlations to two other peaks of the histidine ring, but not to the water molecule (see FIG. 59). This indicates that there is no water molecule simultaneously coordinating both the $^{175}$Lu and the His-NH in $^{175}$Lu-DO3A-monoamide-Aoc-QWAVGHLM-NH$_2$. Thus, the difference between the two molecules is significant. In the $^{175}$Lu-L70 a secondary structure of the peptide is stabilized via the bound water molecule, and this may be responsible for increased in vivo stability.

TABLE 19

Chemical Shifts (ppm) of $^{175}$Lu-L70 in DMSO-d$_6$ at 25° C.

| Position Assignment | Chemical Shift Proton (Carbon) |
|---|---|
| 2/12 | — |
| 3/11 | — |
| 5/9 | — |
| 6/8 | — |
| 13 | — |
| 15 | — |
| 20 | — |
| 17 | 3.69/3.62 |
| 22 | 9.95/9.73 |
| 23 | 4.04/4.16 (43.57) |
| 26 | 10.47 |
| 28/32 | 7.62 (118.9) |
| 29/31 | 7.79 (128.7) |
| 35a | 8.54 |
| 36 | 4.29 (54.26) |
| 39 | 1.83/1.91 (27.26) |
| 40 | 2.16 (32.08) |
| 47 | 6.84/7.30 |
| 43 | 7.97 |
| 44 | 4.54 (53.37) |
| 48 | 2.98/3.12 (27.74) |
| 50 | 7.12 (123.9) |
| 51 | 10.79 |
| 53 | 7.53 (118.7) |
| 54 | 6.93 (118.6) |
| 55 | 7.03 (121.3) |
| 56 | 7.28 (111.7) |
| 58 | 8.09 |
| 59 | 4.32 (48.71) |
| 62 | 1.16 (17.86) |
| 63 | 7.65 |
| 64 | 4.12 (58.28) |
| 67 | 1.98 (30.96) |
| 68/73 | 0.84 (18.42) |
|  | 0.85 (19.52) |
| 69 | 8.19 |
| 70 | 3.70/3.74 (42.45) |
| 74 | 8.10 |
| 75 | 4.60 (51.85) |
| 78 | 2.95/3.08 (27.50) |
| 80 | 14.15 |
| 81 | 8.91 |
| 83 | 7.32 |
| 84 | 8.14 |
| 85 | 4.23 (51.93) |
| 86 | 1.48 (40.6) |
| 87 | 1.60 (24.61) |
| 88/91 | 0.84 (21.8) |
|  | 0.88 (23.41) |
| 92 | 8.04 |
| 93 | 4.25 (52.25) |
| 96 | 1.76/1.92 (32.16) |
| 97 | 2.41 (29.91) |
| 99 | 2.02 (15.13) |

Example LXII

Synthesis of L500

FIG. 64

The compound L500 was prepared as illustrated in FIG. 64. Specifically, diisopropylethylamine (150 µL) was added to a cooled solution of the acid A (0.19 g, 0.3 mmol) and HATU (0.12 g, 0.32 mmol) in DMF (1 mL) and stirred for 5 min. Purified peptide B (0.11 g, 0.1 mmol) was then added to the reaction mixture and stirred for 18 h. DMF was removed and the oil obtained was dissolved in a mixture of DMF/CH$_3$CN and purified by preparative HPLC. Pure fractions containing the tetra-t-butyl ester were collected and freeze dried to give the tetra-t-butyl ester as a white solid. Yield 80 mg (32%). Tetra-t-butyl ester obtained was dissolved in reagent B and stirred for 8 h. TFA was removed and the resulting pasty solid was purified by HPLC using CH$_3$CN/Water/0.1% TFA. Pure fractions were collected and freeze dried to give L500 as a white solid. Yield 23 mg (38%) MS: 1515.7 (M−H), 757.4 (M−2H)/2.

Example LXIII

Synthesis of L501

FIG. 65

The compound L501 was prepared as illustrated in FIG. 65. Diisopropylethylamine (150 µL) was added to a cooled mixture of A (0.278 g, 0.4 mmol) and HATU (0.152 g, 0.4 mmol) in DMF (1 mL) and stirred for 5 min. Purified peptide B (0.12 g .0.11 mmol) was added to the reaction mixture and stirred for 18 h. DMF was removed and the oil obtained was dissolved in a mixture of DMF/CH$_3$CN and purified by preparative HPLC. Pure fractions containing the tetra-t-butyl ester were collected and freeze dried to give the tetra t-butylester. Yield 62 mg (32%). Tetra t-butyl ester (36.0 mg, 0.02 mmol) was dissolved in reagent B and stirred for 8 h. TFA was removed and the resulting thick oil was purified by HPLC using CH$_3$CN/Water/0.1% TFA. Pure fractions were collected and freeze dried to give L501 as a white solid. Yield 12 mg (38%). MS: 1569.7 (M−H), 784.4 (M−2H/2), 803.3 (M+K−2H)/2.

Example LXIV

Radiolabeling ($^{177}$Lu) and Biodistribution of L500 and L501 Radiolabeling and HPLC Analysis of $^{177}$Lu-Complexes of L500 and L501

Radiolabeling Procedure:

Typically, a 1 mg/mL solution of ligand was prepared in 0.2 M sodium acetate buffer (pH 4.8). An aliquot of this solution (2 to 5 µL) and 6 to 10 mCi of $^{177}$LuCl$_3$ (in 0.05 NHCl, specific activity 2.8-4.09 Ci/µmol) were added to 100 to 200 µL of 0.2 M, pH 4.8 NaOAc buffer to achieve a ligand to Lu molar ratio of 2:1. After incubation at room temperature for 5 min, 10 µL of 10 mM Na$_2$EDTA.2H$_2$O was added to terminate the reaction and scavenge any remaining free $^{177}$Lu in the solution. A 9:1 (v/v) mixture of Bacteriostatic 0.9% Sodium Chloride Injection USP/ASCOR L500® Ascorbic Acid Injection USP (0.2 mL) was then added to inhibit radiolysis of the resulting radiocomplex. The radiochemical purity (RCP) was determined by HPLC. Complete coordination of Lu-177 was observed within 5 min of incubation at room temperature for all the tested ligands.

Radiolabeled Complex Prepared for In Vivo Biodistribution Studies:

For biodistribution studies, the radiolabeled compounds were prepared as described above except that a 1:1 molar ratio of ligand to Lutetium was used to guarantee complete chelation of all starting ligand. The HPLC peak containing the resulting $^{177}$Lu complex was collected in 1 mL of 9:1 Bacteriostatic saline/ASCOR L500® solution containing 0.1% HSA, and the organic solvents were removed using a speed-vacuum device. The remaining solution was further diluted to the required radioconcentration using Bacteriostatic saline/ASCOR L500® Ascorbic Acid Injection USP mixed in a 9 to 1 [v/v]) ratio. The radiochemical purity of all samples was ≧95%.

HPLC analysis: All HPLC studies were performed at a flow rate of 1.5 mL/min using a column temperature of 37° C.

1. $^{177}$Lu-L500

HPLC column: Zorbax Bonus-RP, 5 µm, 80 Å pore size, 250 mm×4.6 mm (Agilent).

Mobile phase: The following gradient was used, where A=water; B=water containing 30 mM (NH4)2SO4; C=methanol; D=acetonitrile

TABLE 20

|  | A (%) | B (%) | C (%) | D (%) |
|---|---|---|---|---|
| 0-2 min | 70 | 30 | 0 | 0 |
| 15 min | 36 | 30 | 16 | 16 |
| 30 min | 30 | 30 | 20 | 20 |
| 35-40 min | 0 | 30 | 35 | 35 |
| 45 min | 70 | 30 | 0 | 0 |
| 55 min | 70 | 30 | 0 | 0 |

Retention time: $^{177}$Lu-L500 = 25.5 min.

2. $^{177}$Lu-L501

HPLC column: Zorbax Bonus-RP, 5 µm, 80 Å pore, 250 mm×4.6 mm (Agilent).

Mobile phase: The following gradient was used, where A=water; B=water containing 30 mM (NH$_4$)$_2$SO$_4$; C=methanol; D=acetonitrile.

TABLE 21

|  | A (%) | B (%) | C (%) | D (%) |
|---|---|---|---|---|
| 0-2 min | 70 | 30 | 0 | 0 |
| 15 min | 32 | 30 | 19 | 19 |
| 30 min | 28 | 30 | 21 | 21 |
| 35-40 min | 0 | 30 | 35 | 35 |
| 45 min | 70 | 30 | 0 | 0 |
| 55 min | 70 | 30 | 0 | 0 |

Retention time: $^{177}$Lu-L501 = 23.1 min.

Biodistribution Studies:

The tumor targeting capacity, biodistribution and kinetics of $^{177}$Lu-L500, $^{177}$Lu-XX100, $^{177}$Lu-L501 and $^{177}$Lu-L70 were evaluated in the human PC-3 nude mouse model. 10-50 µCi of the HPLC purified compounds were administered to each mouse by i.v. tail vein injection, n=4 per group. At 1 h, 1 and 7 days post injection, the mice were terminated and the organs and tissues were harvested. Radioactivity was assayed in a gamma counter. The data was expressed as percentage of the total administered radioactivity (% ID) for the urine combined with the bladder, as well as for the blood pool; and percentage of the total administered radioactivity per gram (% ID/g) for all the other tested organs.

related derivative) is derivatised with the GRP targeting peptide (as in L500 and L501) the radioactivity shows localization in the tumor. The data are similar to those of $^{177}$Lu-L70, which as shown herein, has demonstrated efficacy for delivering radioactivity to PC-3 tumors for radiotherapeutic purposes. The tumor localization and lack of retention of radioactivity in the other tissue of the body show the utility of compounds of the invention containing these two chelators for radioimaging and radiotherapy.

The structure of $^{177}$Lu-XX100 is:

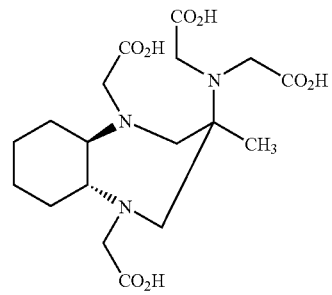

Example LXIV

Reduction of Aberrant Vascular Permeability in LNCaP Tumors

FIGS. 66-68

Referring now to FIG. 66, in a preferred embodiment, LNCaP cells grown as xenografts in CrTAC:NCr:Foxn1$^{nu/nu}$ mice exhibit a low profile invasive habit with extensive extravasation of blood from the tumor vasculature into the skin, resulting in a nonelevated, rounded or irregular, dark or darker patch (ecchymosis) (FIG. 67). Ecchymosis is clearly visible and provides a measure of the leakiness of the tumour vasculature. It has now been shown that treatment of LNCaP tumours with $^{177}$Lu-L70 decreases ecchymosis, indicating that it decreases aberrant vascular permeability, as is shown in FIGS. 65 and 68. Due to its effects on vascular permeability, treatment with radioactive L70 in combination with another therapeutic agent would be expected to improve the delivery of the other therapeutic agent.

As shown in FIGS. 66-68, in a preferred embodiment, radiotherapy studies were performed using the LNCaP (androgen sensitive prostate adenocarcinoma) tumor-bearing

TABLE 22

| Cmpd | Tumor 1 h % ID/g | Tumor 24 h % ID/g | Tumor 7 d % ID/g | Blood 1 h % ID | Blood 24 h % ID | Blood 7 d % ID | Urine/Blad 1 h % ID | Femur 7 d % ID/g | Carcass 7 d % ID/g |
|---|---|---|---|---|---|---|---|---|---|
| XX100 | 0.47 ± .21 | 0.03 ± 0.01 | 0.01 ± 0.00* | 0.39 ± 0.29 | 0.01 ± 0.01 | 0.00 ± 0.00* | 53.9 ± 30.6 | 0.19 ± 0.04* | 0.38 ± 0.02* |
| L500 | 4.49 ± 1.72 | 1.89 ± 0.55 | 0.49 ± 0.13 | 0.39 ± 0.07 | 0.01 ± 0.00 | 0.00 ± 0.00 | 56.6 ± 12.3 | 0.14 ± 0.02 | 0.50 ± 0.01 |
| L501 | 1.82 ± 0.06 | 0.76 ± 0.35 | 0.12 ± 0.04 | 1.82 ± 0.06 | 0.00 ± 0.00 | 0.00 ± 0.00 | 51.9 ± 19.7 | ND | 0.07 ± 0.01 |
| L70 | 5.86 ± 1.91 | 1.82 ± 0.06 | 0.34 ± 0.16 | 1.23 ± 0.58 | 0.02 ± 0.00 | 0.00 ± 0.00 | 43.4 ± 4.3 | 0.06 ± 0.03 | 0.17 ± 0.01 |

*72 h timepoint, ND—not done

The data show that the Lu-177 administered as a complex of the underivatized cyclohexylaazta chleator (XX100), which does not include a GRP receptor targeting moiety, is rapidly cleared from the body with little residual localization in any organs or tissue. When the complex (or its closely nude mouse model. The $^{177}$Lu labeled compound of the invention was compared to an untreated control group. (n=12 for each group for 60 days), Treated mice were administered 100 µL of $^{177}$Lu-labeled compound of the invention at 30 mCi/kg total dose, i.v, or s.c. under sterile conditions. The subjects were housed in a barrier environment for the duration of the study. Body weight, tumor size (by caliper measurement), and clinical observations were collected on each subject 3 times per week for the duration of the study. Criteria for early termination included: death; loss of total body weight (TBW) equal to or greater than 20%; tumor size equal to or greater than 2 cm³. Treatment with $^{177}$Lu-L70 does not increase survival over the control animals given no treatment, but the mice treated with $^{177}$Lu-L70 had a significant reduction in observable ecchymosis, P=0.0056. The occurrence of ecchymosis over the duration of the study is shown in FIG. 66, and is depicted in FIGS. 67 and 68.

Time to Progression is an alternative means to assess the anti-cancer activity of new agents. It is defined as the time point at which the tumor shows a 20% increase in diameter. The Mean Time to Progression is the study day when half of the animals in a group reach that point. In a preferred embodiment, it has now been found that the mean time to tumor progression in LNCap tumours is increased by about 100% with $^{177}$Lu-L70 treatment. The Mean Time to Progression data is shown in Table 23.

TABLE 23

| Group | Mean Time to Progression (Study Day) |
|---|---|
| Control | 14 |
| $^{177}$Lu-L70 | 28 |

Time to Progression = increase of at least 20% > 2r, where r = average (L × W)/2.

As shown in FIG. 67, control mice which did not receive $^{177}$Lu-L70 had LNCaP xenografts which presented with ecchymosis extending into the ipsilateral hind limb. By comparison, in FIG. 68, experimental mice which received $^{177}$Lu-L70 had LNCaP xenografts showing reduced ecchymosis when compared to control mice.

As described in this example, treatment with $^{177}$Lu-L70 provides a beneficial response in the LNCap tumours, that is, normalization of blood vessels in the tumour and substantially increased time to progression.

Example LXV

Low GRP-Receptor Model Therapeutic Response to L70

DU145 cells are derived from a prostate cancer brain metastasis, and, like PC-3, are representative of later stage prostate cancer (AR-, androgen insensitive). They have been shown to vascularize primarily in response to hypoxia. The vasculature is not as tortuous as LNCaP, and they do not exhibit ecchymosis. The PC-3 tumor cell line has a high number of GRP receptors (2.5×10⁵/cell), whereas DU145 and LNCaP express a lower receptor number (1.2×10⁴, and 5.9×10³/cell, respectively).

Radiotherapy studies were performed using a DU145 tumor-bearing nude mouse model. The DU145 tumor mice were established by xenografting 5 million DU145 cells/mouse suspended in Matrigel™ to the flank; at the start of the radiotherapy the average tumor size was 151 mm³. The $^{177}$Lu labeled compound of the invention was compared to an untreated control group, (n=12 for each group for 60 days). Treated mice were administered 100 μL of $^{177}$Lu-labeled compound of the invention at 30 mCi/kg total dose, i.v, or s.c. under sterile conditions. The subjects were housed in a barrier environment for the duration of the study. Body weight, tumor size (by caliper measurement), and clinical observations were collected on each subject 3 times per week for the duration of the study. Criteria for early termination included: death; loss of total body weight (TBW) equal to or greater than 20%; tumor size equal to or greater than 2 cm³. At termination, the tumors were harvested for histology and immunohistochemistry (1HC) consisting of Vimentin staining to confirm human origin of the cells; anti-human ki67 nuclear staining for cell proliferation, and hematoxylin and eosin staining for structure.

Results:

Data was analyzed in terms of the Mean Time to Progression, defined as the time point at which 50% of the study animal tumors (per group) demonstrate a 20% increase in diameter. As shown in Table 24 Mice treated with $^{177}$Lu-AMBA demonstrated a 57% increase in the Mean Time to Progression over the control group.

TABLE 24

Mean Time to Progression: DU145 Radiotherapy

| Group | Mean Time to Progression (Day) |
|---|---|
| Control | 7 |
| $^{177}$Lu-AMBA | 11 |

Time to Progression = increase of at least 20% > 2r, where r = average (L × W)/2.

Referring now to FIGS. 69 and 70, the reduced proliferation rate of treated DU145 tumors was confirmed by anti-human Ki67 immunohistochemistry. Ki67 is a cell cycle related nuclear protein expressed by cells in all phases of the active cell cycle, but absent in the resting phase. As shown in FIGS. 69 and 70, an average of 85% (range 60-100%) of the control DU145 tumor cells demonstrated Ki67 positive staining, as compared to an average of 53% (range 20-80%) of the DU145 cells in tumors from $^{177}$Lu-AMBA treated subjects.

To assess efficacy, a version of the World Health Organization (WHO) two dimensional tumor measurement criteria which includes all all three prostate cancer cell lines, PC-3, LNCaP, and DU145, was applied to the study data, the results of which are shown in Table 25 below. The results were then confirmed by histology.

The DU145 radiotherapy resulted in 92% of the control group mice with progressive disease, and 8% partial recovery. Treatment with $^{177}$LuAMBA resulted in a reduction of progressive disease in DU145 to 42%, with 58% partial recovery. There were no complete remissions of the tumor in this study.

In comparison the LNCaP radiotherapy (Example LXIV) demonstrated 91% of the control group mice with progressive disease, and 9% partial recovery. There were no complete responses or cases of stable disease. Treatment with $^{177}$LuAMBA resulted in a reduction of progressive disease in LNCaP to 42%, partial recovery to 8%, and complete remission of the tumor as seen in 50% of the $^{177}$LuAMBA treated group.

In the PC-3 radiotherapy (Example LV) Controls showed 100% Progressive disease. The treated PC-3 had 22% with Progressive Disease, 3% Stable Disease, 44% Partial Response and 31% Complete Responses.

These combined data demonstrate that treatment with $^{177}$LuAMBA demonstrates efficacy in prostate cancer tumor models with high GRPR as well as slows the progression of the low GRP receptor expressing LNCaP and DU145 tumors, and can result in complete remission of the LNCaP tumors.

TABLE 25

Modified WHO Two Dimensional Tumor Measurement Criteria

| Classification | Control PC-3 120 Day | Control LNCaP 60 Day | Control DU145 60 Day | Treated PC-3 120 Day | Treated LNCaP 60 Day | Treated DU145 60 Day |
|---|---|---|---|---|---|---|
| Progressive Disease | 100% | 91% | 92% | 22% | 42% | 42% |
| Stable Disease | 0% | 0% | 0% | 3% | 0% | 0% |
| Partial Response | 0% | 9% | 8% | 44% | 8% | 58% |
| Complete Response | 0% | 0% | 0% | 31% | 50% | 0% |

Complete Response: measures 0 at Day 60, or remaining mass is devoid of tumor cells.
Partial Response: 30-90% decrease from starting volume of tumor at anytime during the study, calculated from the smallest measurement during the study.
Stable Disease: neither PR nor PD criteria met.
Progressive Disease: steady increase in volume totaling 25% or more over the start volume As confirmed by the results in Table 25, $^{177}$Lu-AMBA decreases tumor load and increases survival in high GRPR expressing PC-3 xenografts. These radiotherapy results illustrate that, even at low GRPR receptor levels, $^{177}$Lu-AMBA provides ameliorative effects in androgen insensitive prostate cancer xenografts by reducing cell proliferation and increasing the time to tumor progression, and may useful as an adjunct to chemotherapy.

Embodiments of the Invention

The following is provided to illustrate without limitation the various embodiments of the present invention:

1. A compound of the general formula:

M-N-O-P-G wherein
M is an optical label or a metal chelator, optionally complexed with a radionuclide;
N is 0, an alpha or non-alpha amino acid or other linking group;
O is an alpha or non-alpha amino acid; and
P is 0, an alpha or non-alpha amino acid or other linking group, and G is a GRP receptor targeting peptide, wherein at least one of N, O or P is a non-alpha amino acid.

2. The compound of embodiment 1, wherein G is an agonist or a peptide which confers agonist activity.

3. The compound of embodiment 1, wherein the non-alpha amino acid is selected from the group consisting of:
8-amino-3,6-dioxaoctanoic acid;
N-4-aminoethyl-N-1-piperazine-acetic acid; and
polyethylene glycol derivatives having the formula $NH_2$—$(CH_2CH_2O)n$-$CH_2CO_2H$ or $NH_2$—$(CH_2CH_2O)n$-$CH_2CH_2CO_2H$ where n=2 to 100.

4. The compound of embodiment 1, wherein the metal chelator is selected from the group consisting of DTPA, DOTA, DO3A, HP-DO3A, EDTA, TETA, EHPG, HBED, NOTA, DOTMA, TETMA, PDTA, TTHA, LICAM, MECAM and CMDOTA.

5. The compound of embodiment 1, wherein the metal chelator is selected from the group consisting of
N,N-dimethylGly-Ser-Cys;
N,N-dimethylGly-Thr-Cys;
N,N-diethylGly-Ser-Cys; and
N,N-dibenzylGly-Ser-Cys.

6. The compound of embodiment 1, wherein the metal chelator is selected from the group consisting of
N,N-dimethylGly-Ser-Cys-Gly;
N,N-dimethylGly-Thr-Cys-Gly;
N,N-diethylGly-Ser-Cys-Gly; and
N,N-dibenzylGly-Ser-Cys-Gly.

7. The compound of embodiment 1, selected from the group consisting of:
N,N-dimethylglycine-Ser-Cys(Acm)-Gly-Lys-8-amino-3,6-dioxaoctanoic acid-BBN(7-14) wherein the BBN(7-14) sequence is SEQ ID NO: 1;
N,N-dimethylglycine-Ser-Cys(Acm)-Gly-Arg-8-amino-3,6-dioxaoctanoic acid-BBN (7-14) wherein the BBN(7-14) sequence is SEQ ID NO: 1;
N,N-dimethylglycine-Ser-Cys(Acm)-Gly-Asp-8-amino-3,6-dioxaoctanoic acid-BBN (7-14) wherein the BBN(7-14) sequence is SEQ ID NO: 1;
N,N-dimethylglycine-Ser-Cys(Acm)-Gly-Ser-8-amino-3,6-dioxaoctanoic acid-BBN (7-14) wherein the BBN(7-14) sequence is SEQ ID NO: 1;
N,N-dimethylglycine-Ser-Cys(Acm)-Gly-Gly-8-amino-3,6-dioxaoctanoic acid-BBN(7-14) wherein the BBN(7-14) sequence is SEQ ID NO: 1;
N,N-dimethylglycine-Ser-Cys(Acm)-Gly-Glu-8-amino-3,6-dioxaoctanoic acid-BBN(7-14) wherein the BBN(7-14) sequence is SEQ ID NO: 1;
N,N-dimethylglycine-Ser-Cys(Acm)-Gly-Dala-8-amino-3,6-dioxaoctanoic acid-BBN(7-14) wherein the BBN(7-14) sequence is SEQ ID NO: 1;
N,N-dimethylglycine-Ser-Cys(Acm)-Gly-8-amino-3,6-dioxaoctanoic acid-Lys-BBN(7-14) wherein the BBN(7-14) sequence is SEQ ID NO: 1;
N,N-dimethylglycine-Ser-Cys(Acm)-Gly-8-amino-3,6-dioxaoctanoic acid-Arg-BBN(7-14) wherein the BBN(7-14) sequence is SEQ ID NO: 1;
N,N-dimethylglycine-Ser-Cys(Acm)-Gly-8-amino-3,6-dioxaoctanoic acid-Asp-BBN(7-14) wherein the BBN(7-14) sequence is SEQ ID NO: 1;
N,N-dimethylglycine-Ser-Cys(Acm)-Gly-8-amino-3,6-dioxaoctanoic acid-Ser-BBN(7-14) wherein the BBN(7-14) sequence is SEQ ID NO: 1;
N,N-dimethylglycine-Ser-Cys(Acm)-Gly-8-amino-3,6-dioxaoctanoic acid-Gly-BBN(7-14) wherein the BBN(7-14) sequence is SEQ ID NO: 1;
N,N-dimethylglycine-Ser-Cys(Acm)-Gly-8-amino-3,6-dioxaoctanoic acid-Glu-BBN(7-14) wherein the BBN(7-14) sequence is SEQ ID NO: 1;
N,N-dimethylglycine-Ser-Cys(Acm)-Gly-8-amino-3,6-dioxaoctanoic acid-Dala-BBN(7-14) wherein the BBN(7-14) sequence is SEQ ID NO: 1;
N,N-dimethylglycine-Ser-Cys(Acm)-Gly-8-amino-3,6-dioxaoctanoic acid-8-amino-3,6-dioxaoctanoic acid-BBN (7-14) wherein the BBN(7-14) sequence is SEQ ID NO: 1;
N,N-dimethylglycine-Ser-Cys(Acm)-Gly-8-amino-3,6-dioxaoctanoic acid-2,3-diaminopropionic acid-BBN(7-14) wherein the BBN(7-14) sequence is SEQ ID NO: 1;
N,N-dimethylglycine-Ser-Cys(Acm)-Gly-8-amino-3,6-dioxaoctanoic acid-BBN(7-14) wherein the BBN(7-14) sequence is SEQ ID NO: 1;
N,N-dimethylglycine-Ser-Cys(Acm)-Gly-2,3-diaminopropionic acid-8-amino-3,6-dioxaoctanoic acid-BBN(7-14) wherein the BBN(7-14) sequence is SEQ ID NO: 1;
N,N-dimethylglycine-Ser-Cys(Acm)-Gly-Asp-8-amino-3,6-dioxaoctanoic acid-Gly-BBN(7-14) wherein the BBN (7-14) sequence is SEQ ID NO: 1;

N,N-dimethylglycine-Ser-Cys(Acm)-Gly-8-amino-3,6-dioxaoctanoic acid-Asp-Gly-BBN(7-14) wherein the BBN (7-14) sequence is SEQ ID NO: 1;
N,N-dimethylglycine-Ser-Cys(Acm)-Gly-8-amino-3,6-dioxaoctanoic acid-Ser-Gly-BBN(7-14) wherein the BBN (7-14) sequence is SEQ ID NO: 1;
N,N-dimethylglycine-Ser-Cys(Acm)-Gly-8-amino-3,6-dioxaoctanoic acid-Arg-Gly-BBN(7-14) wherein the BBN (7-14) sequence is SEQ ID NO: 1;
N,N-dimethylglycine-Ser-Cys(Acm)-Gly-8-amino-3,6-dioxaoctanoic acid-8-amino-3,6-dioxaoctanoic acid-Gly-BBN(7-14) wherein the BBN(7-14) sequence is SEQ ID NO: 1;
N,N-dimethylglycine-Ser-Cys(Acm)-Gly-8-amino-3,6-dioxaoctanoic acid-2,3-diaminopropionic acid-Gly-BBN(7-14) wherein the BBN(7-14) sequence is SEQ ID NO: 1;
N,N-dimethylglycine-Ser-Cys(Acm)-Gly-8-amino-3,6-dioxaoctanoic acid-Lys-Gly-BBN(7-14) wherein the BBN (7-14) sequence is SEQ ID NO: 1;
N,N-dimethylglycine-Ser-Cys(Acm)-Gly-2,3-diaminopropionic acid-8-amino-3,6-dioxaoctanoic acid-Gly-BBN(7-14) wherein the BBN(7-14) sequence is SEQ ID NO: 1;
N,N-dimethylglycine-Ser-Cys(Acm)-Gly-N-4-aminoethyl-N-1-piperazineacetic acid-Asp-BBN(7-14) wherein the BBN(7-14) sequence is SEQ ID NO: 1;
N,N-dimethylglycine-Ser-Cys(Acm)-Gly-N-4-aminoethyl-N-1-piperazineacetic acid-Ser-BBN(7-14) wherein the BBN(7-14) sequence is SEQ ID NO: 1;
N,N-dimethylglycine-Ser-Cys(Acm)-Gly-N-4-aminoethyl-N-1-piperazineacetic acid-Arg-BBN(7-14) wherein the BBN(7-14) sequence is SEQ ID NO: 1;
N,N-dimethylglycine-Ser-Cys(Acm)-Gly-N-4-aminoethyl-N-1-piperazineacetic acid-8-amino-3,6-dioxaoctanoic acid-BBN(7-14) wherein the BBN(7-14) sequence is SEQ ID NO: 1;
N,N-dimethylglycine-Ser-Cys(Acm)-Gly-N-4-aminoethyl-N-1-piperazineacetic acid-2,3-diaminopropionic acid-BBN(7-14) wherein the BBN(7-14) sequence is SEQ ID NO: 1;
N,N-dimethylglycine-Ser-Cys(Acm)-Gly-N-4-aminoethyl-N-1-piperazineacetic acid-Lys-BBN(7-14) wherein the BBN(7-14) sequence is SEQ ID NO: 1;
N,N-dimethylglycine-Ser-Cys(Acm)-Gly-N-1-piperazineacetic acid-Asp-BBN(7-14) wherein the BBN(7-14) sequence is SEQ ID NO: 1;
N,N-dimethylglycine-Ser-Cys(Acm)-Gly-N-1-piperazineacetic acid-Ser-BBN(7-14) wherein the BBN(7-14) sequence is SEQ ID NO: 1;
N,N-dimethylglycine-Ser-Cys(Acm)-Gly-N-1-piperazineacetic acid-Arg-BBN(7-14) wherein the BBN(7-14) sequence is SEQ ID NO: 1;
N,N-dimethylglycine-Ser-Cys(Acm)-Gly-N-1-piperazineacetic acid-8-amino-3,6-dioxaoctanoic acid-BBN(7-14) wherein the BBN(7-14) sequence is SEQ ID NO: 1;
N,N-dimethylglycine-Ser-Cys(Acm)-Gly-N-1-piperazineacetic acid-2,3-diaminopropionic acid BBN(7-14) wherein the BBN(7-14) sequence is SEQ ID NO: 1;
N,N-dimethylglycine-Ser-Cys(Acm)-Gly-N-1-piperazineacetic acid-Lys-BBN(7-14) wherein the BBN(7-14) sequence is SEQ ID NO: 1;
N,N-dimethylglycine-Ser-Cys(Acm)-Gly-4-Hydroxyproline-8-amino-3,6-dioxaoctanoic acid-BBN(7-14) wherein the BBN(7-14) sequence is SEQ ID NO: 1;
N,N-dimethylglycine-Ser-Cys(Acm)-Gly-4-aminoproline-8-amino-3,6-dioxaoctanoic acid-BBN(7-14) wherein the BBN(7-14) sequence is SEQ ID NO: 1;
N,N-dimethylglycine-Ser-Cys(Acm)-Gly-Lys-8-amino-3,6-dioxaoctanoic acid-Gly-BBN(7-14) wherein the BBN(7-14) sequence is SEQ ID NO: 1;
N,N-dimethylglycine-Ser-Cys(Acm)-Gly-Arg-8-amino-3,6-dioxaoctanoic acid-Gly-BBN(7-14) wherein the BBN(7-14) sequence is SEQ ID NO: 1;
N,N-dimethylglycine-Ser-Cys(Acm)-Gly-Ser-8-amino-3,6-dioxaoctanoic acid-Gly-BBN(7-14) wherein the BBN(7-14) sequence is SEQ ID NO: 1;
N,N-dimethylglycine-Ser-Cys(Acm)-Gly-Asp-8-amino-3,6-dioxaoctanoic acid-Gly-BBN(7-14) wherein the BBN (7-14) sequence is SEQ ID NO: 1;
N,N-dimethylglycine-Ser-Cys(Acm)-Gly-8-amino-3,6-dioxaoctanoic acid-Asp-Gly-BBN(7-14) wherein the BBN (7-14) sequence is SEQ ID NO: 1;
N,N-dimethylglycine-Ser-Cys(Acm)-Gly-8-amino-3,6-dioxaoctanoic acid-Ser-Gly-BBN(7-14) wherein the BBN (7-14) sequence is SEQ ID NO: 1;
N,N-dimethylglycine-Ser-Cys(Acm)-Gly-8-amino-3,6-dioxaoctanoic acid-Arg-Gly-BBN(7-14) wherein the BBN (7-14) sequence is SEQ ID NO: 1;
N,N-dimethylglycine-Ser-Cys(Acm)-Gly-8-amino-3,6-dioxaoctanoic acid-8-amino-3,6-dioxaoctanoic acid-Gly-BBN(7-14) wherein the BBN(7-14) sequence is SEQ ID NO: 1;
N,N-dimethylglycine-Ser-Cys(Acm)-Gly-8-amino-3,6-dioxaoctanoic acid-2,3-diaminopropionic acid-Gly-BBN(7-14) wherein the BBN(7-14) sequence is SEQ ID NO: 1;
N,N-dimethylglycine-Ser-Cys(Acm)-Gly-8-amino-3,6-dioxaoctanoic acid-Lys-Gly-BBN(7-14) wherein the BBN (7-14) sequence is SEQ ID NO: 1; and
N,N-dimethylglycine-Ser-Cys(Acm)-Gly-2,3-diaminopropionic acid-8-amino-3,6-dioxaoctanoic acid-Gly-BBN(7-14) wherein the BBN(7-14) sequence is SEQ ID NO: 1.

8. The compound of embodiment 1, selected from the group consisting of:
N,N-dimethylglycine-Ser-Cys-Gly-Lys-8-amino-3,6-dioxaoctanoic acid-BBN(7-14) wherein the BBN(7-14) sequence is SEQ ID NO: 1;
N,N-dimethylglycine-Ser-Cys-Gly-Arg-8-amino-3,6-dioxaoctanoic acid-BBN(7-14) wherein the BBN(7-14) sequence is SEQ ID NO: 1;
N,N-dimethylglycine-Ser-Cys-Gly-Asp-8-amino-3,6-dioxaoctanoic acid-BBN(7-14) wherein the BBN(7-14) sequence is SEQ ID NO: 1;
N,N-dimethylglycine-Ser-Cys-Gly-Ser-8-amino-3,6-dioxaoctanoic acid-BBN(7-14) wherein the BBN(7-14) sequence is SEQ ID NO: 1;
N,N-dimethylglycine-Ser-Cys-Gly-Gly-8-amino-3,6-dioxaoctanoic acid-BBN(7-14) wherein the BBN(7-14) sequence is SEQ ID NO: 1;
N,N-dimethylglycine-Ser-Cys-Gly-Glu-8-amino-3,6-dioxaoctanoic acid-BBN(7-14) wherein the BBN(7-14) sequence is SEQ ID NO: 1;
N,N-dimethylglycine-Ser-Cys-Gly-Dala-8-amino-3,6-dioxaoctanoic acid-BBN(7-14) wherein the BBN(7-14) sequence is SEQ ID NO: 1;
N,N-dimethylglycine-Ser-Cys-Gly-8-amino-3,6-dioxaoctanoic acid-Lys-BBN(7-14) wherein the BBN(7-14) sequence is SEQ ID NO: 1;
N,N-dimethylglycine-Ser-Cys-Gly-8-amino-3,6-dioxaoctanoic acid-Arg-BBN(7-14) wherein the BBN(7-14) sequence is SEQ ID NO: 1;
N,N-dimethylglycine-Ser-Cys-Gly-8-amino-3,6-dioxaoctanoic acid-Asp-BBN(7-14) wherein the BBN(7-14) sequence is SEQ ID NO: 1;

N,N-dimethylglycine-Ser-Cys-Gly-8-amino-3,6-dioxaoctanoic acid-Ser-BBN(7-14) wherein the BBN(7-14) sequence is SEQ ID NO: 1;
N,N-dimethylglycine-Ser-Cys-Gly-8-amino-3,6-dioxaoctanoic acid-Gly-BBN(7-14) wherein the BBN(7-14) sequence is SEQ ID NO: 1;
N,N-dimethylglycine-Ser-Cys-Gly-8-amino-3,6-dioxaoctanoic acid-Glu-BBN(7-14) wherein the BBN(7-14) sequence is SEQ ID NO: 1;
N,N-dimethylglycine-Ser-Cys-Gly-8-amino-3,6-dioxaoctanoic acid-Dala-BBN(7-14) wherein the BBN(7-14) sequence is SEQ ID NO: 1;
N,N-dimethylglycine-Ser-Cys-Gly-8-amino-3,6-dioxaoctanoic acid-8-amino-3,6-dioxaoctanoic acid-BBN(7-14) wherein the BBN(7-14) sequence is SEQ ID NO: 1;
N,N-dimethylglycine-Ser-Cys-Gly-8-amino-3,6-dioxaoctanoic acid-2,3-diaminopropionic acid-BBN(7-14) wherein the BBN(7-14) sequence is SEQ ID NO: 1;
N,N-dimethylglycine-Ser-Cys-Gly-8-amino-3,6-dioxaoctanoic acid-BBN(7-14) wherein the BBN(7-14) sequence is SEQ ID NO: 1;
N,N-dimethylglycine-Ser-Cys-Gly-2,3-diaminopropionic acid-8-amino-3,6-dioxaoctanoic acid-BBN(7-14) wherein the BBN(7-14) sequence is SEQ ID NO: 1;
N,N-dimethylglycine-Ser-Cys-Gly-Asp-8-amino-3,6-dioxaoctanoic acid-Gly-BBN(7-14) wherein the BBN(7-14) sequence is SEQ ID NO: 1;
N,N-dimethylglycine-Ser-Cys-Gly-8-amino-3,6-dioxaoctanoic acid-Asp-Gly-BBN(7-14) wherein the BBN(7-14) sequence is SEQ ID NO: 1;
N,N-dimethylglycine-Ser-Cys-Gly-8-amino-3,6-dioxaoctanoic acid-Ser-Gly-BBN(7-14) wherein the BBN(7-14) sequence is SEQ ID NO: 1;
N,N-dimethylglycine-Ser-Cys-Gly-8-amino-3,6-dioxaoctanoic acid-Arg-Gly-BBN(7-14) wherein the BBN(7-14) sequence is SEQ ID NO: 1;
N,N-dimethylglycine-Ser-Cys-Gly-8-amino-3,6-dioxaoctanoic acid-8-amino-3,6-dioxaoctanoic acid-Gly-BBN(7-14) wherein the BBN(7-14) sequence is SEQ ID NO: 1;
N,N-dimethylglycine-Ser-Cys-Gly-8-amino-3,6-dioxaoctanoic acid-2,3-diaminopropionic acid-Gly-BBN(7-14) wherein the BBN(7-14) sequence is SEQ ID NO: 1;
N,N-dimethylglycine-Ser-Cys-Gly-8-amino-3,6-dioxaoctanoic acid-Lys-Gly-BBN(7-14) wherein the BBN(7-14) sequence is SEQ ID NO: 1;
N,N-dimethylglycine-Ser-Cys-Gly-2,3-diaminopropionic acid-8-amino-3,6-dioxaoctanoic acid-Gly-BBN(7-14) wherein the BBN(7-14) sequence is SEQ ID NO: 1;
N,N-dimethylglycine-Ser-Cys-Gly-N-4-aminoethyl-N-1-piperazineacetic acid-Asp-BBN(7-14) wherein the BBN(7-14) sequence is SEQ ID NO: 1;
N,N-dimethylglycine-Ser-Cys-Gly-N-4-aminoethyl-N-1-piperazineacetic acid-Ser-BBN(7-14) wherein the BBN(7-14) sequence is SEQ ID NO: 1;
N,N-dimethylglycine-Ser-Cys-Gly-N-4-aminoethyl-N-1-piperazineacetic acid-Arg-BBN(7-14) wherein the BBN(7-14) sequence is SEQ ID NO: 1;
N,N-dimethylglycine-Ser-Cys(Acm)-Gly-N-4-aminoethyl-N-1-piperazineacetic acid-8-amino-3,6-dioxaoctanoic acid-BBN(7-14) wherein the BBN(7-14) sequence is SEQ ID NO: 1;
N,N-dimethylglycine-Ser-Cys-Gly-N-4-aminoethyl-N-1-piperazineacetic acid-2,3-diaminopropionic acid-BBN(7-14) wherein the BBN(7-14) sequence is SEQ ID NO: 1;
N,N-dimethylglycine-Ser-Cys-Gly-N-4-aminoethyl-N-1-piperazineacetic acid-Lys-BBN(7-14) wherein the BBN(7-14) sequence is SEQ ID NO: 1;
N,N-dimethylglycine-Ser-Cys-Gly-N-1-piperazineacetic acid-Asp-BBN(7-14) wherein the BBN(7-14) sequence is SEQ ID NO: 1;
N,N-dimethylglycine-Ser-Cys-Gly-N-1-piperazineacetic acid-Ser-BBN(7-14) wherein the BBN(7-14) sequence is SEQ ID NO: 1;
N,N-dimethylglycine-Ser-Cys-Gly-N-1-piperazineacetic acid-Arg-BBN(7-14) wherein the BBN(7-14) sequence is SEQ ID NO: 1;
N,N-dimethylglycine-Ser-Cys-Gly-N-1-piperazineacetic acid-8-amino-3,6-dioxaoctanoic acid-BBN(7-14) wherein the BBN(7-14) sequence is SEQ ID NO: 1;
N,N-dimethylglycine-Ser-Cys-Gly-N-1-piperazineacetic acid-2,3-diaminopropionic acid BBN(7-14) wherein the BBN(7-14) sequence is SEQ ID NO: 1;
N,N-dimethylglycine-Ser-Cys-Gly-N-1-piperazineacetic acid-Lys-BBN(7-14) wherein the BBN(7-14) sequence is SEQ ID NO: 1;
N,N-dimethylglycine-Ser-Cys-Gly-4-Hydroxyproline-8-amino-3,6-dioxaoctanoic acid-BBN(7-14) wherein the BBN(7-14) sequence is SEQ ID NO: 1;
N,N-dimethylglycine-Ser-Cys-Gly-4-aminoproline-8-amino-3,6-dioxaoctanoic acid-BBN(7-14) wherein the BBN(7-14) sequence is SEQ ID NO: 1;
N,N-dimethylglycine-Ser-Cys-Gly-Lys-8-amino-3,6-dioxaoctanoic acid-Gly-BBN(7-14) wherein the BBN(7-14) sequence is SEQ ID NO: 1;
N,N-dimethylglycine-Ser-Cys-Gly-Arg-8-amino-3,6-dioxaoctanoic acid-Gly-BBN(7-14) wherein the BBN(7-14) sequence is SEQ ID NO: 1;
N,N-dimethylglycine-Ser-Cys-Gly-Ser-8-amino-3,6-dioxaoctanoic acid-Gly-BBN(7-14) wherein the BBN(7-14) sequence is SEQ ID NO: 1;
N,N-dimethylglycine-Ser-Cys-Gly-Asp-8-amino-3,6-dioxaoctanoic acid-Gly-BBN(7-14) wherein the BBN(7-14) sequence is SEQ ID NO: 1;
N,N-dimethylglycine-Ser-Cys-Gly-8-amino-3,6-dioxaoctanoic acid-Asp-Gly-BBN(7-14) wherein the BBN(7-14) sequence is SEQ ID NO: 1;
N,N-dimethylglycine-Ser-Cys-Gly-8-amino-3,6-dioxaoctanoic acid-Ser-Gly-BBN(7-14) wherein the BBN(7-14) sequence is SEQ ID NO: 1;
N,N-dimethylglycine-Ser-Cys-Gly-8-amino-3,6-dioxaoctanoic acid-Arg-Gly-BBN(7-14) wherein the BBN(7-14) sequence is SEQ ID NO: 1;
N,N-dimethylglycine-Ser-Cys-Gly-8-amino-3,6-dioxaoctanoic acid-8-amino-3,6-dioxaoctanoic acid-Gly-BBN(7-14) wherein the BBN(7-14) sequence is SEQ ID NO: 1;
N,N-dimethylglycine-Ser-Cys-Gly-8-amino-3,6-dioxaoctanoic acid-2,3-diaminopropionic acid-Gly-BBN(7-14) wherein the BBN(7-14) sequence is SEQ ID NO: 1;
N,N-dimethylglycine-Ser-Cys-Gly-8-amino-3,6-dioxaoctanoic acid-Lys-Gly-BBN(7-14) wherein the BBN(7-14) sequence is SEQ ID NO: 1; and
N,N-dimethylglycine-Ser-Cys-Gly-2,3-diaminopropionic acid-8-amino-3,6-dioxaoctanoic acid-Gly-BBN(7-14) wherein the BBN(7-14) sequence is SEQ ID NO: 1.

9. The compound of embodiment 1, selected from the group consisting of:
DO3A-monoamide-8-amino-3,6-dioxaoctanoic acid-diaminopropionic acid-BBN(7-14) wherein the BBN(7-14) sequence is SEQ ID NO: 1;
DO3A-monoamide-8-amino-3,6-dioxaoctanoic acid-biphenylalanine-BBN(7-14) wherein the BBN(7-14) sequence is SEQ ID NO: 1;

DO3A-monoamide-8-amino-3,6-dioxaoctanoic acid-diphenylalanine-BBN(7-14) wherein the BBN(7-14) sequence is SEQ ID NO: 1;

DO3A-monoamide-8-amino-3,6-dioxaoctanoic acid-4-benzoylphenylalanine-BBN(7-14) wherein the BBN(7-14) sequence is SEQ ID NO: 1;

DO3A-monoamide-5-aminopentanoic acid-8-amino-3,6-dioxaoctanoic acid-BBN(7-14) wherein the BBN(7-14) sequence is SEQ ID NO: 1;

DO3A-monoamide-8-amino-3,6-dioxaoctanoic acid-D-phenylalanine-BBN(7-14) wherein the BBN(7-14) sequence is SEQ ID NO: 1; and DO3A-monoamide-8-aminooctanoic acid-8-amino-3,6-dioxaoctanoic acid-BBN(7-14) wherein the BBN(7-14) sequence is SEQ ID NO: 1.

10. The compound of any one of embodiments 1, 2 or 3, wherein the optical label is selected from the group consisting of organic chromophores, organic fluorophores, light-absorbing compounds, light-reflecting compounds, light-scattering compounds, and bioluminescent molecules.

11. A method of imaging comprising the steps of:
administering to a patient a diagnostic imaging agent comprising the compound of embodiment 1 wherein M is a metal chelator complexed with a diagnostic radionuclide, and
imaging said patient.

12. A method of imaging comprising the steps of:
administering to a patient a diagnostic imaging agent comprising the compound of embodiment 8 complexed with a diagnostic radionuclide, and
imaging said patient.

13. A method of imaging comprising the steps of:
administering to a patient a diagnostic imaging agent comprising the compound of embodiment 1 wherein M is an optical label, and
imaging said patient.

14. A method of imaging comprising the steps of:
administering to a patient a diagnostic imaging agent comprising the compound of embodiment 10, and
imaging said patient.

15. A method for preparing a diagnostic imaging agent comprising the step of adding to an injectable medium a substance comprising the compound of embodiment 1.

16. A method of treating a patient comprising the step of administering to a patient a radiotherapeutic agent comprising the compound of embodiments 7, 8 or 9 complexed with a therapeutic radionuclide.

17. A method of treating a patient comprising the step of administering to a patient a radiotherapeutic agent comprising the compound of embodiment 4 complexed with a therapeutic radionuclide.

18. A method of preparing a radiotherapeutic agent comprising the step of adding to an injectable medium a substance comprising the compound of embodiments 7, 8, or 9.

19. A method of preparing a radiotherapeutic agent comprising the step of adding to an injectable medium a substance comprising the compound of embodiment 4.

20. A compound of the general formula:

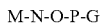

wherein
M is an optical label or a metal chelator, optionally complexed with a radionuclide;
N is 0, an alpha amino acid, a substituted bile acid or other linking group;
O is an alpha amino acid or a substituted bile acid; and
P is 0, an alpha amino acid, a substituted bile acid or other linking group; and
G is a GRP receptor targeting peptide, and
wherein at least one of N, O or P is a substituted bile acid.

21. The compound of embodiment 20, wherein G is an agonist or a peptide which confers agonist activity.

22. The compound of embodiment 20, wherein the substituted bile acid is selected from the group consisting of:
3β-amino-3-deoxycholic acid;
(3β,5β)-3-aminocholan-24-oic acid;
(3β,5β,12α)-3-amino-12-hydroxycholan-24-oic acid;
(3β,5β,7α,12α)-3-amino-7,12-dihydroxycholan-24-oic acid;
Lys-(3,6,9)-trioxaundecane-1,11-dicarbonyl-3,7-dideoxy-3-aminocholic acid);
(3β,5β,7α,12α)-3-amino-7-hydroxy-12-oxocholan-24-oic acid; and
(3β,5β,7α)-3-amino-7-hydroxycholan-24-oic acid.

23. The compound of embodiment 20, wherein M is selected from the group consisting of: DTPA, DOTA, DO3A, HPDO3A, EDTA, TETA and CMDOTA.

24. The compound of embodiment 20, wherein M is selected from the group consisting of EHPG and derivatives thereof 25. The compound of embodiment 20, wherein M is selected from the group consisting of 5-C1-EHPG, 5-Br-EHPG, 5-Me-EHPG, 5-t-Bu-EHPG, and 5-sec-Bu-EHPG.

26. The compound of embodiment 20, wherein M is selected from the group consisting of benzodiethylenetriamine pentaacetic acid (benzo-DTPA) and derivatives thereof 27. The compound of embodiment 20, wherein M is selected from the group consisting of dibenzo-DTPA, phenyl-DTPA, diphenyl-DTPA, benzyl-DTPA, and dibenzyl DTPA.

28. The compound of embodiment 20, wherein M is selected from the group consisting of HBED and derivatives thereof.

29. The compound of embodiment 20, wherein M is a macrocyclic compound which contains at least 3 carbon atoms and at least two heteroatoms (0 and/or N), which macrocyclic compounds can consist of one ring, or two or three rings joined together at the hetero ring elements.

30. The compound of embodiment 20, wherein M is selected from the group consisting of benzo-DOTA, dibenzo-DOTA, and benzo-NOTA, benzo-TETA, benzo-DOTMA, and benzo-TETMA.

31. The compound of embodiment 20, wherein M is selected from the group consisting of derivatives of 1,3-propylenediaminetetraacetic acid (PDTA) and triethylenetetraaminehexaacetic acid (TTHA); derivatives of 1,5,10-N,N',N"-tris(2,3-dihydroxybenzoyl)-tricatecholate (LICAM) and 1,3,5-N,N',N"-tris(2,3-dihydroxybenzoyl) aminomethylbenzene (MECAM).

32. A compound of embodiment 20 selected from the group consisting of:
DO3A-monoamide-Gly-(3β,5β)-3-aminocholan-24-oic acid-BBN(7-14) wherein the BBN(7-14) sequence is SEQ ID NO: 1;
DO3A-monoamide-Gly-(3β,5β,12α)-3-amino-12-hydroxycholan-24-oic acid-BBN(7-14) wherein the BBN (7-14) sequence is SEQ ID NO: 1;
DO3A-monoamide-Gly-(3β,5β,7α,12α)-3-amino-7,12-dihydroxycholan-24-oic acid-BBN(7-14) wherein the BBN(7-14) sequence is SEQ ID NO: 1;
DO3A-monoamide-Gly-Lys-(3,6,9)-trioxaundecane-1, 11-dicarbonyl-3,7-dideoxy-3-aminocholic acid)-Arg-BBN(7-14) wherein the BBN(7-14) sequence is SEQ ID NO: 1;

(3β,5β,7α,12α)-3-amino-7,12-dihydroxycholan-24-oic acid-3,6,9-trioxaundecane-1,11-dicarbonyl Lys (DO3A-monoamide-Gly)-Arg-BBN(7-14) wherein the BBN(7-14) sequence is SEQ ID NO: 1;

DO3A-monoamide-Gly-(3β,5β,7α,12α)-3-amino-12-oxocholan-24-oic acid-BBN(7-14) wherein the BBN(7-14) sequence is SEQ ID NO: 1;

DO3A-monoamide-1-amino-3,6-dioxaoctanoic acid-(3β,5β,7α,12α)-3-amino-7,12-dihydroxycholan-24-oic acid-BBN(7-14) wherein the BBN(7-14) sequence is SEQ ID NO: 1;

DO3A-monoamide-Gly-(3β,5β7α,12α)-3-amino-7,12-dihydroxycholan-24-oic acid-QWAVaHLM-NH$_2$ wherein QWAVaHLM-NH$_2$ is SEQ ID NO: 14;

DO3A-monoamide-Gly-(3β,5β7α,12α)-3-amino-7,12-dihydroxycholan-24-oic acid-f-QWAVGHLM-NH$_2$ wherein QWAVGHLM-NH$_2$ is SEQ ID NO: 1;

DO3A-monoamide-Gly-(3β,5β7α,12α)-3-amino-7,12-dihydroxycholan-24-oic acid-f-WAVGHLL-NH$_2$ wherein WAVGHLL-NH$_2$ is SEQ ID NO: 26;

DO3A-monoamide-Gly-(3β,5β7α,12α)-3-amino-7,12-dihydroxycholan-24-oic acid-f-QWAVGHL-NH-pentyl wherein QWAVGHL-NH-pentyl is SEQ ID NO: 6;

DO3A-monoamide-Gly-(3β,5β7α,12α)-3-amino-7,12-dihydroxycholan-24-oic acid-y-QWAV-Bala-H-F-Nle-NH$_2$ wherein QWAV-Bala-H-F-Nle-NH$_2$ is SEQ ID NO: 9;

DO3A-monoamide-Gly-(3β,5β7α,12α)-3-amino-7,12-dihydroxycholan-24-oic acid-f-QWAV-Bala-H-F-Nle-NH$_2$ wherein QWAV-Bala-H-F-Nle-NH$_2$ is SEQ ID NO: 9;

DO3A-monoamide-Gly-(3β,5β7α,12α)-3-amino-7,12-dihydroxycholan-24-oic acid-QWAVGHFL-NH$_2$ wherein QWAVGHFL-NH$_2$ is SEQ ID NO: 22

DO3A-monoamide-Gly-(3β,5β7α,12α)-3-amino-7,12-dihydroxycholan-24-oic acid-QWAVGNMeH-L-M-NH$_2$ wherein QWAVGNMeH-L-M-NH$_2$ is SEQ ID NO: 15;

DO3A-monoamide-Gly-(3β,5β7α,12α)-3-amino-7,12-dihydroxycholan-24-oic acid-LWAVGSF-M-NH$_2$ wherein LWAVGSF-M-NH$_2$ is SEQ ID NO: 11;

DO3A-monoamide-Gly-(3β,5β7α,12α)-3-amino-7,12-dihydroxycholan-24-oic acid-HWAVGHLM-NH$_2$ wherein HWAVGHLM-NH$_2$ is SEQ ID NO: 12;

DO3A-monoamide-Gly-(3β,5β7α,12α)-3-amino-7,12-dihydroxycholan-24-oic acid-LWAGHFM-NH$_2$ wherein LWAGHFM-NH$_2$ is SEQ ID NO: 20;

DO3A-monoamide-Gly-(3β,5β7α,12α)-3-amino-7,12-dihydroxycholan-24-oic acid-QWAVGHFM-NH$_2$ wherein QWAVGHFM-NH$_2$ is SEQ ID NO: 13;

DO3A-monoamide-Gly-(3β,5β7α,12α)-3-amino-7,12-dihydroxycholan-24-oic acid-QRLGNQWAVGHLM-NH$_2$ wherein QRLGNQWAVGHLM-NH$_2$ is SEQ ID NO: 3;

DO3A-monoamide-Gly-(3β,5β7α,12α)-3-amino-7,12-dihydroxycholan-24-oic acid-QRYGNQWAVGHLM-NH$_2$ wherein QRYGNQWAVGHLM-NH$_2$ is SEQ ID NO: 4;

DO3A-monoamide-Gly-(3β,5β7α,12α)-3-amino-7,12-dihydroxycholan-24-oic acid-QKYGNQWAVGHLM-NH$_2$ wherein QKYGNQWAVGHLM-NH$_2$ is SEQ ID NO: 5;

Pglu-Q-Lys (DO3A-monoamide)-Gly-(3β,5β7α,12α)-3-amino-7,12-dihydroxycholan-24-oic acid-LGNQWAVGHLM-NH$_2$ wherein LGNQWAVGHLM-NH$_2$ is SEQ ID NO: 18.

DO3A-monoamide-Gly-3-amino-3-deoxycholic acid-QRLGNQWAVGHLM-NH$_2$ wherein QRLGNQWAVGHLM-NH$_2$ is SEQ ID NO: 3;

DO3A-monoamide-Gly-3-amino-3-deoxycholic acid-QRYGNQWAVGHLM-NH$_2$ wherein QRYGNQWAVGHLM-NH$_2$ is SEQ ID NO: 4;

DO3A-monoamide-Gly-3-amino-3-deoxycholic acid-QKYGNQWAVGHLM-NH$_2$ wherein QKYGNQWAVGHLM-NH$_2$ is SEQ ID NO: 5; and Pglu-Q-Lys(DO3A-monoamide-G-3-amino-3-deoxycholic acid)-LGNQWAVGHLM-NH$_2$ wherein LGNQWAVGHLM-NH$_2$ is SEQ ID NO: 18.

33. The compound of any one of embodiments 20, 21 or 22, wherein the optical label is selected from the group consisting of organic chromophores, organic fluorophores, light-absorbing compounds, light-reflecting compounds, light-scattering compounds, and bioluminescent molecules.

34. A method of imaging comprising the steps of:
administering to a patient a diagnostic imaging agent comprising the compound of embodiment 20 wherein M is a metal chelator complexed with a diagnostic radionuclide, and
imaging said patient.

35. A method of imaging comprising the steps of:
administering to a patient a diagnostic imaging agent comprising the compound of embodiment 32, and
imaging said patient.

36. A method of imaging comprising the steps of:
administering to a patient a diagnostic imaging agent comprising the compound of embodiment 20 wherein M is an optical label, and
imaging said patient.

37. A method of imaging comprising the steps of:
administering to a patient a diagnostic imaging agent comprising the compound of embodiment 33, and
imaging said patient.

38. A method for preparing a diagnostic imaging agent comprising the step of adding to an injectable medium a substance comprising the compound of embodiment 20.

39. A method of treating a patient comprising the step of administering to a patient a radiotherapeutic agent comprising the compound of embodiment 20 complexed with a therapeutic radionuclide.

40. A method of preparing a radiotherapeutic agent comprising the step of adding to an injectable medium a substance comprising the compound of embodiment 20.

41. A compound DO3A-monoamide-Gly-(3β,5β,7α,12α)-3-amino-7,12-dihydroxycholan-24-oic acid-BBN(7-14) wherein the BBN(7-14) sequence is SEQ ID NO: 1.

42. A method of imaging comprising the steps of:
administering to a patient a diagnostic imaging agent comprising DO3A-monoamide-Gly-(3β,5β,7α,12α)-3-amino-7,12-dihydroxycholan-24-oic acid-BBN(7-14) complexed with a diagnostic radionuclide, wherein the BBN(7-14) sequence is SEQ ID NO: 1, and
imaging said patient.

43. A method for preparing a diagnostic imaging agent comprising the step of adding to an injectable medium a compound comprising DO3A-monoamide-Gly-4-aminobenzoic acid-BBN(7-14) wherein the BBN(7-14) sequence is SEQ ID NO: 1.

44. A method of treating a patient comprising the step of administering to a patient a radiotherapeutic agent comprising the compound of embodiment 41 complexed with a therapeutic radionuclide.

45. A method of preparing a radiotherapeutic agent comprising the step of adding to an injectable medium a substance comprising the compound of embodiment 41.

46. A compound DO3A-monoamide-Gly-4-aminobenzoic acid-BBN(7-14) wherein the BBN(7-14) sequence is SEQ ID NO: 1.

47. A method of imaging comprising the steps of:
administering to a patient a diagnostic imaging agent comprising DO3A-monoamide-Gly-4-aminobenzoic acid-BBN(7-14) complexed with a diagnostic radionuclide, wherein the BBN(7-14) sequence is SEQ ID NO: 1, and imaging said patient.

48. A method for preparing a diagnostic imaging agent comprising the step of adding to an injectable medium a compound comprising DO3A-monoamide-Gly-4-aminobenzoic acid-BBN(7-14) wherein the BBN(7-14) sequence is SEQ ID NO: 1.

49. A method of treating a patient comprising the step of administering to a patient a radiotherapeutic agent comprising the compound of embodiment 46 complexed with a therapeutic radionuclide.

50. A method of preparing a radiotherapeutic agent comprising the step of adding to an injectable medium a substance comprising the compound of embodiment 46.

51. A compound of the general formula:

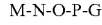

wherein
M is an optical label or a metal chelator optionally complexed with a radionuclide;
N is 0, an alpha amino acid, a non-alpha amino acid with a cyclic group or other linking group;
O is an alpha amino acid or a non-alpha amino acid with a cyclic group;
P is 0, an alpha amino acid, a non-alpha amino acid with a cyclic group, or other linking group; and
G is a GRP receptor targeting peptide,
wherein at least one of N, O or P is a non-alpha amino acid with a cyclic group.

52. The compound of embodiment 51, wherein G is an agonist or a peptide which confers agonist activity.

53. The compound of embodiment 51, wherein the non-alpha amino acid with a cyclic group is selected from the group consisting of:
4-aminobenzoic acid;
4-aminomethyl benzoic acid;
trans-4-aminomethylcyclohexane carboxylic acid;
4-(2-aminoethoxy)benzoic acid; isonipecotic acid;
2-aminomethylbenzoic acid;
4-amino-3-nitrobenzoic acid;
4-(3-carboxymethyl-2-keto-1-benzimidazolyl)-piperidine;
6-(piperazin-1-yl)-4-(3H)-quinazolinone-3-acetic acid;
(2S,5S)-5-amino-1,2,4,5,6,7-hexahydro-azepino[3,21-hi]indole-4-one-2-carboxylic acid;
(4S,7R)-4-amino-6-aza-5-oxo-9-thiabicyclo[4.3.0]nonane-7-carboxylic acid;
3-carboxymethyl-1-phenyl-1,3,8-triazaspiro[4.5]decan-4-one;
N1-piperazineacetic acid;
N-4-aminoethyl-N-1-acetic acid;
(3S)-3-amino-1-carboxymethylcaprolactam; and
(2S,6S,9)-6-amino-2-carboxymethyl-3,8-diazabicyclo-[4,3,0]-nonane-1,4-dione.

54. The compound of embodiment 51, wherein M is selected from the group consisting of: DTPA, DOTA, DO3A, HPDO3A, EDTA, and TETA.

55. The compound of embodiment 51, wherein M is selected from the group consisting of EHPG and derivatives thereof 56. The compound of embodiment 51, wherein M is selected from the group consisting of 5-Cl-EHPG, 5-Br-EHPG, 5-Me-EHPG, 5-t-Bu-EHPG, and 5-sec-Bu-EHPG.

57. The compound of embodiment 51, wherein M is selected from the group consisting of benzodiethylenetriamine pentaacetic acid (benzo-DTPA) and derivatives thereof 58. The compound of embodiment 51, wherein M is selected from the group consisting of dibenzo-DTPA, phenyl-DTPA, diphenyl-DTPA, benzyl-DTPA, and dibenzyl DTPA.

59. The compound of embodiment 51, wherein M is selected from the group consisting of HBED and derivatives thereof.

60. The compound of embodiment 51, wherein M is a macrocyclic compound which contains at least 3 carbon atoms and at least two heteroatoms (0 and/or N), which macrocyclic compounds can consist of one ring, or two or three rings joined together at the hetero ring elements.

61. The compound of embodiment 51, wherein M is selected from the group consisting of benzo-DOTA, dibenzo-DOTA, and benzo-NOTA, benzo-TETA, benzo-DOTMA, and benzo-TETMA.

62. The compound of embodiment 51, wherein M is selected from the group consisting of derivatives of 1,3-propylenediaminetetraacetic acid (PDTA) and triethylenetetraaminehexaacetic acid (TTHA); derivatives of 1,5,10-N,N', N"-tris(2,3-dihydroxybenzoyl)-tricatecholate (LICAM) and 1,3,5-N,N',N"-tris(2,3-dihydroxybenzoyl) aminomethylbenzene (MECAM).

63. The compound of embodiment 51, selected from the group consisting of
DO3A-monoamide-Gly-4-aminobenzoic acid-BBN(7-14) wherein the BBN(7-14) sequence is SEQ ID NO: 1;
DO3A-monoamide-4-aminomethyl benzoic acid-BBN(7-14) wherein the BBN(7-14) sequence is SEQ ID NO: 1;
DO3A-monoamide-trans-4-aminomethylcyclohexyl carboxylic acid-BBN(7-14) wherein the BBN(7-14) sequence is SEQ ID NO: 1;
DO3A-monoamide-4-(2-aminoethoxy)benzoic acid-BBN(7-14) wherein the BBN(7-14) sequence is SEQ ID NO: 1;
DO3A-monoamide-Gly-isonipecotic acid-BBN(7-14) wherein the BBN(7-14) sequence is SEQ ID NO: 1;
DO3A-monoamide-2-aminomethylbenzoic acid-BBN(7-14) wherein the BBN(7-14) sequence is SEQ ID NO: 1;
DO3A-monoamide-4-aminomethyl-3-nitrobenzoic acid-BBN(7-14) wherein the BBN(7-14) sequence is SEQ ID NO: 1;
DO3A-monoamide-8-amino-3,6-dioxaoctanoic acid-1-naphthylalanine-BBN(7-14) wherein the BBN(7-14) sequence is SEQ ID NO: 1;
DO3A-monoamide-4-(3-carboxymethyl-2-keto-1-benzimidazolyl-piperidine-BBN(7-14) wherein the BBN(7-14) sequence is SEQ ID NO: 1;
DO3A-monoamide-6-(piperazin-1-yl)-4-(3H)-quinazolinone-3-acetic acid-BBN(7-14) wherein the BBN(7-14) sequence is SEQ ID NO: 1;
DO3A-monoamide-(2S,5S)-5-amino-1,2,4,5,6,7-hexahydro-azepino[3,21-hi]indole-4-one-2-carboxylic acid-BBN(7-14) wherein the BBN(7-14) sequence is SEQ ID NO: 1;
DO3A-monoamide-(4S,7R)-4-amino-6-aza-5-oxo-9-thiabicyclo[4.3.0]nonane-7-carboxylic acid-BBN(7-14) wherein the BBN(7-14) sequence is SEQ ID NO: 1;

DO3A-monoamide-N,N-dimethylglycine-BBN(7-14) wherein the BBN(7-14) sequence is SEQ ID NO: 1;

DO3A-monoamide-3-carboxymethyl-1-phenyl-1,3,8-triazaspiro[4.5]decan-4-one-BBN(7-14) wherein the BBN(7-14) sequence is SEQ ID NO: 1;

DO3A-monoamide-N1-piperazineacetic acid-BBN(7-14) wherein the BBN(7-14) sequence is SEQ ID NO: 1;

DO3A-monoamide-N-4-aminoethyl-N-1-piperazineacetic acid-BBN(7-14) wherein the BBN(7-14) sequence is SEQ ID NO: 1;

DO3A-monoamide-(3S)-3-amino-1-carboxymethylcaprolactam-BBN(7-14) wherein the BBN(7-14) sequence is SEQ ID NO: 1;

DO3A-monoamide-(2S,6S,9)-6-amino-2-carboxymethyl-3,8-diazabicyclo-[4,3,0]-nonane-1,4-dione-BBN(7-14) wherein the BBN(7-14) sequence is SEQ ID NO: 1;

DO3A-monoamide-5-aminopentanoic acid-trans-4-aminomethylcyclohexane-1-carboxylic acid-BBN(7-14) wherein the BBN(7-14) sequence is SEQ ID NO: 1;

DO3A-monoamide-trans-4-aminomethylcyclohexane-1-carboxylic acid-D-phenylalanine-BBN(7-14) wherein the BBN(7-14) sequence is SEQ ID NO: 1;

DO3A-monoamide-4-aminomethylbenzoic acid-8-amino-3,6-dioxaoctanoic acid-BBN(7-14) wherein the BBN(7-14) sequence is SEQ ID NO: 1;

DO3A-monoamide-4-benzoyl-(L)-phenylalanine-trans-4-aminomethylcyclohexane-1-carboxylic acid-BBN(7-14) wherein the BBN(7-14) sequence is SEQ ID NO: 1;

DO3A-monoamide-trans-4-aminomethylcyclohexane-1-carboxylic acid-Arg-BBN(7-14) wherein the BBN(7-14) sequence is SEQ ID NO: 1;

DO3A-monoamide-trans-4-aminomethylcyclohexane-1-carboxylic acid-Lys-BBN(7-14) wherein the BBN(7-14) sequence is SEQ ID NO: 1;

DO3A-monoamide-trans-4-aminomethylcyclohexane-1-carboxylic acid-diphenylalanine-BBN(7-14) wherein the BBN(7-14) sequence is SEQ ID NO: 1;

DO3A-monoamide-trans-4-aminomethylcyclohexane-1-carboxylic acid-1-naphthylalanine-BBN(7-14) wherein the BBN(7-14) sequence is SEQ ID NO: 1;

DO3A-monoamide-trans-4-aminomethylcyclohexane-1-carboxylic acid-8-amino-3,6-dioxaoctanoic acid-BBN(7-14) wherein the BBN(7-14) sequence is SEQ ID NO: 1;

DO3A-monoamide-trans-4-aminomethylcyclohexane-1-carboxylic acid-Ser-BBN(7-14) wherein the BBN(7-14) sequence is SEQ ID NO: 1;

DO3A-monoamide-trans-4-aminomethylcyclohexane-1-carboxylic acid-2,3-diaminopropionic acid-BBN(7-14) wherein the BBN(7-14) sequence is SEQ ID NO: 1;

DO3A-monoamide-trans-4-aminomethylcyclohexane-1-carboxylic acid-biphenylalanine-BBN(7-14) wherein the BBN(7-14) sequence is SEQ ID NO: 1;

DO3A-monoamide-trans-4-aminomethylcyclohexane-1-carboxylic acid-(2S,5S)-5-amino-1,2,4,5,6,7-hexahydro-azepino[3,21-hi]indole-4-one-2-carboxylic acid-BBN(7-14) wherein the BBN(7-14) sequence is SEQ ID NO: 1;

DO3A-monoamide-trans-4-aminomethylcyclohexane-1-carboxylic acid-trans-4-aminomethylcyclohexane-1-carboxylic acid-BBN(7-14) wherein the BBN(7-14) sequence is SEQ ID NO: 1;

DO3A-monoamide-8-amino-3,6-dioxaoctanoic acid-phenylalanine-BBN(7-14) wherein the BBN(7-14) sequence is SEQ ID NO: 1;

DO3A-monoamide-trans-4-aminomethylcyclohexane-1-carboxylic acid-phenylalanine-BBN(7-14) wherein the BBN(7-14) sequence is SEQ ID NO: 1;

DO3A-monoamide-8-aminooctanoic acid-trans-4-aminomethylcyclohexane-1-carboxylic acid-BBN(7-14) wherein the BBN(7-14) sequence is SEQ ID NO: 1;

DO3A-monoamide-4'-aminomethyl-biphenyl-1-carboxylic acid-BBN(7-14) wherein the BBN(7-14) sequence is SEQ ID NO: 1;

DO3A-monoamide-3'-aminomethyl-biphenyl-3-carboxylic acid-BBN(7-14) wherein the BBN(7-14) sequence is SEQ ID NO: 1;

CMDOTA-Gly-4-aminobenzoic acid-BBN(7-14) wherein the BBN(7-14) sequence is SEQ ID NO: 1;

DO3A-monoamide-4-aminomethylphenoxyacetic acid-BBN(7-14) wherein the BBN(7-14) sequence is SEQ ID NO: 1;

DO3A-monoamide-Gly-4-aminophenylacetic acid-BBN(7-14) wherein the BBN(7-14) sequence is SEQ ID NO: 1;

HPDO3A-4-phenoxy-BBN(7-14) wherein the BBN(7-14) sequence is SEQ ID NO: 1;

DO3A-monoamide-3-aminomethylbenzoic acid-BBN(7-14) wherein the BBN(7-14) sequence is SEQ ID NO: 1;

DO3A-monoamide-4-aminomethylphenylacetic acid-BBN(7-14) wherein the BBN(7-14) sequence is SEQ ID NO: 1;

DO3A-monoamide-4-aminomethyl-3-methoxybenzoic acid-BBN(7-14) wherein the BBN(7-14) sequence is SEQ ID NO: 1;

Boa-Gly-4-aminobenzoic acid-BBN(7-14) wherein the BBN(7-14) sequence is SEQ ID NO: 1;

DO3A-monoamide-Gly-4-hydrazinobenzoyl-BBN(7-14) wherein the BBN(7-14) sequence is SEQ ID NO: 1;

DO3A-monoamide-4-aminobenzoic acid-BBN(7-14) wherein the BBN(7-14) sequence is SEQ ID NO: 1;

DO3A-monoamide-4-aminobenzoic acid-Gly-BBN(7-14) wherein the BBN(7-14) sequence is SEQ ID NO: 1;

DO3A-monoamide-Gly-6-Aminonicotinic acid-BBN(7-14) wherein the BBN(7-14) sequence is SEQ ID NO: 1;

DO3A-monoamide-Gly-4'-Amino-2'-methyl biphenyl-4-carboxylic acid-BBN(7-14) wherein the BBN(7-14) sequence is SEQ ID NO: 1;

DO3A-monoamide-Gly-3'-Aminobiphenyl-3-carboxylic acid-BBN(7-14) wherein the BBN(7-14) sequence is SEQ ID NO: 1;

DO3A-monoamide-Gly-1,2-diaminoethyl-Terephthalic acid-BBN(7-14) wherein the BBN(7-14) sequence is SEQ ID NO: 1;

DO3A-monoamide-Gly-Gly-4-aminobenzoic acid-BBN(7-14) wherein the BBN(7-14) sequence is SEQ ID NO: 1;

DO3A-monoamide-G-4-aminobenzoic acid-EWAVGHLM-NH$_2$ wherein EWAVGHLM-NH$_2$ is SEQ ID NO: 2;

DO3A-monoamide-G-4-aminobenzoic acid-QWAVGHLM-OH wherein QWAVGHLM-OH is SEQ ID NO: 1;

DO3A-monoamide-G-4-aminobenzoic acid-(D)-Phe-BBN(7-14) wherein the BBN(7-14) sequence is SEQ ID NO: 1;

DO3A-monoamide-G-4-aminobenzoic acid-QRLGNQWAVGHLM-NH$_2$ wherein QRLGNQWAVGHLM-NH$_2$ is SEQ ID NO: 3;

DO3A-monoamide-G-4-aminobenzoic acid-QRYGNQWAVGHLM-NH$_2$ wherein QRYGNQWAVGHLM-NH$_2$ is SEQ ID NO: 4;

DO3A-monoamide-G-4-aminobenzoic acid-QKYGNQ-WAVGHLM-NH$_2$ wherein QKYGNQWAVGHLM-NH$_2$ is SEQ ID NO: 5;

DO3A-monoamide-G-4-aminobenzoic acid-(D)-Phe-QWAVGHL-NH-Pentyl wherein QWAVGHL-NH-Pentyl is SEQ ID NO: 6;

DO3A-monoamide-G-4-aminobenzoic acid-QWSVaHLM-NH$_2$ wherein QWSVaHLM-NH$_2$ is SEQ ID NO: 7;

DO3A-monoamide-G-4-aminobenzoic acid-(D)-Phe-QWAVGHLL-NH$_2$ wherein QWAVGHLL-NH$_2$ is SEQ ID NO: 8;

DO3A-monoamide-G-4-aminobenzoic acid-(D)-Tyr-QWAV-Bala-HF-Nle-NH$_2$ wherein QWAV-Bala-HF-Nle-NH$_2$ is SEQ ID NO: 9;

DO3A-monoamide-G-4-aminobenzoic acid-Phe-QWAV-Bala-HF-Nle-NH$_2$ wherein QWAV-Bala-HF-Nle-NH$_2$ is SEQ ID NO: 9;

DO3A-monoamide-G-4-aminobenzoic acid-QWAGHFL-NH$_2$ wherein QWAGHFL-NH$_2$ is SEQ ID NO: 10;

DO3A-monoamide-G-4-aminobenzoic acid-LWAVGSFM-NH$_2$ wherein LWAVGSFM-NH$_2$ is SEQ ID NO: 11;

DO3A-monoamide-G-4-aminobenzoic acid-HWAVGHLM-NH$_2$ wherein HWAVGHLM-NH$_2$ is SEQ ID NO: 12;

DO3A-monoamide-G-4-aminobenzoic acid-LWAVGSFM-NH$_2$ wherein LWAVGSFM-NH$_2$ is SEQ ID NO: 11;

DO3A-monoamide-G-4-aminobenzoic acid-QWAVGHFM-NH$_2$ wherein QWAVGHFM-NH$_2$ is SEQ ID NO: 13;

DO3A-monoamide-Gly-3-aminobenzoic acid-BBN(7-14) wherein the BBN(7-14) sequence is SEQ ID NO: 1;

DO3A-monoamide-Gly-6-aminonaphthoic acid-BBN(7-14) wherein the BBN(7-14) sequence is SEQ ID NO: 1;

DO3A-monoamide-Gly-4-methylaminobenzoic acid-BBN(7-14) wherein the BBN(7-14) sequence is SEQ ID NO: 1;

Cm4 pm10d2a-Gly-4-aminobenzoic acid-BBN(7-14) wherein the BBN(7-14) sequence is SEQ ID NO: 1;

N,N-dimethylglycine-Ser-Cys(Acm)-Gly-Gly-4-aminobenzoic acid-BBN(7-14) wherein the BBN(7-14) sequence is SEQ ID NO: 1;

N,N-dimethylglycine-Ser-Cys(Acm)-Gly-Gly-3-amino-3-deoxycholic acid-BBN(7-14) wherein the BBN(7-14) sequence is SEQ ID NO: 1;

DO3A-monoamide-Gly-3-methoxy-4-aminobenzoic acid-BBN(7-14) wherein the BBN(7-14) sequence is SEQ ID NO: 1;

DO3A-monoamide-Gly-3-chloro-4-aminobenzoic acid-BBN(7-14) wherein the BBN(7-14) sequence is SEQ ID NO: 1;

DO3A-monoamide-Gly-3-methyl-4-aminobenzoic acid-BBN(7-14) wherein the BBN(7-14) sequence is SEQ ID NO: 1

DO3A-monoamide-Gly-3-hydroxy-4-aminobenzoic acid-BBN(7-14) wherein the BBN(7-14) sequence is SEQ ID NO: 1;

(DO3A-monoamide)$_2$-N,N'-Bis(2-aminoethyl)-succinamic acid-BBN(7-14) wherein the BBN(7-14) sequence is SEQ ID NO: 1;

DO3A-monoamide-G-4-aminobenzoic acid-QWAVGHFL-NH$_2$ wherein QWAVGHFL-NH$_2$ is SEQ ID NO: 22

DO3A-monoamide-4-aminomethylbenzoic acid-L-1-Naphthylalanine-QWAVGHLM-NH$_2$ wherein QWAVGHLM-NH$_2$ is SEQ ID NO: 1; and DO3A-monoamide-G-4-aminobenzoic acid-QWAVGN-MeHLM-NH$_2$ wherein QWAVGNMeHLM-NH$_2$ is SEQ ID NO: 15.

64. The compound of any one of embodiments 51, 52 or 53, wherein the optical label is selected from the group consisting of organic chromophores, organic fluorophores, light-absorbing compounds, light-reflecting compounds, light-scattering compounds, and bioluminescent molecules.

65. A method of imaging comprising the steps of:
administering to a patient a diagnostic imaging agent comprising the compound of embodiment 51 wherein M is a metal chelator complexed with a diagnostic radionuclide, and
imaging said patient.

66. A method of imaging comprising the steps of:
administering to a patient a diagnostic imaging agent comprising the compound of embodiment 63, and
imaging said patient.

67. A method of imaging comprising the steps of:
administering to a patient a diagnostic imaging agent comprising the compound of embodiment 51, wherein M is an optical label, and
imaging said patient.

68. A method for preparing a diagnostic imaging agent comprising the step of adding to an injectable medium a substance comprising the compound of embodiment 51.

69. A method of treating a patient comprising the step of administering to a patient a radiotherapeutic agent comprising the compound of embodiment 51 complexed with a therapeutic radionuclide.

70. A method of preparing a radiotherapeutic agent comprising the step of adding to an injectable medium a substance comprising the compound of embodiment 51.

71. A method of synthesizing DO3A-monoamide-Gly-(3β,5β,7α,12α)-3-amino-7,12-dihydroxycholan-24-oic acid-BBN(7-14) wherein the BBN(7-14) sequence is SEQ ID NO: 1 comprising the steps of:
(a) shaking a solution in a solid phase peptide synthesis vessel, said solution comprising a resin and at least one peptide building ingredient,
(b) flushing said solution, and
(c) washing said resin with DMA,
wherein said at least one peptide building ingredient includes DMA morpholine, (3β,5β,7α,12α)-3-[[(9H-fluoren-9-ylmethoxy)amino]acetyl]amino-7,12-dihydroxycholan-24-oic acid, HOBt, DIC, HATU or mixtures thereof, and
wherein each of steps (a), (b) and (c) are repeated until the compound DO3A-monoamide-Gly-(3β,5β,7α,12α)-3-amino-7,12-dihydroxycholan-24-oic acid-BBN(7-14) wherein the BBN(7-14) sequence is SEQ ID NO: 1 is obtained.

72. A method of synthesizing DO3A-monoamide-Gly-4-aminobenzoic acid-BBN(7-14) wherein the BBN(7-14) sequence is SEQ ID NO: 1 comprising the steps of:
(a) shaking a solution in a solid phase peptide synthesis vessel or reaction block, said solution comprising a resin and at least one peptide building ingredient,
(b) flushing said solution, and
(c) washing said resin with DMA,
wherein said at least one peptide building ingredient includes DMA, morpholine, Fmoc-4-aminobenzoic acid, HOBt, DIC, HBTU, HATU or mixtures thereof, and wherein each of steps (a), (b) and (c) are repeated until the compound DO3A-monoamide-Gly-4-aminobenzoic acid-BBN(7-14) wherein the BBN(7-14) sequence is SEQ ID NO: 1 is obtained.

73. A method for labeling DO3A-monoamide-Gly-(3β,5β,7α,12α)-3-amino-7,12-dihydroxycholan-24-oic acid-BBN(7-14) wherein the BBN(7-14) sequence is SEQ ID NO: 1 comprising the steps of
incubating a first solution comprising
DO3A-monoamide-Gly-(3β,5β,7α,12α)-3-amino-7,12-dihydroxycholan-24-oic acid-BBN(7-14) wherein the BBN(7-14) sequence is SEQ ID NO: 1,
ammonium acetate,
a radioactive metal precursor selected from the group consisting of $^{177}LuCl_3$ or $^{111}InCl_3$,
HCl, and
adding to said first solution a second solution comprising $Na_2EDTA.2H_2O$ and water to obtain a radiochemical purity greater than 95%.

74. A method for labeling DO3A-monoamide-Gly-4-aminobenzoic acid-BBN(7-14) wherein the BBN(7-14) sequence is SEQ ID NO: 1 comprising the steps of
incubating a first solution comprising
DO3A-monoamide-Gly-4-aminobenzoic acid-BBN(7-14) wherein the BBN(7-14) sequence is SEQ ID NO: 1,
ammonium acetate,
a radioactive metal precursor selected from the group consisting of $^{177}LuCl_3$ or $^{111}InCl_3$,
HCl, and
adding to said first solution a second solution comprising $Na_2EDTA.2H_2O$ and water to obtain a radiochemical purity greater than 95%.

75. A method of synthesizing DO3A-monoamide-Gly-(3β,5β,7α,12α)-3-amino-7,12-dihydroxycholan-24-oic acid-BBN(7-14) wherein the BBN(7-14) sequence is SEQ ID NO: 1 by coupling of individual amino acids, protected amino acids or modified amino acids, with any required additional treatments with reagents or processing steps before or after the coupling steps in solution.

76. A method of synthesizing DO3A-monoamide-Gly-4-aminobenzoic acid-BBN(7-14) wherein the BBN(7-14) sequence is SEQ ID NO: 1 by segment coupling of modified, protected, unprotected or otherwise variable peptide fragments combined with any required additional treatments with reagents or processing steps before or after the coupling steps in solution or on solid phase or via a combined solution and solid phase synthesis steps and methods.

77. A method of synthesizing DO3A-monoamide-Gly-(3β,5β,7α,12α)-3-amino-7,12-dihydroxycholan-24-oic acid-BBN(7-14) wherein the BBN(7-14) sequence is SEQ ID NO: 1 by coupling of individual amino acids protected amino acids or modified amino acids, with any required additional treatments with reagents or processing steps before or after the coupling steps in solution.

78. A compound of the general formula:

M-N-O-P-G wherein
M is DO3A, optionally complexed with a radionuclide;
N is 0, an alpha or non-alpha amino acid or other linking group;
O is an alpha or non-alpha amino acid; and
P is 0, an alpha or non-alpha amino acid or other linking group,
and G is a GRP receptor targeting peptide,
wherein at least one of N, O or P is 8-amino-3,6-dioxoctanoic acid.

79. The compound of embodiment 78, wherein the GRP receptor targeting peptide is selected from the group consisting of QWAVGHLM-OH (SEQ ID NO: 1), QWAVGHLM-NH$_2$ (SEQ ID NO: 1), QWAVGNMeHLM-NH$_2$ (SEQ ID NO: 15), QWAVGHFL-NH$_2$ (SEQ ID NO: 22), QRLGNQ-WAVGHLM-NH$_2$ (SEQ ID NO: 3), QRYGNQWAVGHLM-NH$_2$ (SEQ ID NO: 4), QKYGNQWAVGHLM-NH$_2$ (SEQ ID NO: 5), QWAVGHL-NH-Pentyl (SEQ ID NO: 6), QWS-VaHLM-NH$_2$ (SEQ ID NO: 7), QWAVGHLL-NH$_2$ (SEQ ID NO: 8), QWAV-Bala-HF-Nle-NH$_2$ (SEQ ID NO: 9), QWAGHFL-NH$_2$ (SEQ ID NO: 10), LWAVGSFM-NH$_2$ (SEQ ID NO: 11), HWAVGHLM-NH$_2$ (SEQ ID NO: 12), LWATGSFM-NH$_2$ (SEQ ID NO: 17), LWAVGSFM-NH$_2$ (SEQ ID NO: 11), QWAVaHLM-NH$_2$ (SEQ ID NO: 14), and QWAVGHFM-NH$_2$ (SEQ ID NO: 13).

80. A compound of the general formula:

M-N-O-P-G wherein
M is DO3A, optionally complexed with a radionuclide;
N is 0, an alpha or non-alpha amino acid or other linking group;
O is an alpha or non-alpha amino acid; and
P is 0, an alpha or non-alpha amino acid or other linking group,
and G is a GRP receptor targeting peptide,
wherein at least one of N, O or P is (3β,5β,12α)-3-amino-12-hydroxycholan-24-oic acid.

81. The compound of embodiment 80 wherein the GRP receptor targeting peptide is selected from the group consisting of QWAVGHLM-OH (SEQ ID NO: 1), QWAVGHLM-NH$_2$ (SEQ ID NO: 1), QWAVGNMeHLM-NH$_2$ (SEQ ID NO: 15), QWAVGHFL-NH$_2$ (SEQ ID NO: 22), QRLGNQ-WAVGHLM-NH$_2$ (SEQ ID NO: 3), QRYGNQWAVGHLM-NH$_2$ (SEQ ID NO: 4), QKYGNQWAVGHLM-NH$_2$ (SEQ ID NO: 5), QWAVGHL-NH-Pentyl (SEQ ID NO: 6), QWS-VaHLM-NH$_2$ (SEQ ID NO: 7), QWAVGHLL-NH$_2$ (SEQ ID NO: 8), QWAV-Bala-HF-Nle-NH$_2$ (SEQ ID NO: 9) QWAGHFL-NH$_2$ (SEQ ID NO: 10), LWAVGSFM-NH$_2$ (SEQ ID NO: 11), HWAVGHLM-NH$_2$ (SEQ ID NO: 12), LWATGSFM-NH$_2$ (SEQ ID NO: 17), LWAVGSFM-NH$_2$ (SEQ ID NO: 11), QWAVaHLM-NH$_2$ (SEQ ID NO: 14), and QWAVGHFM-NH$_2$ (SEQ ID NO: 13).

82. A compound of the general formula:

M-N-O-P-G wherein
M is DO3A, optionally complexed with a radionuclide;
N is 0, an alpha or non-alpha amino acid or other linking group;
O is an alpha or non-alpha amino acid; and
P is 0, an alpha or non-alpha amino acid or other linking group,
and G is a GRP receptor targeting peptide,
wherein at least one of N, O or P is 4-aminobenzoic acid.

83. The compound of embodiment 82, wherein the GRP receptor targeting peptide is selected from the group consisting of QWAVGHLM-OH (SEQ ID NO: 1), QWAVGHLM-NH$_2$ (SEQ ID NO: 1), QWAVGNMeHLM-NH$_2$ (SEQ ID NO: 15), QWAVGHFL-NH$_2$ (SEQ ID NO: 22), QRLGNQ-WAVGHLM-NH$_2$ (SEQ ID NO: 3), QRYGNQWAVGHLM-NH$_2$ (SEQ ID NO: 4), QKYGNQWAVGHLM-NH$_2$ (SEQ ID NO: 5), QWAVGHL-NH-Pentyl (SEQ ID NO: 6), QWS-VaHLM-NH$_2$ (SEQ ID NO: 7), QWAVGHLL-NH$_2$ (SEQ ID NO: 8), QWAV-Bala-HF-Nle-NH$_2$ (SEQ ID NO: 9)

QWAGHFL-NH$_2$ (SEQ ID NO: 10), LWAVGSFM-NH$_2$ (SEQ ID NO: 11), HWAVGHLM-NH$_2$ (SEQ ID NO: 12), LWATGSFM-NH$_2$ (SEQ ID NO: 17), LWAVGSFM-NH$_2$ (SEQ ID NO: 11), QWAVaHLM-NH$_2$ (SEQ ID NO: 14), QWAVGHFM-NH$_2$ (SEQ ID NO: 13), Nme-QWAVGHLM-NH$_2$ wherein QWAVGHLM-NH$_2$ is (SEQ ID NO: 1), Q-Ψ[CSNH]WAVGHLM-NH$_2$, Q-Ψ[CH$_2$NH]-WAVGHLM-NH$_2$, Q-ΨCH=CH]WAVGHLM-NH$_2$, α-MeQWAVGHLM-NH$_2$, QNme-WAVGHLM-NH$_2$, QW-Ψ[CSNH]-AVGHLM-NH$_2$, QW-Ψ[CH$_2$NH]-AVGHLM-NH$_2$, QW-Ψ[CH=CH]-AVGHLM-NH$_2$, Q-α-Me-WAVGHLM-NH$_2$, QW-Nme-AVGHLM-NH$_2$, QWA=Ψ[CSNH]-VGHLM-NH$_2$, QWA-Ψ[CH$_2$NH]-VGHLM-NH$_2$, QW-Aib-VGHLM-NH$_2$, QWAV-Sar-HLM-NH$_2$, QWAVG-T[CSNH]-HLM-NH$_2$, QWAVG-Ψ[CH=CH]-HLM-NH$_2$, QWAV-Dala-HLM-NH$_2$, QWAVG-Nme-His-LM-NH$_2$, QWAVG-H-Ψ[CSNH]-L-M-NH$_2$, QWAVG-H-Ψ[CH$_2$NH]-LM-NH$_2$, QWAVGH-Ψ[CH=CH]-LM-NH$_2$, QWAVG-α-Me-HLM-NH$_2$, QWAVGH-Nme-LM-NH$_2$, QWAVGH-α-MeLM-NH$_2$, QWAVGHF-L-NH$_2$ and QWAVGHLM-NH$_2$, wherein QWAVGHLM-NH$_2$ is SEQ ID NO: 1 and QWAVGHFL-NH$_2$ is SEQ ID NO: 22.

84. A method of phototherapy comprising administering to a patient a compound of any one of embodiments 1, 20 or 51 wherein M is an optical label useful in phototherapy.

85. A compound selected from the group consisting of:
DO3A-monoamide-G-4-aminobenzoic acid-QWAVaHLM-NH$_2$ wherein QWAVaHLM-NH$_2$ is SEQ ID NO: 14;
DO3A-monoamide-G-4-aminobenzoic acid-fQ-WAVGHLM-NH$_2$ wherein QWAVGHLM-NH$_2$ is SEQ ID NO: 1;
DO3A-monoamide-G-4-aminobenzoic acid-fQWAVGHLL-NH$_2$ wherein QWAVGHLL-NH$_2$ is SEQ ID NO: 8;
DO3A-monoamide-G-4-aminobenzoic acid-fQWAVGHL-NH-pentyl wherein QWAVGHL-NH-pentyl is SEQ ID NO: 6;
DO3A-monoamide-G-4-aminobenzoic acid-yQWAV-Bala-HFNle-NH$_2$ wherein QWAV-Bala-HFNle-NH$_2$ is SEQ ID NO: 9;
DO3A-monoamide-G-4-aminobenzoic acid-fQWAV-Bala-HFNle-NH$_2$ wherein QWAV-Bala-HFNle-NH$_2$ is SEQ ID NO: 9;
DO3A-monoamide-G-4-aminobenzoic acid-QWAVGHFL-NH$_2$ wherein QWAVGHFL-NH$_2$ is SEQ ID NO: 22;
DO3A-monoamide-G-4-aminobenzoic acid-QWAVGNMe-HisLM-NH$_2$ wherein QWAVGNMeHisLM-NH$_2$ is SEQ ID NO: 15;
DO3A-monoamide-G-4-aminobenzoic acid-LWAVGSFM-NH$_2$ wherein LWAVGSFM-NH$_2$ is SEQ ID NO: 11;
DO3A-monoamide-G-4-aminobenzoic acid-HWAVGHLM-NH$_2$ wherein HWAVGHLM-NH$_2$ is SEQ ID NO: 12;
DO3A-monoamide-G-4-aminobenzoic acid-LWATGHFM-NH$_2$ wherein LWATGHFM-NH$_2$ is SEQ ID NO: 16;
DO3A-monoamide-G-4-aminobenzoic acid-QWAVGHFM-NH$_2$ wherein QWAVGHFM-NH$_2$ is SEQ ID NO: 13;
DO3A-monoamide-G-4-aminobenzoic acid-QRLGNQ-WAVGHLM-NH$_2$ wherein QRLGNQWAVGHLM-NH$_2$ is SEQ ID NO: 3;
DO3A-monoamide-G-4-aminobenzoic acid-QRYGNQ-WAVGHLM-NH$_2$ wherein QRYGNQWAVGHLM-NH$_2$ is SEQ ID NO: 4;
DO3A-monoamide-G-4-aminobenzoic acid-QKYGNQ-WAVGHLM-NH$_2$ wherein QKYGNQWAVGHLM-NH$_2$ is SEQ ID NO: 5;
Pglu-Q-Lys(DO3A-monoamide-G-4-aminobenzoic acid)-LGNQWAVGHLM-NH$_2$ wherein LGNQWAVGHLM-NH$_2$ is SEQ ID NO: 18;
DO3A-monoamide-G-3-amino-3-deoxycholic acid-QWAVaHLM-NH$_2$ wherein QWAVaHLM-NH$_2$ is SEQ ID NO: 14;
DO3A-monoamide-G-3-amino-3-deoxycholic acid-fQ-WAVGHLM-NH$_2$ wherein QWAVGHLM-NH$_2$ is SEQ ID NO: 1;
DO3A-monoamide-G-3-amino-3-deoxycholic acid-fQ-WAVGHLL-NH$_2$ wherein QWAVGHLL-NH$_2$ is SEQ ID NO: 8;
DO3A-monoamide-G-3-amino-3-deoxycholic acid-fQ-WAVGHL-NH-pentyl wherein QWAVGHL-NH-pentyl is SEQ ID NO: 6;
DO3A-monoamide-G-3-amino-3-deoxycholic acid-yQ-WAV-Bala-HFNle-NH$_2$ wherein QWAV-Bala-HFNle-NH$_2$ is SEQ ID NO: 9;
DO3A-monoamide-G-3-amino-3-deoxycholic acid-fQ-WAV-Bala-HFNle-NH$_2$ wherein QWAV-Bala-HFNle-NH$_2$ is SEQ ID NO: 9;
DO3A-monoamide-G-3-amino-3-deoxycholic acid-QWAVGHFL-NH$_2$ wherein QWAVGHFL-NH$_2$ is SEQ ID NO: 22
DO3A-monoamide-G-3-amino-3-deoxycholic acid-QWAVGNMeHLMNH$_2$ wherein QWAVGNMeHLMNH$_2$ is SEQ ID NO: 15;
DO3A-monoamide-G-3-amino-3-deoxycholic acid-LWAVGSFM-NH$_2$ wherein LWAVGSFM-NH$_2$ is SEQ ID NO: 11;
DO3A-monoamide-G-3-amino-3-deoxycholic acid-HWAVGHLM-NH$_2$ wherein HWAVGHLM-NH$_2$ is SEQ ID NO: 12;
DO3A-monoamide-G-3-amino-3-deoxycholic acid-LWATGHFM-NH$_2$ wherein LWATGHFM-NH$_2$ is SEQ ID NO: 16;
DO3A-monoamide-G-3-amino-3-deoxycholic acid-QWAVGHFM-NH$_2$ wherein QWAVGHFM-NH$_2$ is SEQ ID NO: 13
DO3A-monoamide-G-3-amino-3-deoxycholic acid-QRLGNQWAVGlyHLM-NH$_2$ wherein QRLGNQWAVGHLM-NH$_2$ is SEQ ID NO: 3;
DO3A-monoamide-G-3-amino-3-deoxycholic acid-QRYGNQWAVGHLM-NH$_2$ wherein QRYGNQWAVGHLM-NH$_2$ is SEQ ID NO: 4;
DO3A-monoamide-G-3-amino-3-deoxycholic acid-QKYGNQWAVGHLM-NH$_2$ wherein QKYGNQWAVGHLM-NH$_2$ is SEQ ID NO: 5; and
Pglu-Q-Lys(DO3A-monoamide-G-3-amino-3-deoxycholic acid)-LGNQWAVGHLM-NH$_2$ wherein LGNQWAVGHLM-NH$_2$ is SEQ ID NO: 18.

86. The method of any one of embodiments 16, 17, 39, 44, 49 or 69 further comprising administering a chemotherapeutic or other therapeutic agent.

87. A compound of any one of embodiments 78 or 80, wherein the GRP receptor targeting peptide is selected from the group consisting of Nme-QWAVGHLM-NH$_2$, Q-Ψ[CSNH]WAVGHLM-NH$_2$, Q-Ψ[CH$_2$NH]-WAVGHLM-NH$_2$, Q-Ψ[CH=CH]WAVGHLM-NH$_2$, α-MeQ-WAVGHLM-NH$_2$, QNme-WAVGHLM-NH$_2$, QW-Ψ[CSNH]-AVGHLM-NH$_2$, QW-Ψ[CH$_2$NH]-AVGHLM-NH$_2$, QW-Ψ[CH=CH]-AVGHLM-NH$_2$, Q-α-Me-WAVGHLM-NH$_2$, QW-Nme-AVGHLM-NH$_2$, QWA=Ψ[CSNH]-VGHLM-NH$_2$, QWA-Ψ[CH$_2$NH]-VGHLM-NH$_2$, QW-Aib-VGHLM-NH$_2$, QWAV-Sar-HLM-NH$_2$, QWAVG-Ψ[CSNH]-HLM-NH$_2$, QWAVG-Ψ[CH=CH]-HLM-NH$_2$, QWAV-Dala-HLM-NH$_2$, QWAVG-Nme-His-LM-NH$_2$, QWAVG-H-Ψ[CSNH]-L-M-NH$_2$, QWAVG-H-Ψ[CH$_2$NH]-LM-NH$_2$, QWAVGH-Ψ[CH=CH]-LM-NH$_2$, QWAVG-α-Me-HLM-NH$_2$, QWAVGH-Nme-LM-NH$_2$, QWAVGH-α-

MeLM-NH$_2$, QWAVGHF-L-NH$_2$ and QWAVGHLM-NH$_2$, wherein QWAVGHLM-NH$_2$ is SEQ ID NO: 1 and QWAVGHFL-NH$_2$ is SEQ ID NO: 22.

88. A method for targeting the gastrin releasing peptide receptor (GRP-R) and neuromedin-B receptor (NMB-R), said method comprising administering a compound of the general formula:

M-N-O-P-G wherein
M is an optical label or a metal chelator, optionally complexed with a radionuclide;
N is 0, an alpha or non-alpha amino acid or other linking group;
O is an alpha or non-alpha amino acid; and
P is 0, an alpha or non-alpha amino acid or other linking group,
and G is a GRP receptor targeting peptide,
wherein at least one of N, O or P is a non-alpha amino acid.

89. The method of embodiment 88, wherein at least one of N, O or P is a non-alpha amino acid with a cyclic group.

90. The method of embodiment 89, wherein N is Gly, O is 4-aminobenzoic acid and P is none.

91. A method of targeting the GRP-R and the NMB-R, said method comprising administering a compound of the general formula:

M-N-O-P-G wherein
M is an optical label or a metal chelator, optionally complexed with a radionuclide;
N is 0, an alpha amino acid, a substituted bile acid or other linking group;
O is an alpha amino acid or a substituted bile acid; and
P is 0, an alpha amino acid, a substituted bile acid or other linking group; and
G is a GRP receptor targeting peptide, and
wherein at least one of N, O or P is a substituted bile acid.

92. The method of embodiment 91, wherein N is Gly, O is (3β,5β,7α,12α)-3-amino-7,12-dihydroxycholan-24-oic acid, and P is none.

93. The method of any one of embodiments 88, 89 or 91, wherein the GRP receptor targeting peptide is selected from the group consisting of:
Nme-QWAVGHLM-NH$_2$,
Q-Ψ[CSNH]WAVGHLM-NH$_2$,
Q-Ψ[CH$_2$NH]-WAVGHLM-NH$_2$,
Q-Ψ[CH=CMWAVGHLM-NH$_2$,
α-MeQWAVGHLM-NH$_2$,
QNme-WAVGHLM-NH$_2$,
QW-Ψ[CSNH]-AVGHLM-NH$_2$,
QW-Ψ[CH$_2$NH]-AVGHLM-NH$_2$,
QW-Ψ[CH=CH]-AVGHLM-NH$_2$,
Q-α-Me-WAVGHLM-NH$_2$,
QW-Nme-AVGHLM-NH$_2$,
QWA=Ψ[CSNH]-VGHLM-NH$_2$,
QWA-Ψ[CH$_2$NH]-VGHLM-NH$_2$,
QW-Aib-VGHLM-NH$_2$,
QWAV-Sar-HLM-NH$_2$,
QWAVG-Ψ[CSNH]-HLM-NH$_2$,
QWAVG-Ψ[CH=CH]-HLM-NH$_2$,
QWAV-Dala-HLM-NH$_2$,
QWAVG-Nme-His-LM-NH$_2$,
QWAVG-H-Ψ[CSNH]-L-M-NH$_2$,
QWAVG-H-Ψ[CH$_2$NH]-LM-NH$_2$,
QWAVGH-Ψ[CH=CH]-LM-NH$_2$,
QWAVG-α-Me-HLM-NH$_2$,
QWAVGH-Nme-LM-NH$_2$, and
QWAVGH-α-MeLM-NH$_2$
wherein QWAVGHLM-NH$_2$ is SEQ ID NO: 1 and QWAVGHFL-NH$_2$ is SEQ ID NO: 22.

94. A method of improving the in vivo activity of a compound of any one of embodiments 1, 20, 51, 78, 80, or 82, comprising the step of modifying the GRP receptor targeting peptide so as to reduce proteolytic cleavage of said peptide.

95. The method of embodiment 94, wherein the modified GRP-R targeting peptide is an agonist.

96. A method of reducing proteolytic cleavage of a gastrin releasing peptide (GRP) analogue of any one of embodiments 1, 20, 51, 78, 80, or 82, said method comprising the step of modifying the peptide bond in the GRP-R targeting moiety.

97. The method of embodiment 96, wherein the modified GRP-R targeting peptide is an agonist.

98. A method of reducing proteolytic cleavage of a gastrin releasing peptide (GRP) analogue having a gastrin releasing peptide receptor (GRP-R) targeting moiety that is an agonist, said method comprising the step of modifying the peptide bond in the GRP-R targeting moiety.

99. The method of any one of embodiments 94, 96 or 98, wherein the GRP-R targeting moiety is selected from the group consisting of:
Nme-QWAVGHLM-NH$_2$,
Q-Ψ[CSNH]WAVGHLM-NH$_2$,
Q-Ψ[CH$_2$NH]-WAVGHLM-NH$_2$,
Q-Ψ[CH=CH]WAVGHLM-NH$_2$,
α-MeQWAVGHLM-NH$_2$,
QNme-WAVGHLM-NH$_2$,
QW-Ψ[CSNH]-AVGHLM-NH$_2$,
QW-Ψ[CH$_2$NH]-AVGHLM-NH$_2$,
QW-Ψ[CH=CH]-AVGHLM-NH$_2$,
Q-α-Me-WAVGHLM-NH$_2$,
QW-Nme-AVGHLM-NH$_2$,
QWA=Ψ[CSNH]-VGHLM-NH$_2$,
QWA-Ψ[CH$_2$NH]-VGHLM-NH$_2$,
QW-Aib-VGHLM-NH$_2$,
QWAV-Sar-HLM-NH$_2$,
QWAVG-Ψ[CSNH]-HLM-NH$_2$,
QWAVG-ΨP[CH=CH]-HLM-NH$_2$,
QWAV-Dala-HLM-NH$_2$,
QWAVG-Nme-His-LM-NH$_2$,
QWAVG-H-Ψ[CSNH]-L-M-NH$_2$,
QWAVG-H-Ψ[CH$_2$NH]-LM-NH$_2$,
QWAVGH-Ψ[CH=CH]-LM-NH$_2$,
QWAVG-α-Me-HLM-NH$_2$,
QWAVGH-Nme-LM-NH$_2$, and
QWAVGH-α-MeLM-NH$_2$
wherein QWAVGHLM-NH$_2$ is SEQ ID NO: 1 and QWAVGHFL-NH$_2$ is SEQ ID NO: 22.

100. A compound according to any one of embodiments 1, 20, 51, 78, 80, or 82, wherein G is a GRP receptor targeting peptide that has been modified so as to reduce proteolytic cleavage.

101. A method of conferring specificity for the GRP-R and/or the NMB-R on a compound comprising an optical label or metal chelator optionally complexed with a radionuclide and a GRP-R targeting peptide, comprising including in such compound a linker of the general formula:

N-O-P wherein
N is 0, an alpha or non-alpha amino acid or other linking group;
O is an alpha or non-alpha amino acid; and P is 0, an alpha or non-alpha amino acid or other linking group,
wherein at least one of N, O or P is a non-alpha amino acid.

102. A method of conferring specificity for the GRP-R and/or the NMB-R on a compound comprising an optical label or metal chelator optionally complexed with a radionuclide and a GRP-R targeting peptide, comprising including in such compound a linker of the general formula:

N-O-P wherein
N is 0, an alpha amino acid, a substituted bile acid or other linking group;
O is an alpha amino acid or a substituted bile acid; and
P is 0, an alpha amino acid, a substituted bile acid or other linking group,
wherein at least one of N, O or P is a substituted bile acid.

103. A method of conferring specificity for the GRP-R and/or the NMB-R on a compound comprising an optical label or metal chelator optionally complexed with a radionuclide and a GRP-R targeting peptide, comprising including in such compound a linker of the general formula:

N-O-P wherein
N is 0, an alpha amino acid, a non-alpha amino acid with a cyclic group or other linking group;
O is an alpha amino acid or a non-alpha amino acid with a cyclic group; and
P is 0, an alpha amino acid, a non-alpha amino acid with a cyclic group or other linking group,
wherein at least one of N, O or P is a non-alpha amino acid with a cyclic group.

104. A method of improving the in vivo activity of a compound comprising an optical label or metal chelator optionally complexed with a radionuclide and a GRP-R targeting peptide, comprising including in such compound a linker of the general formula:

N-O-P wherein
N is 0, an alpha or non-alpha amino acid or other linking group;
O is an alpha or non-alpha amino acid; and
P is 0, an alpha or non-alpha amino acid or other linking group,
wherein at least one of N, O or P is a non-alpha amino acid.

105. A method of improving the in vivo activity of a compound comprising an optical label or metal chelator optionally complexed with a radionuclide and a GRP-R targeting peptide, comprising including in such compound a linker of the general formula:

N-O-P wherein
N is 0, an alpha amino acid, a substituted bile acid or other linking group;
O is an alpha amino acid or a substituted bile acid; and
P is 0, an alpha amino acid, a substituted bile acid or other linking group,
wherein at least one of N, O or P is a substituted bile acid.

106. A method of improving the in vivo stability of a compound comprising an optical label or metal chelator optionally complexed with a radionuclide and a GRP-R targeting peptide, comprising including in such compound a linker of the general formula:

N-O-P wherein
N is 0, an alpha amino acid, a non-alpha amino acid with a cyclic group or other linking group;
O is an alpha amino acid or a non-alpha amino acid with a cyclic group; and
P is 0, an alpha amino acid, a non-alpha amino acid with a cyclic group or other linking group,
wherein at least one of N, O or P is a non-alpha amino acid with a cyclic group.

107. A compound having the following structure:

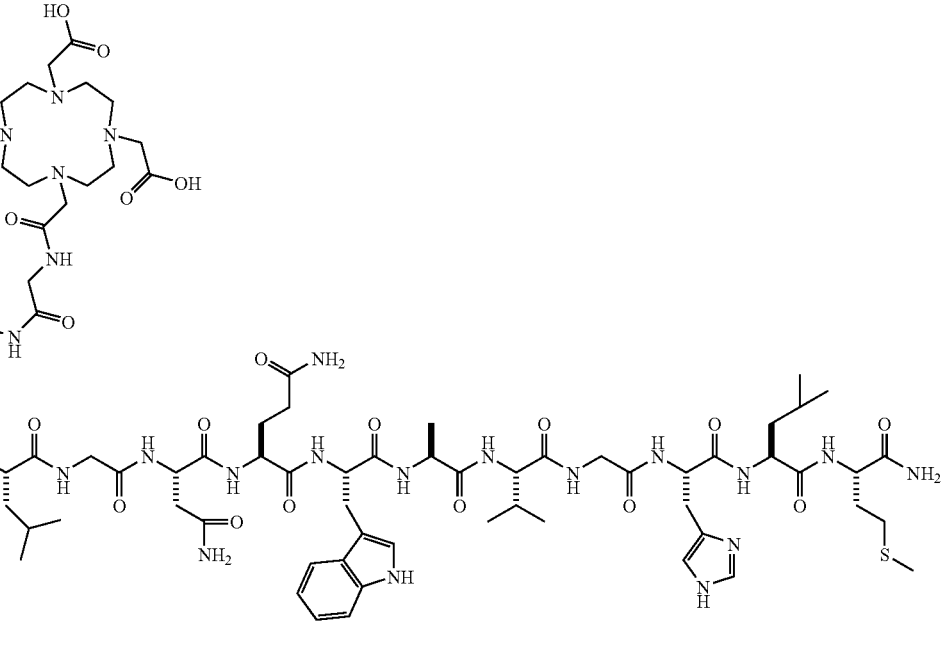

108. A compound of the general formula:

M-N-O-P-G wherein
M is an metal chelator of formula 8:

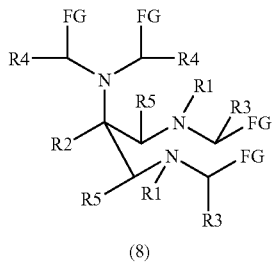

(8)

optionally complexed with a radionuclide, wherein
$R_1$ is hydrogen, $C_1$-$C_{20}$ alkyl optionally substituted with one or more carboxy groups, $C_3$-$C_{10}$ cycloalkyl, $C_4$-$C_{20}$ cycloalkylalkyl, aryl, arylalkyl or the two $R_1$ groups, taken together, form a straight or cyclic $C_2$-$C_{10}$ alkylene group or an ortho-disubstituted arylene;
$R_2$ is hydrogen, carboxy, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety, and a group bearing an amino moiety, each of which may be further optionally substituted with functional groups which allow conjugation with a suitable molecule able to interact with physiological systems;
$R_3$, $R_4$ and $R_5$, which can be the same or different, are hydrogen, carboxy, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amino moiety, each of which may be further optionally substituted with functional groups which allow conjugation with a suitable molecule able to interact with physiological systems; and
FG, which can be the same or different, are carboxy, —$PO_3H_2$ or —RP(O)OH groups, wherein R is hydrogen, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amino moiety, each of which may be further optionally substituted with functional groups which allow conjugation with a suitable molecule able to interact with physiological systems;
N is 0, an alpha amino acid, a non-alpha amino acid with a cyclic group or other linking group;
O is an alpha amino acid or a non-alpha amino acid with a cyclic group;
P is 0, an alpha amino acid, a non-alpha amino acid with a cyclic group, or other linking group; and
G is a GRP receptor targeting peptide,
wherein at least one of N, O or P is a non-alpha amino acid with a cyclic group.

109. A compound of the general formula:

M-N-O-P-G wherein
M is an metal chelator of formula 8:

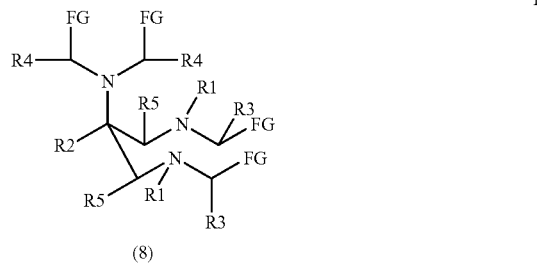

(8)

optionally complexed with a radionuclide, wherein
$R_1$ is hydrogen, $C_1$-$C_{20}$ alkyl optionally substituted with one or more carboxy groups, $C_3$-$C_{10}$ cycloalkyl, $C_4$-$C_{20}$ cycloalkylalkyl, aryl, arylalkyl or the two $R_1$ groups, taken together, form a straight or cyclic $C_2$-$C_{10}$ alkylene group or an ortho-disubstituted arylene;
$R_2$ is hydrogen, carboxy, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety, and a group bearing an amino moiety, each of which may be further optionally substituted with functional groups which allow conjugation with a suitable molecule able to interact with physiological systems;
$R_3$, $R_4$ and $R_5$, which can be the same or different, are hydrogen, carboxy, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amino moiety, each of which may be further optionally substituted with functional groups which allow conjugation with a suitable molecule able to interact with physiological systems; and
FG, which can be the same or different, are carboxy, —$PO_3H_2$ or —RP(O)OH groups, wherein R is hydrogen, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amino moiety, each of which may be further optionally substituted with functional groups which allow conjugation with a suitable molecule able to interact with physiological systems;
N is 0, an alpha or non-alpha amino acid or other linking group;
O is an alpha or non-alpha amino acid; and
P is 0, an alpha or non-alpha amino acid or other linking group, and G is a GRP receptor targeting peptide,
wherein at least one of N, O or P is a non-alpha amino acid.

110. A compound of the general formula:

M-N-O-P-G wherein
M is an metal chelator of formula 8:

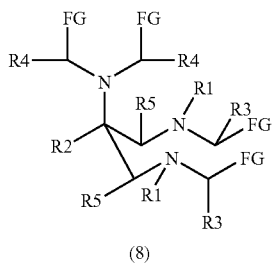

(8)

optionally complexed with a radionuclide, wherein
$R_1$ is hydrogen, $C_1$-$C_{20}$ alkyl optionally substituted with one or more carboxy groups, $C_3$-$C_{10}$ cycloalkyl, $C_4$-$C_{20}$ cycloalkylalkyl, aryl, arylalkyl or the two $R_1$ groups, taken together, form a straight or cyclic $C_2$-$C_{10}$ alkylene group or an ortho-disubstituted arylene;
$R_2$ is hydrogen, carboxy, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety, and a group bearing an amino moiety, each of which may be further optionally substituted with functional groups which allow conjugation with a suitable molecule able to interact with physiological systems;
$R_3$, $R_4$ and $R_5$, which can be the same or different, are hydrogen, carboxy, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amino moiety, each of which may be further optionally substituted with functional groups which allow conjugation with a suitable molecule able to interact with physiological systems; and
FG, which can be the same or different, are carboxy, —$PO_3H_2$ or —$RP(O)OH$ groups, wherein R is hydrogen, or an optionally substituted group selected from $C_1$-$C_{20}$ alkyl, $C_3$-$C_{10}$ cycloalkyl, $C_4$-$C_{20}$ cycloalkylalkyl, aryl, arylalkyl, a group bearing an acidic moiety and a group bearing an amino moiety, each of which may be further optionally substituted with functional groups which allow conjugation with a suitable molecule able to interact with physiological systems;
N is 0, an alpha amino acid, a substituted bile acid or other linking group;
O is an alpha amino acid or a substituted bile acid; and
P is 0, an alpha amino acid, a substituted bile acid or other linking group; and
G is a GRP receptor targeting peptide, and
wherein at least one of N, O or P is a substituted bile acid.
111. A compound of the general formula:
M-N-O-P-G wherein
M is an Aazta metal chelator or a derivative thereof optionally complexed with a radionuclide;
N is 0, an alpha amino acid, a non-alpha amino acid with a cyclic group or other linking group;
O is an alpha amino acid or a non-alpha amino acid with a cyclic group;
P is 0, an alpha amino acid, a non-alpha amino acid with a cyclic group, or other linking group; and
G is a GRP receptor targeting peptide,
wherein at least one of N, O or P is a non-alpha amino acid with a cyclic group.

112. A compound of the general formula:
M-N-O-P-G wherein
M is an Aazta chelator or a derivative thereof, optionally complexed with a radionuclide;
N is 0, an alpha or non-alpha amino acid or other linking group;
O is an alpha or non-alpha amino acid; and
P is 0, an alpha or non-alpha amino acid or other linking group,
and G is a GRP receptor targeting peptide,
wherein at least one of N, O or P is a non-alpha amino acid.
113. A compound of the general formula:
M-N-O-P-G wherein
M is an Aazta metal chelator or a derivative thereof, optionally complexed with a radionuclide;
N is 0, an alpha amino acid, a substituted bile acid or other linking group;
O is an alpha amino acid or a substituted bile acid; and
P is 0, an alpha amino acid, a substituted bile acid or other linking group; and
G is a GRP receptor targeting peptide, and
wherein at least one of N, O or P is a substituted bile acid.
114. The compound of any one of embodiments 108 to 113, wherein G is an agonist or a peptide which confers agonist activity.
115. The compound of embodiment 108 or 111, wherein the non-alpha amino acid with a cyclic group is selected from the group consisting of:
4-aminobenzoic acid;
4-aminomethyl benzoic acid;
trans-4-aminomethylcyclohexane carboxylic acid;
4-(2-aminoethoxy)benzoic acid;
isonipecotic acid;
2-aminomethylbenzoic acid;
4-amino-3-nitrobenzoic acid;
4-(3-carboxymethyl-2-keto-1-benzimidazolyl)-piperidine;
6-(piperazin-1-yl)-4-(3H)-quinazolinone-3-acetic acid;
(2S,5S)-5-amino-1,2,4,5,6,7-hexahydro-azepino[3,21-hi]indole-4-one-2-carboxylic acid;
(4S,7R)-4-amino-6-aza-5-oxo-9-thiabicyclo[4.3.0]nonane-7-carboxylic acid;
3-carboxymethyl-1-phenyl-1,3,8-triazaspiro[4.5]decan-4-one;
N1-piperazineacetic acid;
N-4-aminoethyl-N-1-acetic acid;
(3S)-3-amino-1-carboxymethylcaprolactam; and
(2S,6S,9)-6-amino-2-carboxymethyl-3,8-diazabicyclo-[4,3,0]-nonane-1,4-dione.
116. The compound of embodiment 109 or 112, wherein the non-alpha amino acid is selected from the group consisting of:
8-amino-3,6-dioxaoctanoic acid;
N-4-aminoethyl-N-1-piperazine-acetic acid; and
polyethylene glycol derivatives having the formula $NH_2$—$(CH_2CH_2O)n$—$CH_2CO_2H$ or $NH_2$—$(CH_2CH_2O)n$-$CH_2CH_2CO_2H$ where n=2 to 100.
117. The compound of embodiment 110 or 113, wherein the substituted bile acid is selected from the group consisting of:
3β-amino-3-deoxycholic acid;
(3β,5β)-3-aminocholan-24-oic acid;
(3β,5β,12α)-3-amino-12-hydroxycholan-24-oic acid;
(3β,5β,7α,12α)-3-amino-7,12-dihydroxycholan-24-oic acid;
Lys-(3,6,9)-trioxaundecane-1,11-dicarbonyl-3,7-dideoxy-3-aminocholic acid);
(3β,5β,7α,12α)-3-amino-7-hydroxy-12-oxocholan-24-oic acid; and
(3β,5β,7α)-3-amino-7-hydroxycholan-24-oic acid.

118. A method of imaging comprising the steps of:
administering to a patient a diagnostic imaging agent comprising the compound of any one of embodiments 109 to 113 wherein M is a metal chelator complexed with a radioactive or paramagnetic metal, and
imaging said patient.

119. A method for preparing a diagnostic imaging agent comprising the step of adding to an injectable medium a substance comprising the compound of any one of embodiments 108 to 113.

120. A method of treating a patient comprising the step of administering to a patient a radiotherapeutic agent comprising the compound of any one of embodiments 108 to 113 complexed with a therapeutic radionuclide.

121. A method of preparing a radiotherapeutic agent comprising the step of adding to an injectable medium a substance comprising the compound of any one of embodiments 108 to 113.

122. The compound of embodiment 108, wherein M is Aazta, N is Gly, O is 4-aminobenzoic acid, P is 0, and G is BBN (7-14), wherein BBN(7-14) is SEQ ID NO: 1.

123. The compound of embodiment 108, wherein M is CyAazta, N is Gly, O is 4-aminobenzoic acid, P is 0, and G is BBN (7-14), wherein BBN(7-14) is SEQ ID NO: 1.

124. The compound of embodiment 110, wherein M is Aazta, N is Gly, O is (3β,5β,7α,12α)-3-amino-7,12-dihydroxycholan-24-oic acid, P is 0, and G is BBN (7-14), wherein BBN(7-14) is SEQ ID NO: 1.

125. The compound of embodiment 110, wherein M is CyAazta, N is Gly, O is (3β,5β,7α,12α)-3-amino-7,12-dihydroxycholan-24-oic acid, P is 0, and G is BBN (7-14), wherein BBN(7-14) is SEQ ID NO: 1.

126. A compound having the following structure:

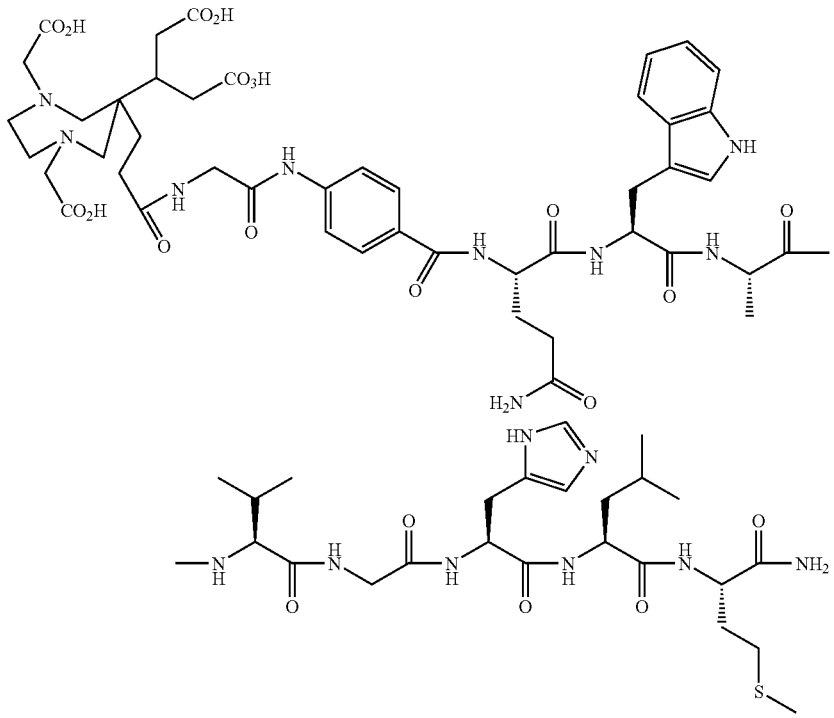

127. A compound having the following structure:

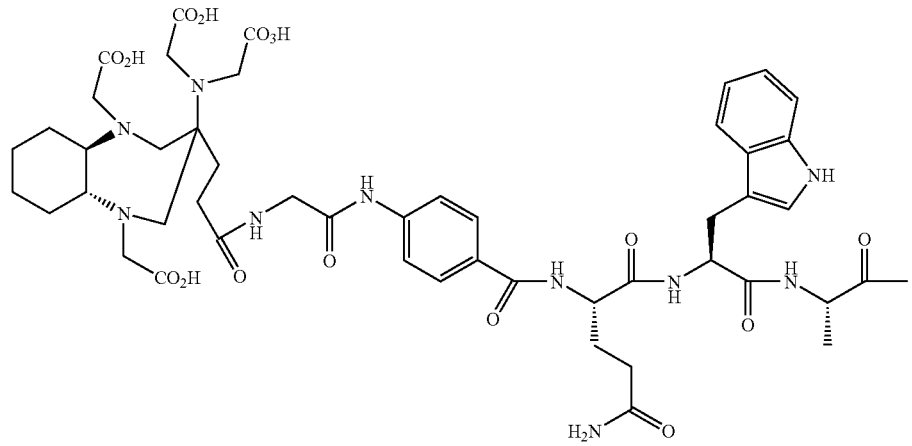

-continued

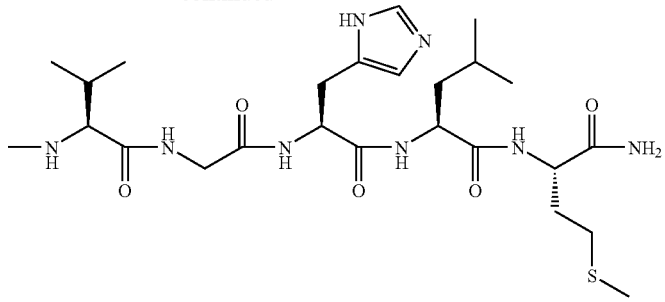

128. A method for increasing the targeting of a labeled compound to a GRP receptor expressing target tissue within a subject comprising the steps of:
administering to a subject a first dose comprising a GRP receptor targeting peptide to occupy a GRP receptor binding site in non-target tissue,
administering to said subject a second dose comprising a labeled compound of the general formula:

M-N-O-P-G wherein
M is an optical label or a metal chelator complexed with a radionuclide;
N is 0, an alpha or non-alpha amino acid or other linking group;
O is an alpha or non-alpha amino acid; and
P is 0, an alpha or non-alpha amino acid or other linking group,
and G is a GRP receptor targeting peptide, and
wherein at least one of N, O or P is a non-alpha amino acid.

129. The method of embodiment 128, wherein the step of administering said first dose and the step of administering said second dose occur contemporaneously.

130. The method of embodiment 128, wherein the GRP receptor targeting peptide in the first dose is conjugated to a linker.

131. The method of embodiment 128, wherein the GRP receptor targeting peptide in the first dose is conjugated to a linker which is attached to one or more metal chelator.

132. The method of embodiment 132, wherein the GRP receptor targeting peptide, linker and metal chelator of said first dose are the same as the GRP receptor targeting peptide, N-O-P linker and metal chelator of the second dose.

133. The method of embodiment 128, wherein the non-alpha amino acid is selected from the group consisting of:
8-amino-3,6-dioxaoctanoic acid;
N-4-aminoethyl-N-1-piperazine-acetic acid; and
polyethylene glycol derivatives having the formula NH$_2$—(CH$_2$CH$_2$O)n-CH$_2$CO$_2$H or NH$_2$—(CH$_2$CH$_2$O)n-CH$_2$CH$_2$CO$_2$H where n=2 to 100.

134. The method of embodiment 128, wherein the metal chelator is selected from the group consisting of DTPA, DOTA, DO3A, HP-DO3A, EDTA, TETA, EHPG, HBED, NOTA, DOTMA, TETMA, PDTA, TTHA, LICAM, MECAM, MDOTA, N,N-dimethylGly-Ser-Cys, Aazta and derivatives thereof.

135. The method of embodiment 128, wherein the labeled compound comprises a compound selected from the group consisting of:

N,N-dimethylglycine-Ser-Cys(Acm)-Gly-Lys-8-amino-3,6-dioxaoctanoic acid-BBN(7-14) wherein the BBN(7-14) sequence is SEQ ID NO: 1;
N,N-dimethylglycine-Ser-Cys(Acm)-Gly-Arg-8-amino-3,6-dioxaoctanoic acid-BBN(7-14) wherein the BBN(7-14) sequence is SEQ ID NO: 1;
N,N-dimethylglycine-Ser-Cys(Acm)-Gly-Asp-8-amino-3,6-dioxaoctanoic acid-BBN(7-14) wherein the BBN(7-14) sequence is SEQ ID NO: 1;
N,N-dimethylglycine-Ser-Cys(Acm)-Gly-Ser-8-amino-3,6-dioxaoctanoic acid-BBN(7-14) wherein the BBN(7-14) sequence is SEQ ID NO: 1;
N,N-dimethylglycine-Ser-Cys(Acm)-Gly-Gly-8-amino-3,6-dioxaoctanoic acid-BBN(7-14) wherein the BBN(7-14) sequence is SEQ ID NO: 1;
N,N-dimethylglycine-Ser-Cys(Acm)-Gly-Glu-8-amino-3,6-dioxaoctanoic acid-BBN(7-14) wherein the BBN(7-14) sequence is SEQ ID NO: 1;
N,N-dimethylglycine-Ser-Cys(Acm)-Gly-Dala-8-amino-3,6-dioxaoctanoic acid-BBN(7-14) wherein the BBN(7-14) sequence is SEQ ID NO: 1;
N,N-dimethylglycine-Ser-Cys(Acm)-Gly-8-amino-3,6-dioxaoctanoic acid-Lys-BBN(7-14) wherein the BBN(7-14) sequence is SEQ ID NO: 1;
N,N-dimethylglycine-Ser-Cys(Acm)-Gly-8-amino-3,6-dioxaoctanoic acid-Arg-BBN(7-14) wherein the BBN(7-14) sequence is SEQ ID NO: 1;
N,N-dimethylglycine-Ser-Cys(Acm)-Gly-8-amino-3,6-dioxaoctanoic acid-Asp-BBN(7-14) wherein the BBN(7-14) sequence is SEQ ID NO: 1;
N,N-dimethylglycine-Ser-Cys(Acm)-Gly-8-amino-3,6-dioxaoctanoic acid-Ser-BBN(7-14) wherein the BBN(7-14) sequence is SEQ ID NO: 1;
N,N-dimethylglycine-Ser-Cys(Acm)-Gly-8-amino-3,6-dioxaoctanoic acid-Gly-BBN(7-14) wherein the BBN(7-14) sequence is SEQ ID NO: 1;
N,N-dimethylglycine-Ser-Cys(Acm)-Gly-8-amino-3,6-dioxaoctanoic acid-Glu-BBN(7-14) wherein the BBN(7-14) sequence is SEQ ID NO: 1;
N,N-dimethylglycine-Ser-Cys(Acm)-Gly-8-amino-3,6-dioxaoctanoic acid-Dala-BBN(7-14) wherein the BBN(7-14) sequence is SEQ ID NO: 1;
N,N-dimethylglycine-Ser-Cys(Acm)-Gly-8-amino-3,6-dioxaoctanoic acid-8-amino-3,6-dioxaoctanoic acid-BBN(7-14) wherein the BBN(7-14) sequence is SEQ ID NO: 1;
N,N-dimethylglycine-Ser-Cys(Acm)-Gly-8-amino-3,6-dioxaoctanoic acid-2,3-diaminopropionic acid-BBN(7-14) wherein the BBN(7-14) sequence is SEQ ID NO: 1;
N,N-dimethylglycine-Ser-Cys(Acm)-Gly-8-amino-3,6-dioxaoctanoic acid-BBN(7-14) wherein the BBN(7-14) sequence is SEQ ID NO: 1;

N,N-dimethylglycine-Ser-Cys(Acm)-Gly-2,3-diaminopropionic acid-8-amino-3,6-dioxaoctanoic acid-BBN(7-14) wherein the BBN(7-14) sequence is SEQ ID NO: 1;

N,N-dimethylglycine-Ser-Cys(Acm)-Gly-Asp-8-amino-3,6-dioxaoctanoic acid-Gly-BBN(7-14) wherein the BBN (7-14) sequence is SEQ ID NO: 1;

N,N-dimethylglycine-Ser-Cys(Acm)-Gly-8-amino-3,6-dioxaoctanoic acid-Asp-Gly-BBN(7-14) wherein the BBN (7-14) sequence is SEQ ID NO: 1;

N,N-dimethylglycine-Ser-Cys(Acm)-Gly-8-amino-3,6-dioxaoctanoic acid-Ser-Gly-BBN(7-14) wherein the BBN (7-14) sequence is SEQ ID NO: 1;

N,N-dimethylglycine-Ser-Cys(Acm)-Gly-8-amino-3,6-dioxaoctanoic acid-Arg-Gly-BBN(7-14) wherein the BBN (7-14) sequence is SEQ ID NO: 1;

N,N-dimethylglycine-Ser-Cys(Acm)-Gly-8-amino-3,6-dioxaoctanoic acid-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-2,3-diaminopropionic acid-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-Lys-Gly-BBN(7-14) wherein the BBN (7-14) sequence is SEQ ID NO: 1;

N,N-dimethylglycine-Ser-Cys(Acm)-Gly-2,3-diaminopropionic acid-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-Asp-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-Ser-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-Arg-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-8-amino-3,6-dioxaoctanoic acid-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-2,3-diaminopropionic acid-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-Lys-BBN(7-14) wherein the BBN(7-14) sequence is SEQ ID NO: 1;

N,N-dimethylglycine-Ser-Cys(Acm)-Gly-N-1-piperazineacetic acid-Asp-BBN(7-14) wherein the BBN(7-14) sequence is SEQ ID NO: 1;

N,N-dimethylglycine-Ser-Cys(Acm)-Gly-N-1-piperazineacetic acid-Ser-BBN(7-14) wherein the BBN(7-14) sequence is SEQ ID NO: 1;

N,N-dimethylglycine-Ser-Cys(Acm)-Gly-N-1-piperazineacetic acid-Arg-BBN(7-14) wherein the BBN(7-14) sequence is SEQ ID NO: 1;

N,N-dimethylglycine-Ser-Cys(Acm)-Gly-N-1-piperazineacetic acid-8-amino-3,6-dioxaoctanoic acid-BBN(7-14) wherein the BBN(7-14) sequence is SEQ ID NO: 1;

N,N-dimethylglycine-Ser-Cys(Acm)-Gly-N-1-piperazineacetic acid-2,3-diaminopropionic acid BBN(7-14) wherein the BBN(7-14) sequence is SEQ ID NO: 1;

N,N-dimethylglycine-Ser-Cys(Acm)-Gly-N-1-piperazineacetic acid-Lys-BBN(7-14) wherein the BBN(7-14) sequence is SEQ ID NO: 1;

N,N-dimethylglycine-Ser-Cys(Acm)-Gly-4-Hydroxyproline-8-amino-3,6-dioxaoctanoic acid-BBN(7-14) wherein the BBN(7-14) sequence is SEQ ID NO: 1;

N,N-dimethylglycine-Ser-Cys(Acm)-Gly-4-aminoproline-8-amino-3,6-dioxaoctanoic acid-BBN(7-14) wherein the BBN(7-14) sequence is SEQ ID NO: 1;

N,N-dimethylglycine-Ser-Cys(Acm)-Gly-Lys-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-Arg-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-Ser-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-Asp-8-amino-3,6-dioxaoctanoic acid-Gly-BBN(7-14) wherein the BBN (7-14) sequence is SEQ ID NO: 1;

N,N-dimethylglycine-Ser-Cys(Acm)-Gly-8-amino-3,6-dioxaoctanoic acid-Asp-Gly-BBN(7-14) wherein the BBN (7-14) sequence is SEQ ID NO: 1;

N,N-dimethylglycine-Ser-Cys(Acm)-Gly-8-amino-3,6-dioxaoctanoic acid-Ser-Gly-BBN(7-14) wherein the BBN (7-14) sequence is SEQ ID NO: 1;

N,N-dimethylglycine-Ser-Cys(Acm)-Gly-8-amino-3,6-dioxaoctanoic acid-Arg-Gly-BBN(7-14) wherein the BBN (7-14) sequence is SEQ ID NO: 1;

N,N-dimethylglycine-Ser-Cys(Acm)-Gly-8-amino-3,6-dioxaoctanoic acid-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-2,3-diaminopropionic acid-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-Lys-Gly-BBN(7-14) wherein the BBN (7-14) sequence is SEQ ID NO: 1; and N,N-dimethylglycine-Ser-Cys(Acm)-Gly-2,3-diaminopropionic acid-8-amino-3,6-dioxaoctanoic acid-Gly-BBN(7-14) wherein the BBN(7-14) sequence is SEQ ID NO: 1.

136. The method of embodiment 128, wherein the labeled compound comprises a compound selected from the group consisting of:

DO3A-monoamide-8-amino-3,6-dioxaoctanoic acid-diaminopropionic acid-BBN(7-14) wherein the BBN(7-14) sequence is SEQ ID NO: 1;

DO3A-monoamide-8-amino-3,6-dioxaoctanoic acid-biphenylalanine-BBN(7-14) wherein the BBN(7-14) sequence is SEQ ID NO: 1;

DO3A-monoamide-8-amino-3,6-dioxaoctanoic acid-diphenylalanine-BBN(7-14) wherein the BBN(7-14) sequence is SEQ ID NO: 1;

DO3A-monoamide-8-amino-3,6-dioxaoctanoic acid-4-benzoylphenylalanine-BBN(7-14) wherein the BBN(7-14) sequence is SEQ ID NO: 1;

DO3A-monoamide-5-aminopentanoic acid-8-amino-3,6-dioxaoctanoic acid-BBN(7-14) wherein the BBN(7-14) sequence is SEQ ID NO: 1;

DO3A-monoamide-8-amino-3,6-dioxaoctanoic acid-D-phenylalanine-BBN(7-14) wherein the BBN(7-14) sequence is SEQ ID NO: 1;

DO3A-monoamide-8-aminooctanoic acid-8-amino-3,6-dioxaoctanoic acid-BBN(7-14) wherein the BBN(7-14) sequence is SEQ ID NO: 1;

DO3A-monoamide-E(G8-amino-3,6-dioxaoctanoic acid-8-amino-3,6-dioxaoctanoic acid QWAVGHLM-NH$_2$)-8- aminooctanoic acid-8-aminooctanoic acid-BBN(7-14) wherein the BBN(7-14) sequence is SEQ ID NO: 1; and
DO3A-monoamide-E(G-Aoa-Aoa-QWAVGHLM-NH$_2$)-8-aminooctanoic acid-8-aminooctanoic acid-BBN(7-14) wherein the BBN(7-14) sequence is SEQ ID NO: 1.

137. A method for increasing the targeting of a labeled compound to a GRP receptor expressing target tissue within a subject comprising the steps of:
administering to a subject a first dose comprising a GRP receptor targeting peptide to occupy GRP receptor binding sites in non-target tissues,
administering to said subject a second dose comprising a labeled compound of the general formula:

M-N-O-P-G wherein
M is an optical label or a metal chelator complexed with a radionuclide;
N is 0, an alpha amino acid, a substituted bile acid or other linking group;
O is an alpha amino acid or a substituted bile acid;
P is 0, an alpha amino acid, a substituted bile acid or other linking group;
G is a GRP receptor targeting peptide, and
wherein at least one of N, O or P is a substituted bile acid.

138. The method of embodiment 137, wherein the step of administering said first dose and the step of administering said second dose occur contemporaneously.

139. The method of embodiment 137, wherein the GRP receptor targeting peptide in the first dose is conjugated to a linker.

140. The method of embodiment 137 wherein the GRP receptor targeting peptide in the first dose is conjugated to a linker which is attached to one or more metal chelator.

141. The method embodiment 140 wherein the GRP receptor targeting peptide, linker and metal chelator of said first dose are the same as the GRP receptor targeting peptide, N-O-P linker and metal chelator of the second dose.

142. The method of embodiment 137, wherein the substituted bile acid is selected from the group consisting of:
3β-amino-3-deoxycholic acid;
(3β,5β)-3-aminocholan-24-oic acid;
(3β,5β,12α)-3-amino-12-hydroxycholan-24-oic acid;
(3β,5β,7α,12α)-3-amino-7,12-dihydroxycholan-24-oic acid;
Lys-(3,6,9)-trioxaundecane-1,11-dicarbonyl-3,7-dideoxy-3-aminocholic acid);
(3β,5β,7α,12α)-3-amino-7-hydroxy-12-oxocholan-24-oic acid; and
(3β,5β,7α)-3-amino-7-hydroxycholan-24-oic acid.

143. The method of embodiment 137, wherein the metal chelator is selected from the group consisting of: DTPA, DOTA, DO3A, HPDO3A, EDTA, TETA, CMDOTA, N,N-dimethylGly-Ser-Cys, Aazta and derivatives thereof 144. The method of embodiment 137, wherein the labeled compound comprises a compound selected from the group consisting of:
DO3A-monoamide-Gly-(3β,5β)-3-aminocholan-24-oic acid-BBN(7-14) wherein the BBN(7-14) sequence is SEQ ID NO: 1;
DO3A-monoamide-Gly-(3β,5β,12α)-3-amino-12-hydroxycholan-24-oic acid-BBN(7-14) wherein the BBN (7-14) sequence is SEQ ID NO: 1;
DO3A-monoamide-Gly-(3β,5β,7α,12α)-3-amino-7,12-dihydroxycholan-24-oic acid-BBN(7-14) wherein the BBN(7-14) sequence is SEQ ID NO: 1;
DO3A-monoamide-Gly-Lys-(3,6,9)-trioxaundecane-1,11-dicarbonyl-3,7-dideoxy-3-aminocholic acid)-Arg-BBN(7-14) wherein the BBN(7-14) sequence is SEQ ID NO: 1;
(3β,5β,7α,12α)-3-amino-7,12-dihydroxycholan-24-oic acid-3,6,9-trioxaundecane-1,11-dicarbonyl Lys (DO3A-monoamide-Gly)-Arg-BBN(7-14) wherein the BBN(7-14) sequence is SEQ ID NO: 1;
DO3A-monoamide-Gly-(3β,5β,7α,12α)-3-amino-12-oxocholan-24-oic acid-BBN(7-14) wherein the BBN(7-14) sequence is SEQ ID NO: 1;
DO3A-monoamide-1-amino-3,6-dioxaoctanoic acid-(3β,5β,7α,12α)-3-amino-7,12-dihydroxycholan-24-oic acid-BBN(7-14) wherein the BBN(7-14) sequence is SEQ ID NO: 1;
DO3A-monoamide-Gly-(3β,5β7α,12α)-3-amino-7,12-dihydroxycholan-24-oic acid-QWAVaHLM-NH$_2$ wherein QWAVaHLM-NH$_2$ is SEQ ID NO: 14;
DO3A-monoamide-Gly-(3β,5β7α,12α)-3-amino-7,12-dihydroxycholan-24-oic acid-f-QWAVGHLM-NH$_2$ wherein QWAVGHLM-NH$_2$ is SEQ ID NO: 1;
DO3A-monoamide-Gly-(3β,5β7α,12α)-3-amino-7,12-dihydroxycholan-24-oic acid-f-WAVGHLL-NH$_2$ wherein WAVGHLL-NH$_2$ is SEQ ID NO: 8;
DO3A-monoamide-Gly-(3β,5β7α,12α)-3-amino-7,12-dihydroxycholan-24-oic acid-f-QWAVGHL-NH-pentyl wherein QWAVGHL-NH-pentyl is SEQ ID NO: 6;
DO3A-monoamide-Gly-(3β,5β7α,12α)-3-amino-7,12-dihydroxycholan-24-oic acid-y-QWAV-Bala-H-F-Nle-NH$_2$ wherein QWAV-Bala-H-F-Nle-NH$_2$ is SEQ ID NO: 9;
DO3A-monoamide-Gly-(3β,5β7α,12α)-3-amino-7,12-dihydroxycholan-24-oic acid-f-QWAV-Bala-H-F-Nle-NH$_2$ wherein QWAV-Bala-H-F-Nle-NH$_2$ is SEQ ID NO: 9;
DO3A-monoamide-Gly-(3β,5β7α,12α)-3-amino-7,12-dihydroxycholan-24-oic acid-QWAVGHFL-NH$_2$ wherein QWAVGHFL-NH$_2$ is SEQ ID NO: 22;
DO3A-monoamide-Gly-(3β,5β7α,12α)-3-amino-7,12-dihydroxycholan-24-oic acid-QWAVGNMeH-L-M-NH$_2$ wherein QWAVGNMeH-L-M-NH$_2$ is SEQ ID NO: 15;
DO3A-monoamide-Gly-(3β,5β7α,12α)-3-amino-7,12-dihydroxycholan-24-oic acid-LWAVGSF-M-NH$_2$ wherein LWAVGSF-M-NH$_2$ is SEQ ID NO: 11;
DO3A-monoamide-Gly-(3β,5β7α,12α)-3-amino-7,12-dihydroxycholan-24-oic acid-HWAVGHLM-NH$_2$ wherein HWAVGHLM-NH$_2$ is SEQ ID NO: 12;
DO3A-monoamide-Gly-(3β,5β7α,12α)-3-amino-7,12-dihydroxycholan-24-oic acid-LWAGHFM-NH$_2$ wherein LWAGHFM-NH$_2$ is SEQ ID NO: 20;
DO3A-monoamide-Gly-(3β,5β7α,12α)-3-amino-7,12-dihydroxycholan-24-oic acid-QWAVGHFM-NH$_2$ wherein QWAVGHFM-NH$_2$ is SEQ ID NO: 13;
DO3A-monoamide-Gly-(3β,5β7α,12α)-3-amino-7,12-dihydroxycholan-24-oic acid-QRLGNQWAVGHLM-NH$_2$ wherein QRLGNQWAVGHLM-NH$_2$ is SEQ ID NO: 3;
DO3A-monoamide-Gly-(3β,5β7α,12α)-3-amino-7,12-dihydroxycholan-24-oic acid-QRYGNQWAVGHLM-NH$_2$ wherein QRYGNQWAVGHLM-NH$_2$ is SEQ ID NO: 4;
DO3A-monoamide-Gly-(3β,5β7α,12α)-3-amino-7,12-dihydroxycholan-24-oic acid-QKYGNQWAVGHLM-NH$_2$ wherein QKYGNQWAVGHLM-NH$_2$ is SEQ ID NO: 5;

Pglu-Q-Lys (DO3A-monoamide)-Gly-(3β,5β7α,12α)-3-amino-7,12-dihydroxycholan-24-oic acid-LGNQ-WAVGHLM-NH$_2$ wherein LGNQWAVGHLM-NH$_2$ is SEQ ID NO: 18;

DO3A-monoamide-Gly-3-amino-3-deoxycholic acid-QRLGNQWAVGHLM-NH$_2$ wherein QRLGNQ-WAVGHLM-NH$_2$ is SEQ ID NO: 3;

DO3A-monoamide-Gly-3-amino-3-deoxycholic acid-QRYGNQWAVGHLM-NH$_2$ wherein QRYGNQ-WAVGHLM-NH$_2$ is SEQ ID NO: 4;

DO3A-monoamide-Gly-3-amino-3-deoxycholic acid-QKYGNQWAVGHLM-NH$_2$ wherein QKYGNQ-WAVGHLM-NH$_2$ is SEQ ID NO: 5;

Pglu-Q-Lys(DO3A-monoamide-G-3-amino-3-deoxycholic acid)-LGNQWAVGHLM-NH$_2$ wherein LGNQ-WAVGHLM-NH$_2$ is SEQ ID NO: 18;

Aazta-Gly-(3β,5β,7α,12α)-3-amino-7,12-dihydroxycholan-24-oic acid-BBN(7-14) wherein the BBN(7-14) sequence is SEQ ID NO: 1; and CyAazta-Gly-(3β,5β,7α,12α)-3-amino-7,12-dihydroxycholan-24-oic acid-BBN(7-14) wherein the BBN(7-14) sequence is SEQ ID NO: 1.

145. The method of embodiment 137 wherein said labeled compound comprises DO3A-monoamide-Gly-(3β,5β,7α,12α)-3-amino-7,12-dihydroxycholan-24-oic acid-BBN(7-14) wherein the BBN(7-14) sequence is SEQ ID NO: 1.

146. A method for increasing the targeting of a labeled compound to a GRP receptor expressing target tissue within a subject comprising the steps of:
administering to a subject a first dose comprising a GRP receptor targeting peptide to occupy a GRP receptor binding site in non-target tissue,
administering to said subject a second dose comprising a labeled compound of the general formula:

M-N-O-P-G wherein
M is an optical label or a metal chelator complexed with a radionuclide;
N is 0, an alpha amino acid, a non-alpha amino acid with a cyclic group or other linking group;
O is an alpha amino acid or a non-alpha amino acid with a cyclic group;
P is 0, an alpha amino acid, a non-alpha amino acid with a cyclic group, or other linking group; and
G is a GRP receptor targeting peptide,
wherein at least one of N, O or P is a non-alpha amino acid with a cyclic group.

147. The method of embodiment 146, wherein the step of administering said first dose and the step of administering said second dose occur contemporaneously.

148. The method of embodiment 146, wherein the GRP receptor targeting peptide in the first dose is conjugated to a linker.

149. The method of embodiment 146, wherein the GRP receptor targeting peptide in the first dose is conjugated to a linker which is attached to one or more metal chelator.

150. The method of embodiment 149, wherein said GRP receptor peptide, linker and metal chelator of said first dose are the same as the GRP receptor targeting peptide, N-O-P linker and metal chelator of the second dose.

151. The method of embodiment 146, wherein the non-alpha amino acid with a cyclic group is selected from the group consisting of:
4-aminobenzoic acid;
4-aminomethyl benzoic acid;
trans-4-aminomethylcyclohexane carboxylic acid;
4-(2-aminoethoxy)benzoic acid;
Isonipecotic acid;
2-aminomethylbenzoic acid;
4-amino-3-nitrobenzoic acid;
4-(3-carboxymethyl-2-keto-1-benzimidazolyl)-piperidine;
6-(piperazin-1-yl)-4-(3H)-quinazolinone-3-acetic acid;
(2S,5S)-5-amino-1,2,4,5,6,7-hexahydro-azepino[3,21-hi]indole-4-one-2-carboxylic acid;
(4S,7R)-4-amino-6-aza-5-oxo-9-thiabicyclo[4.3.0]nonane-7-carboxylic acid;
3-carboxymethyl-1-phenyl-1,3,8-triazaspiro[4.5]decan-4-one;
N1-piperazineacetic acid;
N-4-aminoethyl-N-1-acetic acid;
(3S)-3-amino-1-carboxymethylcaprolactam; and
(2S,6S,9)-6-amino-2-carboxymethyl-3,8-diazabicyclo-[4,3,0]-nonane-1,4-dione.

152. The method of embodiment 146 wherein the metal chelator is selected from the group consisting of: DTPA, DOTA, DO3A, HPDO3A, EDTA, TETA, N,N-dimethylGly-Ser-Cys, Aazta and derivatives thereof 153. The method of embodiment 146, wherein the labeled compound comprises a compound selected from the group consisting of
DO3A-monoamide-Gly-4-aminobenzoic acid-BBN(7-14) wherein the BBN(7-14) sequence is SEQ ID NO: 1;
DO3A-monoamide-4-aminomethyl benzoic acid-BBN(7-14) wherein the BBN(7-14) sequence is SEQ ID NO: 1;
DO3A-monoamide-trans-4-aminomethylcyclohexyl carboxylic acid-BBN(7-14) wherein the BBN(7-14) sequence is SEQ ID NO: 1;
DO3A-monoamide-4-(2-aminoethoxy)benzoic acid-BBN(7-14) wherein the BBN(7-14) sequence is SEQ ID NO: 1;
DO3A-monoamide-Gly-isonipecotic acid-BBN(7-14) wherein the BBN(7-14) sequence is SEQ ID NO: 1;
DO3A-monoamide-2-aminomethylbenzoic acid-BBN(7-14) wherein the BBN(7-14) sequence is SEQ ID NO: 1;
DO3A-monoamide-4-aminomethyl-3-nitrobenzoic acid-BBN(7-14) wherein the BBN(7-14) sequence is SEQ ID NO: 1;
DO3A-monoamide-8-amino-3,6-dioxaoctanoic acid-1-naphthylalanine-BBN(7-14) wherein the BBN(7-14) sequence is SEQ ID NO: 1;
DO3A-monoamide-4-(3-carboxymethyl-2-keto-1-benzimidazolyl-piperidine-BBN(7-14) wherein the BBN(7-14) sequence is SEQ ID NO: 1;
DO3A-monoamide-6-(piperazin-1-yl)-4-(3H)-quinazolinone-3-acetic acid-BBN(7-14) wherein the BBN(7-14) sequence is SEQ ID NO: 1;
DO3A-monoamide-(2S,5S)-5-amino-1,2,4,5,6,7-hexahydro-azepino[3,21-hi]indole-4-one-2-carboxylic acid-BBN(7-14) wherein the BBN(7-14) sequence is SEQ ID NO: 1;
DO3A-monoamide-(4S,7R)-4-amino-6-aza-5-oxo-9-thiabicyclo[4.3.0]nonane-7-carboxylic acid-BBN(7-14) wherein the BBN(7-14) sequence is SEQ ID NO: 1;
DO3A-monoamide-N,N-dimethylglycine-BBN(7-14) wherein the BBN(7-14) sequence is SEQ ID NO: 1;
DO3A-monoamide-3-carboxymethyl-1-phenyl-1,3,8-triazaspiro[4.5]decan-4-one-BBN(7-14) wherein the BBN(7-14) sequence is SEQ ID NO: 1;
DO3A-monoamide-N1-piperazineacetic acid-BBN(7-14) wherein the BBN(7-14) sequence is SEQ ID NO: 1;
DO3A-monoamide-N-4-aminoethyl-N-1-piperazineacetic acid-BBN(7-14) wherein the BBN(7-14) sequence is SEQ ID NO: 1;

DO3A-monoamide-(3S)-3-amino-1-carboxymethylcaprolactam-BBN(7-14) wherein the BBN(7-14) sequence is SEQ ID NO: 1;
DO3A-monoamide-(2S,6S,9)-6-amino-2-carboxymethyl-3,8-diazabicyclo-[4,3,0]-nonane-1,4-dione-BBN(7-14) wherein the BBN(7-14) sequence is SEQ ID NO: 1;
DO3A-monoamide-5-aminopentanoic acid-trans-4-aminomethylcyclohexane-1-carboxylic acid-BBN(7-14) wherein the BBN(7-14) sequence is SEQ ID NO: 1;
DO3A-monoamide-trans-4-aminomethylcyclohexane-1-carboxylic acid-D-phenylalanine-BBN(7-14) wherein the BBN(7-14) sequence is SEQ ID NO: 1;
DO3A-monoamide-4-aminomethylbenzoic acid-8-amino-3,6-dioxaoctanoic acid-BBN(7-14) wherein the BBN(7-14) sequence is SEQ ID NO: 1;
DO3A-monoamide-4-benzoyl-(L)-phenylalanine-trans-4-aminomethylcyclohexane-1-carboxylic acid-BBN(7-14) wherein the BBN(7-14) sequence is SEQ ID NO: 1;
DO3A-monoamide-trans-4-aminomethylcyclohexane-1-carboxylic acid-Arg-BBN(7-14) wherein the BBN(7-14) sequence is SEQ ID NO: 1;
DO3A-monoamide-trans-4-aminomethylcyclohexane-1-carboxylic acid-Lys-BBN(7-14) wherein the BBN(7-14) sequence is SEQ ID NO: 1;
DO3A-monoamide-trans-4-aminomethylcyclohexane-1-carboxylic acid-diphenylalanine-BBN(7-14) wherein the BBN(7-14) sequence is SEQ ID NO: 1;
DO3A-monoamide-trans-4-aminomethylcyclohexane-1-carboxylic acid-1-naphthylalanine-BBN(7-14) wherein the BBN(7-14) sequence is SEQ ID NO: 1;
DO3A-monoamide-trans-4-aminomethylcyclohexane-1-carboxylic acid-8-amino-3,6-dioxaoctanoic acid-BBN(7-14) wherein the BBN(7-14) sequence is SEQ ID NO: 1;
DO3A-monoamide-trans-4-aminomethylcyclohexane-1-carboxylic acid-Ser-BBN(7-14) wherein the BBN(7-14) sequence is SEQ ID NO: 1;
DO3A-monoamide-trans-4-aminomethylcyclohexane-1-carboxylic acid-2,3-diaminopropionic acid-BBN(7-14) wherein the BBN(7-14) sequence is SEQ ID NO: 1;
DO3A-monoamide-trans-4-aminomethylcyclohexane-1-carboxylic acid-biphenylalanine-BBN(7-14) wherein the BBN(7-14) sequence is SEQ ID NO: 1;
DO3A-monoamide-trans-4-aminomethylcyclohexane-1-carboxylic acid-(2S,5S)-5-amino-1,2,4,5,6,7-hexahydro-azepino[3,21-hi]indole-4-one-2-carboxylic acid-BBN(7-14) wherein the BBN(7-14) sequence is SEQ ID NO: 1;
DO3A-monoamide-trans-4-aminomethylcyclohexane-1-carboxylic acid-trans-4-aminomethylcyclohexane-1-carboxylic acid-BBN(7-14) wherein the BBN(7-14) sequence is SEQ ID NO: 1;
DO3A-monoamide-8-amino-3,6-dioxaoctanoic acid-phenylalanine-BBN(7-14) wherein the BBN(7-14) sequence is SEQ ID NO: 1;
DO3A-monoamide-trans-4-aminomethylcyclohexane-1-carboxylic acid-phenylalanine-BBN(7-14) wherein the BBN(7-14) sequence is SEQ ID NO: 1;
DO3A-monoamide-8-aminooctanoic acid-trans-4-aminomethylcyclohexane-1-carboxylic acid-BBN(7-14) wherein the BBN(7-14) sequence is SEQ ID NO: 1;
DO3A-monoamide-4'-aminomethyl-biphenyl-1-carboxylic acid-BBN(7-14) wherein the BBN(7-14) sequence is SEQ ID NO: 1;
DO3A-monoamide-3'-aminomethyl-biphenyl-3-carboxylic acid-BBN(7-14) wherein the BBN(7-14) sequence is SEQ ID NO: 1;
CMDOTA-Gly-4-aminobenzoic acid-BBN(7-14) wherein the BBN(7-14) sequence is SEQ ID NO: 1;
DO3A-monoamide-4-aminomethylphenoxyacetic acid-BBN(7-14) wherein the BBN(7-14) sequence is SEQ ID NO: 1;
DO3A-monoamide-Gly-4-aminophenylacetic acid-BBN(7-14) wherein the BBN(7-14) sequence is SEQ ID NO: 1;
HPDO3A-4-phenoxy-BBN(7-14) wherein the BBN(7-14) sequence is SEQ ID NO: 1;
DO3A-monoamide-3-aminomethylbenzoic acid-BBN(7-14) wherein the BBN(7-14) sequence is SEQ ID NO: 1;
DO3A-monoamide-4-aminomethylphenylacetic acid-BBN(7-14) wherein the BBN(7-14) sequence is SEQ ID NO: 1;
DO3A-monoamide-4-aminomethyl-3-methoxybenzoic acid-BBN(7-14) wherein the BBN(7-14) sequence is SEQ ID NO: 1;
Boa-Gly-4-aminobenzoic acid-BBN(7-14) wherein the BBN(7-14) sequence is SEQ ID NO: 1;
DO3A-monoamide-Gly-4-hydrazinobenzoyl-BBN(7-14) wherein the BBN(7-14) sequence is SEQ ID NO: 1;
DO3A-monoamide-4-aminobenzoic acid-BBN(7-14) wherein the BBN(7-14) sequence is SEQ ID NO: 1;
DO3A-monoamide-4-aminobenzoic acid-Gly-BBN(7-14) wherein the BBN(7-14) sequence is SEQ ID NO: 1;
DO3A-monoamide-Gly-6-Aminonicotinic acid-BBN(7-14) wherein the BBN(7-14) sequence is SEQ ID NO: 1;
DO3A-monoamide-Gly-4'-Amino-2'-methyl biphenyl-4-carboxylic acid-BBN(7-14) wherein the BBN(7-14) sequence is SEQ ID NO: 1;
DO3A-monoamide-Gly-3'-Aminobiphenyl-3-carboxylic acid-BBN(7-14) wherein the BBN(7-14) sequence is SEQ ID NO: 1;
DO3A-monoamide-Gly-1,2-diaminoethyl-Terephthalic acid-BBN(7-14) wherein the BBN(7-14) sequence is SEQ ID NO: 1;
DO3A-monoamide-Gly-Gly-4-aminobenzoic acid-BBN(7-14) wherein the BBN(7-14) sequence is SEQ ID NO: 1;
DO3A-monoamide-G-4-aminobenzoic acid-EWAVGHLM-NH$_2$ wherein EWAVGHLM-NH$_2$ is SEQ ID NO: 2;
DO3A-monoamide-G-4-aminobenzoic acid-QWAVGHLM-OH wherein QWAVGHLM-OH is SEQ ID NO: 1;
DO3A-monoamide-G-4-aminobenzoic acid-(D)-Phe-BBN(7-14) wherein the BBN(7-14) sequence is SEQ ID NO: 1;
DO3A-monoamide-G-4-aminobenzoic acid-QRLGNQWAVGHLM-NH$_2$ wherein QRLGNQWAVGHLM-NH$_2$ is SEQ ID NO: 3;
DO3A-monoamide-G-4-aminobenzoic acid-QRYGNQWAVGHLM-NH$_2$ wherein QRYGNQWAVGHLM-NH$_2$ is SEQ ID NO: 4;
DO3A-monoamide-G-4-aminobenzoic acid-QKYGNQWAVGHLM-NH$_2$ wherein QKYGNQWAVGHLM-NH$_2$ is SEQ ID NO: 5;
DO3A-monoamide-G-4-aminobenzoic acid-(D)-Phe-QWAVGHL-NH-Pentyl wherein QWAVGHL-NH-Pentyl is SEQ ID NO: 6;
DO3A-monoamide-G-4-aminobenzoic acid-QWSVaHLM-NH$_2$ wherein QWSVaHLM-NH$_2$ is SEQ ID NO: 7;
DO3A-monoamide-G-4-aminobenzoic acid-(D)-Phe-QWAVGHLL-NH$_2$ QWAVGHLL-NH$_2$ is SEQ ID NO: 8;

DO3A-monoamide-G-4-aminobenzoic acid-(D)-Tyr-QWAV-Bala-HF-Nle-NH₂ wherein QWAV-Bala-HF-Nle-NH₂ is SEQ ID NO: 9;
DO3A-monoamide-G-4-aminobenzoic acid-Phe-QWAV-Bala-HF-Nle-NH₂ wherein QWAV-Bala-HF-Nle-NH₂ is SEQ ID NO: 9;
DO3A-monoamide-G-4-aminobenzoic acid-QWAGHFL-NH₂ wherein QWAGHFL-NH₂ is SEQ ID NO: 10;
DO3A-monoamide-G-4-aminobenzoic acid-LWAVGSFM-NH₂ wherein LWAVGSFM-NH₂ is SEQ ID NO: 11;
DO3A-monoamide-G-4-aminobenzoic acid-HWAVGHLM-NH₂ wherein HWAVGHLM-NH₂ is SEQ ID NO: 12;
DO3A-monoamide-G-4-aminobenzoic acid-LWAVGSFM-NH₂ wherein LWAVGSFM-NH₂ is SEQ ID NO: 11;
DO3A-monoamide-G-4-aminobenzoic acid-QWAVGHFM-NH₂ wherein QWAVGHFM-NH₂ is SEQ ID NO: 13;
DO3A-monoamide-Gly-3-aminobenzoic acid-BBN(7-14) wherein the BBN(7-14) sequence is SEQ ID NO: 1;
DO3A-monoamide-Gly-6-aminonaphthoic acid-BBN(7-14) wherein the BBN(7-14) sequence is SEQ ID NO: 1;
DO3A-monoamide-Gly-4-methylaminobenzoic acid-BBN(7-14) wherein the BBN(7-14) sequence is SEQ ID NO: 1;
Cm4 pm10d2a-Gly-4-aminobenzoic acid-BBN(7-14) wherein the BBN(7-14) sequence is SEQ ID NO: 1;
N,N-dimethylglycine-Ser-Cys(Acm)-Gly-Gly-4-aminobenzoic acid-BBN(7-14) wherein the BBN(7-14) sequence is SEQ ID NO: 1;
N,N-dimethylglycine-Ser-Cys(Acm)-Gly-Gly-3-amino-3-deoxycholic acid-BBN(7-14) wherein the BBN(7-14) sequence is SEQ ID NO: 1;
DO3A-monoamide-Gly-3-methoxy-4-aminobenzoic acid-BBN(7-14) wherein the BBN(7-14) sequence is SEQ ID NO: 1;
DO3A-monoamide-Gly-3-chloro-4-aminobenzoic acid-BBN(7-14) wherein the BBN(7-14) sequence is SEQ ID NO: 1;
DO3A-monoamide-Gly-3-methyl-4-aminobenzoic acid-BBN(7-14) wherein the BBN(7-14) sequence is SEQ ID NO: 1;
DO3A-monoamide-Gly-3-hydroxy-4-aminobenzoic acid-BBN(7-14) wherein the BBN(7-14) sequence is SEQ ID NO: 1;
(DO3A-monoamide)₂-N,N'-Bis(2-aminoethyl)-succinamic acid-BBN(7-14) wherein the BBN(7-14) sequence is SEQ ID NO: 1;
DO3A-monoamide-G-4-aminobenzoic acid-QWAVGHFL-NH₂ wherein QWAVGHFL-NH₂ is SEQ ID NO: 22;
DO3A-monoamide-4-aminomethylbenzoic acid-L-1-Naphthylalanine-QWAVGHLM-NH₂ wherein QWAVGHLM-NH₂ is SEQ ID NO: 1;
DO3A-monoamide-G-4-aminobenzoic acid-QWAVGN-MeHisLM-NH₂ wherein QWAVGNMeHisLM-NH₂ is SEQ ID NO: 15;
Aazta-Gly-4-aminobenzoic acid-BBN(7-14) wherein the BBN(7-14) sequence is SEQ ID NO: 1; and
CyAazta-Gly-4-aminobenzoic acid-BBN(7-14) wherein the BBN(7-14) sequence is SEQ ID NO: 1.

154. The method of embodiment 146, wherein the labeled compound comprise DO3A-monoamide-Gly-4-aminobenzoic acid-BBN(7-14) wherein the BBN(7-14) sequence is SEQ ID NO: 1.

155. A method for increasing the targeting of a labeled compound to a GRP receptor expressing target tissue within a subject comprising the step of administering to a subject a dose comprising a combination of:
a first GRP receptor targeting peptide to occupy a GRP receptor binding site in non-target tissue, and
a labeled compound of the general formula:

M-N-O-P-G wherein
M is an optical label or a metal chelator complexed with a radionuclide;
N is 0, an alpha or non-alpha amino acid or other linking group;
O is an alpha or non-alpha amino acid; and
P is 0, an alpha or non-alpha amino acid or other linking group,
and G is a second GRP receptor targeting peptide, and
wherein at least one of N, O or P is a non-alpha amino acid.

156. The method of embodiment 155, wherein the first GRP receptor targeting peptide is conjugated to a linker.

157. The method of embodiment 155, wherein the first GRP receptor targeting peptide is conjugated to a linker which is attached to one or more metal chelator.

158. The method of embodiment 157, wherein said first GRP receptor peptide, linker and metal chelator are the same as the second GRP receptor targeting peptide, N-O-P linker and metal chelator of the labeled compound.

159. The method of embodiment 158, wherein the non-alpha amino acid is selected from the group consisting of:
8-amino-3,6-dioxaoctanoic acid;
N-4-aminoethyl-N-1-piperazine-acetic acid; and
polyethylene glycol derivatives having the formula NH₂—(CH₂CH₂O)n-CH₂CO₂H or NH₂—(CH₂CH₂O)n-CH₂CH₂CO₂H where n=2 to 100.

160. The method of embodiment 155, wherein the metal chelator is selected from the group consisting of DTPA, DOTA, DO3A, HP-DO3A, EDTA, TETA, EHPG, HBED, NOTA, DOTMA, TETMA, PDTA, TTHA, LICAM, MECAM, CMDOTA, N,N-dimethylGly-Ser-Cys, Aazta and derivatives thereof.

161. The method of embodiment 155, wherein the labeled compound comprises a compound selected from the group consisting of:
N,N-dimethylglycine-Ser-Cys(Acm)-Gly-Lys-8-amino-3,6-dioxaoctanoic acid-BBN(7-14) wherein the BBN(7-14) sequence is SEQ ID NO: 1;
N,N-dimethylglycine-Ser-Cys(Acm)-Gly-Arg-8-amino-3,6-dioxaoctanoic acid-BBN (7-14) wherein the BBN(7-14) sequence is SEQ ID NO: 1;
N,N-dimethylglycine-Ser-Cys(Acm)-Gly-Asp-8-amino-3,6-dioxaoctanoic acid-BBN (7-14) wherein the BBN(7-14) sequence is SEQ ID NO: 1;
N,N-dimethylglycine-Ser-Cys(Acm)-Gly-Ser-8-amino-3,6-dioxaoctanoic acid-BBN (7-14) wherein the BBN(7-14) sequence is SEQ ID NO: 1;
N,N-dimethylglycine-Ser-Cys(Acm)-Gly-Gly-8-amino-3,6-dioxaoctanoic acid-BBN(7-14) wherein the BBN(7-14) sequence is SEQ ID NO: 1;
N,N-dimethylglycine-Ser-Cys(Acm)-Gly-Glu-8-amino-3,6-dioxaoctanoic acid-BBN(7-14) wherein the BBN(7-14) sequence is SEQ ID NO: 1;
N,N-dimethylglycine-Ser-Cys(Acm)-Gly-Dala-8-amino-3,6-dioxaoctanoic acid-BBN(7-14) wherein the BBN(7-14) sequence is SEQ ID NO: 1;

N,N-dimethylglycine-Ser-Cys(Acm)-Gly-8-amino-3,6-dioxaoctanoic acid-Lys-BBN(7-14) wherein the BBN(7-14) sequence is SEQ ID NO: 1;

N,N-dimethylglycine-Ser-Cys(Acm)-Gly-8-amino-3,6-dioxaoctanoic acid-Arg-BBN(7-14) wherein the BBN(7-14) sequence is SEQ ID NO: 1;

N,N-dimethylglycine-Ser-Cys(Acm)-Gly-8-amino-3,6-dioxaoctanoic acid-Asp-BBN(7-14) wherein the BBN(7-14) sequence is SEQ ID NO: 1;

N,N-dimethylglycine-Ser-Cys(Acm)-Gly-8-amino-3,6-dioxaoctanoic acid-Ser-BBN(7-14) wherein the BBN(7-14) sequence is SEQ ID NO: 1;

N,N-dimethylglycine-Ser-Cys(Acm)-Gly-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-Glu-BBN(7-14) wherein the BBN(7-14) sequence is SEQ ID NO: 1;

N,N-dimethylglycine-Ser-Cys(Acm)-Gly-8-amino-3,6-dioxaoctanoic acid-Dala-BBN(7-14) wherein the BBN(7-14) sequence is SEQ ID NO: 1;

N,N-dimethylglycine-Ser-Cys(Acm)-Gly-8-amino-3,6-dioxaoctanoic acid-8-amino-3,6-dioxaoctanoic acid-BBN(7-14) wherein the BBN(7-14) sequence is SEQ ID NO: 1;

N,N-dimethylglycine-Ser-Cys(Acm)-Gly-8-amino-3,6-dioxaoctanoic acid-2,3-diaminopropionic acid-BBN(7-14) wherein the BBN(7-14) sequence is SEQ ID NO: 1;

N,N-dimethylglycine-Ser-Cys(Acm)-Gly-8-amino-3,6-dioxaoctanoic acid-BBN(7-14) wherein the BBN(7-14) sequence is SEQ ID NO: 1;

N,N-dimethylglycine-Ser-Cys(Acm)-Gly-2,3-diaminopropionic acid-8-amino-3,6-dioxaoctanoic acid-BBN(7-14) wherein the BBN(7-14) sequence is SEQ ID NO: 1;

N,N-dimethylglycine-Ser-Cys(Acm)-Gly-Asp-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-Asp-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-Ser-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-Arg-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-2,3-diaminopropionic acid-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-Lys-Gly-BBN(7-14) wherein the BBN(7-14) sequence is SEQ ID NO: 1;

N,N-dimethylglycine-Ser-Cys(Acm)-Gly-2,3-diaminopropionic acid-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-Asp-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-Ser-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-Arg-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-8-amino-3,6-dioxaoctanoic acid-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-2,3-diaminopropionic acid-BBN(7-14) wherein the BBN(7-14) sequence is SEQ ID NO: 1;

N,N-dimethylglycine-Ser-Cys(Acm)-Gly-N-4-aminoethyl-N-1-piperazineacetic acid-Lys-BBN(7-14) wherein the BBN(7-14) sequence is SEQ ID NO: 1;

N,N-dimethylglycine-Ser-Cys(Acm)-Gly-N-1-piperazineacetic acid-Asp-BBN(7-14) wherein the BBN(7-14) sequence is SEQ ID NO: 1;

N,N-dimethylglycine-Ser-Cys(Acm)-Gly-N-1-piperazineacetic acid-Ser-BBN(7-14) wherein the BBN(7-14) sequence is SEQ ID NO: 1;

N,N-dimethylglycine-Ser-Cys(Acm)-Gly-N-1-piperazineacetic acid-Arg-BBN(7-14) wherein the BBN(7-14) sequence is SEQ ID NO: 1;

N,N-dimethylglycine-Ser-Cys(Acm)-Gly-N-1-piperazineacetic acid-8-amino-3,6-dioxaoctanoic acid-BBN(7-14) wherein the BBN(7-14) sequence is SEQ ID NO: 1;

N,N-dimethylglycine-Ser-Cys(Acm)-Gly-N-1-piperazineacetic acid-2,3-diaminopropionic acid BBN(7-14) wherein the BBN(7-14) sequence is SEQ ID NO: 1;

N,N-dimethylglycine-Ser-Cys(Acm)-Gly-N-1-piperazineacetic acid-Lys-BBN(7-14) wherein the BBN(7-14) sequence is SEQ ID NO: 1;

N,N-dimethylglycine-Ser-Cys(Acm)-Gly-4-Hydroxyproline-8-amino-3,6-dioxaoctanoic acid-BBN(7-14) wherein the BBN(7-14) sequence is SEQ ID NO: 1;

N,N-dimethylglycine-Ser-Cys(Acm)-Gly-4-aminoproline-8-amino-3,6-dioxaoctanoic acid-BBN(7-14) wherein the BBN(7-14) sequence is SEQ ID NO: 1;

N,N-dimethylglycine-Ser-Cys(Acm)-Gly-Lys-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-Arg-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-Ser-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-Asp-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-Asp-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-Ser-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-Arg-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-8-amino-3,6-dioxaoctanoic acid-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-2,3-diaminopropionic acid-Gly-BBN(7-14) wherein the BBN(7-14) sequence is SEQ ID NO: 1;

N,N-dimethylglycine-Ser-Cys(Acm)-Gly-8-amino-3,6-dioxaoctanoic acid-Lys-Gly-BBN(7-14) wherein the BBN(7-14) sequence is SEQ ID NO: 1; and N,N-dimethylglycine-Ser-Cys(Acm)-Gly-2,3-diaminopropionic acid-8-amino-3,6-dioxaoctanoic acid-Gly-BBN(7-14) wherein the BBN(7-14) sequence is SEQ ID NO: 1.

162. The method of embodiment 155, wherein the labeled compound comprises a compound selected from the group consisting of:
DO3A-monoamide-8-amino-3,6-dioxaoctanoic acid-diaminopropionic acid-BBN(7-14) wherein the BBN(7-14) sequence is SEQ ID NO: 1;
DO3A-monoamide-8-amino-3,6-dioxaoctanoic acid-biphenylalanine-BBN(7-14) wherein the BBN(7-14) sequence is SEQ ID NO: 1;
DO3A-monoamide-8-amino-3,6-dioxaoctanoic acid-diphenylalanine-BBN(7-14) wherein the BBN(7-14) sequence is SEQ ID NO: 1;
DO3A-monoamide-8-amino-3,6-dioxaoctanoic acid-4-benzoylphenylalanine-BBN(7-14) wherein the BBN(7-14) sequence is SEQ ID NO: 1;
DO3A-monoamide-5-aminopentanoic acid-8-amino-3,6-dioxaoctanoic acid-BBN(7-14) wherein the BBN(7-14) sequence is SEQ ID NO: 1;
DO3A-monoamide-8-amino-3,6-dioxaoctanoic acid-D-phenylalanine-BBN(7-14) wherein the BBN(7-14) sequence is SEQ ID NO: 1;
DO3A-monoamide-8-aminooctanoic acid-8-amino-3,6-dioxaoctanoic acid-BBN(7-14) wherein the BBN(7-14) sequence is SEQ ID NO: 1;
DO3A-monoamide-E(G8-amino-3,6-dioxaoctanoic acid-8-amino-3,6-dioxaoctanoic acid QWAVGHLM-NH$_2$)-8-aminooctanoic acid-8-aminooctanoic acid-BBN(7-14) wherein the BBN(7-14) sequence is SEQ ID NO: 1; and
DO3A-monoamide-E(G-Aoa-Aoa-QWAVGHLM-NH$_2$)-8-aminooctanoic acid-8-aminooctanoic acid-BBN(7-14) wherein the BBN(7-14) sequence is SEQ ID NO: 1.

163. A method for increasing the targeting of a labeled compound to a GRP receptor expressing target tissue within a subject comprising the step of administering to a subject a dose comprising a combination of:
a first GRP receptor targeting peptide to occupy a GRP receptor binding site in non-target tissue, and
a labeled compound of the general formula:

M-N-O-P-G wherein
M is an optical label or a metal chelator complexed with a radionuclide;
N is 0, an alpha amino acid, a substituted bile acid or other linking group;
O is an alpha amino acid or a substituted bile acid;
P is 0, an alpha amino acid, a substituted bile acid or other linking group;
G is a second GRP receptor targeting peptide, and
wherein at least one of N, O or P is a substituted bile acid.

164. The method of embodiment 163, wherein the first GRP receptor targeting peptide is conjugated to a linker.

165. The method of embodiment 163, wherein the first GRP receptor targeting peptide is conjugated to a linker which is attached to one or more metal chelator.

166. The method of embodiment 166, wherein said first GRP receptor peptide, linker and metal chelator are the same as the second GRP receptor targeting peptide, N-O-P linker and metal chelator of the labeled compound.

167. The method of embodiment 163, wherein the substituted bile acid is selected from the group consisting of:
3β-amino-3-deoxycholic acid;
(3β,5β)-3-aminocholan-24-oic acid;
(3β,5β,12α)-3-amino-12-hydroxycholan-24-oic acid;
(3β,5β,7α,12α)-3-amino-7,12-dihydroxycholan-24-oic acid;
Lys-(3,6,9)-trioxaundecane-1,11-dicarbonyl-3,7-dideoxy-3-aminocholic acid);
(3β,5β,7α,12α)-3-amino-7-hydroxy-12-oxocholan-24-oic acid; and
(3β,5β,7α)-3-amino-7-hydroxycholan-24-oic acid.

168. The method of embodiment 163, wherein the metal chelator is selected from the group consisting of: DTPA, DOTA, DO3A, HPDO3A, EDTA, TETA, CMDOTA, N,N-dimethylGly-Ser-Cys, Aazta and derivatives thereof.

169. The method of embodiment 163, wherein the labeled compound comprises a compound selected from the group consisting of:
DO3A-monoamide-Gly-(3β,5β)-3-aminocholan-24-oic acid-BBN(7-14) wherein the BBN(7-14) sequence is SEQ ID NO: 1;
DO3A-monoamide-Gly-(3β,5β,12α)-3-amino-12-hydroxycholan-24-oic acid-BBN(7-14) wherein the BBN(7-14) sequence is SEQ ID NO: 1;
DO3A-monoamide-Gly-(3β,5β,7α,12α)-3-amino-7,12-dihydroxycholan-24-oic acid-BBN(7-14) wherein the BBN(7-14) sequence is SEQ ID NO: 1;
DO3A-monoamide-Gly-Lys-(3,6,9)-trioxaundecane-1,11-dicarbonyl-3,7-dideoxy-3-aminocholic acid)-Arg-BBN(7-14) wherein the BBN(7-14) sequence is SEQ ID NO: 1;
(3β,5β,7α,12α)-3-amino-7,12-dihydroxycholan-24-oic acid-3,6,9-trioxaundecane-1,11-dicarbonyl Lys (DO3A-monoamide-Gly)-Arg-BBN(7-14) wherein the BBN(7-14) sequence is SEQ ID NO: 1;
DO3A-monoamide-Gly-(3β,5β,7α,12α)-3-amino-12-oxocholan-24-oic acid-BBN(7-14) wherein the BBN(7-14) sequence is SEQ ID NO: 1;
DO3A-monoamide-1-amino-3,6-dioxaoctanoic acid-(3β,5β,7α,12α)-3-amino-7,12-dihydroxycholan-24-oic acid-BBN(7-14) wherein the BBN(7-14) sequence is SEQ ID NO: 1;
DO3A-monoamide-Gly-(3β,5β7α,12α)-3-amino-7,12-dihydroxycholan-24-oic acid-QWAVaHLM-NH$_2$ wherein QWAVaHLM-NH$_2$ is SEQ ID NO: 14;
DO3A-monoamide-Gly-(3β,5β7α,12α)-3-amino-7,12-dihydroxycholan-24-oic acid-f-QWAVGHLM-NH$_2$ wherein QWAVGHLM-NH$_2$ is SEQ ID NO: 1;
DO3A-monoamide-Gly-(3β,5β7α,12α)-3-amino-7,12-dihydroxycholan-24-oic acid-f-WAVGHLL-NH$_2$ wherein WAVGHLL-NH$_2$ is SEQ ID NO: 26;
DO3A-monoamide-Gly-(3β,5β7α,12α)-3-amino-7,12-dihydroxycholan-24-oic acid-f-QWAVGHL-NH-pentyl wherein QWAVGHL-NH-pentyl is SEQ ID NO: 6;
DO3A-monoamide-Gly-(3β,5β7α,12α)-3-amino-7,12-dihydroxycholan-24-oic acid-y-QWAV-Bala-H-F-Nle-NH$_2$ wherein QWAV-Bala-H-F-Nle-NH$_2$ is SEQ ID NO: 9;
DO3A-monoamide-Gly-(3β,5β7α,12α)-3-amino-7,12-dihydroxycholan-24-oic acid-f-QWAV-Bala-H-F-Nle-NH$_2$ wherein QWAV-Bala-H-F-Nle-NH$_2$ is SEQ ID NO: 9;
DO3A-monoamide-Gly-(3β,5β7α,12α)-3-amino-7,12-dihydroxycholan-24-oic acid-QWAVGHFL-NH$_2$ wherein QWAVGHFL-NH$_2$ is SEQ ID NO: 22;
DO3A-monoamide-Gly-(3β,5β7α,12α)-3-amino-7,12-dihydroxycholan-24-oic acid-QWAVGNMeH-L-M-NH$_2$ wherein QWAVGNMeH-L-M-NH$_2$ wherein QWAVGNMeH-L-M-NH$_2$ is SEQ ID NO: 15;

DO3A-monoamide-Gly-(3β,5β7α,12α)-3-amino-7,12-dihydroxycholan-24-oic acid-LWAVGSF-M-NH₂ wherein LWAVGSF-M-NH₂ is SEQ ID NO: 11;

DO3A-monoamide-Gly-(3β,5β7α,12α)-3-amino-7,12-dihydroxycholan-24-oic acid-HWAVGHLM-NH₂ wherein HWAVGHLM-NH₂ is SEQ ID NO: 12;

DO3A-monoamide-Gly-(3β,5β7α,12α)-3-amino-7,12-dihydroxycholan-24-oic acid-LWAGHFM-NH₂ wherein LWAGHFM-NH₂ is SEQ ID NO: 20;

DO3A-monoamide-Gly-(3β,5β7α,12α)-3-amino-7,12-dihydroxycholan-24-oic acid-QWAVGHFM-NH₂ wherein QWAVGHFM-NH₂ is SEQ ID NO: 13;

DO3A-monoamide-Gly-(3β,5β7α,12α)-3-amino-7,12-dihydroxycholan-24-oic acid-QRLGNQWAVGHLM-NH₂ wherein QRLGNQWAVGHLM-NH₂ is SEQ ID NO: 3;

DO3A-monoamide-Gly-(3β,5β7α,12α)-3-amino-7,12-dihydroxycholan-24-oic acid-QRYGNQWAVGHLM-NH₂ wherein QRYGNQWAVGHLM-NH₂ is SEQ ID NO: 4;

DO3A-monoamide-Gly-(3β,5β7α,12α)-3-amino-7,12-dihydroxycholan-24-oic acid-QKYGNQWAVGHLM-NH₂ wherein QKYGNQWAVGHLM-NH₂ is SEQ ID NO: 5;

Pglu-Q-Lys (DO3A-monoamide)-Gly-(3β,5β7α,12α)-3-amino-7,12-dihydroxycholan-24-oic acid-LGNQWAVGHLM-NH₂ wherein LGNQWAVGHLM-NH₂ is SEQ ID NO: 18;

DO3A-monoamide-Gly-3-amino-3-deoxycholic acid-QRLGNQWAVGHLM-NH₂ wherein QRLGNQWAVGHLM-NH₂ is SEQ ID NO: 3;

DO3A-monoamide-Gly-3-amino-3-deoxycholic acid-QRYGNQWAVGHLM-NH₂ wherein QRYGNQWAVGHLM-NH₂ is SEQ ID NO: 4;

DO3A-monoamide-Gly-3-amino-3-deoxycholic acid-QKYGNQWAVGHLM-NH₂ wherein QKYGNQWAVGHLM-NH₂ is SEQ ID NO: 5;

Pglu-Q-Lys(DO3A-monoamide-G-3-amino-3-deoxycholic acid)-LGNQWAVGHLM-NH₂ wherein LGNQWAVGHLM-NH₂ is SEQ ID NO: 18;

Aazta-Gly-(3β,5β,7α,12α)-3-amino-7,12-dihydroxycholan-24-oic acid-BBN(7-14) wherein the BBN(7-14) sequence is SEQ ID NO: 1; and CyAazta-Gly-(3β,5β,7α,12α)-3-amino-7,12-dihydroxycholan-24-oic acid-BBN(7-14) wherein the BBN(7-14) sequence is SEQ ID NO: 1.

170. The method of embodiment 163, wherein said labeled compound comprises DO3A-monoamide-Gly-(3β,5β,7α,12α)-3-amino-7,12-dihydroxycholan-24-oic acid-BBN(7-14) wherein the BBN(7-14) sequence is SEQ ID NO: 1.

171. A method for increasing the targeting of a labeled compound to a GRP receptor expressing target tissue within a subject comprising the step of administering to a subject a dose comprising a combination of:
a first GRP receptor targeting peptide to occupy a GRP receptor binding site in non-target tissue, and
a labeled compound of the general formula:

M-N-O-P-G wherein
M is an optical label or a metal chelator complexed with a radionuclide;
N is 0, an alpha amino acid, a non-alpha amino acid with a cyclic group or other linking group;
O is an alpha amino acid or a non-alpha amino acid with a cyclic group;
P is 0, an alpha amino acid, a non-alpha amino acid with a cyclic group, or other linking group; and
G is a second GRP receptor targeting peptide,
wherein at least one of N, O or P is a non-alpha amino acid with a cyclic group.

172. The method of embodiment 171, wherein the first GRP receptor targeting peptide is conjugated to a linker.

173. The method of embodiment 171, wherein the first GRP receptor targeting peptide is conjugated to a linker which is attached to one or more metal chelator.

174. The method of embodiment 173, wherein said first GRP receptor peptide, linker and metal chelator are the same as the GRP receptor targeting peptide, N-O-P linker and metal chelator of the labeled compound.

175. The method of embodiment 171, wherein the non-alpha amino acid with a cyclic group is selected from the group consisting of:
4-aminobenzoic acid;
4-aminomethyl benzoic acid;
trans-4-aminomethylcyclohexane carboxylic acid;
4-(2-aminoethoxy)benzoic acid;
Isonipecotic acid;
2-aminomethylbenzoic acid;
4-amino-3-nitrobenzoic acid;
4-(3-carboxymethyl-2-keto-1-benzimidazolyl)-piperidine;
6-(piperazin-1-yl)-4-(3H)-quinazolinone-3-acetic acid;
(2S,5S)-5-amino-1,2,4,5,6,7-hexahydro-azepino[3,21-hi]indole-4-one-2-carboxylic acid;
(4S,7R)-4-amino-6-aza-5-oxo-9-thiabicyclo[4.3.0]nonane-7-carboxylic acid;
3-carboxymethyl-1-phenyl-1,3,8-triazaspiro[4.5]decan-4-one;
N1-piperazineacetic acid;
N-4-aminoethyl-N-1-acetic acid;
(3S)-3-amino-1-carboxymethylcaprolactam; and
(2S,6S,9)-6-amino-2-carboxymethyl-3,8-diazabicyclo-[4,3,0]-nonane-1,4-dione.

176. The method of embodiment 171, wherein the metal chelator is selected from the group consisting of: DTPA, DOTA, DO3A, HPDO3A, EDTA, TETA, N,N-dimethylGly-Ser-Cys, Aazta and derivatives thererof.

177. The method of embodiment 171, wherein the labeled compound comprises a compound selected from the group consisting of DO3A-monoamide-Gly-4-aminobenzoic acid-BBN(7-14) wherein the BBN(7-14) sequence is SEQ ID NO: 1;

DO3A-monoamide-4-aminomethyl benzoic acid-BBN(7-14) wherein the BBN(7-14) sequence is SEQ ID NO: 1;

DO3A-monoamide-trans-4-aminomethylcyclohexyl carboxylic acid-BBN(7-14) wherein the BBN(7-14) sequence is SEQ ID NO: 1;

DO3A-monoamide-4-(2-aminoethoxy)benzoic acid-BBN(7-14) wherein the BBN(7-14) sequence is SEQ ID NO: 1;

DO3A-monoamide-Gly-isonipecotic acid-BBN(7-14) wherein the BBN(7-14) sequence is SEQ ID NO: 1;

DO3A-monoamide-2-aminomethylbenzoic acid-BBN(7-14) wherein the BBN(7-14) sequence is SEQ ID NO: 1;

DO3A-monoamide-4-aminomethyl-3-nitrobenzoic acid-BBN(7-14) wherein the BBN(7-14) sequence is SEQ ID NO: 1;

DO3A-monoamide-8-amino-3,6-dioxaoctanoic acid-1-naphthylalanine-BBN(7-14) wherein the BBN(7-14) sequence is SEQ ID NO: 1;

DO3A-monoamide-4-(3-carboxymethyl-2-keto-1-benzimidazolyl-piperidine-BBN(7-14) wherein the BBN(7-14) sequence is SEQ ID NO: 1;

DO3A-monoamide-6-(piperazin-1-yl)-4-(3H)-quinazolinone-3-acetic acid-BBN(7-14) wherein the BBN(7-14) sequence is SEQ ID NO: 1;
DO3A-monoamide-(2S,5S)-5-amino-1,2,4,5,6,7-hexahydro-azepino[3,21-hi]indole-4-one-2-carboxylic acid-BBN(7-14) wherein the BBN(7-14) sequence is SEQ ID NO: 1;
DO3A-monoamide-(4S,7R)-4-amino-6-aza-5-oxo-9-thiabicyclo[4.3.0]nonane-7-carboxylic acid-BBN(7-14) wherein the BBN(7-14) sequence is SEQ ID NO: 1;
DO3A-monoamide-N,N-dimethylglycine-BBN(7-14) wherein the BBN(7-14) sequence is SEQ ID NO: 1;
DO3A-monoamide-3-carboxymethyl-1-phenyl-1,3,8-triazaspiro[4.5]decan-4-one-BBN(7-14) wherein the BBN(7-14) sequence is SEQ ID NO: 1;
DO3A-monoamide-N1-piperazineacetic acid-BBN(7-14) wherein the BBN(7-14) sequence is SEQ ID NO: 1;
DO3A-monoamide-N-4-aminoethyl-N-1-piperazineacetic acid-BBN(7-14) wherein the BBN(7-14) sequence is SEQ ID NO: 1;
DO3A-monoamide-(3S)-3-amino-1-carboxymethylcaprolactam-BBN(7-14) wherein the BBN(7-14) sequence is SEQ ID NO: 1;
DO3A-monoamide-(2S,6S,9)-6-amino-2-carboxymethyl-3,8-diazabicyclo-[4,3,0]-nonane-1,4-dione-BBN(7-14) wherein the BBN(7-14) sequence is SEQ ID NO: 1;
DO3A-monoamide-5-aminopentanoic acid-trans-4-aminomethylcyclohexane-1-carboxylic acid-BBN(7-14) wherein the BBN(7-14) sequence is SEQ ID NO: 1;
DO3A-monoamide-trans-4-aminomethylcyclohexane-1-carboxylic acid-D-phenylalanine-BBN(7-14) wherein the BBN(7-14) sequence is SEQ ID NO: 1;
DO3A-monoamide-4-aminomethylbenzoic acid-8-amino-3,6-dioxaoctanoic acid-BBN(7-14) wherein the BBN(7-14) sequence is SEQ ID NO: 1;
DO3A-monoamide-4-benzoyl-(L)-phenylalanine-trans-4-aminomethylcyclohexane-1-carboxylic acid-BBN(7-14) wherein the BBN(7-14) sequence is SEQ ID NO: 1;
DO3A-monoamide-trans-4-aminomethylcyclohexane-1-carboxylic acid-Arg-BBN(7-14) wherein the BBN(7-14) sequence is SEQ ID NO: 1;
DO3A-monoamide-trans-4-aminomethylcyclohexane-1-carboxylic acid-Lys-BBN(7-14) wherein the BBN(7-14) sequence is SEQ ID NO: 1;
DO3A-monoamide-trans-4-aminomethylcyclohexane-1-carboxylic acid-diphenylalanine-BBN(7-14) wherein the BBN(7-14) sequence is SEQ ID NO: 1;
DO3A-monoamide-trans-4-aminomethylcyclohexane-1-carboxylic acid-1-naphthylalanine-BBN(7-14) wherein the BBN(7-14) sequence is SEQ ID NO: 1;
DO3A-monoamide-trans-4-aminomethylcyclohexane-1-carboxylic acid-8-amino-3,6-dioxaoctanoic acid-BBN(7-14) wherein the BBN(7-14) sequence is SEQ ID NO: 1;
DO3A-monoamide-trans-4-aminomethylcyclohexane-1-carboxylic acid-Ser-BBN(7-14) wherein the BBN(7-14) sequence is SEQ ID NO: 1;
DO3A-monoamide-trans-4-aminomethylcyclohexane-1-carboxylic acid-2,3-diaminopropionic acid-BBN(7-14) wherein the BBN(7-14) sequence is SEQ ID NO: 1;
DO3A-monoamide-trans-4-aminomethylcyclohexane-1-carboxylic acid-biphenylalanine-BBN(7-14) wherein the BBN(7-14) sequence is SEQ ID NO: 1;
DO3A-monoamide-trans-4-aminomethylcyclohexane-1-carboxylic acid-(2S,5S)-5-amino-1,2,4,5,6,7-hexahydro-azepino[3,21-hi]indole-4-one-2-carboxylic acid-BBN(7-14) wherein the BBN(7-14) sequence is SEQ ID NO: 1;
DO3A-monoamide-trans-4-aminomethylcyclohexane-1-carboxylic acid-trans-4-aminomethylcyclohexane-1-carboxylic acid-BBN(7-14) wherein the BBN(7-14) sequence is SEQ ID NO: 1;
DO3A-monoamide-8-amino-3,6-dioxaoctanoic acid-phenylalanine-BBN(7-14) wherein the BBN(7-14) sequence is SEQ ID NO: 1;
DO3A-monoamide-trans-4-aminomethylcyclohexane-1-carboxylic acid-phenylalanine-BBN(7-14) wherein the BBN(7-14) sequence is SEQ ID NO: 1;
DO3A-monoamide-8-aminooctanoic acid-trans-4-aminomethylcyclohexane-1-carboxylic acid-BBN(7-14) wherein the BBN(7-14) sequence is SEQ ID NO: 1;
DO3A-monoamide-4'-aminomethyl-biphenyl-1-carboxylic acid-BBN(7-14) wherein the BBN(7-14) sequence is SEQ ID NO: 1;
DO3A-monoamide-3'-aminomethyl-biphenyl-3-carboxylic acid-BBN(7-14) wherein the BBN(7-14) sequence is SEQ ID NO: 1;
CMDOTA-Gly-4-aminobenzoic acid-BBN(7-14) wherein the BBN(7-14) sequence is SEQ ID NO: 1;
DO3A-monoamide-4-aminomethylphenoxyacetic acid-BBN(7-14) wherein the BBN(7-14) sequence is SEQ ID NO: 1;
DO3A-monoamide-Gly-4-aminophenylacetic acid-BBN(7-14) wherein the BBN(7-14) sequence is SEQ ID NO: 1;
HPDO3A-4-phenoxy-BBN(7-14) wherein the BBN(7-14) sequence is SEQ ID NO: 1;
DO3A-monoamide-3-aminomethylbenzoic acid-BBN(7-14) wherein the BBN(7-14) sequence is SEQ ID NO: 1;
DO3A-monoamide-4-aminomethylphenylacetic acid-BBN(7-14) wherein the BBN(7-14) sequence is SEQ ID NO: 1;
DO3A-monoamide-4-aminomethyl-3-methoxybenzoic acid-BBN(7-14) wherein the BBN(7-14) sequence is SEQ ID NO: 1;
Boa-Gly-4-aminobenzoic acid-BBN(7-14) wherein the BBN(7-14) sequence is SEQ ID NO: 1;
DO3A-monoamide-Gly-4-hydrazinobenzoyl-BBN(7-14) wherein the BBN(7-14) sequence is SEQ ID NO: 1;
DO3A-monoamide-4-aminobenzoic acid-BBN(7-14) wherein the BBN(7-14) sequence is SEQ ID NO: 1;
DO3A-monoamide-4-aminobenzoic acid-Gly-BBN(7-14) wherein the BBN(7-14) sequence is SEQ ID NO: 1;
DO3A-monoamide-Gly-6-Aminonicotinic acid-BBN(7-14) wherein the BBN(7-14) sequence is SEQ ID NO: 1;
DO3A-monoamide-Gly-4'-Amino-2'-methyl biphenyl-4-carboxylic acid-BBN(7-14) wherein the BBN(7-14) sequence is SEQ ID NO: 1;
DO3A-monoamide-Gly-3'-Aminobiphenyl-3-carboxylic acid-BBN(7-14) wherein the BBN(7-14) sequence is SEQ ID NO: 1;
DO3A-monoamide-Gly-1,2-diaminoethyl-Terephthalic acid-BBN(7-14) wherein the BBN(7-14) sequence is SEQ ID NO: 1;
DO3A-monoamide-Gly-Gly-4-aminobenzoic acid-BBN(7-14) wherein the BBN(7-14) sequence is SEQ ID NO: 1;
DO3A-monoamide-G-4-aminobenzoic acid-EWAVGHLM-NH$_2$ wherein EWAVGHLM-NH$_2$ is SEQ ID NO: 2;

DO3A-monoamide-G-4-aminobenzoic acid-QWAVGHLM-OH wherein QWAVGHLM-OH is SEQ ID NO: 1;

DO3A-monoamide-G-4-aminobenzoic acid-(D)-Phe-BBN(7-14) wherein the BBN(7-14) sequence is SEQ ID NO: 1;

DO3A-monoamide-G-4-aminobenzoic acid-QRLGNQWAVGHLM-NH$_2$ wherein QRLGNQWAVGHLM-NH$_2$ is SEQ ID NO: 3;

DO3A-monoamide-G-4-aminobenzoic acid-QRYGNQWAVGHLM-NH$_2$ wherein QRYGNQWAVGHLM-NH$_2$ is SEQ ID NO: 4;

DO3A-monoamide-G-4-aminobenzoic acid-QKYGNQWAVGHLM-NH$_2$ wherein QKYGNQWAVGHLM-NH$_2$ is SEQ ID NO: 5;

DO3A-monoamide-G-4-aminobenzoic acid-(D)-Phe-QWAVGHL-NH-Pentyl wherein QWAVGHL-NH-Pentyl is SEQ ID NO: 6;

DO3A-monoamide-G-4-aminobenzoic acid-QWSVaHLM-NH$_2$ wherein QWSVaHLM-NH$_2$ is SEQ ID NO: 7;

DO3A-monoamide-G-4-aminobenzoic acid-(D)-Phe-QWAVGHLL-NH$_2$ wherein QWAVGHLL-NH$_2$ is SEQ ID NO: 8;

DO3A-monoamide-G-4-aminobenzoic acid-(D)-Tyr-QWAV-Bala-HF-Nle-NH$_2$ wherein QWAV-Bala-HF-Nle-NH$_2$ is SEQ ID NO: 9;

DO3A-monoamide-G-4-aminobenzoic acid-Phe-QWAV-Bala-HF-Nle-NH$_2$ wherein QWAV-Bala-HF-Nle-NH$_2$ is SEQ ID NO: 9;

DO3A-monoamide-G-4-aminobenzoic acid-QWAGHFL-NH$_2$ wherein QWAGHFL-NH$_2$ is SEQ ID NO: 10;

DO3A-monoamide-G-4-aminobenzoic acid-LWAVGSFM-NH$_2$ wherein LWAVGSFM-NH$_2$ is SEQ ID NO: 11;

DO3A-monoamide-G-4-aminobenzoic acid-HWAVGHLM-NH$_2$ wherein HWAVGHLM-NH$_2$ is SEQ ID NO: 12;

DO3A-monoamide-G-4-aminobenzoic acid-LWAVGSFM-NH$_2$ wherein LWAVGSFM-NH$_2$ is SEQ ID NO: 11;

DO3A-monoamide-G-4-aminobenzoic acid-QWAVGHFM-NH$_2$ wherein QWAVGHFM-NH$_2$ is SEQ ID NO: 13;

DO3A-monoamide-Gly-3-aminobenzoic acid-BBN(7-14) wherein the BBN(7-14) sequence is SEQ ID NO: 1;

DO3A-monoamide-Gly-6-aminonaphthoic acid-BBN(7-14) wherein the BBN(7-14) sequence is SEQ ID NO: 1;

DO3A-monoamide-Gly-4-methylaminobenzoic acid-BBN(7-14) wherein the BBN(7-14) sequence is SEQ ID NO: 1;

Cm4 pm10d2a-Gly-4-aminobenzoic acid-BBN(7-14) wherein the BBN(7-14) sequence is SEQ ID NO: 1;

N,N-dimethylglycine-Ser-Cys(Acm)-Gly-Gly-4-aminobenzoic acid-BBN(7-14) wherein the BBN(7-14) sequence is SEQ ID NO: 1;

N,N-dimethylglycine-Ser-Cys(Acm)-Gly-Gly-3-amino-3-deoxycholic acid-BBN(7-14) wherein the BBN(7-14) sequence is SEQ ID NO: 1;

DO3A-monoamide-Gly-3-methoxy-4-aminobenzoic acid-BBN(7-14) wherein the BBN(7-14) sequence is SEQ ID NO: 1;

DO3A-monoamide-Gly-3-chloro-4-aminobenzoic acid-BBN(7-14) wherein the BBN(7-14) sequence is SEQ ID NO: 1;

DO3A-monoamide-Gly-3-methyl-4-aminobenzoic acid-BBN(7-14) wherein the BBN(7-14) sequence is SEQ ID NO: 1;

DO3A-monoamide-Gly-3-hydroxy-4-aminobenzoic acid-BBN(7-14) wherein the BBN(7-14) sequence is SEQ ID NO: 1;

(DO3A-monoamide)$_2$-N,N'-Bis(2-aminoethyl)-succinamic acid-BBN(7-14) wherein the BBN(7-14) sequence is SEQ ID NO: 1;

DO3A-monoamide-G-4-aminobenzoic acid-QWAVGHFL-NH$_2$ wherein QWAVGHFL-NH$_2$ is SEQ ID NO: 22;

DO3A-monoamide-4-aminomethylbenzoic acid-L-1-Naphthylalanine-QWAVGHLM-NH$_2$ wherein QWAVGHLM-NH$_2$ is SEQ ID NO: 1;

DO3A-monoamide-G-4-aminobenzoic acid-QWAVGNMeHisLM-NH$_2$ wherein QWAVGNMeHisLM-NH$_2$ is SEQ ID NO: 15;

Aazta-Gly-4-aminobenzoic acid-BBN(7-14) wherein the BBN(7-14) sequence is SEQ ID NO: 1; and CyAazta-Gly-4-aminobenzoic acid-BBN(7-14) wherein the BBN(7-14) sequence is SEQ ID NO: 1.

178. The method of embodiment 171, wherein the labeled compound comprises DO3A-monoamide-Gly-4-aminobenzoic acid-BBN(7-14) wherein the BBN(7-14) sequence is SEQ ID NO: 1.

179. The method of embodiment 128, wherein the GRP receptor targeting peptide of said first dose is an agonist.

180. The method of embodiment 137, wherein the GRP receptor targeting peptide of said first dose is an agonist.

181. The method of embodiment 146, wherein the GRP receptor targeting peptide of said first dose is an agonist.

182. The method of embodiment 155, wherein the first GRP receptor targeting peptide is an agonist.

183. The method of embodiment 163, wherein the first GRP receptor targeting peptide is an agonist.

184. The method of embodiment 171, wherein the first GRP receptor targeting peptide is an agonist.

185. A method of treating bone or soft tissue metastases of prostate cancer comprising the step of administering to a subject a dose comprising:

an amount of radioactively labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

186. The method of embodiment 185, wherein said radioactive label is $^{177}$Lu.

187. The method of embodiment 185, wherein said dose is about 3-30 mCi/kg of $^{177}$Lu-labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-t tophyl-L-alanyl-L-valyl-glycyl-L-histidyl-L-leucyl-L-methioninamide.

188. The method of embodiment 185 wherein said dose is administered intravenously.

189. The method of embodiment 185 wherein said tumor exhibits a reduction in aberrant vasculature.

190. The method of embodiment 185 wherein time to progression is increased by at least about 15%.

191. A method of treating hormone sensitive prostate cancer comprising the step of administering to a subject a dose comprising:

an amount of radioactively labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

192. The method of embodiment 191 wherein said radioactive label is $^{177}$Lu.

193. The method of embodiment 191 wherein said dose is about 3-30 mCi/kg of $^{177}$Lu-labeled L70, N-[4-[[[[[4,7,10-Tris(carboxymethyl)-1,4,7,10-tetraazacyclododec-1yl] acetyl]amino]acetyl]amino]benzoyl]-L-glutaminyl-L-tophyl-L-alanyl-L-valyl-glycyl-L-histidyl-L-leucyl-L-methioninamide.

194. The method of embodiment 191 wherein said dose is administered intravenously.

195. The method of embodiment 191 wherein said tumor exhibits a reduction in aberrant vasculature.

196. The method of embodiment 191 wherein time to progression is increased by at least about 15%.

197. A method of treating hormone refractory prostate cancer comprising the step of administering to a subject a dose comprising:
an amount of radioactively labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

198. The method of embodiment 197 wherein said radioactive label is $^{177}$Lu.

199. The method of embodiment 197 wherein said dose is about 3-30 mCi/kg of $^{177}$Lu-labeled L70, N-[4-[[[[[4,7,10-Tris(carboxymethyl)-1,4,7,10-tetraazacyclododec-1yl] acetyl]amino]acetyl]amino]benzoyl]-L-glutaminyl-L-tophyl-L-alanyl-L-valyl-glycyl-L-histidyl-L-leucyl-L-methioninamide.

200. The method of embodiment 197 wherein said dose is administered intravenously.

201. A method of delaying progression of hormone sensitive prostate cancer comprising the step of administering to a subject a dose comprising:
an amount of radioactively labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide, sufficient to cause a reduction in aberrant vasculature in a tumor or increased time to progression.

202. The method of embodiment 201 wherein said radioactive label is $^{177}$Lu.

203. The method of embodiment 201 wherein said dose is about 3-30 mCi/kg of $^{177}$Lu-labeled L70, N-[4-[[[[4,7,10-Tris(carboxymethyl)-1,4,7,10-tetraazacyclododec-1-yl] acetyl]amino]acetyl]amino]benzoyl]-L-glutaminyl-L-tophyl-L-alanyl-L-valyl-glycyl-L-histidyl-L-leucyl-L-methioninamide.

204. The method of embodiment 201 wherein said dose is administered intravenously.

205. The method of embodiment 201 wherein said tumor exhibits a reduction in aberrant vasculature.

206. The method of embodiment 201 wherein time to progression is increased by at least about 15%.

207. The method of embodiment 201 wherein time to progression is increased by at least about 50%.

208. The method of embodiment 201 wherein time to progression is increased by about 100%.

209. A method of facilitating combination therapy in hormone sensitive prostate cancer comprising the step of administering to a subject a dose comprising:
an amount of radioactively labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide, sufficient to cause a reduction in aberrant vasculature in a tumor or increased time to progression.

210. The method of embodiment 209 wherein said radioactive label is $^{177}$Lu.

211. The method of embodiment 209 wherein said dose is about 3-30 mCi/kg of $^{177}$Lu-labeled L70, N-[4-[[[[[4,7,10-Tris(carboxymethyl)-1,4,7,10-tetraazacyclododec-1-yl] acetyl]amino]acetyl]amino]benzoyl]-L-glutaminyl-L-tophyl-L-alanyl-L-valyl-glycyl-L-histidyl-L-leucyl-L-methioninamide.

212. The method of embodiment 209 wherein said dose is administered intravenously.

213. The method of embodiment 209 wherein said tumor exhibits a reduction in aberrant vasculature.

214. The method of embodiment 209 wherein time to progression is increased by at least about 15%.

215. A method of decreasing aberrant vascular permeability in patients with hormone sensitive prostate cancer comprising the step of administering to a subject a dose comprising:
an amount of radioactively labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

216. The method of embodiment 215 wherein said radioactive label is $^{177}$Lu.

217. The method of embodiment 215 wherein said dose is about 3-30 mCi/kg of $^{177}$Lu-labeled L70, N-[4-[[[[[4,7,10-Tris(carboxymethyl)-1,4,7,10-tetraazacyclododec-1-yl] acetyl]amino]acetyl]amino]benzoyl]-L-glutaminyl-L-tophyl-L-alanyl-L-valyl-glycyl-L-histidyl-L-leucyl-L-methioninamide.

218. The method of embodiment 215 wherein said dose is administered intravenously.

We claim:

1. A method of treating bone or soft tissue metastases of prostate cancer comprising the step of administering to a subject a dose comprising:
   an amount of radioactively labeled L70, N[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

2. The method of claim 1 wherein said radioactive label is $^{177}$Lu.

3. The method of claim 1 wherein said dose is about 3-30 mCi/kg of $^{177}$Lu-labeled L70, N4-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

4. The method of claim 1 wherein said dose is administered intravenously.

5. The method of claim 1 wherein said tumor exhibits a reduction in aberrant vasculature as shown by a visible reduction in bruising due to ecchymosis.

6. The method of claim 1 wherein time to progression is increased by at least 15%.

7. A method of treating hormone sensitive prostate cancer comprising the step of administering to a subject a dose comprising:
   an amount of radioactively labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

8. The method of claim 7 wherein said radioactive label is $^{177}$Lu.

9. The method of claim 7 wherein said dose is about 3-30 mCi/kg of $^{177}$Lu-labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

10. The method of claim 7 wherein said dose is administered intravenously.

11. The method of claim 7 wherein said tumor exhibits a reduction in aberrant vasculature as shown by a visible reduction in bruising due to ecchymosis.

12. The method of claim 7 wherein time to progression is increased by at least 15%.

13. A method of treating hormone refractory prostate cancer comprising the step of administering to a subject a dose comprising:
   an amount of radioactively labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

14. The method of claim 13 wherein said radioactive label is $^{177}$Lu.

15. The method of claim 13 wherein said dose is about 3-30 mCi/kg of $^{177}$Lu-labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

16. The method of claim 13 wherein said dose is administered intravenously.

17. A method of delaying progression of hormone sensitive prostate cancer comprising the step of administering to a subject a dose comprising: an amount of radioactively labeled L70, N-[4-[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide, sufficient to cause a reduction in aberrant vasculature as shown by a visible reduction in bruising due to ecchymosis in a tumor or statistically significant increase in the time to progression.

18. The method of claim 17 wherein said radioactive label is $^{177}$Lu.

19. The method of claim 17 wherein said dose is about 3-30 mCi/kg of $^{177}$Lu-labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

20. The method of claim 17 wherein said dose is administered intravenously.

21. The method of claim 17 wherein said tumor exhibits a reduction in aberrant vasculature as shown by a visible reduction in bruising due to ecchymosis.

22. The method of claim 17 wherein statistically significant increase in the time to progression is increased by at least 15%.

23. The method of claim 17 wherein statistically significant increase in the time to progression is increased by at least 50%.

24. The method of claim 17 wherein statistically significant increase in the time to progression is increased by about 100%.

25. A method of facilitating combination therapy in hormone sensitive prostate cancer comprising the step of administering to a subject a dose comprising:

an amount of radioactively labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide, sufficient to cause a reduction in aberrant vasculature as shown by a visible reduction in bruising due to ecchymosis in a tumor or statistically significant increase in the time to progression.

26. The method of claim 25 wherein said radioactive label is $^{177}$Lu.

27. The method of claim 25 wherein said dose is about 3-30 mCi/kg of $^{177}$Lu-labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

28. The method of claim 25 wherein said dose is administered intravenously.

29. The method of claim 25 wherein said tumor exhibits a reduction in aberrant vasculature as shown by a visible reduction in bruising due to ecchymosis.

30. The method of claim 25 wherein statistically significant increase in the time to progression is increased by at least 15%.

31. A method of decreasing aberrant vascular permeability in patients with hormone sensitive prostate cancer comprising the step of administering to a subject a dose comprising:

an amount of radioactively labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

32. The method of claim 31 wherein said radioactive label is $^{177}$Lu.

33. The method of claim 31 wherein said dose is about 3-30 mCi/kg of $^{177}$Lu-labeled L70, N-[4-[[[[[4,7,10-Tris(carboxymethyl)-1,4,7,10-tetraazacyclododec-1-yl]acetyl]amino]acetyl]amino]benzoyl]-L-glutaminyl-L-tryptophyl-L-alanyl-L-valyl-glycyl-L-histidyl-L-leucyl-L-methioninamide.

34. The method of claim 31 wherein said dose is administered intravenously.

* * * * *

SEQUENCE LISTING

```
<160> NUMBER OF SEQ ID NOS: 26

<210> SEQ ID NO 1
<211> LENGTH: 8
<212> TYPE: PRT
<213> ORGANISM: Artificial
<220> FEATURE:
<223> OTHER INFORMATION: Description of Artificial Sequence:  This
      peptide is known as bombesin (i.e., BBN (7-14)) and binds to
      gastrin releasing peptide (GRP) receptors.
<220> FEATURE:
```

```
<221> NAME/KEY: MOD_RES
<222> LOCATION: (1)..(1)
<223> OTHER INFORMATION: Optionally includes the following amide bond
      modifications: Nme-Q, Q-[CSNH], Q-[CH2NH], Q-[CH=CH] or MeQ
<220> FEATURE:
<221> NAME/KEY: MOD_RES
<222> LOCATION: (2)..(2)
<223> OTHER INFORMATION: Optionally includes the following amide bond
      modifications: Nme-W, W-[CSNH], W-[CH2NH], W-[CH=CH] or MeW
<220> FEATURE:
<221> NAME/KEY: MOD_RES
<222> LOCATION: (3)..(3)
<223> OTHER INFORMATION: Optionally includes the following amide bond
      modifications: Nme-A, A-[CSNH], A-[CH2NH] or Aib
<220> FEATURE:
<221> NAME/KEY: MOD_RES
<222> LOCATION: (5)..(5)
<223> OTHER INFORMATION: Optionally includes the following amide bond
      modifications: G-[CSNH] or G-[CH=CH].  Also includes the following
      substitutions for G: Sar or Dala.
<220> FEATURE:
<221> NAME/KEY: MOD_RES
<222> LOCATION: (6)..(6)
<223> OTHER INFORMATION: Optionally includes the following amide bond
      modifications: Nme-His, H-[CSNH], H-[CH2NH], H-[CH=CH] or MeH
<220> FEATURE:
<221> NAME/KEY: MOD_RES
<222> LOCATION: (7)..(7)
<223> OTHER INFORMATION: Optionally includes the following amide bond
      modifications: Nme-L or MeL
<220> FEATURE:
<221> NAME/KEY: MOD_RES
<222> LOCATION: (8)..(8)
<223> OTHER INFORMATION: M-NH2 or M-OH

<400> SEQUENCE: 1

Gln Trp Ala Val Gly His Leu Met
1               5

<210> SEQ ID NO 2
<211> LENGTH: 8
<212> TYPE: PRT
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
<222> LOCATION: (8)..(8)
<223> OTHER INFORMATION: M-NH2

<400> SEQUENCE: 2

Glu Trp Ala Val Gly His Leu Met
1               5

<210> SEQ ID NO 3
<211> LENGTH: 13
<212> TYPE: PRT
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
<222> LOCATION: (13)..(13)
<223> OTHER INFORMATION: M-NH2

<400> SEQUENCE: 3

Gln Arg Leu Gly Asn Gln Trp Ala Val Gly His Leu Met
1               5                   10

<210> SEQ ID NO 4
<211> LENGTH: 13
<212> TYPE: PRT
```

```
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
<222> LOCATION: (13)..(13)
<223> OTHER INFORMATION: M-NH2

<400> SEQUENCE: 4

Gln Arg Tyr Gly Asn Gln Trp Ala Val Gly His Leu Met
1               5                   10

<210> SEQ ID NO 5
<211> LENGTH: 13
<212> TYPE: PRT
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
<222> LOCATION: (13)..(13)
<223> OTHER INFORMATION: M-NH2

<400> SEQUENCE: 5

Gln Lys Tyr Gly Asn Gln Trp Ala Val Gly His Leu Met
1               5                   10

<210> SEQ ID NO 6
<211> LENGTH: 7
<212> TYPE: PRT
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
<222> LOCATION: (7)..(7)
<223> OTHER INFORMATION: L-NH-Pentyl

<400> SEQUENCE: 6

Gln Trp Ala Val Gly His Leu
1               5

<210> SEQ ID NO 7
<211> LENGTH: 7
<212> TYPE: PRT
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
<222> LOCATION: (7)..(7)
<223> OTHER INFORMATION: M-NH2

<400> SEQUENCE: 7

Gln Trp Ser Val His Leu Met
1               5

<210> SEQ ID NO 8
<211> LENGTH: 8
<212> TYPE: PRT
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
<222> LOCATION: (8)..(8)
<223> OTHER INFORMATION: L-NH2
```

```
<400> SEQUENCE: 8

Gln Trp Ala Val Gly His Leu Leu
1               5

<210> SEQ ID NO 9
<211> LENGTH: 8
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: Nle-NH2

<400> SEQUENCE: 9

Gln Trp Ala Val Ala His Phe Leu
1               5

<210> SEQ ID NO 10
<211> LENGTH: 7
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (7)..(7)
<223> OTHER INFORMATION: L-NH2

<400> SEQUENCE: 10

Gln Trp Ala Gly His Phe Leu
1               5

<210> SEQ ID NO 11
<211> LENGTH: 8
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (8)..(8)
<223> OTHER INFORMATION: M-NH2

<400> SEQUENCE: 11

Leu Trp Ala Val Gly Ser Phe Met
1               5

<210> SEQ ID NO 12
<211> LENGTH: 8
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (8)..(8)
<223> OTHER INFORMATION: M-NH2

<400> SEQUENCE: 12

His Trp Ala Val Gly His Leu Met
```

-continued

<210> SEQ ID NO 13
<211> LENGTH: 8
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (8)..(8)
<223> OTHER INFORMATION: M-NH2

<400> SEQUENCE: 13

Gln Trp Ala Val Gly His Phe Met
1               5

<210> SEQ ID NO 14
<211> LENGTH: 7
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (7)..(7)
<223> OTHER INFORMATION: M-NH2

<400> SEQUENCE: 14

Gln Trp Ala Val His Leu Met
1               5

<210> SEQ ID NO 15
<211> LENGTH: 9
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (7)..(7)
<223> OTHER INFORMATION: MeH

<400> SEQUENCE: 15

Gln Trp Ala Val Gly Asn His Leu Met
1               5

<210> SEQ ID NO 16
<211> LENGTH: 8
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (8)..(8)
<223> OTHER INFORMATION: M-NH2

<400> SEQUENCE: 16

Leu Trp Ala Thr Gly His Phe Met
1               5

<210> SEQ ID NO 17
<211> LENGTH: 8
<212> TYPE: PRT
<213> ORGANISM: Artificial
<220> FEATURE:

```
<223> OTHER INFORMATION: Description of Artificial Sequence:  GRP
      Receptor Targeting Peptide
<220> FEATURE:
<221> NAME/KEY: MOD_RES
<222> LOCATION: (8)..(8)
<223> OTHER INFORMATION: M-NH2

<400> SEQUENCE: 17

Leu Trp Ala Thr Gly Ser Phe Met
1               5

<210> SEQ ID NO 18
<211> LENGTH: 11
<212> TYPE: PRT
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
<222> LOCATION: (11)..(11)
<223> OTHER INFORMATION: M-NH2

<400> SEQUENCE: 18

Leu Gly Asn Gln Trp Ala Val Gly His Leu Met
1               5                   10

<210> SEQ ID NO 19
<211> LENGTH: 9
<212> TYPE: PRT
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
<222> LOCATION: (9)..(9)
<223> OTHER INFORMATION: NH2
<220> FEATURE:
<221> NAME/KEY: MOD_RES
<222> LOCATION: (9)..(9)
<223> OTHER INFORMATION: M-NH2

<400> SEQUENCE: 19

Gly Gln Trp Ala Val Gly His Leu Met
1               5

<210> SEQ ID NO 20
<211> LENGTH: 7
<212> TYPE: PRT
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
<222> LOCATION: (7)..(7)
<223> OTHER INFORMATION: M-NH2

<400> SEQUENCE: 20

Leu Trp Ala Gly His Phe Met
1               5

<210> SEQ ID NO 21
<211> LENGTH: 8
<212> TYPE: PRT
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
```

```
<222> LOCATION: (8)..(8)
<223> OTHER INFORMATION: M-NH-C5H12

<400> SEQUENCE: 21

Gln Trp Ala Val Gly His Leu Met
1               5

<210> SEQ ID NO 22
<211> LENGTH: 8
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (8)..(8)
<223> OTHER INFORMATION: L-NH2

<400> SEQUENCE: 22

Gln Trp Ala Val Gly His Phe Leu
1               5

<210> SEQ ID NO 23
<211> LENGTH: 8
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (5)..(5)
<223> OTHER INFORMATION: Ala2
<220> FEATURE:
<221> NAME/KEY: MOD_RES
<222> LOCATION: (8)..(8)
<223> OTHER INFORMATION: Nle-NH2

<400> SEQUENCE: 23

Gln Trp Ala Val Ala His Phe Leu
1               5

<210> SEQ ID NO 24
<211> LENGTH: 10
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (10)..(10)
<223> OTHER INFORMATION: M-NH2

<400> SEQUENCE: 24

Gly Asn Leu Trp Ala Thr Gly His Phe Met
1               5                   10

<210> SEQ ID NO 25
<211> LENGTH: 7
<212> TYPE: PRT
<213> ORGANISM: Artificial
<220> FEATURE:
<223> OTHER INFORMATION: Description of Artificial Sequence: GRP
      Receptor Targeting Peptide
<220> FEATURE:
<221> NAME/KEY: MOD_RES
<222> LOCATION: (7)..(7)
<223> OTHER INFORMATION: M-NH2

<400> SEQUENCE: 25
```

```
Trp Ala Val Gly His Leu Met
1               5

<210> SEQ ID NO 26
<211> LENGTH: 7
<212> TYPE: PRT
<213> ORGANISM: Artificial
<220> FEATURE:
<223> OTHER INFORMATION: Description of Artificial Sequence:  GRP
      Receptor Targeting Peptide
<220> FEATURE:
<221> NAME/KEY: MOD_RES
<222> LOCATION: (7)..(7)
<223> OTHER INFORMATION: L-NH2

<400> SEQUENCE: 26

Trp Ala Val Gly His Leu Leu
1               5
```